(12) United States Patent
Baca et al.

(10) Patent No.: US 9,212,231 B2
(45) Date of Patent: Dec. 15, 2015

(54) TRAIL R2-SPECIFIC MULTIMERIC SCAFFOLDS

(75) Inventors: Manuel Baca, Gaithersburg, MD (US); Thomas Thisted, Gaithersburg, MD (US); Jeffrey Swers, Gaithersburg, MD (US); David Tice, Gaithersburg, MD (US)

(73) Assignee: MEDIMMUNE, LLC, Gaithersburg, MD (US)

( * ) Notice: Subject to any disclaimer, the term of this patent is extended or adjusted under 35 U.S.C. 154(b) by 26 days.

(21) Appl. No.: 13/639,381

(22) PCT Filed: Apr. 12, 2011

(86) PCT No.: PCT/US2011/032188
§ 371 (c)(1),
(2), (4) Date: Dec. 6, 2012

(87) PCT Pub. No.: WO2011/130328
PCT Pub. Date: Oct. 20, 2011

(65) Prior Publication Data
US 2013/0096058 A1 Apr. 18, 2013

Related U.S. Application Data

(60) Provisional application No. 61/323,708, filed on Apr. 13, 2010.

(51) Int. Cl.
*C07K 19/00* (2006.01)
*C07K 14/47* (2006.01)
(Continued)

(52) U.S. Cl.
CPC .............. *C07K 19/00* (2013.01); *C07K 14/001* (2013.01); *C07K 14/78* (2013.01); *C07K 16/1027* (2013.01); *C07K 16/2878* (2013.01); *C07K 16/468* (2013.01); *A61K 2039/505* (2013.01); *C07K 2317/73* (2013.01);
(Continued)

(58) Field of Classification Search
None
See application file for complete search history.

(56) References Cited

U.S. PATENT DOCUMENTS 6,160,089 A 12/2000 Honjo et al.
6,482,410 B1 11/2002 Crossin et al.
(Continued)

FOREIGN PATENT DOCUMENTS

CN 101371124 A 2/2009
CN 101445559 A 6/2009
(Continued)

OTHER PUBLICATIONS

Li et al., Activation of the proapoptotic death receptor DR5 by oligomeric peptide and antibody agonists, J. Mol. Biol. 361(3):522-536, Aug. 18, 2006.*
(Continued)

*Primary Examiner* — Claire Kaufman

(57) ABSTRACT

The present invention provides Tenascin-3 FnIII domain-based multimeric scaffolds that specifically bind to TRAIL Receptor 2 (TRAIL R2), a cell membrane receptor involved in apoptosis. The invention further provides engineered variants with increased affinity for the target, increased stability, and reduced immunogenicity. Furthermore, the present invention is related to engineered multivalent scaffolds as prophylactic, diagnostic, or therapeutic agents, and their uses against diseases caused by cells expressing TRAIL R2, in particular to a therapeutic use against cancer.

24 Claims, 41 Drawing Sheets

(51) Int. Cl.

| | | |
|---|---|---|
| *C07K 14/78* | (2006.01) | |
| *C07K 16/10* | (2006.01) | |
| *C07K 16/28* | (2006.01) | |
| *C07K 16/46* | (2006.01) | |
| *C07K 14/00* | (2006.01) | |
| *C07K 14/715* | (2006.01) | |
| *A61K 39/00* | (2006.01) | |

(52) U.S. Cl.
CPC ........ *C07K 2317/90* (2013.01); *C07K 2318/20* (2013.01); *C07K 2319/00* (2013.01); *C07K 2319/30* (2013.01); *C07K 2319/33* (2013.01); *C07K 2319/70* (2013.01); *C07K 2319/74* (2013.01)

(56) References Cited

U.S. PATENT DOCUMENTS

| | | | |
|---|---|---|---|
| 6,624,295 | B1 * | 9/2003 | Adams et al. |
| 6,818,418 | B1 | 11/2004 | Lipovsek et al. |
| 8,633,297 | B2 * | 1/2014 | Wu et al. |
| 2005/0038229 | A1 | 2/2005 | Lipovsek et al. |
| 2006/0073559 | A1 | 4/2006 | Ferrari et al. |
| 2007/0098681 | A1 | 5/2007 | Kelley et al. |
| 2008/0108798 | A1 | 5/2008 | Lipovsek et al. |
| 2008/0206229 | A1 | 8/2008 | Ono et al. |
| 2009/0176654 | A1 | 7/2009 | Cappuccilli et al. |
| 2009/0289213 | A1 | 11/2009 | Pipper |
| 2010/0105620 | A1 | 4/2010 | Bowdish et al. |
| 2010/0216708 | A1 | 8/2010 | Jacobs et al. |
| 2010/0298541 | A1 | 11/2010 | Wu et al. |

FOREIGN PATENT DOCUMENTS

| | | | |
|---|---|---|---|
| EP | 2 065 402 A1 | 6/2009 | |
| WO | WO 9856915 A2 | 12/1998 | |
| WO | WO 0034784 A1 | 6/2000 | |
| WO | WO 0164942 A1 | 9/2001 | |
| WO | WO 0204523 A2 | 1/2002 | |
| WO | WO 0232925 A2 | 4/2002 | |
| WO | WO 03104418 A2 | 12/2003 | |
| WO | WO 2005056764 A2 | 6/2005 | |
| WO | WO 2006013468 A2 | 2/2006 | |
| WO | WO 2008031098 A1 | 3/2008 | |
| WO | WO 2008066752 A2 | 6/2008 | |
| WO | WO 2009023184 A2 | 2/2009 | |
| WO | WO 2009058379 A2 | 5/2009 | |
| WO | WO 2009058379 A3 | 5/2009 | |
| WO | WO 2009083804 A2 | 7/2009 | |
| WO | WO 2009133208 A1 | 11/2009 | |
| WO | WO 2009142773 A2 | 11/2009 | |
| WO | WO 2010051274 A2 | 5/2010 | |
| WO | WO 2010060095 A1 | 5/2010 | |
| WO | WO 2010093627 A2 | 8/2010 | |
| WO | WO 2011020033 A2 | 2/2011 | |
| WO | WO 2011035202 A2 | 3/2011 | |

OTHER PUBLICATIONS

Kuruca et al., Retargeting of CTL by an efficient refolded bispecific single-chain Fv dimer produced in bateria, J. Immunol. 154:4576-4582, 1995.*

Baca, M., "A New Platform for Non-antibody Protein Drugs," 15thHuman Antibodies & Hybridomas Conference, pp. 1-22 (2010).

Baca, M., "Beyond Antibodies: Challenges and Opportunities for Alternative Scaffold Protein Drugs," Antibody Interest Group, NIH, pp. 1-24 (2010).

Baca, M., "Tn3: A New Platform for Non-antibody Protein Drugs," Protein and Antibody Engineering Summit, pp. 1-2 (2010).

Batori, V., et al., "Exploring the potential of the monobody scaffold: effects of loop elongation on the stability of a fibronectin type III domain," Protein Engineering, vol. 15, No. 12, pp. 1015-1020, Oxford University Press (2002).

Binz, H.K., et al., "Engineering novel binding proteins from nonimmunoglobulin domains," Nature Biotechnology, vol. 23, No. 10, pp. 1257-1268, Nature publishing Group (2005).

Bloom, L, and Calabro, V., "FN3: a new protein scaffold reaches the clinic," Drug Discovery Today, vol. 14, No. 19-20, pp. 949-955, Elsevier Ltd. (2009).

Bork, P, and Doolittle, R.F., "Proposed acquisition of an animal protein domain by bacteria," Proc. Natl. Acad. Sci, vol. 89, pp. 8990-8994, (1992).

Bork, P., et al., "The Immunoglobulin Fold Structural Classification, Sequence Patterns and Common Core," J. Mol. Bio., vol. 242, pp. 309-320, Academic Press Limited (1994).

Chothia, C, and Jones, E.Y., "The Molecular Structure of Cell Adhesion Molecules," Annu. Rev. Biochem., vol. 66, pp. 823-862, Annual Reviews Inc., (1997).

Coussen, F., et al., "Trimers of the fibronectin cell adhesion domain localize to actin filament bundles and undergo rearward translocation," Journal of Cell Science, vol. 115, pp. 2581-2590, The Company of Biologists Ltd (2002).

Dineen, Sean P. et al., The Adnectin CT-322 is a novel VEGF receptor 2 inhibitor that decreases tumor burden in an orthotopic mouse model of pancreatic cancer, BMC Cancer, pp. 1-10 (2008).

Duan, J., et al., "Fibronectin Type III Domain Based Monobody with High Avidity," Biochemistry, vol. 46, No. 44, pp. 12656-12664, American Chemical Society (2007).

Dutta, S., "High-affinity fragment complementation of a fibronectin type III domain and its application to stability enhancement," Protein Science, vol. 14, pp. 2838-2848, The Protein Society (2005).

Emanuel, S.L., et al., "Functional activity of a bispecific Adnectin inhibitor to EGFR and IGFR," AACR, p. 1, Denver, CO (2009).

Friedman, M, and StÅhl, S., "Engineered affinity proteins for tumour-targeting applications," Biotechnol. Appl. Biochem. vol. 53, pp. 1-29, Portland Press Ltd (2009).

Gebauer, M, and Skerra, A., "Engineered protein scaffolds as next-generation antibody therapeutics," Current Opinion in Chemical Biology, vol. 13, pp. 245-255, Elsevier Ltd. (2009).

Getmanova, E.V., et al., "Antagonists to Human and Mouse Vascular Endothelial Growth Factor Receptor 2 Generated by Directed Protein Evolution In Vitro," Chemistry & Biology, vol. 13, Issue 5, pp. 549-556, Elsevier Ltd (2006).

Gill, D.S and Damle, N.K., "Biopharmaceutical drug discovery using novel protein scaffolds," Current Opinion in Biotechnology, vol. 17, pp. 653-658, Elsevier Ltd. (2006).

Hackel, B.J, and Wittrup, K.D., "High Affinity Fn3 Domains Using Loop Length Diversity and Population Maturation," AIChE SBE's 1st International Converence on Biomolecular Engineering (2007).

Hackel, B.J., et al., "Picomolar Affinity Fibronectin Domains Engineered Utilizing Loop Length Diversity, Recursive Mutagenesis, and Loop Shuffling," J. Mol. Biol., vol. 381, pp. 1238-1252, Elsevier Ltd. (2008).

Hsia, H.C, and Schwarzbauer, J.E., "Meet the Tenascins: Multifunctional and Mysterious," The Journal of Biological Chemistry, vol. 280, No. 29, pp. 26641-26644, The American Society for Biochemistry and Molecular Biology, Inc. (2005).

Karatan, E., et al., "Molecular Recognition Properties of FN3 Monobodies that Bind the Src SH3 Domain," Chemistry & Biology, vol. 11, pp. 835-844, Elsevier Ltd. (2004).

Kashiwagi, K., et al., "Frame shuffling: a novel method for in vitro protein evolution," Protein Engineering, Design & Selection, vol. 19, No. 3, pp. 135-140 (2006).

Koide, A, and Koide, S., "Monobodies Antibody Mimics based on the Scaffold of the Fibronectin Type III Domain," Methods in Molecular Biology, vol. 352, pp. 95-96, Humana Press Inc. (2007).

Koide, A., et al., "High-affinity single-domain binding proteins with a binary-code interface," PNAS, vol. 104, No. 16, pp. 6632-6637, The National Academy of Sciences of the USA (2007).

Koide, A., et al., "The Fibronectin Type III Domain as a Scaffold for Novel Binding Proteins," J. Mol. Biol., vol. 284, pp. 1141-1151, Academic Press (1998).

Kolkman, J.A, and Stemmer, W.P.C., "Directed evolution of proteins by exon shuffling," Nature Biotechnology, vol. 19, pp. 423-428, Nature Publishing Group (2001).

(56) References Cited

OTHER PUBLICATIONS

Lipovšek "Evolution of an Interloop Disulfide Bond in High-Affinity Antibody Mimics Based on Fibronectin Type III Domain and Selected by Yeast Surface Display: Molecular Convergence with Single-Domain Camelid and Shark Antibodies," J. Mol. Biol., vol. 368, pp. 1024-1041, Elsevier Ltd. (2007).

Meinke, A., et al., "Cellulose-Binding Polypeptides from *Cellulomonas fimi*: Endoglucanase D (CenD), a Family A β-1,4-Glucanase," Journal of Bacteriology, vol. 175, No. 7, pp. 1910-1918, American Society for Microbiology (1993).

NG. S.P., et al., "Designing an extracellular matrix protein with enhanced mechanical stability," PNAS, vol. 104, No. 23, pp. 9633-9637, The National Academy of Sciences of the USA (2007).

Nuttall, S.D, and Walsh, R.B., "Display scaffolds: protein engineering for novel therapeutics," Current Opinion in Pharmacology, vol. 8, pp. 609-615, Elsevier Ltd. (2008).

O'Neil, K., "Centyrin Alternative Scaffolds: A New Biotherapeutic Platform for J&J," Beyond Antibodies conference, pp. 1-24 (2009).

Olson, C.A, and Roberts, R.W., "Design, expression, and stability of a diverse protein library based on the human fibronectin type III domain," Protein Science, vol. 16, pp. 476-484, The Protein Society (2007).

Parker, M.H., et al., "Antibody mimics based on human fibronectin type three domain engineered for thermostability and high-affinity binding to vascular endothelial growth factor receptor two," Protein Engineering, Design & Selection, vol. 18, No. 9, pp. 435-444 (2005).

Peleshok, J, and Saragovi, H.U., "Functional mimetics of neurotrophins and their receptors," Biochemical Society Transactions, vol. 34, Part 4, pp. 612-617, Biochemical Society (2006).

Schellenberger, V., "Tuning the Half-life of Protein Therapeutics by Fusion to XTEN," VP Drug Discovery, Amunix Inc., pp. 1-25 (2010).

Sheridan, C., "Pharma consolidates its grip on post-antibody landscape," Nature Biotechnology, vol. 25, No. 4, pp. 365-366, Nature Publishing Group (2007).

Siggers, Keri et al., "Conformational Dynamics in Loop Swap Mutants of Homologous Fibronectin Type III Domains", Biophysical Journal, vol. 93(7):2447-2456 (2007).

Silverman, J., et al., "Multivalent avimer proteins evolved by exon shuffling of a family of human receptor domains," vol. 23, No. 12, Nature Biotechnology, pp. 1556-1561, Nature Publishing Group (2005).

Skerra, A., "Alternative non-antibody scaffolds for molecular recognition", Current Opinion in Biotechnology, 18:295-304, (2007).

Swers, Jeffery S. et al., "Multivalent Scaffold Proteins as Superagonists of TRAIL Receptor 2-Induced Apoptosis", Molecular Cancer Therapeutics, vol. 12(7):1235-1244 (2013).

Thisted, T., "Tn3: A New Platform for Non-antibody Protein Drugs," 5th Annual Biological Therapeutics Conference, pp. 1-21 (2010).

ThØgersen, H.C, and Holldack, J., "A Tetranectin-Based Platform for Protein Engineering," Innovations in Pharmaceutical Technology, pp. 27-31 (2005).

Watanabe, T., et al., "Gene Cloning of Chitinase A1 from *Bacillus circulans* WL-12 Revealed Its Evolutionary Relationship to *Serratia* Chitinase and to the Type III Homology Units Fibronectin," The Journal of Biological Chemistry, vol. 265, No. 26, pp. 15659-15665, The American Society for Biochemistry and Molecular Biology, Inc. (1990).

Wurch, T., et al., "Development of Novel Protein Scaffolds as Alternatives to Whole Antibodies for Imaging and Therapy: Status on Discovery Research and Clinical Validation," Current Pharmaceutical Biotechnology, vol. 9, No. 6, pp. 502-509, Bentham Science Publishers Ltd (2008).

International Preliminary Report on Patentability (IPRP) with Written Opinion for International Application No. PCT/US2008/012398, The International Bureau of WIPO, Switzerland, mailed on Apr. 24, 2009.

International Search Report corresponding to PCT/US2011/32188 mailed May 31, 2011.

Supplementary European Search Report corresponding to EP 08 84 5766 dated Jun. 30, 2011.

\* cited by examiner

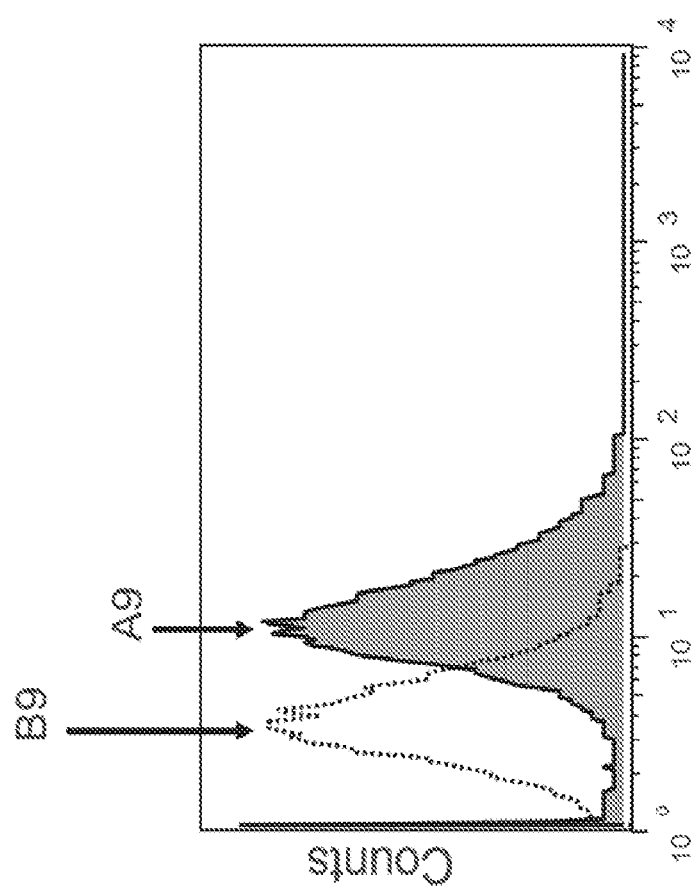

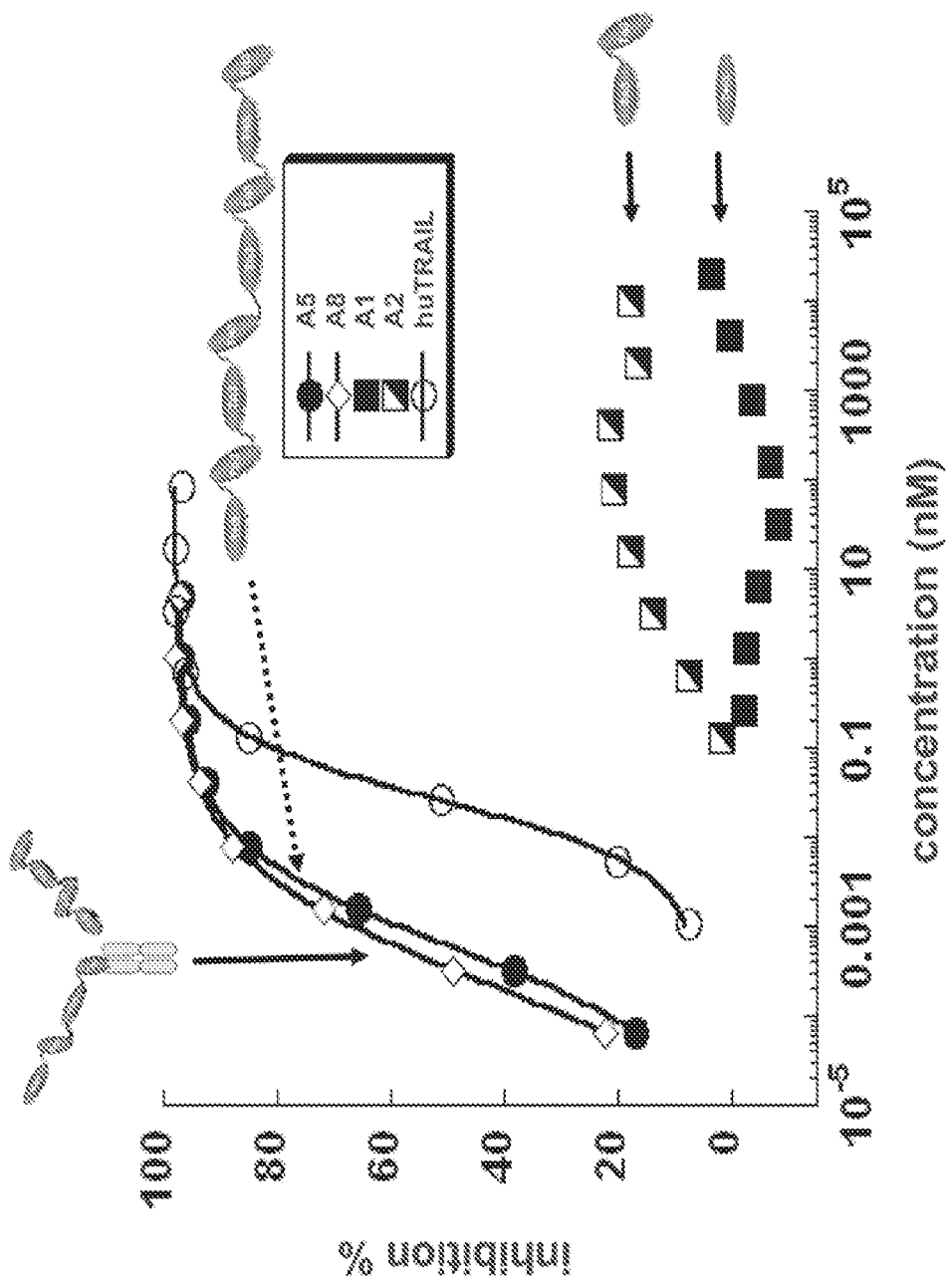

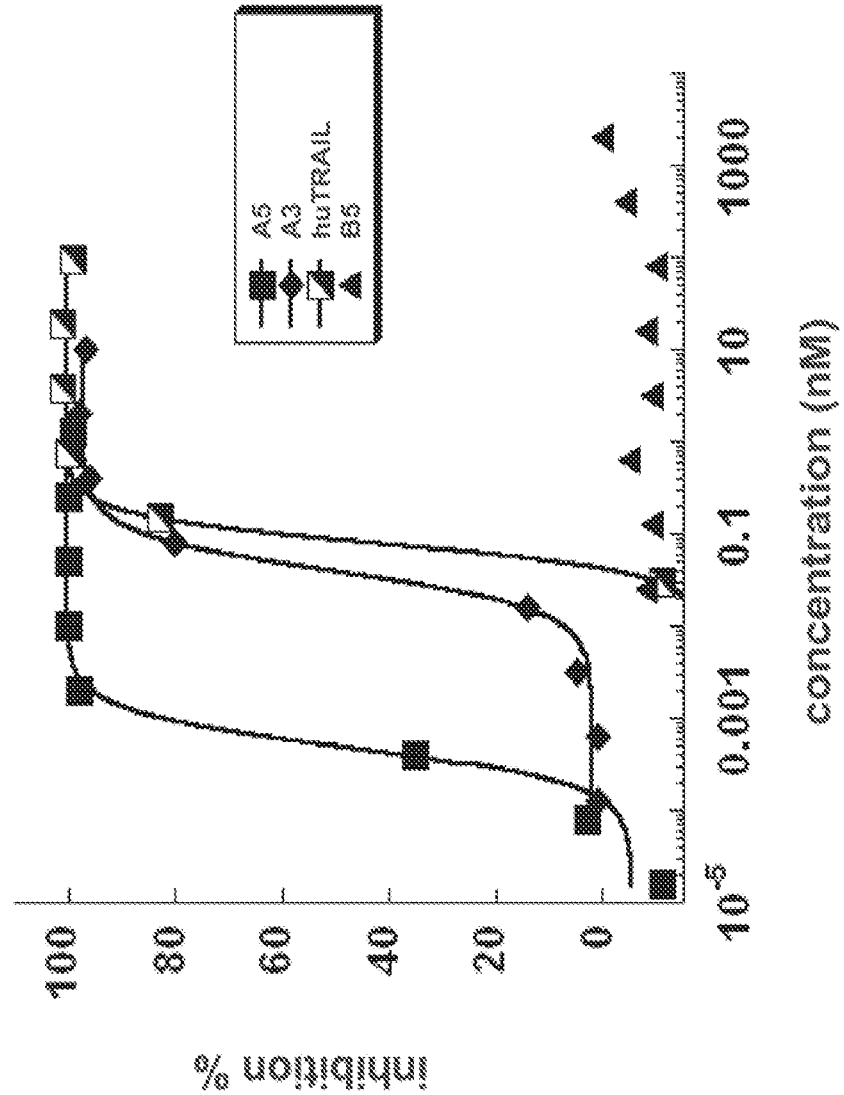

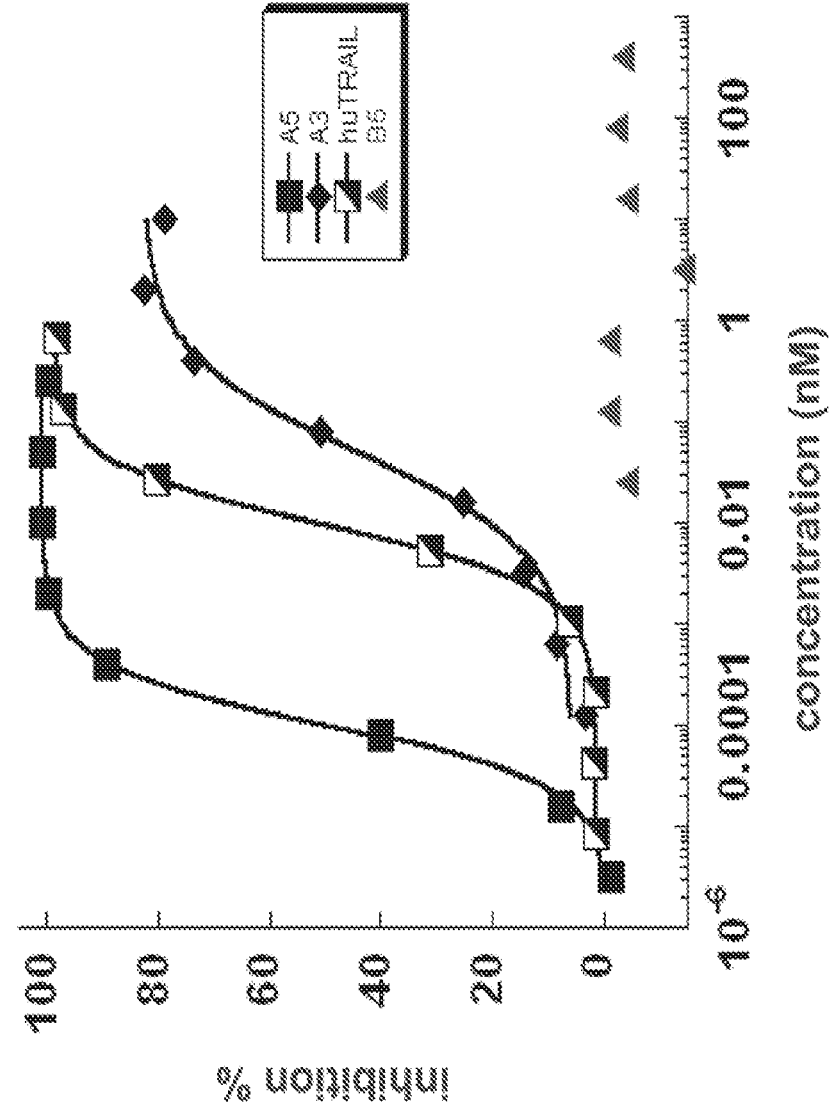

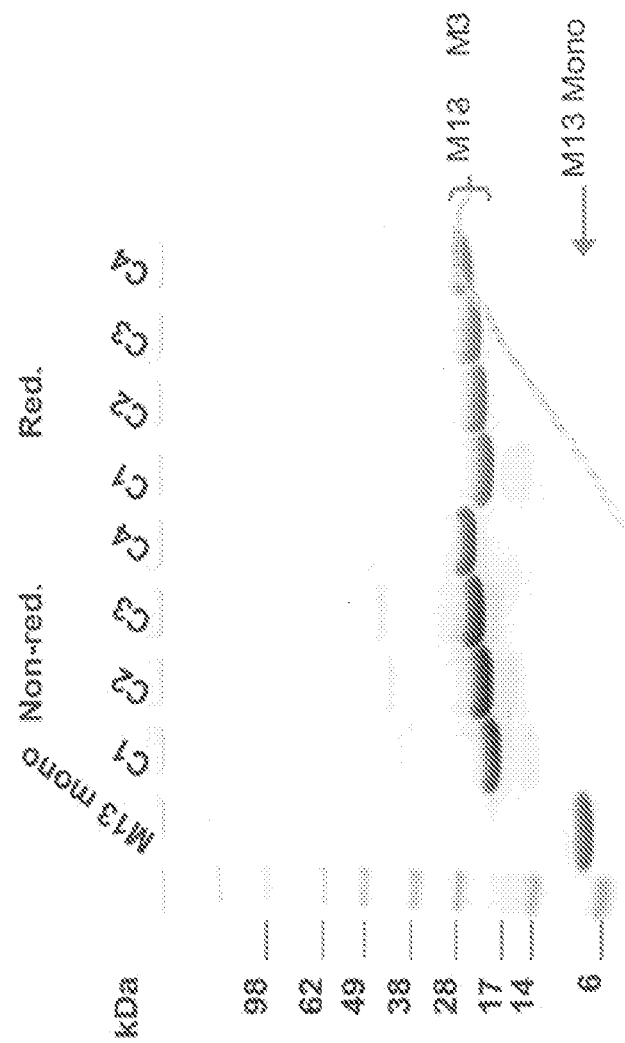

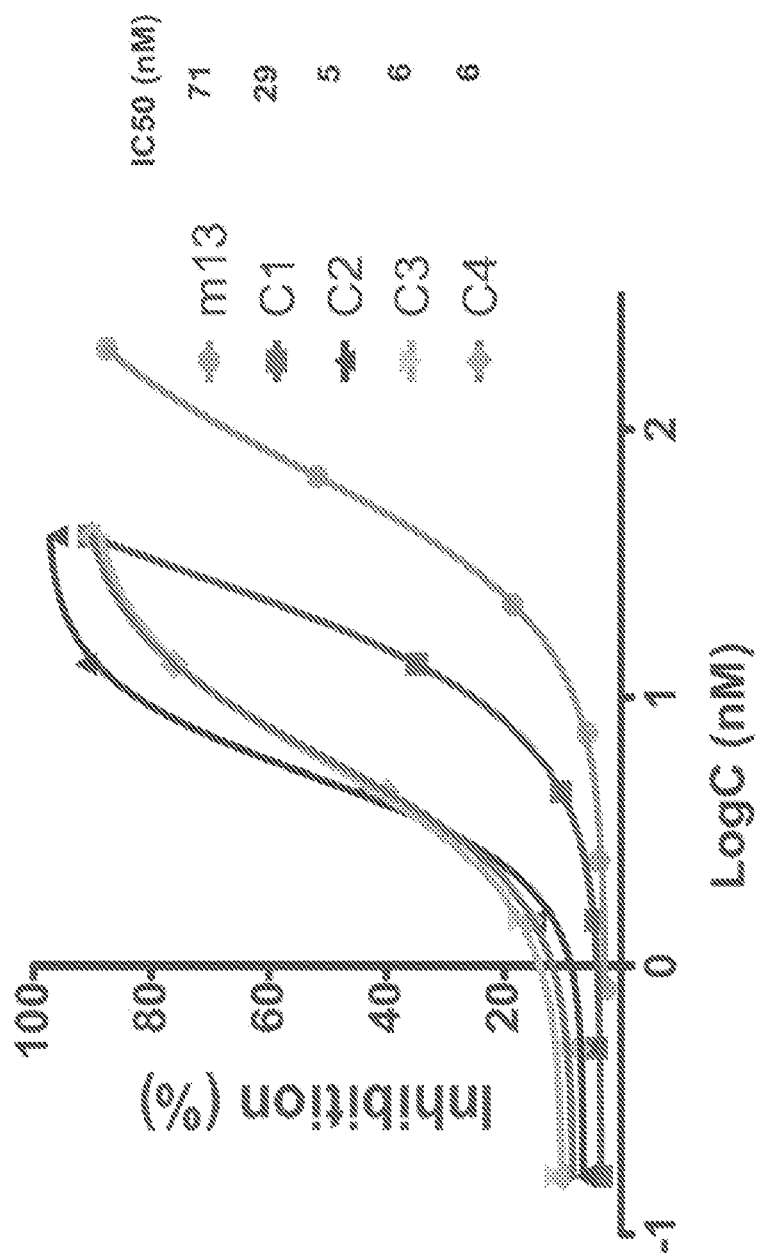

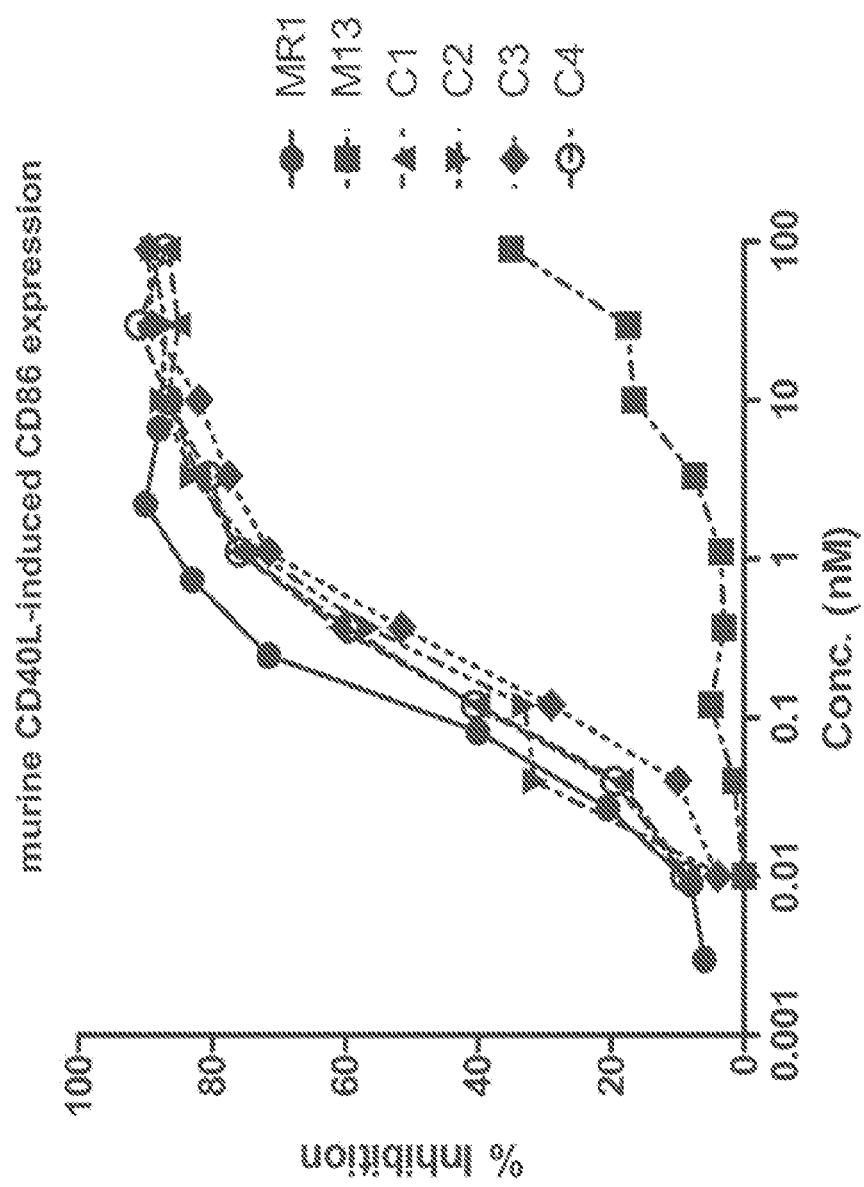

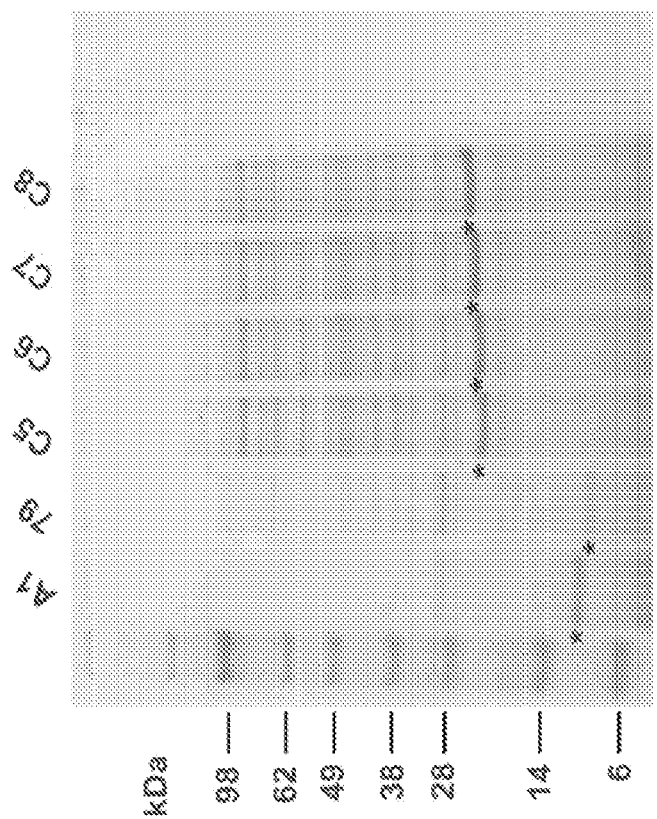

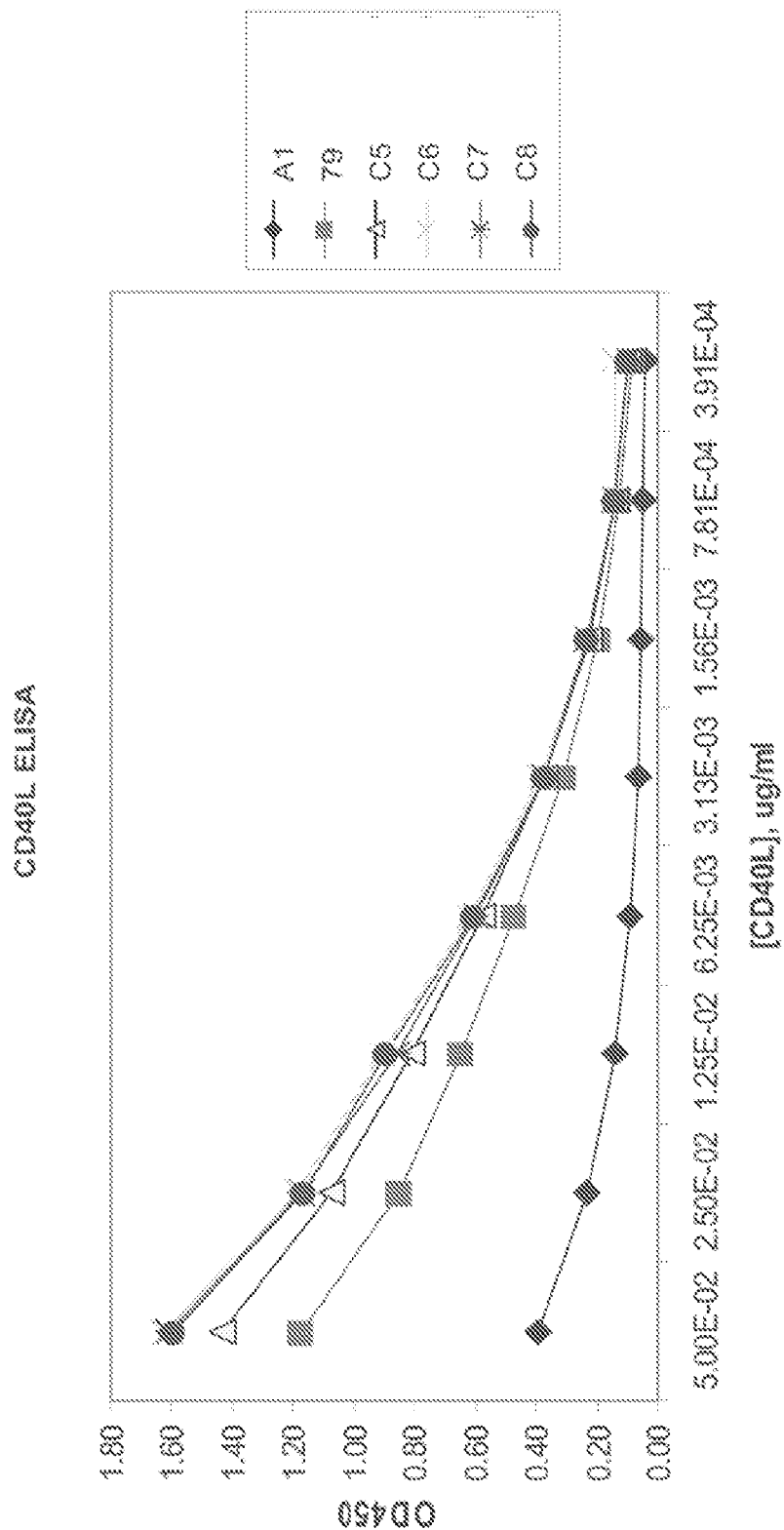

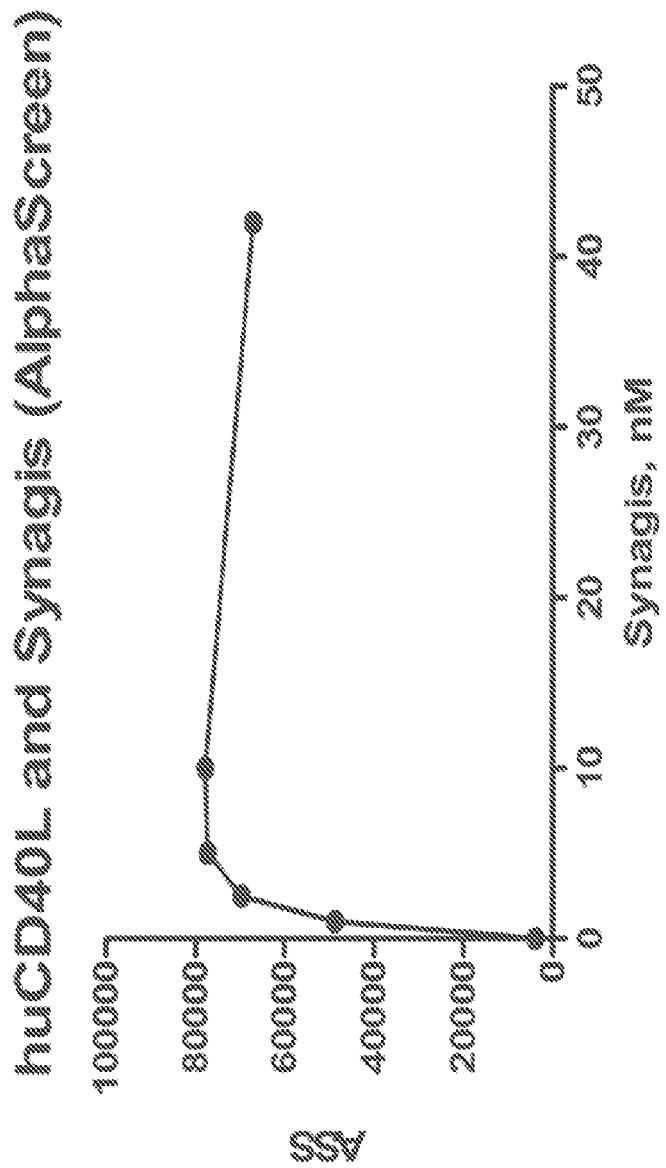

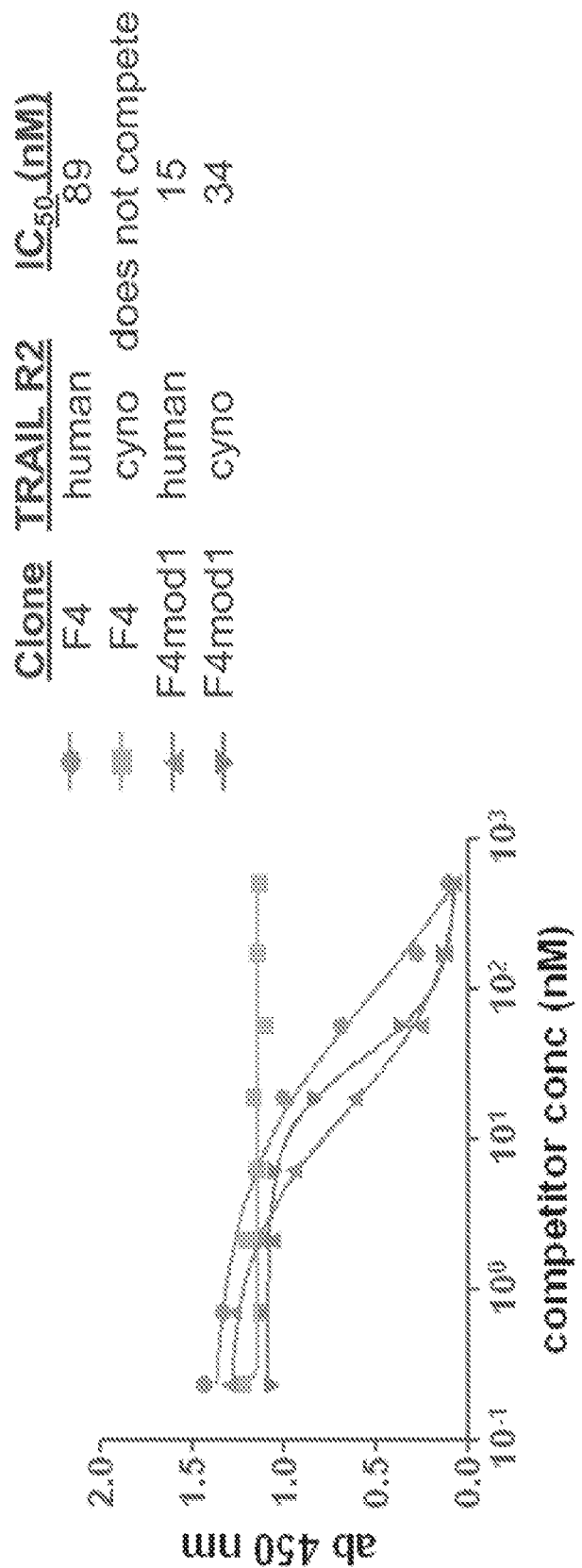

Figure 23A

|  | FW1 (A strand-B strand) | BC Loop | FW2 (C strand-D strand) | SEQ ID NO |
|---|---|---|---|---|
| 3rd Fn III of Tenascin | T E D N Q Y S I G N L K P D T E Y | T F K P L A E I D | G I E L T Y G I K D V P G D R T T I D L | |
| F4 | A I E V K D V T D T T A L I T W | A K P M Y D P P P L | G C E L T Y G I K D V P G D R T T I D L | 4 |
| F4 mod 1 | A I E V K D V T D T T A L I T W | A K P M Y D P P L W | G C E L T Y G I K D V P G D R T T I D L | 202 |
| F4 mod 12 | S Q E V R D V T D T T A L I T W | A K P M Y D P P L W | G C E L T Y G I K D V P G D R T T I G L | 203 |

Residues reverted to germline without affecting binding

|  | DE Loop | FW3 (E strand-F strand) | FG Loop | FW4 (G strand) | |
|---|---|---|---|---|---|
| 3rd Fn III of Tenascin | T E D N Q | Y S I G N L K P D T E Y E V S L I S R K G D M S S N | P A K E T F T T G L | | |
| F4 | Q Q S H T | Y S I G N L K P D T E Y E V S L I C F P P Y G K S R | P A K E T F T T G L | | |
| F4 mod 1 | Q Q S H T | Y S I G N L K P D T E Y E V S L I C F P P Y G K S R | P A K E T F T T G L | | |
| F4 mod 12 | Q Q K H N | Y S I G N L K P D T E Y E V S L I P P Y G L K S R | P A K E T F T T G L | |

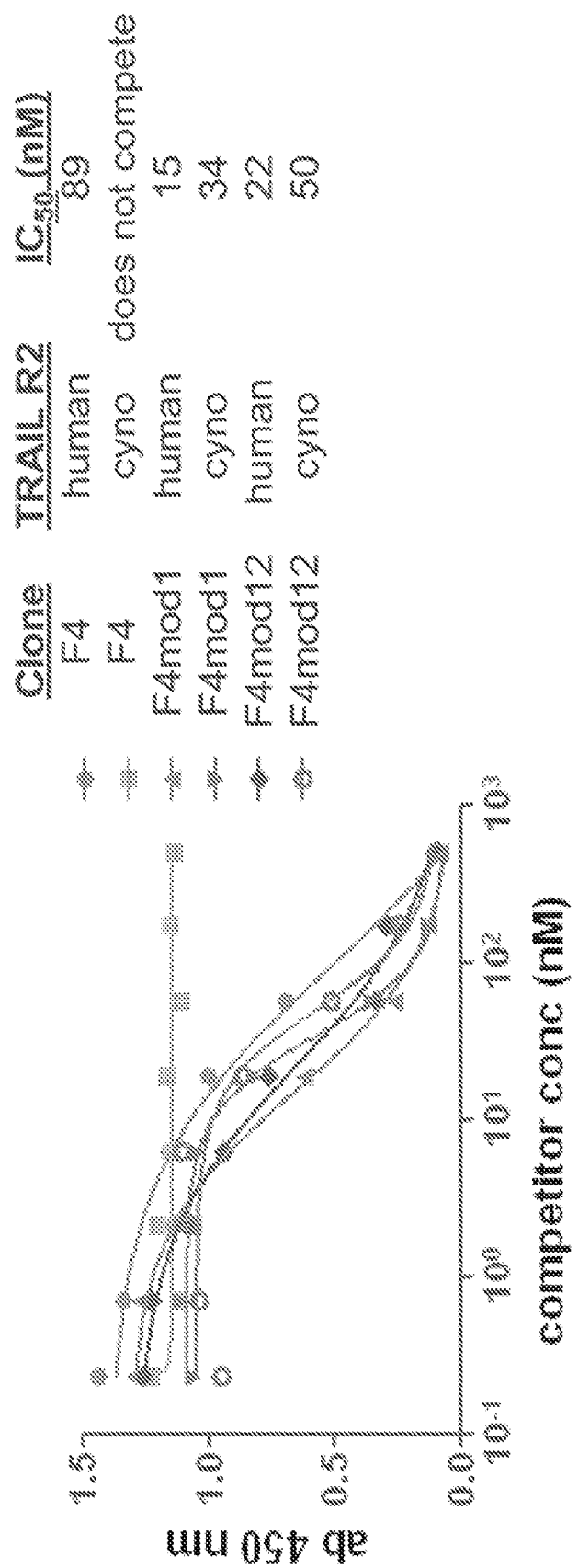

Figure 25

|  | FW1 (A strand-B strand) | BC Loop | FW2 (C strand-D strand) |
|---|---|---|---|
| wild type Tn3 | SQIEVKDVTDTTALITW | RKPLAEDG | QCELFYQIKDVPGDRTTIGL |
| F4 mod 12 | SQIEVKDVTDTTALITW | AKPWVDPPPLW G | QCELTYGIKDVPGDRTTIGL |
| A07-Alt | SQIEVKDVTDTTALITW | GQPWVDPPPLW G | QCELTYGIKDVPGDRTTIGL |
| G09-Alt | SQIEVKDVTDTTALITW | AKPWVDPPPLW G | QCELTYGIKDVPGDRTTIGL |
| A10-Alt | SQIEVKDVTDTTALITW | AKPWVDPPPLW G | QCELTYGIKDVPGDRTTIGL |
| F11-Alt | SQIEVKDVTDTTALITW | AKPWVDPPPLW G | QCELTYGIKDVPGDRTTIGL |

|  | DE Loop | FW3 (E strand-F strand) | FG Loop | FW4 (G strand) | SEQ ID NO |
|---|---|---|---|---|---|
| wild type Tn3 | TEDEN | QYSIGNLKPDTEYEVSLICFD | RGSDNSSN-PA | KETFTTGL | 201 |
| F4 mod 12 | QQKHN | QYSIGNLKPDTEYEVSLICFD | PPYGLKSRPA | KETFTTGL | 204 |
| A07-Alt | QQKHN | QYSIGNLKPDTEYEVSLICFD | PPYGLHSRPT | KETFTTGL | 205 |
| G09-Alt | QQKHN | QYSIGNLKPDTEYEVSLICFD | PPYGNKSPPL | KETFTTGL | 206 |
| A10-Alt | QQKHN | QYSIGNLKPDTEYEVSLICFD | PPYGQKSRPI | KETFTTGL | 207 |
| F11-Alt | QQKHN | QYSIGNLKPDTEYEVSLICFD | PPYGMKSPPS | KETFTTGL | 208 |

TRAIL R2-SPECIFIC MULTIMERIC SCAFFOLDS

CROSS-REFERENCE TO RELATED APPLICATIONS

This application is a U.S. National Stage application of International Application No. PCT/US2011/032188, filed on Apr. 12, 2011, said International Application No. PCT/US2011/032188 claims benefit under 35 U.S.C. §119(e) of the U.S. Provisional Application No. 61/323,708, filed Apr. 13, 2010. Each of the above listed applications is incorporated by reference herein in its entirety for all purposes.

REFERENCE TO THE SEQUENCE LISTING

The application incorporates by reference a Sequence Listing submitted with this application via EFS-Web as text file entitled TN3TR-100US1_SL.txt created on Apr. 13, 2015 and having a size of 390,000 bytes.

BACKGROUND OF THE INVENTION

1. Field of the Invention

The present invention relates in general to the field of antibody mimetics, specifically to multimeric scaffolds based on the fibronectin type III (Fn3) domain useful, for example, for the generation of products having novel binding characteristics. In particular, the invention relates to TRAIL R2-specific multimeric scaffolds derived from the third FnIII domain of human Tenascin C and their use for TRAIL R2 receptor detection and modulation of TRAIL R2-mediated function such as treatment of cancer and other disorders.

2. Background Art

Biomolecules capable of specific binding to a desired target epitope are of great importance as therapeutics, research, and medical diagnostic tools. A well known example of this class of molecules is the antibody. Antibodies can be selected that bind specifically and with affinity to almost any structural epitope. However, classical antibodies are structurally complex heterotetrameric molecules with are difficult to express in simple eukaryotic systems. As a result, most antibodies are produced using complex and expensive mammalian cell expression systems.

Proteins having relatively defined three-dimensional structures, commonly referred to as protein scaffolds, may be used as reagents for the design of engineered products. One particular area in which such scaffolds are useful is the field of antibody mimetic design. Antibody mimetics, i.e., small, non-antibody protein therapeutics, capitalize on the advantages of antibodies and antibody fragments, such as high affinity binding of targets and low immunogenicity and toxicity, while avoiding some of the shortfalls, such as the tendency for antibody fragments to aggregate and be less stable than full-length IgGs.

These drawbacks can be addressed by using antibody fragments created by the removal of parts of the antibody native fold. However, this often causes aggregation when amino acid residues which would normally be buried in a hydrophobic environment such as an interface between variable and constant domain become exposed to the solvent. One example of a scaffold-based antibody mimetic is based on the structure of a fibronectin module of type III (FnIII), a domain found widely across phyla and protein classes, such as in mammalian blood and structural proteins.

TRAIL (tumor necrosis factor-related apoptosis-inducing ligand, also referred to in the literature as Apo2L and TNFSF10) belongs to the tumor necrosis factor (TNF) superfamily and has been identified as an activator of programmed cell death, or apoptosis, in tumor cells. Both the membrane-bound and soluble forms of TRAIL are able to trigger apoptosis via interaction with TRAIL receptors located on target cells. In humans, five receptors have been identified to have binding activity for TRAIL. Upon binding of TRAIL to TRAIL R1 or TRAIL R2, caspase-related cell death is triggered. In light of this cell death activity, TRAIL-based therapeutic approaches are being pursued. Several therapeutic approaches based on TRAIL or TRAIL R1 or R2 human agonistic antibodies have been developed, however, TRAIL has a very short life, it binds to decoy receptors, and the large size of antibodies can limit their tumor penetration. Accordingly, there is a need for novel molecules that can bind to TRAIL receptors, pharmaceutical compositions comprising those molecules, methods for screening for such molecules, and methods for using such molecules in the therapeutic treatment of a wide variety of cancers.

Citation or discussion of a reference herein shall not be construed as an admission that such is prior art to the present invention.

SUMMARY OF THE INVENTION

The invention provides a TRAIL R2-specific recombinant multimeric scaffold comprising two Tn3 monomer scaffolds, wherein (a) each Tn3 monomer scaffold comprises seven beta strands designated A, B, C, D, E, F, and G, and six loop regions designated AB, BC, CD, DE, EF, and FG, (b) the Tn3 monomer scaffolds are connected in tandem, and (c) the recombinant multimeric scaffold specifically binds to TRAIL R2. In some embodiments, a TRAIL R2-specific multimeric scaffold comprises 3, 4, 5, 6, 7, or 8 Tn3 monomer scaffolds. In some other embodiments, all of the Tn3 monomer scaffolds in a TRAIL R2-specific multimeric scaffold of the invention are in tandem.

In some embodiments, at least one Tn3 monomer scaffold of a TRAIL R2-specific multimeric scaffold is connected directly, by a linker, or by a heterologous moiety to 1, 2, 3, 4, 5, 6, or 7 other Tn3 monomer scaffolds. In certain embodiments, at least two Tn3 monomer scaffolds of a TRAIL R2-specific multimeric scaffold are directly connected without a linker interposed between the Tn3 monomer scaffolds. In some embodiments, at least two Tn3 monomer scaffolds of a TRAIL R2-specific multimeric scaffold are connected by a linker. In some embodiments, the linker comprises a peptide linker. In some embodiments, the peptide linker is a flexible peptide linker. In certain embodiments, the peptide linker comprises a $(G_xS)_y$ sequence wherein x and y are integers, wherein x=1, 2, 3 or 4, and wherein y=1, 2, 3, 4, 5, 6, or 7 (SEQ ID NO: 212).

In some embodiments, the binding of a TRAIL R2-specific multimeric scaffold of the invention to TRAIL R2 is improved over that of a TRAIL R2 specific Tn3 monomer scaffold. In some embodiments, the binding of the of the TRAIL R2-specific multimeric scaffold to TRAIL R2 improves the action on the target over that of a TRAIL R2 specific Tn3 monomer scaffold.

In some embodiments, the improvement in binding of a TRAIL R2 specific scaffold of the invention to TRAIL R2 over that of a TRAIL R2 specific Tn3 monomer scaffold is an improvement in binding affinity and/or an improvement in binding avidity. In other embodiments, the binding affinity for TRAIL R2 and protein stability are improved over those of a TRAIL R2 specific Tn3 monomer scaffold. In some embodiments, the binding avidity for TRAIL R2 and protein stability are improved over those of a TRAIL R2 specific Tn3 monomer scaffold.

In some embodiments, a TRAIL R2-specific multimeric scaffold contains a linker comprising a functional moiety. In some embodiments, the functional moiety is an immunoglobulin or a fragment thereof. In certain embodiments, the immunoglobulin or fragment thereof is selected from the group consisting of: a Fab fragment, a Fab' fragment, a Fd fragment, a Fd' fragment, a Fv fragment, a dAb fragment, a F(ab')2 fragment, an scFv, a diabody, a linear antibody, a full length antibody, an Fc region, and a combination of two or more of said moieties. In certain embodiments, the immunoglobulin or fragment thereof comprises an Fc domain and a hinge region of an IgG. In other embodiments, the immunoglobulin or fragment thereof further comprises a CH1 domain. In some embodiments, the immunoglobulin or fragment thereof comprises a Ckappa domain or a Clambda domain of an IgG.

In some embodiments, at least one of the Tn3 monomer scaffolds of a TRAIL R2-specific multimeric scaffold is fused to a heterologous moiety. In some embodiments, the heterologous moiety comprises a composition selected from the group consisting of: a protein, a peptide, a protein domain, a linker, a drug, a toxin, a cytotoxic agent, an imaging agent, a radionuclide, a radioactive compound, an organic polymer, an inorganic polymer, a polyethylene glycol (PEG), biotin, a human serum albumin (HSA), a HSA FcRn binding portion, an antibody, a domain of an antibody, an antibody fragment, a single chain antibody, a domain antibody, an albumin binding domain, an enzyme, a ligand, a receptor, a binding peptide, a non-FnIII scaffold, an epitope tag, a recombinant polypeptide polymer, a cytokine, and a combination of two or more of said moieties.

In some specific embodiments, a TRAIL R2-specific multimeric scaffold is conjugated to PEG. In other embodiments, more than two of the Tn3 monomer scaffolds are connected by linkers and wherein at least one linker is structurally and/or functionally different from the other linkers.

In some embodiments, the Tn3 monomer scaffolds in a TRAIL R2-specific multimeric scaffold are connected in a branched format. In other embodiments, some Tn3 monomer scaffolds in a TRAIL R2-specific multimeric scaffold of the invention are connected in a linear tandem format and some Tn3 monomer scaffolds are connected in a branched format. In some embodiments, at least two Tn3 monomer scaffolds in a TRAIL R2-specific multimeric scaffold are identical. In other embodiments, at least two Tn3 monomer scaffolds in a TRAIL R2-specific multimeric scaffold are different.

In some embodiments, a TRAIL R2-specific multimeric scaffold of the invention binds to at least an additional target, which may be a T cell antigen. In some embodiments, this T cell antigen is CD40L.

In some embodiments, a TRAIL R2-specific multimeric scaffold of the invention is a receptor agonist. In some embodiments, at least two Tn3 monomer scaffolds in a TRAIL R2-specific multimeric scaffold of the invention bind the same epitope on TRAIL R2. In other embodiments, at least two Tn3 monomer scaffolds in a TRAIL R2-specific multimeric scaffold of the invention bind different epitopes on TRAIL R2. In some embodiments, the different TRAIL R2 epitopes are non-overlapping epitopes. In other embodiments, the different TRAIL R2 epitopes are overlapping epitopes.

In some embodiments, the beta strands of at least two Tn3 monomer scaffolds in a TRAIL R2-specific multimeric scaffold of the invention have at least 90% sequence identity to the beta strands of SEQ ID NO: 1. In some embodiments, at least two Tn3 monomer scaffolds in a TRAIL R2-specific multimeric scaffold of the invention comprise the amino acid sequence (SEQ ID NO: 213):
IEV$(X_{AB})$nALITW$(X_{BC})_n$CELX$_1$YGI$(X_{CD})_n$TTIX$_2$L$(X_{DE})_n$YSI$(X_{EF})_n$YEVSLIC$(X_{FG})_n$KX$_3$TFTT wherein X$_{AB}$, X$_{BC}$, X$_{CD}$, X$_{DE}$, X$_{EF}$, and X$_{FG}$ represent the amino acid residues present in the AB, BC, CD, DE, EF, and FG loops, respectively, wherein X$_1$ represents amino acid residue A or T, wherein X$_2$ represents amino acid residue D or G, wherein X$_3$ represents amino acid E or G, and wherein the length of the loop n is an integer between 2 and 26. In some embodiments, the AB loop comprises SEQ ID NO: 35, the CD loop comprises SEQ ID NO: 37, and the EF loop comprises SEQ ID NO: 39. In some embodiments, the BC loop comprises a sequence selected from the group consisting of SEQ ID NOs: 97, 98, or 168. In some embodiments, the DE loop comprises a sequence selected from the group consisting of SEQ ID NOs: 102, 103, and 179. In some embodiments, the FG loop comprises a sequence selected from the groups consisting of SEQ ID NOs: 106, 108, 109, 169 and 170. In some embodiments, the BC loop comprises SEQ ID NO: 97, the DE loop comprises SEQ ID NO: 179, and the FG loop comprises SEQ ID NO: 170. In some embodiments, a TRAIL R2-specific multimeric scaffold of the invention comprises SEQ ID NO: 209 or 204.

In some embodiments, a TRAIL R2-specific multimeric scaffold of the invention binds to a TRAIL R2 receptor with an affinity (K$_d$) of 1 µM or less. In another embodiment, a TRAIL R2-specific multimeric scaffold of the invention binds to a TRAIL R2 receptor with an affinity (K$_d$) of 500 nM or less. In yet another embodiment, a TRAIL R2-specific multimeric scaffold of the invention binds to a TRAIL R2 receptor with an affinity (Kd) of 100 nM or less.

The invention also provides for an isolated nucleic acid molecule encoding any of the multimeric scaffolds described above. In some embodiments, an expression vector comprises the nucleic acid. In other embodiments, a host cell can comprise the vector.

The invention also provides a method of producing a TRAIL R2-specific multimeric scaffold of the invention comprising culturing a host cell under conditions in which the multimeric scaffold encoded by the nucleic acid molecule is expressed. The invention also provides a composition comprising a recombinant TRAIL R2-specific multimeric scaffold of the invention in a pharmaceutically acceptable excipient. The invention also provides a method of preventing, treating, ameliorating, or managing cancer in a patient in need thereof by administering an effective amount of a composition comprising a TRAIL R2-specific multimeric scaffold of the invention. In some embodiments, the cancer is selected from lung cancer, non-Hodgkin's lymphoma, ovarian cancer, colon cancer, colorectal cancer, pancreatic cancer, and multiple myeloma.

The invention also provides a method for diagnosing or imaging a disease in a patient with a composition comprising a TRAIL R2-specific multimeric scaffold of the invention. Also provided is a method of inducing apoptosis in a cell expressing TRAIL R2 comprising contacting the cell with a TRAIL R2-specific multimeric scaffold of the invention. In some embodiments, the method of preventing, treating, ameliorating, or managing cancer in a patient in need thereof further comprises an additional therapy, wherein said therapy is immunotherapy, biological therapy, chemotherapy, radiation therapy, or small molecule drug therapy.

In some embodiments, the TRAIL R2-specific multimeric scaffold specifically binds to human TRAIL R2. In some specific embodiments, the TRAIL R2-specific multimeric scaffold of the invention binds TRAIL R2 and (a) agonizes the TRAIL R2 receptor, (b) mimics the binding of TRAIL to TRAIL R2 receptor, (c) facilitates TRAIL R2 receptor dimerization or oligomerization, (d) induces apoptosis, (e) reduces or inhibits cell viability, or (f) a combination of activities (a), (b), (c), (d) and (e).

In other embodiments, the invention provides a method of altering an activity in a TRAIL R2 expressing cell comprising contacting the cell with the TRAIL R2 specific multimeric scaffold of any one of claims 1-47, wherein the multimeric scaffold binds TRAIL R2 and (a) agonizes the TRAIL R2 receptor, (b) mimics the binding of TRAIL to TRAIL R2 receptor, (c) facilitates TRAIL R2 receptor dimerization or oligomerization, (d) induces apoptosis, (e) reduces or inhibits cell viability, or (f) a combination of activities (a), (b), (c), (d), and (e).

In some embodiments, PEG is conjugated to the TRAIL R2-specific multimeric scaffold of the invention at the N-terminus or the C-terminus.

BRIEF DESCRIPTION OF THE DRAWINGS

For the purpose of illustrating the invention, there are depicted in the drawings certain embodiments of the invention. However, the invention is not limited to the precise arrangements and instrumentalities of the embodiments depicted in the drawings.

FIG. 5. shows a flow cytometric histogram of the TRAIL R2-specific multivalent scaffold A9 binding to H2122 cells compared to a cognate control scaffold (B9) that does not bind TRAIL R2.

FIG. 7B shows the effect of molecular format on killing of H2122 cells by TRAIL R2-specific multivalent scaffolds comprising 8 Tn3 modules.

FIG. 8A shows the specific killing of colorectal adenocarcinoma cell line Colo205 cells expressing TRAIL R2 by linearly fused tetra-(A3) and octavalent (A5) TRAIL R2-specific Tn3 scaffolds.

FIG. 8B shows the specific killing of leukemic line Jurkat cells expressing TRAIL R2 by linearly fused tetra-(A3) and octavalent (A5) TRAIL R2-specific Tn3 scaffolds.

FIG. 9B shows the SDS-PAGE analysis of a purified monovalent M13 construct (CD40L-specific Tn3 construct), or tandem bivalent scaffolds with linkers containing 1, 3, 5 or 7 Gly$_4$Ser units (denoted as GS) joining two M13 modules. Monovalent M13 construct was run in lane 2, Construct C1 in lanes 3 and 7, Construct C2 in lanes 4 and 8, construct C3 in lanes 5 and 9, and construct C4 in lanes 6 and 10. Samples were run either non-reduced conditions (lanes 2-6) or reduced conditions (lanes 7-10).

FIG. 9C shows the competitive inhibition of MuCD40L binding to Murine CD40 receptor immobilized on a biosensor chip by MuCD40L-specific monovalent (M13) or bivalent tandem scaffolds. The half maximal inhibitory concentration ($IC_{50}$) for the various constructs is indicated.

FIG. 9D shows the inhibitory effect of MuCD40L-specific monovalent (M13) Tn3, bivalent tandem scaffolds, or antibody MR1 (an anti-MuCD40L antibody) on MuCD40L-induced CD86 expression on B cells.

FIG. 10 shows the expression levels of soluble monovalent and TRAIL R2/CD40L-bispecific tandem bivalent Tn3 scaffold constructs recombinantly expressed in *E. coli* analyzed by SDS-PAGE of the bacterial culture media. Monovalent scaffolds, A1 and 79 are shown in lanes 2 and 3, respectively. Tandem scaffold constructs comprising A1 and 79, joined in tandem by a Gly$_4$Ser amino acid linker of increasing length (cognate to constructs C5, C6, C7 and C8) are shown in lanes 4-7. The expressed constructs are indicated on the stained gel by an asterisk.

FIG. 11B shows the binding of bispecific Tn3 scaffolds to Human. CD40L assayed using capture ELISA.

FIG. 17B shows the simultaneous binding of the trispecific/trivalent Tn3 scaffold D1-1E11-79 to huCD40L and Synagis® using AlphaScreen binding analysis. AlphaScreen signal (ASS) shown as a function of Synagis® concentration.

FIG. 19 shows a sequence alignment of parental TRAIL R2 binding clone 1C12 and its affinity matured derivatives. The position of the engineered disulfide bond is highlighted, the arrow indicates the location of the one framework mutation, and changes in the loops that arise during affinity maturation are shown in highlighted blocks A, B, C, and D.

FIG. 22A shows a sequence alignment corresponding to the engineered enhancement of cyno cross reactivity for clone F4. The common feature among all of these clones is a mutation from D to G two amino acids before the DE loop.

FIG. 22B shows ELISA measurements of the inhibition of binding of either human or cyno TRAIL R2-Fc to F4 mod 1 coated plates by F4 or F4 mod 1 monomer.

FIG. 23A shows a sequence alignment corresponding to germlining of the clone F4 mod 1, specifically a comparison of F4, F4 mod 1 and F4 mod 12 to the TN3 germline.

FIG. 23B shows ELISA measurements of the inhibition of binding of either human or cyno TRAIL-R2-Fc to F4 mod 1 coated plates by F4, F4 mod 1, or F4 mod 12 monomer.

FIG. 25 shows a sequence alignment corresponding to the clones tested in Antitope EpiScreen Immunogenicity analyses. Differences with respect to clone F4 mod 12 are highlighted.

DETAILED DESCRIPTION OF THE INVENTION

Definitions

Figure 1:
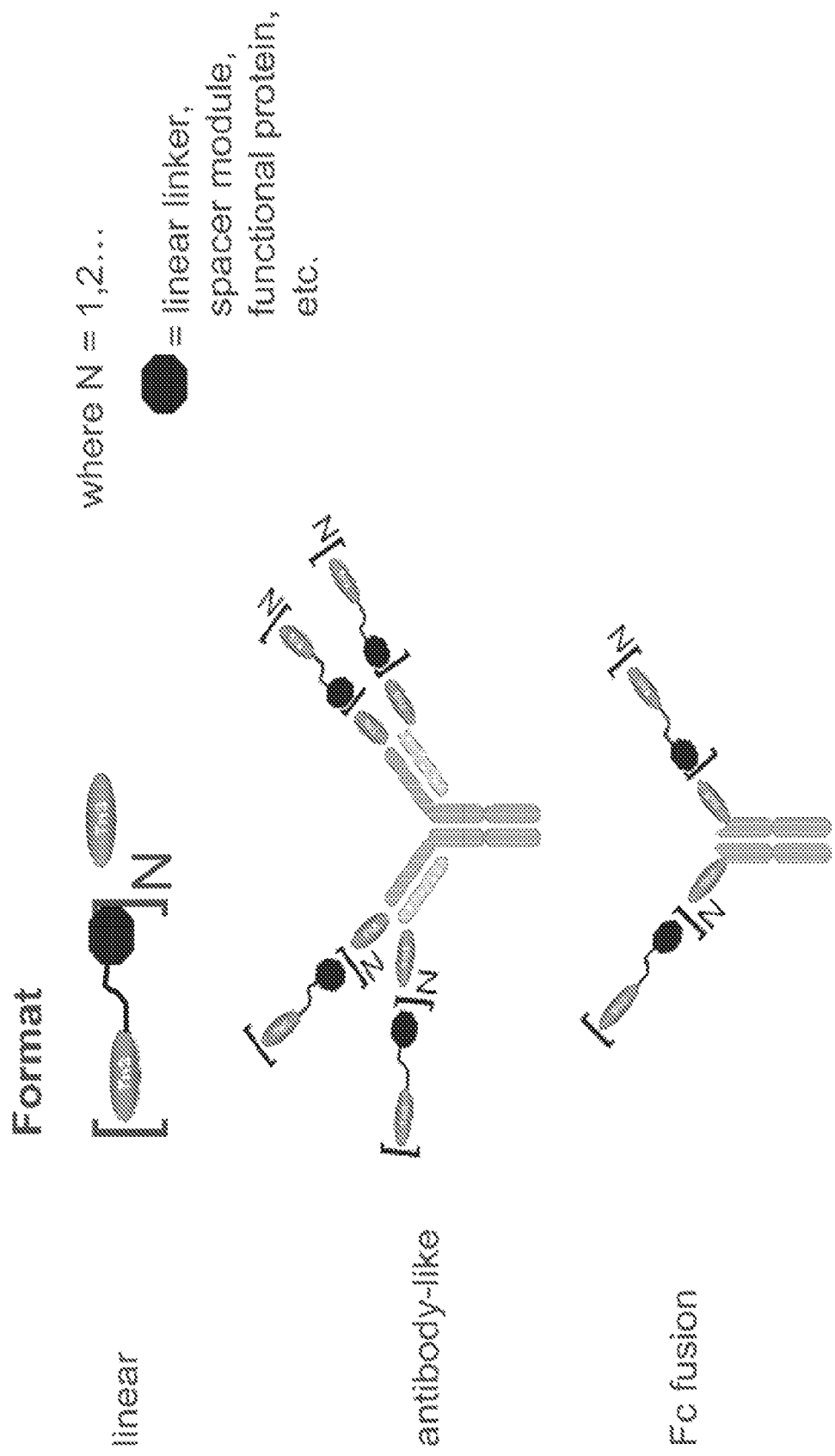
FIG. 1 shows linear, antibody-like and fusion formats of multivalent Tn3 scaffolds. Multivalent Tn3 scaffolds contain two or more Tn3 modules attached by a spacer indicated by a black octagonal block, where the spacer can be, e.g., a linker.

Before describing the present invention in detail, it is to be understood that this invention is not limited to specific compositions or process steps, as such can vary. It must be noted that, as used in this specification and the appended claims, the singular forms "a", "an" and "the" include plural referents unless the context clearly dictates otherwise. The terms "a" (or "an"), as well as the terms "one or more," and "at least one" can be used interchangeably herein.

Furthermore, "and/or" where used herein is to be taken as specific disclosure of each of the two specified features or components with or without the other. Thus, the term "and/or" as used in a phrase such as "A and/or B" herein is intended to include "A and B," "A or B," "A," (alone) and "B" (alone). Likewise, the term "and/or" as used in a phrase such as "A, B, and/or C" is intended to encompass each of the following embodiments: A, B, and C; A, B, or C; A or C; A or B; B or C; A and C; A and B; B and C; A (alone); B (alone); and C (alone).

Unless defined otherwise, all technical and scientific terms used herein have the same meaning as commonly understood by one of ordinary skill in the art to which this invention is related. For example, the Concise Dictionary of Biomedicine and Molecular Biology, Juo, Pei-Show, 2nd ed., 2002, CRC Press; The Dictionary of Cell and Molecular Biology, 3rd ed., 1999, Academic Press; and the Oxford Dictionary Of Biochemistry And Molecular Biology, Revised, 2000, Oxford University Press, provide one of skill with a general dictionary of many of the terms used in this invention.

Units, prefixes, and symbols are denoted in their Systéme International de Unites (SI) accepted form. Numeric ranges are inclusive of the numbers defining the range. Unless otherwise indicated, amino acid sequences are written left to right in amino to carboxy orientation. The headings provided herein are not limitations of the various aspects or embodiments of the invention, which can be had by reference to the specification as a whole. Accordingly, the terms defined immediately below are more fully defined by reference to the specification in its entirety.

It is understood that wherever embodiments are described herein with the language "comprising," otherwise analogous embodiments described in terms of "consisting of" and/or "consisting essentially of" are also provided.

Amino acids are referred to herein by either their commonly known three letter symbols or by the one-letter symbols recommended by the IUPAC-IUB Biochemical Nomenclature Commission. Nucleotides, likewise, are referred to by their commonly accepted single-letter codes.

The term "epitope" as used herein refers to a protein determinant capable of binding to a scaffold of the invention. Epitopes usually consist of chemically active surface groupings of molecules such as amino acids or sugar side chains and usually have specific three dimensional structural characteristics, as well as specific charge characteristics. Conformational and non-conformational epitopes are distinguished in that the binding to the former but not the latter is lost in the presence of denaturing solvents.

The terms "fibronectin type III (FnIII) domain" and "FnIII domain" refer to polypeptides homologous to the human fibronectin type III domain having at least 7 beta strands which are distributed between two beta sheets, which themselves pack against each other to form the core of the protein, and further containing solvent exposed loops which connect the beta strands to each other. There are at least three such loops at each edge of the beta sheet sandwich, where the edge is the boundary of the protein perpendicular to the direction of the beta strands. In certain embodiments, an FnIII domain comprises 7 beta strands designated A, B, C, D, E, F, and G linked to six loop regions designated AB, BC, CD, DE, EF, and FG, wherein a loop region connects each beta strand.

The term "DNA" refers to a sequence of two or more covalently bonded, naturally occurring or modified deoxyribonucleotides.

The term "fusion protein" refers to protein that includes (i) one or more scaffolds of the invention joined to (ii) a second, different protein (i.e., a "heterologous" protein).

The term "heterologous moiety" is used herein to indicate the addition of a composition to a scaffold of the invention wherein the composition is not normally part of an FnIII domain. Exemplary heterologous moieties include proteins, peptides, protein domains, linkers, drugs, toxins, imaging agents, radioactive compounds, organic and inorganic polymers, and any other compositions which might provide an activity that is not inherent in the FnIII domain itself, including, but are not limited to, polyethylene glycol (PEG), a cytotoxic agent, a radionuclide, imaging agent, biotin, a dimerization domain (e.g. leucine zipper domain), human serum albumin (HSA) or an FcRn binding portion thereof, a domain or fragment of an antibody (e.g., antibody variable domain, a CH1 domain, a Ckappa domain, a Clambda domain, a CH2, or a CH3 domain), a single chain antibody, a domain antibody, an albumin binding domain, an IgG molecule, an enzyme, a ligand, a receptor, a binding peptide, a non-FnIII scaffold, an epitope tag, a recombinant polypeptide polymer, a cytokine, and the like.

The term "linker" as used herein refers to any molecular assembly that joins or connects two or more scaffolds. The linker can be a molecule whose function is to act as a "spacer" between modules in a scaffold, or it can also be a molecule with additional function (i.e., a "functional moiety"). A molecule included in the definition of "heterologous moiety" can also function as a linker.

The terms "linked" and "fused" are used interchangeably. These terms refer to the joining together of two or more scaffolds, heterologous moieties, or linkers by whatever means including chemical conjugation or recombinant means.

The terms "multimer," "multimeric scaffold" and "multivalent scaffold" refer to a molecule that comprises at least two FnIII scaffolds in association. The scaffolds forming a multimeric scaffold can be linked through a linker that permits each scaffold to function independently. "Multimeric" and "multivalent" can be used interchangeably herein. A multivalent scaffold can be monospecific or bispecific.

The terms "domain" or "protein domain" refer to a region of a protein that can fold into a stable three-dimensional structure, often independently of the rest of the protein, and which can be endowed with a particular function. This structure maintains a specific function associated with the domain's function within the original protein, e.g., enzymatic activity, creation of a recognition motif for another molecule, or to provide necessary structural components for a protein to exist in a particular environment of proteins. Both within a protein family and within related protein superfamilies, protein domains can be evolutionarily conserved regions. When describing the component of a multimeric scaffold, the terms "domain." "Monomeric scaffold" and "module" can be used interchangeably. By "native FnIII domain" is meant any non-recombinant FnIII domain that is encoded by a living organism.

A "protein sequence" or "amino acid sequence" means a linear representation of the amino acid constituents in a polypeptide in an amino-terminal to carboxyl-terminal direction in which residues that neighbor each other in the representation are contiguous in the primary structure of the polypeptide.

The term "nucleic acid" refers to any two or more covalently bonded nucleotides or nucleotide analogs or derivatives. As used herein, this term includes, without limitation, DNA, RNA, and PNA. "Nucleic acid" and "polynucleotide" are used interchangeably herein.

The term "polynucleotide" is intended to encompass a singular nucleic acid as well as plural nucleic acids, and refers to an isolated nucleic acid molecule or construct, e.g., messenger RNA (mRNA) or plasmid DNA (pDNA). The term "isolated" nucleic acid or polynucleotide is intended refers to a nucleic acid molecule, DNA or RNA that has been removed from its native environment. For example, a recombinant polynucleotide encoding, e.g., a scaffold of the invention contained in a vector is considered isolated for the purposes of the present invention. Further examples of an isolated polynucleotide include recombinant polynucleotides maintained in heterologous host cells or purified (partially or substantially) polynucleotides in solution. Isolated RNA molecules include in vivo or in vitro RNA transcripts of polynucleotides of the present invention. Isolated polynucleotides or nucleic acids according to the present invention further include such molecules produced synthetically. In addition, a polynucleotide or a nucleic acid can be or can include a regulatory element such as a promoter, ribosome binding site, or a transcription terminator.

The term "pharmaceutically acceptable" refers to a compound or protein that can be administered to an animal (for example, a mammal) without significant adverse medical consequences.

The term "physiologically acceptable carrier" refers to a carrier which does not have a significant detrimental impact on the treated host and which retains the therapeutic properties of the compound with which it is administered. One exemplary physiologically acceptable carrier is physiological saline. Other physiologically acceptable carriers and their formulations are known to one skilled in the art and are described, for example, in Remington's Pharmaceutical Sciences, ($18^{th}$ edition), ed. A. German), 1990, Mack Publishing Company, Easton, Pa., incorporated herein by reference.

By a "polypeptide" is meant any sequence of two or more amino acids linearly linked by amide bonds (peptide bonds) regardless of length, post-translation modification, or function. "Polypeptide," "peptide," and "protein" are used interchangeably herein. Thus, peptides, dipeptides, tripeptides, or oligopeptides are included within the definition of "polypeptide," and the term "polypeptide" can be used instead of, or interchangeably with any of these terms. The term "polypeptide" is also intended to refer to the products of post-expression modifications of the polypeptide, including without limitation glycosylation, acetylation, phosphorylation, amidation, derivatization by known protecting/blocking groups, proteolytic cleavage, or modification by non-naturally occurring amino acids. A polypeptide can be derived from a natural biological source or produced by recombinant technology, but is not necessarily translated from a designated nucleic acid sequence. A polypeptide can be generated in any manner, including by chemical synthesis.

Also included as polypeptides of the present invention are fragments, derivatives, analogs, or variants of the foregoing polypeptides, and any combination thereof. Variants can occur naturally or be non-naturally occurring. Non-naturally occurring variants can be produced using art-known mutagenesis techniques. Variant polypeptides can comprise conservative or non-conservative amino acid substitutions, deletions, or additions. Also included as "derivatives" are those peptides that contain one or more naturally occurring amino acid derivatives of the twenty standard amino acids.

By "randomized" or "mutated" is meant including one or more amino acid alterations, including deletion, substitution or addition, relative to a template sequence. By "randomizing" or "mutating" is meant the process of introducing, into a sequence, such an amino acid alteration. Randomization or mutation can be accomplished through intentional, blind, or spontaneous sequence variation, generally of a nucleic acid coding sequence, and can occur by any technique, for example, PCR, error-prone PCR, or chemical DNA synthesis. The terms "randomizing", "randomized", "mutating", "mutated" and the like are used interchangeably herein.

By a "cognate" or "cognate, non-mutated protein" is meant a protein that is identical in sequence to a variant protein, except for the amino acid mutations introduced into the variant protein, wherein the variant protein is randomized or mutated.

By "RNA" is meant a sequence of two or more covalently bonded, naturally occurring or modified ribonucleotides. One example of a modified RNA included within this term is phosphorothioate RNA.

The terms "scaffold of the invention" or "scaffolds of the invention" as used herein, refers to multimeric scaffolds as well as monomeric FnIII scaffolds. The term "target" refers to a compound recognized by a specific scaffold of the invention. Typical targets include proteins, polysaccharides, polynucleotides and small molecules. The terms "target" and "antigen" are used interchangeably herein. The term "specificity" as used herein, e.g., in the terms "specifically binds" or "specific binding," refers to the relative affinity by which a scaffold of the invention binds to one or more antigens via one or more antigen binding domains, and that binding entails some complementarity between one or more antigen binding domains and one or more antigens. According to this definition, a scaffold of the invention is said to "specifically bind" to an epitope when it binds to that epitope more readily than it would bind to a random, unrelated epitope.

The term "affinity" as used herein refers to a measure of the strength of the binding of a certain scaffold of the invention to an individual epitope.

The term "avidity" as used herein refers to the overall stability of the complex between a population of scaffolds of the invention and a certain epitope, i.e., the functionally combined strength of the binding of a plurality of scaffolds with the antigen. Avidity is related to both the affinity of individual antigen-binding domains with specific epitopes, and also the valency of the scaffold of the invention.

The term "action on the target" refers to the binding of a multimeric scaffold of the invention to one or more targets and to the biological effects resulting from such binding. In this respect, multiple antigen binding units in a multimeric scaffold can interact with a variety of targets and/or epitopes and, for example, bring two targets physically closer, trigger metabolic cascades through the interaction with distinct targets, etc. With reference to TRAIL R2, "action on the target" refers to the effect achieved, for example, by the enhancement, stimulation or activation, of one or more biological activities of TRAIL R2.

The term "valency" as used herein refers to the number of potential antigen-binding modules, e.g., the number of FnIII modules in a scaffold of the invention. When a scaffold of the invention comprises more than one antigen-binding module, each binding module can specifically bind, e.g., the same epitope or a different epitope, in the same target or different targets.

The term "disulfide bond" as used herein includes the covalent bond formed between two sulfur atoms. The amino acid cysteine comprises a thiol group that can form a disulfide bond or bridge with a second thiol group.

The terms "Tn3 module" and "Tn3 scaffold" as used herein, refers to a FnIII scaffold wherein the A beta strand comprises SEQ ID NO: 42, the B beta strand comprises SEQ ID NO: 43, the C beta strand SEQ ID NO: 45 or 131, the D beta strand comprises SEQ ID NO: 46, the E beta strand comprises SEQ ID NO: 47, the F beta strand comprises SEQ ID NO: 49, and the beta strand G comprises SEQ ID NO: 52, wherein at least one loop is a non-naturally occurring variant of the loops in the "wild type Tn3 scaffold." In certain embodiments, one or more of the beta strands of a Tn3 module comprise at least one amino acid substitution except that the cysteine residues in the C beta strand (e.g., the cysteine in SEQ ID NOs: 45 or 131) and F beta strands (SEQ ID NO: 49) are not substituted.

The term "wild type Tn3 scaffold" as used herein refers to an FnIII scaffold comprising SEQ ID NO: 1, i.e., an engineered FnIII scaffold derived from the $3^{rd}$ FnIII of human tenascin C.

The term "immunoglobulin" and "antibody" comprises various broad classes of polypeptides that can be distinguished biochemically. Those skilled in the art will appreciate that heavy chains are classified as gamma, mu, alpha, delta, or epsilon. It is the nature of this chain that determines the "class" of the antibody as IgG, IgM, IgA IgG, or IgE, respectively. Modified versions of each of these classes are readily discernable to the skilled artisan. As used herein, the term "antibody" includes but not limited to an intact antibody, a modified antibody, an antibody VL or VL domain, a CH1 domain, a Ckappa domain, a Clambda domain, an Fc domain (see supra), a CH2, or a CH3 domain.

As used herein, the term "modified antibody" includes synthetic forms of antibodies which are altered such that they are not naturally occurring, e.g., antibodies that comprise at least two heavy chain portions but not two complete heavy chains (as, e.g., domain deleted antibodies or minibodies); multispecific forms of antibodies (e.g., bispecific, trispecific, etc.) altered to bind to two or more antigens or to different epitopes of a single antigen). In addition, the term "modified antibody" includes multivalent forms of antibodies (e.g., trivalent, tetravalent, etc., antibodies that to three or more copies of the same antigen). (See, e.g., Antibody Engineering, Kontermann & Dubel, eds., 2010, Springer Protocols, Springer).

The term "in vivo half-life" is used in its normal meaning, i.e., the time at which 50% of the biological activity of a polypeptide is still present in the body/target organ, or the time at which the activity of the polypeptide is 50% of its initial value. As an alternative to determining functional in vivo half-life, "serum half-life" may be determined, i.e., the time at which 50% of the polypeptide molecules circulate in the plasma or bloodstream prior to being cleared. Determination of serum-half-life is often more simple than determining functional in vivo half-life and the magnitude of serum-half-life is usually a good indication of the magnitude of functional in vivo half-life. Alternative terms to serum half-life include plasma half-life, circulating half-life, circulatory half-life, serum clearance, plasma clearance, and clearance half-life. The functionality to be retained is normally selected from procoagulant, proteolytic, co-factor binding, receptor binding activity, or other type of biological activity associated with the particular protein.

The term "increased" with respect to the functional in vivo half-life or plasma half-life is used to indicate that the relevant half-life of the polypeptide is statistically significantly increased relative to that of a reference molecule (for example an unmodified polypeptide), as determined under comparable conditions.

The term "expression" as used herein refers to a process by which a gene produces a biochemical, for example, a scaffold of the invention or a fragment thereof. The process includes any manifestation of the functional presence of the gene within the cell including, without limitation, gene knockdown as well as both transient expression and stable expression. It includes without limitation transcription of the gene into one or more mRNAs, and the translation of such mRNAs into one or more polypeptides. If the final desired product is a biochemical, expression includes the creation of that biochemical and any precursors.

An "expression product" can be either a nucleic acid, e.g., a messenger RNA produced by transcription of a gene, or a polypeptide. Expression products described herein further include nucleic acids with post transcriptional modifications, e.g., polyadenylation, or polypeptides with post translational modifications, e.g., methylation, glycosylation, the addition of lipids, association with other protein subunits, proteolytic cleavage, and the like.

The term "vector" or "expression vector" is used herein to mean vectors used in accordance with the present invention as a vehicle for introducing into and expressing a desired expression product in a host cell. As known to those skilled in the art, such vectors can easily be selected from the group consisting of plasmids, phages, viruses and retroviruses. In general, vectors compatible with the instant invention will comprise a selection marker, appropriate restriction sites to facilitate cloning of the desired nucleic acid and the ability to enter and/or replicate in eukaryotic or prokaryotic cells.

The term "host cells" refers to cells that harbor vectors constructed using recombinant DNA techniques and encoding at least one expression product. In descriptions of processes for the isolation of an expression product from recombinant hosts, the terms "cell" and "cell culture" are used interchangeably to denote the source of the expression product unless it is clearly specified otherwise, i.e., recovery of the expression product from the "cells" means either recovery from spun down whole cells, or recovery from the cell culture containing both the medium and the suspended cells.

The terms "treat" or "treatment" as used herein refer to both therapeutic treatment and prophylactic or preventative measures, wherein the object is to prevent or slow down (lessen) an undesired physiological change or disorder in a subject, such as the progression of an inflammatory disease or condition. Beneficial or desired clinical results include, but are not limited to, alleviation of symptoms, diminishment of extent of disease, stabilized (i.e., not worsening) state of disease, delay or slowing of disease progression, amelioration or palliation of the disease state, and remission (whether partial or total), whether detectable or undetectable.

The term "treatment" also means prolonging survival as compared to expected survival if not receiving treatment. Those in need of treatment include those already with the condition or disorder as well as those prone to have the condition or disorder or those in which the condition or disorder is to be prevented.

The terms "subject," "individual," "animal," "patient," or "mammal" refer to any individual, patient or animal, in particularly a mammalian subject, for whom diagnosis, prognosis, or therapy is desired. Mammalian subjects include humans, domestic animals, farm animals, and zoo, sports, or pet animals such as dogs, cats, guinea pigs, rabbits, rats, mice, horses, cattle, cows, and so on.

The term "TRAIL receptor" as used herein refers to a protein that binds TRAIL and, upon binding TRAIL, activates programmed cell death (apoptosis) in tumor cells. A non-limiting example of a TRAIL receptor includes the TRAIL-R2 receptor.

The terms "TRAIL R2" or "TRAIL R2 receptor" are used interchangeably herein to refer to the full length TRAIL receptor sequence and soluble, extracellular domain forms of the receptor described in Sheridan et al., Science, 277:818-821 (1997); Pan et al., Science, 277:815-818 (1997), U.S. Pat. Nos. 6,072,047 and 6,342,369: PCT Publ. Nos. WO98/51793, WO98/41629, WO98/35986, WO99/02653, WO99/09165, WO98/46643, and WO99/11791; Screaton et al., Curr. Biol., 7:693-696 (1997); Walczak et al., EMBO J., 16:5386-5387 (1997); Wu et al., Nature Genetics, 17:141-143 (1997). Representative full length TRAIL receptor sequences are available at GenBank Accession Nos. AAC51778.1 and O14763.2.

The term "TRAIL receptor agonist" or "agonist" is used in the broadest sense, and includes any molecule that partially or fully enhances, stimulates or activates one or more biological activities of TRAIL R2, and biologically active variants thereof, in vitro, in situ, or in vivo. Examples of such biological activities include apoptosis as well as those further reported in the literature. An agonist may function in a direct or indirect manner. For instance, a TRAIL receptor agonist may function to partially or fully enhance, stimulate or active one or more biological activities of one or more TRAIL R2 receptors, or one or more TRAIL R2 receptors and other targets, in vivo, in vitro or in situ, as a result of its binding to TRAIL R2 which causes receptor activation or signal transduction.

"TRAIL" or "TRAIL polypeptide" refers to a ligand that binds to one or more TRAIL receptors, including TRAIL R2, as well as biologically active fragments thereof. Representative TRAIL sequences are available at GenBank Accession Nos. AAH32722.1 and P50591.1. Fragments include, but are not limited to, sequences having about 5 to about 50 amino acid residues, or about 5 to about 25, or about 10 to 20 residues, or about 12 to about 20 amino acid residues of a TRAIL polypeptide sequence. Optionally, the TRAIL peptide consists of no more than 25 amino acid residues (e.g., 25, 23, 21, 19, 17, or less amino acid residues).

The terms "apoptosis" and "apoptotic activity" are used in a broad sense and refer to the orderly or controlled form of cell death in mammals that is typically accompanied by one or characteristic cell changes, including condensation of cytoplasm, loss of plasma membrane microvilli, segmentation of the nucleus, degradation of chromosomal DNA or loss of mitochondrial function. This activity can be determined and measured using well known art methods, for instance, by cell viability assays, FACS analysis or DNA electrophoresis, binding to annexin V, fragmentation of DNA, cell shrinkage, dilation of endoplasmic reticulum, cell fragmentation, and/or formation of membrane vesicles (apoptotic bodies).

Introduction

The TRAIL-R2 protein is encoded by a member of the TNF-receptor superfamily gene, and contains an intracellular death domain. In some instances, it may also be known as TNFRSF10B; CD262, DR5, KILLER, KILLER/DR5, TRAILR2, TRICK2, TRICK2A, TRICK2B, TRICKB, or ZTNFR9. This receptor can be activated by tumor necrosis factor-related apoptosis inducing ligand (TNFSF 10/TRAIL/APO-2L), and transduces an apoptotic signal. Further, TRAIL-R2 induced apoptosis involves caspases and the intracellular adapter molecule FADD/MORT1 (Walczak et al. EMBO J, (1997), 16, 5386-97).

Although several types of normal cells express TRAIL R2, apoptosis signaling through this receptor appears to be restricted primarily to tumor cells, which become more susceptible to death receptor-mediated apoptosis in the context of their transformation by oncogenes such as Myc or Ras (Wang et al., Cancer Cell 5:501-12 (2004); Nesterov et al., Cancer Res. 64:3922-7 (2004)). TRAIL-R2 is frequently expressed by human cancer cell lines as well as primary tumors.

The present invention provides a family of recombinant, non-naturally occurring protein scaffolds capable of binding to TRAIL R2. In particular, the proteins described herein may be used to display defined loops which are analogous to the complementarity-determining regions ("CDRs") of an antibody variable region. These loops may be subjected to randomization or restricted evolution to generate diversity capable of binding to a multitude of target compounds. The proteins may be assembled into multispecific scaffolds capable of binding to TRAIL R2 and to different targets.

In specific embodiments, the invention provides TRAIL-R2 specific binders which are useful for preventing ameliorating, detecting, diagnosing, or monitoring diseases, such as but not limited to cancer. In other specific embodiments, TRAIL-R2 specific binding scaffolds of the invention are useful for the treatment of cancers in which cancer cells express TRAIL-R2. In some embodiments, cancers may include, but are not limited to, lung cancer, non-Hodgkin's lymphoma, ovarian cancer, colon cancer, colorectal cancer, pancreatic cancer, and multiple myeloma. The invention also provides methods of using the scaffolds to deplete a cell population. In one embodiment, methods of the invention are useful in the depletion of the following cell types: eosinophil, basophil, neutrophil, T cell, B cell, mast cell, monocytes and tumor cell.

The scaffolds of the invention are multimeric scaffolds comprising monomeric scaffolds derived from the third FnIII domain of human tenascin C, in which at least one non-naturally occurring intramolecular disulfide bond has been engineered. The Tn3 scaffolds that make up the multimeric scaffolds of the invention correctly fold independently of each other, retain their binding specificity and affinity, and each of the monomeric scaffolds retains its functional properties. When the Tn3 scaffolds that make up the multimeric scaffolds of the invention are assembled in high valency multimeric scaffolds, e.g., hexavalent or octavalent scaffolds, the monomer scaffolds correctly fold independently of each other, retain their binding specificity and affinity, and each one of the monomer scaffold retains its functional properties.

Multimeric Tn3 scaffolds, including high valency scaffolds (e.g., hexavalent or octavalent), fold correctly even when the topology of construct is not linear, e.g., when the monomeric Tn3 or multimeric Tn3 scaffolds are assembled in complex branched structures (e.g., Fc fusion constructs or antibody-like constructs).

Native FnIII domains such as the 10th FnIII domain of human fibronectin and the vast majority of naturally occurring FnIII domains contain no disulfide bonds or free cysteines. When multidomain proteins are engineered by introducing multiple cysteines, lack of protein expression, precipitation of the resulting proteins, or production of non-functional proteins, are common occurrences. These deleterious effects are due to the incorrect formation of intramolecular intradomain and/or interdomain disulfide bonds, and/or the incorrect formation of intermolecular disulfide bonds, which result in incorrect protein folding. These effects are generally intensified when the number of cysteines and/or protein domains is increased.

For example, a linear multimeric scaffold comprising 8 wild type Tn3 scaffolds (SEQ ID NO: 1) would contain 16 cysteines along a single polypeptide amino acid sequence. In another exemplary embodiment, an antibody-like construct comprising 4 Tn3 modules, wherein two Tn3 modules are linked to IgG heavy chains and two Tn3 are linked to IgG light chains, would comprise 8 cysteines distributed among 4 different polypeptide chains. Multimeric scaffolds of the present invention, such as those containing 4, 6, or 8 linear Tn3 modules, comprising such number of cysteines and such structural complexity fold correctly and display improved stability and target binding properties when compared to their respective monomers.

When Tn3 scaffolds comprising one or more engineered disulfide bridges are assembled in high valency multimeric formats, each individual monomer scaffold folds correctly retaining its binding specificity and affinity, as well as its functional properties. In addition, the monomeric scaffolds are capable of forming stable, functional, and correctly folded multimeric scaffolds.

An advantage of the multimeric scaffolds of the invention is their ability to bind to multiple epitopes, e.g., (i) binding to multiple epitopes in a single target, (ii) binding to a single epitope in multiple targets, (iii) binding to multiple epitopes located on different subunits of one target, or (iv) binding to multiple epitopes on multiple targets, thus increasing avidity.

In addition, due to the flexibility of the multimeric scaffolds and to the possibility of varying the distance between multiple Tn3 monomers via linkers, the multimeric Tn3 scaffolds are capable of binding to multiple target molecules on a surface (either on the same cell/surface or in different cells/surfaces).

As a result of their ability to bind simultaneously to more than one target, the multimeric scaffolds of the invention can be used to modulate multiple pathways, crosslink receptors on a cell surface, bind cell surface receptors on separate cells, and/or bind target molecules or cells to a substrate.

From prior sequence analysis of FnIII domains, large variations were seen in the BC and FG loops, suggesting that these loops are not crucial to stability (see, for example, PCT Publication No: WO 2009/058379). The present invention provides Tn3 scaffolds having improved stability, which vary in amino acid sequence but which comprise an FG loop having a shorter length than that of the corresponding FG loop of the third FnIII of human tenascin C. It has been observed that shortening the FG loops results in a mutated Tn3 scaffold that has increased stability. Consequently, another aspect of the invention provides variants of the wild type Tn3 scaffold (SEQ ID NO: 1) having increased protein stability.

In certain embodiments, a Tn3 monomer scaffold of the invention comprises an FG loop having 9 amino acids and an increased stability compared to a scaffold comprising the native third FnIII domain of human tenascin C which has an FG loop length of 10 amino acids. Additionally the present invention provides libraries of diverse Tn3 scaffolds having specified FG loop lengths which are useful for isolating Tn3 scaffolds having increased stability.

In addition, the present invention provides multispecific scaffolds that can bind to TRAIL R2 and one or more additional targets, affinity matured scaffolds wherein the affinity of a scaffold for a specific target is modulated via mutation, and scaffolds whose immunogenicity and/or cross-reactivity among animal species is modulated via mutation. Also, the invention provides methods to produce the scaffolds of the invention as well as methods to engineer scaffolds with desirable physicochemical, pharmacological, or immunological properties. Furthermore, the present invention provides uses for such scaffolds and methods for therapeutic, prophylactic, and diagnostic use.

The FnIII Structural Motif

The Tn3 scaffolds of the present invention are based on the structure of a fibronectin module of type III (FnIII), a domain found widely across all three domains of life and viruses, and in multitude of protein classes.

In specific embodiments, the scaffolds of the invention are derived from the third FnIII domain of human tenascin C (SEQ ID NO: 4). In one specific embodiment, the scaffolds of the invention comprise a Tn3 module. The overall tridimensional fold of this domain is closely related to that of the smallest functional antibody fragment, the variable region of the heavy chain (VH), which in the single domain antibodies of camels and camelids (e.g., llamas) comprises the entire antigen recognition unit.

The Tn3 monomeric scaffolds of the invention and the native FnIII domain from tenascin C are characterized by the same tridimensional structure, namely a beta-sandwich structure with three beta strands (A, B, and E) on one side and four beta strands (C, D, F, and G) on the other side, connected by six loop regions. These loop regions are designated according to the beta-strands connected to the N- and C-terminus of each loop. Accordingly, the AB loop is located between beta strands A and B, the BC loop is located between strands B and C, the CD loop is located between beta strands C and D, the DE loop is located between beta strands D and E, the EF loop is located between beta strands E and F, and the FG loop is located between beta strands F and G. FnIII domains possess solvent exposed loop s tolerant of randomization, which facilitates the generation of diverse pools of protein scaffolds capable of binding specific targets with high affinity.

In one aspect of the invention, Tn3 domains are used as scaffolds which are subjected to directed evolution designed to randomize one or more of the loops which are analogous to the complementarity-determining regions (CDRs) of an antibody variable region. Such a directed evolution approach results in the production of antibody-like molecules with high affinities for targets of interest, e.g., TRAIL R2. In addition, in some embodiments the scaffolds described herein can be used to display defined exposed loops (for example, loops previously randomized and selected on the basis of target binding) in order to direct the evolution of molecules that bind to such introduced loops. This type of selection can be carried out to identify recognition molecules for any individual CDR-like loop or, alternatively, for the recognition of two or all three CDR-like loops combined into a nonlinear epitope binding moiety.

The scaffolds of the invention are molecules based on the third FnIII domain of human tenascin C structural motif described in PCT Publication No: WO 2009/058379. A set of three loops (designated BC, DE, and FG), which can confer specific target binding, run between the B and C strands; the D and E strands, and the F and G beta strands, respectively. The BC, DE, and FG loops of the third FnIII domain of human tenascin C are 9, 6, and 10 amino acid residues long, respectively. The length of these loops falls within the narrow range of the cognate antigen-recognition loops found in antibody heavy chains, that is, 7-10, 4-8, and 4-28 amino acids in length, respectively. Similarly, a second set of loops, the AB, CD, and EF loops (7, 7, and 8, amino acids in length respectively) run between the A and B beta strands; the C and D beta strands; and the E and F beta strands, respectively.

Once randomized and selected for high affinity binding to a target, the loops in the Tn3 domain may make contacts with targets equivalent to the contacts of the cognate CDR loops in antibodies. Accordingly, in some embodiments the AB, CD, and EF loops are randomized and selected for high affinity binding to one or more targets, e.g., TRAIL R2. In some embodiments, this randomization and selection process may be performed in parallel with the randomization of the BC, DE, and FG loops, whereas in other embodiments this randomization and selection process is performed in series.

Monomeric Scaffolds of the Invention

The invention provides recombinant, non-naturally occurring FnIII scaffolds comprising, a plurality of beta strand domains linked to a plurality of loop regions, wherein one or more of said loop regions vary by deletion, substitution or addition of at least one amino acid from the cognate loops in wild type Tn3 (SEQ ID NO: 1).

To generate improved Tn3 modules with novel binding characteristics, an wild type Tn3 is subjected to amino acid additions, deletions or substitutions. It will be understood that, when comparing the sequence of an improved scaffold to the sequence of Tn3, the same definition of the beta strands and loops is utilized. Improved Tn3 scaffolds can be generated using the third FnIII domain of human tenascin C), a wild type Tn3 scaffold, or a previously improved Tn3 scaffold. In some embodiments, the monomeric scaffolds of the invention comprise the amino acid sequence (SEQ ID NO: 215):
IEV($X_{AB}$)$_n$ALITW($X_{BC}$)$_n$CELX$_1$YGI($X_{CD}$)$_n$TTIDL($X_{DE}$)$_n$YSI($X_{EF}$)$_n$YEVSLIC($X_{FG}$)$_n$KETFTT, wherein $X_{AB}$, $X_{BC}$, $X_{CD}$, $X_{DE}$, $X_{EF}$, and $X_{FG}$ represent the amino acid residues present in the AB, BC, CD, DE, EF, and FG loops, respectively, wherein $X_1$ represents amino acid residue A or T, and wherein n=2-26.

In one embodiment, $X_{AB}$ consists of SEQ ID NO: 35. In one embodiment, $X_{BC}$ consists of SEQ ID NO: 36. In one embodiment, $X_{CD}$ consists of SEQ ID NO: 37. In one embodiment, $X_{DE}$ consists of SEQ ID NO: 38. In one embodiment, $X_{EF}$ consists of SEQ ID NO: 39. In one embodiment, $X_{FG}$ consists of SEQ ID NO: 40.

In one embodiment, $X_{AB}$ comprises SEQ ID NO: 35. In one embodiment, $X_{BC}$ comprises SEQ ID NO: 36. In one embodiment, $X_{CD}$ comprises SEQ ID NO: 37. In one embodiment, $X_{DE}$ comprises SEQ ID NO: 38. In one embodiment, $X_{EF}$ comprises SEQ ID NO: 39. In one embodiment, $X_{FG}$ comprises SEQ ID NO: 40.

In certain embodiments, $X_{AB}$ consists of SEQ ID NO: 35, $X_{CD}$ consists of SEQ ID NO: 37, and $X_{EF}$ consists of SEQ ID NO: 39. In one embodiment, $X_{BC}$ consists of SEQ ID NO: 36, $X_{DE}$ consists of SEQ ID NO: 38, and $X_{FG}$ consists of SEQ ID NO: 40.

In certain embodiments, $X_{AB}$ comprises SEQ ID NO: 35, $X_{CD}$ comprises SEQ ID NO: 37, and $X_{EF}$ comprises SEQ ID NO: 39. In one embodiment, $X_{BC}$ comprises SEQ ID NO: 36, $X_{DE}$ comprises SEQ ID NO: 38, and $X_{FG}$ comprises SEQ ID NO: 40.

In some embodiments, the monomeric scaffolds of the invention comprise a Tn3 module. In still other embodiments, scaffolds of the invention comprise a Tn3 module (SEQ ID NO: 1), wherein beta strand C of a third FnIII domain of human tenascin C (SEQ ID NO; 4) is replaced by a variant beta strand C (SEQ ID NO: 45 or SEQ ID NO; 131) comprising an N-terminal cysteine and wherein beta strand F of a third FnIII domain of human tenascin C (SEQ ID NO: 48) is replaced by a variant beta strand F (SEQ ID NO: 49) comprising a C-terminal cysteine. In some embodiments the scaffolds of the invention comprise a Tn3 module wherein one or more of the beta strands comprise at least one amino acid substitution except that the cysteine residues in the C and F beta strands (SEQ ID NOs: 45 or 131; and SEQ ID NO: 49, respectively) may not be substituted.

The loops connecting the various beta strands of the scaffolds of the invention can be randomized for length and/or sequence diversity. In one embodiment, the scaffolds of the invention have at least one loop that is randomized for length and/or sequence diversity. In one embodiment, at least one, at least two, at least three, at least four, at least five or at least six loops of a scaffold are randomized for length and/or sequence diversity. In one embodiment, at least one loop of the scaffolds of the invention is kept constant while at least one additional loop is randomized for length and/or sequence diversity. In another embodiment, at least one, at least two, or all three of loops AB, CD, and EF are kept constant while at least one, at least two, or all three of loops BC, DE, and FG are randomized for length or sequence diversity. In another embodiment, at least one, at least two, or at least all three of loops AB, CD, and EF are randomized while at least one, at least two, or all three of loops BC, DE, and FG are randomized for length and/or sequence diversity. In still another embodiment, at least one, at least two, at least three of loops, at least 4, at least five, or all six of loops AB, CD, EF, BC, DE, and FG are randomized for length or sequence diversity.

In some embodiments, one or more residues within a loop are held constant while other residues are randomized for length and/or sequence diversity. In some embodiments, one or more residues within a loop are held to a predetermined and limited number of different amino acids while other residues are randomized for length and/or sequence diversity. Accordingly, scaffolds of the invention can comprise one or more loops having a degenerate consensus sequence and/or one or more invariant amino acid residues. In one embodiment, the scaffolds of the invention comprise an AB loop which is randomized with the following consensus sequence: K-X-X-X-X-X-a (SEQ ID NO: 216), wherein X represents asparagine, aspartic acid, histidine, tyrosine, isoleucine, valine, leucine, phenylalanine, threonine, alanine, proline, or serine, and wherein (a) represents serine, threonine, alanine, or glycine. In another embodiment, the scaffolds of the invention comprise an AB loop which is randomized with the following consensus sequence: K-X-X-X-X-X-X-X-a (SEQ ID NO: 217), wherein X represents asparagine, aspartic acid, histidine, tyrosine, isoleucine, valine, leucine, phenylalanine, threonine, alanine, proline, or serine, and wherein (a) represents serine, threonine, alanine, or glycine.

In another embodiment, the scaffolds of the invention comprise a BC loop which is randomized with the following consensus sequence: S-X-a-X-b-X-X-X-G (SEQ ID NO: 218), wherein X represents any amino acid, wherein (a) represents proline or alanine and wherein (b) represents alanine or glycine. In another embodiment, the scaffolds of the invention comprise a BC loop which is randomized with the following consensus sequence: S-P-c-X-X-X-X-X-X-T-G (SEQ ID NO: 219), wherein X represents any amino acid and wherein (c) represents proline, serine or glycine. In still another embodiment, the scaffolds of the invention comprise a BC loop which is randomized with the following consensus sequence: A-d-P-X-X-X-e-f-X-I-X-G (SEQ ID NO: 220), wherein X represents any amino acid, wherein (d) represents proline, glutamate or lysine, wherein (e) represents asparagine or glycine, and wherein (f) represents serine or glycine.

In one embodiment, the scaffolds of the invention comprise a CD loop which is randomized with the following consensus sequence: $X_n$ (SEQ ID NO: 221), wherein X represents any amino acid, and wherein n=6, 7, 8, 9, or 10. In another embodiment, the scaffolds of the invention comprise an CD loop which is randomized with the following consensus sequence: $X_n$, wherein X represents asparagine, aspartic acid, histidine, tyrosine, isoleucine, valine, leucine, phenylalanine, threonine, alanine, proline, or serine, and wherein n=7, 8, or 9.

In one embodiment, the scaffolds of the invention comprise a DE loop which is randomized with the following consensus sequence: X-X-X-X-X-X (SEQ ID NO: 222), wherein X represents any amino acid.

In one embodiment, the scaffolds of the invention comprise an EF loop which is randomized with the following consensus sequence: X-b-L-X-P-X-c-X (SEQ ID NO: 223), wherein X represents asparagine, aspartic acid, histidine, tyrosine, isoleucine, valine, leucine, phenylalanine, threonine, alanine, proline, or serine, wherein (b) represents asparagine, lysine, arginine, aspartic acid, glutamic acid, or glycine, and wherein (c) represents isoleucine, threonine, serine, valine, alanine, or glycine In one embodiment, the scaffolds of the invention comprise an FG loop which is randomized with the following consensus sequence: X-a-X-X-G-X-X-X-b (SEQ ID NO: 224), wherein X represents any amino acid, wherein (a) represents asparagine, threonine or lysine, and wherein (b) represents serine or alanine. In another embodiment, the scaffolds of the invention comprise an FG loop which is randomized with the following consensus sequence: X-X-X-X-X-X-X-X-X ($X_9$) (SEQ ID NO: 225), wherein X represents any amino acid. In still another embodiment, the scaffolds of the invention comprise an FG loop which is randomized with the following consensus sequence: X-a-X-X-X-X-b-N-P-A (SEQ ID NO: 226), wherein X represents any amino acid, wherein (a) represents asparagine, threonine or lysine and wherein (b) represents serine or glycine. In a specific embodiment, the scaffolds of the invention comprise an FG loop which is randomized with the following consensus sequence: X-a-X-X-G-X-X-S-N-P-A (SEQ ID NO: 227), wherein X represents any amino acid, and wherein (a) represents asparagine, threonine or lysine.

In certain embodiments, the scaffolds of the invention comprise an FG loop which is held to be at least one amino acid residue shorter than the cognate FG loop of the third FnIII domain of human tenascin C and is further randomized at one or more positions.

In specific embodiments, at least one of loops BC, DE, and FG is randomized, wherein the A beta strand comprises SEQ ID NO:41 or 42, the B beta strand comprises SEQ ID NO:43, the C beta strand comprises SEQ ID NO:44, the D beta strand comprises SEQ ID NO:46, the E beta strand comprises SEQ ID NO:47, the F beta strand comprises SEQ ID NO:48, 49, 50, or 51, and the G beta strand comprises SEQ ID NO:52 or 53, the AB loop comprises SEQ ID NO:35, the CD loop comprises SEQ ID NO:37 and the EF loop comprises SEQ ID NO:39.

In other specific embodiments, at least one of loops AB, CD, and EF are randomized, wherein the A beta strand comprises SEQ ID NO:41 or 42, the B beta strand comprises SEQ ID NO:43, the C beta strand comprises SEQ ID NO:44 or 45, the D beta strand comprises SEQ ID NO:46, the E beta strand comprises SEQ ID NO:47, the F beta strand comprises SEQ ID NO:48, 49, 50, or 51, and the G beta strand comprises SEQ ID NO:52 or 53, the BC loop comprises SEQ ID NO:36, the DE loop comprises SEQ ID NO:38 and the FG loop comprises SEQ ID NO:40.

Enhanced Scaffold Stability
Non-Naturally Occurring Disulfide Bonds

The stability of Tn3 scaffolds of the invention may be increased by many different approaches. In some embodiments, scaffolds of the invention can be stabilized by elongating the N- and/or C-terminal regions. The N- and/or C-terminal regions can be elongated by 1, 2, 3, 4, 5, 6, 7, 8, 9, 10 or more than 10 amino acids. In other embodiments, the Tn3 scaffolds of the invention can be stabilized by introducing an alteration that increases serum half-life, as described herein. In yet another embodiment, the Tn3 scaffolds of the invention comprise an addition, deletion or substitution of at least one amino acid residue to stabilize the hydrophobic core of the scaffold.

Tn3 scaffolds of the invention can be effectively stabilized by engineering non-natural disulfide bonds. Such engineered scaffolds can be efficiently expressed as part of multimeric scaffolds. The correct formation of the disulfide bonds and the correct folding of the engineered scaffold are evidenced by the preservation of the biological activity of the scaffold. The fact that an engineered scaffold comprising non-natural disulfide bonds can bind simultaneously to at least two targets (see, e.g., Example 8) or three targets (see, e.g., Example 12) provides evidence that the tridimensional structure of the scaffold is not significantly altered by the engineered disulfide bonds and that the relative positions of the target-binding loops are preserved. In some embodiments, scaffolds of the invention comprise non-naturally occurring disulfide bonds, as described in PCT Publication No: WO 2009/058379. A bioinformatics approach may be utilized to identify candidate positions suitable for engineering disulfide bonds.

In one embodiment, a Tn3 monomer scaffold of the invention comprises at least one, at least two, at least three, at least four, or at least five non-naturally occurring intramolecular disulfide bonds. In a specific embodiment, the invention provides a method of obtaining a Tn3 scaffold having increased stability as compared to the third FnIII domain of human tenascin C comprising two, three, four, or more engineered intramolecular disulfide bonds.

In one embodiment, a Tn3 monomer scaffold of the invention comprises at least one non-naturally occurring intramolecular disulfide bond, wherein said at least one non-naturally occurring disulfide bond stabilizes a monomer scaffold.

In another embodiment, multimeric scaffolds of the invention comprise at least one non-naturally occurring disulfide bond, wherein the bond is located between two distinct monomer scaffolds in the same multimeric scaffold. In yet another embodiment, scaffolds of the invention comprise at least one non-naturally occurring disulfide bond, wherein the bond is located between two distinct multimeric scaffolds, i.e., the disulfide bond is an intermolecular disulfide bond. For example, a disulfide bond can link distinct scaffolds (for example, two isolated Tn3 monomer scaffolds, an isolated Tn3 monomer scaffold and a multimeric scaffold, or two multimeric scaffolds), a Tn3 scaffold and a linker, a Tn3 scaffold and an Fn domain, or a Tn3 scaffold and an antibody or fragment thereof. In some embodiments, scaffolds of the invention comprise at least one non-naturally occurring intermolecular disulfide bond that links a scaffold and an isolated heterologous moiety, a scaffold and a heterologous moiety fused or conjugated to the same scaffold, or a scaffold and heterologous moiety fused or conjugated to a different scaffold.

In some embodiments, scaffolds of the invention comprise a disulfide bond that forms a multimeric scaffold of at least 2, at least 3, at least 4 or more scaffolds.

In another embodiment, scaffolds of the invention may comprise an elongation of the N and/or C terminal regions. In one embodiment, the scaffolds of the invention comprise an alteration to increase serum half-life, as described herein. In yet another embodiment, the scaffolds of the invention comprise an addition, deletion or substitution of at least one amino acid residue to stabilize the hydrophobic core of the scaffold.

In a specific embodiment, scaffolds of the invention comprise at least one non-naturally occurring intramolecular disulfide bond, wherein the A beta strand domain comprises SEQ ID NO:42, the B beta strand comprises SEQ ID NO:43, the C beta strand comprises SEQ ID NO:45, the D beta strand comprises SEQ ID NO:46, the E beta strand comprises SEQ ID NO:47, the F beta strand comprises SEQ ID NO:49, and the G beta strand comprises SEQ ID NO:52.

In a specific embodiment, scaffolds of the invention comprise at least one non-naturally occurring intramolecular disulfide bond, wherein the A beta strand domain consists of SEQ ID NO:42, the B beta strand consists of SEQ ID NO:43, the C beta strand consists of SEQ ID NO:45, the D beta strand consists of SEQ ID NO:46, the E beta strand consists of SEQ ID NO:47, the F beta strand consists of SEQ ID NO:49, and the G beta strand consists of SEQ ID NO:52.

In a specific embodiment, scaffolds of the invention comprise at least one non-naturally occurring intramolecular disulfide bond, wherein the A beta strand domain consists essentially of SEQ ID NO:42, the B beta strand consists essentially of SEQ ID NO:43, the C beta strand consists essentially of SEQ ID NO:45, the D beta strand consists essentially of SEQ ID NO:46, the E beta strand consists essentially of SEQ ID NO:47, the F beta strand consists essentially of SEQ ID NO:49, and the G beta strand consists essentially of SEQ ID NO:52.

Enhanced Scaffold Stability: FG Loop Length

The inventors have discovered that the length of the FG loop plays a role in the stability of Tn3 scaffolds. In particular, Tn3 scaffolds comprising non-naturally occurring variant FG loops which are at least one amino acid shorter than that found in the FG loop of an FOI are shown to have enhanced stability. In certain embodiments, scaffolds of the invention comprise a non-naturally occurring variant FG loop which is at least one amino acid residue shorter than the FG loop of the third FnIII domain of human tenascin C.

In a specific embodiment, the stability of a Tn3 scaffold is enhanced by deletion of at least one amino acid in the FG loop. In another embodiment, the stability of a Tn3 scaffold can be enhanced by deletion of at least 1, or at least 2, or at least 3, or at least 4, or at least 5, or at least 6, or at least 7, or at least 8, or at least 9, or at least 10 amino acids in the FG loop. It is specifically contemplated that the stabilized Tn3 scaffold can comprise at least one non-naturally occurring disulfide bond.

In certain embodiments, the Tn3 scaffold variant also comprises at least one loop, (i.e., AB, BC, CD, DE, EF, and/or FG) that has been randomized for length and/or sequence. It is specifically contemplated that the Tn3 scaffold variant may comprise at least one non-naturally occurring disulfide bond.

In certain embodiments, a Tn3 scaffold variant comprises an FG loop which is at least one, or at least two, or at least 3, or at least 4, or at least 5, or at least 6, or at least 7, or at least 8, or at least 9, or at least 10 amino acid residues shorter than the FG loop of a wild type Tn3 scaffold, wherein the Tn3 scaffold variant further comprises at least one amino acid substitution.

Stability Measurements

The increase in stability of the stabilized FnIII scaffolds of the invention, isolated or as part of a multimeric scaffold, can be readily measured by techniques well known in the art, such as thermal ($T_m$) and chaotropic denaturation (such as treatment with urea, or guanidine salts), protease treatment (such as treatment with thermolysin) or another art accepted methodology to determine protein stability. A comprehensive review of techniques used to measure protein stability can be found, for example in "Current Protocols in Molecular Biology" and "Current Protocols in Protein Science" by John Wiley and Sons. 2007.

Multimeric Scaffolds

One aspect of the present invention provides multimeric scaffolds comprising at least two Tn3 monomer scaffolds of the invention joined in tandem. Such multimeric scaffolds can be assembled in multiple formats. In some embodiments the Tn3 monomer scaffolds are assembled in linear formats whereas in other embodiments the scaffolds are assembled in branched formats (see, e.g., FIG. 1). In a specific aspect, the invention provides multimeric scaffolds, wherein at least two Tn3 scaffolds are connected in tandem via a peptide linker. In some embodiments, a Tn3 scaffold in the multimeric scaffolds of the invention binds to TRAIL R2, whereas a second Tn3 scaffold binds to a different target, thereby demonstrating multiple functions, and/or to the same target, thereby increasing the valency and/or avidity of target binding, other action of the target(s). In some embodiments, the increase in valency and/or avidity of target binding is accomplished when multiple scaffolds bind to the same target. In some embodiments, the increase in valency improves a specific action on the target, such as increasing the dimerization of a target protein.

In a specific embodiment, the multimeric scaffold of the invention comprises at least two Tn3 scaffolds of the invention connected in tandem, wherein each Tn3 scaffold binds at least one target, and wherein each Tn3 scaffold comprises a plurality of beta strands linked to a plurality of loop regions, wherein at least one loop is a non-naturally occurring variant of the cognate loop in a wild type Tn3 domain.

Multimeric Tandem Scaffolds

In one embodiment, the multimeric scaffolds of the invention comprise two, three, four, five, six, eight or more Tn3 monomer scaffolds of the invention. In some embodiments some of the Tn3 monomer scaffolds are connected in tandem. In yet another embodiment, some of the Tn3 monomer scaffolds are connected in tandem and some of the Tn3 monomer scaffolds are not connected in tandem. In a specific embodiment, the multimeric scaffolds of the invention comprise two, or three, or four, or five, or six, or seven, or eight, or nine, or ten, or more scaffolds of the invention connected in tandem (see, e.g., FIG. 1 and FIG. 2).

In one embodiment, the multimeric scaffolds are generated through covalent binding between Tn3 monomer scaffolds, for example, by directly linking the Tn3 scaffolds, or by the inclusion of a linker, e.g., a peptide linker. In particular examples, covalently bonded scaffolds are generated by constructing fusion genes that encode the monomeric Tn3 scaffolds or, alternatively, by engineering codons for cysteine residues into monomer Tn3 scaffolds and allowing disulfide bond formation to occur between the expression products.

In one embodiment, the multimeric scaffolds of the invention comprise at least two Tn3 scaffolds that are connected directly to each other without any additional intervening amino acids. In another embodiment, the multimeric scaffolds of the invention comprise at least two Tn3 scaffolds that are connected in tandem via a linker, e.g., a peptide linker. In a specific embodiment, the multimeric scaffolds of the invention comprise at least two Tn3 scaffolds that are connected in tandem via a peptide linker, wherein the peptide linker comprises 1 to about 1000, or 1 to about 500, or 1 to about 250, or 1 to about 100, or 1 to about 50, or 1 to about 25, amino acids. In a specific embodiment, the multimeric scaffolds of the invention comprise at least two Tn3 scaffolds that are connected in tandem via a peptide linker, wherein the peptide linker comprises 1 to about 20, or 1 to about 15, or 1 to about 10, or 1 to about 5, amino acids.

In a specific embodiment, the multimeric scaffolds of the invention comprise at least two Tn3 scaffolds that are connected in tandem via a linker, e.g., a peptide linker, wherein the linker is a functional moiety. The functional moiety will be selected based on the desired function and/or characteristics of the multimeric scaffold. For example, a functional moiety useful for purification (e.g., a histidine tag) may be used as a linker. Functional moieties useful as linkers include, but are not limited to, polyethylene glycol (PEG), a cytotoxic agent, a radionuclide, imaging agent, biotin, a dimerization domain, human serum albumin (HSA) or an FcRn binding portion thereof, a domain or fragment of an antibody, a single chain antibody, a domain antibody, an albumin binding domain, an IgG molecule, an enzyme, a ligand, a receptor, a binding peptide, a non-Tn3 scaffold, an epitope tag, a recombinant polypeptide polymer, a cytokine, and the like. Specific peptide linkers and functional moieties which may be used as linkers are disclosed infra.

In some embodiments, the multimeric Tn3 scaffold comprises at least two Tn3 scaffolds that are connected via one or more linkers, wherein the linkers interposed between each Tn3 scaffold can be the same linkers or different linkers. In some embodiments, a linker can comprise multiple linkers, which can be the same linker or different linkers. In some embodiments, when a plurality of linkers are concatenated, some or all the linkers can be functional moieties.

Multimeric Scaffold Binding Stoichiometry

In some embodiments, the multimeric Tn3 scaffold comprise scaffolds that are specific for TRAIL R2. In other embodiments, multimeric scaffolds of the invention comprise scaffolds that are specific for different epitopes, which can be different epitopes on TRAIL R2 or on different targets.

In a specific embodiment, the multimeric Tn3 scaffold can bind two or more different epitopes (e.g., non-overlapping epitopes) on the same TRAIL R2 molecule. In another specific embodiment, the multimeric Tn3 scaffold can bind two or more different epitopes on TRAIL R2. In yet another specific embodiment, the multimeric Tn3 scaffold can bind two or more different epitopes on the TRAIL R2 and additionally, bind at least one epitope on one or more different target molecules. In still another specific embodiment, the multimeric Tn3 scaffold can bind to the same epitope on a TRAIL R2 dimer. In yet another embodiment, the multimeric Tn3 scaffold can bind to the same epitope on at least two TRAIL R2 molecules. In certain embodiments, the multimeric Tn3 scaffold can bind the same epitope on two or more copies of the TRAIL R2 molecule on an adjacent cell surface. In some embodiments, the multimeric Tn3 scaffold can bind to the same epitope or different epitopes on TRAIL R2 or on different targets with the same or different binding affinities and/or avidities.

In another embodiment, the monomer scaffolds in a multimeric Tn3 scaffold can bind to epitopes on one or more copies of TRAIL R2 according to a specific binding pattern designed to achieve or enhance (e.g., synergistically) a desired action on the target, e.g., target dimerization. For example, the Tn3 scaffolds in a linear multimeric scaffold can bind to a single TRAIL R2 or to multiple TRAIL R2 according to a certain pattern, e.g., Tn3 scaffolds in a 6 module linear multivalent scaffold can bind to two TRAIL R2 targets A and B according to an AAABBB pattern, an AABBAA pattern, an ABABAB pattern, an AAAABB pattern, etc.; to three targets according to an AABBCC pattern, an ABCABC pattern, and ABCCBA pattern, etc.; to four targets according to an ABCDDA patterns, ABCADA pattern, etc.; etc. In addition, when a multimeric scaffold of the invention comprises a plurality of engineered (e.g., disulfide engineered, loop engineered, or both disulfide and loop engineered) and non-engineered scaffolds, such monomeric scaffolds can be arranged according to a certain pattern to achieve or enhance a certain biological effect. Such combinations of monomeric Tn3 scaffolds can be combinatorially assembled and subsequently evaluated using methods known in the art.

In some embodiments, multimeric Tn3 scaffolds in branched constructs, e.g., multimeric scaffolds in an Fc fusion or antibody-like format, can also bind to a single TRAIL R2 or to multiple TRAIL R2 targets according to a certain pattern. For instance, in certain embodiments a linear format Tn3 scaffold fused to the IgG heavy chains in an antibody-like format Tn3 multimeric scaffold can bind to a first target whereas a multivalent Tn3 linear scaffold fused to the IgG light chains in an antibody-like format Tn3 scaffold can bind to a second target. In another embodiment, linear format Tn3 scaffolds fused to the IgG heavy chains of an antibody-like format Tn3 scaffold can bind to a target with a certain affinity whereas the linear format scaffolds fused to the IgG light chains of an antibody-like format scaffold can bind to the same target with a different affinity. In some embodiments, the Tn3 scaffolds fused to the chains in the left arm of the "Y" of an antibody can bind to a first target, whereas the Tn3 scaffolds fused to the chains of the right of the "Y" of an antibody can bind to a second target.

Fusions

The invention further provides multimeric Tn3 scaffolds comprising at least two Tn3 monomer scaffolds, wherein at least one Tn3 monomer scaffold may be fused to a heterologous moiety. In this context the heterologous moiety is not used to link the scaffolds as a spacer but may provide additional functionality to the multimeric Tn3 scaffold. For example, in some embodiments, a multimeric Tn3 scaffold that binds TRAIL R2 may be fused to a cytotoxic agent to facilitate target specific cell killing. In some embodiments, a heterologous moiety can function as a linker.

The present invention encompasses the use of multimeric Tn3 scaffolds conjugated or fused to one or more heterologous moieties, including but not limited to, peptides, polypeptides, proteins, fusion proteins, nucleic acid molecules, small molecules, mimetic agents, synthetic drugs, inorganic molecules, and organic molecules. The present invention encompasses the use of multimeric Tn3 scaffolds recombinantly fused or chemically conjugated to a heterologous protein or polypeptide or fragment thereof. Conjugation includes both covalent and non-covalent conjugation. In some embodiments, a multimeric Tn3 scaffold can be fused or chemically conjugated to a polypeptide of at least 10, at least 20, at least 30, at least 40, at least 50, at least 60, at least 70, at least 80, at least 90, at least 100, at least 200, at least 300, at least 500, or at least 1000 amino acids) to generate fusion proteins.

The fusion or conjugation of a multimeric Tn3 scaffold to one or more heterologous moieties can be direct, i.e., without a linker interposed between a Tn3 scaffold and a heterologous moiety, or via one or more linker sequences described herein. In some embodiments, scaffolds can be used to target heterologous polypeptides to particular cell types, either in vitro or in vivo, by fusing or conjugating the Tn3 scaffolds to antibodies specific for particular cell surface receptors in the target cells, such as TRAIL R2. Multimeric Tn3 scaffolds fused or conjugated to heterologous polypeptides can also be used in in vitro immunoassays and purification methods using methods known in the art. See e.g., International Publication No. WO 93/21232; European Patent No. EP 439,095; Naramura et al. Immunol. Lett. 39:91-99, 1994; U.S. Pat. No. 5,474,981; Gillies et al., PNAS 89:1428-1432, 1992; and Fell et al., J. Immunol. 146:2446-2452, 1991, which are incorporated by reference in their entireties.

In some embodiments, the multimeric Tn3 scaffolds can be integrated with the human immune response by fusing or conjugating a scaffold with an immunoglobulin or domain thereof including, but not limited to, the constant region of an IgG (Fc), e.g., through the N or C-terminus. Similarly, a fusion between a scaffold and a complement protein, such as C1q, can be used to target cells. A fusion between a multimeric Tn3 scaffold and a toxin can be used to specifically destroy cells that carry a particular antigen as described herein.

Various publications describe methods for obtaining physiologically active molecules whose half-lives are modified by introducing an FcRn-binding polypeptide into the molecules (see, e.g., WO 97/43316; U.S. Pat. No. 5,869,046; U.S. Pat. No. 5,747,035; WO 96/32478; and WO 91/14438), by fusing the molecules with antibodies whose FcRn-binding affinities are preserved but affinities for other Fc receptors have been greatly reduced (see, e.g., WO 99/43713), or by fusing the molecules with FcRn binding domains of antibodies (see, e.g., WO 00/09560; U.S. Pat. No. 4,703,039). Specific techniques and methods of increasing half-life of physiologically active molecules can also be found in U.S. Pat. No. 7,083,784. Specifically, it is contemplated that the multimeric Tn3 scaffolds can be fused to an Fc region from an IgG, wherein the Fc region comprises amino acid residue mutations M252Y/S254T/T256E or H433K/N434F/Y436H, wherein amino acid positions are designated according to the Kabat numbering schema. In some embodiments, the half life of the multimeric Tn3 scaffold can be increased by genetically fusing the multivalent Tn3 scaffold with an intrinsically unstructured recombinant polypeptide (e.g., an XTEN™ polypeptide) or by conjugation with polyethylene glycol (PEG).

In some embodiments, the multimeric Tn3 scaffold can be fused with molecules that increase or extend in vivo or serum half life. In some embodiments, the scaffold can be fused or conjugated with albumin, such as human serum albumin (HSA), a neonatal Fc receptor (FcRn) binding fragment thereof, PEG, polysaccharides, antibodies, complement, hemoglobin, a binding peptide, lipoproteins and other factors to increase its half-life in the bloodstream and/or its tissue penetration. Any of these fusions may be generated by standard techniques, for example, by expression of the fusion protein from a recombinant fusion gene constructed using publicly available gene sequences.

Moreover, the scaffolds of the invention can be fused to marker sequences, such as a peptide to facilitate purification. In some embodiments, the marker amino acid sequence is a poly-histidine peptide (His-tag), e.g., a octa-histidine-tag (His-8-tag) (SEQ ID NO: 211) or hexa-histidine-tag (His-6-tag) (SEQ ID NO: 228) such as the tag provided in a pQE expression vector (QIAGEN, Inc., 9259 Eton Avenue, Chatsworth, Calif., 91311), among other vectors, many of which are commercially available. As described in Gentz et al., Proc. Natl. Acad. Sci. USA 86:821-824, 1989, for instance, poly-histidine provides for convenient purification of the fusion protein. Other peptide tags useful for purification include, but are not limited to, a hemagglutinin ("HA") tag, which corresponds to an epitope derived from the influenza hemagglutinin protein (see, e.g., Wilson et al., Cell 37:767, 1984), a FLAG tag, a Strep-tag, a myc-tag, a V5 tag, a GFP-tag, an AU1-tag, an AU5-tag, an ECS-tag, a GST-tag, or an OLLAS tag.

Additional fusion proteins comprising scaffolds of the invention may be generated through the techniques of gene-shuffling, motif-shuffling, exon-shuffling, and/or codon-shuffling (collectively referred to as "DNA shuffling").

DNA shuffling may be employed to alter the action of Tn3 scaffolds on the target (e.g., generate scaffolds with higher affinities and lower dissociation rates, or scaffold with increased ability to dimerize TRAIL R2). Tn3 scaffolds may be altered by random mutagenesis by error-prone PCR, random nucleotide insertion, or other methods prior to recombination. One or more portions of a polynucleotide encoding a scaffold, which bind to a specific target may be recombined with one or more components, motifs, sections, parts, domains, fragments, etc. of one or more heterologous molecules.

Antibody-Like Multimeric Scaffolds

In some embodiments, the multimeric scaffold of the invention comprise at least two Tn3 scaffolds, wherein at least one Tn3 scaffold is fused to a domain or fragment of an antibody (e.g., an IgG), including but not limited to an intact antibody, an antibody variable domain, a CH1 domain, a Ckappa domain, a Clambda domain, an Fc domain, a CH2, or a CH3 domain.

In some embodiments, a Tn3 scaffold can be fused to a domain or fragment of an antibody. The domain or fragment of an antibody can further enhances the avidity and/or affinity of the multimeric scaffold by providing, similarly to the Fc domain described below, a dimerization or multimerization domain which facilitates the formation of multimeric scaffolds of the invention. Furthermore, the domain or fragment of an antibody can further enhance the scaffold's action on the target, e.g., more efficiently dimerizing or multimerizing a target.

In some embodiments, only one multimeric Tn3 tandem scaffold comprising two Tn3 domains is conjugated or fused to a domain or fragment of an antibody. For instance, a single multimeric tandem scaffold can be fused to the N-terminus of a polypeptide of a domain or fragment of an antibody (e.g., a heavy chain or a light chain of an antibody). In some embodiments, multimeric Tn3 scaffolds are created by fusing or conjugating one or more Tn3 scaffolds to the N-terminus and/or the C-terminus a polypeptide of a domain or fragment of an antibody (e.g., a heavy chain and/or a light chain of an antibody. In some embodiments, some or all the Tn3 scaffolds fused to a domain or fragment of an antibody are identical. In some other embodiments, some or all the Tn3 scaffolds fused to a domain or fragment of an antibody are different.

In some embodiments, the tandem Tn3 scaffolds used to generate an antibody-like multivalent Tn3 scaffold can contain the same number of Tn3 modules. In other embodiments, the tandem Tn3 scaffolds used to generate an antibody-like multivalent Tn3 scaffold can contain a different number of Tn3 modules. For example, a tetravalent Tn3 scaffold can be formed, e.g., by fusing a linear format tetravalent Tn3 scaffold to a single position, or by fusing one Tn3 monomer scaffold in one position and a trimeric linear format Tn3 scaffold to another position, or by fusing two dimeric Tn3 linear format scaffolds to two different positions, or by fusing 4 Tn3 monomer scaffolds, each one to a single position.

In a specific embodiment, multimeric Tn3 scaffolds of the invention comprise four multimeric linear Tn3 scaffolds fused to a domain or fragment of an antibody wherein each multimeric linear Tn3 scaffold comprises two Tn3 monomer scaffolds that are connected in tandem via a linker (FIG. 1). In other embodiments, multimeric Tn3 scaffolds of the invention comprise at least one, at least two, at least three, at least four, at least five, at least six, at least seven or at least eight monomeric or multimeric Tn3 scaffolds of the invention fused to a domain or fragment of an antibody.

Figure 2:
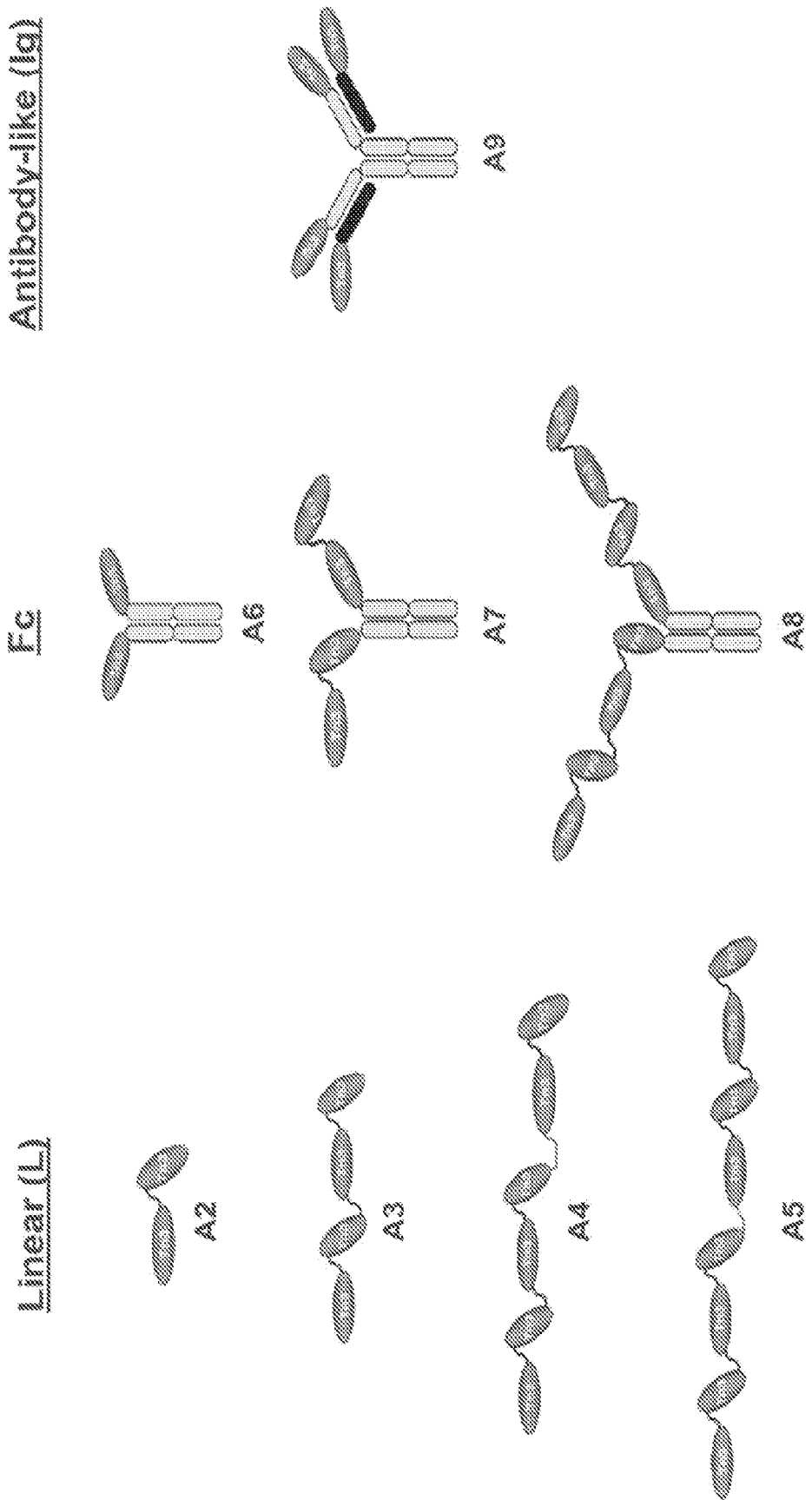
FIG. 2 shows TRAIL R2-specific multivalent Tn3 scaffolds, designated as A2 to A9, which were generated according to the three different molecular formats shown in FIG. 1 with valencies (number of Tn3 modules) varying from 2 to 8.

In one specific embodiment, a tetravalent Tn3 scaffold can be generated by fusing one Tn3 scaffold to the N-terminus of each of the light chains and heavy chains of a domain or fragment of an antibody (see, e.g., A9 construct in FIG. 2).

An antibody-like format multivalent Tn3 scaffold can be generated by fusing any combination of Tn3 scaffolds to a domain or fragment of an antibody or modified antibody. Examples of modified antibodies include domain deleted antibodies, minibodies (see, e.g., U.S. Pat. No. 5,837,821), tetravalent minibodies, tetravalent antibodies (see, e.g., Coloma & Morrison, Nature Biotechnol. 15:159-163, 1997; PCT Publication No. WO 95/09917), thermally stabilized antibodies, humanized antibodies, etc.

Each of the linear Tn3 scaffolds of the invention used to generate an antibody-like multivalent Tn3 scaffold according to FIG. 1 can contain the same linkers and linker distributions, or different linkers and different linker distributions.

Fc-Fusion Multimeric Scaffolds

In some embodiments, a multimeric Tn3 scaffold of the invention comprises a plurality of monomeric or multimeric Tn3 scaffolds connected to an Fc domain. The fusion of a multimeric Tn3 scaffold of the invention to an antibody fragment comprising an Fc domain further enhances the avidity and/or activity of the multimeric FnIII scaffold by providing a dimerization domain which facilitates the formation of dimers of the multimeric Tn3 scaffolds.

In some embodiments, only one multimeric Tn3 scaffold is fused to an Fc domain. In a specific embodiment, multimeric Tn3 scaffolds of the invention comprise two multimeric Tn3 scaffolds fused to an Fc domain wherein each multimeric Tn3 scaffold comprises two or more Tn3 scaffolds that are connected via one or more linkers (FIG. 1). In one specific embodiment, the multimeric Tn3 scaffolds fuse to the Fc domain are linear format scaffolds.

In one specific embodiment, two linear format Tn3 scaffolds comprising two Tn3 domains in tandem are fused to an Fc domain to yield a multimeric Tn3 scaffold with a valency of 4 (see, e.g., A7 construct in FIG. 2). In another specific embodiment, two linear format scaffolds, each one of them comprising four Tn3 monomer scaffolds are fused to an Fc domain to yield an multimeric Tn3 scaffold with a valency of 8 (see, e.g., A8 construct in FIG. 2).

In some embodiments, the Tn3 scaffolds fused to the Fc domain comprise the same number of Tn3 modules. In some embodiments, the Tn3 scaffolds fused to the Fc domain comprise a different number of Tn3 modules. In some embodiments, the Tn3 scaffolds fused to the Fc domain comprise the same linkers. In other embodiments, the Tn3 scaffolds fused to the Fc domain comprise different linkers.

In some embodiments, different multimeric Tn3 scaffolds of the invention can be dimerized by the use of Fc domain mutations which favor the formation of heterodimers. It is known in the art that variants of the Fc region (e.g., amino acid substitutions and/or additions and/or deletions) enhance or diminish effector function of the antibody and can alter the pharmacokinetic properties (e.g. half-life) of the antibody. Thus, in certain embodiments, the multispecific Tn3 scaffolds of the invention comprise Fc domain(s) that comprise an altered Fc region in which one or more alterations have been made in the Fc region in order to change functional and/or pharmacokinetic properties of the multimeric Tn3 scaffold.

It is also known that the glycosylation of the Fc region can be modified to increase or decrease effector function and/or anti-inflammatory activity. Accordingly, in one embodiment the Fc regions of the multimeric FnIII scaffolds of the invention comprise altered glycosylation of amino acid residues in order to change cytotoxic and/or anti-inflammatory properties of the multimeric scaffolds.

Multimeric Scaffold Topologies

One skilled in the art would appreciate that multimeric scaffolds discussed above, in FIG. 1 and FIG. 2, and throughout the specification are just illustrative examples. The construct topologies or formats shown in FIG. 1 and FIG. 2 illustrate that in some embodiments the scaffolds of the invention are fused to the N-termini of the constituent polypeptides of Fc domains and antibodies. The scaffolds of the invention can be fused to the C-terminus of the Fc domains, antibody light chains, and antibody heavy chains in any suitable spatial arrangement. For example, an some embodiments a tetravalent scaffold can be created by fusing an FnIII monomer scaffold to the N-terminus of each heavy chain and an FnIII monomer scaffold to the C-terminus domain of each light chain of an antibody, by fusing an FnIII monomer scaffold to the N-terminus of each light chain and an FnIII monomer scaffold to the C-terminus of each heavy chain of an antibody, or by fusing an FnIII monomer scaffold to the N-terminus of each heavy chain and an FnIII monomer scaffold to the N-terminus of each light chain of an antibody. Monomeric and/or multimeric FnIII scaffolds can be fused to full length heavy and/or light chains comprising both variable regions and constant regions. Alternatively, the FnIII monomer and/or multimer scaffolds can be fused to truncated heavy and/or light chains comprising only constant regions (e.g., as in the A9 construct shown in FIG. 2).

Multimeric Tn3 scaffolds can be created by using the formats shown in FIG. 1 as building blocks. For example, the antibody-like and Fc fusion formats are combinations comprising simpler linear format Tn3 modules. Accordingly, in some embodiments more complex multimeric Tn3 scaffolds formats can be created by combining the building blocks shown in FIG. 1.

FIGS. 1 and 2 also illustrate that in some embodiments the multimeric Tn3 scaffolds can be linear or branched and exhibit different levels of branching. For example, the Fc format provides an example of first order branched format, whereas the antibody-like format provides an example of a second-order branched format. Higher order branched constructs can be obtained by replacing the linear format building blocks in the antibody-like format or the Fc fusion format with Fc fusion format building blocks or antibody-like building blocks, and connect them to either the C-termini or N-termini of the constituent polypeptides of the Fc or antibody.

FIGS. 1 and 2, and TABLE 1 illustrate the fact that in some embodiments the linkers in a multimeric Tn3 scaffold can be structurally and functionally diverse and can provide a plurality of attachment points. For example, all the Tn3 modules in the A4 and A5 constructs are connected by (Gly$_4$Ser)$_3$Ala linkers (SEQ ID NO: 88), except for the 4th and 5th Tn3 modules, which are connected by a (Gly$_4$Ser)$_2$GlyThrGly-SerAlaMetAlaSer (Gly$_4$Ser)$_1$Ala linker (SEQ ID NO: 89). For example, in the A7 construct, the first and second Tn3 domains and the third and fourth Tn3 domain are connected by (Gly$_4$Ser)$_3$Ala linkers (SEQ ID NO: 88), whereas the second and third Tn3 domains are connected by an Fc domain as a functional moiety linker.

The Fc fusion shown in FIG. 1 exemplifies that in some embodiments monomeric or multimeric Tn3 scaffolds can be fused to the N-termini of the polypeptides of the functional moiety linker. In some embodiments, monomeric or multimeric Tn3 scaffolds of the invention can readily be fused to the C-terminus of the Fc domain in an Fc fusion format construct.

Similarly, the antibody or modified antibody in an antibody-like format construct is also a functional moiety linker. In this case, instead of two attachment points as in a (Gly$_4$Ser)$_3$Ala (SEQ ID NO: 88) or in a (Gly$_4$Ser)$_2$GlyThr-GlySerAlaMetAlaSer (Gly$_4$Ser)$_1$Ala linker (SEQ ID NO: 89), or four possible attachment points as in the Fc domain case, the antibody shown in the antibody-like example of FIG. 1 provides 6 possible attachment points. The antibody-like format shown in FIG. 1 exemplifies that in some embodiments only the N-terminal attachment points in the functional moiety linker are occupied by Tn3 scaffolds. In an antibody-like format construct some or all the Tn3 scaffolds of the invention can readily be fused to the C-termini of the heavy chains and the light chains of an antibody or modified antibody domain. Other fusion stoichiometries can be applied, i.e., one, two, three, four, five, six, seven, eight, or more Tn3 scaffolds of the invention can be fused to an antibody or modified antibody.

FIGS. 1 and 2 also illustrate that in some embodiments multimeric Tn3 scaffolds can be generated by combining other Tn3 multimeric scaffolds. For example, the Fc format A6, A7, and A8 scaffolds of FIG. 2 are homodimeric Tn3 scaffolds wherein the multimeric Tn3 scaffold is formed by two polypeptide chains, each one comprising a linear format Tn3 scaffold fused to an Fc domain, which in turn are connected via intermolecular disulfide bonds. The antibody-like scaffold of FIGS. 1 and 2 exemplifies a heterotetrameric Tn3 scaffold wherein 4 polypeptides corresponding to two different types of scaffolds (2 Tn3 scaffolds formed by fusing an Tn3 monomer scaffold to an IgG light chain constant region, and 2 Tn3 scaffolds formed by fusing an Tn3 monomer scaffold to an CH1-hinge-region-Fc region of an IgG) are connected via intermolecular disulfide bonds.

Generation of Scaffolds of the Invention

The Tn3 scaffolds described herein may be used in any technique for evolving new or improved target binding proteins. In one particular example, the target is immobilized on a solid support, such as a column resin or microtiter plate well, and the target contacted with a library of candidate scaffold-based binding proteins. Such a library may consist of clones constructed from a Tn3 scaffold, through randomization of the sequence and/or the length of the CDR-like loops.

In this regard, bacteriophage (phage) display is one well known technique which allows one to screen large oligopeptide libraries to identify member(s) of those libraries which are capable of specifically binding to a target. Phage display is a technique by which variant polypeptides are displayed as fusion proteins to the coat protein on the surface of bacteriophage particles (Scott, J. K. and Smith, G. P. (1990) Science 249: 386). A bioinformatics approach may be employed to determine the loop length and diversity preferences of naturally occurring FnIII domains. Using this analysis, the preferences for loop length and sequence diversity may be employed to develop a "restricted randomization" approach. In this restricted randomization, the relative loop length and sequence preferences are incorporated into the development of a library strategy. Integrating the loop length and sequence diversity analysis into library development results in a restricted randomization (i.e. certain positions within the randomized loop are limited in which amino acid could reside in that position).

The invention also provides recombinant libraries comprising diverse populations of non-naturally occurring Tn3 scaffolds. In one embodiment, the libraries comprise non-naturally occurring Tn3 scaffolds comprising, a plurality of beta strand domains linked to a plurality of loop regions, wherein one or more of said loops vary by deletion, substitution or addition by at least one amino acid. In a specific embodiment, the libraries comprise Tn3 scaffolds derived from the wild type Tn3 scaffold.

As detailed above, the loops connecting the various beta strands of the scaffolds may be randomized for length and/or sequence diversity. In one embodiment, the libraries of the invention comprise Tn3 scaffolds having at least one loop that is randomized for length and/or sequence diversity. In one embodiment, at least one, at least two, at least three, at least four, at least five or at least six loops of the Tn3 scaffolds are randomized for length and/or sequence diversity. In one embodiment, at least one loop is kept constant while at least one additional loop is randomized for length and/or sequence diversity. In another embodiment, at least one, at least two, or all three of loops AB, CD, and EF are kept constant while at least one, at least two, or all three of loops BC, DE, and FG are randomized for length or sequence diversity. In another embodiment, at least one, at least two, or at least all three of loops AB, CD, and EF are randomized while at least one, at least two, or all three of loops BC, DE, and FG are randomized for length and/or sequence diversity.

We have found that FG loops which are at least one amino acid shorter than that found in the FG loop of an FOI show enhanced stability. Accordingly, the present invention provides libraries comprising Tn3 scaffolds, wherein at least one loop is randomized for length and/or sequence diversity, except that length of the FG loops are held to be at least one amino acid shorter than the cognate FG loop of the third FnIII domain of human tenascin C comprises 10 amino acid residues. In some embodiments, the libraries of the invention comprise Tn3 scaffolds, wherein each scaffold comprises seven beta strands designated A, B, C, D, E, F, and G linked to six loop regions, wherein a loop region connects each beta strand and is designated AB, BC, CD, DE, EF, and FG; and wherein at least one loop is a non-naturally occurring variant of a wild Tn3 scaffold loop, and wherein the FG loop is at least one amino acid shorter than the cognate loop in the wild type Tn3 scaffold.

In a specific embodiment, the libraries of the invention comprise FnIII scaffolds, wherein the A beta strand comprises SEQ ID NO: 42, the B beta strand comprises SEQ ID NO: 43, the C beta strand comprises SEQ ID NO: 45, the D beta strand comprises SEQ ID NO: 46, the E beta strand comprises SEQ ID NO: 47, the F beta strand comprises SEQ ID NO: 49, and the G beta strand comprises SEQ ID NO: 52.

In a specific embodiment, the libraries of the invention comprise FnIII scaffolds, wherein the A beta stand consists of SEQ ID NO: 42, the B beta strand consists of SEQ ID NO: 43, the C beta strand consists of SEQ ID NO: 45, the D beta strand consists of SEQ ID NO: 46, the E beta strand consists of SEQ ID NO: 47, the F beta strand consists of SEQ ID NO: 49, and the G beta strand consists of SEQ ID NO: 52.

In a specific embodiment, the libraries of the invention comprise FnIII scaffolds, wherein the A beta strand consists essentially of SEQ ID NO: 42, the B beta strand consists essentially of SEQ ID NO: 43, the C beta strand consists essentially of SEQ ID NO: 45, the D beta strand consists essentially of SEQ ID NO: 46, the E beta strand consists essentially of SEQ ID NO: 47, the F beta strand consists essentially of SEQ ID NO: 49, and the G beta strand consists essentially of SEQ ID NO: 52.

As detailed above, one or more residues within a loop may be held constant while other residues are randomized for length and/or sequence diversity. Optionally or alternatively, one or more residues within a loop may be held to a predetermined and limited number of different amino acids while other residues are randomized for length and/or sequence diversity. Accordingly, libraries of the invention comprise Tn3 scaffolds that may comprise one or more loops having a degenerate consensus sequence and/or one or more invariant amino acid residues.

In another embodiment, the libraries of the invention comprise Tn3 scaffolds having BC loops which are randomized with the following consensus sequence: S-X-a-X-b-X-X-X-G (SEQ ID NO: 218), wherein X represents any amino acid, wherein (a) represents proline or alanine and wherein (b) represents alanine or glycine. In another embodiment, the libraries of the invention comprise Tn3 scaffolds having BC loops which are randomized with the following consensus sequence: S-P-c-X-X-X-X-X-X-T-G (SEQ ID NO: 219), wherein X represents any amino acid and wherein (c) represents proline, serine or glycine. In still another embodiment, the libraries of the invention comprise Tn3 scaffolds having BC loops which are randomized with the following consensus sequence: A-d-P-X-X-X-e-f-X-I-X-G (SEQ ID NO: 220), wherein X represents any amino acid, wherein (d) represents proline, glutamate or lysine, wherein (e) represents asparagine or glycine, and wherein (f) represents serine or glycine.

In one embodiment the libraries of the invention comprise Tn3 scaffolds having DE loops which are randomized with the following consensus sequence: X-X-X-X-X-X (SEQ ID NO: 221), wherein X represents any amino acid.

In one embodiment, the libraries of the invention comprise Tn3 scaffolds having FG loops which are randomized with the following consensus sequence: X-a-X-X-G-X-X-X-b (SEQ ID NO: 222), wherein X represents any amino acid, wherein (a) represents asparagine, threonine or lysine, and wherein (b) represents serine or alanine. In another embodiment, the libraries of the invention comprise FnIII scaffolds having FG loops which are randomized with the following consensus sequence: X-X-X-X-X-X-X-X-X ($X_9$) (SEQ ID NO: 223), wherein X represents any amino acid.

In a specific embodiment, the libraries of the invention comprise scaffolds, wherein the scaffolds comprise the amino acid sequence (SEQ ID NO: 229): IEV$(X_{AB})_n$ALITW$(X_{BC})_n$CELX$_1$YGI$(X_{CD})_n$TTIDL $(X_{DE})_n$YSI$(X_{EF})_n$YEVSLIC$(X_{FG})_n$KETFTT, wherein $X_{AB}$, $X_{BC}$, $X_{CD}$, $X_{DE}$, $X_{EF}$, and $X_{FG}$ represent the amino acid residues present in the AB, BC, CD, DE, EF, and FG loops, respectively, wherein $X_1$ represents amino acid residue A or T, and wherein n=2-26 and m=1-9.

The invention further provides methods for identifying a recombinant Tn3 scaffold that binds a target, e.g., TRAIL R2, and has increased stability or improved action on the target, e.g., TRAIL R2, as compared to a wild type Tn3 scaffold by screening the libraries of the invention.

In certain embodiments, the method for identifying a recombinant Tn3 scaffold having increased protein stability as compared to a wild type Tn3 scaffold, and which specifically binds a target, comprises:

a. contacting the target ligand with a library of the invention under conditions suitable for forming a scaffold:target ligand complex;
b. obtaining from the complex, the scaffold that binds the target ligand;
c. determining if the stability of the scaffold obtained in step (b) is greater than that of the wild type Tn3 scaffold.

The same method can be used to identify recombinant Tn3 scaffold with improved binding affinity, avidity, etc. to the target. In one embodiment, in step (a) the scaffold library of the invention is incubated with immobilized target. In one embodiment, in step (b) the scaffold:target ligand complex is washed to remove non-specific binders, and the tightest binders are eluted under very stringent conditions and subjected to PCR to recover the sequence information. It is specifically contemplated that the binders and/or sequence information obtained in step (b) can be used to create a new library using the methods disclosed herein or known to one of skill in the art, which may be used to repeat the selection process, with or without further mutagenesis of the sequence. In some embodiments, a number of rounds of selection may be performed until binders of sufficient affinity for the antigen are obtained.

A further embodiment of the invention is a collection of isolated nucleic acid molecules encoding a library comprising the scaffolds of the invention and as described above.

The scaffolds of the invention may be subjected to affinity maturation. In this art-accepted process, a specific binding protein is subject to a scheme that selects for increased affinity for a specific target (see Wu et al., Proc. Natl. Acad. Sci.

USA. 95(11):6037-42). The resultant scaffolds of the invention may exhibit binding characteristics at least as high as compared to the scaffolds prior to affinity maturation.

The invention also provides methods of identifying the amino acid sequence of a protein scaffold capable of binding to target so as to form a scaffold:target complex. In one embodiment, the method comprises: a) contacting a library of the invention with an immobilized or separable target; b) separating the scaffold:target complexes from the free scaffolds; c) causing the replication of the separated scaffolds of (b) so as to result in a new polypeptide display library distinguished from that in (a) by having a lowered diversity and by being enriched in displayed scaffolds capable of binding the target; d) optionally repeating steps (a), and (b) with the new library of (c); and e) determining the nucleic acid sequence of the region encoding the displayed scaffold of a species from (d) and hence deducing the peptide sequence capable of binding to the target.

In another embodiment, the scaffolds of the invention may be further randomized after identification from a library screen. In one embodiment, methods of the invention comprise further randomizing at least one, at least two, at least three, at least four, at least five or at least six loops of a scaffold identified from a library using a method described herein. In another embodiment, the further randomized scaffold is subjected to a subsequent method of identifying a scaffold capable of binding a target. This method comprises (a) contacting said further randomized scaffold with an immobilized or separable target, (b) separating the further randomized scaffold:target complexes from the free scaffolds, (c) causing the replication of the separated scaffolds of (b), optionally repeating steps (a)-(c), and (d) determining the nucleic acid sequence of the region encoding said farther randomized scaffold and hence, deducing the peptide sequence capable of binding to the target.

In a further embodiment, the further randomized scaffolds comprise at least one, at least two, at least three, at least four, at least five, or at least six randomized loops which were previously randomized in the first library. In an alternate further embodiment, the further randomized scaffolds comprise at least one, at least two, at least three, at least four, at least five, or at least six randomized loops which were not previously randomized in the first library.

The invention also provides a method for obtaining at least two Tn3 scaffolds that bind to at least one or more targets. This method allows for the screening of agents that act cooperatively to elicit a particular response. It may be advantageous to use such a screen when an agonistic activity requiring the cooperation of more than one scaffold is required (for example, but not limited to, agonism of a receptor belonging to the TNF receptor family). This method allows for the screening of cooperative agents without the reformatting of the library to form multimeric complexes. In one embodiment, the method of the invention comprises contacting a target ligand with a library of the invention under conditions that allow a scaffold:target ligand complex to form, engaging said scaffolds with a crosslinking agent (defined as an agent that brings together, in close proximity, at least two identical or distinct scaffolds) wherein the crosslinking of the scaffolds elicits a detectable response and obtaining from the complex, said scaffolds that bind the target. In a further embodiment, the crosslinking agent is a scaffold specific antibody, or fragment thereof, an epitope tag specific antibody of a fragment thereof, a dimerization domain, such as Fc region, a coiled coil motif (for example, but not limited to, a leucine zipper), a chemical crosslinker, or another dimerization domain known in the art.

The invention also provides methods of detecting a compound utilizing the scaffolds of the invention. Based on the binding specificities of the scaffolds obtained by library screening, it is possible to use such scaffolds in assays to detect the specific target in a sample, such as for diagnostic methods. In one embodiment, the method of detecting a compound comprises contacting said compound in a sample with a scaffold of the invention, under conditions that allow a compound:scaffold complex to form and detecting said scaffold, thereby detecting said compound in a sample. In farther embodiments, the scaffold is labeled (i.e., radiolabel, fluorescent, enzyme-linked or colorimetric label) to facilitate the detection of the compound.

The invention also provides methods of capturing a compound utilizing the scaffolds of the invention. Based on the binding specificities of the scaffolds obtained by library screening, it is possible to use such scaffolds in assays to capture the specific target in a sample, such as for purification methods. In one embodiment, the method of capturing a compound in a sample comprises contacting said compound in a sample with a scaffold of the invention under conditions that allow the formation of a compound:scaffold complex and removing said complex from the sample, thereby capturing said compound in said sample. In further embodiments, the scaffold is immobilized to facilitate the removing of the compound:scaffold complex.

In some embodiments, scaffolds isolated from libraries of the invention comprise at least one, at least two, at least four, at least five, at least six, or more randomized loops. In some embodiments, isolated scaffold loop sequences may be swapped from a donor scaffold to any loop in a receiver scaffold (for example, an FG loop sequence from a donor scaffold may be transferred to any loop in a receiver scaffold). In specific embodiments, an isolated loop sequences may be transferred to the cognate loop in the receiving scaffold (for example, an FG loop sequence from a donor scaffold may be transferred to a receiver scaffold in the FG loop position). In some embodiments, isolated loop sequences may be "mix and matched" randomly with various receiver scaffolds.

In other embodiments, isolated scaffolds sequences may be identified by the loop sequence. For example, a library is used to pan against a particular target and a collection of specific binders are isolated. The randomized loop sequences may be characterized as specific sequences independently of the scaffold background (i.e., the scaffold that binds target X wherein said scaffold comprises an FG loop sequence of SEQ ID NO:X). In alternative embodiments, where a scaffold exhibits two loop sequences that bind target X, the loop sequences may be characterized as binding target X in the absence of the scaffold sequence. In other words, it is contemplated that scaffolds isolated from a library that bind a particular target may be expressed as the variable loop sequences that bind that target independent of the scaffold backbone. This process would be analogous to the concept of CDRs in variable regions of antibodies.

Affinity Maturation

The development of TRAIL R2 Tn3 scaffolds may involve one or more in vitro or in vivo affinity maturation steps. Any affinity maturation approach can be employed that results in amino acid changes in a Tn3 domain or a Tn3 domain loops that improve the binding of the Tn3 scaffold to the desired antigen.

These amino acid changes can, for example, be achieved via random mutagenesis, "walk though" mutagenesis, and "look through" mutagenesis. Such mutagenesis can be achieved by using, for example, error-prone PCR, "mutator" strains of yeast or bacteria, incorporation of random or defined nucleic acid changes during ab initio synthesis of all or part of a FnIII-based binding molecule. Methods for performing affinity maturation and/or mutagenesis are described, for example, in U.S. Pat. Nos. 7,195,880; 6,951,725; 7,078,197; 7,022,479; 5,922,545; 5,830,721; 5,605,793, 5,830,650; 6,194,550; 6,699,658; 7,063,943; 5,866,344 and PCT Publication WO06023144.

Such affinity maturation methods may further require that the stringency of the antigen-binding screening assay is increased to select for Tn3 scaffolds with improved affinity for an antigen. Art recognized methods for increasing the stringency of a protein-protein interaction assay can be used here. In one embodiment, one or more of the assay conditions are varied (for example, the salt concentration of the assay buffer) to reduce the affinity of the Tn3 scaffold for the desired antigen. In another embodiment, the length of time permitted for the Tn3 scaffold to bind to the desired antigen is reduced.

In another embodiment, a competitive binding step can be added to the protein-protein interaction assay. For example, the Tn3 scaffold can be first allowed to bind to a desired immobilized antigen. A specific concentration of non-immobilized antigen is then added which serves to compete for binding with the immobilized antigen such that the Tn3 scaffolds with the lowest affinity for antigen are eluted from the immobilized antigen resulting in selection of Tn3 scaffolds with improved antigen binding affinity. The stringency of the assay conditions can be further increased by increasing the concentration of non-immobilized antigen is added to the assay.

Screening methods may also require multiple rounds of selection to enrich for one or more Tn3 scaffolds with improved antigen binding. In one embodiment, at each round of selection further amino acid mutations are introduce into the Tn3 scaffold. In another embodiment, at each round of selection the stringency of binding to the desired antigen is increased to select for Tn3 scaffolds with increased affinity for antigen.

In some embodiments, affinity maturation is performed by saturation mutagenesis of portions of the BC, DE, and FG loops of Tn3. In some embodiments, saturation mutagenesis is performed using Kunkel mutagenesis. In other embodiments, saturation mutagenesis is performed by using PCR.

In some embodiments, at least one, at least two, at least three, at least four, at least five, or more than five rounds of affinity maturation are applied. In some embodiments, saturation mutagenesis is applied to only one loop, whereas in some other embodiments, only one loop or a portion of a loop is mutated during one round of affinity maturation. In some embodiments, more than one loop or portions of one or more than loop are mutated during the same round of affinity maturation.

In other embodiments, the BC, DE, and FG loops mutated simultaneously during the same round of affinity maturation.

In the case of the Tn3 scaffolds to assemble into multimeric scaffolds binding to different epitopes of the same target or in the case of bispecific Tn3 scaffolds, each binding specificity can be screened independently. Accordingly, in some embodiments, a first screen to identify individual Tn3 binding molecules that bind to a first target, e.g. TRAIL R2, is performed using a first library of Tn3 scaffolds, where one or more amino acids in one or more loops is altered. In some embodiments, additional screens to identify individual Tn3 molecules that bind to a different target or to a different epitope of the same target can be performed.

In some embodiments, the loops are randomized using a phage display library. In some embodiments, the binding of a Tn3 scaffold to a desired target can be determined using methods recognized in the art. Also, the amino acid sequences of the Tn3 scaffolds identified in the screens can be determined using art recognized methods.

In some embodiments, the monomeric affinity matured scaffolds of the invention exhibit an increased in affinity for TRAIL R2 of at least 5-fold, at least 10-fold, at least 20-fold, at least 40-fold, at least 60-fold, at least 80-fold, or at least 100-fold or more compared to the same Tn3 scaffold prior to affinity maturation, as measured by Surface Plasmon Resonance or by other assays known in the art. In some embodiments, the monomeric affinity matured scaffolds of the invention have a dissociation constant ($K_d$) of less than 5 μM, less than 1 μM, less than 500 μM, less than 250 μM, less than 100 μM, or less than 50 μM, as measured by Surface Plasmon Resonance or by other assays known in the art.

These affinity maturation methods can be applied to develop Tn3 scaffolds with desirable improved binding properties such as increased affinity or other desirable characteristics, such as favorable pharmacokinetic properties, high potency, low immunogenicity, increased or decreased cross-reactivity with TRAIL R2 receptors from other organisms, etc.

Generation of Tandem Repeats

Linking of tandem constructs may be generated by ligation of oligonucleotides at restriction sites using restriction enzymes known in the art, including but not limited to type II and type IIS restriction enzymes.

The multimeric Tn3 scaffolds of the invention may comprise a linker at the C-terminus and/or the N-terminus and/or between domains as described herein. Further, scaffolds of the invention comprising at least 1, at least 2, at least 3, at least 4, at least 5, at least 6, at least 7, at least 8 or polypeptide scaffolds may be fused or conjugated to a dimerization domain, including but not limited to an antibody moiety selected from:

(i) a Fab fragment, having VL, CL, VH and CH1 domains;
(ii) a Fab' fragment, which is a Fab fragment having one or more cysteine residues at the C-terminus of the CH1 domain;
(iii) a Fd fragment having VH and CH1 domains;
(iv) a Fd' fragment having VH and CH1 domains and one or more cysteine residues at the C-terminus of the CH1 domain;
(v) a Fv fragment having the VL and VH domains of a single arm of an antibody;
(vi) a dAb fragment which consists of a VH domain;
(vii) isolated CDR regions;
(viii) F(ab')2 fragments, a bivalent fragment including two Fab' fragments linked by a disulfide bridge at the hinge region;
(ix) single chain antibody molecules (e.g., single chain Fv; scFv);
(x) a "diabody" with two antigen binding sites, comprising a heavy chain variable domain (VH) connected to a light chain variable domain (VL) in the same polypeptide chain;
(xi) a "linear antibody" comprising a pair of tandem Fd segments (VH-CH1-VH-CH1) which, together with complementary light chain polypeptides, form a pair of antigen binding regions;
(xii) a full length antibody; and
(xiii) an Fc region comprising CH2-CH3, which may further comprise all or a portion of a hinge region and/or a CH1 region. Various valency, affinity, and spatial orientation schemes are exemplified below in the Examples.

Scaffold Production

Recombinant expression of a scaffold of the invention requires construction of an expression vector containing a polynucleotide that encodes the scaffold. Once a polynucleotide encoding a scaffold has been obtained, the vector for the production of scaffold may be produced by recombinant DNA technology using techniques well known in the art. Thus, methods for preparing a protein by expressing a polynucleotide containing a scaffold encoding nucleotide sequence are described herein. Methods that are well known to those skilled in the art can be used to construct expression vectors containing scaffold polypeptide coding sequences and appropriate transcriptional and translational control signals. These methods include, for example, in vitro recombinant DNA techniques, synthetic techniques, and in vivo genetic recombination. The invention, thus, provides replicable vectors comprising a nucleotide sequence encoding a scaffold of the invention, operably linked to a promoter.

The expression vector is transferred to a host cell by conventional techniques and the transfected cells are then cultured by conventional techniques to produce a scaffold of the invention. Thus, the invention includes host cells containing a polynucleotide encoding a scaffold of the invention, operably linked to a heterologous promoter. Suitable host cells include, but are not limited to, microorganisms such as bacteria (e.g., *E. coli* and *B. subtilis*).

A variety of host-expression vector systems may be utilized to express the scaffolds of the invention. Such host-expression systems represent vehicles by which the coding sequences of interest may be produced and subsequently purified, but also represent cells which may, when transformed or transfected with the appropriate nucleotide coding sequences, express a scaffold of the invention in situ. These include but are not limited to microorganisms such as bacteria (e.g., *E. coli* and *B. subtilis*) transformed with recombinant bacteriophage DNA, plasmid DNA or cosmid DNA expression vectors containing scaffold coding sequences or mammalian cell systems (e.g., COS, CHO, BHK, 293, NSO, and 3T3 cells).

Methods useful for the production of scaffolds of the invention are disclosed, for example, in Publication No: WO 2009/058379. Once a scaffold of the invention has been produced by recombinant expression, it may be purified by any method known in the art for purification of a protein.

Production of the scaffolds of the invention in the research laboratory can be scaled up to produce scaffolds in analytical scale reactors or production scale reactors, as described in U.S. Patent Publication No. US 2010-0298541 A1.

Scalable Production of Secreted Scaffolds

The Tn3 scaffolds of the invention may be produced intracellularly or as a secreted form. In some embodiments, the secreted scaffolds are properly folded and fully functional. Tn3 scaffolds of the invention can be produced by a scalable process. In some embodiments, scaffolds may be produced by a scalable process of the invention in the research laboratory that may be scaled up to produce the scaffolds of the invention in analytical scale bioreactors (for example, but not limited to 5 L, 10 L, 15 L, 30 L, or 50 L bioreactors). In other embodiments, the Tn3 scaffolds may be produced by a scalable process of the invention in the research laboratory that may be scaled up to produce the Tn3 scaffolds of the invention in production scale bioreactors (for example, but not limited to 75 L, 100 L, 150 L, 300 L, or 500 L). In some embodiments, the scalable process of the invention results in little or no reduction in production efficiency as compared to the production process performed in the research laboratory.

Linkers

The Tn3 scaffolds in a multimeric scaffold can be connected by protein and/or nonprotein linkers, wherein each linker is fused to at least two Tn3 scaffolds of the invention. A suitable linker can consist of a protein linker, a nonprotein linker, and combinations thereof. Combinations of linkers can be homomeric or heteromeric. In some embodiments, a multimeric Tn3 scaffold of the invention comprises a plurality of monomer Tn3 scaffolds wherein are all the linkers are identical. In other embodiments, a multimeric Tn3 scaffold comprises a plurality of monomeric Tn3 scaffolds wherein at least one of the linkers is functionally or structurally different from the rest of the linkers. In some embodiments, linkers can themselves contribute to the activity of a multimeric FnIII scaffold by participating directly or indirectly in the binding to a target.

In some embodiments, the protein linker is a polypeptide. The linker polypeptide should have a length, which is adequate to link two or more monomer scaffolds of the invention or two or more multimeric scaffolds of the invention in such a way that they assume the correct conformation relative to one another so that they retain the desired activity.

In one embodiment, the polypeptide linker comprises 1 to about 1000 amino acids residues, 1 to about 50 amino acid residues, 1-25 amino acid residues, 1-20 amino acid residues, 1-15 amino acid residues, 1-10 amino acid residues, 1-5 amino acid residues, 1-3 amino acid residues. The invention further provides nucleic acids, such as DNA, RNA, or combinations of both, encoding the polypeptide linker sequence. The amino acid residues selected for inclusion in the polypeptide linker should exhibit properties that do not interfere significantly with the activity or function of the multimeric Tn3 scaffold of the invention. Thus, a polypeptide linker should on the whole not exhibit a charge which would be inconsistent with the activity or function of the multimeric scaffold of the invention, or interfere with internal folding, or form bonds or other interactions with amino acid residues in one or more of the Tn3 monomer domains which would seriously impede the binding of the multimeric scaffold of the invention to TRAIL R2.

The use of naturally occurring as well as artificial peptide linkers to connect polypeptides into novel linked fusion polypeptides is well known in the literature. Accordingly, the linkers fusing two or more scaffolds of the invention are natural linkers, artificial linkers, or combinations thereof. In some embodiments, the amino acid sequences of all peptide linkers present in a multimeric scaffold of the invention are identical. In other embodiments, the amino acid sequences of at least two of the peptide linkers present in a multimeric scaffold of the invention are different.

In some embodiments, a polypeptide linker possesses conformational flexibility. In a specific embodiment, a polypeptide linker sequence comprises a $(G-G-G-G-S)_x$ (SEQ ID NO: 210) amino acid sequence where x is a positive integer. In some embodiments, a polypeptide linker is an inherently unstructured natural or artificial polypeptide (see, e.g., Schellenberger et al., Nature Biotechnol. 27:1186-1190, 2009; see also, Sickmeier et al., Nucleic Acids Res. 35:D786-93, 2007).

The peptide linker can be modified in such a way that an amino acid residue comprising an attachment group for a non-polypeptide moiety is introduced. Examples of such amino acid residues may be a cysteine residue (to which the non-polypeptide moiety is then subsequently attached) or the amino acid sequence may include an in vivo N-glycosylation site (thereby attaching a sugar moiety (in vivo) to the peptide linker).

In some embodiments, the amino acid sequences of all peptide linkers present in the polypeptide multimer are identical. Alternatively, the amino acid sequences of all peptide linkers present in the polypeptide multimer may be different.

Labeling or Conjugation of Scaffolds

The scaffolds of the invention can be used in non-conjugated form or conjugated to at least one of a variety of heterologous moieties to facilitate target detection or for imaging or therapy. The scaffolds of the can be labeled or conjugated either before or after purification, when purification is performed.

Many heterologous moieties lack suitable functional groups to which scaffolds of the invention can be linked. Thus, in some embodiments, the effector molecule is attached to the scaffold through a linker, wherein the linker contains reactive groups for conjugation. In some embodiments, the heterologous moiety conjugated to a scaffold of the invention can function as a linker. In other embodiments, the moiety is conjugated to the scaffold via a linker that can be cleavable or non-cleavable. In one embodiment, the cleavable linking molecule is a redox cleavable linking molecule, such that the linking molecule is cleavable in environments with a lower redox potential, such as the cytoplasm and other regions with higher concentrations of molecules with free sulfhydryl groups. Examples of linking molecules that may be cleaved due to a change in redox potential include those containing disulfides.

In some embodiments, scaffolds of the invention are engineered to provide reactive groups for conjugation. In such scaffolds, the N-terminus and/or C-terminus can also serve to provide reactive groups for conjugation. In other embodiments, the N-terminus can be conjugated to one moiety (such as, but not limited to PEG) while the C-terminus is conjugated to another moiety (such as, but not limited to biotin), or vice versa.

The term "polyethylene glycol" or "PEG" means a polyethylene glycol compound or a derivative thereof, with or without coupling agents, coupling or activating moieties (e.g., with thiol, triflate, tresylate, aziridine, oxirane, N-hydroxysuccinimide or a maleimide moiety). The term "PEG" is intended to indicate polyethylene glycol of a molecular weight between 500 and 150,000 Da, including analogues thereof, wherein for instance the terminal OH-group has been replaced by a methoxy group (referred to as mPEG).

The scaffolds of the invention can be derivatized with polyethylene glycol (PEG). PEG is a linear, water-soluble polymer of ethylene oxide repeating units with two terminal hydroxyl groups. PEGs are classified by their molecular weights which typically range from about 500 daltons to about 40,000 daltons. In a specific embodiment, the PEGs employed have molecular weights ranging from 5,000 daltons to about 20,000 daltons. PEGs coupled to the scaffolds of the invention can be either branched or unbranched. See, for example, Monfardini, C. et al. 1995 Bioconjugate Chem 6:62-69. PEGs are commercially available from Nektar Inc., Sigma Chemical Co. and other companies. Such PEGs include, but are not limited to, monomethoxypolyethylene glycol (MePEG-OH), monomethoxypolyethylene glycol-succinate (MePEG-S), monomethoxypolyethylene glycol-succinimidyl succinate (MePEG-S-NHS), monomethoxypolyethylene glycol-amine (MePEG-NH2), monomethoxypolyethylene glycol-tresylate (MePEG-TRES), and monomethoxypolyethylene glycol-imidazolyl-carbonyl (MePEG-IM).

Briefly, the hydrophilic polymer which is employed, for example, PEG, is capped at one end by an unreactive group such as a methoxy or ethoxy group. Thereafter, the polymer is activated at the other end by reaction with a suitable activating agent, such as cyanuric halides (for example, cyanuric chloride, bromide or fluoride), carbonyldiimidazole, an anhydride reagent (for example, a dihalo succinic anhydride, such as dibromosuccinic anhydride), acyl azide, p-diazoniumbenzyl ether, 3-(p-diazoniumphenoxy)-2-hydroxypropylether) and the like. The activated polymer is then reacted with a polypeptide as described herein to produce a polypeptide derivatized with a polymer. Alternatively, a functional group in the scaffolds of the invention can be activated for reaction with the polymer, or the two groups can be joined in a concerted coupling reaction using known coupling methods. It will be readily appreciated that the polypeptides of the invention can be derivatized with PEG using a myriad of other reaction schemes known to and used by those of skill in the art. A PEG can be coupled to a scaffold of the invention at one or more functional groups at either end of the scaffold or within the scaffold. In certain embodiments, the PEG is coupled at either the N-terminus or the C-terminus.

In other embodiments, scaffolds of the invention, analogs or derivatives thereof may be conjugated to a diagnostic or detectable agent. Such scaffolds can be useful for monitoring or prognosing the development or progression of a disease as part of a clinical testing procedure, such as determining the efficacy of a particular therapy.

The present invention further encompasses uses of scaffolds conjugated to a therapeutic moiety. A scaffold may be conjugated to a therapeutic moiety such as a cytotoxin, e.g., a cytostatic or cytocidal agent, a therapeutic agent or a radioactive metal ion, e.g., alpha-emitters. A cytotoxin or cytotoxic agent includes any agent that is detrimental to cells.

Assaying Scaffolds

The binding affinity and other binding properties of a scaffold to an antigen may be determined by a variety of in vitro assay methods known in the art including for example, equilibrium methods (e.g., enzyme-linked immunoabsorbent assay (ELISA) or kinetics (e.g., BIACORE® analysis), and other methods such as indirect binding assays, competitive binding assays, gel electrophoresis and chromatography (e.g., gel filtration). These and other methods may utilize a label on one or more of the components being examined and/or employ a variety of detection methods including but not limited to chromogenic, fluorescent, luminescent, or isotopic labels. A detailed description of binding affinities and kinetics can be found in Paul, W. E., ed., Fundamental Immunology, 4th Ed., Lippincott-Raven, Philadelphia (1999).

In some embodiments, scaffolds of the invention specifically bind a target with specific kinetics. In some embodiments, scaffolds of the invention may have a dissociation constant or $K_d(k_{off}/k_{on})$ of less than $1\times10^{-2}$M, $1\times10^{-3}$M, $1\times10^{-4}$M, $1\times10^{-5}$M, $1\times10^{-6}$M, $1\times10^{-7}$M, $1\times10^{-8}$M, $1\times10^{-9}$M, $1\times10^{-10}$M, $1\times10^{-11}$M, $1\times10^{-12}$M, $1\times10^{-13}$M, $1\times10^{-14}$M or less than $1\times10^{-15}$M. In specific embodiments, scaffolds of the invention have a $K_d$ of 500 µM, 100 µM, 500 nM, 100 nM, 1 nM, 500 pM, 100 pM or less as determined by a BIAcore Assay® or by other assays known in the art. In an alternative embodiment, the affinity of the scaffolds of the invention is described in terms of the association constant ($K_a$), which is calculated as the ratio $k_{on}/k_{off}$, of at least $1\times10^2$M$^{-1}$, $1\times10^3$M$^{-1}$, $1\times10^4$M$^{-1}$, $1\times10^5$M$^{-1}$, $1\times10^6$M$^{-1}$, $1\times10^7$M$^{-1}$, $1\times10^8$M$^{-1}$, $1\times10^9$M$^{-1}$, $1\times10^{10}$M$^{-1}$ $1\times10^{11}$M$^{-1}$ $1\times10^{12}$M$^{-1}$, $1\times10^{13}$M$^{-1}$, $1\times10^{14}$M$^{-1}$, $1\times10^{15}$M$^{-1}$, or at least $5\times10^{15}$ M$^{-1}$. In certain embodiments the rate at which the scaffolds of the invention dissociate from a target epitope may be more relevant than the value of the $K_d$ or the $K_a$. In some embodiments, the scaffolds of the invention have a $k_{off}$ of less than $10^{-3}$ s$^{-1}$, less than $5\times10^{-3}$ s$^{-1}$, less than $10^{-4}$ s$^{-1}$, less than $5\times10^{-4}$ s$^{-1}$, less than $10^{-5}$ s$^{-1}$, less than $5\times10^{-5}$ s$^{-1}$, less than $10^{-6}$ s$^{-1}$, less than $5\times10^{-6}$ s$^{-1}$, less than $10^{-7}$ s$^{-1}$, less than $5\times10^{-7}$ s$^{-1}$, less than $10^{-8}$ s$^{-1}$, less than $5\times10^{-8}$ s$^{-1}$, less than $10^{-9}$ s$^{-1}$, less than $5\times10^{-9}$ s$^{-1}$, or less than $10^{-10}$ s$^{-1}$. In certain other embodiments, the rate at which the scaffolds of the invention associate with a target epitope may be more relevant than the value of the $K_d$ or the $K_a$. In this instance, the scaffolds of the invention bind to a target with a $k_{on}$ rate of at least $10^5 M^{-1}s^{-1}$, at least $5\times10^5 M^{-1}s^{-1}$, at least $10^6 M^{-1}s^{-1}$, at least $5\times10^6 M^{-1}s^{-1}$, at least $10^7 M^{-1}s^{-1}$, at least $5\times10^7 M^{-1}s^{-1}$, or at least $10^8 M^{-1}s^{-1}$, or at least $10^9 M^{-1}s^{-1}$.

Scaffolds of the invention may also be attached to solid supports, which are particularly useful for immunoassays or purification of the target antigen. Such solid supports include, but are not limited to, glass, cellulose, polyacrylamide, nylon, polystyrene, polyvinyl chloride or polypropylene.

TRAIL R2-specific Tn3 Scaffolds

The TRAIL R2 protein is encoded by a member of the TNF-receptor superfamily gene, and contains an intracellular death domain. In some instances, it may also be known as TNFRSFlOB; CD262, DR5, KILLER, KILLER/DR5, TRAILR2, TRICK2, TRICK2A, TRICK2B, TRICKB, or ZTNFR9. This receptor can be activated by tumor necrosis factor-related apoptosis inducing ligand (TNFSF 10/TRAIL/APO-2L), and transduces an apoptotic signal. Further, TRAIL R2 induced apoptosis involves caspases and the intracellular adapter molecule FADD/MORT1 (Walczak et al. EMBO J, (1997), 16, 5386-97).

The invention provides Tn3 scaffolds that specifically bind to TRAIL R2. In specific embodiments, scaffolds of the invention specifically bind to human TRAIL R2. In other specific embodiments, Tn3 scaffolds of the invention bind to TRAIL R2 homologs from mouse, chicken, Rhesus, cynomolgus, rat, or rabbit. In some embodiments, Tn3 scaffolds of the invention bind to an exposed epitope of TRAIL R2. Such embodiments include TRAIL R2 endogenously expressed on cells and/or cells transfected to ectopically express the receptor.

In other embodiments, Tn3 scaffolds of the invention recognize epitopes displayed on a monomeric TRAIL R2. In other embodiments, Tn3 scaffolds of the invention recognize epitopes displayed on a homodimeric form of TRAIL R2. In yet other embodiments, Tn3 scaffolds of the invention bind monomeric TRAIL R2 and facilitate dimerization or oligomerization of 2 or more TRAIL R2 molecules (for example, but not limited to multimeric scaffolds). In yet other embodiments, scaffolds of the invention reduce or inhibit interaction of TRAIL R2 with TRAIL ligand. In other embodiments, scaffolds of the invention mimic the interaction of TRAIL ligand with TRAIL R2. In further embodiments, Tn3 scaffolds of the invention agonize cellular signaling by TRAIL-R2.

The invention also provides methods of modulating TRAIL R2 activity using the Tn3 scaffolds described herein. In some embodiments, methods of the invention comprise contacting a cell expressing TRAIL R2 with TRAIL R2 specific scaffolds and blocking interaction with TRAIL ligand. In other embodiments, methods of the invention comprise contacting a cell expressing TRAIL R2 with a TRAIL R2-specific Tn3 scaffold and mimicking the interaction of TRAIL ligand with TRAIL R2.

In other embodiments, methods of the invention comprise agonizing TRAIL R2 by contacting with a TRAIL R2-specific Tn3 scaffold. In other embodiments, methods of the invention comprise dimerizing or oligomerizing TRAIL R2 by contacting a monomer of TRAIL R2 expressed on cells with a TRAIL R2 specific scaffold and facilitating dimerization or oligomerization. In further embodiments, dimerization of TRAIL R2 may be achieved through the use of, for example, but not limited to, multimeric Tn3 scaffolds that: mimic TRAIL R2 dimers, stabilize TRAIL R2 dimer formation, destabilize TRAIL R2 monomers, or only recognize TRAIL R2 dimers displayed on cells.

In other embodiments, dimerization or oligomerization of TRAIL R2 may be achieved through the use of monomeric Tn3 scaffolds coupled with a scaffold dimerization or oligomerization agents. Such scaffolds dimerization or oligomerization agents may include, for example, but not limited to, an anti-scaffold antibody, use of scaffolds with epitope tags coupled with antibodies to epitope tag, or the incorporation of various protein dimerization or oligomerization motifs described herein and known in the art. In a further embodiment, TRAIL R2 dimers or oligomers may be induced by the administration of monomeric scaffolds followed by the administration of a scaffold dimerization or oligomerization agent.

In some embodiments, methods of the invention comprise the administration of a TRAIL R2 specific scaffold that reduces cell viability as measured by routine assays known in the art. In further embodiments, the reduction in cell viability is activation of apoptosis as measured by known assays in the art. In other embodiments, reduction in cell viability is the inhibition of cell division as measured by art accepted methods. In some embodiments, cell viability is reduced by at least 10%, at least 20%, at least 30%, at least 40%, at least 50%, at least 60%, at least 70%, at least 80%, at least 90%, or more as compared to cell viability in the absence of treatment.

In some embodiments, TRAIL R2-binding Tn3 scaffolds of the invention agonize TRAIL R2 with similar activity as the ligand for TRAIL R2, known as TRAIL. In other embodiments, TRAIL R2-binding Tn3 scaffolds of the invention are capable of sufficiently activating TRAIL R2 to result in the activation of one or more intracellular signaling pathways, including the activation of caspase 3, caspase 8, caspase 10, or FADD. In other embodiments, TRAIL R2-binding Tn3 scaffolds of the invention activate apoptosis in at least one cancer cell type. In further embodiments, TRAIL R2-binding Tn3 scaffolds of the invention demonstrate an enhanced activation of apoptosis in at least one cell type as compared to TRAIL.

In other embodiments, the TRAIL R2-binding Tn3 scaffolds of the invention may bind or compete with binding for the same epitope on TRAIL R2 as TRAIL (ligand). In such embodiments, the TRAIL R2 binding scaffolds are capable of blocking or inhibiting the interaction of TRAIL R2 with TRAIL by at least 50%, at least 60%, at least 70%, at least 80%, at least 90%, or more which may be determined in an in vitro competitive assay using the soluble TRAIL ligand (such as the 114-281 fragment of TRAIL ligand), crystallographic studies, or other known in vivo or in vitro studies.

Methods of Using Tn3 TRAIL R2-Specific Scaffolds in Therapy

TRAIL R2 is known to mediate apoptosis signaling. Although several types of normal cells express TRAIL R2, apoptosis signaling through this receptor appears to be restricted primarily to tumor cells, which become more susceptible to death receptor-mediated apoptosis in the context of their transformation by oncogenes such as Myc or Ras (Wang et al., Cancer Cell 5:501-12 (2004); Nesterov et al., Cancer Res. 64:3922-7 (2004)). TRAIL R2 is frequently expressed by human cancer cell lines as well as primary tumors.

In some embodiments, TRAIL R2 specific scaffolds of the invention are administered to a subject in need of treatment (i.e., a patient with cancer). In such embodiments, a sterile, pyrogen-free composition comprising a TRAIL R2 specific scaffold is administered to a subject in need thereof. The efficiency of treatment may be measured using a variety of in vitro and in vivo assays well known in the art, such as, but not limited to apoptotic activity, using caspases activation of Annexin V binding, as well as a reduction in tumor burden or volume.

In other embodiments, TRAIL R2 specific scaffolds of the invention are useful for the diagnosis and detection of cancer or other TRAIL R2 associated diseases. In such embodiments, TRAIL R2 specific scaffolds of the invention are linked to a detection agent, such as, but not limited to a radioisotope, fluorescent or chemiluminescent label. Such linked binders are useful in methods that detect or diagnose cancer or TRAIL R2 associated diseases in a subject, or a sample taken from said subject. In addition, TRAIL R2 specific scaffolds are useful in the diagnosis and treatment of other TRAIL R2 associated pathological conditions, such as immune-related diseases in mammals, including humans.

Specific TRAIL R2 Binding Sequences

In some embodiments TRAIL R2 specific Tn3 monomer scaffolds of the invention comprise at least one, at least two, at least three, at least four, at least five, or at least six loop sequences that bind to TRAIL R2.

In some embodiments, TRAIL R2 specific Tn3 scaffolds comprise at least one, at least two, at least three, at least four, at least five, or at least six loop sequences of TRAIL R2 binding monomer scaffold clones selected from: 1C12 (SEQ ID NO: 132), G3 (SEQ ID NO: 133), 1E11 (SEQ ID NO: 134), C4 (SEQ ID NO: 135), C11 (SEQ ID NO: 136), F4 (SEQ ID NO: 137), and G6 (SEQ ID NO: 138).

In some embodiments, TRAIL R2 specific Tn3 monomer scaffolds comprise at least one loop sequence selected from the loop sequences listed in TABLE 4. In other embodiments, TRAIL R2 specific monomer scaffolds comprise at least one BC loop sequence selected from the BC loop sequences listed in TABLE 4. In other embodiments, TRAIL R2 specific monomer scaffolds comprise at least one DE loop sequence selected from the DE loop sequences listed in TABLE 4. In other embodiments, TRAIL R2 specific monomer scaffolds comprise at least one FG loop sequence selected from the FG loop sequences listed in TABLE 4.

In some embodiments, TRAIL R2 specific Tn3 monomer scaffolds comprise a BC loop sequence selected from the BC loop sequences listed in TABLE 4; and a DE loop sequence selected from the DE loop sequences listed in TABLE 4. In other embodiments, TRAIL R2 specific monomer scaffolds comprise a BC loop sequence selected from the BC loop sequences listed in TABLE 4; and an FG loop sequence selected from the FG loop sequences listed in TABLE 4. In other embodiments, TRAIL R2 specific scaffolds comprise a DE loop sequence selected from the DE loop sequences listed in TABLE 4; and an FG loop sequence selected from the FG loop sequences listed in TABLE 4. In some embodiments, a TRAIL R2 specific Tn3 monomer scaffold comprises loop sequences corresponding to loop sequences from one, two or three different Tn3 clones.

In some embodiments, the TRAIL R2 specific Tn3 multimeric scaffolds are linear multimers, e.g., dimers such as the 1E11 tandem 2 scaffold of SEQ ID NO: 139, tetramers such as the 1E11 tandem 4 scaffold of SEQ ID NO: 140 or the G6 tandem 4 scaffold of SEQ ID NO: 143, hexamers such as the 1E11 tandem 6 scaffold of SEQ ID NO: 141, the G6 tandem 6 scaffold of SEQ ID NO: 144 or the F4 mod 12 tandem 6 of SEQ ID NO: 167, or octamers such as the 1E11 tandem 8 scaffold of SEQ ID NO: 142, the G6 tandem 8 scaffold of SEQ ID NO: 145, or the F4 mod 12 tandem 8 scaffold of SEQ ID NO: 166.

In some embodiments, the TRAIL R2 specific Tn3 multimeric scaffolds are Fc fusions, e.g., the 1C12 Fc fusion of SEQ ID NO: 149, the G3 Fc fusion of SEQ ID NO: 150, the 1E11 Fc fusion of SEQ ID NO: 151, the C4 Fc fusion of SEQ ID NO: 152, or the G6 Fc fusion of SEQ ID NO: 153.

In some embodiments, the TRAIL R2 specific Tn3 multimeric scaffolds are antibody-like fusions, e.g., the scaffold resulting from the association of the 1C12 IgG1 heavy chain constant region scaffold of SEQ ID NO: 154 with the 1C12 kappa light chain scaffold of SEQ ID NO: 155, the scaffold resulting from the association of the G3 IgG1 heavy chain scaffold of SEQ ID NO: 156 with the G3 kappa light chain scaffold of SEQ ID NO: 157, the scaffold resulting from the association of the 1E11 IgG1 heavy chain scaffold of SEQ ID NO: 158 with the 1E11 kappa light chain scaffold of SEQ ID NO: 159, the scaffold resulting from the association of the C4 IgG1 heavy chain scaffold of SEQ ID NO: 160 with the C4 kappa light chain scaffold of SEQ ID NO: 161, or the scaffold resulting from the association of the G6 IgG1 heavy chain scaffold of SEQ ID NO: 162 with the G6 kappa light chain scaffold of SEQ ID NO: 163.

In some embodiments, the TRAIL R2 specific Tn3 multimeric scaffold combine a Fc fusion format with a linear format, e.g., the 1E11 tandem 2 Fc fusion of SEQ ID NO: 164, or the 1E11 tandem 4 Fc fusion of SEQ ID NO: 165.

In certain embodiments, where the TRAIL R2 specific Tn3 multimeric scaffold sequence contains a linker and/or a Histidine tag at the C-terminus of the sequence, this C-terminal linker and/or Histidine tag can be removed, the corresponding amino acid sequence thus containing a deletion of the C-terminal linker and His tag sequences.

In some embodiments, TRAIL R2 specific Tn3 multimeric scaffolds are conjugated to PEG. In specific embodiments, the F4 mod 12 tandem 6 (SEQ ID NO: 167) or the F4 mod 12 tandem 8 (SEQ ID NO: 166) scaffolds are conjugated to PEG. In further embodiments, the PEG is conjugated at either the N-terminus or the C-terminus of the multimeric scaffold molecule.

Pharmaceutical Compositions

In another aspect, the present invention provides a composition, for example, but not limited to, a pharmaceutical composition, containing one or a combination of scaffolds or multimeric scaffolds of the present invention, formulated together with a pharmaceutically acceptable carrier. Such compositions may include one or a combination of, for example, but not limited to two or more different scaffolds of the invention. For example, a pharmaceutical composition of the invention may comprise a combination of scaffolds that bind to different epitopes on the target antigen or that have complementary activities. In a specific embodiment, a pharmaceutical composition comprises a multimeric scaffold of the invention.

Pharmaceutical compositions of the invention also can be administered in combination therapy, such as, combined with other agents. For example, the combination therapy can include a scaffold of the present invention combined with at least one other therapy wherein the therapy may be immunotherapy, chemotherapy, radiation treatment, or drug therapy. The pharmaceutical compounds of the invention may include one or more pharmaceutically acceptable salts.

Pharmaceutical Dosing and Administration

To prepare pharmaceutical or sterile compositions including a Tn3 scaffold of the invention, a scaffold is mixed with a pharmaceutically acceptable carrier or excipient. Selecting an administration regimen for a therapeutic depends on several factors, including the serum or tissue turnover rate of the entity, the level of symptoms, the immunogenicity of the entity, and the accessibility of the target cells in the biological matrix. In certain embodiments, an administration regimen maximizes the amount of therapeutic delivered to the patient consistent with an acceptable level of side effects. Actual dosage levels of the active ingredients in the pharmaceutical compositions of the present invention may be varied so as to obtain an amount of the active ingredient which is effective to achieve the desired therapeutic response for a particular patient, composition, and mode of administration, without being toxic to the patient. The selected dosage level will depend upon a variety of pharmacokinetic factors including the activity of the particular compositions of the present invention employed, or the ester, salt or amide thereof, the route of administration, the time of administration, the rate of excretion of the particular compound being employed, the duration of the treatment, other drugs, compounds and/or materials used in combination with the particular compositions employed, the age, sex, weight, condition, general health and prior medical history of the patient being treated, and like factors well known in the medical arts.

A composition of the present invention may also be administered via one or more routes of administration using one or more of a variety of methods known in the art. In certain embodiments, the Tn3 scaffolds of the invention can be formulated to ensure proper distribution in vivo.

Methods of Using Scaffolds

The Tn3 scaffolds of the present invention have in vitro and in vivo diagnostic and therapeutic utilities. For example, these molecules can be administered to cells in culture, e.g. in vitro or ex vivo, or in a subject, e.g., in vivo, to treat, prevent or diagnose a variety of disorders.

Also, many cell surface receptors activate or deactivate as a consequence of cross-linking of sub units. The Tn3 scaffolds of the invention may be used to stimulate or inhibit a response in a target cell by cross-linking of cell surface receptors such as TRAIL R2. In another embodiment, the scaffolds of the invention of the invention may be used to block the interaction of multiple cell surface receptors with antigens. In another embodiment, the Tn3 scaffolds of the invention may be used to strengthen the interaction of multiple cell surface receptors with antigens. In another embodiment, it may be possible to crosslink homo- or heterodimers of a cell surface receptor using the Tn3 scaffolds of the invention containing binding domains that share specificity for the same antigen, or bind two different antigens. In another embodiment, the Tn3 scaffolds of the invention could be used to deliver a ligand, or ligand analogue to a specific cell surface receptor.

The invention also provides methods of targeting epitopes not easily accomplished with traditional antibodies. For example, in one embodiment, the Tn3 scaffolds and of the invention may be used to first target an adjacent antigen and while binding, another binding domain may engage the cryptic antigen.

The invention also provides methods of using the Tn3 scaffolds of the invention to bring together distinct cell types. In one embodiment, the scaffolds of the invention may bind a target cell with one binding domain and recruit another cell via another binding domain. In another embodiment, the first cell may be a cancer cell and the second cell is an immune effector cell such as an NK cell. In another embodiment, the Tn3 scaffolds of the invention may be used to strengthen the interaction between two distinct cells, such as an antigen presenting cell and a T cell to possibly boost the immune response.

The invention also provides methods of using the Tn3 scaffolds to ameliorate, treat, or prevent cancer or symptoms thereof. In one embodiment, the invention provides a method of using the Tn3 scaffolds of the invention to deplete TRAIL resistant cell populations. In this respect, Tn3 scaffolds of the invention can be used to treat some types of therapy resistant cancers.

The invention also provides methods of using Tn3 scaffolds to deplete a cell population. In one embodiment, methods of the invention are useful in the depletion of the following cell types: eosinophil, basophil, neutrophil, T cell, B cell, mast cell, monocytes and tumor cell. The invention also provides methods of using scaffolds to inactivate, inhibit, or deplete cytokines. The invention also provides methods of using Tn3 scaffolds proteins as diagnostic reagents. In this respect, in some embodiments the binding of the Tn3 scaffolds of the invention to TRAIL R2 receptors can be used diagnostically to detect cells expressing TRAIL R2. In other embodiments, the ability of the Tn3 scaffolds of the invention to differentiate between cell populations resistant to TRAIL but sensitive to TRAIL mimetics, and cell populations resistant to TRAIL and also to TRAIL mimetics (see, e.g., Example 19) can be used for diagnostic purposes. The Tn3 scaffolds of the invention may be useful in kits or reagents where different antigens need to be efficiently captured concurrently. It is also contemplated that cancers caused by aberrations in apoptosis can also be treated by the methods and compositions of the invention.

In another embodiment, the invention provides methods for preventing, managing, treating or ameliorating cancer. TRAIL R2 specific multimeric Tn3 scaffold can be used to treat cancer, e.g., lung cancer, non-Hodgkin's lymphoma, ovarian cancer, colon cancer, colorectal cancer, pancreatic cancer, and multiple myeloma. Treatment of cancer with TRAIL R2 specific multimeric Tn3 can further comprise an additional therapy, such as immunotherapy, biological therapy, chemotherapy, radiation therapy, or small molecule drug therapy.

Methods to treat cancer can comprise the administering to a subject in need thereof a dose of a prophylactically or therapeutically effective amount of one or more Tn3 scaffolds of the invention in combination with surgery, alone or in further combination with the administration of a standard or experimental chemotherapy, a hormonal therapy, a biological therapy/immunotherapy and/or a radiation therapy. In accordance with these embodiments, the Tn3 scaffolds of the invention utilized to prevent, manage, treat or ameliorate cancer, autoimmune, inflammatory or infectious diseases or one or more symptoms or one or more symptoms thereof may or may not be conjugated or fused to a moiety (e.g., therapeutic agent or drug).

EQUIVALENTS

Those skilled in the art will recognize, or be able to ascertain using no more than routine experimentation, many equivalents to the specific embodiments of the invention described herein. Such equivalents are intended to be encompassed by the following claims.

All publications, patents and patent applications mentioned in this specification are herein incorporated by reference into the specification to the same extent as if each individual publication, patent or patent application was specifically and individually indicated to be incorporated herein by reference. This application claims the benefit of priority to U.S. Provisional Patent Application No. 61/323,708, filed Apr. 13, 2010, the entire contents of which are incorporated herein by reference. Additionally, PCT Application No. PCT/US2008/012398, filed on Oct. 10, 2008 and published as International Publication No. WO 2009/058379 A2 is hereby incorporated by reference in its entirety for all purposes.

TABLE 1

Sequences and SEQ ID Nos of molecular components to assemble representative scaffolds of the invention:

| Name/Brief Description | Sequence | SEQ ID NO |
|---|---|---|
| Tn3 | IEVKDVTDTTALITWFKPLAEIDGCELTYGIKDVPGDRTTIDLTEDENQY SIGNLKPDTEYEVSLICRRGDMSSNPAKETFTT (cys residues of disulfide bond are underlined) | 1 |
| SS3 | IEVKDVTDTTALITWFKPLAEIDGIELTYGIKDVPGDRTTIDLTEDENQYS IGNLKPDTEYCVSLISRRGDMSSNPAKECFTT (cys residues of disulfide bond are underlined) | 2 |
| Tn3 + SS3 | IEVKDVTDTTALITWFKPLAEIDGCELTYGIKDVPGDRTTIDLTEDENQY SIGNLKPDTEYCVSLICRRGDMSSNPAKECFTT (cys residues of disulfide bonds are underlined) | 3 |
| 3rd FnIII of tenascin C (w/N-term aa) | RLDAPSQIEVKDVTDTTALITWFKPLAEIDGIELTYGIKDVPGDRTTIDLT EDENQYSIGNLKPDTEYEVSLISRRGDMSSNPAKETFTT (underlined A beta strand residues may be removed) | 4 |
| 10th FnIII of fibronectin | LEVVAATPTSLLISWDAPAVTVRYYRITYGETGGNSPVQEFTVPGSKST ATISGLKPGVDYTITVYAVTGRGDSPASSKPISINYRT | 5 |
| 3rd FnIII of fibronectin | PTVDQVDDTSIVVRWSRPQAPITGYRIVYSPSVEGSSTELNLPETANSVT LSDLQPGVQYNITIYAVEENQESTPVVIQQET | 6 |
| 6th FnIII of fibronectin | PYNTEVTETTIVITWTPAPRIGFKLGVRPSQGGEAPREVTSDSGSIVVSGL TPGVEYVYTIQVLRDGQERDAPIVNKVVT | 7 |
| FnIII from growth hormone R | PPIALNWTLLNVSLTGIHADIQVRWEAPRNADIQKGWMVLEYELQYKE VNETKWKMMDPILTTSVPVYSLKVDKEYEVRVRSKQRNSGNYGEFSE VLYVTLP | 8 |
| FnIII from β common R | PPSLNVTKDGDSYSLRWETMKMRYEHIDHTFEIQYRKDTATWKDSKTE TLQNAHSMALPALEPSTRYWARVRVRTSRTGYNGIWSEWSEARSWDT E | 9 |
| FnIII from IL-5R | PPVNFTIKVTGLAQVLLQWKPNPDQEQRNVNLEYQVKINAPKEDDYET RITESKIVTILHKGFSASVRTILQNDHSLLASSWASAELHA | 10 |
| 29th FnIII from Tenascin XB | LSVTDVTTSSLRLNWEAPPGAFDSFLLRFGVPSPSTLEPHPRPLLQRELM VPGTRHSAVLRDLRSGTLYSLTLYGLRGPHKADSIQGTART | 11 |
| 31st FnIII from Tenascin XB | LRALNLTEGFAVLHWKPPQNPVDTYDIQVTAPGAPPLQAETPGSAVDY PLHDLVLHTNYTATVRGLRGPNLTSPASITFTT | 12 |
| 32nd FnIII from Tenascin XB | LEAKEVTPRTALLTWTEPPVRPAGYLLSFHTPGGQTQEILLPGGITSHQL LGLFPSTSYNARLQAMWGQSLLPPVSTSFTT | 13 |
| Truncated 3rd FnIII of tenascin C | IEVKDVTDTTALITWFKPLAEIDGIELTYGIKDVPGDRTTIDLTEDENQYS IGNLKPDTEYEVSLISRRGDMSSNPAKETFTT | 14 |
| FnIII - growth hormone R | PKFTKCRSPERETFSCHWTDEVHHGTKNLGPIQLFYTRRNTQEWTQEW KECPDYVSAGENSCYFNSSFTSIWIPYCIKLTSNGGTVDEKCFSV | 15 |
| FnIII from PTPR-F | PSGFPQNLHVTGLTTSTTELAWDPPVLAERNGRIISYTVVFRDINSQQEL QNITTDTRFTLTGLKPDTTYDIKVRAWTSKGSGPLSPSIQSRTMPVE | 16 |
| FnIII from PTPR-F | PKPPIDLVVTETTATSVTLTWDSGNSEPVTYYGIQYRAAGTEGPFQEVD GVATTRYSIGGLSPFSEYAFRVLAVNSIGRGPPSEAVARTGE | 17 |
| FnIII from collagen type XIV | LSPPRNLRISNVGSNSARLTWDPTSRQINGYRIVYNNADGTEINEVEVDP ITTFPLKGLTPLTEYTIAIFSIYDEGQSEPLTGVFTT | 18 |
| 3rd FnIII of tenascin C - charge variant | IEVKDVTDTTALITWFKPLAEIDGIQLTYGIKDVPGDRTTINLTEDENQYS IGNLKPDTEYEVSLISRRGDMSSNPAKQTFTT | 19 |
| Archaeoglobus fulgidus DSM 4304 NCBI Acc. #: NC_000917 | PAISNVRVSDVTNSSATIRWDVSLAANNRVLFSTNSDLSSPQWSAWDNS TDSPMITLSGLSAGTAYYFSVYSFRPDNASLYSNSSIMSFTT | 20 |

TABLE 1-continued

Sequences and SEQ ID Nos of molecular components to assemble representative scaffolds of the invention:

| Name/Brief Description | Sequence | SEQ ID NO |
|---|---|---|
| *Staphylothermus marinus* F1<br>NCBI Acc. #:<br>NC_009033 | SEPQNLKATAGNNNITLTWDPPIDDGGCRIVEYRIVRGTNNNNLEVYAS<br>VNGSTTTFIDKNIVYSQTYYYKVSAVNNIVEGPKSNTASATPTSS | 21 |
| *Sulfolobus acidocaldarius* DSM 639<br>NCBI Acc. #:<br>NC_007181<br>1st FnIII | PPPKPVIRFAQAGNNSISLSWYDTNTSGYYIQWWSSIDNNKSTINVGNVS<br>SYLFINLTNGVTYYFRIIPYNQAGNGTSSDIISLTPGAV | 22 |
| *Sulfolobus acidocaldarius* DSM 639<br>NCBI Acc. #:<br>NC_007181<br>2nd FnIII | PDSPSVKVIVGDRNATVIWSKPYNGGFPILGYYLTVKTDNSSYTINVGN<br>VSKYTLTNLTPEVLYEVMVVAYNKLGNSSPGIVNFVALTT | 23 |
| *Sulfolobus acidocaldarius* DSM 639<br>NCBI Acc. #:<br>NC_007181<br>3rd FnIII | LTTASISVSVYKKVNGVLISWNKTENTTYNLLISDKKGKIIVNITTTNTSY<br>FAYIPYGIYNVTIRATNQVGTNSTSFPIVFYIPPFI | 24 |
| *Sulfolobus acidocaldarius* DSM 639<br>NCBI Acc. #:<br>NC_007181<br>4th FnIII | PLVKFSIGNNSILNLKWNNVTGATFYLVYVNTTLIANVTTDSYSLNLTP<br>GFHVIRVVAANPIYNSSPASLGILIQQHSVTSSIT | 25 |
| *Sulfolobus solfataricus* P2<br>NCBI Acc. #:<br>NC_002754<br>1st FnIII | PLPPKITSYSAGNESVTLGWNPVRLSSGYEIIYWNNMGFNSSINVGNVTS<br>YTVTGLKDGITYYFEVLAYNSIGYSSPSSILALTPASV | 26 |
| *Sulfolobus solfataricus* P2<br>NCBI Acc. #:<br>NC_002754<br>2nd FnIII | PNPPQLVSVKYGNDNVTLNWLPPTFSGGYLLLGYYVIVKNENSMVSSH<br>FVNSTSLTISNLTPNVTYNVFIYAVNKLGNSSPLVLTVVPITKA | 27 |
| *Sulfolobus solfataricus* P2<br>NCBI Acc. #:<br>NC_002754<br>3rd FnIII | PITKASVFAFITKLGNGILVNWTTSFPANITLELYNPNGNLISQIAAIKGNS<br>SYLFRVPQGNYTLVIIASNSAGVSKYVYQVVYYL | 28 |
| *Sulfolobus solfataricus* P2<br>NCBI Acc. #:<br>NC_002754<br>4th FnIII | PPASPQVSLIGFGNNLYISWNNEANVITYLVYVNNSLVYEGPSNSIVTNI<br>SNGTYLVKVIGVNPAGSSSPGIAVIHYTGDYVT | 29 |
| *Sulfolobus tokodaii* str. 7<br>NCBI Acc. #:<br>NC_003106<br>1st FnIII | PPKPQIASIASGNETITVKWYDTNASGYYITYWSNFSQKVTINVGNVTSY<br>TIKHLKDGVTYYIQIVPYNSLGNGTPSDIISATPSSV | 30 |
| *Sulfolobus tokodaii* str. 7<br>NCBI Arc. #:<br>NC_003106<br>2nd FnIII | PNPPIIKVKIGNLNATLTWYDTFNGGYPIEGYYLYVNGKGINVGNITSYV<br>LTNLTAGELYTIELIAYNKIGNSSISSVSFIAASKA | 31 |

TABLE 1-continued

Sequences and SEQ ID Nos of molecular components to assemble representative scaffolds of the invention:

| Name/Brief Description | Sequence | SEQ ID NO |
|---|---|---|
| *Sulfolobus tokodaii* str. 7 NCBI Acc. #: NC_003106 3rd FnIII | ASKANLTVTVYKKINGFLVSWNSTSKAKYILTVSKENVVLLNVSTTNTS YFVKVPFGVYNISLEAVNIVGITKYAFILIYYIQ | 32 |
| *Sulfolobus tokodaii* str. 7 NCBI Acc. #: NC_003106 4th FnIII | PASPTVNWSITLNTVSLNWSKVSGAEYYLIYDNGKLITNTTNTAFTFNL TIGQNEIEVYAANAYYKSAPYIINDVANYIVV | 33 |
| 14th FnIII of fibronectin | ARVTDATETTITISWRTKTETITGFQVDAVPANGQTPIQRTIKPDVRSYTITG LQPGTDYKIYLYTLNDNARSSPVVIDAST | 34 |
| 3rd FnIII of tenascin C, AB loop | KDVTDTT | 35 |
| 3rd FnIII of tenascin C, BC loop | FKPLAEIDG | 36 |
| 3rd FnIII of tenascin C, CD loop | KDVPGDR | 37 |
| 3rd FnIII of tenascin C, DE loop | TEDENQ | 38 |
| 3rd FnIII of tenascin C, EF loop | GNLKPDTE | 39 |
| 3rd FnIII of tenascin C, FG loop | RRGDMSSNPA | 40 |
| 3rd FnIII of tenascin C, beta strand A | RLDAPSQIEV | 41 |
| 3rd FnIII of tenascin C, beta strand A N-terminal truncation | IEV | 42 |
| 3rd FnIII of tenascin C, beta strand B | ALITW | 43 |
| 3rd FnIII of tenascin C, beta strand C | IELTYGI | 44 |
| 3rd FnIII of tenascin C, beta strand C (Tn3) | CELTYGI | 45 |
| 3rd FnIII of tenascin C, beta strand D | TTIDL | 46 |
| 3rd FnIII of tenascin C, beta strand E | YSI | 47 |
| 3rd FnIII of tenascin C, beta strand F | YEVSLIS | 48 |

TABLE 1-continued

Sequences and SEQ ID Nos of molecular components to assemble representative scaffolds of the invention:

| Name/Brief Description | Sequence | SEQ ID NO |
|---|---|---|
| 3rd FnIII of tenascin C, beta strand F (Tn3) | YEVSLIC | 49 |
| 3rd FnIII of tenascin C, beta strand F (SS3) | YCVSLIS | 50 |
| 3rd FnIII of tenascin C, beta strand F (Tn3 + SS3) | YCVSLIC | 51 |
| 3rd FnIII of tenascin C, beta strand G | KETFTT | 52 |
| 3rd FnIII of tenascin C, beta strand G (SS3 & Tn3 + SS3) | KECFTT | 53 |
| WT 10FnIII of fibronectin (w/N-term aa) | <u>VSDVPRDLEV</u>VAATPTSLLISWDAPAVTVRYYRITYGETGGNSPVQEFT VPGSKSTATISGLKPGVDYTITVYAVTGRGDSPASSKPISINYRT (underlined A beta strand residues may be removed) | 54 |
| WT 10FnIII of fibronectin, AB loop | VAATPTS | 55 |
| WT 10FnIII of fibronectin, BC loop | DAPAVTVRY | 56 |
| WT 10FnIII of fibronectin, CD loop | TGGNSPV | 57 |
| WT 10FnIII of fibronectin, DE loop | PGSKST | 58 |
| WT 10FnIII of fibronectin, EF loop | SGLKPGVD | 59 |
| WT 10FnIII of fibronectin, FG loop | VTGRGDSPASSKPI | 60 |
| WT 10FnIII of fibronectin, beta strand A | VSDVPRDLEV | 61 |
| WT 10FnIII of fibronectin, beta strand A N-terminal truncation | LEV | 62 |
| WT 10FnIII of fibronectin, beta strand B | LLISW | 63 |
| WT 10FnIII of fibronectin, beta strand C | YRITYGE | 64 |

TABLE 1-continued

Sequences and SEQ ID Nos of molecular components to assemble representative scaffolds of the invention:

| Name/Brief Description | Sequence | SEQ ID NO |
|---|---|---|
| WT 10FnIII of fibronectin, beta strand D | QEFTV | 65 |
| WT 10FnIII of fibronectin, beta strand E | ATI | 66 |
| WT 10FnIII of fibronectin, beta strand F | YTITVYA | 67 |
| WT 10FnIII of fibronectin, beta strand G | SINYRT | 68 |
| WT 14FnIII of fibronectin, (w/N-term aa) | VSPPRRARVTDATETTITISWRTKTETITGFQVDAVPANGQTPIQRTIKPD VRSYTITGLQPGTDYKIYLYTLNDNARSSPVVIDAST (underlined A beta strand residues may be removed) | 69 |
| WT 14FnIII of fibronectin, AB loop | TDATETT | 70 |
| WT 14FnIII of fibronectin, BC loop | RTKTETITG | 71 |
| WT 14FnIII of fibronectin, CD loop | ANGQTP | 72 |
| WT 14FnIII of fibronectin, DE loop | KPDVRS | 73 |
| WT 14FnIII of fibronectin, EF loop | TGLQPGTD | 74 |
| WT 14FnIII of fibronectin, FG loop | LNDNARSSPV | 75 |
| WT 14FnIII of fibronectin, Beta strand A | SPPRRARV | 76 |
| WT 14FnIII of fibronectin, Beta strand A N-terminal truncation | ARV | 77 |
| WT 14FnIII of fibronectin, Beta strand B | ITISW | 230 |
| WT 14FnIII of fibronectin, Beta strand C | FQVDAVP | 79 |
| WT 14FnIII of fibronectin, Beta strand D | IQRTI | 80 |

TABLE 1-continued

Sequences and SEQ ID Nos of molecular components to assemble representative scaffolds of the invention:

| Name/Brief Description | Sequence | SEQ ID NO |
|---|---|---|
| WT 14FnIII of fibronectin, Beta strand E | YTI | 81 |
| WT 14FnIII of fibronectin, Beta strand F | YKIYLYT | 82 |
| WT 14FnIII of fibronectin, Beta strand G | VIDAST | 83 |
| Fc region with hinge | EPKSCDKTHTCPPCPAPELLGGPSVFLFPPKPKDTLMISRTPEVTCVVVD VSHEDPEVKFNWYVDGVEVHNAKTKPREEQYNSTYRVVSVLTVLHQD WLNGKEYKCKVSNKALPAPIEKTISKAKGQPREPQVYTLPPSREEMTKN QVSLTCLVKGFYPSDIAVEWESNGQPENNYKTTPPVLDSDGSFFLYSKL TVDKSRWQQGNVFSCSVMHEALHNHYTQKSLSLSPGK | 84 |
| CH1-hinge-Fc region | ASTKGPSVFPLAPSSKSTSGGTAALGCLVKDYFPEPVTVSWNSGALTSG VHTFPAVLQSSGLYSLSSVVTVPSSSLGTQTYICNVNHKPSNTKVDKRV EPKSCDKTHTCPPCPAPELLGGPSVFLFPPKPKDTLMISRTPEVTCVVVD VSHEDPEVKFNWYVDGVEVHNAKTKPREEQYNSTYRVVSVLTVLHQD WLNGKEYKCKVSNKALPAPIEKTISKAKGQPREPQVYTLPPSREEMTKN QVSLTCLVKGFYPSDIAVEWESNGQPENNYKTIPPVLDSDGSFTLYSKL TVDKSRWQQGNVFSCSVMHEALHNHYTQKSLSLSPGK | 85 |
| Kappa light chain | RTVAAPSVFIFPPSDEQLKSGTASVVCLLNNFYPREAKVQWKVDNALQS GNSQESVTEQDSKDSTYSLSSTLTLSKADYEKHKVYACEVTHQGLSSPV TKSFNRGEC | 86 |
| Lambda light chain | QPKAAPSVTLFPPSSEELQANKATLVCLISDFYPGAVTVAWKADSSPVK AGVETTTPSKQSNNKYAASSYLSLTPEQWKSHRSYSCQVTHEGSTVEK TVAPTEC | 87 |
| Linker region 1 | GGGGSGGGGSGGGGSA | 88 |
| Linker region 2 | GGGGSGGGGSGTGSAMASGGGGSA | 89 |
| Linker region from C1 | *AGGGGS*RLDAPGQ (G-G-G-G-S SEQ ID NO: 210)) units are in bold; natural tenascin C sequence underlined | 90 |
| Linker region from C2 and C8 | *GGGGSGGGGSGGGGS*RLDAPGQ (G-G-G-G-S SEQ ID NO: 210)) units are in bold; natural tenascin C sequence underlined | 91 |
| Linker region from C3 | *GGGGSGGGGSGGGGSGGGGSGGGGS*RLDAPGQ (G-G-G-G-S) units are in bold; natural tenascin C sequence underlined | 92 |
| Linker region from C4 | *GGGGSGGGGSGGGGSGGGGSGGGGSGGGGSGGGGS*RLDAPGQ (G-G-G-G-S SEQ ID NO: 210)) units are in bold; natural tenascin C sequence underlined | 93 |
| Linker region from C5 | *T*RLDAPGQ natural tenascin C sequence underlined | 94 |
| Linker region from C6 | *GGGGS*RLDAPGQ (G-G-G-G-S SEQ ID NO: 210)) units are in bold; natural tenascin C sequence underlined | 95 |
| Linker region from C7 | *GGGGSGGGGS*RLDAPGQ (G-G-G-G-S SEQ ID NO: 210)) units are in bold; natural tenascin C sequence underlined | 96 |

EXAMPLES

The invention is now described with reference to the following examples. These examples are illustrative only and the invention should in no way be construed as being limited to these examples but rather should be construed to encompass any and all variations which become evident as a result of the teachings provided herein.

Example 1

Design of Various Multivalent Tn3 Formats

Multivalent formats of the Tn3 scaffold have been designed. The multivalent formats contain one or more Tn3 modules fused to themselves, fused to other protein motifs that can oligomerize, or fused to themselves and to other protein motifs that can oligomerize are shown in FIG. 1. In each case, the resulting molecular entity contains at least 2 Tn3 modules. The polypeptide linkers connecting the Tn3 modules to each other or to other protein motifs can be structured or unstructured and with or without a function. Three exemplary classes of multivalent Tn3 scaffold proteins are specifically provided: (i) linear (L) multivalent proteins containing Tn3 modules fused to each other via a polypeptide linker; (ii) antibody-like (Ig) multivalent proteins containing one or more linearly fused Tn3 modules fused to the light and heavy chains of an antibody or antibody fragment and (iii) Fc-containing multivalent proteins containing one or more linearly fused Tn3 modules fused to an antibody Fc region (FIG. 1).

Example 2

Expression and Purification of Multivalent TRAIL R2-Specific Tn3-Containing Proteins A series of eight multivalent Tn3-module containing scaffold proteins (also referred to as "Tn3 proteins" or "Tn3 scaffolds") with binding specificity for human TRAIL R2 were prepared. Examples were prepared from each of the three multivalent formats described in Example 1, and all of these proteins presented 2 or more of the TRAIL R2-binding Tn3 module A1 (clone 1E11, G6 or 1C12). For several TRAIL R2-specific multivalent Tn3 protein, a corresponding control Tn3 protein (clone D1, a Tn3 domain specific for the Synagis® antibody) that did not bind TRAIL R2 was also generated, this differing only in the sequence and binding specificity of the component Tn3 modules. Tn3 clone D1 is a Tn3 protein wherein the BC, DE, and FG loops of a 1E11 clone are replaced with alternative loops with sequences corresponding to SEQ ID NO: 99, 38, and 107, respectively (see TABLE 4). Sequence identity numbers of the multivalent Tn3 protein constructs that were expressed are shown in TABLE 2, and all the possible constructs are represented schematically in TABLE 3 and FIG. 2. The loop sequences for the clones are provided in TABLE 4.

TABLE 2

Names, formats, valencies, and specificities of expressed Tn3-containing proteins

| Name (clone) | Format type | SEQ ID NO | Number of Tn3 modules | Specificity |
|---|---|---|---|---|
| A1(1E11) | Monomer | 134 | 1 | TRAIL R2 |
| A2(1E11) | L | 139 | 2 | TRAIL R2 |
| A3(1E11) | L | 140 | 4 | TRAIL R2 |
| A4(1E11) | L | 141 | 6 | TRAIL R2 |
| A5(1E11) | L | 142 | 8 | TRAIL R2 |
| A5(G6) | L | 145 | 8 | TRAIL R2 |
| A6(1E11) | Fc | 151 | 2 | TRAIL R2 |
| A7(1E11) | Fc | 164 | 4 | TRAIL R2 |
| A8(1E11) | Fc | 165 | 8 | TRAIL R2 |
| A9(1C12) | Ig | 154 (HC), 154 (LC) | 4 | TRAIL R2 |
| A9(1E11) | Ig | 158 (HC), 159 (LC) | 4 | TRAIL R2 |
| B1(D1) | Monomer | 180 | 1 | Non TRAIL R2-binding control of A1 |
| B2(D1) | L | not expressed | 2 | non TRAIL R2-binding control of A2 |
| B3(D1) | L | 146 | 4 | non TRAIL R2-binding control of A3 |
| B4(D1) | L | 147 | 6 | non TRAIL R2-binding control of A4 |
| B5(D1) | L | 148 | 8 | non TRAIL R2-binding control of A5 |
| B6(D1) | Fc | 181 | 2 | non TRAIL R2-binding control of A6 |
| B7(D1) | Fc | not expressed | 4 | non TRAIL R2-binding control of A7 |
| B8(D1) | Fc | not expressed | 8 | non TRAIL R2-binding control of A8 |
| B9(D1) | Ig | 182 (HC), 183 (LC) | 4 | non TRAIL R2-binding control of A9 |

L = linear Tn3 fusions, Fc = Fc-Tn3 fusions, Ig = antibody-like Tn3 fusions

TABLE 3

Schematic Representation of Tn3 Scaffold Constructs

| | Construct Components |
|---|---|
| Tn3 Module (Tn3) | IEV($X_{AB}$)$_n$ALITW($X_{BC}$)$_n$CELX$_1$YGI($X_{CD}$)$_n$TTIDL($X_{DE}$)$_n$YSI($X_{EF}$)$_n$YEVSLIC($X_{FG}$)$_n$KE TFTT (SEQ IS NO: 215) $X_{AB}$, $X_{BC}$, $X_{CD}$, $X_{DE}$, $X_{EF}$, and $X_{FG}$ represent the amino acid residues present in the AB, BC, CD, DE, EF, and FG loops, respectively where n = 2-26, $X_1$ represents amino acid residue A or T. |
| Gly-Ser linker module, $(G_4S)_n$ where n = 1-7 (SEQ ID NO: 231) | GGGGS (SEQ IS NO: 215) The $(G_4S)_n$ module wherein n = 1 is shown above |
| Poly-Histidine | HHHHHHHH (SEQ ID NO: 211) An optional component of the constructs detailed |

TABLE 3-continued

Schematic Representation of Tn3 Scaffold Constructs

| Tag (H$_8$) (SEQ ID NO: 211) | below - useful for purification |
|---|---|

| Name | Construct Overview |
|---|---|
| A1 or B1 | A(Tn3)GGGTLGH$_8$ (SEQ IS NO: 232) |
| A2 or B2 | S(G$_4$S)$_1$A(Tn3)(G$_4$S)$_3$A(Tn3)(G$_4$S)$_2$GTLGH$_8$ (SEQ IS NO: 233) |
| A3 or B3 | S(G$_4$S)$_1$A(Tn3)(G$_4$S)$_3$A(Tn3)(G$_4$S)$_3$A(Tn3)(G$_4$S)$_2$GTLGH$_8$ (SEQ IS NO: 234) |
| A4 or B4 | S(G$_4$S)$_1$A(Tn3)(G$_4$S)$_3$A(Tn3)(G$_4$S)$_3$A(Tn3)(G$_4$S)$_3$A(Tn3)(G$_4$S)$_2$GTGSAMAS(G$_4$S)$_1$A(Tn3)(G$_4$S)$_3$A(Tn3)(G$_4$S)$_2$GTLGH$_8$ (SEQ IS NO: 235) |
| A5 or B5 | S(G$_4$S)$_1$A(Tn3)(G$_4$S)$_3$A(Tn3)(G$_4$S)$_3$A(Tn3)(G$_4$S)$_3$A(Tn3)(G$_4$S)$_2$GTGSAMAS(G$_4$S)$_1$A(Tn3)(G$_4$S)$_3$A(Tn3)(G$_4$S)$_3$A(Tn3)(G$_4$S)$_2$GTLGH$_8$ (SEQ IS NO: 236) |
| A6 or B6 | (Tn3)GAEPKSCDKTHTCPPCPAPELLGGPSVFLFPPKPKDTLMISRTPEVTCVVV DVSHEDPEVKFNWYVDGVEVHNAKTKPREEQYNSTYRVVSVLTVLHQDWLN GKEYKCKVSNKALPAPIEKTISKAKGQPREPQVYTLPPSREEMTKNQVSLTCLV KGFYPSDIAVEWESNGQPENNYKTTPPVLDSDGSFFLYSKLTVDKSRWQQGNV FSCSVMHEALHNHYTQKSLSLSPGK (SEQ IS NO: 237) |
| A7 or B7 | AMAS(G$_4$S)$_1$A(Tn3)(G$_4$S)$_3$A(Tn3)(G$_4$S)$_2$GTGAEPKSCDKTHTCPPCPAPELLGGPS VFLFPPKPKDTLMISRTPEVTCVVVDVSHEDPEVKFNWYVDGVEVHNAKTKPR EEQYNSTYRVVSVLTVLHQDWLNGKEYKCKVSNKALPAPIEKTISKAKGQPRE PQVYTLPPSREEMTKNQVSLTCLVKGFYPSDIAVEWESNGQPENNYKTTPPVL DSDGSFELYSKLTVDKSRWQQGNVFSCSVMHEALHNHYTQKSLSLSPGK (SEQ IS NO: 238) |
| A8 or B8 | AMAS(G$_4$S)$_1$A(Tn3)(G$_4$S)$_3$A(Tn3)(G$_4$S)$_3$A(Tn3)(G$_4$S)$_2$GTGAEPKSCD KTHTCPPCPAPELLGGPSVFLFPPKPKDTLMISRTPEVTCVVVDVSHEDPEVKFN WYVDGVEVHNAKTKPREEQYNSTYRVVSVLTVLHQDWLNGKEYKCKVSNK ALPAPIEKTISKAKGQPREPQVYTLPPSREEMTKNQVSLTCLVKGFYPSDIAVE WESNGQPENNYKTTPPVLDSDGSFFLYSKLTVDKSRWQQGNVFSCSVMHEAL HNHYTQKSLSLSPGK (SEQ IS NO: 239) |
| A9 or B9 heavy chain constant region fusion | SQ(Tn3)GGGTPTSSASTKGPSVFPLAPSSKSTSGGTAALGCLVKDYFPEPVTVSW NSGALTSGVHTFPAVLQSSGLYSLSSVVTVPSSSLGTQTYICNVNHKPSNTKVD KRVEPKSCDKTHTCPPCPAPELLGGPSVFLFPPKPKDTLMISRTPEVTCVVVDVS HEDPEVKFNWYVDGVEVHNAKTKPREEQYNSTYRVVSVLTVLHQDWLNGKE YKCKVSNKALPAPIEKTISKAKGQPREPQVYTLPPSREEMTKNQVSLTCLVKGF YPSDIAVEWESNGQPENNYKTTPPVLDSDGSFFLYSKLTVDKSRWQQGNVFSC SVMHEALHNHYTQKSLSLSPGK (SEQ IS NO: 240) |
| A9 or B9 light chain constant region fusion | SQ(Tn3)GGGTPTRTVAAPSVFIFPPSDEQLKSGTASVVCLLNNFYPREAKVQWK VDNALQSGNSQESVTEQDSKDSTYSLSSTLTLSKADYEKHKVYACEVTHQGLS SPVTKSFNRGEC (SEQ IS NO: 241) |
| M13 or 79 | A(Tn3)GGGTLGH$_8$ (SEQ IS NO: 242) |
| C1 | A(Tn3)A(G$_4$S)$_1$RLDAPGQ(Tn3)GGGTLGH$_8$ (SEQ IS NO: 243) |
| C2 | A(Tn3)(G$_4$S)$_3$RLDAPGQ(Tn3)GGGTLGH$_8$ (SEQ IS NO: 244) |
| C3 | A(Tn3)(G$_4$S)$_5$RLDAPGQ(Tn3)GGGTLGH$_8$ (SEQ IS NO: 245) |
| C4 | A(Tn3)(G$_4$S)$_7$RLDAPGQ(Tn3)GGGTLGH$_8$ (SEQ IS NO: 246) |
| C5 | A(Tn3)TRLDAPGQ(Tn3)GGGTLGH$_8$ (SEQ IS NO: 247) |
| C6 | A(Tn3)(G$_4$S)$_1$RLDAPGQ(Tn3)GGGTLGH$_8$ (SEQ IS NO: 248) |
| C7 | A(Tn3)(G$_4$S)$_2$RLDAPGQ(Tn3)GGGTLGH$_8$ (SEQ IS NO: 249) |
| C8 | A(Tn3)(G$_4$S)$_3$RLDAPGQ(Tn3)GGGTLGH$_8$ (SEQ IS NO: 250) |

TABLE 4

Loop Sequences of Tn3 Clones Used in These Studies

| Clone | AB Loop (SEQ ID NO) | BC Loop (SEQ ID NO) | CD Loop (SEQ ID NO) | DE Loop (SEQ ID NO) | EF Loop (SEQ ID NO) | FG Loop (SEQ ID NO) |
|---|---|---|---|---|---|---|
| 1E11† | KDVTDTT (NO: 35) | AKPWVDPPPLWG (NO: 97) | KDVPGDR (NO: 37) | QQKHTA (NO: 102) | GNLKPDTE (NO: 39) | FDPYGAKSNPA (NO: 106) |
| D1 | KDVTDTT (NO: 35) | SPGERIWMFTG (NO: 99) | KDVPGDR (NO: 37) | TEDENQ (NO: 38) | GNLKPDTE (NO: 39) | PNYERISNPA (NO: 107) |
| G6† | KDVTDTT (NO: 35) | AKPWVDPPPLWG (NO: 97) | KDVPGDR (NO: 37) | QQKHTA (NO: 102) | GNLKPDTE (NO: 39) | FDPYGMRSKPA (NO: 108) |
| 1C12† | KDVTDTT (NO: 35) | AKPEKWDGSIYG (NO: 98) | KDVPGDR (NO: 37) | NSRHTA (NO: 103) | GNLKPDTE (NO: 39) | FTPYGAKSNPA (NO: 109) |
| M13 | KDVTDTT (NO: 35) | HDAFGYDFG (NO: 100) | KDVPGDR (NO: 37) | PDHFHN (NO: 104) | GNLKPDTE (NO: 39) | ANDHGFDSNPA (NO: 110) |
| 79 | KDVTDTT (NO: 35) | IPPHNADSSIIG (NO: 101) | KDVPGDR (NO: 37) | YDVAFD (NO: 105) | GNLKPDTE (NO: 39) | DTFYGFDSNPA (NO: 111) |
| G3† | KDVTDTT (NO: 35) | AKPEKWDGPPLW (NO: 168) | KDVPGDR (NO: 37) | NSRHTA (NO: 103) | GNLKPDTE (NO: 39) | FTPYGAKSNPA (NO: 109) |
| C4† | KDVTDTT (NO: 35) | AKPWVDPPPLWG (NO: 97) | KDVPGDR (NO: 37) | QQKHTA (NO: 102) | GNLKPDTE (NO: 39) | FDPYNKRNVPA (NO: 169) |
| F4† | KDVTDTT (NO: 35) | AKPWVDPPPLWG (NO: 97) | KDVPGDR (NO: 37) | QQKHTA (NO: 102) | GNLKPDTE (NO: 39) | FDPYGLKSRPA (NO: 170) |
| F4mod 1† | KDVTDTT (NO: 35) | AKPWVDPPPLWG (NO: 97) | KDVPGDR (NO: 37) | QQKHTA (NO: 102) | GNLKPDTE (NO: 39) | FDPYGLKSRPA (NO: 170) |
| F4mod 2 | KDVTDTT (NO: 35) | AKPWVDPPPLWG (NO: 97) | KDVPGDR (NO: 37) | QQKHNQ (NO: 179) | GNLKPDTE (NO: 39) | FDPYGLKSRPA (NO: 170) |

†Clones comprising a C beta strand having the sequence CELAYGI (SEQ ID NO: 131), all other clones comprise a C beta strand having the sequence CELTYGI (SEQ ID NO: 45)

Preparation of Expression Constructs:

Enzymes used were from New England Biolabs (Ipswich, Mass.), DNA purification kits were from Qiagen (Germantown, Md.), and DNA primers were from IDT (Coralville, Iowa). Preparation of expression constructs encoding 2 or more linearly fused Tn3 modules was as follows. The DNA encoding a TRAIL R2-specific Tn3 module (e.g., 1E11; SEQ ID NO: 134; G6, SEQ ID NO: 138; etc.) was amplified by PCR with the primers "Tn3 gly4ser1 module forward" (SEQ ID NO: 112) and "Tn3 gly4ser2 module reverse" (SEQ ID NO: 113) (TABLE 5).

After cleanup of the PCR product, the amplified DNA was divided in two, with one half digested with BpmI, and the other half digested with AcuI. The digested samples were purified using a PCR cleanup kit and ligated with T4 DNA ligase to make a DNA product encoding two Tn3 modules (A2). This material was purified by agarose gel electrophoresis and again split into two. Digestion with NcoI and KpnI followed by ligation into NcoI KpnI digested pSec-oppA (L25M) (described in WO 2009/058379 A2, Example 18) yielded the bacterial expression construct for protein A2. Ligation of undigested product into pCR 2.1-TOPO vector (Invitrogen, Carlsbad, Calif.) provided genetic material for generation of higher order fusions. To make a DNA fragment encoding four Tn3 modules (A3), the TOPO cloned A2 DNA was PCR amplified with primers "module amp forward" (SEQ ID NO: 114) and "module amp reverse" (SEQ ID NO: 115) (TABLE 5), purified, and split in two for digestion with AcuI or BpmI. The rest of the process for making the A3 expression construct was the same as that used for making the A2 construct, wherein the DNA encoding A3 was assembled from A2 building blocks. Again, concurrent cloning of assembled A3 DNA into pCR 2.1-TOPO provided genetic material for generation of higher order fusions.

For preparation of A4 and A5 bacterial expression constructs, an adapter module was introduced at the 3' end of the multi-Tn3 coding sequence within the A3 expression construct. To do this, the A3 expression vector was first digested with KpnI and EcoRI, and the excised fragment was replaced with a duplex cassette containing the oligonucleotides "insert BamHI in pSec forward" (SEQ ID NO: 116) and "insert BamHI in pSec reverse" (SEQ ID NO: 117) (TABLE 5). PCR amplification of A2 and A3 sequences from the corresponding pCR 2.1 TOPO constructs was performed with the primers "module insert BamHI forward" (SEQ ID NO: 118) and "module amp reverse" (SEQ ID NO: 115) (TABLE 5). Amplified products were double digested with BamHI/KpnI, and cloned into similarly digested A3 expression construct.

Proteins A6-A9 were expressed by transient transfection of 293F cells, as described in Example 16 of WO 2009/058379 A2. Briefly, expression vectors were generated by PCR amplifying the Tn3 module (or modules) from the bacterial expression constructs, and cloning these into in house vectors encoding the Fc region, the kappa light chain constant region and/or the CH1-hinge-CH2-CH3 heavy chain constant regions for expression of Fc fusion or antibody proteins. For protein A9, a Tn3 module replaces the antibody variable regions in the human IgG1 heavy chain and kappa light chain. The primers that add compatible NheI and KasI sites for making Fc fusions of the tandem constructs are shown in TABLE 5.

TABLE 5

Primer Sequences Used in the Construction of Multivalent Tn3 Proteins

| Sequence Name | Sequence | SEQ ID NO |
|---|---|---|
| Tn3 gly4ser1 module forward | GGCGCTAGGCTGAGTAGGTCCTGGAGTGCGGCCATGGC CAGCGGGGCGGAGGGAGTGCCATTGAAGTGAAAGATG TGACCGATACC | 112 |
| Tn3 gly4ser2 module reverse | CCTCAGCCGATCACCACCTGAAGGCTACGCAGGTACCGC TACCGCCACCTCCGCTCCCACCGCCACCGGTGGTAAAGG TTTC | 113 |
| Module amp forward | GGCGCTAGGCTGAGTAGGTCCTGGAGTGCGG | 114 |
| Module amp reverse | CCTCAGCCGATCACCACCTGAAGGCTACGCAGG | 115 |
| Module insert BamHI in pSec forward | GGGATCCGCTACGGGCCACTCGATCGAGGTCCGTGCTGA TCGAGCGATCGGTACCCTGGGCCATCATCATCATCATCA CCACCACTGAG | 116 |
| Module insert BamHI in pSec reverse | AATTCTCAGTGGTGGTGATGATGATGATGATGGCCCAGG GTACCGATCGCTCGATCAGCACGGACCTCGATCGAGTGG CCCGTAGCGGATCCCGTAC | 117 |
| Module insert BamHI forward | GGCGCTAGGCTGAGTAGGTCCTGGGGATCCGCCATGGCC AGC | 118 |
| Module insert NheI forward | GGCGCTAGGCTGAGTAGGTCCTGGCTAGCTGCCATGGCC AGC | 119 |
| Module insert KasI reverse | CCTCAGCCGATCACCACCTGAAGGCGGCGCCGGTACC | 120 |

Figure 3:
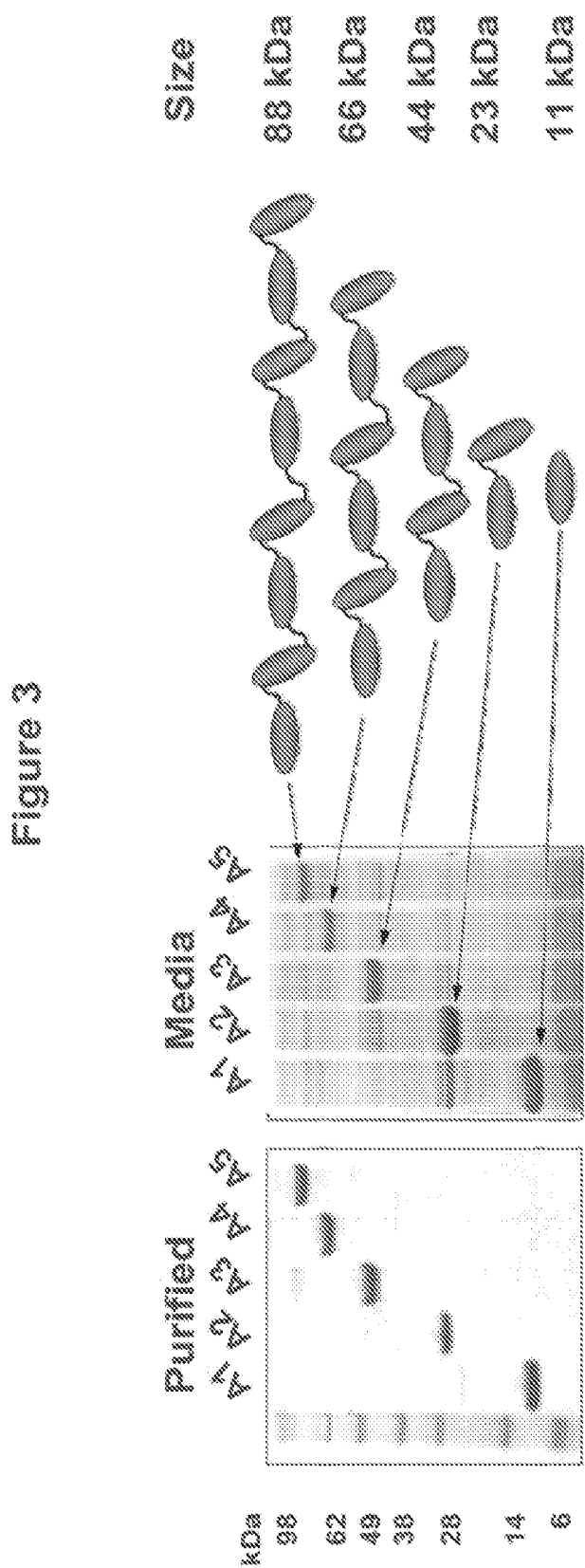
FIG. 3 shows non reducing SDS-PAGE analysis of crude bacterial media (right gel) and affinity purified samples (left gel) corresponding to linear tandem constructs designated A1 to A5, with valencies varying from 1 to 8, expressed in *E. coli*.

Expression and Purification of Proteins:

Monovalent or linear Tn3 proteins were expressed in BL21 (DE3) *E. coli* (EMD/Novagen, Gibbstown, N.J.) and the His-tagged proteins were purified from the culture media using Ni NTA Superflow resin (Qiagen). Surprisingly, despite large differences in the molecular weights, all of these constructs expressed at medium to high levels in *E. coli* and were efficiently secreted into the media (TABLE 6 and FIG. 3).

To express Fc fusion and antibody-like proteins (A6-A9), 293F cells were transiently transfected with the appropriate expression constructs. Harvests of supernatant were performed on days 6 and 10 and the protein was purified by protein A affinity chromatography.

All purified proteins were analysed by SDS-PAGE on NuPage Novex 4-12% bis tris gels in MES buffer without reducing agent, and were visualized using SimplyBlue SafeStain (Invitrogen, Carlsbad, Calif.). Size exclusion chromatography was also used to analyze purified proteins, and where necessary, aggregated material was removed on either a Superdex 75 10/300GL or Superdex 200 10/300GL column (GE Healthcare, Piscataway, N.J.), to a final level below 10% of total protein. An Acrodisc unit with a Mustang E membrane (Pall Corporation, Port Washington, N.Y.) was used as indicated by the manufacturer to remove endotoxin from bacterially expressed protein preparations.

TABLE 6

Yield After Purification of Representative Multivalent Tn3 Protein Formats

| Protein (Clone) | Yield (mg/L) |
|---|---|
| A1 (1E11) | 400 |
| A2 (1E11) | 300 |

TABLE 6-continued

Yield After Purification of Representative Multivalent Tn3 Protein Formats

| Protein (Clone) | Yield (mg/L) |
|---|---|
| A3 (1E11) | 135 |
| A4 (1E11) | 90 |
| A5 (1E11) | 40 |

Example 3

TRAIL R2 Binding Affinity for Mono- and Polyvalent Tn3 Proteins

Figure 4:
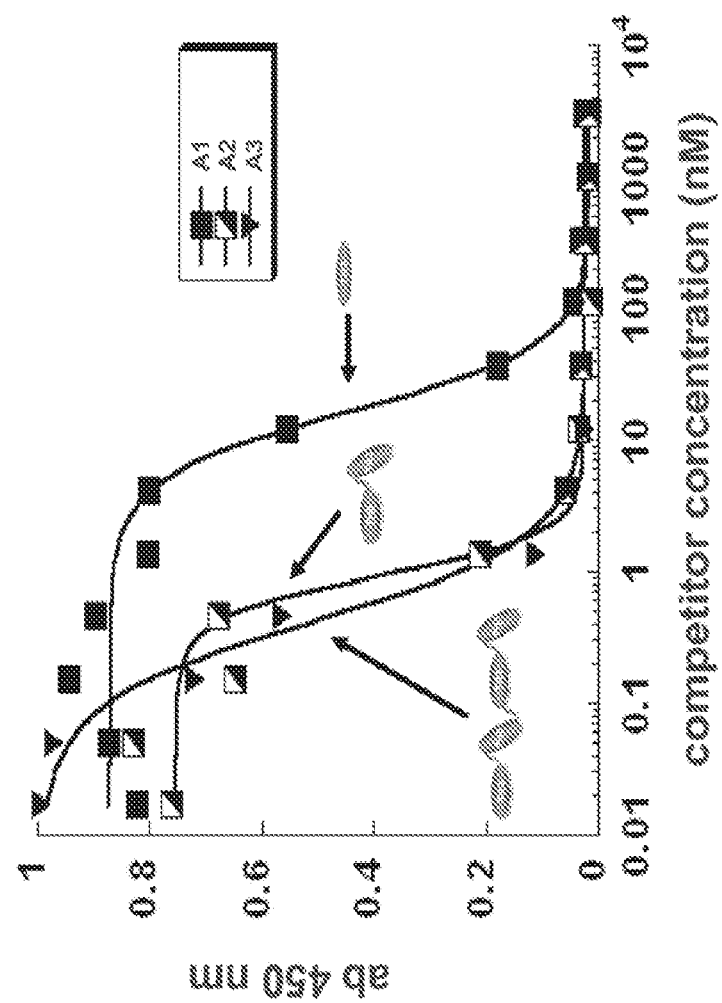
FIG. 4 shows a competition ELISA measuring binding of monovalent (A1) and multivalent (A2, A3) Tn3 scaffolds to TRAIL R2.

To measure the effect of Tn3 valency on binding affinity for a series of TRAIL R2-specific Tn3 proteins, a competition ELISA experiment was performed. A 96-well NUNC MaxiSorp plate (Thermo Fisher, Rochester, N.Y.), was coated with A9(1C12) (SEQ ID NO: 154+SEQ ID NO: 145) a TRAIL R2 specific scaffold in an antibody-like format, in PBS at 2 μg/ml overnight at 4° C. Plates were blocked with PBS 0.1% Tween 20+10 mg/ml BSA. Dilutions of A1 (1E11 monomer), and linear format A2 (1E11 bivalent) or A3 (1E11 tetravalent) multimeric scaffolds were incubated on the coated plate with 0.75 nM of biotinylated TRAIL R2-Fc for two hours at room temperature in PBS 0.1% Tween 20+1 mg/ml BSA, washed. Bound biotinylated TRAIL R2 Fc was detected with streptavidin HRP, TMB, and neutralized with acid. Absorbance was read at 450 nm. Data is shown in FIG. 4. Binding affinities ($IC_{50}$) are shown in TABLE 7 and were calculated as the concentration of competing protein required to reduce maximal binding of biotinylated TRAIL R2-Fc by 50%.

The $IC_{50}$ values for A2 and A3 were at least 30-fold lower than those of the monomer A1 and are at the limit of this assay (i.e., approx. equal to the concentration of biotinylated TRAIL R2-Fc). Binding of biotinylated TRAIL R2-Fc to immobilized TRAIL R2-specific Tn3 was displaced by the TRAIL R2 binding constructs.

Relative to the monomeric A1 protein, the bi- and tetravalent A2 and A3 proteins bound TRAIL R2-Fc with 30-40-fold higher affinity, which is an indication that the multiple Tn3 modules retain their binding activity and contribute to higher affinity through an avidity effect. The true difference in affinity between mono- and bi- or tetravalent Tn3 proteins may be greater than 30-40-fold given the $IC_{50}$ values for A2 and A3 were approximately equal to the concentration of biotinylated TRAIL R2-Fc used in the assay (0.75 nM).

TABLE 7

$IC_{50}$ Values for the Inhibition of Binding of TRAIL R2-Fc to immobilized TRAIL R2 Binding A9(1C12) Tn3 Protein

| Clone | Valency | $IC_{50}$ (nM) |
|---|---|---|
| A1 (1E11) | 1 | 16 |
| A2 (1E11) | 2 | 0.5 |
| A3 (1E11) | 4 | 0.4 |

Example 4

Flow Cytometry for Confirmation of Cell Binding

Flow cytometry was used to confirm the specificity of binding of a multivalent TRAIL R2-specific Tn3 protein to endogenous TRAIL R2 expressed on the cell surface of H2122 cells. Adherent H2122 cells (a non-small cell lung cancer adenocarcinoma cell line), were detached from tissue culture flasks using Accutase (Innovative Cell Technologies, San Diego, Calif.). Cells were rinsed with complete medium (RPMI 1640 medium supplemented with 10% FBS) and resuspended in PBS/2% FBS at approximately $2 \times 10^6$ cells/mL. Tn3 protein A9(1E11) (SEQ ID NO: 158+SEQ ID NO: 159), a tetravalent antibody-like format multimeric scaffold, or the format-matched control Tn3 protein B9 (clone D1), were prepared at 40 nM concentrations in PBS/2% FBS.

Cells were plated on 96 well U-bottom plates at 75 µl per well, and protein samples were added at 25 µl per well (to a final concentration of 10 nM). The plate was incubated at 4° C. for approximately 1 hour, then washed 3 times with PBS/2% FBS. Anti-human IgG Alexa Fluor 488 conjugated secondary antibody added was added (100 µl/well), and the plate was incubated at 4° C. for approximately 30 minutes and washed as described above. Cells were resuspended in 100 µl of PBS/2% FBS, and flow cytometry analysis was performed using a BD LSR II cytometer (BD Biosciences, San Jose, Calif.). A shift (increase) in fluorescently labeled H2122 cells when incubated with the TRAIL R2 specific Tn3 protein relative to control confirmed that the TRAIL R2 specific Tn3 protein could bind to cellular TRAIL R2 (FIG. 5).

Example 5

Effect of Valency and Format on Apoptosis of H2122 Cells by TRAIL R2-Specific Tn3 Proteins Apoptotic cell death can be induced in cancer cells lines by crosslinking of cell surface TRAIL R2. This effect can be determined in cell assays that measure the number of viable cells. To this end, lung carcinoma cell lines H2122 cells were plated in 96 well plates at a density of 10,000 cells/well in 75 µl of complete medium (RPMI 1640 medium supplemented with 10% FBS). Following overnight incubation at 37° C., media was supplemented with 25 µl of additional media containing a serial dilution of TRAIL R2-specific (clone 1E11) or negative control (clone D1) Tn3 proteins. All treatments were performed in duplicate wells. Commercially available TRAIL ligand (Chemicon/Millipore, Billerica, Mass.) was used as a positive control for TRAIL receptor-induced cell death. After 72 hrs, the CellTiter-Glo kit from Promega (Madison, Wis.) was used according to the manufacturer's instructions to assay ATP levels, which is a measure of the number of viable cells in the culture. Assay luminescence was measured on an Envision Plate reader (PerkinElmer, Waltham, Mass.). Inhibition of cell viability was determined by dividing the luminescence values for treated cells by the average luminescence for untreated viable cells. Dose response plots of inhibition vs. compound concentration were generated, and cell killing potency ($EC_{50}$) was determined as the concentration of protein required to inhibit 50% of the cell viability.

Figure 6A:
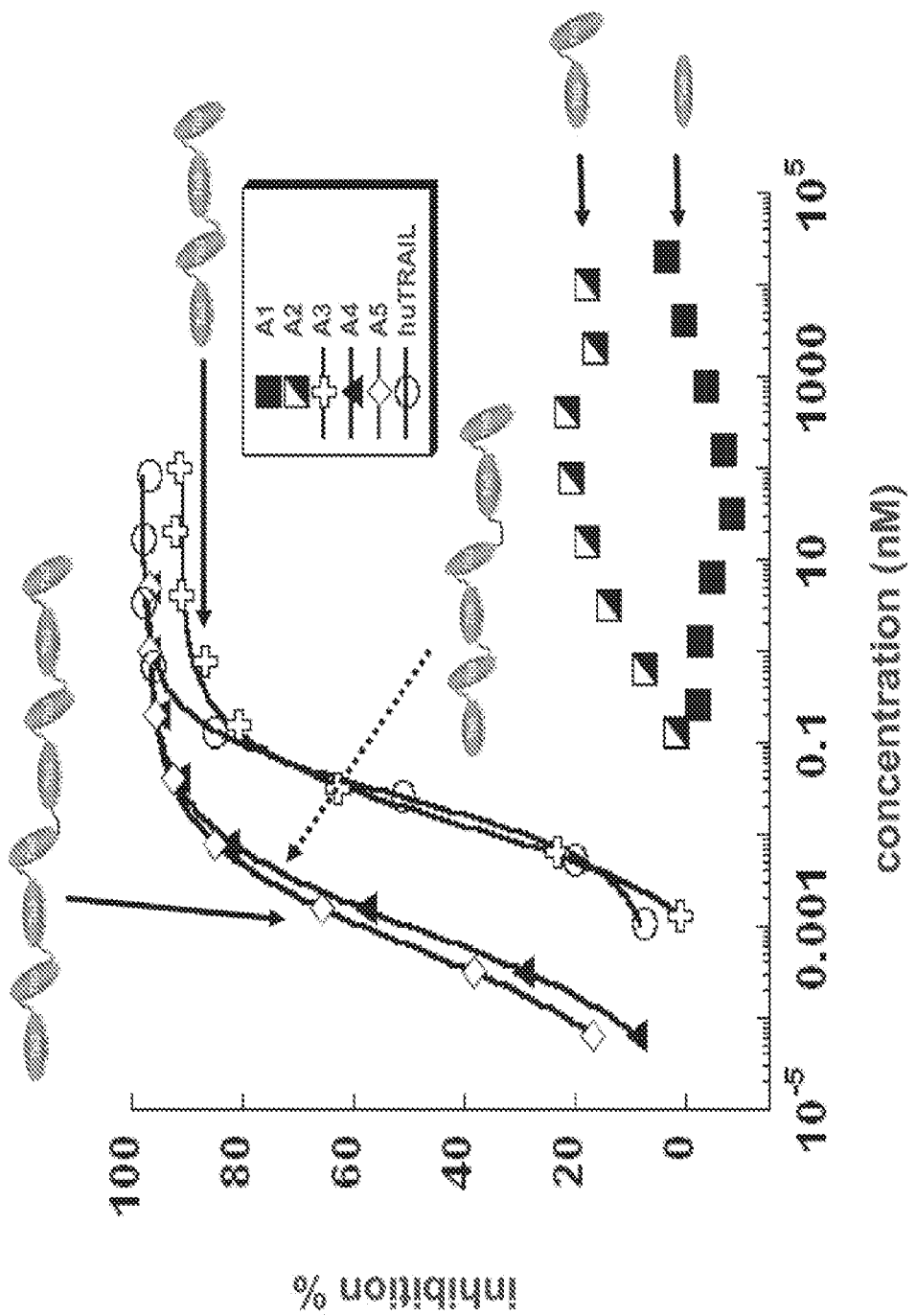
FIG. 6A shows the effect of valency on the specific killing of the TRAIL R2-expressing cell line H2122 by multivalent scaffolds.

To test the effect of valency on the proapoptotic activity of multivalent TRAIL R2-specific Tn3 proteins, H2122 cells were treated with the monovalent Tn3 protein A1 (clone 1E11), and the series of linearly fused Tn3 proteins A2-A5 (each clone 1E11) which contain 2, 4, 6 or 8 Tn3 modules. While the mono- and bivalent Tn3 proteins showed no or negligible killing activity, proteins containing 4, 6 and 8 Tn3 modules potently inhibited H2122 cell viability, with potency increasing as a function of valency (FIG. 6A; TABLE 8). Protein A3 (tetravalent) had a similar potency to TRAIL, the natural TRAIL R2 ligand, while proteins A4 (hexavalent) and A5 (octavalent) were 1-2 logs more potent. It is clear from this assay that for a given molecular format, cell killing improves with higher valency, up to a point where the assay can no longer discriminate.

TABLE 8

$EC_{50}$ Values for Killing of H2122 by Multivalent Constructs

| Clone | $EC_{50}$ (nM) | Maximum Inhibition % |
|---|---|---|
| A3 (1E11) | 0.013 | 91 |
| A4 (1E11) | 0.0009 | 97 |
| A5 (1E11) | 0.0006 | 97 |
| human TRAIL | 0.027 | 98 |

Figure 6B:
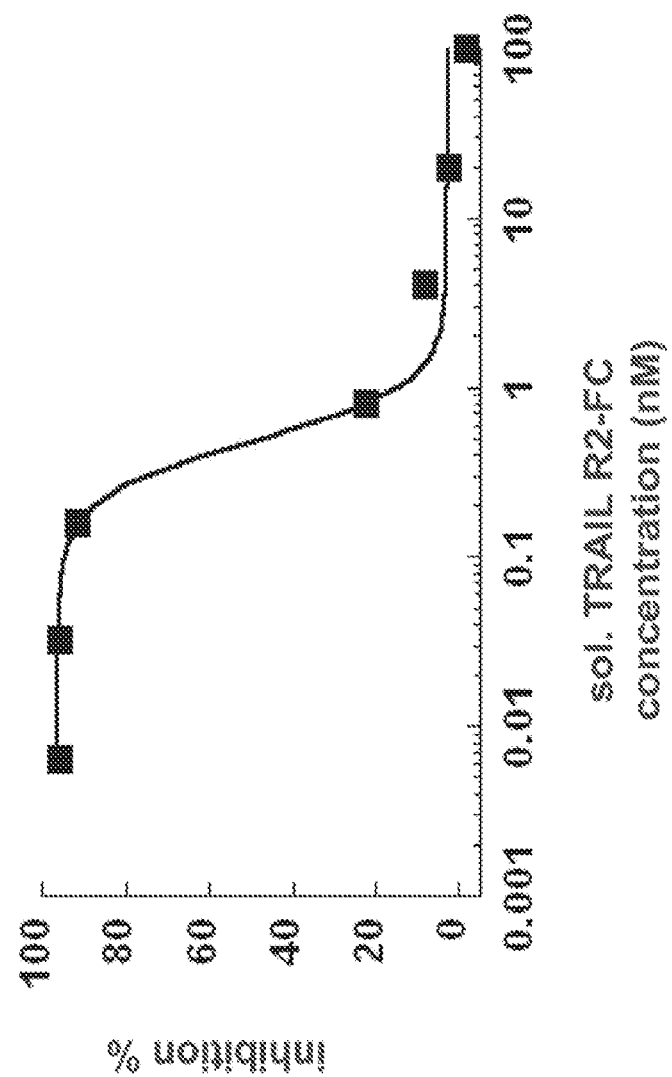
FIG. 6B shows the specificity of H2122 tumor cell killing by TRAIL R2-specific multivalent scaffolds.

To demonstrate that inhibition of cell viability is dependent on TRAIL R2 binding, 100 µM of protein A5 (clone G6) (i.e., 167× the $EC_{50}$) was incubated with H2122 cells in the presence of soluble TRAIL R2-Fc protein. Dose dependent repression of cell killing by soluble TRAIL R2-Fc is an indication that cell killing is dependent on protein A5 binding to cell surface TRAIL R2 (FIG. 6B). Similar results were seen with protein A5 comprising clone 1E11 loops (data not shown).

Figure 7A:
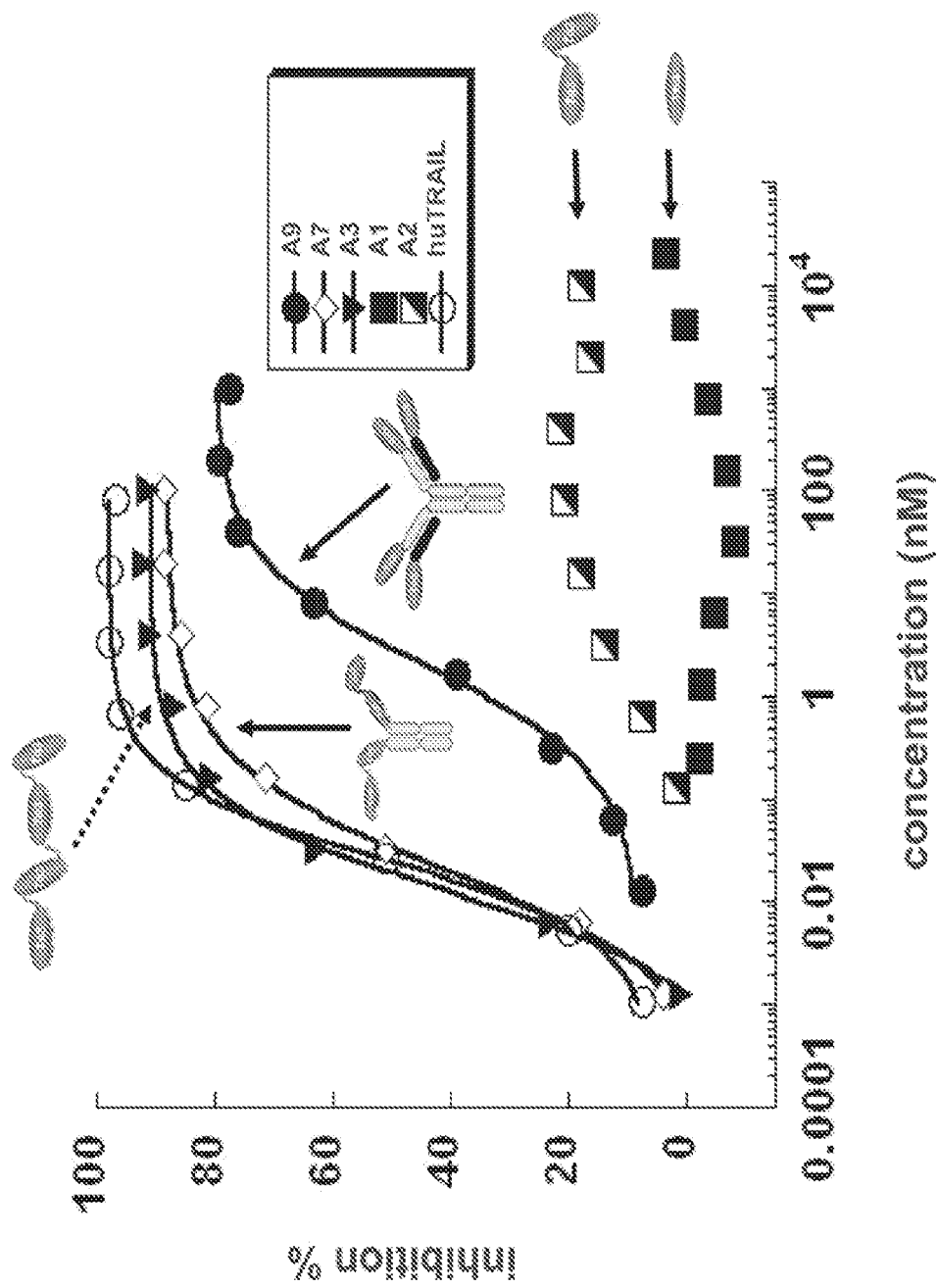
FIG. 7A shows the effect of molecular format on killing of H2122 cells by TRAIL R2-specific multivalent scaffolds comprising 4 Tn3 modules.

In addition to the number of binding modules, the activity of multivalent Tn3 proteins may also be affected by the molecular format used to present the individual binding units. To test the effect of molecular format on activity, H2122 cells were treated with different TRAIL R2-specific Tn3 proteins presenting the same number of Tn3 binding modules. The ability of the tetravalent proteins A3, A7 and A9 (each clone 1E11) to induce killing of H2122 cells was tested in the cell viability assay, as was the pair of octavalent Tn3 proteins A5 and A8 (each clone 1E11). Inactive mono- and bivalent proteins were included as negative controls, and TRAIL as a positive control (FIG. 7; TABLE 9 and TABLE 10). In FIG. 7A, for the three constructs tested with a valency of four, it is apparent that A3 (linear format) and A7 (Fc-fusion format) are similar in their cell killing activity and are more potent in killing H2122 cells than A9 (antibody-like fusion format). This clearly shows that the spatial orientation of Tn3 modules can have a considerable effect on bioactivity, wherein A3 is approximately 150-fold more potent than A9 protein in inhibiting H2122 cell viability (TABLE 9). FIG. 7B shows that both formats of octavalent TRAIL R2-binding Tn3 proteins, A5 (linear) and A8 (Fe-fusion), have similar efficacy in inhibiting the viability of H2122 cells. The $EC_{50}$ data for these constructs is shown in TABLE 9. The ability to fine tune affinity, valency, and spatial orientation affords great flexibility in terms of the ability to precisely engineer a desired therapeutic outcome.

TABLE 9

$EC_{50}$ Values for Killing of H2122 by Multivalent Constructs with a Valency of Four

| Clone | $EC_{50}$ (nM) | Maximum Inhibition % |
|---|---|---|
| A9 (1E11) | 1.98 | 80 |
| A7 (1E11) | 0.02 | 88 |
| A3 (1E11) | 0.013 | 91 |
| human TRAIL | 0.027 | 98 |

TABLE 10

$EC_{50}$ Values for Killing of H2122 by Multivalent Constructs with a Valency of Eight

| Clone | $EC_{50}$ (nM) | Maximum Inhibition % |
|---|---|---|
| A5 (1E11) | 0.0006 | 97 |
| A8 (1E11) | 0.0002 | 98 |
| human TRAIL | 0.027 | 98 |

Example 6

Dose Dependent Cell Killing in the Cell Lines Colo205 and Jurkat

To demonstrate that multivalent TRAIL R2-specific Tn3 proteins could kill cancer cell lines other than H2122, other TRAIL R2 expressing cell lines were also tested. The colorectal adenocarcinoma cell line Colo205 (FIG. 8A) and Jurkat T cell leukemia line (FIG. 8B) were tested for their ability to be killed by proteins A3 (tetravalent, linear format) (SEQ ID NO: 143) and A5 (octavalent, linear format) (SEQ ID NO: 145) (each clone G6). Each cell line was incubated with A3, A5, the positive control TRAIL, or a negative control protein B5 (SEQ ID NO: 148) which does not bind TRAIL R2, and the cell viability assay was performed as described for H2122. In each of these cell lines, A5 shows extremely potent inhibition of cell viability. The lower valency A3 protein also induces cell killing, albeit with lower potency than A5. Thus, the higher valency construct shows greater activity. As expected, TRAIL could also inhibit cell viability, but not octavalent negative control protein B5, which does not bind TRAIL R2.

TABLE 11

$EC_{50}$ Values for Killing of Colo205 by Linear Tandem Constructs

| Clone | $EC_{50}$ (nM) | Maximum Inhibition % |
|---|---|---|
| A3 (G6) | 0.04 | 97 |
| A5 (G6) | 0.0005 | 100 |
| human TRAIL | 0.08 | 100 |

TABLE 12

$EC_{50}$ Values for Killing of Jurkat cells by Linear Tandem Constructs

| Clone | $EC_{50}$ (nM) | Maximum Inhibition % |
|---|---|---|
| A3 (G6) | 0.05 | 83 |
| A5 (G6) | 0.0001 | 100 |
| human TRAIL | 0.009 | 99 |

Cells were analyzed by the CellTiter-Glo assay as in Example 5.

Example 7

Figure 9A:
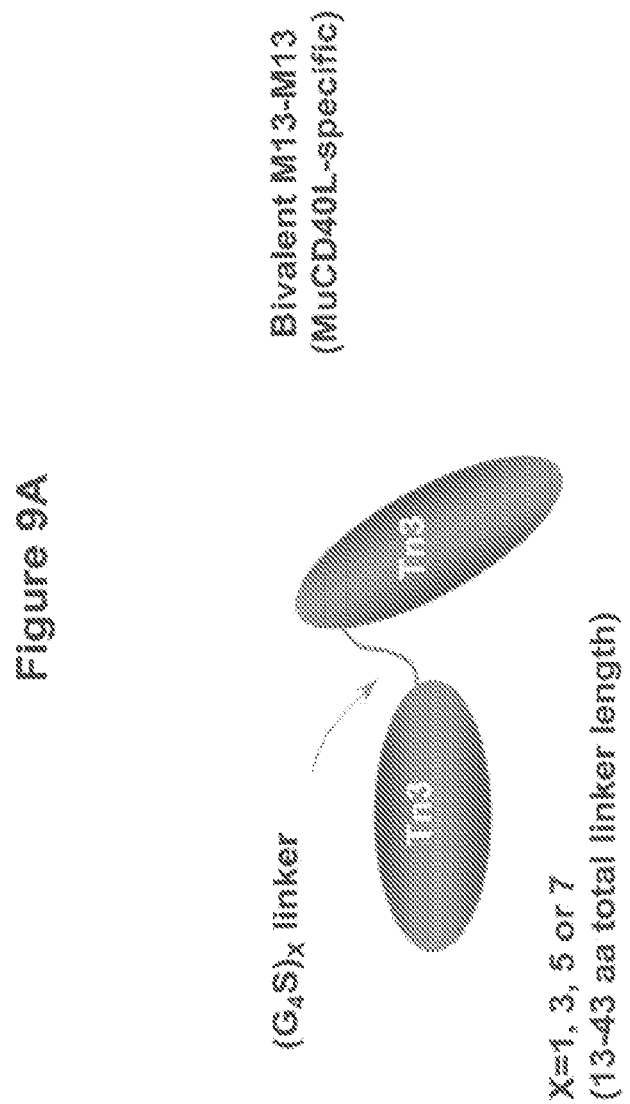
FIG. 9A shows the design of murine CD40L-specific tandem bivalent Tn3 scaffolds (M13 constructs).

Design, Expression, and Activity of Mouse CD40L-Specific Bivalent Tandem Scaffolds Bivalent murine CD40L-specific Tn3 proteins (TABLE 13) were prepared by fusing a pair of identical Tn3 modules. M13 is a Tn3 protein that specifically binds Murine CD40L. The M13 sequence corresponds to the sequence of Tn3 wherein the sequences of the BC, DE, and FG loops are replaced with alternative loops with sequences corresponding to SEQ ID NOs: 100, 104, and 110, respectively (see TABLE 4). Linkers containing 1 (Construct C1(M13)), 3 (Construct C2(M13)), 5 (Construct C3(M13)), or 7 (Construct C4(M13)) copies of the $Gly_4Ser$ (SEQ ID NO: 210) (GS) unit were used resulting in total linker lengths between 13 and 43 amino acids (see FIG. 9A and TABLE 3).

TABLE 13

Names, valencies, and specificities of expressed Tn3-containing proteins

| Name (clone) | Number of Tn3 modules | Linker length | Specificity |
|---|---|---|---|
| M13 (M13) | 1 | N/A | Murine CD40L |
| C1(M13) | 2 | 13 | Murine CD40L |
| C2(M13) | 2 | 23 | Murine CD40L |
| C3(M13) | 2 | 33 | Murine CD40L |
| C4(M13) | 2 | 43 | Murine CD40L |

Briefly, the expression constructs were generated as follows: Fragment A was generated by PCR amplification of Murine CD40L binder pSec-M13 cloned in the pSec-oppA (L25M) vector described in Example 1 with a primer specific for the pSec vector upstream of the Tn3 gene and primer "1-3 GS linker reverse" (SEQ ID NO: 123) (see TABLE 14 for sequences of Tn3 specific primers used). Fragments B1GS and B3GS were generated by PCR amplification of the same template with primers "1 GS linker" (SEQ ID NO: 121) or "3 GS linker" (SEQ ID NO: 122), respectively, and a primer specific for the pSec vector downstream of the Tn3 gene. Upon gel-purification of the fragments, Fragment A and B1OS or Fragment A and B3GS were mixed, and the tandem constructs were generated by overlap PCR in a PCR reaction with the two pSec vector specific primers. The products were digested with NcoI and KpnI and cloned back into the pSec-oppA(L25M) vector as described in Example 1, yielding the two constructs: C1(M13) and C2(M13). In order to generate the 5 and 7 GS linker constructs, linker inserts generated by PCR amplification of the oligonucleotides "5 GSLinker" (SEQ ID NO: 124) and "7 GSLinker" (SEQ ID NO: 125), respectively, with primers "GS L Amp forward" (SEQ ID NO: 126) and "GS L Amp reverse" (SEQ ID NO: 127) were digested with PstI and XmaI and cloned into a vector fragment generated by cutting pSecM13-1GS-M13 with PstI and XmaI yielding the constructs C3(M13) and C4(M13).

TABLE 14

Primer sequences used in the construction of Tandem bivalent MuCD40L specific constructs

| Sequence Name | Sequence | SEQ ID NO |
|---|---|---|
| 1 GSLinker | AAAGAAACCTTTACCACTGCAGGTGGCGGAGGTTCACG CTTGGATGCCCCCGGGCAGATTGAAGTGAAAGATGTGA CCGAT | 121 |
| 3 GSLinker | AAAGAAACCTTTACCACTGCAGGTGGCGGAGGTTCAGG TGGCGGAGGTTCAGGTGGCGGAGGTTCACGCTTGGATGC CCCCGGGCAGATTGAAGTGAAAGATGTGACCGAT | 122 |
| 1-3 GSlinker reverse | CTGCAGTGGTAAAGGTTTCTTTCG | 123 |
| 5 GSLinker | AAAGAAACCTTTACCACTGCAGGTGGCGGGGGTAGCGG TGGCGGAGGTTCTGGTGGCGGGGGTAGCGGTGGCGGAG GTTCTGGTGGCGGGGGTAGCCGCTTGGATGCCCCCGGGC A | 124 |
| 7 GSLinker | AAAGAAACCTTTACCACTGCAGGTGGCGGGGGTAGCGG TGGCGGAGGTTCTGGTGGCGGGGGTAGCGGTGGCGGAG GTTCTGGTGGCGGGGGTAGCGGTGGCGGAGGTTCTGGTG GCGGGGGTAGCCGCTTGGATGCCCCCGGGCA | 125 |
| GS L Amp forward | AAAGAAACCTTTACCACTGCAGGT | 126 |
| GS L Amp reverse | TTCAATCTGCCCGGGGGCATCCAA | 127 |

Monovalent and bivalent tandem constructs comprising identical Tn3 scaffolds were recombinantly expressed and purified from *E. coli* as described in Example 2. FIG. 9B depicts an SDS-PAGE analysis of the purified protein preps under reducing and non-reducing conditions.

In order to test the binding efficiencies of the bivalent tandem M13-M13 constructs and compare them to the monovalent M13 scaffold, their competitive inhibition of Murine CD40L binding to Murine CD40 receptor immobilized on a biosensor chip was tested.

Briefly, a fragment of the Murine CD40 receptor in the form of a chimeric fusion with the Fc region of IgG1 was immobilized onto a GLC chip (Bio-Rad) at a density of about 3000 response units. For competition binding assays, 3-fold serial dilutions of monovalent M13 or the M13 tandem bivalent constructs with different linker length were incubated for 20 min with a fixed concentration of *E. coli* produced recombinant Murine CD40L (0.5 μg/ml) in PBS containing 0.1% (v/v) Tween-20 and 0.5 mg/mL BSA. These samples were then injected over the GLC chip at a flow rate of 304/min for 300 seconds and the level of bound CD40L was recorded at a fixed time point within the sensorgram and compared to the corresponding level of bound protein in the absence of any competitor. After each binding measurement, residual CD40L was desorbed from the chip surface by injecting 10 mM glycine-HCl (pH 2.0). Non-specific binding effects were corrected by subtracting sensorgrams from interspots of the chip. $IC_{50}$ values corresponding to the concentrations of Tn3 constructs required to displace 50% of murine CD40L were calculated using GraphPad Prism.

As shown in FIG. 9C, the half maximal inhibitory concentration ($IC_{50}$) for the M13 monomer was 71 nM while the $IC_{50}$ for the bivalent tandem construct C1(M13) was 29 nM. Similar $IC_{50}$ values of 5 or 6 nM were obtained for the bivalent constructs containing longer linkers (constructs C2(M13), C3(M13) and C4(M13), respectively). Due to the concentration of CD40L used in the assay, this is at the lower limit of $IC_{50}$s that can be observed be in this assay. The bivalent constructs all had a lower $IC_{50}$ value compared to the monovalent construct, indicating enhanced binding activity of the bivalent tandem constructs compared to a single M13 Tn3 module. The linker length in these bivalent constructs exhibits some effect on assay potency, with the shortest linker length construct having intermediate potency, while those constructs with linkers of 23 or more amino acids are equivalent in this assay.

To test the activity of the bivalent tandem Tn3 constructs in a cell based activity and compare them to the monovalent M13 scaffold, inhibition of Murine CD40L-induced CD86 expression on B-cells was tested. As a control, the commercially available anti-murine CD40L specific antibody (MR1) was tested in parallel.

The assay utilizes PBMC prepared from blood from healthy volunteers. Briefly, freshly drawn blood was collected in BD Vacutainer® CPT™ Cell Preparation Tube with heparin. After centrifugation, the cell layer containing PBMCs was collected and washed twice with PBS and once with RPMI 1640 medium. The cells were resuspended in complete RPMI 1640 medium (supplemented with 10% heat-inactivated fetal bovine serum, 1% P/S) at a concentration of $5 \times 10^6$ cells/ml.

The murine CD40L-expressing Th2 cell line D10.G4.1 was washed and resuspended in complete RPMI 160 medium at a concentration of $1 \times 10^6$ cells/ml.

M13, M13-M13 tandem bivalent constructs C1-C4, or MR1 antibody (BioLegend Cat. No: 106508) were serially diluted (1:3) in complete RPMI 1640 medium. A 50 μl sample of each dilution was added to wells in a 96 well U bottom tissue culture plate. Each well then received 50 nl of D10.G4.1 cells ($5 \times 10^4$), and after mixing, plates were incubated at 37° C. for 1 hr. 100 μl of resuspended PBMC ($5 \times 10^5$ cells) were then added to each well and incubated at 37° C. for 20-24 hrs.

PBMC were collected and stained with APC-anti-human CD86 (BD bioscience, Cat #555660) and FITC-anti-human CD19 (BD bioscience, Cat #555412) in FACS buffer (PBS pH 7.4, 1% BSA, 0.1% sodium azide) at 4° C. for 30 min in the dark. After two washes in FACS buffer, samples were then analyzed by FACS LSR11 (Becton Dickinson). CD86 expression on CD19 gated B cells was evaluated. The analysis of CD86 expression as a function of test protein was performed using GraphPad Prism software.

As shown in FIG. 9D, the bivalent M13-M13 tandem constructs all inhibited CD86 expression with an $IC_{50}$ of 100 to 200 μM, comparable to the $IC_{50}$ of the MR1 antibody (100 μM) and about 3 logs more potent than the M13 monovalent scaffold itself. In contrast to the biochemical assay, no effect of linker length was observed in this cell based assay, and bivalent constructs with linkers ranging from 13 to 43 amino acids in length all show equivalent ability to enhanced potency relative to the monovalent protein.

Example 8

Expression of Bi-Specific Tandem Scaffolds

To generate bispecific Tn3 constructs with specificity for TRAIL R2 and Human CD40L (HuCD40L), two Tn3 modules, one with specificity for TRAIL R2 (clone 1E11) and one with specificity for human CD40L (clone 79), were fused together with variable length linkers separating the two modules (TABLE 3 and TABLE 15). The sequence of the clone 79 protein (SEQ ID NO: 184) corresponds to the sequence of a Tn3 module wherein the BC, DE, and EF loops have been replaced with alternative loops corresponding to SEQ ID NOs: 101, 105, and 111, respectively. Expression constructs for the tandem bispecific scaffolds containing linkers with 1 and 3 Gly$_4$Ser (GS) repeats (constructs C6 and C8, respectively) were generated as described in Example 7 except that plasmids carrying the Tn3 variants A1 and 79 were used initially as PCR templates. Construct C5 (containing a short linker derived from the natural sequence linking the second and third FnIII domains in human tenascin C, which may be considered part of the A beta strand of the third FnIII domain although it is not required for scaffold binding) and construct C7 were generated in a similar way to C6 and C8, using the additional primers listed in TABLE 16, except that "0 GSlinker reverse" was used in place of "1-3 GSLinker reverse" for C5.

TABLE 15

Names, valencies, and specificities of expressed Tn3-containing proteins

| Name | Number of Tn3 modules | Linker length | Specificity |
|---|---|---|---|
| A1 (1E11) | 1 | N/A | TRAIL R2 |
| 79 (79) | 1 | N/A | HuCD40L |
| C5 (1E11 & 79) | 2 | 8 | TRAIL R2 + HuCD40L |
| C6 (1E11 & 79) | 2 | 13 | TRAIL R2 + HuCD40L |
| C7 (1E11 & 79) | 2 | 18 | TRAIL R2 + HuCD40L |
| C8 (1E11 & 79) | 2 | 23 | TRAIL R2 + HuCD40L |

TABLE 16

Additional Primer sequences used in the construction of bispecific tandem constructs

| Sequence Name | Sequence | SEQ ID NO |
|---|---|---|
| 0 GSLinker | AAAGAAACCTTTACCACCACGCGTTTGGATGCCCCCG GGCAGATTGAAGTGAAAGATGTGACCGAT | 128 |
| 0 GSlinker reverse | CGTGGTGGTAAAGGTTTCTTTCG | 129 |
| 2 GSLinker | AAAGAAACCTTTACCACTGCAGGTGGCGGAGGTTCA GGTGGCGGAGGTTCACGCTTGGATGCCCCCGGGCAG ATTGAAGTGAAAGATGTGACCGAT | 130 |

Monovalent as well as tandem bispecific Tn3 scaffolds were recombinantly expressed in *E. coli* media as described in Example 2. Expression levels of the soluble constructs were analyzed using SDS-PAGE. FIG. 10 demonstrates acceptable expression levels for the constructs tested.

Example 9

Specific Binding of BiSpecific Tandem Scaffolds

Figure 11A:
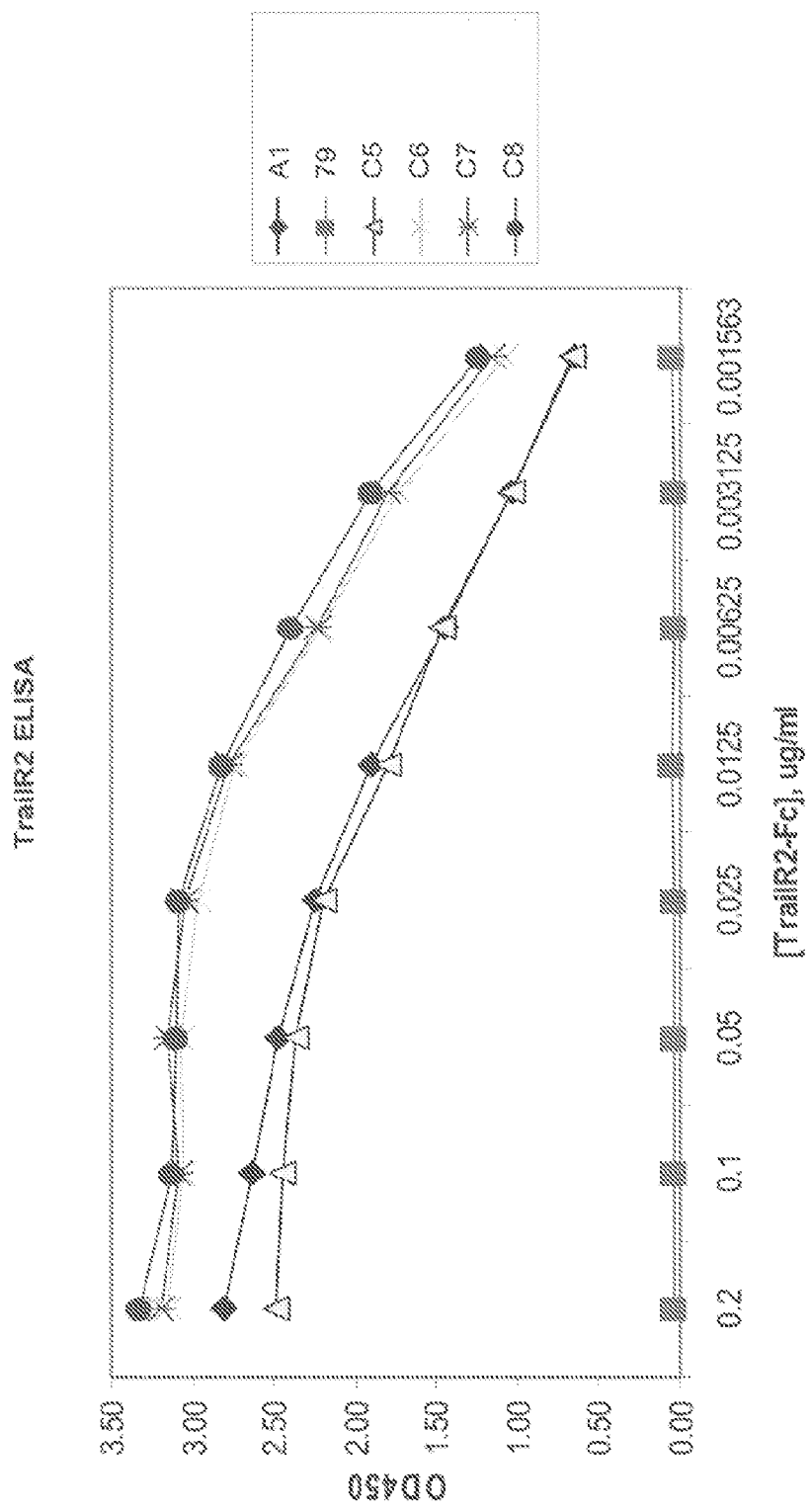
FIG. 11A shows the binding of bispecific Tn3 scaffolds to TRAIL R2 assayed using capture ELISA.

To measure the binding of bispecific Tn3 constructs to CD40L and TRAIL R2, a capture ELISA assay was employed. Briefly, 8× His-tagged protein constructs ("8× His" disclosed as SEQ ID NO: 211): A1, 79, C5, C6, C7 or C8 (see TABLE 15 for details) were captured from *E. coli* media onto anti-His antibody coated wells as follows. A 96-well MaxiSorb plate was coated with Qiagen anti-His antibody at 2 µg/ml overnight. The coated plate was blocked with PBS containing 0.1% v/v Tween-20 and 4% w/v skim milk powder (PBST 4% milk) for 1.5 hours. The coated plate was washed with PBST and diluted bacterial media (diluted 30-fold) containing soluble expressed proteins was added and plates were incubated at room temperature for 2 hours. After washing with PBST, wells containing the captured constructs were incubated for 1.5 hours with varying concentrations of either biotinylated TRAIL R2 (FIG. 11A) or a complex generated by preincubation of *E. coli* produced His-tagged HuCD40L with biotinylated anti-His antibody (FIG. 11B). After washing with PBST, bound TRAIL R2 or HuCD40L/anti-His antibody complex was detected with streptavidin-horseradish peroxidase (RPN1231V; GE Healthcare; 1000× working dilution) for 20 min., washing with PBST, and detecting colorimetrically by addition of TMB substrate (Pierce). The absorbance was read at 450 nm.

Binding of the bispecific tandem TRAIL R2-HuCD40L-specific scaffolds to TRAIL R2, and binding of the bispecific tandem TRAIL R2-HuCD40L-specific scaffolds to HuCD40L are depicted in FIG. 11A and FIG. 11B, respectively. Bispecific tandem scaffolds, designated C5 to C8, comprising a TRAIL R2 specific Tn3 domain fused to a HuCD40L specific Tn3 domain bound TRAIL R2 and HuCD40L; however, the monomeric/monospecific Tn3 constructs A1 and 79 bound either TRAIL R2 or HuCD40L according to their known specificities but not both targets.

Simultaneous binding of tandem TRAIL R2-HuCD40L-specific constructs to TRAIL R2 and HuCD40L was determined using an AlphaScreen™ assay. Dilutions of *E. coli* media containing proteins A1, 79, C5, C6, C7 and C8 were incubated with 10 nM TRAIL R2-Fc fusion protein, 50 nM biotinylated HuCD40L (produced in *E. coli*), streptavidin AlphaScreen donor beads (0.02 mg/ml) and Protein A AlphaScreen acceptor beads (0.02 mg/ml) in PBS+0.01% Tween+0.1% BSA. Samples were incubated 1 h in the dark prior to reading in a PerkinElmer Envision reader. The donor bead population was excited with a laser at 680 nm causing the release of singlet oxygen. Singlet oxygen has a limited lifetime allowing it to travel up to 200 nm by diffusion before falling back to ground state. Singlet oxygen excites the acceptor beads causing light emission between 520-620 nm which is measured by the Envision reader. Only when donor and acceptor beads are in proximity is a signal generated. Thus, an increase in signal is observed when the two bead types are brought together by molecules interacting with the two targets simultaneously. In the absence of binding to either target no signal should be detected.

Figure 12:
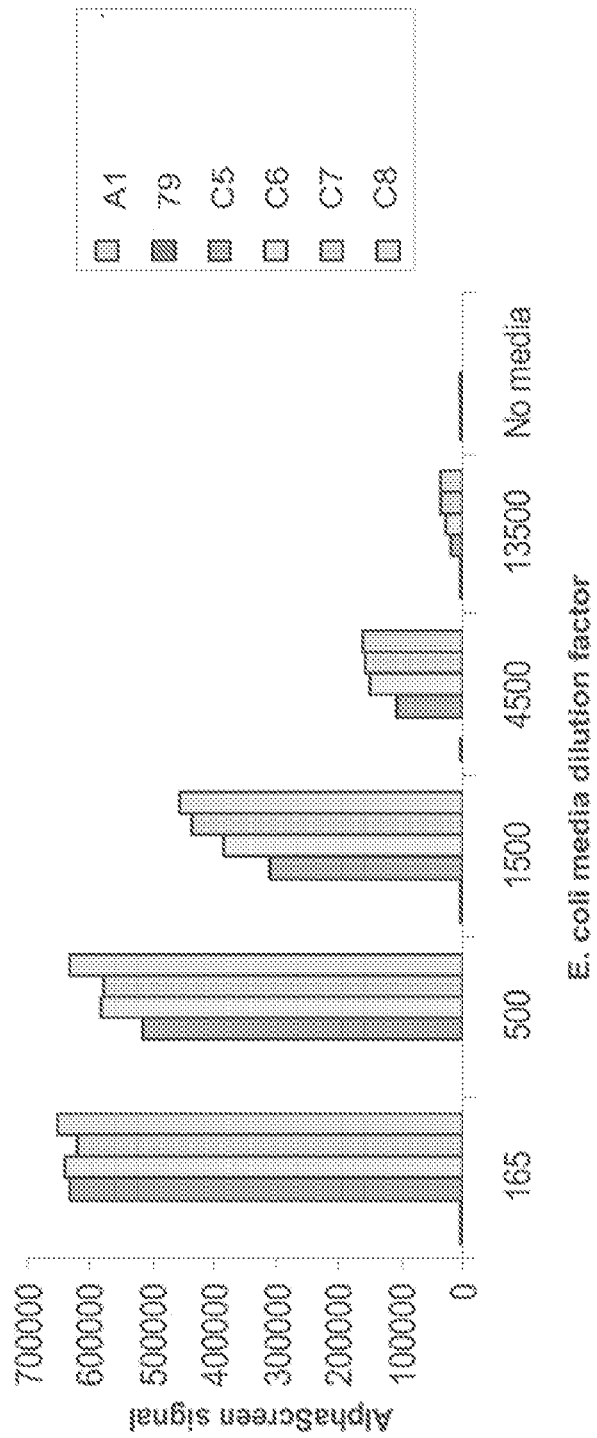
FIG. 12 shows the simultaneous binding of bispecific tandem Tn3 scaffolds C5, C6, C7, and C8 to TRAIL R2 and CD40L assayed using an AlphaScreen™ assay.

As shown in FIG. 12, the tandem bispecific constructs simultaneously bound TRAIL R2 and HuCD40L generating a strong AlphaScreen signal; however, the monovalent Tn3 scaffolds, A1 and 79, did not generate a signal indicating they could not bring donor and acceptor beads in proximity by simultaneously binding both targets.

Example 10

Increased Stability of Tn3 Scaffolds Having 9 Amino Acid Length FG Loop

Figure 13:
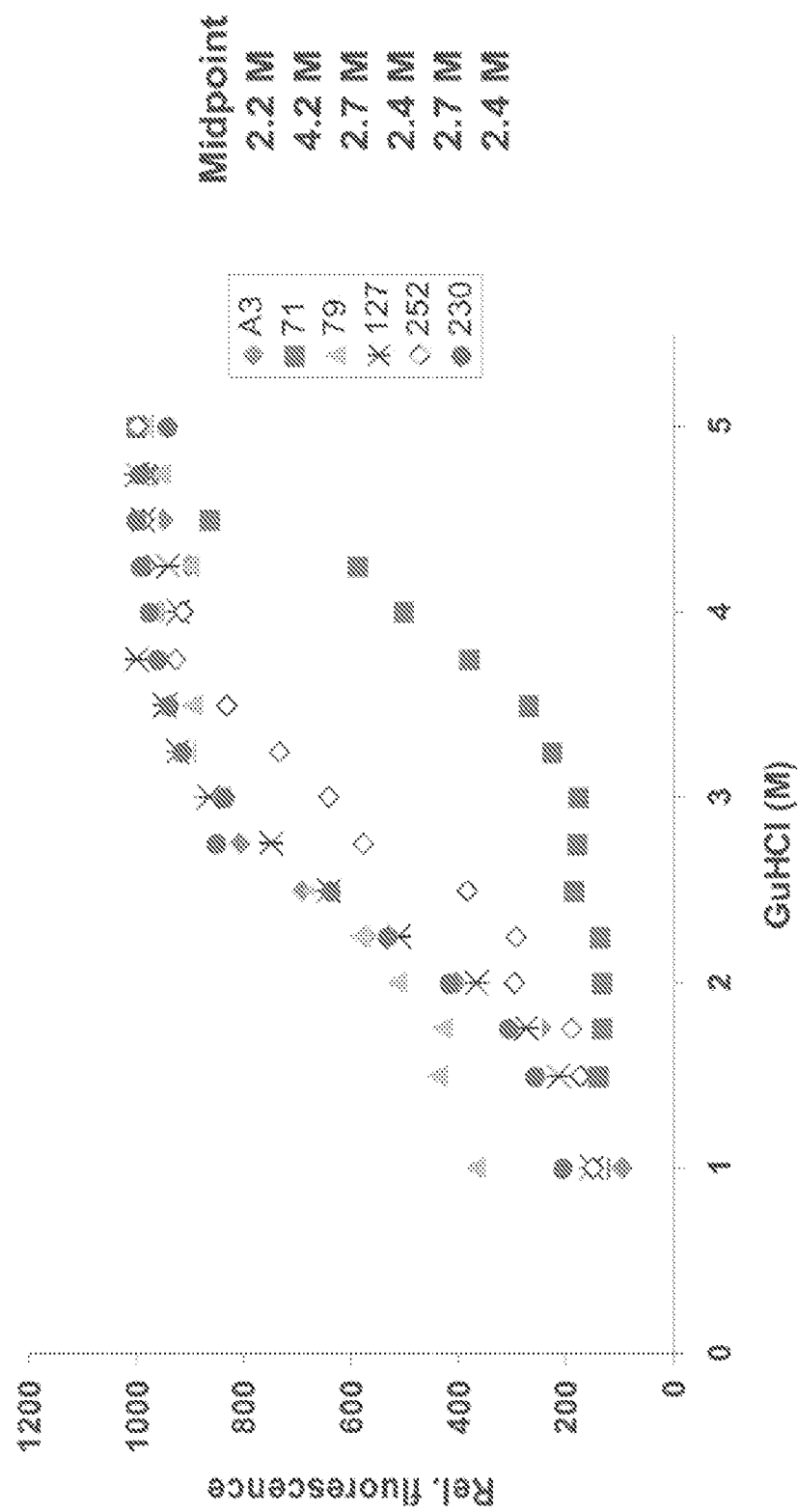
FIG. 13 shows the stability of Tn3 scaffolds in the present of guanidine-HCl. $C_m$ (midpoint value) for each tested scaffold is indicated.

To measure the effect of FG loop length on Tn3 stability, unfolding of six HuCD40L-specific Tn3 scaffolds by guanidine hydrochloride (GuHCl) at pH 7.0 was assessed by intrinsic tryptophan fluorescence. These Tn3 monomeric scaffolds contained FG loop lengths of 9, 10 or 11 amino acids. Samples of 0.05 mg/mL Tn3 scaffold containing different concentrations of guanidine hydrochloride were prepared in 50 mM sodium phosphate pH 7.0. Fluorescence emission spectra were acquired on a Horiba Fluoromax-4 spectrofluorometer at an excitation wavelength of 280 nm. Relative fluorescence emission intensity at 360 nm was plotted as a function of GuHCl concentration for each protein. Each scaffold contained unique BC, DE, and FG loop sequences. Clones A3 (SEQ ID NO:185; note that the A3 monomeric scaffold in this example is distinct from the construct designated as A3 as provided in Table 3), 71 (SEQ ID NO: 186), 79 (SEQ ID NO: 184), 127 (SEQ ID NO: 187), 252 (SEQ ID NO: 188), and 230 (SEQ ID NO: 189) were more than 50% unfolded in 3.0M GuHCl at pH 7.0, which is the GuHCl concentration required to effect 50% unfolding ($C_m$) of parental Tn3. $C_m$ values for clones A3, 79, 127, 252, and 230 were 2.2M, 2.7M, 2.4M, 2.7M, 2.4M, respectively. The FG loop lengths for these clones is 11, 11, 11, 10 and 11 amino acids respectively, while the FG loop length for parental Tn3 is 10 amino acids. Surprisingly, clone 71, the only variant having an FG loop length of 9 amino acids, exhibited a Cm of 4.2M, a significantly higher stability than parental Tn3 scaffold or the other five variants tested. Results are shown in FIG. 13.

Figure 14:
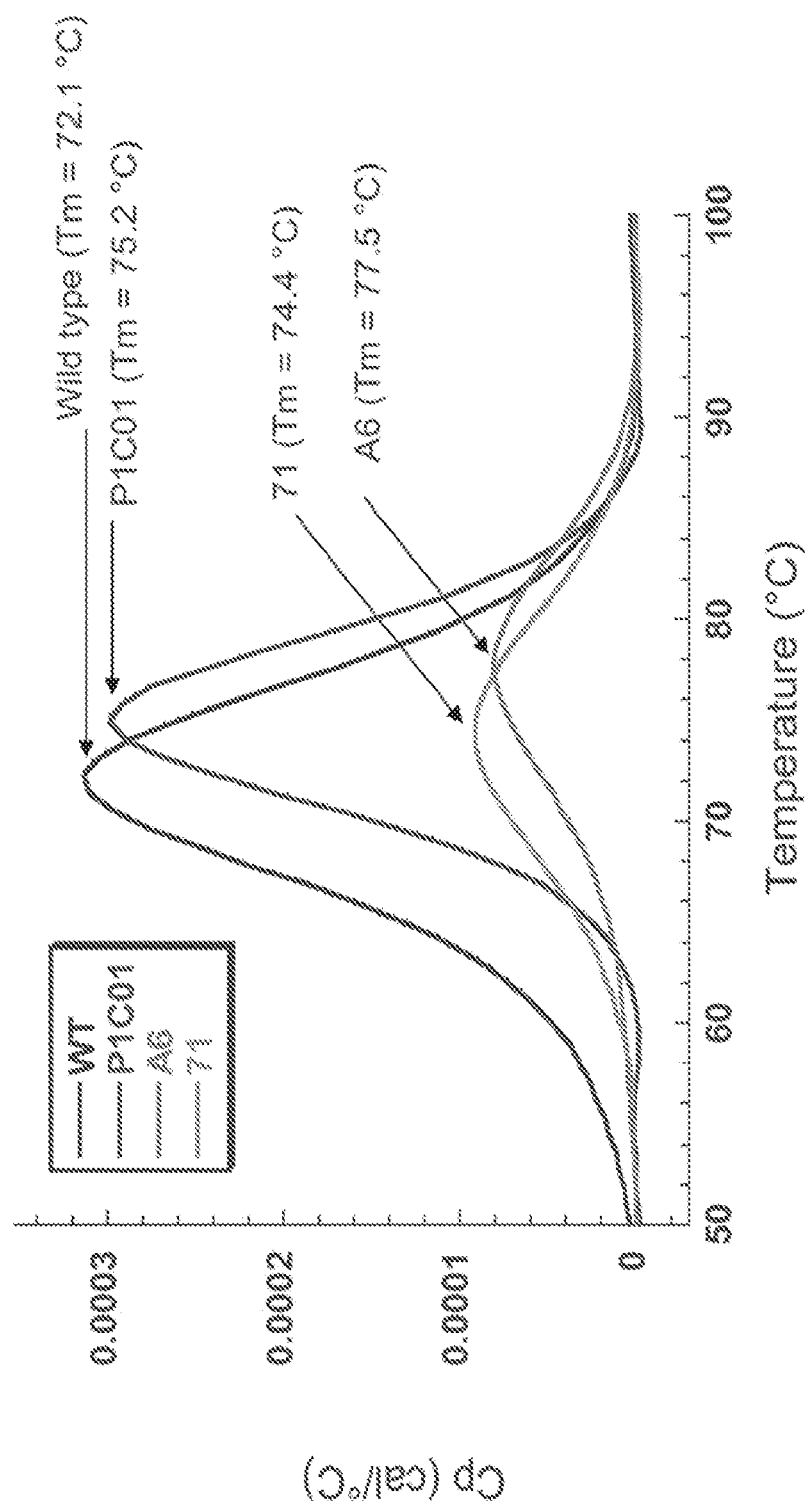
FIG. 14 shows the thermostability of three different Tn3 scaffolds with different loop sequences, but the same length FG loop (nine amino acids) compared to the parental Tn3 scaffold which has a longer FG loop analyzed by differential scanning calorimetry (DSC).

To determine whether the enhanced stability of Tn3 clone 71 was intrinsic to its sequence, or a consequence of the shortened FG loops length, this clone and two additional monomeric Tn3 scaffold proteins, (A6 (SEQ ID NO: 190; note that the A6 monomeric scaffold in this example is distinct from the construct designated A6 as provided in Table 3) and P1C01 (SEQ ID NO: 191)) with an FG loop length of 9 amino acids (but different BC, DE and FG loop sequences) were analyzed by differential scanning calorimetry (DSC) and compared to the parental Tn3 scaffold which contains an FG loop that is 10 amino acids long. Tn3 protein samples at 1 mg/mL in PBS pH 7.2 were analyzed. In all cases, the midpoint of thermal unfolding was higher for clones with the 9 residue FG loops as compared to parental (WT) Tn3, which has a 10 residue FG loop. Thermal unfolding was reversible, or partially reversible (clone A6) as evidenced by superimposable thermograms when the same sample was cooled and reheated. As shown in FIG. 14, the melting temperature ($T_m$) for parental Tn3 was 72.1° C., for P1C01 the Tm was 75.2° C., for A6 the $T_m$ was 77.5° C., and for 71 the $T_m$ was 74.4° C.

Figure 15:
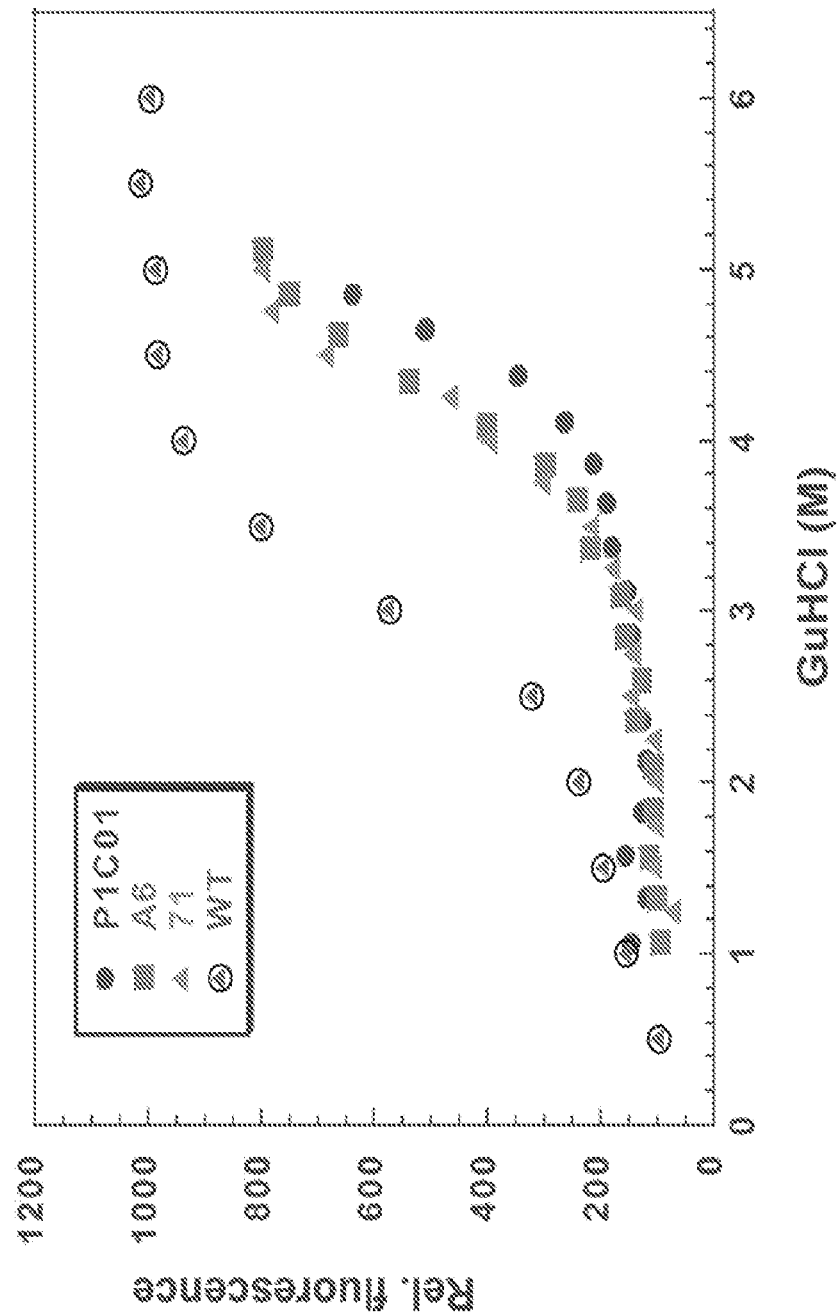
FIG. 15 shows the increase in stability in the presence of guanidine-HCl of Tn3 scaffolds having a nine amino acid length FG loop (P1C01, A6, and 71) compared to the parental (WT) Tn3 scaffold.

These findings were corroborated by testing the same Tn3 protein variants in a guanidine hydrochloride stability experiment. Unfolding of parental (WT) Tn3, P1C01, A6, and 71 by guanidine hydrochloride (GuHCl) at pH 7.0 was assessed by intrinsic tryptophan fluorescence as described above. As shown in FIG. 15, in agreement with the DSC data in FIG. 14, Tn3 clones A6, 71, and P1C01 all have midpoints of unfolding at significantly higher GuHCl concentrations than parental (WT) Tn3 scaffold, indicating the stability of Tn3 proteins having FG loops that are 9 amino acids in length, i.e. shorter than that in the parental Tn3 scaffold, is enhanced.

Example 11

Stability Analysis of FG Loop Length

As described above, preliminary analysis indicated that Tn3 molecules having an FG loop length of 9 residues are significantly more stable than those having longer FG loops. In these studies, we conducted stability analysis on a set of random Tn3s to assess the effect of FG loop length on thermal stability.

A Tn3 library was subcloned into the pSEC expression vector. This library codes for Tn3s with BC, DE, and FG loops of varying sequence as well as varying but defined length. The FG loop, which is the focus of these studies, can be 9, 10, or 11 residues long. The BC loop may be 9, 11, or 12 residues long. The DE loop in this library has a fixed length of 6 residues. The subcloned library was used to transform DH5α competent cells, from which a plasmid pool was purified and used to transform BL21(DE3) cells. BL21 colonies were sequenced to identify 96 clones which coded for full-length Tn3s. The final 96 clones were grown in a 96 deep-well plate at a 500 µl scale using standard Magic Media expression (37° C. shaking for 24 hours post-inoculation) and analyzed on SDS-PAGE. 29 random clones having moderate-to-high expression levels were scaled up to 50 mL scale expression and purified using standard immobilized metal affinity chromatography. Identities of all proteins were confirmed by mass spectrometry.

The random clones were analyzed for stability by DSC. Briefly, DSC measurements were conducted on a VP-Capillary DSC (MicroCal). Proteins were exchanged into PBS (pH 7.2) through extensive dialysis, and adjusted to a concentration of 0.25-0.5 mg/ml for DSC analysis. Samples were scanned from 20-95° C. at a scan rate of 90° C./hour, with no repeat scan. The results are shown in TABLE 17.

TABLE 17

Comparison of $T_m$ values of Tn3s with FG9 vs FG10/11

| FG9 | $T_m$(° C.) | FG10/11 | $T_m$(° C.) |
|---|---|---|---|
| A1 | 64.8 | E12 (FG10) | 65.0 |
| A3 | 71.8 | F5 (FG10) | 60.0 |
| B2 | 70.0 | G1 (FG11) | 64.3 |
| B4 | 69.4 | G4 (FG11) | 67.6 |
| C5 | 66.6 | G8 (FG11) | 64.2 |
| C7 | 66.0 | H6 (FG11) | 70.3 |
| C8 | 64.1 | H7 (FG11) | 71.7 |
| C11 | 59.5 | H8 (FG10) | 61.9 |
| D1 | 73.7 | H9 (FG10) | 59.5 |
| D8 | 72.1 | H10 (FG11) | 67.6 |
| D10 | 65.6 | H11 (FG11) | 63.7 |
| D11 | 65.6 | H12 (FG11) | 65.6 |
| D12 | 66.4 | | |
| E1 | 75.0 | | |
| E3 | 66.0 | | |
| E9 | 75.3 | | |
| E11 | 61.9 | | |
| n = 17 | | n = 12 | |
| Mean | 67.9 | Mean | 65.1 |

In this study, the thermal stability of Tn3s with loop length FG9 or FG10 and 11 was compared. The trend shows that Tn3 domains having an FG loop of length 9 are more thermostable than those with loop length FG10 or 11. A control, the wild-type Tn3 domain (with an FG loop of 10 residues) had a Tm of 72° C. when run in parallel with the above samples. The range of $T_m$ values seen with each loop length indicates that other factors also play a role in determining Tn3 domain thermostability.

Example 12

Generation and Characterization of a Trispecific Tn3

Figure 16:
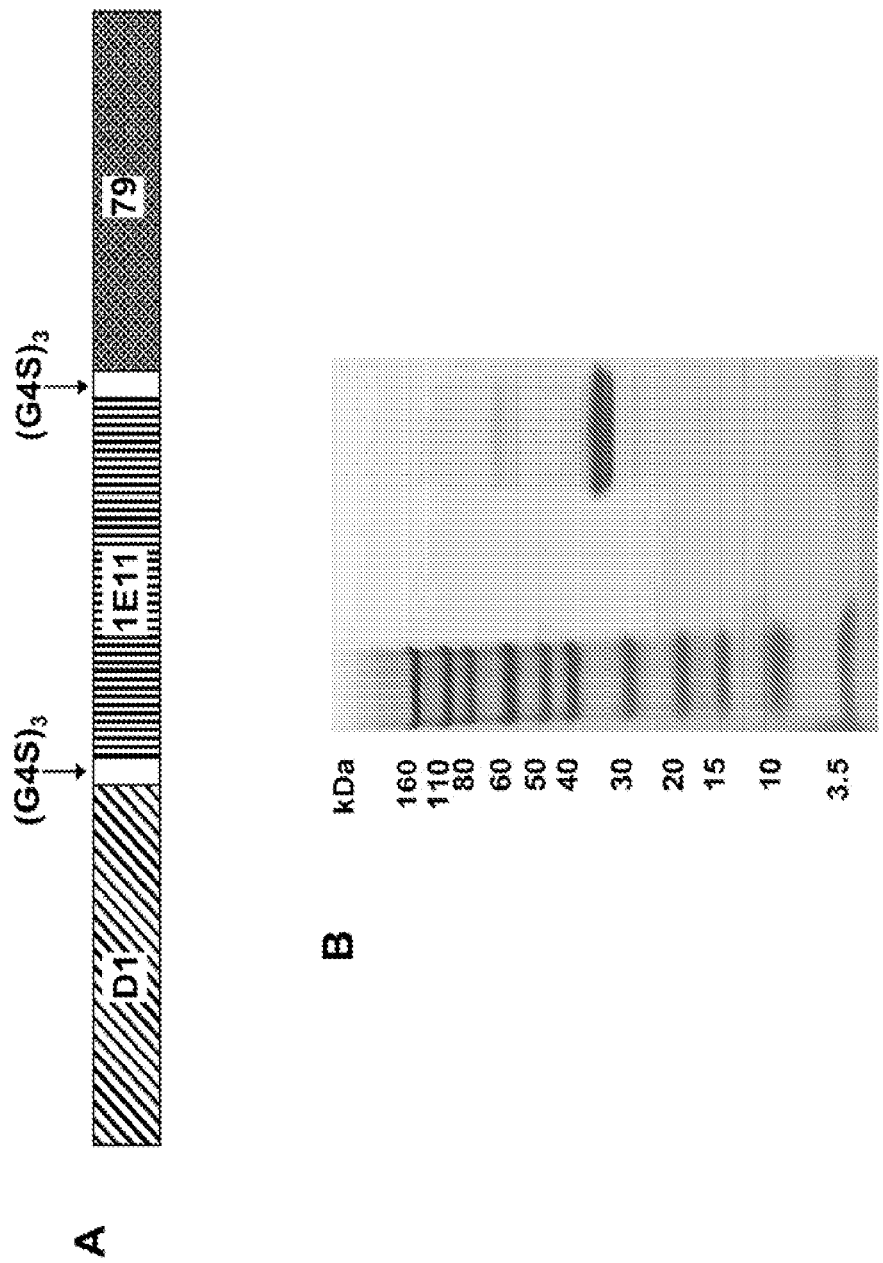
FIG. 16A shows a schematic representation and expression of a trispecific/trivalent Tn3 scaffold. The D1-1E11-79 scaffold contains a Synagis®-binding domain (D1), followed by a TRAIL R2-Fc binding domain (1E11), and a C-terminal Tn3 domain specific for human CD40L (79). A flexible (Gly$_4$Ser)$_3$ linker (SEQ ID NO: 214) separates each domain.
FIG. 16B shows a SDS-PAGE (4-12% Bis-Tris) gel of the expressed and purified D1-1E11-79 scaffold. The expected molecular weight of this construct is approximately 34,081 Dalton.

In these experiments, a Tn3 molecule having binding specificity for three different targets was generated and characterized. D1, the Tn3 domain specific for the Synagis® antibody, was linked to 1E11, a Tn3 domain specific for TRAIL receptor 2, and 79, a Tn3 domain specific for CD40L, respectively (FIG. 16A). The construct was expressed in BL21(DE3) E. coli cells and purified using standard methods (see FIG. 16B).

Figure 17A:
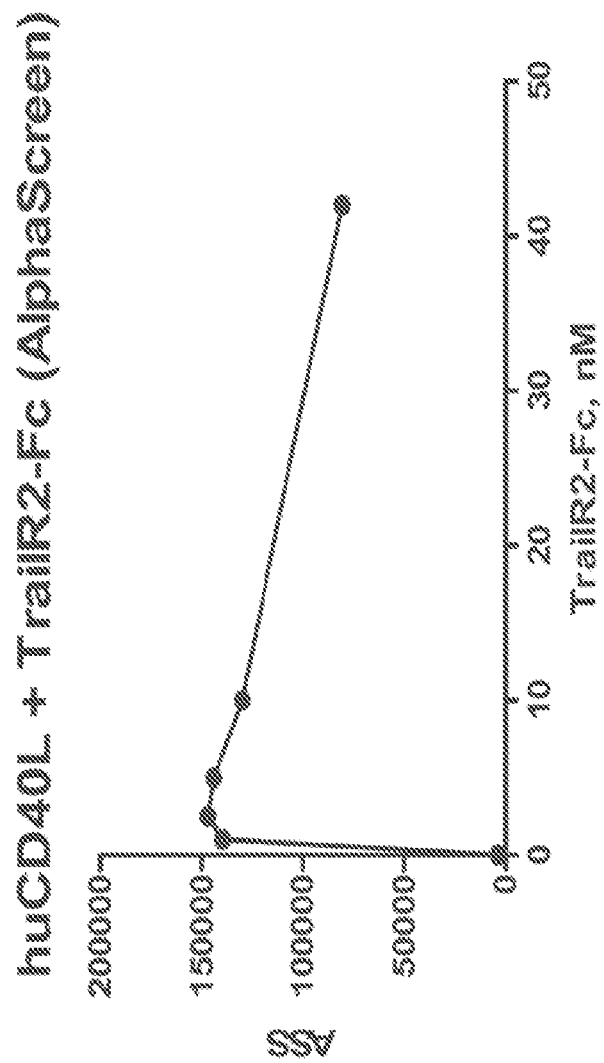
FIG. 17A shows the simultaneous binding of the trispecific/trivalent Tn3 scaffold D1-1E11-79 to huCD40L and TRAIL R2-Fc using AlphaScreen binding analysis. AlphaScreen signal (ASS) shown as a function of TrailR2-Fc concentration.
Figure 18:
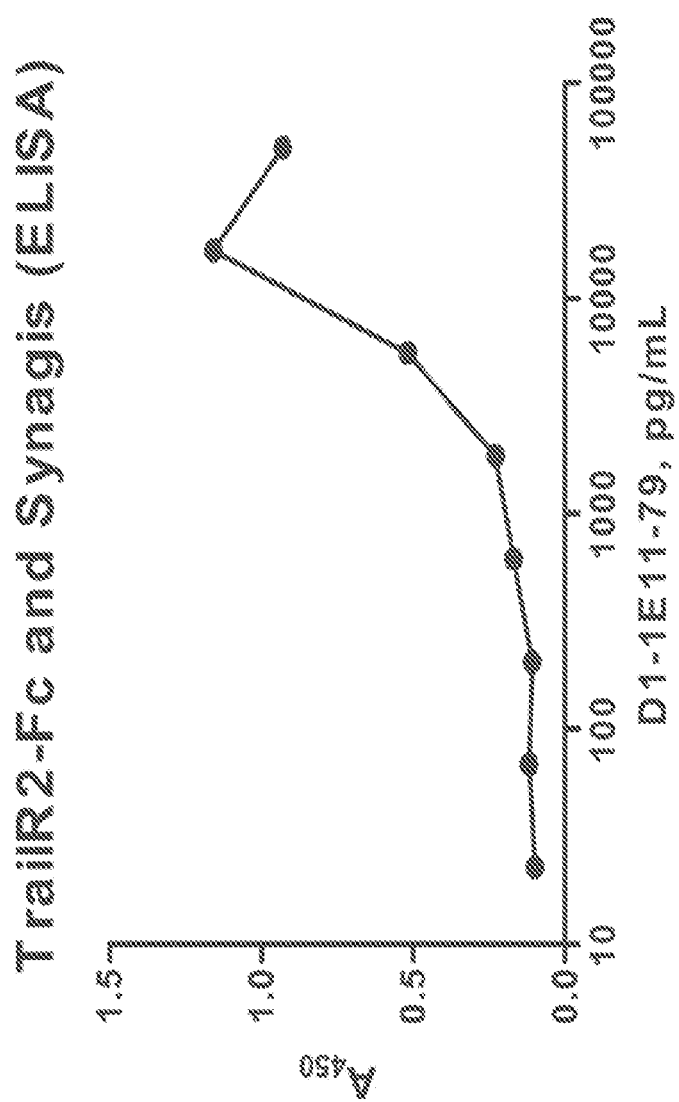
FIG. 18 shows the simultaneous binding of the trispecific/trivalent Tn3 scaffold D1-1E11-79 to TRAIL R2-Fc and Synagis® using ELISA.

To confirm that the trispecific constructs were capable of binding pairs of all three targets simultaneously, both AlphaScreen and ELISA experiments were conducted. For AlphaScreen experiments, trispecific Tn3, subsets of two of the three total target molecules (one biotinylated and the other containing an antibody Fc region), Protein A donor beads, and streptavidin acceptor beads were combined in a 384-well white Optiplate, as described above. AlphaScreen signal can only be observed when the streptavidin donor bead and Protein A acceptor bead are within proximity of each other (200 nm of each other), which in this assay is accomplished through bridging by the trispecific molecule. The ability of D1-1E11-79 to simultaneously bind huCD40L and TRAIL R2-Fc (FIG. 17A), and to simultaneously bind huCD40L and Synagis® (FIG. 17B) was confirmed by AlphaScreen as follows: in a 384-well white Optiplate, the following components were combined in a total volume of 30 20 mM purified D1-1E11-79, 50 mM biotinylated-huCD40L, (0, 1, 2.5, 5, 10, or 42 nM) TrailR2-Fc (FIG. 18A) or (0, 1, 2.5, 5, 10, or 42 nM) Synagis (FIG. 18B), 5 µl each of 1/50 dilutions of AlphaScreen Protein A acceptor beads and streptavidin donor beads. After 1 hour incubation in the dark, the plate was read on an Envision plate reader in AlphaScreen mode.

Because Synagis® and TRAIL R2-Fc both contain an Fc domain, the AlphaScreen assay could not be used to demonstrate simultaneous binding of these molecules to the trispecific construct. In place of this, an ELISA experiment was conducted. MaxiSorp plates were coated with TRAIL R2-Fc (100 µl at 1 µg/ml), blocked with 4% milk, then followed by addition of varying concentrations of the trispecific construct. Biotinylated Synagis, the second target ligand, was added and detected by the addition of HRP-streptavidin (FIG. 18). of D1-1E11-79 was also shown to be capable of binding both TRAIL R2-Fc and Synagis® simultaneously, as indicated by the ELISA results in FIG. 18. Therefore we can conclude that this construct can bind all three pairs of its targets simultaneously.

Example 13

Lead Isolation

The first step in developing an agonist Tn3 is to isolate a Tn3 monomer that can bind to TRAIL R2 and when linked into a multivalent format can bind two or more TRAIL R2 extracellular domains in a way that engages the apoptotic pathway. Since not all binders may act as agonists, we decided to first isolate a panel of binders and then screen for agonism in a secondary in vitro cell killing assay. We first panned a large phage displayed library of Tn3's with variation in the BC, DE, and FG loops on recombinant TRAIL R2-Fc to isolate an initial panel of binders. The Tn3 scaffold chosen as the basis for this library was not a native $3^{rd}$ FnIII domain from tenascin C but a version that had an engineered disulfide to improve stability. An in house Tn3/gene 3 fused phage display library was constructed containing randomization in the BC, DE, and FG loops. Multiple binders were found by a phage ELISA in which TRAIL R2 was directly coated on a plate and binding of 1:3 diluted phage in PBS+0.1% Tween 20 (PBST) 1% milk was detected by anti-M13-peroxidase conjugated antibody (GE Healthcare Biosciences, Piscataway, N.J.). A majority of the binders had an undesirable free cysteine in one of the loops and were not chosen for further study. A subset of the clones lacking an unpaired cysteine were cloned into expression vectors generating either an Fc fusion or antibody-like construct (FIG. 1) and tested in the tumor cell line H2122 for cell killing (data not shown). Although the Fc fusion format failed to kill cells regardless of its fused Tn3, the antibody-like format did elicit a response for more than one binder.

Example 14

Affinity Maturation

Clone 1C12 (SEQ ID NO: 132) (see FIG. 19) showed the best cell killing in the initial screening assays and was therefore chosen for affinity maturation. Affinity maturation was performed by saturation mutagenesis of portions of the loops using either Kunkel mutagenesis or PCR with oligonucleotides containing randomization, assembly, and ligation into the phage display vector. Round one and three consisted of saturation mutagenesis in parts of the BC and FG loops respectively and round 2 combined saturation mutagenesis of parts of all three loops separately, panning, gene shuffling, and then panning of the shuffled mutants to obtain the highest affinity output clone. Pools of affinity matured clones were recovered after panning by PCR directly from the phage or by prepping the single stranded DNA using a Qiagen kit (Qiagen, Valencia, Calif.) and then PCR. PCR products were digested NcoI to KpnI (New England Biolabs, Ipswich, Mass.) and cloned into our in house expression vector pSEC. The clones were expressed in MagicMedia (Invitrogen, Carlsbad, Calif.) and run on a gel to verify that expression did not differ greatly between clones. Improved clones were identified by a competition ELISA in which plates were coated with tetravalent, antibody-like 1C12 (SEQ ID NOs: 154 and 155), and the inhibition in binding of 0.75 nM TRAIL R2 biotin in the presence of dilutions of Tn3 in MagicMedia was measured using streptavidin-horseradish peroxidase (GE Healthcare Biosciences, Piscataway, N.J.). TMB (KPL, Gaithersburg, Md.) was added and neutralized with acid. Absorbance was read at 450 nm.

Figure 19:
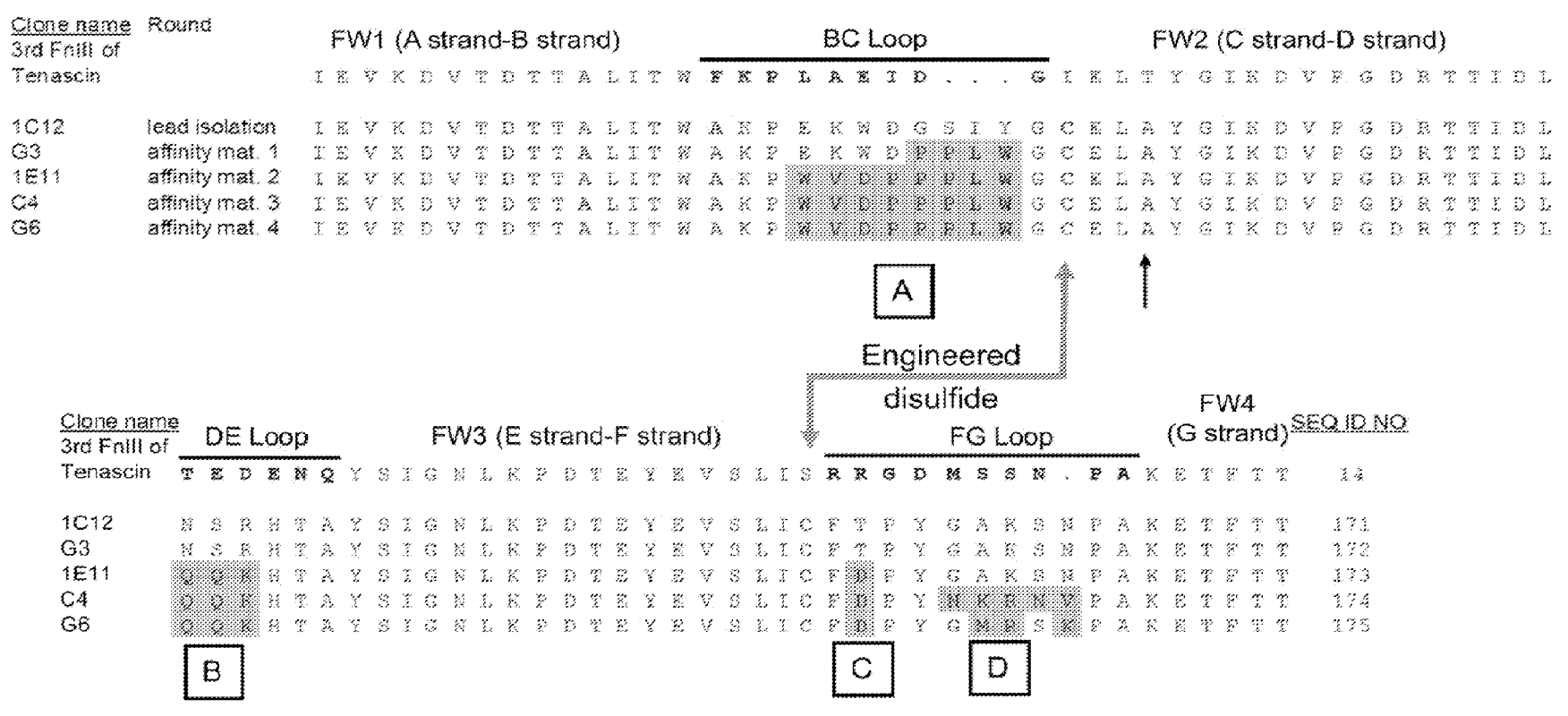

Affinity measurements were performed on the ProteOn XPR36 protein interaction array system (Bio-Rad, Hercules, Calif.) with GLC sensor chip at 25° C. ProteOn phosphate buffered saline with 0.005% Tween 20, pH 7.4 (PBS/Tween) was used as running buffer. TRAIL R2 was immobilized on the chip and a two-fold, 12 point serial dilution of the Tn3 binders (1C12 (SEQ ID NO: 132), 1E11 (SEQ ID NO: 134), G3 (SEQ ID NO: 133), C4 (SEQ ID NO: 135), and G6 (SEQ ID NO: 138)) were prepared in PBS/Tween/0.5 mg/ml BSA, pH 7.4 at starting concentrations ranging from 36 µM to 700 nM. Samples of each concentration were injected into the six analyte channels at a flow rate of 30 µl/min. for 300 seconds. The $K_d$ was determined by using the equilibrium analysis setting within the ProteOn software. The sequences of the best clones from each round are shown in FIG. 19. The total improvement in affinity after three rounds of affinity maturation was almost two orders of magnitude with the best clones having affinities in the 40-50 nM range (TABLE 18).

TABLE 18

Equilibrium binding constants of monomeric best clones from affinity maturation of lead clone 1C12 as measured by Surface Plasmon Resonance (SPR).

| Round | Clone | $K_d$(nM) | Fold Improvement |
|---|---|---|---|
| Lead isolation | 1C12 | 4130 ± 281 | |
| Affinity maturation 1 | G3 | 422 ± 45 | 10 |
| Affinity maturation 2 | 1E11 | 103 ± 9 | 40 |
| Affinity maturation 3 | C4 | 50 ± 2 | 83 |
| Affinity maturation 3 | G6 | 43 ± 2 | 96 |

Example 15

Effect of Tn3 Affinity on Potency in Antibody-Like Format

In order to assess the effect of affinity of the individual TN3 subunit on potency, all of the clones in TABLE 18 were reformatted into the antibody-like construct depicted in FIG. 1. To express the antibody-like proteins, 293F cells were transiently transfected with the appropriate expression constructs. Harvests of supernatant were performed on days 6 and 10 and the protein was purified by protein A affinity chromatography. All purified proteins were analyzed by SDS-PAGE on NuPage Novex 4-12% bis tris gels in MES buffer without reducing agent, and were visualized using Simply-Blue SafeStain (Invitrogen, Carlsbad, Calif.).

Size exclusion chromatography was also used to analyze purified proteins, and where necessary, aggregated material was removed on either a Superdex 75 10/300GL or Superdex 200 10/300GL column (GE Healthcare, Piscataway, N.J.), to a final level below 10% of total protein. An Acrodisc unit with a Mustang E membrane (Pall Corporation, Port Washington, N.Y.) was used as indicated by the manufacturer to remove endotoxin from bacterially expressed protein preparations.

H2122 cells were then tested for sensitivity to the agonistic antibody-like constructs using a CellTiter-Glo cell viability assay. In this assay, luminescence is directly proportional to the levels of ATP within a given well of a 96 well plate, which in turn is directly proportional to the amount of metabolically active viable cells. For the H2122 cell line, cells were plated in 96 well plates at a density of 10,000 cells/well in 75 µl of complete medium (RPMI 1640 medium supplemented with 10% FBS). Following overnight incubation at 37° C., media was supplemented with 25 µl of additional media containing a serial dilution of TRAIL R2-specific or negative control proteins. All treatments were performed in duplicate wells. Commercially available TRAIL ligand (Chemicon/Millipore, Billerica, Mass.) was used as a positive control for TRAIL receptor-induced cell death.

After 72 hours, the CellTiter-Glo kit was used according to the manufacturer's instructions. Assay luminescence was measured on an Envision Plate reader (PerkinElmer, Waltham, Mass.). Inhibition of cell viability was determined by dividing the luminescence values for treated cells by the average luminescence for untreated viable cells.

Figure 20:
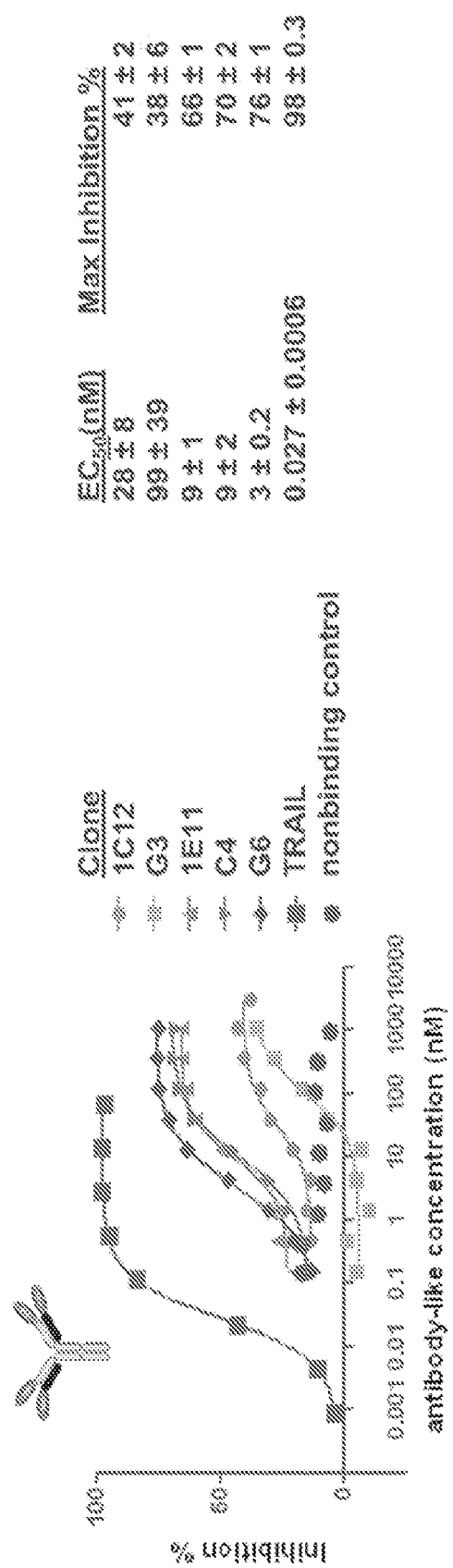
FIG. 20 shows a CellTiter-Glo cell viability assay of the 1C12 clone and its affinity matured derivatives.
Figure 21:
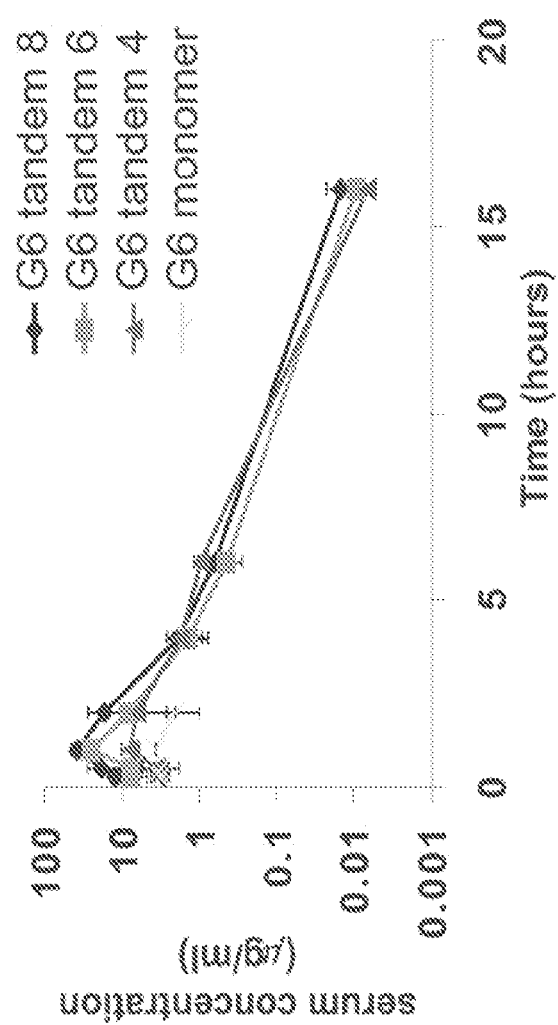
FIG. 21 shows concentration of G6 tandems as a function of time in mouse serum.

Two variables determine potency: the concentration at which a construct inhibits the viability of cells by 50% ($EC_{50}$) and the maximum inhibition of cell viability. FIG. 20 shows that as a general trend, greater affinity of the Tn3 monomer leads to a lower $EC_{50}$ of the antibody-like constructs as G6 has a lower $EC_{50}$ than 1E11 and 1E11 has a lower $EC_{50}$ than 1C12.

Example 16

Pharmacokinetics of Linear Tn3's

To determine the half life of the linear Tn3 tandems as a function of the number of Tn3 modules per tandem, the G6 monomer (SEQ ID NO: 138), G6 tandem 4 (SEQ ID NO: 143), G6 tandem 6 (SEQ ID NO: 192), and G6 tandem 8 (SEQ ID NO: 145) were injected into a mouse and serum concentration of the Tn3s was monitored by an ELISA. The route of administration was intraperitoneal (IP) injection. The experimental design is shown in TABLE 19. Mice were bled 150 µL per time point. Tn3's were detected in serum by an ELISA in which in house produced TRAIL R2 coated plates were incubated with serum diluted in PBST 1% milk. Initial ELISAs were performed to determine for a given time point the correct dilution range in order for the signal to be within the dynamic range of the assay. Bound Tn3 was detected with a 1 in 1,000 dilution of polyclonal anti-Tn3 serum from rabbit in PBST 1% milk (Covance, Princeton, N.J.) followed by a 1 in 10,000 dilution in PBST 1% milk of donkey anti-rabbit HRP (Jackson ImmunoResearch, West Grove, Pa.). For each construct, a standard curve was made. Statistical analysis was performed using an in house statistical program.

The term "maximum plasma concentration" ("$C_{max}$") refers to the highest observed concentration of tandem Tn3 in plasma following administration of the test material to the patient.

The term "$T_{max}$" refers to the time to maximum plasma concentration $C_{max}$.

The term "area under the curve" ("AUC") is the area under the curve in a plot of the concentration of tandem Tn3 in plasma against time. AUC can be a measure of the integral of the instantaneous plasma concentrations ($C_p$) during a time interval and has the units of mass*time/volume. However, AUC is usually given for the time interval zero to infinity. Thus, as used herein "$AUC_{inf}$" refers to an AUC from over an infinite time period.

The term "biological half-life" ("$T_{1/2}$") is defined as the time required for the plasmatic concentration of tandem Tn3 to reach half of its original value.

The term "CL/F" refers to the apparent total body clearance calculated as $Dose/AUC_{inf}$.

Tn3 biological half-life ($T_{1/2}$) increases with increasing number of tandem Tn3's per linear molecule. Adding seven Tn3's to make a tandem 8 from a monomer increased the half life by almost 50%. Increases in valency did not affect the $T_{max}$. However, increases in valency from 1 to 8 resulted in approximately ten-fold and 7-fold increases in $C_{max}$ and $AUC_{inf}$ respectively. Furthermore, when valency increase from 1 to 8, an approximately 7-fold decrease in clearance (CL/F) was observed.

TABLE 19

Experimental design of anti-TRAIL R2 linear tandem pharmacokinetic assay.

| Group # | Test | Dose | Route | Volume | Time points | # Mice |
|---|---|---|---|---|---|---|
| 1 | G6 monomer | 10 mg/kg | IP | 10 ml/kg | (15 min, 1 hr, 16 hr), (30 min, 4 hr, 24 hr) (2 hr, 6 hr, 48 hr) | (3) (3) (3) |

TABLE 19-continued

Experimental design of anti-TRAIL R2 linear tandem pharmacokinetic assay.

| Group # | Test | Dose | Route | Volume | Time points | # Mice |
|---|---|---|---|---|---|---|
| 2 | G6 tandem 4 | 10 mg/kg | IP | 10 ml/kg | (15 min, 1 hr, 16 hr), (30 min, 4 hr, 24 hr) (2 hr, 6 hr, 48 hr) | (3) (3) (3) |
| 3 | G6 tandem 6 | 10 mg/kg | IP | 10 ml/kg | (15 min, 1 hr, 16 hr), (30 min, 4 hr, 24 hr) (2 hr, 6 hr, 48 hr) | (3) (3) (3) |
| 4 | G6 tandem 8 | 10 mg/kg | IP | 10 ml/kg | (15 min, 1 hr, 16 hr), (30 min, 4 hr, 24 hr) (2 hr, 6 hr, 48 hr) | (3) (3) (3) |
| | | | | | Total | 36 |

TABLE 20

Pharmacokinetic properties of Tandem Tn3's

| Test Material | $C_{max}$ (µg/mL) | $T_{max}$ (hr) | $AUC_{inf}$ (hr·µg/mL) | $T_{1/2}$ (hr) | CL/F (mL/hr/kg) |
|---|---|---|---|---|---|
| G6 monomer | 3.65 | 1 | 9.31 | 1.22 | 1070 |
| G6 tandem 4 | 8.07 | 1 | 23.2 | 1.46 | 431 |
| G6 tandem 6 | 24.6 | 1 | 36.5 | 1.69 | 274 |
| G6 tandem 8 | 38.6 | 1 | 64.2 | 1.76 | 156 |

Example 17

Engineered Enhancement of Cyno Cross-Reactivity

For pre-clinical toxicity testing in cynomolgus monkeys (*Macaca fascicularis*), it is desirable to develop an anti-TRAIL R2-Tn3 that cross reacts with cynomolgus TRAIL R2 (cyno TRAIL R2). Our initial affinity matured lead clones had poor cross reactivity with cyno TRAIL R2, although the homology to human TRAIL R2 is 88%. The cross reactivity was enhanced by making a library based upon clone F4 (SEQ ID NO: 137), which was the clone with the best cyno cross reactivity among the clones that resulted from affinity maturation.

Two libraries were made by saturation mutagenesis: one with diversity in the FG loop alone and one with diversity in the BC and FG loops. A low error rate mutagenic PCR was also used to allow for mutations outside the loops that may be beneficial for enhanced cyno TRAIL R2 binding. Four rounds of phage panning were done on in house produced cyno TRAIL R2, and outputs were cloned into the pSEC expression vector. For screening of initial hits in an ELISA format, Tn3's were secreted into MagicMedia (Invitrogen, Carlsbad, Calif.) and were captured from supernatant using an anti-his tag antibody (R and D Systems, Minneapolis, Minn.).

Figure 22A:
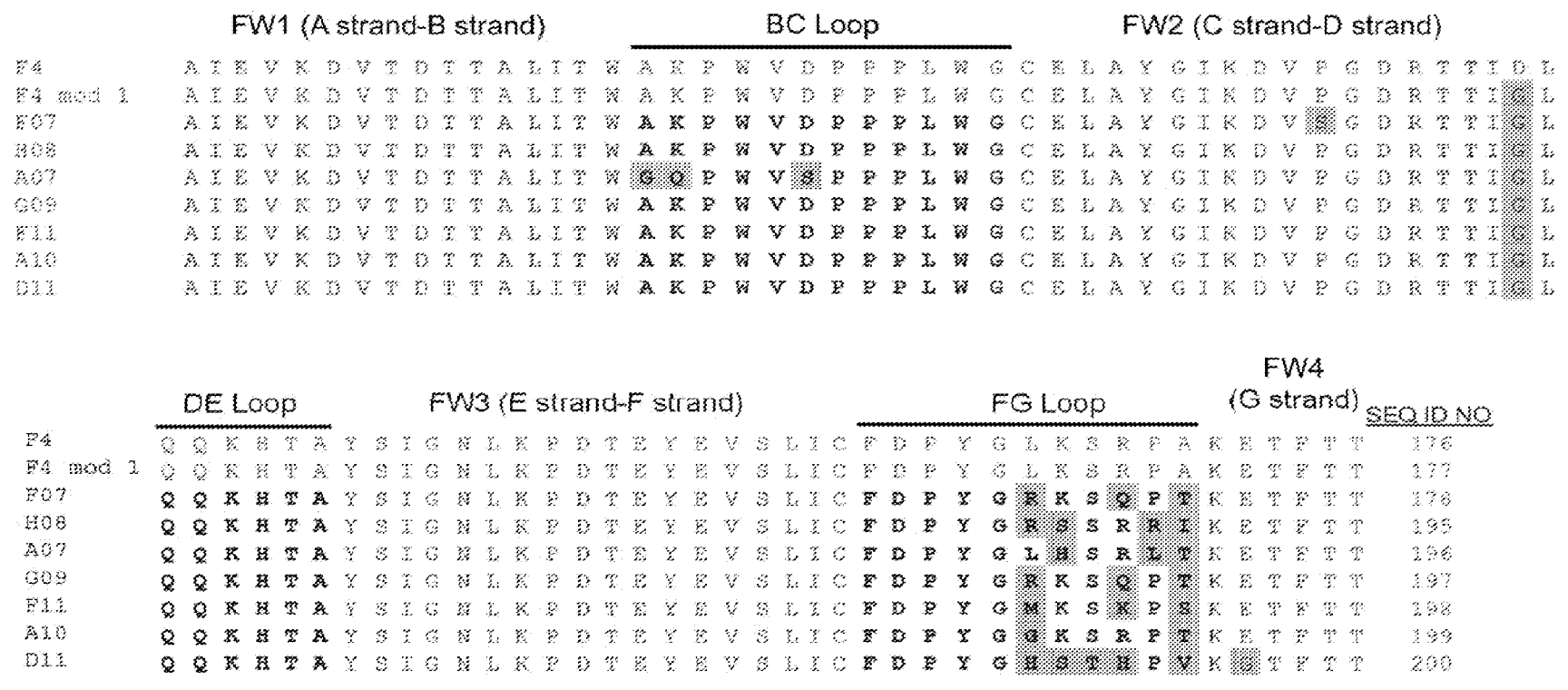

Binding of either human or cyno TRAIL R2-Fc in solution to captured Tn3 was detected by anti-human-Fc-HRP. Clones that had significant binding to cyno TRAIL R2-Fc and did not appear to lose binding to human TRAIL R2-Fc were selected for a subsequent screening ELISA in which either human or cyno TRAIL R2-Fc was coated on a plate and Tn3 supernatants were titrated and then detected with anti-his tag HRP. Because the level of variation in expression levels from clone to clone was low, and also because avidity from having divalent TRAIL R2-Fc in solution could not mask differences in Tn3 affinity, this ELISA allowed for affinity discrimination. It was found that one mutation, a mutation from D to G two amino acids before the DE loop, was present in all engineered cyno cross reactive clones (FIG. 22A). This D to G mutation was engineered into the original F4 to make a clone named F4 mod 1 (SEQ ID NO: 193) and the cross reactivity for cyno was greatly improved without sacrificing binding to human TRAIL R2 (FIG. 22B). In this ELISA, inhibition of binding of 0.75 nM of human or cyno TRAIL R2-Fc to F4 mod 1 coated plates by purified F4 or F4 mod 1 was measured.

It is desired that the binding of a cyno cross reactive enhanced clone to cyno TRAIL-R2-Fc be within tenfold of its binding to human TRAIL R2-Fc. Also, it is desired that the binding of a cyno cross reactive enhanced clone to cyno TRAIL-R2-Fc be within tenfold of the binding of F4 to human TRAIL R2-Fc. The $IC_{50}$ for F4 mod 1 binding to cyno TRAIL R2 differs by less than three fold from the $IC_{50}$ for F4 mod 1 binding to human TRAIL R2. In addition, the $IC_{50}$ for F4 mod 1 binding to human TRAIL R2 is sixfold stronger than the $IC_{50}$ for F4 binding to human TRAIL R2. Accordingly, F4 mod 1 meets the intended cross reactivity requirements.

Example 18

Germline Engineering of Enhanced Cyno Cross Reactive Clone

Clone F4 mod 1 was further engineered to eliminate non essential mutations from germline in order to reduce possible immunogenicity risk. A panel of twelve different modifications was made to determine if there was an effect from a given mutation on the binding to both human and cyno TRAIL R2. FIG. 23A shows a comparison of the final clone F4 mod 12 (SEQ ID NO: 194), which incorporates all tested germline mutations that do not affect binding, to other constructs, namely the Tn3 germline, the original F4 parent, and clone F4 mod 1 (initial enhanced cyno cross reactive engineered).

The amino acid sequence of F4 mod 12 starts with the native Tn3 sequence SQ, ends with L, has a reversion of the framework 2 mutation from A to T, and has a reversion of the final two amino acids of the DE loop from TA to NQ. FIG. 23B shows that F4, F4 mod 1, and F4 mod 12 all are within sixfold of each other in their binding to human TRAIL R2. It also shows that F4 mod 1 and F4 mod 12 are within twofold of each other in their binding to cyno TRAIL R2.

Figure 23C:
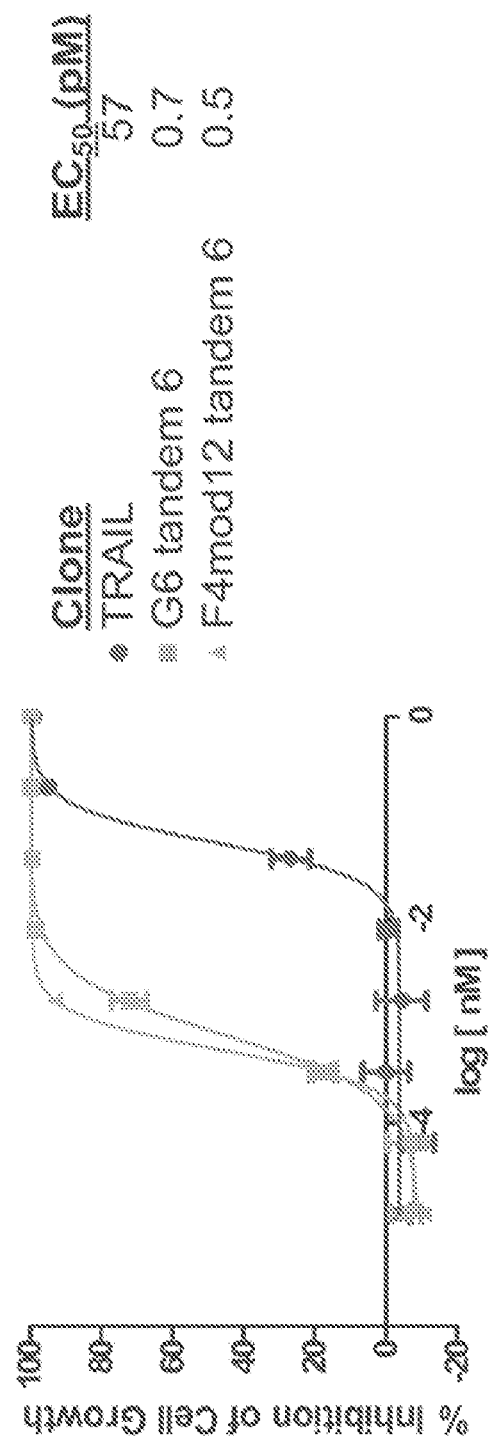
FIG. 23C shows a Colo205 cell killing assay comparing G6 tandem 6 to F4 mod 12 tandem 6.
Figure 23D:
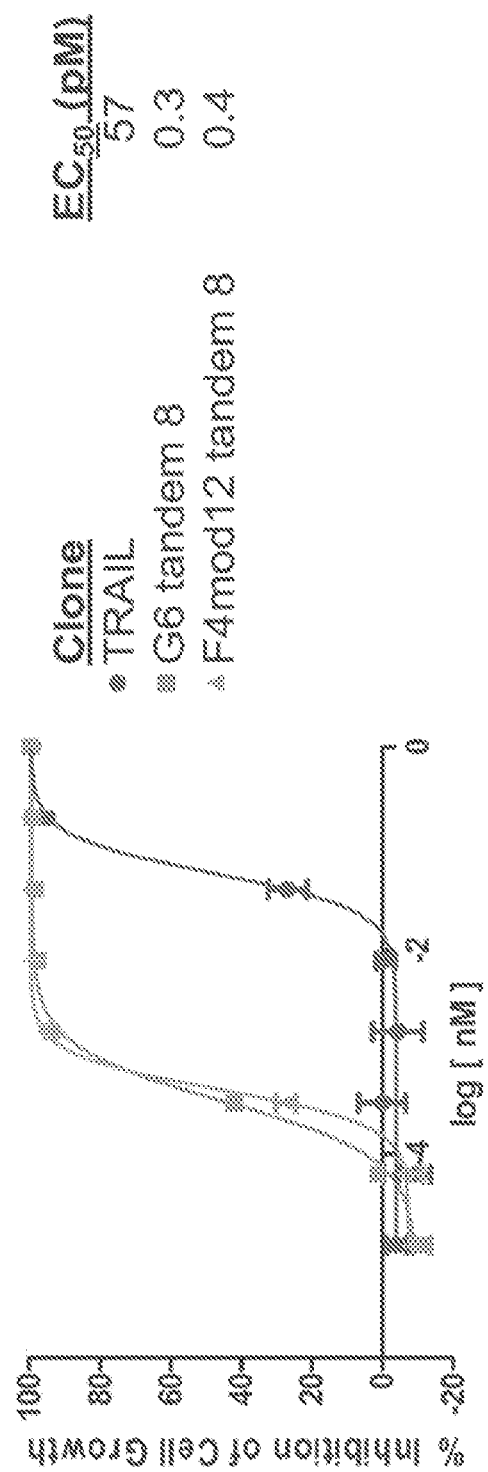
FIG. 23D shows a Colo205 cell killing assay comparing G6 tandem 8 to F4 mod 12 tandem 8.

F4 mod 12 was reformatted into a tandem 6 (SEQ ID NO: 167) and tandem 8 (SEQ ID NO: 166) construct and tested to confirm that there is not loss in potency relative to G6 tandem 6 (SEQ ID NO: 144) and tandem 8 (SEQ ID NO: 145). FIG. 23C and FIG. 23D show no loss in potency for the germline engineered, enhanced cyno cross reactive F4 mod 12 tandems in comparison to the G6 tandems in the Colo205 cell line.

Example 19

Activity of G6 Tandem 8 in TRAIL Resistant Cell Lines

Figure 24:
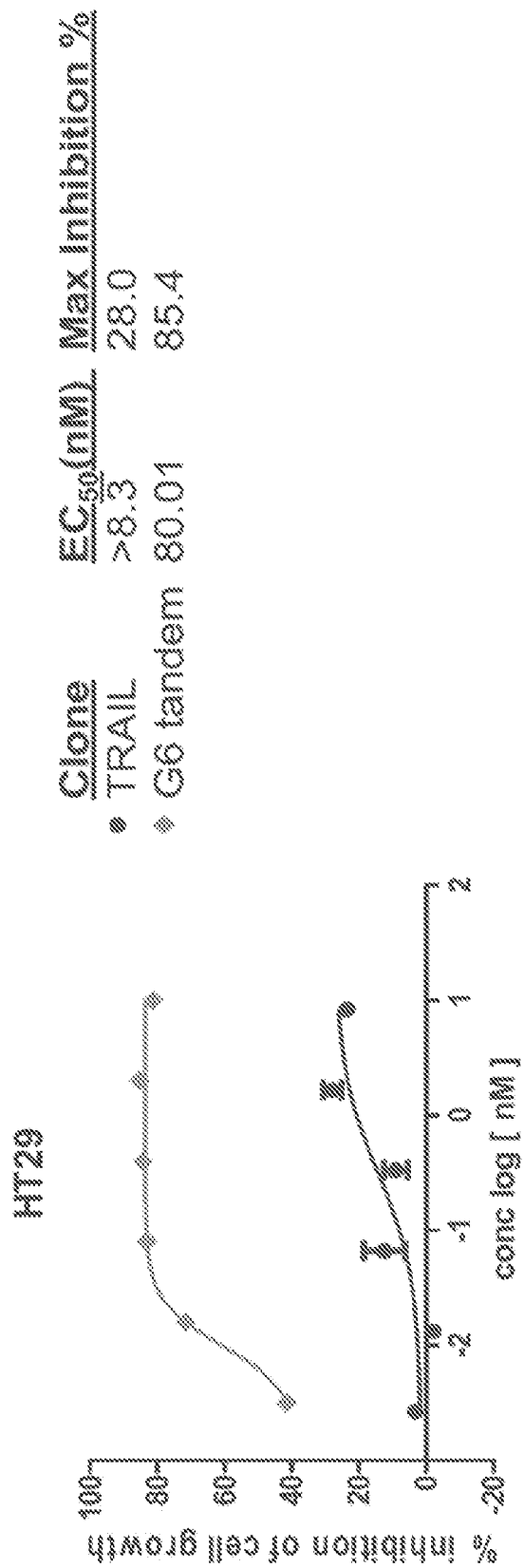
FIG. 24 shows an HT29 cell killing assay comparing the activity of G6 tandem 8 to F4 mod 12 tandem 8 in the TRAIL resistant cell line HT29.

Multiple cell lines are resistant to killing by TRAIL. Thus, we evaluated whether the enhanced potency of G6 tandem 8 constructs relative to TRAIL in TRAIL sensitive cell lines will translate into potency of G6 tandem 8 in TRAIL resistant cell lines. Sensitivity to Apo2L/TRAIL in several cancer cell lines was determined with the CellTiter-Glo Luminescent Cell Viability Assay (Promega, Madison, Wis.). Briefly, cells were plated in 96-well plates, allowed to adhere overnight and then treated with various concentrations of recombinant human Apo2L/TRAIL and TRAIL mimetic G6 Tandem 8 in medium containing 10% FBS. After a period of 48-72 hrs, cell viability was determined following manufacturer's protocols. FIG. 24 shows that for the TRAIL resistant cell line HT29 G6 tandem 8 shows potent cell killing activity while TRAIL does not. TABLE 21 shows that G6 tandem 8 has cell killing activity in many, but not all of the TRAIL resistant cell lines tested. Enhanced potency may be due to the higher valency of the tandem relative to TRAIL, although spatial orientation of the binding modules may also have an effect.

TABLE 21

Activity of G6 tandem 8 and TRAIL in TRAIL resistant cell lines.

|  |  | TRAIL IC50 [nM] | G6 Tandem 8 IC50 [nM] | TRAIL % Max Kill | G6 Tandem 8 % Max Kill |
|---|---|---|---|---|---|
| Resistant to TRAIL but sensitive to TRAIL mimetics | T84 | >8.3 | 0.247 | 14.44 | 71.53 |
|  | LoVo | >8.3 | 0.005 | 45.99 | 74.22 |
|  | CaCo-2 | >8.3 | 0.044 | 18.23 | 54.84 |
|  | HT29 | >8.3 | 0.01 | 28.00 | 85.40 |
|  | HPAF-II | >8.3 | 0.016 | 45.33 | 91.33 |
|  | Hep3B | >8.3 | 0.023 | 13.35 | 70.15 |
|  | SKHEP-1 | >8.3 | 0.055 | 19.48 | 80.19 |
|  | Hep G2 | >8.3 | 0.040 | 33.31 | 84.00 |
| Resistant to TRAIL and TRAIL mimetics | SW820 | >8.3 | >10 | −5.71 | 4.65 |
|  | SW837 | >8.3 | >10 | 19.98 | 25.32 |
|  | Hs766T | >8.3 | >10 | 20.99 | 47.86 |
|  | NCI-H522 | >8.3 | >10 | 32.69 | 31.33 |
|  | NCI-H23 | >8.3 | >10 | 22.08 | 39.53 |
|  | BT-649 | >8.3 | >10 | 4.49 | 27.99 |
|  | SNB-75 | >8.3 | >10 | 8.9 | 4.7 |
|  | 786-0 | >8.3 | >10 | −0.12 | 7.19 |
|  | SNU-387 | >8.3 | >10 | −0.63 | 33.7 |
|  | SNU-475 | >8.3 | >10 | 0.49 | 20.83 |
|  | SNU-398 | >8.3 | >10 | 1.50 | 0.46 |

Example 20

Immunogenicity Study of TRAIL R2 Binding Monomers

Immunogenicity is a potential issue for any therapeutic protein even if it is human in origin. Immunogenic responses can limit efficacy through neutralizing antibodies that can lead to inflammation. One of the most important factors in the development of an immune response is the presence of epitopes that can stimulate CD4+ T cell proliferation. In the EpiScreen test (Antitope, Cambridge, UK), CD8+ T cell depleted Peripheral Blood Mononuclear Cells (PBMCs) are incubated with test proteins and CD4+ T cell proliferation and IL-2 secretion are monitored (see, Baker & Jones, *Curr. Opin. Drug Discovery Dev.* 10:219-227, 2007; Jaber & Baker, *J. Pharma. Biomed. Anal.* 43:1256-1261, 2007; Jones et al., *J. Thrombosis and Haemostasis* 3:991-1000, 2005; Jones et al., *J. Interferon Cytokine Res.* 24:560-72, 2004). The PBMCs are isolated from a pool of donors which represent the HLA-DR allotypes expressed in the world's population.

The Tn3 monomers shown in FIG. 25 were expressed (with a GGGGHHHHHHHH linker-His tag (SEQ ID NO: 251)), purified, and verified to be monomeric by SEC, and filtered for endotoxin removal as described above. All non-wild type clones tested were from the engineering round to enhance cyno cross reactivity (FIG. 22A). However, these clones had mutations to germline that have been shown not to affect binding in the F4 mod 1 background. These clones were tested in an ELISA to verify that the germlining mutations did not affect binding. In both the T cell proliferation assay and the IL-2 secretion assay, a stimulation index (SI) of greater than two had been previously established as a positive response for a given donor. The mean SI, or average of the SI of the positive responding population, is indicative of the strength of the response. A control protein known to induce a strong response, keyhole limpet haemocyanin (KLH), was included in both assays.

TABLE 22 shows mean SI for all test proteins, which are significantly lower than for KLH and was not much higher than the cutoff of 2 for a positive mean SI. In addition, the frequency of response for the test proteins was very low (ten percent or less for all tested proteins except for the control which had a response in excess of 90%). Previous studies by Antitope have revealed that an EpiScreen response of less than 10% is indicative of low clinical immunogenicity risk. Thus, our observation that all Tn3s tested have 10% or less frequency of response indicates a low risk of clinical immunogenicity.

TABLE 22

Results of Antitope EpiScreen immunogenicity assay. Tested Tn3s are ranked from 1 (most immunogenic) to 4 (least immunogenic).

|  | Mean SI | | Frequency (%) of Response | | |
|---|---|---|---|---|---|
| Sample | Prolif | iL-2 | Prolif | iL-2 | Ranking |
| F4mod12 | 2.82 | 2.30 | 4 | 4 | 4= |
| 00322S-A07 | 2.91 | 2.06 | 8 | 8 | 2 |
| 00322S-G09 | 2.88 | 2.26 | 10 | 10 | 1 |
| 00322V-A10 | 2.67 | 2.33 | 8 | 6 | 3= |
| 00322V-F11 | 3.14 | 2.37 | 6 | 6 | 3= |
| wild type | 2.05 | 2.00 | 6 | 4 | 4= |
| KLH | 6.51 | 3.98 | 96 | 92 | N/A |

Example 21

Aggregation State of Unpurified and Purified G6 Tandem 8 Tn3's

Figure 26A:
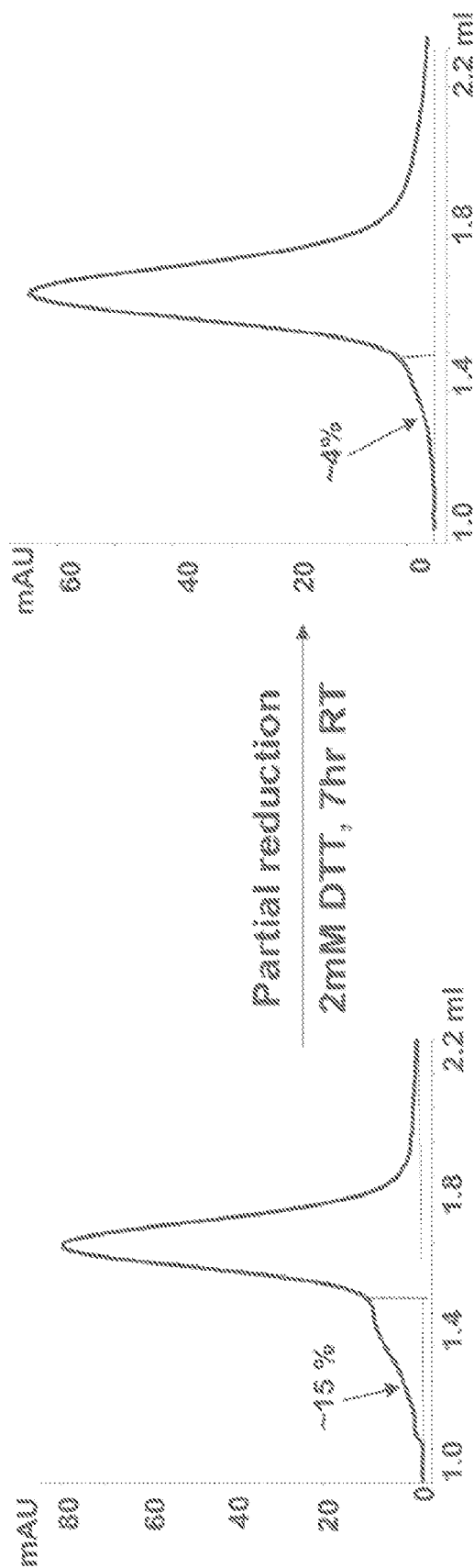
FIG. 26A shows SEC traces of non-SEC-purified G6 tandem 8.
Figure 26B:
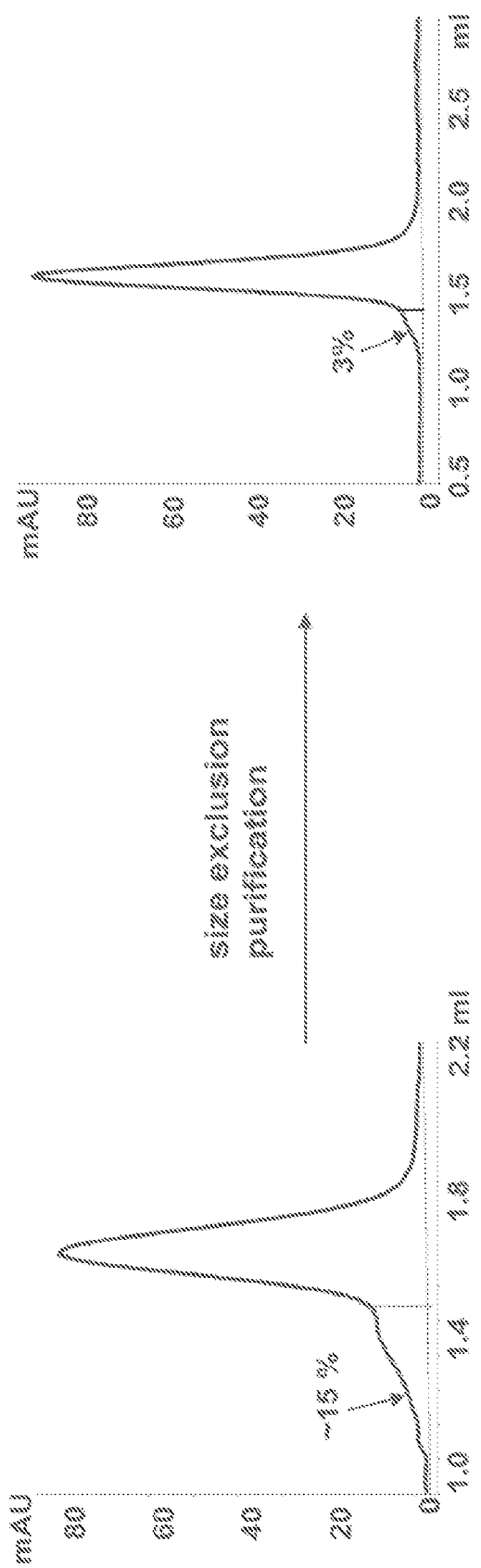
FIG. 26B shows SEC traces of SEC-purified G6 tandem 8.

It is known in the art that proteins containing multiple cysteines, e.g., a protein made up of tandem repeats that contains an internal disulfide bond, often does not exhibit proper disulfide pairing. Scrambling of disulfides can reduce or eliminate expression into media. If the protein does express into media, it may be a mixture of improperly folded protein with intermolecular as well as mismatched intramolecular disulfide pairs leading to aggregation. Our SEC data revealed that the majority of tandem proteins in the bacterial expression media were in a monomeric, properly folded state. After Ni-NTA purification of the Hi-tagged G6 tandem 8 protein, approximately 15% of the protein was aggregated. The observed aggregation was reduced to 4% (FIG. 26A) by reduction with 2 mM DTT, indicating that most of the aggregation was disulfide mediated. Most of the aggregates were removed by SEC purification (FIG. 26B), as described above.

Example 22

Determination of TRAIL Mimetics, G6TN6 and G6TN8, Tumor Growth Inhibition of in Colo205 Colorectal Cancer Xenograft Models The anti-tumor activity of TRAIL Tn3 mimetics, G6 tandem 6 (G6TN6) (SEQ ID NO: 144) and G6 tandem 8 (G6TN8) (SEQ ID NO: 145), were evaluated in Colo205, a human colorectal carcinoma xenograft model. Colo205 cells were maintained as a semiadhesive monolayer culture at 37° C. under 5% $CO_2$ in Roswell Park Memorial Institute (RPMI) 1640 medium that contained 10% fetal bovine serum (FBS). Cells harvested by trypsinization were resuspended to a final concentration of $3 \times 10^7$ cells/mL in Hank's balanced salt solution (HBSS). Athymic female nude mice were each injected subcutaneously (SC) in the right flank with $3 \times 10^6$ Colo205 cells. The study was initiated when tumors reached an average of ~177 $mm^3$. The study design is summarized in TABLE 23. TRAIL was diluted from stock solution with 20 mM Tris-HCl 300 mM Arginine-HCl PH 7 and administered intravenously (IV) at dose indicated in TABLE 23, daily for a total of 5 doses according to body weight (10 mL/kg). G6 tandem 6 (G6TN6) and G6 tandem 8 (G6TN8) were each diluted from a stock solution with PBS and administered intravenously (IV) at doses indicated in TABLE 23, daily for a total of 5 doses according to body weight (10 mL/kg). Tumor volumes and body weight measurements were recorded. Tumor measurements were made using an electronic caliper and tumor volume ($mm^3$) was calculated using the formula tumor volume=[length (mm)×width $(mm)^2$]/2. Tumor growth inhibition (TGI) was calculated as percent TGI=(1−T/C)× 100, where T=final tumor volumes from a treated group after the last dose, and C=final tumor volumes from the control group after the last dose.

Figure 27:
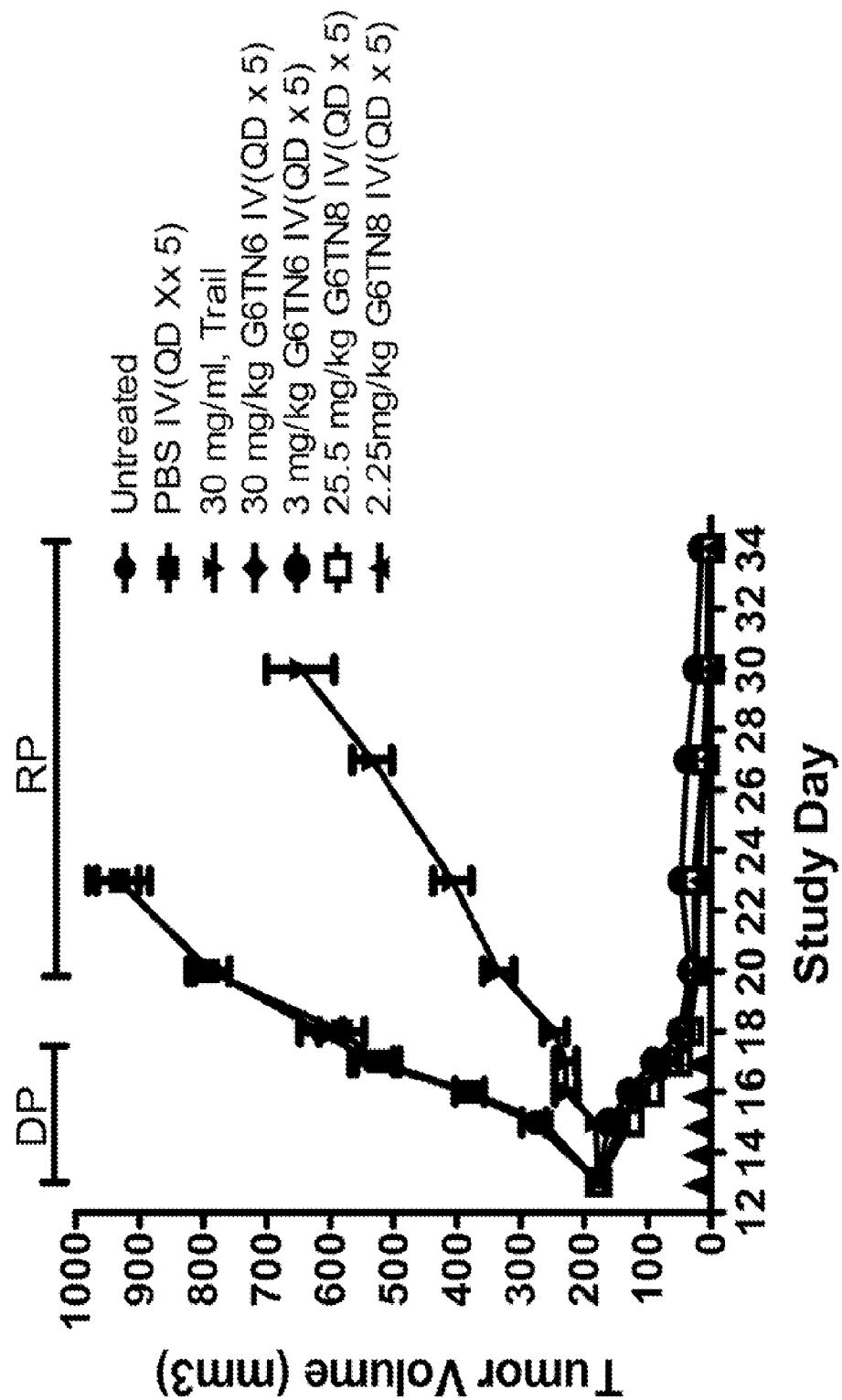
FIG. 27 shows changes in tumor volume in Colo205 colorectal cancer xenograft models in response to different doses of the Tn3 TRAIL R2 agonists G6 tandem 6 and G6 tandem 8.

During the dosing phase (DP) (FIG. 27), 3 mg/kg and 30 mg/kg of G6TN6 resulted in significant TGI of 92% (p<0.0001) and 93% (p<0.0001), respectively (TABLE 24). Similarly, after equimolar adjustment for final concentration, 2.25 mg/kg and 25.5 mg/kg of G6TN8 resulted in significant TGI of 93% (p<0.0001) and 94% (p<0.0001), respectively (TABLE 24). 30 mg/kg of TRAIL resulted in TGI of 60% (p<0.001), (TABLE 24).

By day 34 of the regrowth phase (RP) (FIG. 27), while 3 mg/kg G6TN6 did not result in any CR (CR; percentage of mice in group where no palpable tumor detectable for two successive measurements), 2.25 mg/kg G6TN8 resulted in a 90% CR. At a higher dose of 30 mg/kg G6TN6 50% CR was achieved. On the other hand, 25.5 mg/kg G6TN8 resulted in 100% CR (TABLE 25). Results from both doses suggest that G6TN8 resulted in greater efficacy in comparison to G6TN6. However, both G6TN6 and G6TN8 showed efficacy at certain doses. More importantly, both constructs significantly outperformed TRAIL which did not result in any PR or CR.

Figure 28:
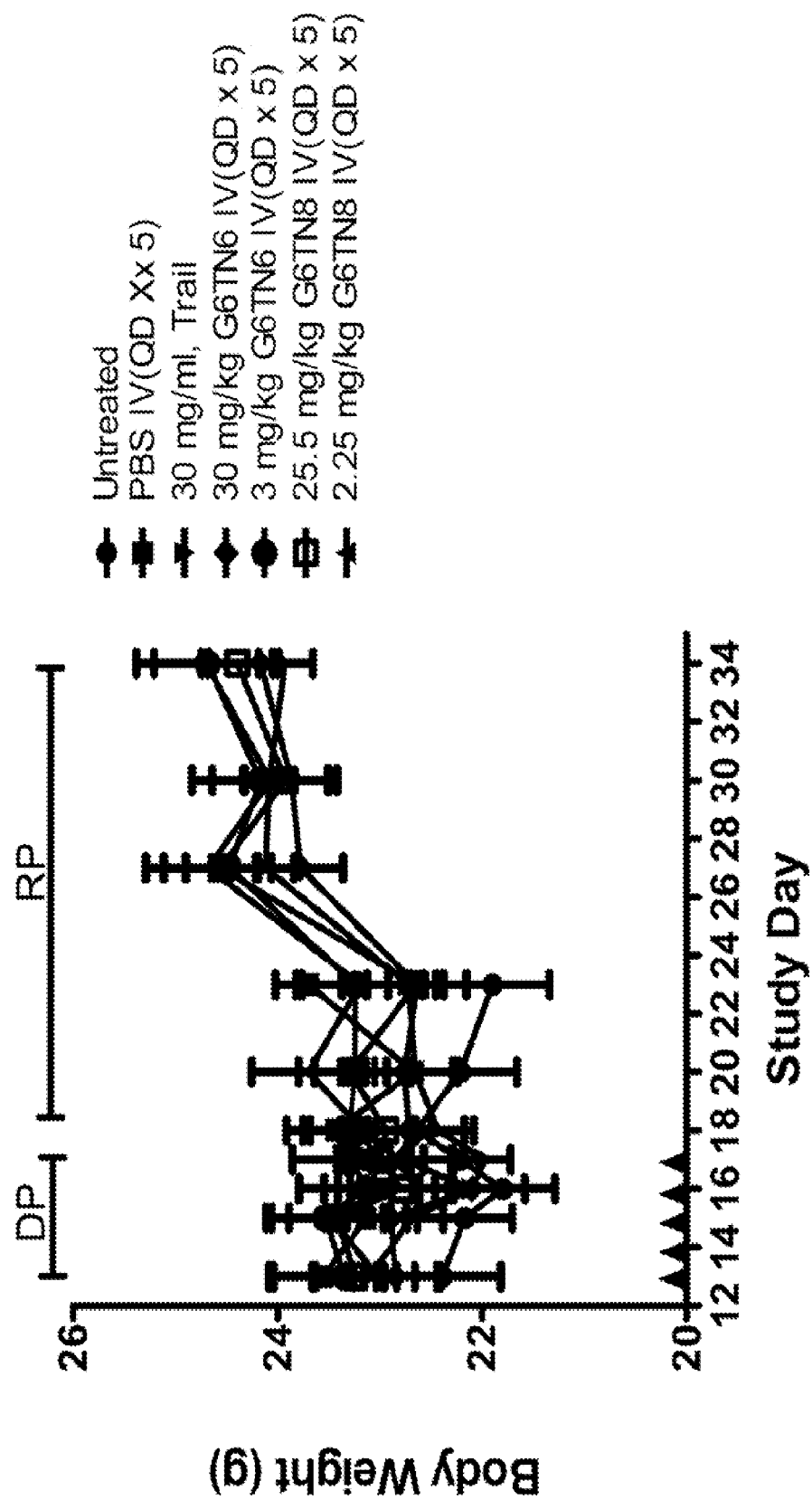
FIG. 28 shows changes in body weight in Colo205 colorectal xenograft models in response to different doses of the Tn3 TRAIL R2 agonists G6 tandem 6 and G6 tandem 8.

As shown in FIG. 28, no body weight loss was observed for both G6TN6 and G6TN8 at all doses during the dosing and regrowth phase of the study.

TABLE 23

Study design for TRAIL and TRAIL mimetics (G6TN6 and G6TN8) in Colo205 tumor xenograft model

| Group | Test Material | Dose (mg/kg) | Dose Volume (mL/kg) | Route | Dose Schedule |
|---|---|---|---|---|---|
| 1 | Untreated | NA | NA | NA | NA |
| 2 | PBS | NA | 10 | IV | QDX5 |
| 3 | TRAIL | 30 mg/kg | 10 | IV | QDX5 |
| 4 | G6TN6 | 30 mg/kg | 10 | IV | QDX5 |
| 5 | G6TN6 | 3 mg/kg | 10 | IV | QDX5 |
| 6 | G6TN8 | 25.5 mg/kg | 10 | IV | QDX5 |
| 7 | G6TN8 | 2.25 mg/kg | 10 | IV | QDX5 |

TABLE 24

Effect of TRAIL and TRAIL mimetics (G6TN6 and G6TN8) on TGI during dosing phase of the study.

| Treatment group | % TGI | P Value (compared to untreated control) |
|---|---|---|
| TRAIL 30 mg/kg | 60 | P < 0.001 |
| G6TN6 30 mg/kg | 93 | P < 0.0001 |
| G6TN6 3 mg/kg | 92 | P < 0.0001 |
| G6TN8 25.5 mg/kg | 94 | P < 0.0001 |
| G6TN8 2.25 mg/kg | 93 | P < 0.0001 |

TABLE 25

Effect of TRAIL and TRAIL mimetics (G6TN6 and G6TN8) on TGI during regrowth phase by day 34 of the study.

| Treatment group | $PR^a$ (%) | $CR^b$ (%) |
|---|---|---|
| Trail | — | — |
| G6TN6 30 mg/kg | 50 | 50 |
| G6TN6 3 mg/kg | 100 | — |
| G6TN8 25.5 mg/kg | — | 100 |
| G6TN8 2.25 mg/kg | 10 | 90 |

[a] percent partial regression (PR; percentage of mice in group where tumor volume is less than 50% of volume at time of staging for two successive measurements)
[b] percent complete regression (CR; percentage of mice in group where no palpable tumor detectable for two successive measurements)

The examples shown above illustrate various aspects of the invention and practice of the methods of the invention. These examples are not intended to provide an exhaustive description of the many different embodiments of the invention. Thus, although the invention has been described in some detail by way of illustration and example for purposes of clarity of understanding, those of ordinary skill in the art will realize readily that many changes and modifications can be made without departing from the spirit or scope of the appended claims.

All publications, patents and patent applications mentioned in this specification are herein incorporated by reference into the specification to the same extent as if each individual publication, patent or patent application was specifically and individually indicated to be incorporated herein by reference.

The foregoing examples illustrate various aspects of the invention and practice of the methods of the invention. The examples are not intended to provide an exhaustive description of the many different embodiments of the invention. Thus, although the forgoing invention has been described in some detail by way of illustration and example for purposes of clarity of understanding, those of ordinary skill in the art will realize readily that many changes and modifications can be made thereto without departing from the spirit or scope of the appended claims.

All publications, patents and patent applications mentioned in this specification are herein incorporated by reference into the specification to the same extent as if each individual publication, patent or patent application was specifically and individually indicated to be incorporated herein by reference.

What is claimed is:

1. A TRAIL R2-specific recombinant multimeric scaffold comprising at least two Tn3 monomer scaffolds, wherein
   (a) each Tn3 monomer scaffold comprises seven beta strands designated A, B, C, D, E, F, and G, and six loop regions designated AB, BC, CD, DE, EF, and FG, wherein the AB loop comprises SEQ ID NO: 35, the BC loop comprises a sequence selected from the group consisting of SEQ ID NOs: 97, 98, or 168, the CD loop comprises SEQ ID NO: 37, the DE loop comprises a sequence selected from the group consisting of SEQ ID NOs: 102, 103, and 179, the EF loop comprises SEQ ID NO: 39, and FG loop comprises a sequence selected from the groups consisting of SEQ ID NOs: 106, 108, 109, 169, and 170,
   (b) the Tn3 monomer scaffold comprises at least one disulfide bond to link any two of the seven beta strand domains,
   (c) the Tn3 monomer scaffolds are connected in tandem, and
   (d) the recombinant multimeric scaffold specifically binds to TRAIL R2.

2. The multimeric scaffold of claim 1, wherein the multimeric scaffold comprises 3, 4, 5, 6, 7, or 8 Tn3 monomer scaffolds.

3. The multimeric scaffold of claim 2, wherein all of the Tn3 monomer scaffolds are in linear tandem format.

4. The multimeric scaffold of claim 1, wherein at least two Tn3 monomer scaffolds are connected by a linker.

5. The multimeric scaffold of claim 4, wherein the linker comprises a peptide linker.

6. The multimeric scaffold of claim 5, wherein the peptide linker comprises a (GxS)y sequence wherein x and y are integers, wherein x=1, 2, 3 or 4, and wherein y=1, 2, 3, 4, 5, 6, or 7 (SEQ ID NO: 212).

7. The multimeric scaffold of claim 6, wherein the peptide linker is Gly4Ser (SEQ ID NO: 210).

8. The multimeric scaffold of claim 1, wherein at least one of the Tn3 monomer scaffolds is fused to a heterologous moiety.

9. The multimeric scaffold of claim 8, wherein the heterologous moiety comprises a composition selected from the group consisting of: a protein, a peptide, a protein domain, a linker, a drug, a toxin, a cytotoxic agent, an imaging agent, a radionuclide, a radioactive compound, an organic polymer, an inorganic polymer, a polyethylene glycol (PEG), biotin, a human serum albumin (HSA), a HSA FeRn binding portion, an antibody, a domain of an antibody, an antibody fragment, a single chain antibody, a domain antibody, an albumin binding domain, an enzyme, a ligand, a receptor, a binding peptide, a non-FnIII scaffold, an epitope tag, a recombinant polypeptide polymer, a cytokine, and a combination of two or more of said moieties.

10. The multimeric scaffold of claim 9, wherein the multimeric scaffold is conjugated to PEG at the N-terminus or C-terminus.

11. The multimeric scaffold of claim 9, wherein the scaffold is conjugated to PEG.

12. The multimeric scaffold of claim 11, wherein the PEG is conjugated to the scaffold at the N-terminus or the C-terminus.

13. The multimeric scaffold of claim 1, wherein the multimeric scaffold is a receptor agonist.

14. The multimeric scaffold of claim 1, wherein at least two Tn3 monomer scaffolds bind the same epitope on TRAIL R2.

15. The multimeric scaffold of claim 1, wherein at least two Tn3 monomer scaffolds bind different epitopes on TRAIL R2.

16. The multimeric scaffold of claim 1, wherein said TRAIL R2 is human TRAIL R2.

17. A composition comprising the recombinant multimeric scaffold of claim 1 in a pharmaceutically acceptable excipient.

18. The TRAIL R2-specific recombinant multimeric scaffold of claim 1, wherein at least two Tn3 monomer scaffolds comprise the amino acid sequence (SEQ ID NO: 213):

IEV$(X_{AB})_n$ALITW$(X_{BC})_n$CELX$_1$YGI$(X_{CD})$nTTIX$_2$L$(X_{DE})_n$YSI$(X_{EF})_n$YEVSLIC$(X_{FG})_n$KX$_3$TFTT wherein $X_{AB}$, $X_{BC}$, $X_{CD}$, $X_{DE}$, $X_{EF}$, and $X_{FG}$ represent the amino acid residues present in the AB, BC, CD, DE, EF, and FG loops, respectively, wherein $X_1$ represents amino acid residue A or T, wherein $X_2$ represents amino acid residue D or G, and wherein $X_3$ represents amino acid E or G.

19. The multimeric scaffold of claim 1, wherein the multimeric scaffold comprises SEQ ID NO. 202.

20. The multimeric scaffold of claim 1, wherein the multimeric scaffold comprises SEQ ID NO. 203.

21. The multimeric scaffold of claim 1, wherein the multimeric scaffold comprises SEQ ID NO. 204.

22. The multimeric scaffold of claim 1, wherein the multimeric scaffold comprises SEQ ID NO. 167.

23. The multimeric scaffold of claim 18, wherein the scaffold comprises SEQ ID NO: 202.

24. The multimeric scaffold of claim 18, wherein the scaffold comprises SEQ ID NO: 203.

* * * * *

SEQUENCE LISTING

<160> NUMBER OF SEQ ID NOS: 251

<210> SEQ ID NO 1
<211> LENGTH: 83
<212> TYPE: PRT
<213> ORGANISM: Artificial Sequence
<220> FEATURE:
<223> OTHER INFORMATION: Description of Artificial Sequence: Synthetic
      Disulfide-bonded variant polypeptide

<400> SEQUENCE: 1

Ile Glu Val Lys Asp Val Thr Asp Thr Thr Ala Leu Ile Thr Trp Phe
1               5                   10                  15

Lys Pro Leu Ala Glu Ile Asp Gly Cys Glu Leu Thr Tyr Gly Ile Lys
                20                  25                  30

Asp Val Pro Gly Asp Arg Thr Thr Ile Asp Leu Thr Glu Asp Glu Asn
            35                  40                  45

Gln Tyr Ser Ile Gly Asn Leu Lys Pro Asp Thr Glu Tyr Glu Val Ser
        50                  55                  60

Leu Ile Cys Arg Arg Gly Asp Met Ser Ser Asn Pro Ala Lys Glu Thr
65                  70                  75                  80

Phe Thr Thr

<210> SEQ ID NO 2
<211> LENGTH: 83
<212> TYPE: PRT
<213> ORGANISM: Artificial Sequence
<220> FEATURE:
<223> OTHER INFORMATION: Description of Artificial Sequence: Synthetic
      Disulfide-bonded variant polypeptide

<400> SEQUENCE: 2

Ile Glu Val Lys Asp Val Thr Asp Thr Thr Ala Leu Ile Thr Trp Phe
1               5                   10                  15

Lys Pro Leu Ala Glu Ile Asp Gly Ile Glu Leu Thr Tyr Gly Ile Lys
                20                  25                  30

Asp Val Pro Gly Asp Arg Thr Thr Ile Asp Leu Thr Glu Asp Glu Asn
            35                  40                  45

Gln Tyr Ser Ile Gly Asn Leu Lys Pro Asp Thr Glu Tyr Cys Val Ser
        50                  55                  60

Leu Ile Ser Arg Arg Gly Asp Met Ser Ser Asn Pro Ala Lys Glu Cys
65                  70                  75                  80

Phe Thr Thr

<210> SEQ ID NO 3
<211> LENGTH: 83
<212> TYPE: PRT
<213> ORGANISM: Artificial Sequence
<220> FEATURE:
<223> OTHER INFORMATION: Description of Artificial Sequence: Synthetic
      Disulfide-bonded variant polypeptide

<400> SEQUENCE: 3

Ile Glu Val Lys Asp Val Thr Asp Thr Thr Ala Leu Ile Thr Trp Phe
1               5                   10                  15

Lys Pro Leu Ala Glu Ile Asp Gly Cys Glu Leu Thr Tyr Gly Ile Lys
                20                  25                  30

Asp Val Pro Gly Asp Arg Thr Thr Ile Asp Leu Thr Glu Asp Glu Asn
            35                  40                  45

Gln Tyr Ser Ile Gly Asn Leu Lys Pro Asp Thr Glu Tyr Cys Val Ser

```
                    50                  55                  60
Leu Ile Cys Arg Arg Gly Asp Met Ser Ser Asn Pro Ala Lys Glu Cys
 65                  70                  75                  80

Phe Thr Thr

<210> SEQ ID NO 4
<211> LENGTH: 90
<212> TYPE: PRT
<213> ORGANISM: Homo sapiens

<400> SEQUENCE: 4

Arg Leu Asp Ala Pro Ser Gln Ile Glu Val Lys Asp Val Thr Asp Thr
  1               5                  10                  15

Thr Ala Leu Ile Thr Trp Phe Lys Pro Leu Ala Glu Ile Asp Gly Ile
                 20                  25                  30

Glu Leu Thr Tyr Gly Ile Lys Asp Val Pro Gly Asp Arg Thr Thr Ile
             35                  40                  45

Asp Leu Thr Glu Asp Glu Asn Gln Tyr Ser Ile Gly Asn Leu Lys Pro
         50                  55                  60

Asp Thr Glu Tyr Glu Val Ser Leu Ile Ser Arg Arg Gly Asp Met Ser
 65                  70                  75                  80

Ser Asn Pro Ala Lys Glu Thr Phe Thr Thr
                 85                  90

<210> SEQ ID NO 5
<211> LENGTH: 87
<212> TYPE: PRT
<213> ORGANISM: Homo sapiens

<400> SEQUENCE: 5

Leu Glu Val Val Ala Ala Thr Pro Thr Ser Leu Leu Ile Ser Trp Asp
  1               5                  10                  15

Ala Pro Ala Val Thr Val Arg Tyr Tyr Arg Ile Thr Tyr Gly Glu Thr
                 20                  25                  30

Gly Gly Asn Ser Pro Val Gln Glu Phe Thr Val Pro Gly Ser Lys Ser
             35                  40                  45

Thr Ala Thr Ile Ser Gly Leu Lys Pro Gly Val Asp Tyr Thr Ile Thr
         50                  55                  60

Val Tyr Ala Val Thr Gly Arg Gly Asp Ser Pro Ala Ser Ser Lys Pro
 65                  70                  75                  80

Ile Ser Ile Asn Tyr Arg Thr
                 85

<210> SEQ ID NO 6
<211> LENGTH: 82
<212> TYPE: PRT
<213> ORGANISM: Homo sapiens

<400> SEQUENCE: 6

Pro Thr Val Asp Gln Val Asp Asp Thr Ser Ile Val Val Arg Trp Ser
  1               5                  10                  15

Arg Pro Gln Ala Pro Ile Thr Gly Tyr Arg Ile Val Tyr Ser Pro Ser
                 20                  25                  30

Val Glu Gly Ser Ser Thr Glu Leu Asn Leu Pro Glu Thr Ala Asn Ser
             35                  40                  45

Val Thr Leu Ser Asp Leu Gln Pro Gly Val Gln Tyr Asn Ile Thr Ile
         50                  55                  60
```

Tyr Ala Val Glu Glu Asn Gln Glu Ser Thr Pro Val Val Ile Gln Gln
65                  70                  75                  80

Glu Thr

<210> SEQ ID NO 7
<211> LENGTH: 80
<212> TYPE: PRT
<213> ORGANISM: Homo sapiens

<400> SEQUENCE: 7

Pro Tyr Asn Thr Glu Val Thr Glu Thr Thr Ile Val Ile Thr Trp Thr
1               5                   10                  15

Pro Ala Pro Arg Ile Gly Phe Lys Leu Gly Val Arg Pro Ser Gln Gly
                20                  25                  30

Gly Glu Ala Pro Arg Glu Val Thr Ser Asp Ser Gly Ser Ile Val Val
            35                  40                  45

Ser Gly Leu Thr Pro Gly Val Glu Tyr Val Tyr Thr Ile Gln Val Leu
    50                  55                  60

Arg Asp Gly Gln Glu Arg Asp Ala Pro Ile Val Asn Lys Val Val Thr
65                  70                  75                  80

<210> SEQ ID NO 8
<211> LENGTH: 102
<212> TYPE: PRT
<213> ORGANISM: Homo sapiens

<400> SEQUENCE: 8

Pro Pro Ile Ala Leu Asn Trp Thr Leu Leu Asn Val Ser Leu Thr Gly
1               5                   10                  15

Ile His Ala Asp Ile Gln Val Arg Trp Glu Ala Pro Arg Asn Ala Asp
                20                  25                  30

Ile Gln Lys Gly Trp Met Val Leu Glu Tyr Glu Leu Gln Tyr Lys Glu
            35                  40                  45

Val Asn Glu Thr Lys Trp Lys Met Met Asp Pro Ile Leu Thr Thr Ser
    50                  55                  60

Val Pro Val Tyr Ser Leu Lys Val Asp Lys Glu Tyr Glu Val Arg Val
65                  70                  75                  80

Arg Ser Lys Gln Arg Asn Ser Gly Asn Tyr Gly Glu Phe Ser Glu Val
                85                  90                  95

Leu Tyr Val Thr Leu Pro
            100

<210> SEQ ID NO 9
<211> LENGTH: 96
<212> TYPE: PRT
<213> ORGANISM: Homo sapiens

<400> SEQUENCE: 9

Pro Pro Ser Leu Asn Val Thr Lys Asp Gly Asp Ser Tyr Ser Leu Arg
1               5                   10                  15

Trp Glu Thr Met Lys Met Arg Tyr Glu His Ile Asp His Thr Phe Glu
                20                  25                  30

Ile Gln Tyr Arg Lys Asp Thr Ala Thr Trp Lys Asp Ser Lys Thr Glu
            35                  40                  45

Thr Leu Gln Asn Ala His Ser Met Ala Leu Pro Ala Leu Glu Pro Ser
    50                  55                  60

Thr Arg Tyr Trp Ala Arg Val Arg Val Arg Thr Ser Arg Thr Gly Tyr
65                  70                  75                  80

Asn Gly Ile Trp Ser Glu Trp Ser Glu Ala Arg Ser Trp Asp Thr Glu
            85                  90                  95

<210> SEQ ID NO 10
<211> LENGTH: 89
<212> TYPE: PRT
<213> ORGANISM: Homo sapiens

<400> SEQUENCE: 10

Pro Pro Val Asn Phe Thr Ile Lys Val Thr Gly Leu Ala Gln Val Leu
1               5                   10                  15

Leu Gln Trp Lys Pro Asn Pro Asp Gln Glu Gln Arg Asn Val Asn Leu
            20                  25                  30

Glu Tyr Gln Val Lys Ile Asn Ala Pro Lys Glu Asp Asp Tyr Glu Thr
        35                  40                  45

Arg Ile Thr Glu Ser Lys Leu Val Thr Ile Leu His Lys Gly Phe Ser
    50                  55                  60

Ala Ser Val Arg Thr Ile Leu Gln Asn Asp His Ser Leu Leu Ala Ser
65                  70                  75                  80

Ser Trp Ala Ser Ala Glu Leu His Ala
            85

<210> SEQ ID NO 11
<211> LENGTH: 91
<212> TYPE: PRT
<213> ORGANISM: Homo sapiens

<400> SEQUENCE: 11

Leu Ser Val Thr Asp Val Thr Ser Ser Leu Arg Leu Asn Trp Glu
1               5                   10                  15

Ala Pro Pro Gly Ala Phe Asp Ser Phe Leu Leu Arg Phe Gly Val Pro
            20                  25                  30

Ser Pro Ser Thr Leu Glu Pro His Pro Arg Pro Leu Leu Gln Arg Glu
        35                  40                  45

Leu Met Val Pro Gly Thr Arg His Ser Ala Val Leu Arg Asp Leu Arg
    50                  55                  60

Ser Gly Thr Leu Tyr Ser Leu Thr Leu Tyr Gly Leu Arg Gly Pro His
65                  70                  75                  80

Lys Ala Asp Ser Ile Gln Gly Thr Ala Arg Thr
            85                  90

<210> SEQ ID NO 12
<211> LENGTH: 81
<212> TYPE: PRT
<213> ORGANISM: Homo sapiens

<400> SEQUENCE: 12

Leu Arg Ala Leu Asn Leu Thr Glu Gly Phe Ala Val Leu His Trp Lys
1               5                   10                  15

Pro Pro Gln Asn Pro Val Asp Thr Tyr Asp Ile Gln Val Thr Ala Pro
            20                  25                  30

Gly Ala Pro Pro Leu Gln Ala Glu Thr Pro Gly Ser Ala Val Asp Tyr
        35                  40                  45

Pro Leu His Asp Leu Val Leu His Thr Asn Tyr Thr Ala Thr Val Arg
    50                  55                  60

Gly Leu Arg Gly Pro Asn Leu Thr Ser Pro Ala Ser Ile Thr Phe Thr
65                  70                  75                  80

Thr

<210> SEQ ID NO 13
<211> LENGTH: 81
<212> TYPE: PRT
<213> ORGANISM: Homo sapiens

<400> SEQUENCE: 13

Leu Glu Ala Lys Glu Val Thr Pro Arg Thr Ala Leu Leu Thr Trp Thr
1               5                   10                  15

Glu Pro Pro Val Arg Pro Ala Gly Tyr Leu Leu Ser Phe His Thr Pro
            20                  25                  30

Gly Gly Gln Thr Gln Glu Ile Leu Leu Pro Gly Gly Ile Thr Ser His
        35                  40                  45

Gln Leu Leu Gly Leu Phe Pro Ser Thr Ser Tyr Asn Ala Arg Leu Gln
    50                  55                  60

Ala Met Trp Gly Gln Ser Leu Leu Pro Pro Val Ser Thr Ser Phe Thr
65                  70                  75                  80

Thr

<210> SEQ ID NO 14
<211> LENGTH: 83
<212> TYPE: PRT
<213> ORGANISM: Homo sapiens

<400> SEQUENCE: 14

Ile Glu Val Lys Asp Val Thr Asp Thr Thr Ala Leu Ile Thr Trp Phe
1               5                   10                  15

Lys Pro Leu Ala Glu Ile Asp Gly Ile Glu Leu Thr Tyr Gly Ile Lys
            20                  25                  30

Asp Val Pro Gly Asp Arg Thr Thr Ile Asp Leu Thr Glu Asp Glu Asn
        35                  40                  45

Gln Tyr Ser Ile Gly Asn Leu Lys Pro Asp Thr Glu Tyr Glu Val Ser
    50                  55                  60

Leu Ile Ser Arg Arg Gly Asp Met Ser Ser Asn Pro Ala Lys Glu Thr
65                  70                  75                  80

Phe Thr Thr

<210> SEQ ID NO 15
<211> LENGTH: 93
<212> TYPE: PRT
<213> ORGANISM: Homo sapiens

<400> SEQUENCE: 15

Pro Lys Phe Thr Lys Cys Arg Ser Pro Glu Arg Glu Thr Phe Ser Cys
1               5                   10                  15

His Trp Thr Asp Glu Val His His Gly Thr Lys Asn Leu Gly Pro Ile
            20                  25                  30

Gln Leu Phe Tyr Thr Arg Arg Asn Thr Gln Glu Trp Thr Gln Glu Trp
        35                  40                  45

Lys Glu Cys Pro Asp Tyr Val Ser Ala Gly Glu Asn Ser Cys Tyr Phe
    50                  55                  60

Asn Ser Ser Phe Thr Ser Ile Trp Ile Pro Tyr Cys Ile Lys Leu Thr
65                  70                  75                  80

Ser Asn Gly Gly Thr Val Asp Glu Lys Cys Phe Ser Val
                85                  90

```
<210> SEQ ID NO 16
<211> LENGTH: 97
<212> TYPE: PRT
<213> ORGANISM: Homo sapiens

<400> SEQUENCE: 16

Pro Ser Gly Phe Pro Gln Asn Leu His Val Thr Gly Leu Thr Thr Ser
1               5                   10                  15

Thr Thr Glu Leu Ala Trp Asp Pro Pro Val Leu Ala Glu Arg Asn Gly
            20                  25                  30

Arg Ile Ile Ser Tyr Thr Val Val Phe Arg Asp Ile Asn Ser Gln Gln
        35                  40                  45

Glu Leu Gln Asn Ile Thr Thr Asp Thr Arg Phe Thr Leu Thr Gly Leu
    50                  55                  60

Lys Pro Asp Thr Thr Tyr Asp Ile Lys Val Arg Ala Trp Thr Ser Lys
65                  70                  75                  80

Gly Ser Gly Pro Leu Ser Pro Ser Ile Gln Ser Arg Thr Met Pro Val
                85                  90                  95

Glu

<210> SEQ ID NO 17
<211> LENGTH: 92
<212> TYPE: PRT
<213> ORGANISM: Homo sapiens

<400> SEQUENCE: 17

Pro Lys Pro Pro Ile Asp Leu Val Val Thr Glu Thr Thr Ala Thr Ser
1               5                   10                  15

Val Thr Leu Thr Trp Asp Ser Gly Asn Ser Glu Pro Val Thr Tyr Tyr
            20                  25                  30

Gly Ile Gln Tyr Arg Ala Ala Gly Thr Glu Gly Pro Phe Gln Glu Val
        35                  40                  45

Asp Gly Val Ala Thr Thr Arg Tyr Ser Ile Gly Leu Ser Pro Phe
    50                  55                  60

Ser Glu Tyr Ala Phe Arg Val Leu Ala Val Asn Ser Ile Gly Arg Gly
65                  70                  75                  80

Pro Pro Ser Glu Ala Val Arg Ala Arg Thr Gly Glu
                85                  90

<210> SEQ ID NO 18
<211> LENGTH: 87
<212> TYPE: PRT
<213> ORGANISM: Homo sapiens

<400> SEQUENCE: 18

Leu Ser Pro Pro Arg Asn Leu Arg Ile Ser Asn Val Gly Ser Asn Ser
1               5                   10                  15

Ala Arg Leu Thr Trp Asp Pro Thr Ser Arg Gln Ile Asn Gly Tyr Arg
            20                  25                  30

Ile Val Tyr Asn Asn Ala Asp Gly Thr Glu Ile Asn Val Glu Val
        35                  40                  45

Asp Pro Ile Thr Thr Phe Pro Leu Lys Gly Leu Thr Pro Leu Thr Glu
    50                  55                  60

Tyr Thr Ile Ala Ile Phe Ser Ile Tyr Asp Glu Gly Gln Ser Glu Pro
65                  70                  75                  80

Leu Thr Gly Val Phe Thr Thr
                85
```

```
<210> SEQ ID NO 19
<211> LENGTH: 83
<212> TYPE: PRT
<213> ORGANISM: Artificial Sequence
<220> FEATURE:
<223> OTHER INFORMATION: Description of Artificial Sequence: Synthetic
      Charge variant polypeptide

<400> SEQUENCE: 19

Ile Glu Val Lys Asp Val Thr Asp Thr Thr Ala Leu Ile Thr Trp Phe
1               5                   10                  15

Lys Pro Leu Ala Glu Ile Asp Gly Ile Gln Leu Thr Tyr Gly Ile Lys
                20                  25                  30

Asp Val Pro Gly Asp Arg Thr Thr Ile Asn Leu Thr Glu Asp Glu Asn
            35                  40                  45

Gln Tyr Ser Ile Gly Asn Leu Lys Pro Asp Thr Glu Tyr Glu Val Ser
    50                  55                  60

Leu Ile Ser Arg Arg Gly Asp Met Ser Ser Asn Pro Ala Lys Gln Thr
65                  70                  75                  80

Phe Thr Thr

<210> SEQ ID NO 20
<211> LENGTH: 91
<212> TYPE: PRT
<213> ORGANISM: Archaeoglobus fulgidus DSM 4304

<400> SEQUENCE: 20

Pro Ala Ile Ser Asn Val Arg Val Ser Asp Val Thr Asn Ser Ser Ala
1               5                   10                  15

Thr Ile Arg Trp Asp Val Ser Leu Ala Ala Asn Asn Arg Val Leu Phe
                20                  25                  30

Ser Thr Asn Ser Asp Leu Ser Ser Pro Gln Trp Ser Ala Trp Asp Asn
            35                  40                  45

Ser Thr Asp Ser Pro Met Ile Thr Leu Ser Gly Leu Ser Ala Gly Thr
    50                  55                  60

Ala Tyr Tyr Phe Ser Val Tyr Ser Phe Arg Pro Asp Asn Ala Ser Leu
65                  70                  75                  80

Tyr Ser Asn Ser Ser Ile Met Ser Phe Thr Thr
                85                  90

<210> SEQ ID NO 21
<211> LENGTH: 94
<212> TYPE: PRT
<213> ORGANISM: Staphylothermus marinus F1

<400> SEQUENCE: 21

Ser Glu Pro Gln Asn Leu Lys Ala Thr Ala Gly Asn Asn Asn Ile Thr
1               5                   10                  15

Leu Thr Trp Asp Pro Pro Ile Asp Asp Gly Gly Cys Arg Ile Val Glu
                20                  25                  30

Tyr Arg Ile Tyr Arg Gly Thr Asn Asn Asn Asn Leu Glu Tyr Tyr Ala
            35                  40                  45

Ser Val Asn Gly Ser Thr Thr Thr Phe Ile Asp Lys Asn Ile Val Tyr
    50                  55                  60

Ser Gln Thr Tyr Tyr Lys Val Ser Ala Val Asn Asn Ile Val Glu
65                  70                  75                  80

Gly Pro Lys Ser Asn Thr Ala Ser Ala Thr Pro Thr Ser Ser
                85                  90
```

<210> SEQ ID NO 22
<211> LENGTH: 89
<212> TYPE: PRT
<213> ORGANISM: Sulfolobus acidocaldarius DSM 639

<400> SEQUENCE: 22

Pro Pro Pro Lys Pro Val Ile Arg Phe Ala Gln Ala Gly Asn Asn Ser
1               5                   10                  15

Ile Ser Leu Ser Trp Tyr Asp Thr Asn Thr Ser Gly Tyr Tyr Ile Gln
            20                  25                  30

Trp Trp Ser Ser Ile Asp Asn Asn Lys Ser Thr Ile Asn Val Gly Asn
        35                  40                  45

Val Ser Ser Tyr Leu Phe Ile Asn Leu Thr Asn Gly Val Thr Tyr Tyr
    50                  55                  60

Phe Arg Ile Ile Pro Tyr Asn Gln Ala Gly Asn Gly Thr Ser Ser Asp
65                  70                  75                  80

Ile Ile Ser Leu Thr Pro Gly Ala Val
                85

<210> SEQ ID NO 23
<211> LENGTH: 89
<212> TYPE: PRT
<213> ORGANISM: Sulfolobus acidocaldarius DSM 639

<400> SEQUENCE: 23

Pro Asp Ser Pro Ser Val Lys Val Ile Val Gly Asp Arg Asn Ala Thr
1               5                   10                  15

Val Ile Trp Ser Lys Pro Tyr Asn Gly Gly Phe Pro Ile Leu Gly Tyr
            20                  25                  30

Tyr Leu Thr Val Lys Thr Asp Asn Ser Ser Tyr Thr Ile Asn Val Gly
        35                  40                  45

Asn Val Ser Lys Tyr Thr Leu Thr Asn Leu Thr Pro Glu Val Leu Tyr
    50                  55                  60

Glu Val Met Val Ala Tyr Asn Lys Leu Gly Asn Ser Ser Pro Gly
65                  70                  75                  80

Ile Val Asn Phe Val Ala Leu Thr Thr
                85

<210> SEQ ID NO 24
<211> LENGTH: 87
<212> TYPE: PRT
<213> ORGANISM: Sulfolobus acidocaldarius DSM 639

<400> SEQUENCE: 24

Leu Thr Thr Ala Ser Ile Ser Val Ser Val Tyr Lys Lys Val Asn Gly
1               5                   10                  15

Val Leu Ile Ser Trp Asn Lys Thr Glu Asn Thr Thr Tyr Asn Leu Leu
            20                  25                  30

Ile Ser Asp Lys Lys Gly Lys Ile Val Asn Ile Thr Thr Thr Asn
        35                  40                  45

Thr Ser Tyr Phe Ala Tyr Ile Pro Tyr Gly Ile Tyr Asn Val Thr Ile
    50                  55                  60

Arg Ala Thr Asn Gln Val Gly Thr Asn Ser Thr Ser Phe Pro Ile Val
65                  70                  75                  80

Phe Tyr Ile Pro Pro Phe Ile
                85

<210> SEQ ID NO 25
<211> LENGTH: 84
<212> TYPE: PRT
<213> ORGANISM: Sulfolobus acidocaldarius DSM 639

<400> SEQUENCE: 25

Pro Leu Val Lys Phe Ser Ile Gly Asn Asn Ser Ile Leu Asn Leu Lys
1               5                   10                  15

Trp Asn Asn Val Thr Gly Ala Thr Phe Tyr Leu Val Tyr Val Asn Thr
            20                  25                  30

Thr Leu Ile Ala Asn Val Thr Thr Asp Ser Tyr Ser Leu Asn Leu Thr
        35                  40                  45

Pro Gly Phe His Val Ile Arg Val Val Ala Ala Asn Pro Ile Tyr Asn
    50                  55                  60

Ser Ser Pro Ala Ser Leu Gly Ile Leu Gln Gln His Ser Val Thr
65                  70                  75                  80

Ser Ser Ile Thr

<210> SEQ ID NO 26
<211> LENGTH: 88
<212> TYPE: PRT
<213> ORGANISM: Sulfolobus solfataricus P2

<400> SEQUENCE: 26

Pro Leu Pro Pro Lys Ile Thr Ser Tyr Ser Ala Gly Asn Glu Ser Val
1               5                   10                  15

Thr Leu Gly Trp Asn Pro Val Arg Leu Ser Ser Gly Tyr Glu Ile Ile
            20                  25                  30

Tyr Trp Asn Asn Met Gly Phe Asn Ser Ser Ile Asn Val Gly Asn Val
        35                  40                  45

Thr Ser Tyr Thr Val Thr Gly Leu Lys Asp Gly Ile Thr Tyr Tyr Phe
    50                  55                  60

Glu Val Leu Ala Tyr Asn Ser Ile Gly Tyr Ser Ser Pro Ser Ser Ile
65                  70                  75                  80

Ile Ala Leu Thr Pro Ala Ser Val
                85

<210> SEQ ID NO 27
<211> LENGTH: 92
<212> TYPE: PRT
<213> ORGANISM: Sulfolobus solfataricus P2

<400> SEQUENCE: 27

Pro Asn Pro Pro Gln Leu Val Ser Val Lys Tyr Gly Asn Asp Asn Val
1               5                   10                  15

Thr Leu Asn Trp Leu Pro Pro Thr Phe Ser Gly Gly Tyr Leu Leu Leu
            20                  25                  30

Gly Tyr Tyr Val Ile Val Lys Asn Glu Asn Ser Met Val Ser Ser His
        35                  40                  45

Phe Val Asn Ser Thr Ser Leu Thr Ile Ser Asn Leu Thr Pro Asn Val
    50                  55                  60

Thr Tyr Asn Val Phe Ile Tyr Ala Val Asn Lys Leu Gly Asn Ser Ser
65                  70                  75                  80

Pro Leu Val Leu Thr Val Val Pro Ile Thr Lys Ala
                85                  90

<210> SEQ ID NO 28

-continued

```
<211> LENGTH: 86
<212> TYPE: PRT
<213> ORGANISM: Sulfolobus solfataricus P2

<400> SEQUENCE: 28

Pro Ile Thr Lys Ala Ser Val Phe Ala Phe Ile Thr Lys Leu Gly Asn
1               5                   10                  15

Gly Ile Leu Val Asn Trp Thr Thr Ser Phe Pro Ala Asn Ile Thr Leu
            20                  25                  30

Glu Leu Tyr Asn Pro Asn Gly Asn Leu Ile Ser Gln Ile Ala Ala Ile
        35                  40                  45

Lys Gly Asn Ser Ser Tyr Leu Phe Arg Val Pro Gln Gly Asn Tyr Thr
50                  55                  60

Leu Val Ile Ile Ala Ser Asn Ser Ala Gly Val Ser Lys Tyr Val Tyr
65                  70                  75                  80

Gln Val Val Tyr Tyr Leu
                85

<210> SEQ ID NO 29
<211> LENGTH: 83
<212> TYPE: PRT
<213> ORGANISM: Sulfolobus solfataricus P2

<400> SEQUENCE: 29

Pro Pro Ala Ser Pro Gln Val Ser Leu Ile Gly Phe Gly Asn Asn Leu
1               5                   10                  15

Tyr Ile Ser Trp Asn Asn Glu Ala Asn Val Ile Thr Tyr Leu Val Tyr
            20                  25                  30

Val Asn Asn Ser Leu Val Tyr Glu Gly Pro Ser Asn Ser Ile Val Thr
        35                  40                  45

Asn Ile Ser Asn Gly Thr Tyr Leu Val Lys Val Ile Gly Val Asn Pro
50                  55                  60

Ala Gly Ser Ser Pro Gly Ile Ala Val Ile His Tyr Thr Gly Asp
65                  70                  75                  80

Tyr Val Thr

<210> SEQ ID NO 30
<211> LENGTH: 87
<212> TYPE: PRT
<213> ORGANISM: Sulfolobus tokodaii
<220> FEATURE:
<223> OTHER INFORMATION: str. 7

<400> SEQUENCE: 30

Pro Pro Lys Pro Gln Ile Ala Ser Ile Ala Ser Gly Asn Glu Thr Ile
1               5                   10                  15

Thr Val Lys Trp Tyr Asp Thr Asn Ala Ser Gly Tyr Tyr Ile Thr Tyr
            20                  25                  30

Trp Ser Asn Phe Ser Gln Lys Val Thr Ile Asn Val Gly Asn Val Thr
        35                  40                  45

Ser Tyr Thr Ile Lys His Leu Lys Asp Gly Val Thr Tyr Tyr Ile Gln
50                  55                  60

Ile Val Pro Tyr Asn Ser Leu Gly Asn Gly Thr Pro Ser Asp Ile Ile
65                  70                  75                  80

Ser Ala Thr Pro Ser Ser Val
                85

<210> SEQ ID NO 31
```

```
<211> LENGTH: 86
<212> TYPE: PRT
<213> ORGANISM: Sulfolobus tokodaii
<220> FEATURE:
<223> OTHER INFORMATION: str. 7

<400> SEQUENCE: 31

Pro Asn Pro Pro Ile Ile Lys Val Lys Ile Gly Asn Leu Asn Ala Thr
1               5                   10                  15

Leu Thr Trp Tyr Asp Thr Phe Asn Gly Gly Tyr Pro Ile Glu Gly Tyr
            20                  25                  30

Tyr Leu Tyr Val Asn Gly Lys Gly Ile Asn Val Gly Asn Ile Thr Ser
        35                  40                  45

Tyr Val Leu Thr Asn Leu Thr Ala Gly Glu Leu Tyr Thr Ile Glu Leu
50                  55                  60

Ile Ala Tyr Asn Lys Ile Gly Asn Ser Ser Ile Ser Val Ser Phe
65                  70                  75                  80

Ile Ala Ala Ser Lys Ala
                85

<210> SEQ ID NO 32
<211> LENGTH: 83
<212> TYPE: PRT
<213> ORGANISM: Sulfolobus tokodaii
<220> FEATURE:
<223> OTHER INFORMATION: str. 7

<400> SEQUENCE: 32

Ala Ser Lys Ala Asn Leu Thr Val Thr Val Tyr Lys Lys Ile Asn Gly
1               5                   10                  15

Phe Leu Val Ser Trp Asn Ser Thr Ser Lys Ala Lys Tyr Ile Leu Thr
            20                  25                  30

Val Ser Lys Glu Asn Val Val Leu Leu Asn Val Ser Thr Thr Asn Thr
        35                  40                  45

Ser Tyr Phe Val Lys Val Pro Phe Gly Val Tyr Asn Ile Ser Leu Glu
50                  55                  60

Ala Val Asn Ile Val Gly Ile Thr Lys Tyr Ala Phe Ile Leu Ile Tyr
65                  70                  75                  80

Tyr Ile Gln

<210> SEQ ID NO 33
<211> LENGTH: 81
<212> TYPE: PRT
<213> ORGANISM: Sulfolobus tokodaii
<220> FEATURE:
<223> OTHER INFORMATION: str. 7

<400> SEQUENCE: 33

Pro Ala Ser Pro Thr Val Asn Trp Ser Ile Thr Leu Asn Thr Val Ser
1               5                   10                  15

Leu Asn Trp Ser Lys Val Ser Gly Ala Glu Tyr Tyr Leu Ile Tyr Asp
            20                  25                  30

Asn Gly Lys Leu Ile Thr Asn Thr Thr Asn Thr Ala Phe Thr Phe Asn
        35                  40                  45

Leu Thr Ile Gly Gln Asn Glu Ile Glu Val Tyr Ala Ala Asn Ala Tyr
50                  55                  60

Tyr Lys Ser Ala Pro Tyr Ile Ile Asn Asp Val Arg Asn Tyr Ile Val
65                  70                  75                  80

Val
```

<210> SEQ ID NO 34
<211> LENGTH: 82
<212> TYPE: PRT
<213> ORGANISM: Homo sapiens

<400> SEQUENCE: 34

Ala Arg Val Thr Asp Ala Thr Glu Thr Thr Ile Thr Ile Ser Trp Arg
1               5                   10                  15

Thr Lys Thr Glu Thr Ile Thr Gly Phe Gln Val Asp Ala Val Pro Ala
            20                  25                  30

Asn Gly Gln Thr Pro Ile Gln Arg Thr Ile Lys Pro Asp Val Arg Ser
        35                  40                  45

Tyr Thr Ile Thr Gly Leu Gln Pro Gly Thr Asp Tyr Lys Ile Tyr Leu
    50                  55                  60

Tyr Thr Leu Asn Asp Asn Ala Arg Ser Ser Pro Val Val Ile Asp Ala
65                  70                  75                  80

Ser Thr

<210> SEQ ID NO 35
<211> LENGTH: 7
<212> TYPE: PRT
<213> ORGANISM: Homo sapiens

<400> SEQUENCE: 35

Lys Asp Val Thr Asp Thr Thr
1               5

<210> SEQ ID NO 36
<211> LENGTH: 9
<212> TYPE: PRT
<213> ORGANISM: Homo sapiens

<400> SEQUENCE: 36

Phe Lys Pro Leu Ala Glu Ile Asp Gly
1               5

<210> SEQ ID NO 37
<211> LENGTH: 7
<212> TYPE: PRT
<213> ORGANISM: Homo sapiens

<400> SEQUENCE: 37

Lys Asp Val Pro Gly Asp Arg
1               5

<210> SEQ ID NO 38
<211> LENGTH: 6
<212> TYPE: PRT
<213> ORGANISM: Homo sapiens

<400> SEQUENCE: 38

Thr Glu Asp Glu Asn Gln
1               5

<210> SEQ ID NO 39
<211> LENGTH: 8
<212> TYPE: PRT
<213> ORGANISM: Homo sapiens

<400> SEQUENCE: 39

Gly Asn Leu Lys Pro Asp Thr Glu

<210> SEQ ID NO 40
<211> LENGTH: 10
<212> TYPE: PRT
<213> ORGANISM: Homo sapiens

<400> SEQUENCE: 40

Arg Arg Gly Asp Met Ser Ser Asn Pro Ala
1               5                   10

<210> SEQ ID NO 41
<211> LENGTH: 10
<212> TYPE: PRT
<213> ORGANISM: Homo sapiens

<400> SEQUENCE: 41

Arg Leu Asp Ala Pro Ser Gln Ile Glu Val
1               5                   10

<210> SEQ ID NO 42
<211> LENGTH: 3
<212> TYPE: PRT
<213> ORGANISM: Homo sapiens

<400> SEQUENCE: 42

Ile Glu Val
1

<210> SEQ ID NO 43
<211> LENGTH: 5
<212> TYPE: PRT
<213> ORGANISM: Homo sapiens

<400> SEQUENCE: 43

Ala Leu Ile Thr Trp
1               5

<210> SEQ ID NO 44
<211> LENGTH: 7
<212> TYPE: PRT
<213> ORGANISM: Homo sapiens

<400> SEQUENCE: 44

Ile Glu Leu Thr Tyr Gly Ile
1               5

<210> SEQ ID NO 45
<211> LENGTH: 7
<212> TYPE: PRT
<213> ORGANISM: Artificial Sequence
<220> FEATURE:
<223> OTHER INFORMATION: Description of Artificial Sequence: Synthetic
      Beta-strand C peptide in Disulfide-bonded variant

<400> SEQUENCE: 45

Cys Glu Leu Thr Tyr Gly Ile
1               5

<210> SEQ ID NO 46
<211> LENGTH: 5
<212> TYPE: PRT
<213> ORGANISM: Homo sapiens

<400> SEQUENCE: 46

Thr Thr Ile Asp Leu
1               5

<210> SEQ ID NO 47
<211> LENGTH: 3
<212> TYPE: PRT
<213> ORGANISM: Homo sapiens

<400> SEQUENCE: 47

Tyr Ser Ile
1

<210> SEQ ID NO 48
<211> LENGTH: 7
<212> TYPE: PRT
<213> ORGANISM: Homo sapiens

<400> SEQUENCE: 48

Tyr Glu Val Ser Leu Ile Ser
1               5

<210> SEQ ID NO 49
<211> LENGTH: 7
<212> TYPE: PRT
<213> ORGANISM: Artificial Sequence
<220> FEATURE:
<223> OTHER INFORMATION: Description of Artificial Sequence: Synthetic
      Beta-strand F peptide in Disulfide-bonded variant

<400> SEQUENCE: 49

Tyr Glu Val Ser Leu Ile Cys
1               5

<210> SEQ ID NO 50
<211> LENGTH: 7
<212> TYPE: PRT
<213> ORGANISM: Artificial Sequence
<220> FEATURE:
<223> OTHER INFORMATION: Description of Artificial Sequence: Synthetic
      Beta-strand F peptide in Disulfide-bonded variant

<400> SEQUENCE: 50

Tyr Cys Val Ser Leu Ile Ser
1               5

<210> SEQ ID NO 51
<211> LENGTH: 7
<212> TYPE: PRT
<213> ORGANISM: Artificial Sequence
<220> FEATURE:
<223> OTHER INFORMATION: Description of Artificial Sequence: Synthetic
      Beta-strand F peptide in Disulfide-bonded variant

<400> SEQUENCE: 51

Tyr Cys Val Ser Leu Ile Cys
1               5

<210> SEQ ID NO 52
<211> LENGTH: 6
<212> TYPE: PRT
<213> ORGANISM: Homo sapiens

<400> SEQUENCE: 52

Lys Glu Thr Phe Thr Thr
1               5

-continued

```
<210> SEQ ID NO 53
<211> LENGTH: 6
<212> TYPE: PRT
<213> ORGANISM: Artificial Sequence
<220> FEATURE:
<223> OTHER INFORMATION: Description of Artificial Sequence: Synthetic
      Beta-strand G peptide in Disulfide-bonded variant

<400> SEQUENCE: 53

Lys Glu Cys Phe Thr Thr
1               5

<210> SEQ ID NO 54
<211> LENGTH: 94
<212> TYPE: PRT
<213> ORGANISM: Homo sapiens

<400> SEQUENCE: 54

Val Ser Asp Val Pro Arg Asp Leu Glu Val Val Ala Ala Thr Pro Thr
1               5                   10                  15

Ser Leu Leu Ile Ser Trp Asp Ala Pro Ala Val Thr Val Arg Tyr Tyr
            20                  25                  30

Arg Ile Thr Tyr Gly Glu Thr Gly Gly Asn Ser Pro Val Gln Glu Phe
        35                  40                  45

Thr Val Pro Gly Ser Lys Ser Thr Ala Thr Ile Ser Gly Leu Lys Pro
    50                  55                  60

Gly Val Asp Tyr Thr Ile Thr Val Tyr Ala Val Thr Gly Arg Gly Asp
65                  70                  75                  80

Ser Pro Ala Ser Ser Lys Pro Ile Ser Ile Asn Tyr Arg Thr
                85                  90

<210> SEQ ID NO 55
<211> LENGTH: 7
<212> TYPE: PRT
<213> ORGANISM: Homo sapiens

<400> SEQUENCE: 55

Val Ala Ala Thr Pro Thr Ser
1               5

<210> SEQ ID NO 56
<211> LENGTH: 9
<212> TYPE: PRT
<213> ORGANISM: Homo sapiens

<400> SEQUENCE: 56

Asp Ala Pro Ala Val Thr Val Arg Tyr
1               5

<210> SEQ ID NO 57
<211> LENGTH: 7
<212> TYPE: PRT
<213> ORGANISM: Homo sapiens

<400> SEQUENCE: 57

Thr Gly Gly Asn Ser Pro Val
1               5

<210> SEQ ID NO 58
<211> LENGTH: 6
<212> TYPE: PRT
<213> ORGANISM: Homo sapiens

<400> SEQUENCE: 58
```

```
Pro Gly Ser Lys Ser Thr
1               5

<210> SEQ ID NO 59
<211> LENGTH: 8
<212> TYPE: PRT
<213> ORGANISM: Homo sapiens

<400> SEQUENCE: 59

Ser Gly Leu Lys Pro Gly Val Asp
1               5

<210> SEQ ID NO 60
<211> LENGTH: 14
<212> TYPE: PRT
<213> ORGANISM: Homo sapiens

<400> SEQUENCE: 60

Val Thr Gly Arg Gly Asp Ser Pro Ala Ser Ser Lys Pro Ile
1               5                   10

<210> SEQ ID NO 61
<211> LENGTH: 10
<212> TYPE: PRT
<213> ORGANISM: Homo sapiens

<400> SEQUENCE: 61

Val Ser Asp Val Pro Arg Asp Leu Glu Val
1               5                   10

<210> SEQ ID NO 62
<211> LENGTH: 3
<212> TYPE: PRT
<213> ORGANISM: Homo sapiens

<400> SEQUENCE: 62

Leu Glu Val
1

<210> SEQ ID NO 63
<211> LENGTH: 5
<212> TYPE: PRT
<213> ORGANISM: Homo sapiens

<400> SEQUENCE: 63

Leu Leu Ile Ser Trp
1               5

<210> SEQ ID NO 64
<211> LENGTH: 7
<212> TYPE: PRT
<213> ORGANISM: Homo sapiens

<400> SEQUENCE: 64

Tyr Arg Ile Thr Tyr Gly Glu
1               5

<210> SEQ ID NO 65
<211> LENGTH: 5
<212> TYPE: PRT
<213> ORGANISM: Homo sapiens

<400> SEQUENCE: 65

Gln Glu Phe Thr Val
```

```
<210> SEQ ID NO 66
<211> LENGTH: 3
<212> TYPE: PRT
<213> ORGANISM: Homo sapiens

<400> SEQUENCE: 66

Ala Thr Ile
1

<210> SEQ ID NO 67
<211> LENGTH: 7
<212> TYPE: PRT
<213> ORGANISM: Homo sapiens

<400> SEQUENCE: 67

Tyr Thr Ile Thr Val Tyr Ala
1               5

<210> SEQ ID NO 68
<211> LENGTH: 6
<212> TYPE: PRT
<213> ORGANISM: Homo sapiens

<400> SEQUENCE: 68

Ser Ile Asn Tyr Arg Thr
1               5

<210> SEQ ID NO 69
<211> LENGTH: 88
<212> TYPE: PRT
<213> ORGANISM: Homo sapiens

<400> SEQUENCE: 69

Val Ser Pro Pro Arg Ala Arg Val Thr Asp Ala Thr Glu Thr Thr
1               5                   10                  15

Ile Thr Ile Ser Trp Arg Thr Lys Thr Glu Thr Ile Thr Gly Phe Gln
                20                  25                  30

Val Asp Ala Val Pro Ala Asn Gly Gln Thr Pro Ile Gln Arg Thr Ile
            35                  40                  45

Lys Pro Asp Val Arg Ser Tyr Thr Ile Thr Gly Leu Gln Pro Gly Thr
        50                  55                  60

Asp Tyr Lys Ile Tyr Leu Tyr Thr Leu Asn Asp Asn Ala Arg Ser Ser
65                  70                  75                  80

Pro Val Val Ile Asp Ala Ser Thr
                85

<210> SEQ ID NO 70
<211> LENGTH: 7
<212> TYPE: PRT
<213> ORGANISM: Homo sapiens

<400> SEQUENCE: 70

Thr Asp Ala Thr Glu Thr Thr
1               5

<210> SEQ ID NO 71
<211> LENGTH: 9
<212> TYPE: PRT
<213> ORGANISM: Homo sapiens

<400> SEQUENCE: 71
```

```
Arg Thr Lys Thr Glu Thr Ile Thr Gly
1               5
```

<210> SEQ ID NO 72
<211> LENGTH: 6
<212> TYPE: PRT
<213> ORGANISM: Homo sapiens

<400> SEQUENCE: 72

```
Ala Asn Gly Gln Thr Pro
1               5
```

<210> SEQ ID NO 73
<211> LENGTH: 6
<212> TYPE: PRT
<213> ORGANISM: Homo sapiens

<400> SEQUENCE: 73

```
Lys Pro Asp Val Arg Ser
1               5
```

<210> SEQ ID NO 74
<211> LENGTH: 8
<212> TYPE: PRT
<213> ORGANISM: Homo sapiens

<400> SEQUENCE: 74

```
Thr Gly Leu Gln Pro Gly Thr Asp
1               5
```

<210> SEQ ID NO 75
<211> LENGTH: 10
<212> TYPE: PRT
<213> ORGANISM: Homo sapiens

<400> SEQUENCE: 75

```
Leu Asn Asp Asn Ala Arg Ser Ser Pro Val
1               5                   10
```

<210> SEQ ID NO 76
<211> LENGTH: 8
<212> TYPE: PRT
<213> ORGANISM: Homo sapiens

<400> SEQUENCE: 76

```
Ser Pro Pro Arg Arg Ala Arg Val
1               5
```

<210> SEQ ID NO 77
<211> LENGTH: 3
<212> TYPE: PRT
<213> ORGANISM: Homo sapiens

<400> SEQUENCE: 77

```
Ala Arg Val
1
```

<210> SEQ ID NO 78
<211> LENGTH: 4
<212> TYPE: PRT
<213> ORGANISM: Homo sapiens

<400> SEQUENCE: 78

```
Ile Thr Ile Trp
```

<210> SEQ ID NO 79
<211> LENGTH: 7
<212> TYPE: PRT
<213> ORGANISM: Homo sapiens

<400> SEQUENCE: 79

Phe Gln Val Asp Ala Val Pro
1               5

<210> SEQ ID NO 80
<211> LENGTH: 5
<212> TYPE: PRT
<213> ORGANISM: Homo sapiens

<400> SEQUENCE: 80

Ile Gln Arg Thr Ile
1               5

<210> SEQ ID NO 81
<211> LENGTH: 3
<212> TYPE: PRT
<213> ORGANISM: Homo sapiens

<400> SEQUENCE: 81

Tyr Thr Ile
1

<210> SEQ ID NO 82
<211> LENGTH: 7
<212> TYPE: PRT
<213> ORGANISM: Homo sapiens

<400> SEQUENCE: 82

Tyr Lys Ile Tyr Leu Tyr Thr
1               5

<210> SEQ ID NO 83
<211> LENGTH: 6
<212> TYPE: PRT
<213> ORGANISM: Homo sapiens

<400> SEQUENCE: 83

Val Ile Asp Ala Ser Thr
1               5

<210> SEQ ID NO 84
<211> LENGTH: 232
<212> TYPE: PRT
<213> ORGANISM: Homo sapiens

<400> SEQUENCE: 84

Glu Pro Lys Ser Cys Asp Lys Thr His Thr Cys Pro Pro Cys Pro Ala
1               5                   10                  15

Pro Glu Leu Leu Gly Gly Pro Ser Val Phe Leu Phe Pro Pro Lys Pro
                20                  25                  30

Lys Asp Thr Leu Met Ile Ser Arg Thr Pro Glu Val Thr Cys Val Val
            35                  40                  45

Val Asp Val Ser His Glu Asp Pro Glu Val Lys Phe Asn Trp Tyr Val
        50                  55                  60

Asp Gly Val Glu Val His Asn Ala Lys Thr Lys Pro Arg Glu Glu Gln
65                  70                  75                  80

```
Tyr Asn Ser Thr Tyr Arg Val Ser Val Leu Thr Val Leu His Gln
                85                  90                  95

Asp Trp Leu Asn Gly Lys Glu Tyr Lys Cys Lys Val Ser Asn Lys Ala
            100                 105                 110

Leu Pro Ala Pro Ile Glu Lys Thr Ile Ser Lys Ala Lys Gly Gln Pro
        115                 120                 125

Arg Glu Pro Gln Val Tyr Thr Leu Pro Pro Ser Arg Glu Glu Met Thr
    130                 135                 140

Lys Asn Gln Val Ser Leu Thr Cys Leu Val Lys Gly Phe Tyr Pro Ser
145                 150                 155                 160

Asp Ile Ala Val Glu Trp Glu Ser Asn Gly Gln Pro Glu Asn Asn Tyr
                165                 170                 175

Lys Thr Thr Pro Pro Val Leu Asp Ser Asp Gly Ser Phe Phe Leu Tyr
            180                 185                 190

Ser Lys Leu Thr Val Asp Lys Ser Arg Trp Gln Gln Gly Asn Val Phe
        195                 200                 205

Ser Cys Ser Val Met His Glu Ala Leu His Asn His Tyr Thr Gln Lys
    210                 215                 220

Ser Leu Ser Leu Ser Pro Gly Lys
225                 230

<210> SEQ ID NO 85
<211> LENGTH: 330
<212> TYPE: PRT
<213> ORGANISM: Homo sapiens

<400> SEQUENCE: 85

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Arg Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
```

```
                    210                 215                 220
Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330

<210> SEQ ID NO 86
<211> LENGTH: 107
<212> TYPE: PRT
<213> ORGANISM: Homo sapiens

<400> SEQUENCE: 86

Arg Thr Val Ala Ala Pro Ser Val Phe Ile Phe Pro Pro Ser Asp Glu
1               5                   10                  15

Gln Leu Lys Ser Gly Thr Ala Ser Val Val Cys Leu Leu Asn Asn Phe
            20                  25                  30

Tyr Pro Arg Glu Ala Lys Val Gln Trp Lys Val Asp Asn Ala Leu Gln
        35                  40                  45

Ser Gly Asn Ser Gln Glu Ser Val Thr Glu Gln Asp Ser Lys Asp Ser
    50                  55                  60

Thr Tyr Ser Leu Ser Ser Thr Leu Thr Leu Ser Lys Ala Asp Tyr Glu
65                  70                  75                  80

Lys His Lys Val Tyr Ala Cys Glu Val Thr His Gln Gly Leu Ser Ser
                85                  90                  95

Pro Val Thr Lys Ser Phe Asn Arg Gly Glu Cys
            100                 105

<210> SEQ ID NO 87
<211> LENGTH: 104
<212> TYPE: PRT
<213> ORGANISM: Homo sapiens

<400> SEQUENCE: 87

Gln Pro Lys Ala Ala Pro Ser Val Thr Leu Phe Pro Pro Ser Ser Glu
1               5                   10                  15

Glu Leu Gln Ala Asn Lys Ala Thr Leu Val Cys Leu Ile Ser Asp Phe
            20                  25                  30

Tyr Pro Gly Ala Val Thr Val Ala Trp Lys Ala Asp Ser Ser Pro Val
        35                  40                  45

Lys Ala Gly Val Glu Thr Thr Thr Pro Ser Lys Gln Ser Asn Asn Lys
    50                  55                  60

Tyr Ala Ala Ser Ser Tyr Leu Ser Leu Thr Pro Glu Gln Trp Lys Ser
65                  70                  75                  80

His Arg Ser Tyr Ser Cys Gln Val Thr His Glu Gly Ser Thr Val Glu
                85                  90                  95

Lys Thr Val Ala Pro Thr Glu Cys
```

```
<210> SEQ ID NO 88
<211> LENGTH: 16
<212> TYPE: PRT
<213> ORGANISM: Artificial Sequence
<220> FEATURE:
<223> OTHER INFORMATION: Description of Artificial Sequence: Synthetic
      Linker peptide

<400> SEQUENCE: 88

Gly Gly Gly Gly Ser Gly Gly Gly Ser Gly Gly Gly Gly Ser Ala
1               5                   10                  15

<210> SEQ ID NO 89
<211> LENGTH: 24
<212> TYPE: PRT
<213> ORGANISM: Artificial Sequence
<220> FEATURE:
<223> OTHER INFORMATION: Description of Artificial Sequence: Synthetic
      Linker peptide

<400> SEQUENCE: 89

Gly Gly Gly Gly Ser Gly Gly Gly Gly Ser Gly Thr Gly Ser Ala Met
1               5                   10                  15

Ala Ser Gly Gly Gly Gly Ser Ala
            20

<210> SEQ ID NO 90
<211> LENGTH: 13
<212> TYPE: PRT
<213> ORGANISM: Artificial Sequence
<220> FEATURE:
<223> OTHER INFORMATION: Description of Artificial Sequence: Synthetic
      Linker peptide

<400> SEQUENCE: 90

Ala Gly Gly Gly Gly Ser Arg Leu Asp Ala Pro Gly Gln
1               5                   10

<210> SEQ ID NO 91
<211> LENGTH: 22
<212> TYPE: PRT
<213> ORGANISM: Artificial Sequence
<220> FEATURE:
<223> OTHER INFORMATION: Description of Artificial Sequence: Synthetic
      Linker peptide

<400> SEQUENCE: 91

Gly Gly Gly Gly Ser Gly Gly Gly Ser Gly Gly Gly Gly Ser Arg
1               5                   10                  15

Leu Asp Ala Pro Gly Gln
            20

<210> SEQ ID NO 92
<211> LENGTH: 32
<212> TYPE: PRT
<213> ORGANISM: Artificial Sequence
<220> FEATURE:
<223> OTHER INFORMATION: Description of Artificial Sequence: Synthetic
      Linker peptide

<400> SEQUENCE: 92

Gly Gly Gly Gly Ser Gly Gly Gly Gly Ser Gly Gly Gly Gly Ser Gly
1               5                   10                  15

Gly Gly Gly Ser Gly Gly Gly Gly Ser Arg Leu Asp Ala Pro Gly Gln
```

-continued

```
                  20                  25                  30

<210> SEQ ID NO 93
<211> LENGTH: 42
<212> TYPE: PRT
<213> ORGANISM: Artificial Sequence
<220> FEATURE:
<223> OTHER INFORMATION: Description of Artificial Sequence: Synthetic
      Linker peptide

<400> SEQUENCE: 93

Gly Gly Gly Gly Ser Gly Gly Gly Ser Gly Gly Gly Gly Ser Gly
1               5                   10                  15

Gly Gly Gly Ser Gly Gly Gly Gly Ser Gly Gly Gly Gly Ser Gly Gly
                20                  25                  30

Gly Gly Ser Arg Leu Asp Ala Pro Gly Gln
        35                  40

<210> SEQ ID NO 94
<211> LENGTH: 8
<212> TYPE: PRT
<213> ORGANISM: Artificial Sequence
<220> FEATURE:
<223> OTHER INFORMATION: Description of Artificial Sequence: Synthetic
      Linker peptide

<400> SEQUENCE: 94

Thr Arg Leu Asp Ala Pro Gly Gln
1               5

<210> SEQ ID NO 95
<211> LENGTH: 12
<212> TYPE: PRT
<213> ORGANISM: Artificial Sequence
<220> FEATURE:
<223> OTHER INFORMATION: Description of Artificial Sequence: Synthetic
      Linker peptide

<400> SEQUENCE: 95

Gly Gly Gly Gly Ser Arg Leu Asp Ala Pro Gly Gln
1               5                   10

<210> SEQ ID NO 96
<211> LENGTH: 17
<212> TYPE: PRT
<213> ORGANISM: Artificial Sequence
<220> FEATURE:
<223> OTHER INFORMATION: Description of Artificial Sequence: Synthetic
      Linker peptide

<400> SEQUENCE: 96

Gly Gly Gly Gly Ser Gly Gly Gly Gly Ser Arg Leu Asp Ala Pro Gly
1               5                   10                  15

Gln

<210> SEQ ID NO 97
<211> LENGTH: 12
<212> TYPE: PRT
<213> ORGANISM: Artificial Sequence
<220> FEATURE:
<223> OTHER INFORMATION: Description of Artificial Sequence: Synthetic
      Loop peptide

<400> SEQUENCE: 97

Ala Lys Pro Trp Val Asp Pro Pro Pro Leu Trp Gly
1               5                   10
```

<210> SEQ ID NO 98
<211> LENGTH: 12
<212> TYPE: PRT
<213> ORGANISM: Artificial Sequence
<220> FEATURE:
<223> OTHER INFORMATION: Description of Artificial Sequence: Synthetic
      Loop peptide

<400> SEQUENCE: 98

Ala Lys Pro Glu Lys Trp Asp Gly Ser Ile Tyr Gly
1               5                   10

<210> SEQ ID NO 99
<211> LENGTH: 11
<212> TYPE: PRT
<213> ORGANISM: Artificial Sequence
<220> FEATURE:
<223> OTHER INFORMATION: Description of Artificial Sequence: Synthetic
      Loop peptide

<400> SEQUENCE: 99

Ser Pro Gly Glu Arg Ile Trp Met Phe Thr Gly
1               5                   10

<210> SEQ ID NO 100
<211> LENGTH: 9
<212> TYPE: PRT
<213> ORGANISM: Artificial Sequence
<220> FEATURE:
<223> OTHER INFORMATION: Description of Artificial Sequence: Synthetic
      Loop peptide

<400> SEQUENCE: 100

His Asp Ala Phe Gly Tyr Asp Phe Gly
1               5

<210> SEQ ID NO 101
<211> LENGTH: 12
<212> TYPE: PRT
<213> ORGANISM: Artificial Sequence
<220> FEATURE:
<223> OTHER INFORMATION: Description of Artificial Sequence: Synthetic
      Loop peptide

<400> SEQUENCE: 101

Ile Pro Pro His Asn Ala Asp Ser Ser Ile Ile Gly
1               5                   10

<210> SEQ ID NO 102
<211> LENGTH: 6
<212> TYPE: PRT
<213> ORGANISM: Artificial Sequence
<220> FEATURE:
<223> OTHER INFORMATION: Description of Artificial Sequence: Synthetic
      Loop peptide

<400> SEQUENCE: 102

Gln Gln Lys His Thr Ala
1               5

<210> SEQ ID NO 103
<211> LENGTH: 6
<212> TYPE: PRT
<213> ORGANISM: Artificial Sequence
<220> FEATURE:
<223> OTHER INFORMATION: Description of Artificial Sequence: Synthetic
      Loop peptide

```
<400> SEQUENCE: 103

Asn Ser Arg His Thr Ala
1               5

<210> SEQ ID NO 104
<211> LENGTH: 6
<212> TYPE: PRT
<213> ORGANISM: Artificial Sequence
<220> FEATURE:
<223> OTHER INFORMATION: Description of Artificial Sequence: Synthetic
      Loop peptide

<400> SEQUENCE: 104

Pro Asp His Phe His Asn
1               5

<210> SEQ ID NO 105
<211> LENGTH: 6
<212> TYPE: PRT
<213> ORGANISM: Artificial Sequence
<220> FEATURE:
<223> OTHER INFORMATION: Description of Artificial Sequence: Synthetic
      Loop peptide

<400> SEQUENCE: 105

Tyr Asp Val Ala Phe Asp
1               5

<210> SEQ ID NO 106
<211> LENGTH: 11
<212> TYPE: PRT
<213> ORGANISM: Artificial Sequence
<220> FEATURE:
<223> OTHER INFORMATION: Description of Artificial Sequence: Synthetic
      Loop peptide

<400> SEQUENCE: 106

Phe Asp Pro Tyr Gly Ala Lys Ser Asn Pro Ala
1               5                   10

<210> SEQ ID NO 107
<211> LENGTH: 10
<212> TYPE: PRT
<213> ORGANISM: Artificial Sequence
<220> FEATURE:
<223> OTHER INFORMATION: Description of Artificial Sequence: Synthetic
      Loop peptide

<400> SEQUENCE: 107

Pro Asn Tyr Glu Arg Ile Ser Asn Pro Ala
1               5                   10

<210> SEQ ID NO 108
<211> LENGTH: 11
<212> TYPE: PRT
<213> ORGANISM: Artificial Sequence
<220> FEATURE:
<223> OTHER INFORMATION: Description of Artificial Sequence: Synthetic
      Loop peptide

<400> SEQUENCE: 108

Phe Asp Pro Tyr Gly Met Arg Ser Lys Pro Ala
1               5                   10

<210> SEQ ID NO 109
<211> LENGTH: 11
```

<210> SEQ ID NO 109
<211> LENGTH: 11
<212> TYPE: PRT
<213> ORGANISM: Artificial Sequence
<220> FEATURE:
<223> OTHER INFORMATION: Description of Artificial Sequence: Synthetic
      Loop peptide

<400> SEQUENCE: 109

Phe Thr Pro Tyr Gly Ala Lys Ser Asn Pro Ala
1               5                   10

<210> SEQ ID NO 110
<211> LENGTH: 11
<212> TYPE: PRT
<213> ORGANISM: Artificial Sequence
<220> FEATURE:
<223> OTHER INFORMATION: Description of Artificial Sequence: Synthetic
      Loop peptide

<400> SEQUENCE: 110

Ala Asn Asp His Gly Phe Asp Ser Asn Pro Ala
1               5                   10

<210> SEQ ID NO 111
<211> LENGTH: 11
<212> TYPE: PRT
<213> ORGANISM: Artificial Sequence
<220> FEATURE:
<223> OTHER INFORMATION: Description of Artificial Sequence: Synthetic
      Loop peptide

<400> SEQUENCE: 111

Asp Thr Phe Tyr Gly Phe Asp Ser Asn Pro Ala
1               5                   10

<210> SEQ ID NO 112
<211> LENGTH: 87
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 112
ggcgctaggc tgagtaggtc ctggagtgcg gccatggcca gcggggcgg agggagtgcc        60 attgaagtga aagatgtgac cgatacc                                          87

<210> SEQ ID NO 113
<211> LENGTH: 82
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 113
cctcagccga tcaccacctg aaggctacgc aggtaccgct accgccacct ccgctcccac      60
cgccaccggt ggtaaaggtt tc                                               82

<210> SEQ ID NO 114
<211> LENGTH: 31
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 114
ggcgctaggc tgagtaggtc ctggagtgcg g                                        31

<210> SEQ ID NO 115
<211> LENGTH: 33
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 115
cctcagccga tcaccacctg aaggctacgc agg                                      33

<210> SEQ ID NO 116
<211> LENGTH: 89
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 116
gggatccgct acgggccact cgatcgaggt ccgtgctgat cgagcgatcg gtaccctggg         60
ccatcatcat catcatcacc accactgag                                           89

<210> SEQ ID NO 117
<211> LENGTH: 97
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 117
aattctcagt ggtggtgatg atgatgatga tggcccaggg taccgatcgc tcgatcagca         60
cggacctcga tcgagtggcc cgtagcggat cccgtac                                  97

<210> SEQ ID NO 118
<211> LENGTH: 42
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 118
ggcgctaggc tgagtaggtc ctggggatcc gccatggcca gc                            42

<210> SEQ ID NO 119
<211> LENGTH: 42
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 119
ggcgctaggc tgagtaggtc ctggctagct gccatggcca gc                            42

<210> SEQ ID NO 120
<211> LENGTH: 37
<212> TYPE: DNA
<213> ORGANISM: Artificial Sequence
<220> FEATURE:
<223> OTHER INFORMATION: Description of Artificial Sequence: Synthetic

```
                                        Primer

<400> SEQUENCE: 120
cctcagccga tcaccacctg aaggcggcgc cggtacc                              37

<210> SEQ ID NO 121
<211> LENGTH: 81
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 121
aaagaaacct ttaccactgc aggtggcgga ggttcacgct tggatgcccc cgggcagatt    60
gaagtgaaag atgtgaccga t                                              81

<210> SEQ ID NO 122
<211> LENGTH: 111
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 122
aaagaaacct ttaccactgc aggtggcgga ggttcaggtg gcggaggttc aggtggcgga    60
ggttcacgct tggatgcccc cgggcagatt gaagtgaaag atgtgaccga t            111

<210> SEQ ID NO 123
<211> LENGTH: 24
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 123
ctgcagtggt aaaggtttct ttcg                                           24

<210> SEQ ID NO 124
<211> LENGTH: 116
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 124
aaagaaacct ttaccactgc aggtggcggg ggtagcggtg gcggaggttc tggtggcggg    60
ggtagcggtg gcggaggttc tggtggcggg ggtagccgct tggatgcccc cgggca      116

<210> SEQ ID NO 125
<211> LENGTH: 146
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 125
aaagaaacct ttaccactgc aggtggcggg ggtagcggtg gcggaggttc tggtggcggg    60
ggtagcggtg gcggaggttc tggtggcggg ggtagcggtg gcggaggttc tggtggcggg  120
```

```
ggtagccgct tggatgcccc cgggca                                           146

<210> SEQ ID NO 126
<211> LENGTH: 24
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 126
aaagaaacct ttaccactgc aggt                                              24

<210> SEQ ID NO 127
<211> LENGTH: 24
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 127
ttcaatctgc ccgggggcat ccaa                                              24

<210> SEQ ID NO 128
<211> LENGTH: 66
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 128
aaagaaacct ttaccaccac gcgtttggat gccccgggc agattgaagt gaaagatgtg        60
accgat                                                                  66

<210> SEQ ID NO 129
<211> LENGTH: 23
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 129
cgtggtggta aaggtttctt tcg                                               23

<210> SEQ ID NO 130
<211> LENGTH: 96
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 130
aaagaaacct ttaccactgc aggtggcgga ggttcaggtg gcggaggttc acgcttggat       60 gccccgggc agattgaagt gaaagatgtg accgat                                  96

<210> SEQ ID NO 131
<211> LENGTH: 7
<212> TYPE: PRT
<213> ORGANISM: Homo sapiens

<400> SEQUENCE: 131
```

```
Cys Glu Leu Ala Tyr Gly Ile
1               5
```

<210> SEQ ID NO 132
<211> LENGTH: 102
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 132

```
Ala Ile Glu Val Lys Asp Val Thr Asp Thr Thr Ala Leu Ile Thr Trp
1               5                   10                  15

Ala Lys Pro Glu Lys Trp Asp Gly Ser Ile Tyr Gly Cys Glu Leu Ala
                20                  25                  30

Tyr Gly Ile Lys Asp Val Pro Gly Asp Arg Thr Thr Ile Asp Leu Asn
                35                  40                  45

Ser Arg His Thr Ala Tyr Ser Ile Gly Asn Leu Lys Pro Asp Thr Glu
            50                  55                  60

Tyr Glu Val Ser Leu Ile Cys Phe Thr Pro Tyr Gly Ala Lys Ser Asn
65                  70                  75                  80

Pro Ala Lys Glu Thr Phe Thr Thr Gly Gly Gly Thr Leu Gly His His
                85                  90                  95

His His His His His His
            100
```

<210> SEQ ID NO 133
<211> LENGTH: 102
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 133

```
Ala Ile Glu Val Lys Asp Val Thr Asp Thr Thr Ala Leu Ile Thr Trp
1               5                   10                  15

Ala Lys Pro Glu Lys Trp Asp Pro Pro Leu Trp Gly Cys Glu Leu Ala
                20                  25                  30

Tyr Gly Ile Lys Asp Val Pro Gly Asp Arg Thr Thr Ile Asp Leu Asn
                35                  40                  45

Ser Arg His Thr Ala Tyr Ser Ile Gly Asn Leu Lys Pro Asp Thr Glu
            50                  55                  60

Tyr Glu Val Ser Leu Ile Cys Phe Thr Pro Tyr Gly Ala Lys Ser Asn
65                  70                  75                  80

Pro Ala Lys Glu Thr Phe Thr Thr Gly Gly Gly Thr Leu Gly His His
                85                  90                  95

His His His His His His
            100
```

<210> SEQ ID NO 134
<211> LENGTH: 102
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 134

```
Ala Ile Glu Val Lys Asp Val Thr Asp Thr Thr Ala Leu Ile Thr Trp
```

```
                1               5                  10                 15
Ala Lys Pro Trp Val Asp Pro Pro Leu Trp Gly Cys Glu Leu Ala
                20                  25                 30

Tyr Gly Ile Lys Asp Val Pro Gly Asp Arg Thr Thr Ile Asp Leu Gln
        35                  40                  45

Gln Lys His Thr Ala Tyr Ser Ile Gly Asn Leu Lys Pro Asp Thr Glu
        50                  55                  60

Tyr Glu Val Ser Leu Ile Cys Phe Asp Pro Tyr Gly Ala Lys Ser Asn
65                  70                  75                  80

Pro Ala Lys Glu Thr Phe Thr Thr Gly Gly Gly Thr Leu Gly His His
                85                  90                  95

His His His His His His
            100

<210> SEQ ID NO 135
<211> LENGTH: 102
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 135

Ala Ile Glu Val Lys Asp Val Thr Asp Thr Thr Ala Leu Ile Thr Trp
1               5                   10                  15

Ala Lys Pro Trp Val Asp Pro Pro Leu Trp Gly Cys Glu Leu Ala
                20                  25                  30

Tyr Gly Ile Lys Asp Val Pro Gly Asp Arg Thr Thr Ile Asp Leu Gln
        35                  40                  45

Gln Lys His Thr Ala Tyr Ser Ile Gly Asn Leu Lys Pro Asp Thr Glu
        50                  55                  60

Tyr Glu Val Ser Leu Ile Cys Phe Asp Pro Tyr Asn Lys Arg Asn Val
65                  70                  75                  80

Pro Ala Lys Glu Thr Phe Thr Thr Gly Gly Gly Thr Leu Gly His His
                85                  90                  95

His His His His His His
            100

<210> SEQ ID NO 136
<211> LENGTH: 102
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 136

Ala Ile Glu Val Lys Asp Val Thr Asp Thr Thr Ala Leu Ile Thr Trp
1               5                   10                  15

Ala Lys Pro Trp Val Asp Pro Pro Leu Trp Gly Cys Glu Leu Ala
                20                  25                  30

Tyr Gly Ile Lys Asp Val Pro Gly Asp Arg Thr Thr Ile Asp Leu Gln
        35                  40                  45

Gln Lys His Thr Ala Tyr Ser Ile Gly Asn Leu Lys Pro Asp Thr Glu
        50                  55                  60

Tyr Glu Val Ser Leu Ile Cys Phe Asp Pro Tyr Asn His Arg Ser Leu
65                  70                  75                  80

Pro Ala Lys Glu Thr Phe Thr Thr Gly Gly Gly Thr Leu Gly His His
```

His His His His His His
            100

<210> SEQ ID NO 137
<211> LENGTH: 102
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 137

Ala Ile Glu Val Lys Asp Val Thr Asp Thr Thr Ala Leu Ile Thr Trp
1               5                   10                  15

Ala Lys Pro Trp Val Asp Pro Pro Leu Trp Gly Cys Glu Leu Ala
            20                  25                  30

Tyr Gly Ile Lys Asp Val Pro Gly Asp Arg Thr Thr Ile Asp Leu Gln
        35                  40                  45

Gln Lys His Thr Ala Tyr Ser Ile Gly Asn Leu Lys Pro Asp Thr Glu
    50                  55                  60

Tyr Glu Val Ser Leu Ile Cys Phe Asp Pro Tyr Gly Leu Lys Ser Arg
65                  70                  75                  80

Pro Ala Lys Glu Thr Phe Thr Thr Gly Gly Thr Leu Gly His His
                85                  90                  95

His His His His His His
            100

<210> SEQ ID NO 138
<211> LENGTH: 102
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 138

Ala Ile Glu Val Lys Asp Val Thr Asp Thr Thr Ala Leu Ile Thr Trp
1               5                   10                  15

Ala Lys Pro Trp Val Asp Pro Pro Leu Trp Gly Cys Glu Leu Ala
            20                  25                  30

Tyr Gly Ile Lys Asp Val Pro Gly Asp Arg Thr Thr Ile Asp Leu Gln
        35                  40                  45

Gln Lys His Thr Ala Tyr Ser Ile Gly Asn Leu Lys Pro Asp Thr Glu
    50                  55                  60

Tyr Glu Val Ser Leu Ile Cys Phe Asp Pro Tyr Gly Met Arg Ser Lys
65                  70                  75                  80

Pro Ala Lys Glu Thr Phe Thr Thr Gly Gly Thr Leu Gly His His
                85                  90                  95

His His His His His His
            100

<210> SEQ ID NO 139
<211> LENGTH: 219
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 139

Ser Gly Gly Gly Gly Ser Ala Ile Glu Val Lys Asp Val Thr Asp Thr
1               5                   10                  15

Thr Ala Leu Ile Thr Trp Ala Lys Pro Trp Val Asp Pro Pro Leu
            20                  25                  30

Trp Gly Cys Glu Leu Ala Tyr Gly Ile Lys Asp Val Pro Gly Asp Arg
            35                  40                  45

Thr Thr Ile Asp Leu Gln Gln Lys His Thr Ala Tyr Ser Ile Gly Asn
    50                  55                  60

Leu Lys Pro Asp Thr Glu Tyr Glu Val Ser Leu Ile Cys Phe Asp Pro
65                  70                  75                  80

Tyr Gly Ala Lys Ser Asn Pro Ala Lys Glu Thr Phe Thr Thr Gly Gly
                85                  90                  95

Gly Gly Ser Gly Gly Gly Gly Ser Gly Gly Gly Gly Ser Ala Ile Glu
            100                 105                 110

Val Lys Asp Val Thr Asp Thr Thr Ala Leu Ile Thr Trp Ala Lys Pro
        115                 120                 125

Trp Val Asp Pro Pro Leu Trp Gly Cys Glu Leu Ala Tyr Gly Ile
    130                 135                 140

Lys Asp Val Pro Gly Asp Arg Thr Thr Ile Asp Leu Gln Gln Lys His
145                 150                 155                 160

Thr Ala Tyr Ser Ile Gly Asn Leu Lys Pro Asp Thr Glu Tyr Glu Val
                165                 170                 175

Ser Leu Ile Cys Phe Asp Pro Tyr Gly Ala Lys Ser Asn Pro Ala Lys
            180                 185                 190

Glu Thr Phe Thr Thr Gly Gly Gly Gly Ser Gly Gly Gly Gly Ser Gly
        195                 200                 205

Thr Leu Gly His His His His His His His
210                 215

<210> SEQ ID NO 140
<211> LENGTH: 425
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 140

Ser Gly Gly Gly Gly Ser Ala Ile Glu Val Lys Asp Val Thr Asp Thr
1               5                   10                  15

Thr Ala Leu Ile Thr Trp Ala Lys Pro Trp Val Asp Pro Pro Leu
            20                  25                  30

Trp Gly Cys Glu Leu Ala Tyr Gly Ile Lys Asp Val Pro Gly Asp Arg
            35                  40                  45

Thr Thr Ile Asp Leu Gln Gln Lys His Thr Ala Tyr Ser Ile Gly Asn
    50                  55                  60

Leu Lys Pro Asp Thr Glu Tyr Glu Val Ser Leu Ile Cys Phe Asp Pro
65                  70                  75                  80

Tyr Gly Ala Lys Ser Asn Pro Ala Lys Glu Thr Phe Thr Thr Gly Gly
                85                  90                  95

Gly Gly Ser Gly Gly Gly Gly Ser Gly Gly Gly Gly Ser Ala Ile Glu
            100                 105                 110

Val Lys Asp Val Thr Asp Thr Thr Ala Leu Ile Thr Trp Ala Lys Pro
        115                 120                 125

Trp Val Asp Pro Pro Leu Trp Gly Cys Glu Leu Ala Tyr Gly Ile

```
            130                 135                 140
Lys Asp Val Pro Gly Asp Arg Thr Thr Ile Asp Leu Gln Gln Lys His
145                 150                 155                 160

Thr Ala Tyr Ser Ile Gly Asn Leu Lys Pro Asp Thr Glu Tyr Glu Val
                165                 170                 175

Ser Leu Ile Cys Phe Asp Pro Tyr Gly Ala Lys Ser Asn Pro Ala Lys
            180                 185                 190

Glu Thr Phe Thr Thr Gly Gly Gly Ser Gly Gly Gly Ser Gly
        195                 200                 205

Gly Gly Gly Ser Ala Ile Glu Val Lys Asp Val Thr Asp Thr Thr Ala
        210                 215                 220

Leu Ile Thr Trp Ala Lys Pro Trp Val Asp Pro Pro Leu Trp Gly
225                 230                 235                 240

Cys Glu Leu Ala Tyr Gly Ile Lys Asp Val Pro Gly Asp Arg Thr Thr
                245                 250                 255

Ile Asp Leu Gln Gln Lys His Thr Ala Tyr Ser Ile Gly Asn Leu Lys
            260                 265                 270

Pro Asp Thr Glu Tyr Glu Val Ser Leu Ile Cys Phe Asp Pro Tyr Gly
        275                 280                 285

Ala Lys Ser Asn Pro Ala Lys Glu Thr Phe Thr Thr Gly Gly Gly Gly
        290                 295                 300

Ser Gly Gly Gly Ser Gly Gly Gly Ser Ala Ile Glu Val Lys
305                 310                 315                 320

Asp Val Thr Asp Thr Thr Ala Leu Ile Thr Trp Ala Lys Pro Trp Val
                325                 330                 335

Asp Pro Pro Leu Trp Gly Cys Glu Leu Ala Tyr Gly Ile Lys Asp
            340                 345                 350

Val Pro Gly Asp Arg Thr Thr Ile Asp Leu Gln Gln Lys His Thr Ala
        355                 360                 365

Tyr Ser Ile Gly Asn Leu Lys Pro Asp Thr Glu Tyr Glu Val Ser Leu
        370                 375                 380

Ile Cys Phe Asp Pro Tyr Gly Ala Lys Ser Asn Pro Ala Lys Glu Thr
385                 390                 395                 400

Phe Thr Thr Gly Gly Gly Gly Ser Gly Gly Gly Ser Gly Thr Leu
                405                 410                 415

Gly His His His His His His His
            420                 425

<210> SEQ ID NO 141
<211> LENGTH: 639
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 141

Ser Gly Gly Gly Gly Ser Ala Ile Glu Val Lys Asp Val Thr Asp Thr
1               5                   10                  15

Thr Ala Leu Ile Thr Trp Ala Lys Pro Trp Val Asp Pro Pro Leu
            20                  25                  30

Trp Gly Cys Glu Leu Ala Tyr Gly Ile Lys Asp Val Pro Gly Asp Arg
            35                  40                  45

Thr Thr Ile Asp Leu Gln Gln Lys His Thr Ala Tyr Ser Ile Gly Asn
        50                  55                  60
```

Leu Lys Pro Asp Thr Glu Tyr Glu Val Ser Leu Ile Cys Phe Asp Pro
65                  70                  75                  80

Tyr Gly Ala Lys Ser Asn Pro Ala Lys Glu Thr Phe Thr Thr Gly Gly
                85                  90                  95

Gly Gly Ser Gly Gly Gly Gly Ser Gly Gly Gly Ser Ala Ile Glu
            100                 105                 110

Val Lys Asp Val Thr Asp Thr Thr Ala Leu Ile Thr Trp Ala Lys Pro
        115                 120                 125

Trp Val Asp Pro Pro Leu Trp Gly Cys Glu Leu Ala Tyr Gly Ile
        130                 135                 140

Lys Asp Val Pro Gly Asp Arg Thr Thr Ile Asp Leu Gln Gln Lys His
145                 150                 155                 160

Thr Ala Tyr Ser Ile Gly Asn Leu Lys Pro Asp Thr Glu Tyr Glu Val
                165                 170                 175

Ser Leu Ile Cys Phe Asp Pro Tyr Gly Ala Lys Ser Asn Pro Ala Lys
            180                 185                 190

Glu Thr Phe Thr Thr Gly Gly Gly Ser Gly Gly Gly Gly Ser Gly
        195                 200                 205

Gly Gly Gly Ser Ala Ile Glu Val Lys Asp Val Thr Asp Thr Thr Ala
    210                 215                 220

Leu Ile Thr Trp Ala Lys Pro Trp Val Asp Pro Pro Leu Trp Gly
225                 230                 235                 240

Cys Glu Leu Ala Tyr Gly Ile Lys Asp Val Pro Gly Asp Arg Thr Thr
                245                 250                 255

Ile Asp Leu Gln Gln Lys His Thr Ala Tyr Ser Ile Gly Asn Leu Lys
            260                 265                 270

Pro Asp Thr Glu Tyr Glu Val Ser Leu Ile Cys Phe Asp Pro Tyr Gly
        275                 280                 285

Ala Lys Ser Asn Pro Ala Lys Glu Thr Phe Thr Thr Gly Gly Gly
        290                 295                 300

Ser Gly Gly Gly Ser Gly Gly Gly Ser Ala Ile Glu Val Lys
305                 310                 315                 320

Asp Val Thr Asp Thr Thr Ala Leu Ile Thr Trp Ala Lys Pro Trp Val
                325                 330                 335

Asp Pro Pro Leu Trp Gly Cys Glu Leu Ala Tyr Gly Ile Lys Asp
            340                 345                 350

Val Pro Gly Asp Arg Thr Thr Ile Asp Leu Gln Gln Lys His Thr Ala
        355                 360                 365

Tyr Ser Ile Gly Asn Leu Lys Pro Asp Thr Glu Tyr Glu Val Ser Leu
        370                 375                 380

Ile Cys Phe Asp Pro Tyr Gly Ala Lys Ser Asn Pro Ala Lys Glu Thr
385                 390                 395                 400

Phe Thr Thr Gly Gly Gly Ser Gly Gly Gly Ser Gly Thr Gly
                405                 410                 415

Ser Ala Met Ala Ser Gly Gly Gly Ser Ala Ile Glu Val Lys Asp
            420                 425                 430

Val Thr Asp Thr Thr Ala Leu Ile Thr Trp Ala Lys Pro Trp Val Asp
        435                 440                 445

Pro Pro Leu Trp Gly Cys Glu Leu Ala Tyr Gly Ile Lys Asp Val
        450                 455                 460

Pro Gly Asp Arg Thr Thr Ile Asp Leu Gln Gln Lys His Thr Ala Tyr
465                 470                 475                 480

Ser Ile Gly Asn Leu Lys Pro Asp Thr Glu Tyr Glu Val Ser Leu Ile

```
                        485                 490                 495
Cys Phe Asp Pro Tyr Gly Ala Lys Ser Asn Pro Ala Lys Glu Thr Phe
                    500                 505                 510

Thr Thr Gly Gly Gly Ser Gly Gly Gly Ser Gly Gly Gly Gly
                515                 520                 525

Ser Ala Ile Glu Val Lys Asp Val Thr Asp Thr Thr Ala Leu Ile Thr
            530                 535                 540

Trp Ala Lys Pro Trp Val Asp Pro Pro Leu Trp Gly Cys Glu Leu
545                 550                 555                 560

Ala Tyr Gly Ile Lys Asp Val Pro Gly Asp Arg Thr Thr Ile Asp Leu
                    565                 570                 575

Gln Gln Lys His Thr Ala Tyr Ser Ile Gly Asn Leu Lys Pro Asp Thr
                580                 585                 590

Glu Tyr Glu Val Ser Leu Ile Cys Phe Asp Pro Tyr Gly Ala Lys Ser
            595                 600                 605

Asn Pro Ala Lys Glu Thr Phe Thr Thr Gly Gly Gly Ser Gly Gly
610                 615                 620

Gly Gly Ser Gly Thr Leu Gly His His His His His His
625                 630                 635

<210> SEQ ID NO 142
<211> LENGTH: 845
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 142

Ser Gly Gly Gly Gly Ser Ala Ile Glu Val Lys Asp Val Thr Asp Thr
1               5                   10                  15

Thr Ala Leu Ile Thr Trp Ala Lys Pro Trp Val Asp Pro Pro Leu
                20                  25                  30

Trp Gly Cys Glu Leu Ala Tyr Gly Ile Lys Asp Val Pro Gly Asp Arg
            35                  40                  45

Thr Thr Ile Asp Leu Gln Gln Lys His Thr Ala Tyr Ser Ile Gly Asn
        50                  55                  60

Leu Lys Pro Asp Thr Glu Tyr Glu Val Ser Leu Ile Cys Phe Asp Pro
65                  70                  75                  80

Tyr Gly Ala Lys Ser Asn Pro Ala Lys Glu Thr Phe Thr Thr Gly Gly
                85                  90                  95

Gly Gly Ser Gly Gly Gly Ser Gly Gly Gly Ser Ala Ile Glu
            100                 105                 110

Val Lys Asp Val Thr Asp Thr Thr Ala Leu Ile Thr Trp Ala Lys Pro
        115                 120                 125

Trp Val Asp Pro Pro Leu Trp Gly Cys Glu Leu Ala Tyr Gly Ile
        130                 135                 140

Lys Asp Val Pro Gly Asp Arg Thr Thr Ile Asp Leu Gln Gln Lys His
145                 150                 155                 160

Thr Ala Tyr Ser Ile Gly Asn Leu Lys Pro Asp Thr Glu Tyr Glu Val
                165                 170                 175

Ser Leu Ile Cys Phe Asp Pro Tyr Gly Ala Lys Ser Asn Pro Ala Lys
            180                 185                 190

Glu Thr Phe Thr Thr Gly Gly Gly Gly Ser Gly Gly Gly Ser Gly
        195                 200                 205
```

```
Gly Gly Gly Ser Ala Ile Glu Val Lys Asp Val Thr Asp Thr Thr Ala
            210                 215                 220
Leu Ile Thr Trp Ala Lys Pro Trp Val Asp Pro Pro Leu Trp Gly
225                 230                 235                 240
Cys Glu Leu Ala Tyr Gly Ile Lys Asp Val Pro Gly Asp Arg Thr Thr
                245                 250                 255
Ile Asp Leu Gln Gln Lys His Thr Ala Tyr Ser Ile Gly Asn Leu Lys
            260                 265                 270
Pro Asp Thr Glu Tyr Glu Val Ser Leu Ile Cys Phe Asp Pro Tyr Gly
            275                 280                 285
Ala Lys Ser Asn Pro Ala Lys Glu Thr Phe Thr Thr Gly Gly Gly Gly
            290                 295                 300
Ser Gly Gly Gly Gly Ser Gly Gly Gly Ser Ala Ile Glu Val Lys
305                 310                 315                 320
Asp Val Thr Asp Thr Thr Ala Leu Ile Thr Trp Ala Lys Pro Trp Val
                325                 330                 335
Asp Pro Pro Leu Trp Gly Cys Glu Leu Ala Tyr Gly Ile Lys Asp
            340                 345                 350
Val Pro Gly Asp Arg Thr Thr Ile Asp Leu Gln Gln Lys His Thr Ala
            355                 360                 365
Tyr Ser Ile Gly Asn Leu Lys Pro Asp Thr Glu Tyr Glu Val Ser Leu
370                 375                 380
Ile Cys Phe Asp Pro Tyr Gly Ala Lys Ser Asn Pro Ala Lys Glu Thr
385                 390                 395                 400
Phe Thr Thr Gly Gly Gly Gly Ser Gly Gly Gly Gly Ser Gly Thr Gly
                405                 410                 415
Ser Ala Met Ala Ser Gly Gly Gly Ser Ala Ile Glu Val Lys Asp
            420                 425                 430
Val Thr Asp Thr Thr Ala Leu Ile Thr Trp Ala Lys Pro Trp Val Asp
            435                 440                 445
Pro Pro Leu Trp Gly Cys Glu Leu Ala Tyr Gly Ile Lys Asp Val
            450                 455                 460
Pro Gly Asp Arg Thr Thr Ile Asp Leu Gln Gln Lys His Thr Ala Tyr
465                 470                 475                 480
Ser Ile Gly Asn Leu Lys Pro Asp Thr Glu Tyr Glu Val Ser Leu Ile
                485                 490                 495
Cys Phe Asp Pro Tyr Gly Ala Lys Ser Asn Pro Ala Lys Glu Thr Phe
            500                 505                 510
Thr Thr Gly Gly Gly Gly Ser Gly Gly Gly Gly Ser Gly Gly Gly Gly
            515                 520                 525
Ser Ala Ile Glu Val Lys Asp Val Thr Asp Thr Thr Ala Leu Ile Thr
530                 535                 540
Trp Ala Lys Pro Trp Val Asp Pro Pro Leu Trp Gly Cys Glu Leu
545                 550                 555                 560
Ala Tyr Gly Ile Lys Asp Val Pro Gly Asp Arg Thr Thr Ile Asp Leu
                565                 570                 575
Gln Gln Lys His Thr Ala Tyr Ser Ile Gly Asn Leu Lys Pro Asp Thr
            580                 585                 590
Glu Tyr Glu Val Ser Leu Ile Cys Phe Asp Pro Tyr Gly Ala Lys Ser
            595                 600                 605
Asn Pro Ala Lys Glu Thr Phe Thr Thr Gly Gly Gly Gly Ser Gly Gly
            610                 615                 620
Gly Gly Ser Gly Gly Gly Gly Ser Ala Ile Glu Val Lys Asp Val Thr
```

```
                625                 630                 635                 640
Asp Thr Thr Ala Leu Ile Thr Trp Ala Lys Pro Trp Val Asp Pro Pro
                    645                 650                 655

Pro Leu Trp Gly Cys Glu Leu Ala Tyr Gly Ile Lys Asp Val Pro Gly
                660                 665                 670

Asp Arg Thr Thr Ile Asp Leu Gln Gln Lys His Thr Ala Tyr Ser Ile
            675                 680                 685

Gly Asn Leu Lys Pro Asp Thr Glu Tyr Glu Val Ser Leu Ile Cys Phe
690                 695                 700

Asp Pro Tyr Gly Ala Lys Ser Asn Pro Ala Lys Glu Thr Phe Thr Thr
705                 710                 715                 720

Gly Gly Gly Gly Ser Gly Gly Gly Ser Gly Gly Gly Ser Ala
                725                 730                 735

Ile Glu Val Lys Asp Val Thr Asp Thr Thr Ala Leu Ile Thr Trp Ala
                740                 745                 750

Lys Pro Trp Val Asp Pro Pro Leu Trp Gly Cys Glu Leu Ala Tyr
                755                 760                 765

Gly Ile Lys Asp Val Pro Gly Asp Arg Thr Thr Ile Asp Leu Gln Gln
770                 775                 780

Lys His Thr Ala Tyr Ser Ile Gly Asn Leu Lys Pro Asp Thr Glu Tyr
785                 790                 795                 800

Glu Val Ser Leu Ile Cys Phe Asp Pro Tyr Gly Ala Lys Ser Asn Pro
                805                 810                 815

Ala Lys Glu Thr Phe Thr Thr Gly Gly Gly Ser Gly Gly Gly Gly
                820                 825                 830

Ser Gly Thr Leu Gly His His His His His His
            835                 840                 845

<210> SEQ ID NO 143
<211> LENGTH: 425
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 143

Ser Gly Gly Gly Ser Ala Ile Glu Val Lys Asp Val Thr Asp Thr
1               5                   10                  15

Thr Ala Leu Ile Thr Trp Ala Lys Pro Trp Val Asp Pro Pro Leu
            20                  25                  30

Trp Gly Cys Glu Leu Ala Tyr Gly Ile Lys Asp Val Pro Gly Asp Arg
                35                  40                  45

Thr Thr Ile Asp Leu Gln Gln Lys His Thr Ala Tyr Ser Ile Gly Asn
    50                  55                  60

Leu Lys Pro Asp Thr Glu Tyr Glu Val Ser Leu Ile Cys Phe Asp Pro
65                  70                  75                  80

Tyr Gly Met Arg Ser Lys Pro Ala Lys Glu Thr Phe Thr Thr Gly Gly
                85                  90                  95

Gly Gly Ser Gly Gly Gly Gly Ser Gly Gly Gly Gly Ser Ala Ile Glu
            100                 105                 110

Val Lys Asp Val Thr Asp Thr Thr Ala Leu Ile Thr Trp Ala Lys Pro
        115                 120                 125

Trp Val Asp Pro Pro Leu Trp Gly Cys Glu Leu Ala Tyr Gly Ile
    130                 135                 140
```

Lys Asp Val Pro Gly Asp Arg Thr Thr Ile Asp Leu Gln Gln Lys His
145                 150                 155                 160

Thr Ala Tyr Ser Ile Gly Asn Leu Lys Pro Asp Thr Glu Tyr Glu Val
            165                 170                 175

Ser Leu Ile Cys Phe Asp Pro Tyr Gly Met Arg Ser Lys Pro Ala Lys
            180                 185                 190

Glu Thr Phe Thr Thr Gly Gly Gly Ser Gly Gly Gly Ser Gly
        195                 200                 205

Gly Gly Gly Ser Ala Ile Glu Val Lys Asp Val Thr Asp Thr Thr Ala
        210                 215                 220

Leu Ile Thr Trp Ala Lys Pro Trp Val Asp Pro Pro Leu Trp Gly
225                 230                 235                 240

Cys Glu Leu Ala Tyr Gly Ile Lys Asp Val Pro Gly Asp Arg Thr Thr
            245                 250                 255

Ile Asp Leu Gln Gln Lys His Thr Ala Tyr Ser Ile Gly Asn Leu Lys
            260                 265                 270

Pro Asp Thr Glu Tyr Glu Val Ser Leu Ile Cys Phe Asp Pro Tyr Gly
        275                 280                 285

Met Arg Ser Lys Pro Ala Lys Glu Thr Phe Thr Thr Gly Gly Gly Gly
290                 295                 300

Ser Gly Gly Gly Gly Ser Gly Gly Gly Ser Ala Ile Glu Val Lys
305                 310                 315                 320

Asp Val Thr Asp Thr Thr Ala Leu Ile Thr Trp Ala Lys Pro Trp Val
            325                 330                 335

Asp Pro Pro Leu Trp Gly Cys Glu Leu Ala Tyr Gly Ile Lys Asp
            340                 345                 350

Val Pro Gly Asp Arg Thr Thr Ile Asp Leu Gln Gln Lys His Thr Ala
        355                 360                 365

Tyr Ser Ile Gly Asn Leu Lys Pro Asp Thr Glu Tyr Glu Val Ser Leu
        370                 375                 380

Ile Cys Phe Asp Pro Tyr Gly Met Arg Ser Lys Pro Ala Lys Glu Thr
385                 390                 395                 400

Phe Thr Thr Gly Gly Gly Gly Ser Gly Gly Gly Gly Ser Gly Thr Leu
            405                 410                 415

Gly His His His His His His
        420                 425

<210> SEQ ID NO 144
<211> LENGTH: 639
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 144

Ser Gly Gly Gly Gly Ser Ala Ile Glu Val Lys Asp Val Thr Asp Thr
1               5                   10                  15

Thr Ala Leu Ile Thr Trp Ala Lys Pro Trp Val Asp Pro Pro Leu
            20                  25                  30

Trp Gly Cys Glu Leu Ala Tyr Gly Ile Lys Asp Val Pro Gly Asp Arg
            35                  40                  45

Thr Thr Ile Asp Leu Gln Gln Lys His Thr Ala Tyr Ser Ile Gly Asn
        50                  55                  60

Leu Lys Pro Asp Thr Glu Tyr Glu Val Ser Leu Ile Cys Phe Asp Pro
65                  70                  75                  80

```
Tyr Gly Met Arg Ser Lys Pro Ala Lys Glu Thr Phe Thr Thr Gly Gly
                85                  90                  95
Gly Gly Ser Gly Gly Gly Ser Gly Gly Gly Ser Ala Ile Glu
            100                 105                 110
Val Lys Asp Val Thr Asp Thr Thr Ala Leu Ile Thr Trp Ala Lys Pro
        115                 120                 125
Trp Val Asp Pro Pro Leu Trp Gly Cys Glu Leu Ala Tyr Gly Ile
    130                 135                 140
Lys Asp Val Pro Gly Asp Arg Thr Thr Ile Asp Leu Gln Gln Lys His
145                 150                 155                 160
Thr Ala Tyr Ser Ile Gly Asn Leu Lys Pro Asp Thr Glu Tyr Glu Val
                165                 170                 175
Ser Leu Ile Cys Phe Asp Pro Tyr Gly Met Arg Ser Lys Pro Ala Lys
                180                 185                 190
Glu Thr Phe Thr Thr Gly Gly Gly Ser Gly Gly Gly Gly Ser Gly
            195                 200                 205
Gly Gly Ser Ala Ile Glu Val Lys Asp Val Thr Asp Thr Thr Ala
        210                 215                 220
Leu Ile Thr Trp Ala Lys Pro Trp Val Asp Pro Pro Leu Trp Gly
225                 230                 235                 240
Cys Glu Leu Ala Tyr Gly Ile Lys Asp Val Pro Gly Asp Arg Thr Thr
                245                 250                 255
Ile Asp Leu Gln Gln Lys His Thr Ala Tyr Ser Ile Gly Asn Leu Lys
                260                 265                 270
Pro Asp Thr Glu Tyr Glu Val Ser Leu Ile Cys Phe Asp Pro Tyr Gly
            275                 280                 285
Met Arg Ser Lys Pro Ala Lys Glu Thr Phe Thr Thr Gly Gly Gly Gly
        290                 295                 300
Ser Gly Gly Gly Gly Ser Gly Gly Gly Ser Ala Ile Glu Val Lys
305                 310                 315                 320
Asp Val Thr Asp Thr Thr Ala Leu Ile Thr Trp Ala Lys Pro Trp Val
                325                 330                 335
Asp Pro Pro Leu Trp Gly Cys Glu Leu Ala Tyr Gly Ile Lys Asp
            340                 345                 350
Val Pro Gly Asp Arg Thr Thr Ile Asp Leu Gln Gln Lys His Thr Ala
        355                 360                 365
Tyr Ser Ile Gly Asn Leu Lys Pro Asp Thr Glu Tyr Glu Val Ser Leu
    370                 375                 380
Ile Cys Phe Asp Pro Tyr Gly Met Arg Ser Lys Pro Ala Lys Glu Thr
385                 390                 395                 400
Phe Thr Thr Gly Gly Gly Gly Ser Gly Gly Gly Gly Ser Gly Thr Gly
                405                 410                 415
Ser Ala Met Ala Ser Gly Gly Gly Ser Ala Ile Glu Val Lys Asp
            420                 425                 430
Val Thr Asp Thr Thr Ala Leu Ile Thr Trp Ala Lys Pro Trp Val Asp
        435                 440                 445
Pro Pro Leu Trp Gly Cys Glu Leu Ala Tyr Gly Ile Lys Asp Val
    450                 455                 460
Pro Gly Asp Arg Thr Thr Ile Asp Leu Gln Gln Lys His Thr Ala Tyr
465                 470                 475                 480
Ser Ile Gly Asn Leu Lys Pro Asp Thr Glu Tyr Glu Val Ser Leu Ile
                485                 490                 495
```

```
Cys Phe Asp Pro Tyr Gly Met Arg Ser Lys Pro Ala Lys Glu Thr Phe
                500                 505                 510

Thr Thr Gly Gly Gly Ser Gly Gly Gly Ser Gly Gly Gly Gly
            515                 520                 525

Ser Ala Ile Glu Val Lys Asp Val Thr Asp Thr Thr Ala Leu Ile Thr
            530                 535                 540

Trp Ala Lys Pro Trp Val Asp Pro Pro Leu Trp Gly Cys Glu Leu
545                 550                 555                 560

Ala Tyr Gly Ile Lys Asp Val Pro Gly Asp Arg Thr Thr Ile Asp Leu
                565                 570                 575

Gln Gln Lys His Thr Ala Tyr Ser Ile Gly Asn Leu Lys Pro Asp Thr
            580                 585                 590

Glu Tyr Glu Val Ser Leu Ile Cys Phe Asp Pro Tyr Gly Met Arg Ser
            595                 600                 605

Lys Pro Ala Lys Glu Thr Phe Thr Thr Gly Gly Gly Ser Gly Gly
            610                 615                 620

Gly Gly Ser Gly Thr Leu Gly His His His His His His His
625                 630                 635
```

<210> SEQ ID NO 145
<211> LENGTH: 845
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 145

```
Ser Gly Gly Gly Ser Ala Ile Glu Val Lys Asp Val Thr Asp Thr
1               5                   10                  15

Thr Ala Leu Ile Thr Trp Ala Lys Pro Trp Val Asp Pro Pro Leu
            20                  25                  30

Trp Gly Cys Glu Leu Ala Tyr Gly Ile Lys Asp Val Pro Gly Asp Arg
            35                  40                  45

Thr Thr Ile Asp Leu Gln Gln Lys His Thr Ala Tyr Ser Ile Gly Asn
            50                  55                  60

Leu Lys Pro Asp Thr Glu Tyr Glu Val Ser Leu Ile Cys Phe Asp Pro
65                  70                  75                  80

Tyr Gly Met Arg Ser Lys Pro Ala Lys Glu Thr Phe Thr Thr Gly Gly
                85                  90                  95

Gly Gly Ser Gly Gly Gly Gly Ser Gly Gly Gly Gly Ser Ala Ile Glu
            100                 105                 110

Val Lys Asp Val Thr Asp Thr Thr Ala Leu Ile Thr Trp Ala Lys Pro
            115                 120                 125

Trp Val Asp Pro Pro Leu Trp Gly Cys Glu Leu Ala Tyr Gly Ile
            130                 135                 140

Lys Asp Val Pro Gly Asp Arg Thr Thr Ile Asp Leu Gln Gln Lys His
145                 150                 155                 160

Thr Ala Tyr Ser Ile Gly Asn Leu Lys Pro Asp Thr Glu Tyr Glu Val
                165                 170                 175

Ser Leu Ile Cys Phe Asp Pro Tyr Gly Met Arg Ser Lys Pro Ala Lys
            180                 185                 190

Glu Thr Phe Thr Thr Gly Gly Gly Ser Gly Gly Gly Gly Ser Gly
            195                 200                 205

Gly Gly Ser Ala Ile Glu Val Lys Asp Val Thr Asp Thr Thr Ala
            210                 215                 220
```

```
Leu Ile Thr Trp Ala Lys Pro Trp Val Asp Pro Pro Leu Trp Gly
225                 230                 235                 240

Cys Glu Leu Ala Tyr Gly Ile Lys Asp Val Pro Gly Asp Arg Thr Thr
                245                 250                 255

Ile Asp Leu Gln Gln Lys His Thr Ala Tyr Ser Ile Gly Asn Leu Lys
        260                 265                 270

Pro Asp Thr Glu Tyr Glu Val Ser Leu Ile Cys Phe Asp Pro Tyr Gly
            275                 280                 285

Met Arg Ser Lys Pro Ala Lys Glu Thr Phe Thr Thr Gly Gly Gly
        290                 295                 300

Ser Gly Gly Gly Ser Gly Gly Gly Ser Ala Ile Glu Val Lys
305                 310                 315                 320

Asp Val Thr Asp Thr Thr Ala Leu Ile Thr Trp Ala Lys Pro Trp Val
                325                 330                 335

Asp Pro Pro Leu Trp Gly Cys Glu Leu Ala Tyr Gly Ile Lys Asp
        340                 345                 350

Val Pro Gly Asp Arg Thr Thr Ile Asp Leu Gln Gln Lys His Thr Ala
            355                 360                 365

Tyr Ser Ile Gly Asn Leu Lys Pro Asp Thr Glu Tyr Glu Val Ser Leu
370                 375                 380

Ile Cys Phe Asp Pro Tyr Gly Met Arg Ser Lys Pro Ala Lys Glu Thr
385                 390                 395                 400

Phe Thr Thr Gly Gly Gly Gly Ser Gly Gly Gly Gly Ser Gly Thr Gly
                405                 410                 415

Ser Ala Met Ala Ser Gly Gly Gly Ser Ala Ile Glu Val Lys Asp
            420                 425                 430

Val Thr Asp Thr Thr Ala Leu Ile Thr Trp Ala Lys Pro Trp Val Asp
                435                 440                 445

Pro Pro Leu Trp Gly Cys Glu Leu Ala Tyr Gly Ile Lys Asp Val
        450                 455                 460

Pro Gly Asp Arg Thr Thr Ile Asp Leu Gln Gln Lys His Thr Ala Tyr
465                 470                 475                 480

Ser Ile Gly Asn Leu Lys Pro Asp Thr Glu Tyr Glu Val Ser Leu Ile
                485                 490                 495

Cys Phe Asp Pro Tyr Gly Met Arg Ser Lys Pro Ala Lys Glu Thr Phe
                500                 505                 510

Thr Thr Gly Gly Gly Gly Ser Gly Gly Gly Gly Ser Gly Gly Gly Gly
            515                 520                 525

Ser Ala Ile Glu Val Lys Asp Val Thr Asp Thr Thr Ala Leu Ile Thr
        530                 535                 540

Trp Ala Lys Pro Trp Val Asp Pro Pro Leu Trp Gly Cys Glu Leu
545                 550                 555                 560

Ala Tyr Gly Ile Lys Asp Val Pro Gly Asp Arg Thr Thr Ile Asp Leu
                565                 570                 575

Gln Gln Lys His Thr Ala Tyr Ser Ile Gly Asn Leu Lys Pro Asp Thr
            580                 585                 590

Glu Tyr Glu Val Ser Leu Ile Cys Phe Asp Pro Tyr Gly Met Arg Ser
        595                 600                 605

Lys Pro Ala Lys Glu Thr Phe Thr Thr Gly Gly Gly Ser Gly Gly
        610                 615                 620

Gly Gly Ser Gly Gly Gly Gly Ser Ala Ile Glu Val Lys Asp Val Thr
625                 630                 635                 640
```

Asp Thr Thr Ala Leu Ile Thr Trp Ala Lys Pro Trp Val Asp Pro Pro
                645                 650                 655

Pro Leu Trp Gly Cys Glu Leu Ala Tyr Gly Ile Lys Asp Val Pro Gly
        660                 665                 670

Asp Arg Thr Thr Ile Asp Leu Gln Gln Lys His Thr Ala Tyr Ser Ile
        675                 680                 685

Gly Asn Leu Lys Pro Asp Thr Glu Tyr Glu Val Ser Leu Ile Cys Phe
        690                 695                 700

Asp Pro Tyr Gly Met Arg Ser Lys Pro Ala Lys Glu Thr Phe Thr Thr
705                 710                 715                 720

Gly Gly Gly Gly Ser Gly Gly Gly Ser Gly Gly Gly Gly Ser Ala
                725                 730                 735

Ile Glu Val Lys Asp Val Thr Asp Thr Thr Ala Leu Ile Thr Trp Ala
                740                 745                 750

Lys Pro Trp Val Asp Pro Pro Leu Trp Gly Cys Glu Leu Ala Tyr
        755                 760                 765

Gly Ile Lys Asp Val Pro Gly Asp Arg Thr Thr Ile Asp Leu Gln Gln
        770                 775                 780

Lys His Thr Ala Tyr Ser Ile Gly Asn Leu Lys Pro Asp Thr Glu Tyr
785                 790                 795                 800

Glu Val Ser Leu Ile Cys Phe Asp Pro Tyr Gly Met Arg Ser Lys Pro
                805                 810                 815

Ala Lys Glu Thr Phe Thr Thr Gly Gly Gly Ser Gly Gly Gly Gly
        820                 825                 830

Ser Gly Thr Leu Gly His His His His His His His
        835                 840                 845

<210> SEQ ID NO 146
<211> LENGTH: 417
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 146

Ser Gly Gly Gly Ser Ala Ile Glu Val Lys Asp Val Thr Asp Thr
1               5                   10                  15

Thr Ala Leu Ile Thr Trp Ser Pro Gly Glu Arg Ile Trp Met Phe Thr
                20                  25                  30

Gly Cys Glu Leu Thr Tyr Gly Ile Lys Asp Val Pro Gly Asp Arg Thr
        35                  40                  45

Thr Ile Asp Leu Thr Glu Asp Glu Asn Gln Tyr Ser Ile Gly Asn Leu
50                  55                  60

Lys Pro Asp Thr Glu Tyr Glu Val Ser Leu Ile Cys Pro Asn Tyr Glu
65                  70                  75                  80

Arg Ile Ser Asn Pro Ala Lys Glu Thr Phe Thr Thr Gly Gly Gly Gly
                85                  90                  95

Ser Gly Gly Gly Gly Ser Gly Gly Gly Ser Ala Ile Glu Val Lys
        100                 105                 110

Asp Val Thr Asp Thr Thr Ala Leu Ile Thr Trp Ser Pro Gly Glu Arg
        115                 120                 125

Ile Trp Met Phe Thr Gly Cys Glu Leu Thr Tyr Gly Ile Lys Asp Val
        130                 135                 140

Pro Gly Asp Arg Thr Thr Ile Asp Leu Thr Glu Asp Glu Asn Gln Tyr
145                 150                 155                 160

Ser Ile Gly Asn Leu Lys Pro Asp Thr Glu Tyr Glu Val Ser Leu Ile
          165                 170                 175

Cys Pro Asn Tyr Glu Arg Ile Ser Asn Pro Ala Lys Glu Thr Phe Thr
            180                 185                 190

Thr Gly Gly Gly Ser Gly Gly Gly Ser Gly Gly Gly Ser
        195                 200                 205

Ala Ile Glu Val Lys Asp Val Thr Asp Thr Thr Ala Leu Ile Thr Trp
    210                 215                 220

Ser Pro Gly Glu Arg Ile Trp Met Phe Thr Gly Cys Glu Leu Thr Tyr
225                 230                 235                 240

Gly Ile Lys Asp Val Pro Gly Asp Arg Thr Thr Ile Asp Leu Thr Glu
                245                 250                 255

Asp Glu Asn Gln Tyr Ser Ile Gly Asn Leu Lys Pro Asp Thr Glu Tyr
            260                 265                 270

Glu Val Ser Leu Ile Cys Pro Asn Tyr Glu Arg Ile Ser Asn Pro Ala
        275                 280                 285

Lys Glu Thr Phe Thr Thr Gly Gly Gly Ser Gly Gly Gly Ser
    290                 295                 300

Gly Gly Gly Gly Ser Ala Ile Glu Val Lys Asp Val Thr Asp Thr Thr
305                 310                 315                 320

Ala Leu Ile Thr Trp Ser Pro Gly Glu Arg Ile Trp Met Phe Thr Gly
                325                 330                 335

Cys Glu Leu Thr Tyr Gly Ile Lys Asp Val Pro Gly Asp Arg Thr Thr
            340                 345                 350

Ile Asp Leu Thr Glu Asp Glu Asn Gln Tyr Ser Ile Gly Asn Leu Lys
        355                 360                 365

Pro Asp Thr Glu Tyr Glu Val Ser Leu Ile Cys Pro Asn Tyr Glu Arg
    370                 375                 380

Ile Ser Asn Pro Ala Lys Glu Thr Phe Thr Gly Gly Gly Ser
385                 390                 395                 400

Gly Gly Gly Gly Ser Gly Thr Leu Gly His His His His His His
                405                 410                 415

His

<210> SEQ ID NO 147
<211> LENGTH: 626
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 147

Ser Gly Gly Gly Gly Ser Ala Ile Glu Val Lys Asp Val Thr Asp Thr
1               5                   10                  15

Thr Ala Leu Ile Thr Trp Ser Pro Gly Glu Arg Ile Trp Met Phe Thr
            20                  25                  30

Gly Cys Glu Leu Thr Tyr Gly Ile Lys Asp Val Pro Gly Asp Arg Thr
        35                  40                  45

Thr Ile Asp Leu Thr Glu Asp Glu Asn Gln Tyr Ser Ile Gly Asn Leu
    50                  55                  60

Lys Pro Asp Thr Glu Tyr Glu Val Ser Leu Ile Cys Pro Asn Tyr Glu
65                  70                  75                  80

Arg Ile Ser Asn Pro Ala Lys Glu Thr Phe Thr Thr Gly Gly Gly Gly
                85                  90                  95

```
Ser Gly Gly Gly Gly Ser Gly Gly Gly Ser Ala Ile Glu Val Lys
            100             105             110

Asp Val Thr Asp Thr Thr Ala Leu Ile Thr Trp Ser Pro Gly Glu Arg
            115             120             125

Ile Trp Met Phe Thr Gly Cys Glu Leu Thr Tyr Gly Ile Lys Asp Val
            130             135             140

Pro Gly Asp Arg Thr Thr Ile Asp Leu Thr Glu Asp Glu Asn Gln Tyr
145             150             155             160

Ser Ile Gly Asn Leu Lys Pro Asp Thr Glu Tyr Glu Val Ser Leu Ile
            165             170             175

Cys Pro Asn Tyr Glu Arg Ile Ser Asn Pro Ala Lys Glu Thr Phe Thr
            180             185             190

Thr Gly Gly Gly Gly Ser Gly Gly Gly Ser Gly Gly Gly Gly Ser
            195             200             205

Ala Ile Glu Val Lys Asp Val Thr Asp Thr Thr Ala Leu Ile Thr Trp
            210             215             220

Ser Pro Gly Glu Arg Ile Trp Met Phe Thr Gly Cys Glu Leu Thr Tyr
225             230             235             240

Gly Ile Lys Asp Val Pro Gly Asp Arg Thr Thr Ile Asp Leu Thr Glu
            245             250             255

Asp Glu Asn Gln Tyr Ser Ile Gly Asn Leu Lys Pro Asp Thr Glu Tyr
            260             265             270

Glu Val Ser Leu Ile Cys Pro Asn Tyr Glu Arg Ile Ser Asn Pro Ala
            275             280             285

Lys Glu Thr Phe Thr Thr Gly Gly Gly Gly Ser Gly Gly Gly Gly Ser
            290             295             300

Gly Gly Gly Gly Ser Ala Ile Glu Val Lys Asp Val Thr Asp Thr Thr
305             310             315             320

Ala Leu Ile Thr Trp Ser Pro Gly Glu Arg Ile Trp Met Phe Thr Gly
            325             330             335

Cys Glu Leu Thr Tyr Gly Ile Lys Asp Val Pro Gly Asp Arg Thr Thr
            340             345             350

Ile Asp Leu Thr Glu Asp Glu Asn Gln Tyr Ser Ile Gly Asn Leu Lys
            355             360             365

Pro Asp Thr Glu Tyr Glu Val Ser Leu Ile Cys Pro Asn Tyr Glu Arg
370             375             380

Ile Ser Asn Pro Ala Lys Glu Thr Phe Thr Thr Gly Gly Gly Gly Ser
385             390             395             400

Gly Gly Gly Gly Ser Gly Thr Gly Ser Ala Met Ala Ser Gly Gly Gly
            405             410             415

Gly Ser Ile Glu Val Lys Asp Val Thr Asp Thr Thr Ala Leu Ile Thr
            420             425             430

Trp Ser Pro Gly Glu Arg Ile Trp Met Phe Thr Gly Cys Glu Leu Thr
            435             440             445

Tyr Gly Ile Lys Asp Val Pro Gly Asp Arg Thr Thr Ile Asp Leu Thr
            450             455             460

Glu Asp Glu Asn Gln Tyr Ser Ile Gly Asn Leu Lys Pro Asp Thr Glu
465             470             475             480

Tyr Glu Val Ser Leu Ile Cys Pro Asn Tyr Glu Arg Ile Ser Asn Pro
            485             490             495

Ala Lys Glu Thr Phe Thr Thr Gly Gly Gly Gly Ser Gly Gly Gly Gly
            500             505             510
```

Ser Gly Gly Gly Gly Ser Ala Ile Glu Val Lys Asp Val Thr Asp Thr
            515                 520                 525

Thr Ala Leu Ile Thr Trp Ser Pro Gly Glu Arg Ile Trp Met Phe Thr
        530                 535                 540

Gly Cys Glu Leu Thr Tyr Gly Ile Lys Asp Val Pro Gly Asp Arg Thr
545                 550                 555                 560

Thr Ile Asp Leu Thr Glu Asp Glu Asn Gln Tyr Ser Ile Gly Asn Leu
                565                 570                 575

Lys Pro Asp Thr Glu Tyr Glu Val Ser Leu Ile Cys Pro Asn Tyr Glu
            580                 585                 590

Arg Ile Ser Asn Pro Ala Lys Glu Thr Phe Thr Thr Gly Gly Gly Gly
        595                 600                 605

Ser Gly Gly Gly Gly Ser Gly Thr Leu Gly His His His His His His
    610                 615                 620

His His
625

<210> SEQ ID NO 148
<211> LENGTH: 829
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 148

Ser Gly Gly Gly Gly Ser Ala Ile Glu Val Lys Asp Val Thr Asp Thr
1               5                   10                  15

Thr Ala Leu Ile Thr Trp Ser Pro Gly Glu Arg Ile Trp Met Phe Thr
            20                  25                  30

Gly Cys Glu Leu Thr Tyr Gly Ile Lys Asp Val Pro Gly Asp Arg Thr
        35                  40                  45

Thr Ile Asp Leu Thr Glu Asp Glu Asn Gln Tyr Ser Ile Gly Asn Leu
    50                  55                  60

Lys Pro Asp Thr Glu Tyr Glu Val Ser Leu Ile Cys Pro Asn Tyr Glu
65                  70                  75                  80

Arg Ile Ser Asn Pro Ala Lys Glu Thr Phe Thr Thr Gly Gly Gly Gly
                85                  90                  95

Ser Gly Gly Gly Gly Ser Gly Gly Gly Ser Ala Ile Glu Val Lys
            100                 105                 110

Asp Val Thr Asp Thr Thr Ala Leu Ile Thr Trp Ser Pro Gly Glu Arg
        115                 120                 125

Ile Trp Met Phe Thr Gly Cys Glu Leu Thr Tyr Gly Ile Lys Asp Val
    130                 135                 140

Pro Gly Asp Arg Thr Thr Ile Asp Leu Thr Glu Asp Glu Asn Gln Tyr
145                 150                 155                 160

Ser Ile Gly Asn Leu Lys Pro Asp Thr Glu Tyr Glu Val Ser Leu Ile
                165                 170                 175

Cys Pro Asn Tyr Glu Arg Ile Ser Asn Pro Ala Lys Glu Thr Phe Thr
            180                 185                 190

Thr Gly Gly Gly Gly Ser Gly Gly Gly Gly Ser Gly Gly Gly Gly Ser
        195                 200                 205

Ala Ile Glu Val Lys Asp Val Thr Asp Thr Thr Ala Leu Ile Thr Trp
    210                 215                 220

Ser Pro Gly Glu Arg Ile Trp Met Phe Thr Gly Cys Glu Leu Thr Tyr
225                 230                 235                 240

```
Gly Ile Lys Asp Val Pro Gly Asp Arg Thr Thr Ile Asp Leu Thr Glu
                245                 250                 255

Asp Glu Asn Gln Tyr Ser Ile Gly Asn Leu Lys Pro Asp Thr Glu Tyr
            260                 265                 270

Glu Val Ser Leu Ile Cys Pro Asn Tyr Glu Arg Ile Ser Asn Pro Ala
        275                 280                 285

Lys Glu Thr Phe Thr Thr Gly Gly Gly Ser Gly Gly Gly Gly Ser
    290                 295                 300

Gly Gly Gly Gly Ser Ala Ile Glu Val Lys Asp Val Thr Asp Thr Thr
305                 310                 315                 320

Ala Leu Ile Thr Trp Ser Pro Gly Glu Arg Ile Trp Met Phe Thr Gly
                325                 330                 335

Cys Glu Leu Thr Tyr Gly Ile Lys Asp Val Pro Gly Asp Arg Thr Thr
            340                 345                 350

Ile Asp Leu Thr Glu Asp Glu Asn Gln Tyr Ser Ile Gly Asn Leu Lys
        355                 360                 365

Pro Asp Thr Glu Tyr Glu Val Ser Leu Ile Cys Pro Asn Tyr Glu Arg
    370                 375                 380

Ile Ser Asn Pro Ala Lys Glu Thr Phe Thr Thr Gly Gly Gly Gly Ser
385                 390                 395                 400

Gly Gly Gly Gly Ser Gly Thr Gly Ser Ala Met Ala Ser Gly Gly Gly
                405                 410                 415

Gly Ser Ala Ile Glu Val Lys Asp Val Thr Asp Thr Thr Ala Leu Ile
            420                 425                 430

Thr Trp Ser Pro Gly Glu Arg Ile Trp Met Phe Thr Gly Cys Glu Leu
        435                 440                 445

Thr Tyr Gly Ile Lys Asp Val Pro Gly Asp Arg Thr Thr Ile Asp Leu
    450                 455                 460

Thr Glu Asp Glu Asn Gln Tyr Ser Ile Gly Asn Leu Lys Pro Asp Thr
465                 470                 475                 480

Glu Tyr Glu Val Ser Leu Ile Cys Pro Asn Tyr Glu Arg Ile Ser Asn
                485                 490                 495

Pro Ala Lys Glu Thr Phe Thr Thr Gly Gly Gly Gly Ser Gly Gly Gly
            500                 505                 510

Gly Ser Gly Gly Gly Gly Ser Ala Ile Glu Val Lys Asp Val Thr Asp
        515                 520                 525

Thr Thr Ala Leu Ile Thr Trp Ser Pro Gly Glu Arg Ile Trp Met Phe
    530                 535                 540

Thr Gly Cys Glu Leu Thr Tyr Gly Ile Lys Asp Val Pro Gly Asp Arg
545                 550                 555                 560

Thr Thr Ile Asp Leu Thr Glu Asp Glu Asn Gln Tyr Ser Ile Gly Asn
                565                 570                 575

Leu Lys Pro Asp Thr Glu Tyr Glu Val Ser Leu Ile Cys Pro Asn Tyr
            580                 585                 590

Glu Arg Ile Ser Asn Pro Ala Lys Glu Thr Phe Thr Thr Gly Gly Gly
        595                 600                 605

Gly Ser Gly Gly Gly Gly Ser Gly Gly Gly Gly Ser Ala Ile Glu Val
    610                 615                 620

Lys Asp Val Thr Asp Thr Thr Ala Leu Ile Thr Trp Ser Pro Gly Glu
625                 630                 635                 640

Arg Ile Trp Met Phe Thr Gly Cys Glu Leu Thr Tyr Gly Ile Lys Asp
                645                 650                 655
```

```
Val Pro Gly Asp Arg Thr Thr Ile Asp Leu Thr Glu Asp Glu Asn Gln
            660                 665                 670

Tyr Ser Ile Gly Asn Leu Lys Pro Asp Thr Glu Tyr Glu Val Ser Leu
            675                 680                 685

Ile Cys Pro Asn Tyr Glu Arg Ile Ser Asn Pro Ala Lys Glu Thr Phe
            690                 695                 700

Thr Thr Gly Gly Gly Gly Ser Gly Gly Gly Gly Ser Gly Gly Gly Gly
705                 710                 715                 720

Ser Ala Ile Glu Val Lys Asp Val Thr Asp Thr Thr Ala Leu Ile Thr
            725                 730                 735

Trp Ser Pro Gly Glu Arg Ile Trp Met Phe Thr Gly Cys Glu Leu Thr
            740                 745                 750

Tyr Gly Ile Lys Asp Val Pro Gly Asp Arg Thr Thr Ile Asp Leu Thr
            755                 760                 765

Glu Asp Glu Asn Gln Tyr Ser Ile Gly Asn Leu Lys Pro Asp Thr Glu
            770                 775                 780

Tyr Glu Val Ser Leu Ile Cys Pro Asn Tyr Glu Arg Ile Ser Asn Pro
785                 790                 795                 800

Ala Lys Glu Thr Phe Thr Thr Gly Gly Gly Gly Ser Gly Gly Gly Gly
            805                 810                 815

Ser Gly Thr Leu Gly His His His His His His
            820                 825

<210> SEQ ID NO 149
<211> LENGTH: 321
<212> TYPE: PRT
<213> ORGANISM: Homo sapiens

<400> SEQUENCE: 149

Ile Glu Val Lys Asp Val Thr Asp Thr Thr Ala Leu Ile Thr Trp Ala
1               5                   10                  15

Lys Pro Glu Lys Trp Asp Gly Ser Ile Tyr Gly Cys Glu Leu Ala Tyr
            20                  25                  30

Gly Ile Lys Asp Val Pro Gly Asp Arg Thr Thr Ile Asp Leu Asn Ser
            35                  40                  45

Arg His Thr Ala Tyr Ser Ile Gly Asn Leu Lys Pro Asp Thr Glu Tyr
            50                  55                  60

Glu Val Ser Leu Ile Cys Phe Thr Pro Tyr Gly Ala Lys Ser Asn Pro
65                  70                  75                  80

Ala Lys Glu Thr Phe Thr Thr Gly Ala Glu Pro Lys Ser Cys Asp Lys
            85                  90                  95

Thr His Thr Cys Pro Pro Cys Pro Ala Pro Glu Leu Leu Gly Gly Pro
            100                 105                 110

Ser Val Phe Leu Phe Pro Pro Lys Pro Lys Asp Thr Leu Met Ile Ser
            115                 120                 125

Arg Thr Pro Glu Val Thr Cys Val Val Val Asp Val Ser His Glu Asp
            130                 135                 140

Pro Glu Val Lys Phe Asn Trp Tyr Val Asp Gly Val Glu Val His Asn
145                 150                 155                 160

Ala Lys Thr Lys Pro Arg Glu Glu Gln Tyr Asn Ser Thr Tyr Arg Val
            165                 170                 175

Val Ser Val Leu Thr Val Leu His Gln Asp Trp Leu Asn Gly Lys Glu
            180                 185                 190

Tyr Lys Cys Lys Val Ser Asn Lys Ala Leu Pro Ala Pro Ile Glu Lys
            195                 200                 205
```

```
Thr Ile Ser Lys Ala Lys Gly Gln Pro Arg Glu Pro Gln Val Tyr Thr
            210                 215                 220

Leu Pro Pro Ser Arg Glu Glu Met Thr Lys Asn Gln Val Ser Leu Thr
225                 230                 235                 240

Cys Leu Val Lys Gly Phe Tyr Pro Ser Asp Ile Ala Val Glu Trp Glu
                245                 250                 255

Ser Asn Gly Gln Pro Glu Asn Asn Tyr Lys Thr Thr Pro Pro Val Leu
            260                 265                 270

Asp Ser Asp Gly Ser Phe Phe Leu Tyr Ser Lys Leu Thr Val Asp Lys
        275                 280                 285

Ser Arg Trp Gln Gln Gly Asn Val Phe Ser Cys Ser Val Met His Glu
    290                 295                 300

Ala Leu His Asn His Tyr Thr Gln Lys Ser Leu Ser Leu Ser Pro Gly
305                 310                 315                 320

Lys

<210> SEQ ID NO 150
<211> LENGTH: 321
<212> TYPE: PRT
<213> ORGANISM: Homo sapiens

<400> SEQUENCE: 150

Ile Glu Val Lys Asp Val Thr Asp Thr Ala Leu Ile Thr Trp Ala
1               5                   10                  15

Lys Pro Glu Lys Trp Asp Pro Pro Leu Trp Gly Cys Glu Leu Ala Tyr
            20                  25                  30

Gly Ile Lys Asp Val Pro Gly Asp Arg Thr Thr Ile Asp Leu Asn Ser
        35                  40                  45

Arg His Thr Ala Tyr Ser Ile Gly Asn Leu Lys Pro Asp Thr Glu Tyr
    50                  55                  60

Glu Val Ser Leu Ile Cys Phe Thr Pro Tyr Gly Ala Lys Ser Asn Pro
65                  70                  75                  80

Ala Lys Glu Thr Phe Thr Thr Gly Ala Glu Pro Lys Ser Cys Asp Lys
                85                  90                  95

Thr His Thr Cys Pro Pro Cys Pro Ala Pro Glu Leu Leu Gly Gly Pro
            100                 105                 110

Ser Val Phe Leu Phe Pro Pro Lys Pro Lys Asp Thr Leu Met Ile Ser
        115                 120                 125

Arg Thr Pro Glu Val Thr Cys Val Val Val Asp Val Ser His Glu Asp
130                 135                 140

Pro Glu Val Lys Phe Asn Trp Tyr Val Asp Gly Val Glu Val His Asn
145                 150                 155                 160

Ala Lys Thr Lys Pro Arg Glu Glu Gln Tyr Asn Ser Thr Tyr Arg Val
                165                 170                 175

Val Ser Val Leu Thr Val Leu His Gln Asp Trp Leu Asn Gly Lys Glu
            180                 185                 190

Tyr Lys Cys Lys Val Ser Asn Lys Ala Leu Pro Ala Pro Ile Glu Lys
        195                 200                 205

Thr Ile Ser Lys Ala Lys Gly Gln Pro Arg Glu Pro Gln Val Tyr Thr
    210                 215                 220

Leu Pro Pro Ser Arg Glu Glu Met Thr Lys Asn Gln Val Ser Leu Thr
225                 230                 235                 240

Cys Leu Val Lys Gly Phe Tyr Pro Ser Asp Ile Ala Val Glu Trp Glu
                245                 250                 255
```

```
Ser Asn Gly Gln Pro Glu Asn Asn Tyr Lys Thr Thr Pro Val Leu
            260                 265                 270

Asp Ser Asp Gly Ser Phe Phe Leu Tyr Ser Lys Leu Thr Val Asp Lys
            275                 280                 285

Ser Arg Trp Gln Gln Gly Asn Val Phe Ser Cys Ser Val Met His Glu
    290                 295                 300

Ala Leu His Asn His Tyr Thr Gln Lys Ser Leu Ser Leu Ser Pro Gly
305                 310                 315                 320

Lys

<210> SEQ ID NO 151
<211> LENGTH: 321
<212> TYPE: PRT
<213> ORGANISM: Homo sapiens

<400> SEQUENCE: 151

Ile Glu Val Lys Asp Val Thr Asp Thr Thr Ala Leu Ile Thr Trp Ala
1               5                   10                  15

Lys Pro Trp Val Asp Pro Pro Leu Trp Gly Cys Glu Leu Ala Tyr
            20                  25                  30

Gly Ile Lys Asp Val Pro Gly Asp Arg Thr Thr Ile Asp Leu Gln Gln
            35                  40                  45

Lys His Thr Ala Tyr Ser Ile Gly Asn Leu Lys Pro Asp Thr Glu Tyr
    50                  55                  60

Glu Val Ser Leu Ile Cys Phe Asp Pro Tyr Gly Ala Lys Ser Asn Pro
65                  70                  75                  80

Ala Lys Glu Thr Phe Thr Thr Gly Ala Glu Pro Lys Ser Cys Asp Lys
                85                  90                  95

Thr His Thr Cys Pro Pro Cys Pro Ala Pro Glu Leu Leu Gly Gly Pro
            100                 105                 110

Ser Val Phe Leu Phe Pro Pro Lys Pro Lys Asp Thr Leu Met Ile Ser
        115                 120                 125

Arg Thr Pro Glu Val Thr Cys Val Val Val Asp Val Ser His Glu Asp
130                 135                 140

Pro Glu Val Lys Phe Asn Trp Tyr Val Asp Gly Val Glu Val His Asn
145                 150                 155                 160

Ala Lys Thr Lys Pro Arg Glu Glu Gln Tyr Asn Ser Thr Tyr Arg Val
                165                 170                 175

Val Ser Val Leu Thr Val Leu His Gln Asp Trp Leu Asn Gly Lys Glu
            180                 185                 190

Tyr Lys Cys Lys Val Ser Asn Lys Ala Leu Pro Ala Pro Ile Glu Lys
        195                 200                 205

Thr Ile Ser Lys Ala Lys Gly Gln Pro Arg Glu Pro Gln Val Tyr Thr
210                 215                 220

Leu Pro Pro Ser Arg Glu Glu Met Thr Lys Asn Gln Val Ser Leu Thr
225                 230                 235                 240

Cys Leu Val Lys Gly Phe Tyr Pro Ser Asp Ile Ala Val Glu Trp Glu
                245                 250                 255

Ser Asn Gly Gln Pro Glu Asn Asn Tyr Lys Thr Thr Pro Pro Val Leu
            260                 265                 270

Asp Ser Asp Gly Ser Phe Phe Leu Tyr Ser Lys Leu Thr Val Asp Lys
        275                 280                 285

Ser Arg Trp Gln Gln Gly Asn Val Phe Ser Cys Ser Val Met His Glu
    290                 295                 300
```

Ala Leu His Asn His Tyr Thr Gln Lys Ser Leu Ser Leu Ser Pro Gly
305                 310                 315                 320

Lys

<210> SEQ ID NO 152
<211> LENGTH: 321
<212> TYPE: PRT
<213> ORGANISM: Homo sapiens

<400> SEQUENCE: 152

Ile Glu Val Lys Asp Val Thr Asp Thr Thr Ala Leu Ile Thr Trp Ala
1               5                   10                  15

Lys Pro Trp Val Asp Pro Pro Leu Trp Gly Cys Glu Leu Ala Tyr
            20                  25                  30

Gly Ile Lys Asp Val Pro Gly Asp Arg Thr Thr Ile Asp Leu Gln Gln
            35                  40                  45

Lys His Thr Ala Tyr Ser Ile Gly Asn Leu Lys Pro Asp Thr Glu Tyr
        50                  55                  60

Glu Val Ser Leu Ile Cys Phe Asp Pro Tyr Asn Lys Arg Asn Val Pro
65                  70                  75                  80

Ala Lys Glu Thr Phe Thr Thr Gly Ala Glu Pro Lys Ser Cys Asp Lys
                85                  90                  95

Thr His Thr Cys Pro Pro Cys Pro Ala Pro Glu Leu Leu Gly Gly Pro
            100                 105                 110

Ser Val Phe Leu Phe Pro Pro Lys Pro Lys Asp Thr Leu Met Ile Ser
        115                 120                 125

Arg Thr Pro Glu Val Thr Cys Val Val Val Asp Val Ser His Glu Asp
130                 135                 140

Pro Glu Val Lys Phe Asn Trp Tyr Val Asp Gly Val Glu Val His Asn
145                 150                 155                 160

Ala Lys Thr Lys Pro Arg Glu Glu Gln Tyr Asn Ser Thr Tyr Arg Val
                165                 170                 175

Val Ser Val Leu Thr Val Leu His Gln Asp Trp Leu Asn Gly Lys Glu
            180                 185                 190

Tyr Lys Cys Lys Val Ser Asn Lys Ala Leu Pro Ala Pro Ile Glu Lys
        195                 200                 205

Thr Ile Ser Lys Ala Lys Gly Gln Pro Arg Glu Pro Gln Val Tyr Thr
210                 215                 220

Leu Pro Pro Ser Arg Glu Glu Met Thr Lys Asn Gln Val Ser Leu Thr
225                 230                 235                 240

Cys Leu Val Lys Gly Phe Tyr Pro Ser Asp Ile Ala Val Glu Trp Glu
                245                 250                 255

Ser Asn Gly Gln Pro Glu Asn Asn Tyr Lys Thr Thr Pro Pro Val Leu
            260                 265                 270

Asp Ser Asp Gly Ser Phe Phe Leu Tyr Ser Lys Leu Thr Val Asp Lys
        275                 280                 285

Ser Arg Trp Gln Gln Gly Asn Val Phe Ser Cys Ser Val Met His Glu
290                 295                 300

Ala Leu His Asn His Tyr Thr Gln Lys Ser Leu Ser Leu Ser Pro Gly
305                 310                 315                 320

Lys

<210> SEQ ID NO 153
<211> LENGTH: 321

```
<212> TYPE: PRT
<213> ORGANISM: Homo sapiens

<400> SEQUENCE: 153

Ile Glu Val Lys Asp Val Thr Asp Thr Thr Ala Leu Ile Thr Trp Ala
1               5                   10                  15

Lys Pro Trp Val Asp Pro Pro Leu Trp Gly Cys Glu Leu Ala Tyr
                20                  25                  30

Gly Ile Lys Asp Val Pro Gly Asp Arg Thr Thr Ile Asp Leu Gln Gln
            35                  40                  45

Lys His Thr Ala Tyr Ser Ile Gly Asn Leu Lys Pro Asp Thr Glu Tyr
        50                  55                  60

Glu Val Ser Leu Ile Cys Phe Asp Pro Tyr Gly Met Arg Ser Lys Pro
65                  70                  75                  80

Ala Lys Glu Thr Phe Thr Thr Gly Ala Glu Pro Lys Ser Cys Asp Lys
                85                  90                  95

Thr His Thr Cys Pro Pro Cys Pro Ala Pro Glu Leu Leu Gly Gly Pro
            100                 105                 110

Ser Val Phe Leu Phe Pro Pro Lys Pro Lys Asp Thr Leu Met Ile Ser
        115                 120                 125

Arg Thr Pro Glu Val Thr Cys Val Val Val Asp Val Ser His Glu Asp
130                 135                 140

Pro Glu Val Lys Phe Asn Trp Tyr Val Asp Gly Val Glu Val His Asn
145                 150                 155                 160

Ala Lys Thr Lys Pro Arg Glu Glu Gln Tyr Asn Ser Thr Tyr Arg Val
                165                 170                 175

Val Ser Val Leu Thr Val Leu His Gln Asp Trp Leu Asn Gly Lys Glu
            180                 185                 190

Tyr Lys Cys Lys Val Ser Asn Lys Ala Leu Pro Ala Pro Ile Glu Lys
        195                 200                 205

Thr Ile Ser Lys Ala Lys Gly Gln Pro Arg Glu Pro Gln Val Tyr Thr
210                 215                 220

Leu Pro Pro Ser Arg Glu Glu Met Thr Lys Asn Gln Val Ser Leu Thr
225                 230                 235                 240

Cys Leu Val Lys Gly Phe Tyr Pro Ser Asp Ile Ala Val Glu Trp Glu
                245                 250                 255

Ser Asn Gly Gln Pro Glu Asn Asn Tyr Lys Thr Thr Pro Pro Val Leu
            260                 265                 270

Asp Ser Asp Gly Ser Phe Phe Leu Tyr Ser Lys Leu Thr Val Asp Lys
        275                 280                 285

Ser Arg Trp Gln Gln Gly Asn Val Phe Ser Cys Ser Val Met His Glu
290                 295                 300

Ala Leu His Asn His Tyr Thr Gln Lys Ser Leu Ser Leu Ser Pro Gly
305                 310                 315                 320

Lys

<210> SEQ ID NO 154
<211> LENGTH: 427
<212> TYPE: PRT
<213> ORGANISM: Homo sapiens

<400> SEQUENCE: 154

Ser Gln Ile Glu Val Lys Asp Val Thr Asp Thr Thr Ala Leu Ile Thr
1               5                   10                  15

Trp Ala Lys Pro Glu Lys Trp Asp Gly Ser Ile Tyr Gly Cys Glu Leu
```

```
            20                  25                  30
Ala Tyr Gly Ile Lys Asp Val Pro Gly Asp Arg Thr Thr Ile Asp Leu
            35                  40                  45

Asn Ser Arg His Thr Ala Tyr Ser Ile Gly Asn Leu Lys Pro Asp Thr
 50                  55                  60

Glu Tyr Glu Val Ser Leu Ile Cys Phe Thr Pro Tyr Gly Ala Lys Ser
 65                  70                  75                  80

Asn Pro Ala Lys Glu Thr Phe Thr Thr Gly Gly Thr Pro Thr Ser
                 85                  90                  95

Ser Ala Ser Thr Lys Gly Pro Ser Val Phe Pro Leu Ala Pro Ser Ser
                100                 105                 110

Lys Ser Thr Ser Gly Gly Thr Ala Ala Leu Gly Cys Leu Val Lys Asp
            115                 120                 125

Tyr Phe Pro Glu Pro Val Thr Val Ser Trp Asn Ser Gly Ala Leu Thr
            130                 135                 140

Ser Gly Val His Thr Phe Pro Ala Val Leu Gln Ser Ser Gly Leu Tyr
145                 150                 155                 160

Ser Leu Ser Ser Val Val Thr Val Pro Ser Ser Ser Leu Gly Thr Gln
                165                 170                 175

Thr Tyr Ile Cys Asn Val Asn His Lys Pro Ser Asn Thr Lys Val Asp
                180                 185                 190

Lys Arg Val Glu Pro Lys Ser Cys Asp Lys Thr His Thr Cys Pro Pro
            195                 200                 205

Cys Pro Ala Pro Glu Leu Leu Gly Gly Pro Ser Val Phe Leu Phe Pro
            210                 215                 220

Pro Lys Pro Lys Asp Thr Leu Met Ile Ser Arg Thr Pro Glu Val Thr
225                 230                 235                 240

Cys Val Val Val Asp Val Ser His Glu Asp Pro Glu Val Lys Phe Asn
                245                 250                 255

Trp Tyr Val Asp Gly Val Glu Val His Asn Ala Lys Thr Lys Pro Arg
                260                 265                 270

Glu Glu Gln Tyr Asn Ser Thr Tyr Arg Val Val Ser Val Leu Thr Val
            275                 280                 285

Leu His Gln Asp Trp Leu Asn Gly Lys Glu Tyr Lys Cys Lys Val Ser
            290                 295                 300

Asn Lys Ala Leu Pro Ala Pro Ile Glu Lys Thr Ile Ser Lys Ala Lys
305                 310                 315                 320

Gly Gln Pro Arg Glu Pro Gln Val Tyr Thr Leu Pro Pro Ser Arg Glu
                325                 330                 335

Glu Met Thr Lys Asn Gln Val Ser Leu Thr Cys Leu Val Lys Gly Phe
                340                 345                 350

Tyr Pro Ser Asp Ile Ala Val Glu Trp Glu Ser Asn Gly Gln Pro Glu
            355                 360                 365

Asn Asn Tyr Lys Thr Thr Pro Pro Val Leu Asp Ser Asp Gly Ser Phe
            370                 375                 380

Phe Leu Tyr Ser Lys Leu Thr Val Asp Lys Ser Arg Trp Gln Gln Gly
385                 390                 395                 400

Asn Val Phe Ser Cys Ser Val Met His Glu Ala Leu His Asn His Tyr
                405                 410                 415

Thr Gln Lys Ser Leu Ser Leu Ser Pro Gly Lys
            420                 425

<210> SEQ ID NO 155
```

<211> LENGTH: 202
<212> TYPE: PRT
<213> ORGANISM: Homo sapiens

<400> SEQUENCE: 155

Ser Gln Ile Glu Val Lys Asp Val Thr Asp Thr Thr Ala Leu Ile Thr
1               5                   10                  15

Trp Ala Lys Pro Glu Lys Trp Asp Gly Ser Ile Tyr Gly Cys Glu Leu
            20                  25                  30

Ala Tyr Gly Ile Lys Asp Val Pro Gly Asp Arg Thr Thr Ile Asp Leu
        35                  40                  45

Asn Ser Arg His Thr Ala Tyr Ser Ile Gly Asn Leu Lys Pro Asp Thr
    50                  55                  60

Glu Tyr Glu Val Ser Leu Ile Cys Phe Thr Pro Tyr Gly Ala Lys Ser
65                  70                  75                  80

Asn Pro Ala Lys Glu Thr Phe Thr Gly Gly Thr Pro Thr Arg
                85                  90                  95

Thr Val Ala Ala Pro Ser Val Phe Ile Phe Pro Pro Ser Asp Glu Gln
                100                 105                 110

Leu Lys Ser Gly Thr Ala Ser Val Val Cys Leu Leu Asn Asn Phe Tyr
            115                 120                 125

Pro Arg Glu Ala Lys Val Gln Trp Lys Val Asp Asn Ala Leu Gln Ser
    130                 135                 140

Gly Asn Ser Gln Glu Ser Val Thr Glu Gln Asp Ser Lys Asp Ser Thr
145                 150                 155                 160

Tyr Ser Leu Ser Ser Thr Leu Thr Leu Ser Lys Ala Asp Tyr Glu Lys
                165                 170                 175

His Lys Val Tyr Ala Cys Glu Val Thr His Gln Gly Leu Ser Ser Pro
            180                 185                 190

Val Thr Lys Ser Phe Asn Arg Gly Glu Cys
            195                 200

<210> SEQ ID NO 156
<211> LENGTH: 427
<212> TYPE: PRT
<213> ORGANISM: Homo sapiens

<400> SEQUENCE: 156

Ser Gln Ile Glu Val Lys Asp Val Thr Asp Thr Thr Ala Leu Ile Thr
1               5                   10                  15

Trp Ala Lys Pro Glu Lys Trp Asp Pro Pro Leu Trp Gly Cys Glu Leu
            20                  25                  30

Ala Tyr Gly Ile Lys Asp Val Pro Gly Asp Arg Thr Thr Ile Asp Leu
        35                  40                  45

Asn Ser Arg His Thr Ala Tyr Ser Ile Gly Asn Leu Lys Pro Asp Thr
    50                  55                  60

Glu Tyr Glu Val Ser Leu Ile Cys Phe Thr Pro Tyr Gly Ala Lys Ser
65                  70                  75                  80

Asn Pro Ala Lys Glu Thr Phe Thr Gly Gly Thr Pro Thr Ser
                85                  90                  95

Ser Ala Ser Thr Lys Gly Pro Ser Val Phe Pro Leu Ala Pro Ser Ser
                100                 105                 110

Lys Ser Thr Ser Gly Gly Thr Ala Ala Leu Gly Cys Leu Val Lys Asp
            115                 120                 125

Tyr Phe Pro Glu Pro Val Thr Val Ser Trp Asn Ser Gly Ala Leu Thr
    130                 135                 140

Ser Gly Val His Thr Phe Pro Ala Val Leu Gln Ser Ser Gly Leu Tyr
145                 150                 155                 160

Ser Leu Ser Ser Val Val Thr Val Pro Ser Ser Leu Gly Thr Gln
        165                 170                 175

Thr Tyr Ile Cys Asn Val Asn His Lys Pro Ser Asn Thr Lys Val Asp
            180                 185                 190

Lys Arg Val Glu Pro Lys Ser Cys Asp Lys Thr His Thr Cys Pro Pro
                195                 200                 205

Cys Pro Ala Pro Glu Leu Leu Gly Gly Pro Ser Val Phe Leu Phe Pro
        210                 215                 220

Pro Lys Pro Lys Asp Thr Leu Met Ile Ser Arg Thr Pro Glu Val Thr
225                 230                 235                 240

Cys Val Val Val Asp Val Ser His Glu Asp Pro Glu Val Lys Phe Asn
                245                 250                 255

Trp Tyr Val Asp Gly Val Glu Val His Asn Ala Lys Thr Lys Pro Arg
        260                 265                 270

Glu Glu Gln Tyr Asn Ser Thr Tyr Arg Val Val Ser Val Leu Thr Val
            275                 280                 285

Leu His Gln Asp Trp Leu Asn Gly Lys Glu Tyr Lys Cys Lys Val Ser
    290                 295                 300

Asn Lys Ala Leu Pro Ala Pro Ile Glu Lys Thr Ile Ser Lys Ala Lys
305                 310                 315                 320

Gly Gln Pro Arg Glu Pro Gln Val Tyr Thr Leu Pro Pro Ser Arg Glu
                325                 330                 335

Glu Met Thr Lys Asn Gln Val Ser Leu Thr Cys Leu Val Lys Gly Phe
        340                 345                 350

Tyr Pro Ser Asp Ile Ala Val Glu Trp Glu Ser Asn Gly Gln Pro Glu
            355                 360                 365

Asn Asn Tyr Lys Thr Thr Pro Pro Val Leu Asp Ser Asp Gly Ser Phe
370                 375                 380

Phe Leu Tyr Ser Lys Leu Thr Val Asp Lys Ser Arg Trp Gln Gln Gly
385                 390                 395                 400

Asn Val Phe Ser Cys Ser Val Met His Glu Ala Leu His Asn His Tyr
                405                 410                 415

Thr Gln Lys Ser Leu Ser Leu Ser Pro Gly Lys
            420                 425

<210> SEQ ID NO 157
<211> LENGTH: 202
<212> TYPE: PRT
<213> ORGANISM: Homo sapiens

<400> SEQUENCE: 157

Ser Gln Ile Glu Val Lys Asp Val Thr Asp Thr Thr Ala Leu Ile Thr
1               5                   10                  15

Trp Ala Lys Pro Glu Lys Trp Asp Pro Leu Trp Gly Cys Glu Leu
            20                  25                  30

Ala Tyr Gly Ile Lys Asp Val Pro Gly Asp Arg Thr Ile Asp Leu
        35                  40                  45

Asn Ser Arg His Thr Ala Tyr Ser Ile Gly Asn Leu Lys Pro Asp Thr
    50                  55                  60

Glu Tyr Glu Val Ser Leu Ile Cys Phe Thr Pro Tyr Gly Ala Lys Ser
65                  70                  75                  80

Asn Pro Ala Lys Glu Thr Phe Thr Thr Gly Gly Gly Thr Pro Thr Arg

```
                    85                  90                  95

Thr Val Ala Ala Pro Ser Val Phe Ile Phe Pro Pro Ser Asp Glu Gln
                100                 105                 110

Leu Lys Ser Gly Thr Ala Ser Val Val Cys Leu Leu Asn Asn Phe Tyr
                115                 120                 125

Pro Arg Glu Ala Lys Val Gln Trp Lys Val Asp Asn Ala Leu Gln Ser
            130                 135                 140

Gly Asn Ser Gln Glu Ser Val Thr Glu Gln Asp Ser Lys Asp Ser Thr
145                 150                 155                 160

Tyr Ser Leu Ser Ser Thr Leu Thr Leu Ser Lys Ala Asp Tyr Glu Lys
                165                 170                 175

His Lys Val Tyr Ala Cys Glu Val Thr His Gln Gly Leu Ser Ser Pro
                180                 185                 190

Val Thr Lys Ser Phe Asn Arg Gly Glu Cys
                195                 200

<210> SEQ ID NO 158
<211> LENGTH: 427
<212> TYPE: PRT
<213> ORGANISM: Homo sapiens

<400> SEQUENCE: 158

Ser Gln Ile Glu Val Lys Asp Val Thr Asp Thr Thr Ala Leu Ile Thr
1               5                   10                  15

Trp Ala Lys Pro Trp Val Asp Pro Pro Leu Trp Gly Cys Glu Leu
                20                  25                  30

Ala Tyr Gly Ile Lys Asp Val Pro Gly Asp Arg Thr Thr Ile Asp Leu
            35                  40                  45

Gln Gln Lys His Thr Ala Tyr Ser Ile Gly Asn Leu Lys Pro Asp Thr
50                  55                  60

Glu Tyr Glu Val Ser Leu Ile Cys Phe Asp Pro Tyr Gly Ala Lys Ser
65                  70                  75                  80

Asn Pro Ala Lys Glu Thr Phe Thr Thr Gly Gly Thr Pro Thr Ser
                85                  90                  95

Ser Ala Ser Thr Lys Gly Pro Ser Val Phe Pro Leu Ala Pro Ser Ser
                100                 105                 110

Lys Ser Thr Ser Gly Gly Thr Ala Ala Leu Gly Cys Leu Val Lys Asp
            115                 120                 125

Tyr Phe Pro Glu Pro Val Thr Val Ser Trp Asn Ser Gly Ala Leu Thr
130                 135                 140

Ser Gly Val His Thr Phe Pro Ala Val Leu Gln Ser Ser Gly Leu Tyr
145                 150                 155                 160

Ser Leu Ser Ser Val Val Thr Val Pro Ser Ser Ser Leu Gly Thr Gln
                165                 170                 175

Thr Tyr Ile Cys Asn Val Asn His Lys Pro Ser Asn Thr Lys Val Asp
                180                 185                 190

Lys Arg Val Glu Pro Lys Ser Cys Asp Lys Thr His Thr Cys Pro Pro
            195                 200                 205

Cys Pro Ala Pro Glu Leu Leu Gly Gly Pro Ser Val Phe Leu Phe Pro
210                 215                 220

Pro Lys Pro Lys Asp Thr Leu Met Ile Ser Arg Thr Pro Glu Val Thr
225                 230                 235                 240

Cys Val Val Val Asp Val Ser His Glu Asp Pro Glu Val Lys Phe Asn
                245                 250                 255
```

```
Trp Tyr Val Asp Gly Val Glu Val His Asn Ala Lys Thr Lys Pro Arg
            260                 265                 270

Glu Glu Gln Tyr Asn Ser Thr Tyr Arg Val Val Ser Val Leu Thr Val
        275                 280                 285

Leu His Gln Asp Trp Leu Asn Gly Lys Glu Tyr Lys Cys Lys Val Ser
    290                 295                 300

Asn Lys Ala Leu Pro Ala Pro Ile Glu Lys Thr Ile Ser Lys Ala Lys
305                 310                 315                 320

Gly Gln Pro Arg Glu Pro Gln Val Tyr Thr Leu Pro Pro Ser Arg Glu
                325                 330                 335

Glu Met Thr Lys Asn Gln Val Ser Leu Thr Cys Leu Val Lys Gly Phe
            340                 345                 350

Tyr Pro Ser Asp Ile Ala Val Glu Trp Glu Ser Asn Gly Gln Pro Glu
        355                 360                 365

Asn Asn Tyr Lys Thr Thr Pro Pro Val Leu Asp Ser Asp Gly Ser Phe
    370                 375                 380

Phe Leu Tyr Ser Lys Leu Thr Val Asp Lys Ser Arg Trp Gln Gln Gly
385                 390                 395                 400

Asn Val Phe Ser Cys Ser Val Met His Glu Ala Leu His Asn His Tyr
                405                 410                 415

Thr Gln Lys Ser Leu Ser Leu Ser Pro Gly Lys
            420                 425

<210> SEQ ID NO 159
<211> LENGTH: 202
<212> TYPE: PRT
<213> ORGANISM: Homo sapiens

<400> SEQUENCE: 159

Ser Gln Ile Glu Val Lys Asp Val Thr Asp Thr Thr Ala Leu Ile Thr
1               5                   10                  15

Trp Ala Lys Pro Trp Val Asp Pro Pro Leu Trp Gly Cys Glu Leu
            20                  25                  30

Ala Tyr Gly Ile Lys Asp Val Pro Gly Asp Arg Thr Thr Ile Asp Leu
        35                  40                  45

Gln Gln Lys His Thr Ala Tyr Ser Ile Gly Asn Leu Lys Pro Asp Thr
    50                  55                  60

Glu Tyr Glu Val Ser Leu Ile Cys Phe Asp Pro Tyr Gly Ala Lys Ser
65                  70                  75                  80

Asn Pro Ala Lys Glu Thr Phe Thr Thr Gly Gly Gly Thr Pro Thr Arg
                85                  90                  95

Thr Val Ala Ala Pro Ser Val Phe Ile Phe Pro Pro Ser Asp Glu Gln
            100                 105                 110

Leu Lys Ser Gly Thr Ala Ser Val Val Cys Leu Leu Asn Asn Phe Tyr
        115                 120                 125

Pro Arg Glu Ala Lys Val Gln Trp Lys Val Asp Asn Ala Leu Gln Ser
    130                 135                 140

Gly Asn Ser Gln Glu Ser Val Thr Glu Gln Asp Ser Lys Asp Ser Thr
145                 150                 155                 160

Tyr Ser Leu Ser Ser Thr Leu Thr Leu Ser Lys Ala Asp Tyr Glu Lys
                165                 170                 175

His Lys Val Tyr Ala Cys Glu Val Thr His Gln Gly Leu Ser Ser Pro
            180                 185                 190

Val Thr Lys Ser Phe Asn Arg Gly Glu Cys
        195                 200
```

```
<210> SEQ ID NO 160
<211> LENGTH: 427
<212> TYPE: PRT
<213> ORGANISM: Homo sapiens

<400> SEQUENCE: 160

Ser Gln Ile Glu Val Lys Asp Val Thr Asp Thr Ala Leu Ile Thr
1               5                   10                  15

Trp Ala Lys Pro Trp Val Asp Pro Pro Leu Trp Gly Cys Glu Leu
                20                  25                  30

Ala Tyr Gly Ile Lys Asp Val Pro Gly Asp Arg Thr Thr Ile Asp Leu
            35                  40                      45

Gln Gln Lys His Thr Ala Tyr Ser Ile Gly Asn Leu Lys Pro Asp Thr
        50                  55                  60

Glu Tyr Glu Val Ser Leu Ile Cys Phe Asp Pro Tyr Asn Lys Arg Asn
65              70                  75                      80

Val Pro Ala Lys Glu Thr Phe Thr Thr Gly Gly Gly Thr Pro Thr Ser
                85                  90                  95

Ser Ala Ser Thr Lys Gly Pro Ser Val Phe Pro Leu Ala Pro Ser Ser
                100                 105                 110

Lys Ser Thr Ser Gly Gly Thr Ala Ala Leu Gly Cys Leu Val Lys Asp
        115                 120                 125

Tyr Phe Pro Glu Pro Val Thr Val Ser Trp Asn Ser Gly Ala Leu Thr
    130                 135                 140

Ser Gly Val His Thr Phe Pro Ala Val Leu Gln Ser Ser Gly Leu Tyr
145             150                 155                 160

Ser Leu Ser Ser Val Val Thr Val Pro Ser Ser Leu Gly Thr Gln
                165                 170                 175

Thr Tyr Ile Cys Asn Val Asn His Lys Pro Ser Asn Thr Lys Val Asp
            180                 185                 190

Lys Arg Val Glu Pro Lys Ser Cys Asp Lys Thr His Thr Cys Pro Pro
        195                 200                 205

Cys Pro Ala Pro Glu Leu Leu Gly Gly Pro Ser Val Phe Leu Phe Pro
210                 215                 220

Pro Lys Pro Lys Asp Thr Leu Met Ile Ser Arg Thr Pro Glu Val Thr
225                 230                 235                 240

Cys Val Val Val Asp Val Ser His Glu Asp Pro Glu Val Lys Phe Asn
                245                 250                 255

Trp Tyr Val Asp Gly Val Glu Val His Asn Ala Lys Thr Lys Pro Arg
                260                 265                 270

Glu Glu Gln Tyr Asn Ser Thr Tyr Arg Val Val Ser Val Leu Thr Val
            275                 280                 285

Leu His Gln Asp Trp Leu Asn Gly Lys Glu Tyr Lys Cys Lys Val Ser
        290                 295                 300

Asn Lys Ala Leu Pro Ala Pro Ile Glu Lys Thr Ile Ser Lys Ala Lys
305                 310                 315                 320

Gly Gln Pro Arg Glu Pro Gln Val Tyr Thr Leu Pro Pro Ser Arg Glu
                325                 330                 335

Glu Met Thr Lys Asn Gln Val Ser Leu Thr Cys Leu Val Lys Gly Phe
                340                 345                 350

Tyr Pro Ser Asp Ile Ala Val Glu Trp Glu Ser Asn Gly Gln Pro Glu
            355                 360                 365

Asn Asn Tyr Lys Thr Thr Pro Pro Val Leu Asp Ser Asp Gly Ser Phe
```

```
                    370                 375                 380
Phe Leu Tyr Ser Lys Leu Thr Val Asp Lys Ser Arg Trp Gln Gln Gly
385                 390                 395                 400

Asn Val Phe Ser Cys Ser Val Met His Glu Ala Leu His Asn His Tyr
                405                 410                 415

Thr Gln Lys Ser Leu Ser Leu Ser Pro Gly Lys
            420                 425

<210> SEQ ID NO 161
<211> LENGTH: 202
<212> TYPE: PRT
<213> ORGANISM: Homo sapiens

<400> SEQUENCE: 161

Ser Gln Ile Glu Val Lys Asp Val Thr Asp Thr Thr Ala Leu Ile Thr
1               5                   10                  15

Trp Ala Lys Pro Trp Val Asp Pro Pro Leu Trp Gly Cys Glu Leu
            20                  25                  30

Ala Tyr Gly Ile Lys Asp Val Pro Gly Asp Arg Thr Thr Ile Asp Leu
        35                  40                  45

Gln Gln Lys His Thr Ala Tyr Ser Ile Gly Asn Leu Lys Pro Asp Thr
    50                  55                  60

Glu Tyr Glu Val Ser Leu Ile Cys Phe Asp Pro Tyr Asn Lys Arg Asn
65                  70                  75                  80

Val Pro Ala Lys Glu Thr Phe Thr Thr Gly Gly Thr Pro Thr Arg
            85                  90                  95

Thr Val Ala Ala Pro Ser Val Phe Ile Phe Pro Pro Ser Asp Glu Gln
            100                 105                 110

Leu Lys Ser Gly Thr Ala Ser Val Val Cys Leu Leu Asn Asn Phe Tyr
        115                 120                 125

Pro Arg Glu Ala Lys Val Gln Trp Lys Val Asp Asn Ala Leu Gln Ser
    130                 135                 140

Gly Asn Ser Gln Glu Ser Val Thr Glu Gln Asp Ser Lys Asp Ser Thr
145                 150                 155                 160

Tyr Ser Leu Ser Ser Thr Leu Thr Leu Ser Lys Ala Asp Tyr Glu Lys
                165                 170                 175

His Lys Val Tyr Ala Cys Glu Val Thr His Gln Gly Leu Ser Ser Pro
            180                 185                 190

Val Thr Lys Ser Phe Asn Arg Gly Glu Cys
        195                 200

<210> SEQ ID NO 162
<211> LENGTH: 427
<212> TYPE: PRT
<213> ORGANISM: Homo sapiens

<400> SEQUENCE: 162

Ser Gln Ile Glu Val Lys Asp Val Thr Asp Thr Thr Ala Leu Ile Thr
1               5                   10                  15

Trp Ala Lys Pro Trp Val Asp Pro Pro Leu Trp Gly Cys Glu Leu
            20                  25                  30

Ala Tyr Gly Ile Lys Asp Val Pro Gly Asp Arg Thr Thr Ile Asp Leu
        35                  40                  45

Gln Gln Lys His Thr Ala Tyr Ser Ile Gly Asn Leu Lys Pro Asp Thr
    50                  55                  60

Glu Tyr Glu Val Ser Leu Ile Cys Phe Asp Pro Tyr Gly Met Arg Ser
```

```
                65                  70                  75                  80
Lys Pro Ala Lys Glu Thr Phe Thr Thr Gly Gly Thr Pro Thr Ser
                85                  90                  95

Ser Ala Ser Thr Lys Gly Pro Ser Val Phe Pro Leu Ala Pro Ser Ser
            100                 105                 110

Lys Ser Thr Ser Gly Gly Thr Ala Ala Leu Gly Cys Leu Val Lys Asp
        115                 120                 125

Tyr Phe Pro Glu Pro Val Thr Val Ser Trp Asn Ser Gly Ala Leu Thr
    130                 135                 140

Ser Gly Val His Thr Phe Pro Ala Val Leu Gln Ser Ser Gly Leu Tyr
145                 150                 155                 160

Ser Leu Ser Ser Val Val Thr Val Pro Ser Ser Ser Leu Gly Thr Gln
                165                 170                 175

Thr Tyr Ile Cys Asn Val Asn His Lys Pro Ser Asn Thr Lys Val Asp
            180                 185                 190

Lys Arg Val Glu Pro Lys Ser Cys Asp Lys Thr His Thr Cys Pro Pro
        195                 200                 205

Cys Pro Ala Pro Glu Leu Leu Gly Gly Pro Ser Val Phe Leu Phe Pro
    210                 215                 220

Pro Lys Pro Lys Asp Thr Leu Met Ile Ser Arg Thr Pro Glu Val Thr
225                 230                 235                 240

Cys Val Val Val Asp Val Ser His Glu Asp Pro Glu Val Lys Phe Asn
                245                 250                 255

Trp Tyr Val Asp Gly Val Glu Val His Asn Ala Lys Thr Lys Pro Arg
            260                 265                 270

Glu Glu Gln Tyr Asn Ser Thr Tyr Arg Val Val Ser Val Leu Thr Val
        275                 280                 285

Leu His Gln Asp Trp Leu Asn Gly Lys Glu Tyr Lys Cys Lys Val Ser
    290                 295                 300

Asn Lys Ala Leu Pro Ala Pro Ile Glu Lys Thr Ile Ser Lys Ala Lys
305                 310                 315                 320

Gly Gln Pro Arg Glu Pro Gln Val Tyr Thr Leu Pro Pro Ser Arg Glu
                325                 330                 335

Glu Met Thr Lys Asn Gln Val Ser Leu Thr Cys Leu Val Lys Gly Phe
            340                 345                 350

Tyr Pro Ser Asp Ile Ala Val Glu Trp Glu Ser Asn Gly Gln Pro Glu
        355                 360                 365

Asn Asn Tyr Lys Thr Thr Pro Pro Val Leu Asp Ser Asp Gly Ser Phe
    370                 375                 380

Phe Leu Tyr Ser Lys Leu Thr Val Asp Lys Ser Arg Trp Gln Gln Gly
385                 390                 395                 400

Asn Val Phe Ser Cys Ser Val Met His Glu Ala Leu His Asn His Tyr
                405                 410                 415

Thr Gln Lys Ser Leu Ser Leu Ser Pro Gly Lys
            420                 425

<210> SEQ ID NO 163
<211> LENGTH: 202
<212> TYPE: PRT
<213> ORGANISM: Homo sapiens

<400> SEQUENCE: 163

Ser Gln Ile Glu Val Lys Asp Val Thr Asp Thr Thr Ala Leu Ile Thr
1               5                   10                  15
```

```
Trp Ala Lys Pro Trp Val Asp Pro Pro Leu Trp Gly Cys Glu Leu
            20                  25                  30

Ala Tyr Gly Ile Lys Asp Val Pro Gly Asp Arg Thr Thr Ile Asp Leu
            35                  40                  45

Gln Gln Lys His Thr Ala Tyr Ser Ile Gly Asn Leu Lys Pro Asp Thr
 50                      55                  60

Glu Tyr Glu Val Ser Leu Ile Cys Phe Asp Pro Tyr Gly Met Arg Ser
 65                  70                  75                  80

Lys Pro Ala Lys Glu Thr Phe Thr Thr Gly Gly Thr Pro Thr Arg
                85                  90                  95

Thr Val Ala Ala Pro Ser Val Phe Ile Phe Pro Pro Ser Asp Glu Gln
                100                 105                 110

Leu Lys Ser Gly Thr Ala Ser Val Val Cys Leu Leu Asn Asn Phe Tyr
            115                 120                 125

Pro Arg Glu Ala Lys Val Gln Trp Lys Val Asp Asn Ala Leu Gln Ser
            130                 135                 140

Gly Asn Ser Gln Glu Ser Val Thr Glu Gln Asp Ser Lys Asp Ser Thr
145                 150                 155                 160

Tyr Ser Leu Ser Ser Thr Leu Thr Leu Ser Lys Ala Asp Tyr Glu Lys
                165                 170                 175

His Lys Val Tyr Ala Cys Glu Val Thr His Gln Gly Leu Ser Ser Pro
            180                 185                 190

Val Thr Lys Ser Phe Asn Arg Gly Glu Cys
            195                 200

<210> SEQ ID NO 164
<211> LENGTH: 446
<212> TYPE: PRT
<213> ORGANISM: Homo sapiens

<400> SEQUENCE: 164

Ala Met Ala Ser Gly Gly Gly Ser Ala Ile Glu Val Lys Asp Val
 1               5                  10                  15

Thr Asp Thr Thr Ala Leu Ile Thr Trp Ala Lys Pro Trp Val Asp Pro
            20                  25                  30

Pro Leu Trp Gly Cys Glu Leu Ala Tyr Gly Ile Lys Asp Val Pro
            35                  40                  45

Gly Asp Arg Thr Thr Ile Asp Leu Gln Gln Lys His Thr Ala Tyr Ser
 50                  55                  60

Ile Gly Asn Leu Lys Pro Asp Thr Glu Tyr Glu Val Ser Leu Ile Cys
 65                  70                  75                  80

Phe Asp Pro Tyr Gly Ala Lys Ser Asn Pro Ala Lys Glu Thr Phe Thr
                85                  90                  95

Thr Gly Gly Gly Gly Ser Gly Gly Gly Ser Gly Gly Gly Gly Ser
                100                 105                 110

Ala Ile Glu Val Lys Asp Val Thr Asp Thr Thr Ala Leu Ile Thr Trp
            115                 120                 125

Ala Lys Pro Trp Val Asp Pro Pro Leu Trp Gly Cys Glu Leu Ala
            130                 135                 140

Tyr Gly Ile Lys Asp Val Pro Gly Asp Arg Thr Thr Ile Asp Leu Gln
145                 150                 155                 160

Gln Lys His Thr Ala Tyr Ser Ile Gly Asn Leu Lys Pro Asp Thr Glu
                165                 170                 175

Tyr Glu Val Ser Leu Ile Cys Phe Asp Pro Tyr Gly Ala Lys Ser Asn
            180                 185                 190
```

```
Pro Ala Lys Glu Thr Phe Thr Thr Gly Gly Gly Ser Gly Gly Gly
        195                 200                 205

Gly Ser Gly Thr Gly Ala Glu Pro Lys Ser Cys Asp Lys Thr His Thr
    210                 215                 220

Cys Pro Pro Cys Pro Ala Pro Glu Leu Leu Gly Gly Pro Ser Val Phe
225                 230                 235                 240

Leu Phe Pro Pro Lys Pro Lys Asp Thr Leu Met Ile Ser Arg Thr Pro
                245                 250                 255

Glu Val Thr Cys Val Val Val Asp Val Ser His Glu Asp Pro Glu Val
                260                 265                 270

Lys Phe Asn Trp Tyr Val Asp Gly Val Glu Val His Asn Ala Lys Thr
            275                 280                 285

Lys Pro Arg Glu Glu Gln Tyr Asn Ser Thr Tyr Arg Val Val Ser Val
        290                 295                 300

Leu Thr Val Leu His Gln Asp Trp Leu Asn Gly Lys Glu Tyr Lys Cys
305                 310                 315                 320

Lys Val Ser Asn Lys Ala Leu Pro Ala Pro Ile Glu Lys Thr Ile Ser
                325                 330                 335

Lys Ala Lys Gly Gln Pro Arg Glu Pro Gln Val Tyr Thr Leu Pro Pro
                340                 345                 350

Ser Arg Glu Glu Met Thr Lys Asn Gln Val Ser Leu Thr Cys Leu Val
            355                 360                 365

Lys Gly Phe Tyr Pro Ser Asp Ile Ala Val Glu Trp Glu Ser Asn Gly
        370                 375                 380

Gln Pro Glu Asn Asn Tyr Lys Thr Thr Pro Pro Val Leu Asp Ser Asp
385                 390                 395                 400

Gly Ser Phe Phe Leu Tyr Ser Lys Leu Thr Val Asp Lys Ser Arg Trp
                405                 410                 415

Gln Gln Gly Asn Val Phe Ser Cys Ser Val Met His Glu Ala Leu His
                420                 425                 430

Asn His Tyr Thr Gln Lys Ser Leu Ser Leu Ser Pro Gly Lys
            435                 440                 445

<210> SEQ ID NO 165
<211> LENGTH: 652
<212> TYPE: PRT
<213> ORGANISM: Homo sapiens

<400> SEQUENCE: 165

Ala Met Ala Ser Gly Gly Gly Ser Ala Ile Glu Val Lys Asp Val
1               5                   10                  15

Thr Asp Thr Thr Ala Leu Ile Thr Trp Ala Lys Pro Trp Val Asp Pro
            20                  25                  30

Pro Pro Leu Trp Gly Cys Glu Leu Ala Tyr Gly Ile Lys Asp Val Pro
        35                  40                  45

Gly Asp Arg Thr Thr Ile Asp Leu Gln Gln Lys His Thr Ala Tyr Ser
    50                  55                  60

Ile Gly Asn Leu Lys Pro Asp Thr Glu Tyr Glu Val Ser Leu Ile Cys
65                  70                  75                  80

Phe Asp Pro Tyr Gly Ala Lys Ser Asn Pro Ala Lys Glu Thr Phe Thr
                85                  90                  95

Thr Gly Gly Gly Gly Ser Gly Gly Gly Ser Gly Gly Gly Ser
                100                 105                 110

Ala Ile Glu Val Lys Asp Val Thr Asp Thr Thr Ala Leu Ile Thr Trp
```

```
                    115                 120                 125
        Ala Lys Pro Trp Val Asp Pro Pro Leu Trp Gly Cys Glu Leu Ala
        130                 135                 140

Tyr Gly Ile Lys Asp Val Pro Gly Asp Arg Thr Thr Ile Asp Leu Gln
        145                 150                 155                 160

Gln Lys His Thr Ala Tyr Ser Ile Gly Asn Leu Lys Pro Asp Thr Glu
                        165                 170                 175

Tyr Glu Val Ser Leu Ile Cys Phe Asp Pro Tyr Gly Ala Lys Ser Asn
                    180                 185                 190

Pro Ala Lys Glu Thr Phe Thr Thr Gly Gly Gly Ser Gly Gly
                    195                 200                 205

Gly Ser Gly Gly Gly Ser Ala Ile Glu Val Lys Asp Val Thr Asp
                210                 215                 220

Thr Thr Ala Leu Ile Thr Trp Ala Lys Pro Trp Val Asp Pro Pro
        225                 230                 235                 240

Leu Trp Gly Cys Glu Leu Ala Tyr Gly Ile Lys Asp Val Pro Gly Asp
                            245                 250                 255

Arg Thr Thr Ile Asp Leu Gln Gln Lys His Thr Ala Tyr Ser Ile Gly
                    260                 265                 270

Asn Leu Lys Pro Asp Thr Glu Tyr Glu Val Ser Leu Ile Cys Phe Asp
                    275                 280                 285

Pro Tyr Gly Ala Lys Ser Asn Pro Ala Lys Glu Thr Phe Thr Thr Gly
                290                 295                 300

Gly Gly Ser Gly Gly Gly Ser Gly Gly Gly Ser Ala Ile
        305                 310                 315                 320

Glu Val Lys Asp Val Thr Asp Thr Thr Ala Leu Ile Thr Trp Ala Lys
                        325                 330                 335

Pro Trp Val Asp Pro Pro Leu Trp Gly Cys Glu Leu Ala Tyr Gly
                    340                 345                 350

Ile Lys Asp Val Pro Gly Asp Arg Thr Thr Ile Asp Leu Gln Gln Lys
                    355                 360                 365

His Thr Ala Tyr Ser Ile Gly Asn Leu Lys Pro Asp Thr Glu Tyr Glu
                370                 375                 380

Val Ser Leu Ile Cys Phe Asp Pro Tyr Gly Ala Lys Ser Asn Pro Ala
        385                 390                 395                 400

Lys Glu Thr Phe Thr Thr Gly Gly Gly Ser Gly Gly Gly Ser
                            405                 410                 415

Gly Thr Gly Ala Glu Pro Lys Ser Cys Asp Lys Thr His Thr Cys Pro
                    420                 425                 430

Pro Cys Pro Ala Pro Glu Leu Leu Gly Gly Pro Ser Val Phe Leu Phe
                    435                 440                 445

Pro Pro Lys Pro Lys Asp Thr Leu Met Ile Ser Arg Thr Pro Glu Val
                450                 455                 460

Thr Cys Val Val Val Asp Val Ser His Glu Asp Pro Glu Val Lys Phe
        465                 470                 475                 480

Asn Trp Tyr Val Asp Gly Val Glu Val His Asn Ala Lys Thr Lys Pro
                            485                 490                 495

Arg Glu Glu Gln Tyr Asn Ser Thr Tyr Arg Val Val Ser Val Leu Thr
                    500                 505                 510

Val Leu His Gln Asp Trp Leu Asn Gly Lys Glu Tyr Lys Cys Lys Val
                    515                 520                 525

Ser Asn Lys Ala Leu Pro Ala Pro Ile Glu Lys Thr Ile Ser Lys Ala
                530                 535                 540
```

```
Lys Gly Gln Pro Arg Glu Pro Gln Val Tyr Thr Leu Pro Pro Ser Arg
545                 550                 555                 560

Glu Glu Met Thr Lys Asn Gln Val Ser Leu Thr Cys Leu Val Lys Gly
                565                 570                 575

Phe Tyr Pro Ser Asp Ile Ala Val Glu Trp Glu Ser Asn Gly Gln Pro
            580                 585                 590

Glu Asn Asn Tyr Lys Thr Thr Pro Pro Val Leu Asp Ser Asp Gly Ser
        595                 600                 605

Phe Phe Leu Tyr Ser Lys Leu Thr Val Asp Lys Ser Arg Trp Gln Gln
    610                 615                 620

Gly Asn Val Phe Ser Cys Ser Val Met His Glu Ala Leu His Asn His
625                 630                 635                 640

Tyr Thr Gln Lys Ser Leu Ser Leu Ser Pro Gly Lys
                645                 650

<210> SEQ ID NO 166
<211> LENGTH: 770
<212> TYPE: PRT
<213> ORGANISM: Homo sapiens

<400> SEQUENCE: 166

Ser Gln Ile Glu Val Lys Asp Val Thr Asp Thr Thr Ala Leu Ile Thr
1               5                   10                  15

Trp Ala Lys Pro Trp Val Asp Pro Pro Leu Trp Gly Cys Glu Leu
            20                  25                  30

Thr Tyr Gly Ile Lys Asp Val Pro Gly Asp Arg Thr Thr Ile Gly Leu
            35                  40                  45

Gln Gln Lys His Asn Gln Tyr Ser Ile Gly Asn Leu Lys Pro Asp Thr
    50                  55                  60

Glu Tyr Glu Val Ser Leu Ile Cys Phe Asp Pro Tyr Gly Leu Lys Ser
65              70                  75                  80

Arg Pro Ala Lys Glu Thr Phe Thr Thr Gly Gly Gly Ser Gly Gly
                85                  90                  95

Gly Gly Ser Ile Glu Val Lys Asp Val Thr Asp Thr Thr Ala Leu Ile
            100                 105                 110

Thr Trp Ala Lys Pro Trp Val Asp Pro Pro Leu Trp Gly Cys Glu
            115                 120                 125

Leu Thr Tyr Gly Ile Lys Asp Val Pro Gly Asp Arg Thr Thr Ile Gly
    130                 135                 140

Leu Gln Gln Lys His Asn Gln Tyr Ser Ile Gly Asn Leu Lys Pro Asp
145                 150                 155                 160

Thr Glu Tyr Glu Val Ser Leu Ile Cys Phe Asp Pro Tyr Gly Leu Lys
                165                 170                 175

Ser Arg Pro Ala Lys Glu Thr Phe Thr Thr Gly Gly Gly Ser Gly
            180                 185                 190

Gly Gly Gly Ser Ile Glu Val Lys Asp Val Thr Asp Thr Thr Ala Leu
        195                 200                 205

Ile Thr Trp Ala Lys Pro Trp Val Asp Pro Pro Leu Trp Gly Cys
            210                 215                 220

Glu Leu Thr Tyr Gly Ile Lys Asp Val Pro Gly Asp Arg Thr Thr Ile
225                 230                 235                 240

Gly Leu Gln Gln Lys His Asn Gln Tyr Ser Ile Gly Asn Leu Lys Pro
                245                 250                 255

Asp Thr Glu Tyr Glu Val Ser Leu Ile Cys Phe Asp Pro Tyr Gly Leu
```

```
                   260                 265                 270
Lys Ser Arg Pro Ala Lys Glu Thr Phe Thr Thr Gly Gly Gly Ser
        275                 280                 285
Gly Gly Gly Gly Ser Ile Glu Val Lys Asp Val Thr Asp Thr Ala
        290                 295                 300
Leu Ile Thr Trp Ala Lys Pro Trp Val Asp Pro Pro Leu Trp Gly
305                 310                 315                 320
Cys Glu Leu Thr Tyr Gly Ile Lys Asp Val Pro Gly Asp Arg Thr
                325                 330                 335
Ile Gly Leu Gln Gln Lys His Asn Gln Tyr Ser Ile Gly Asn Leu Lys
        340                 345                 350
Pro Asp Thr Glu Tyr Glu Val Ser Leu Ile Cys Phe Asp Pro Tyr Gly
        355                 360                 365
Leu Lys Ser Arg Pro Ala Lys Glu Thr Phe Thr Thr Gly Gly Gly
        370                 375                 380
Ser Gly Gly Gly Ser Ile Glu Val Lys Asp Val Thr Asp Thr Thr
385                 390                 395                 400
Ala Leu Ile Thr Trp Ala Lys Pro Trp Val Asp Pro Pro Leu Trp
                405                 410                 415
Gly Cys Glu Leu Thr Tyr Gly Ile Lys Asp Val Pro Gly Asp Arg Thr
                420                 425                 430
Thr Ile Gly Leu Gln Gln Lys His Asn Gln Tyr Ser Ile Gly Asn Leu
                435                 440                 445
Lys Pro Asp Thr Glu Tyr Glu Val Ser Leu Ile Cys Phe Asp Pro Tyr
        450                 455                 460
Gly Leu Lys Ser Arg Pro Ala Lys Glu Thr Phe Thr Thr Gly Gly Gly
465                 470                 475                 480
Gly Ser Gly Gly Gly Ser Ile Glu Val Lys Asp Val Thr Asp Thr
                485                 490                 495
Thr Ala Leu Ile Thr Trp Ala Lys Pro Trp Val Asp Pro Pro Leu
                500                 505                 510
Trp Gly Cys Glu Leu Thr Tyr Gly Ile Lys Asp Val Pro Gly Asp Arg
                515                 520                 525
Thr Thr Ile Gly Leu Gln Gln Lys His Asn Gln Tyr Ser Ile Gly Asn
        530                 535                 540
Leu Lys Pro Asp Thr Glu Tyr Glu Val Ser Leu Ile Cys Phe Asp Pro
545                 550                 555                 560
Tyr Gly Leu Lys Ser Arg Pro Ala Lys Glu Thr Phe Thr Thr Gly Gly
                565                 570                 575
Gly Gly Ser Gly Gly Gly Ser Ile Glu Val Lys Asp Val Thr Asp
        580                 585                 590
Thr Thr Ala Leu Ile Thr Trp Ala Lys Pro Trp Val Asp Pro Pro Pro
                595                 600                 605
Leu Trp Gly Cys Glu Leu Thr Tyr Gly Ile Lys Asp Val Pro Gly Asp
        610                 615                 620
Arg Thr Thr Ile Gly Leu Gln Gln Lys His Asn Gln Tyr Ser Ile Gly
625                 630                 635                 640
Asn Leu Lys Pro Asp Thr Glu Tyr Glu Val Ser Leu Ile Cys Phe Asp
                645                 650                 655
Pro Tyr Gly Leu Lys Ser Arg Pro Ala Lys Glu Thr Phe Thr Thr Gly
                660                 665                 670
Gly Gly Gly Ser Gly Gly Gly Ser Ile Glu Val Lys Asp Val Thr
                675                 680                 685
```

```
Asp Thr Thr Ala Leu Ile Thr Trp Ala Lys Pro Trp Val Asp Pro
    690                 695                 700

Pro Leu Trp Gly Cys Glu Leu Thr Tyr Gly Ile Lys Asp Val Pro Gly
705                 710                 715                 720

Asp Arg Thr Thr Ile Gly Leu Gln Gln Lys His Asn Gln Tyr Ser Ile
                725                 730                 735

Gly Asn Leu Lys Pro Asp Thr Glu Tyr Glu Val Ser Leu Ile Cys Phe
            740                 745                 750

Asp Pro Tyr Gly Leu Lys Ser Arg Pro Ala Lys Glu Thr Phe Thr Thr
            755                 760                 765

Gly Leu
    770

<210> SEQ ID NO 167
<211> LENGTH: 576
<212> TYPE: PRT
<213> ORGANISM: Homo sapiens

<400> SEQUENCE: 167

Ser Gln Ile Glu Val Lys Asp Val Thr Asp Thr Thr Ala Leu Ile Thr
1               5                   10                  15

Trp Ala Lys Pro Trp Val Asp Pro Pro Leu Trp Gly Cys Glu Leu
            20                  25                  30

Thr Tyr Gly Ile Lys Asp Val Pro Gly Asp Arg Thr Thr Ile Gly Leu
        35                  40                  45

Gln Gln Lys His Asn Gln Tyr Ser Ile Gly Asn Leu Lys Pro Asp Thr
    50                  55                  60

Glu Tyr Glu Val Ser Leu Ile Cys Phe Asp Pro Tyr Gly Leu Lys Ser
65                  70                  75                  80

Arg Pro Ala Lys Glu Thr Phe Thr Thr Gly Gly Gly Ser Gly Gly
                85                  90                  95

Gly Gly Ser Ile Glu Val Lys Asp Val Thr Asp Thr Thr Ala Leu Ile
            100                 105                 110

Thr Trp Ala Lys Pro Trp Val Asp Pro Pro Leu Trp Gly Cys Glu
        115                 120                 125

Leu Thr Tyr Gly Ile Lys Asp Val Pro Gly Asp Arg Thr Thr Ile Gly
    130                 135                 140

Leu Gln Gln Lys His Asn Gln Tyr Ser Ile Gly Asn Leu Lys Pro Asp
145                 150                 155                 160

Thr Glu Tyr Glu Val Ser Leu Ile Cys Phe Asp Pro Tyr Gly Leu Lys
                165                 170                 175

Ser Arg Pro Ala Lys Glu Thr Phe Thr Thr Gly Gly Gly Ser Gly
            180                 185                 190

Gly Gly Gly Ser Ile Glu Val Lys Asp Val Thr Asp Thr Thr Ala Leu
        195                 200                 205

Ile Thr Trp Ala Lys Pro Trp Val Asp Pro Pro Leu Trp Gly Cys
    210                 215                 220

Glu Leu Thr Tyr Gly Ile Lys Asp Val Pro Gly Asp Arg Thr Thr Ile
225                 230                 235                 240

Gly Leu Gln Gln Lys His Asn Gln Tyr Ser Ile Gly Asn Leu Lys Pro
                245                 250                 255

Asp Thr Glu Tyr Glu Val Ser Leu Ile Cys Phe Asp Pro Tyr Gly Leu
            260                 265                 270

Lys Ser Arg Pro Ala Lys Glu Thr Phe Thr Thr Gly Gly Gly Gly Ser
```

-continued

```
                275                 280                 285
Gly Gly Gly Gly Ser Ile Glu Val Lys Asp Val Thr Asp Thr Thr Ala
        290                 295                 300
Leu Ile Thr Trp Ala Lys Pro Trp Val Asp Pro Pro Leu Trp Gly
305                 310                 315                 320
Cys Glu Leu Thr Tyr Gly Ile Lys Asp Val Pro Gly Asp Arg Thr Thr
                325                 330                 335
Ile Gly Leu Gln Gln Lys His Asn Gln Tyr Ser Ile Gly Asn Leu Lys
            340                 345                 350
Pro Asp Thr Glu Tyr Glu Val Ser Leu Ile Cys Phe Asp Pro Tyr Gly
                355                 360                 365
Leu Lys Ser Arg Pro Ala Lys Glu Thr Phe Thr Thr Gly Gly Gly
370                 375                 380
Ser Gly Gly Gly Ser Ile Glu Val Lys Asp Val Thr Asp Thr Thr
385                 390                 395                 400
Ala Leu Ile Thr Trp Ala Lys Pro Trp Val Asp Pro Pro Leu Trp
                405                 410                 415
Gly Cys Glu Leu Thr Tyr Gly Ile Lys Asp Val Pro Gly Asp Arg Thr
                420                 425                 430
Thr Ile Gly Leu Gln Gln Lys His Asn Gln Tyr Ser Ile Gly Asn Leu
            435                 440                 445
Lys Pro Asp Thr Glu Tyr Glu Val Ser Leu Ile Cys Phe Asp Pro Tyr
        450                 455                 460
Gly Leu Lys Ser Arg Pro Ala Lys Glu Thr Phe Thr Thr Gly Gly
465                 470                 475                 480
Gly Ser Gly Gly Gly Ser Ile Glu Val Lys Asp Val Thr Asp Thr
                485                 490                 495
Thr Ala Leu Ile Thr Trp Ala Lys Pro Trp Val Asp Pro Pro Leu
                500                 505                 510
Trp Gly Cys Glu Leu Thr Tyr Gly Ile Lys Asp Val Pro Gly Asp Arg
                515                 520                 525
Thr Thr Ile Gly Leu Gln Gln Lys His Asn Gln Tyr Ser Ile Gly Asn
            530                 535                 540
Leu Lys Pro Asp Thr Glu Tyr Glu Val Ser Leu Ile Cys Phe Asp Pro
545                 550                 555                 560
Tyr Gly Leu Lys Ser Arg Pro Ala Lys Glu Thr Phe Thr Thr Gly Leu
                565                 570                 575
```

<210> SEQ ID NO 168
<211> LENGTH: 12
<212> TYPE: PRT
<213> ORGANISM: Homo sapiens

<400> SEQUENCE: 168

```
Ala Lys Pro Glu Lys Trp Asp Gly Pro Pro Leu Trp
1               5                   10
```

<210> SEQ ID NO 169
<211> LENGTH: 11
<212> TYPE: PRT
<213> ORGANISM: Homo sapiens

<400> SEQUENCE: 169

```
Phe Asp Pro Tyr Asn Lys Arg Asn Val Pro Ala
1               5                   10
```

<210> SEQ ID NO 170
<211> LENGTH: 11
<212> TYPE: PRT
<213> ORGANISM: Homo sapiens

<400> SEQUENCE: 170

Phe Asp Pro Tyr Gly Leu Lys Ser Arg Pro Ala
1               5                   10

<210> SEQ ID NO 171
<211> LENGTH: 88
<212> TYPE: PRT
<213> ORGANISM: Homo sapiens

<400> SEQUENCE: 171

Ala Ile Glu Val Lys Asp Val Thr Asp Thr Thr Ala Leu Ile Thr Trp
1               5                   10                  15

Ala Lys Pro Glu Lys Trp Asp Gly Ser Ile Tyr Gly Cys Glu Leu Ala
            20                  25                  30

Tyr Gly Ile Lys Asp Val Pro Gly Asp Arg Thr Thr Ile Asp Leu Asn
        35                  40                  45

Ser Arg His Thr Ala Tyr Ser Ile Gly Asn Leu Lys Pro Asp Thr Glu
    50                  55                  60

Tyr Glu Val Ser Leu Ile Cys Phe Thr Pro Tyr Gly Ala Lys Ser Asn
65                  70                  75                  80

Pro Ala Lys Glu Thr Phe Thr Thr
                85

<210> SEQ ID NO 172
<211> LENGTH: 88
<212> TYPE: PRT
<213> ORGANISM: Homo sapiens

<400> SEQUENCE: 172

Ala Ile Glu Val Lys Asp Val Thr Asp Thr Thr Ala Leu Ile Thr Trp
1               5                   10                  15

Ala Lys Pro Glu Lys Trp Asp Pro Pro Leu Trp Gly Cys Glu Leu Ala
            20                  25                  30

Tyr Gly Ile Lys Asp Val Pro Gly Asp Arg Thr Thr Ile Asp Leu Asn
        35                  40                  45

Ser Arg His Thr Ala Tyr Ser Ile Gly Asn Leu Lys Pro Asp Thr Glu
    50                  55                  60

Tyr Glu Val Ser Leu Ile Cys Phe Thr Pro Tyr Gly Ala Lys Ser Asn
65                  70                  75                  80

Pro Ala Lys Glu Thr Phe Thr Thr
                85

<210> SEQ ID NO 173
<211> LENGTH: 88
<212> TYPE: PRT
<213> ORGANISM: Homo sapiens

<400> SEQUENCE: 173

Ala Ile Glu Val Lys Asp Val Thr Asp Thr Thr Ala Leu Ile Thr Trp
1               5                   10                  15

Ala Lys Pro Trp Val Asp Pro Pro Leu Trp Gly Cys Glu Leu Ala
            20                  25                  30

Tyr Gly Ile Lys Asp Val Pro Gly Asp Arg Thr Thr Ile Asp Leu Gln
        35                  40                  45

Gln Lys His Thr Ala Tyr Ser Ile Gly Asn Leu Lys Pro Asp Thr Glu
 50                  55                  60

Tyr Glu Val Ser Leu Ile Cys Phe Asp Pro Tyr Gly Ala Lys Ser Asn
 65                  70                  75                  80

Pro Ala Lys Glu Thr Phe Thr Thr
                 85

<210> SEQ ID NO 174
<211> LENGTH: 88
<212> TYPE: PRT
<213> ORGANISM: Homo sapiens

<400> SEQUENCE: 174

Ala Ile Glu Val Lys Asp Val Thr Asp Thr Thr Ala Leu Ile Thr Trp
 1               5                  10                  15

Ala Lys Pro Trp Val Asp Pro Pro Leu Trp Gly Cys Glu Leu Ala
                 20                  25                  30

Tyr Gly Ile Lys Asp Val Pro Gly Asp Arg Thr Thr Ile Asp Leu Gln
                 35                  40                  45

Gln Lys His Thr Ala Tyr Ser Ile Gly Asn Leu Lys Pro Asp Thr Glu
 50                  55                  60

Tyr Glu Val Ser Leu Ile Cys Phe Asp Pro Tyr Asn Lys Arg Asn Val
 65                  70                  75                  80

Pro Ala Lys Glu Thr Phe Thr Thr
                 85

<210> SEQ ID NO 175
<211> LENGTH: 88
<212> TYPE: PRT
<213> ORGANISM: Homo sapiens

<400> SEQUENCE: 175

Ala Ile Glu Val Lys Asp Val Thr Asp Thr Thr Ala Leu Ile Thr Trp
 1               5                  10                  15

Ala Lys Pro Trp Val Asp Pro Pro Leu Trp Gly Cys Glu Leu Ala
                 20                  25                  30

Tyr Gly Ile Lys Asp Val Pro Gly Asp Arg Thr Thr Ile Asp Leu Gln
                 35                  40                  45

Gln Lys His Thr Ala Tyr Ser Ile Gly Asn Leu Lys Pro Asp Thr Glu
 50                  55                  60

Tyr Glu Val Ser Leu Ile Cys Phe Asp Pro Tyr Gly Met Arg Ser Lys
 65                  70                  75                  80

Pro Ala Lys Glu Thr Phe Thr Thr
                 85

<210> SEQ ID NO 176
<211> LENGTH: 88
<212> TYPE: PRT
<213> ORGANISM: Homo sapiens

<400> SEQUENCE: 176

Ala Ile Glu Val Lys Asp Val Thr Asp Thr Thr Ala Leu Ile Thr Trp
 1               5                  10                  15

Ala Lys Pro Trp Val Asp Pro Pro Leu Trp Gly Cys Glu Leu Ala
                 20                  25                  30

Tyr Gly Ile Lys Asp Val Pro Gly Asp Arg Thr Thr Ile Asp Leu Gln
                 35                  40                  45

Gln Lys His Thr Ala Tyr Ser Ile Gly Asn Leu Lys Pro Asp Thr Glu

```
                    50                  55                  60

Tyr Glu Val Ser Leu Ile Cys Phe Asp Pro Tyr Gly Leu Lys Ser Arg
 65                  70                  75                  80

Pro Ala Lys Glu Thr Phe Thr Thr
                 85
```

<210> SEQ ID NO 177
<211> LENGTH: 88
<212> TYPE: PRT
<213> ORGANISM: Homo sapiens

<400> SEQUENCE: 177

```
Ala Ile Glu Val Lys Asp Val Thr Asp Thr Thr Ala Leu Ile Thr Trp
 1               5                  10                  15

Ala Lys Pro Trp Val Asp Pro Pro Leu Trp Gly Cys Glu Leu Ala
                20                  25                  30

Tyr Gly Ile Lys Asp Val Pro Gly Asp Arg Thr Thr Ile Gly Leu Gln
            35                  40                  45

Gln Lys His Thr Ala Tyr Ser Ile Gly Asn Leu Lys Pro Asp Thr Glu
        50                  55                  60

Tyr Glu Val Ser Leu Ile Cys Phe Asp Pro Tyr Gly Leu Lys Ser Arg
 65                  70                  75                  80

Pro Ala Lys Glu Thr Phe Thr Thr
                 85
```

<210> SEQ ID NO 178
<211> LENGTH: 88
<212> TYPE: PRT
<213> ORGANISM: Homo sapiens

<400> SEQUENCE: 178

```
Ala Ile Glu Val Lys Asp Val Thr Asp Thr Thr Ala Leu Ile Thr Trp
 1               5                  10                  15

Ala Lys Pro Trp Val Asp Pro Pro Leu Trp Gly Cys Glu Leu Ala
                20                  25                  30

Tyr Gly Ile Lys Asp Val Ser Gly Asp Arg Thr Thr Ile Gly Leu Gln
            35                  40                  45

Gln Lys His Thr Ala Tyr Ser Ile Gly Asn Leu Lys Pro Asp Thr Glu
        50                  55                  60

Tyr Glu Val Ser Leu Ile Cys Phe Asp Pro Tyr Gly Arg Lys Ser Gln
 65                  70                  75                  80

Pro Thr Lys Glu Thr Phe Thr Thr
                 85
```

<210> SEQ ID NO 179
<211> LENGTH: 6
<212> TYPE: PRT
<213> ORGANISM: Homo sapiens

<400> SEQUENCE: 179

```
Gln Gln Lys His Asn Gln
 1               5
```

<210> SEQ ID NO 180
<211> LENGTH: 100
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 180

Ala Ile Glu Val Lys Asp Val Thr Asp Thr Thr Ala Leu Ile Thr Trp
1               5                   10                  15

Ser Pro Gly Glu Arg Ile Trp Met Phe Thr Gly Cys Glu Leu Thr Tyr
            20                  25                  30

Gly Ile Lys Asp Val Pro Gly Asp Arg Thr Thr Ile Asp Leu Thr Glu
        35                  40                  45

Asp Glu Asn Gln Tyr Ser Ile Gly Asn Leu Lys Pro Asp Thr Glu Tyr
    50                  55                  60

Glu Val Ser Leu Ile Cys Pro Asn Tyr Glu Arg Ile Ser Asn Pro Ala
65                  70                  75                  80

Lys Glu Thr Phe Thr Thr Gly Gly Thr Leu Gly His His His His
                85                  90                  95

His His His His
            100

<210> SEQ ID NO 181
<211> LENGTH: 319
<212> TYPE: PRT
<213> ORGANISM: Homo sapiens

<400> SEQUENCE: 181

Ile Glu Val Lys Asp Val Thr Asp Thr Thr Ala Leu Ile Thr Trp Ser
1               5                   10                  15

Pro Gly Glu Arg Ile Trp Met Phe Thr Gly Cys Glu Leu Thr Tyr Gly
            20                  25                  30

Ile Lys Asp Val Pro Gly Asp Arg Thr Thr Ile Asp Leu Thr Glu Asp
        35                  40                  45

Glu Asn Gln Tyr Ser Ile Gly Asn Leu Lys Pro Asp Thr Glu Tyr Glu
    50                  55                  60

Val Ser Leu Ile Cys Pro Asn Tyr Glu Arg Ile Ser Asn Pro Ala Lys
65                  70                  75                  80

Glu Thr Phe Thr Thr Gly Ala Glu Pro Lys Ser Cys Asp Lys Thr His
                85                  90                  95

Thr Cys Pro Pro Cys Pro Ala Pro Glu Leu Leu Gly Gly Pro Ser Val
            100                 105                 110

Phe Leu Phe Pro Pro Lys Pro Lys Asp Thr Leu Met Ile Ser Arg Thr
        115                 120                 125

Pro Glu Val Thr Cys Val Val Val Asp Val Ser His Glu Asp Pro Glu
130                 135                 140

Val Lys Phe Asn Trp Tyr Val Asp Gly Val Glu Val His Asn Ala Lys
145                 150                 155                 160

Thr Lys Pro Arg Glu Glu Gln Tyr Asn Ser Thr Tyr Arg Val Val Ser
                165                 170                 175

Val Leu Thr Val Leu His Gln Asp Trp Leu Asn Gly Lys Glu Tyr Lys
            180                 185                 190

Cys Lys Val Ser Asn Lys Ala Leu Pro Ala Pro Ile Glu Lys Thr Ile
        195                 200                 205

Ser Lys Ala Lys Gly Gln Pro Arg Glu Pro Gln Val Tyr Thr Leu Pro
    210                 215                 220

Pro Ser Arg Glu Glu Met Thr Lys Asn Gln Val Ser Leu Thr Cys Leu
225                 230                 235                 240

Val Lys Gly Phe Tyr Pro Ser Asp Ile Ala Val Glu Trp Glu Ser Asn
                245                 250                 255

Gly Gln Pro Glu Asn Asn Tyr Lys Thr Thr Pro Pro Val Leu Asp Ser
            260                 265                 270

Asp Gly Ser Phe Phe Leu Tyr Ser Lys Leu Thr Val Asp Lys Ser Arg
            275                 280                 285

Trp Gln Gln Gly Asn Val Phe Ser Cys Ser Val Met His Glu Ala Leu
            290                 295                 300

His Asn His Tyr Thr Gln Lys Ser Leu Ser Leu Ser Pro Gly Lys
305                 310                 315

<210> SEQ ID NO 182
<211> LENGTH: 425
<212> TYPE: PRT
<213> ORGANISM: Homo sapiens

<400> SEQUENCE: 182

Ser Gln Ile Glu Val Lys Asp Val Thr Asp Thr Thr Ala Leu Ile Thr
1               5                   10                  15

Trp Ser Pro Gly Glu Arg Ile Trp Met Phe Thr Gly Cys Glu Leu Thr
            20                  25                  30

Tyr Gly Ile Lys Asp Val Pro Gly Asp Arg Thr Thr Ile Asp Leu Thr
            35                  40                  45

Glu Asp Glu Asn Gln Tyr Ser Ile Gly Asn Leu Lys Pro Asp Thr Glu
50                  55                  60

Tyr Glu Val Ser Leu Ile Cys Pro Asn Tyr Glu Arg Ile Ser Asn Pro
65                  70                  75                  80

Ala Lys Glu Thr Phe Thr Thr Gly Gly Thr Pro Thr Ser Ser Ala
            85                  90                  95

Ser Thr Lys Gly Pro Ser Val Phe Pro Leu Ala Pro Ser Ser Lys Ser
            100                 105                 110

Thr Ser Gly Gly Thr Ala Ala Leu Gly Cys Leu Val Lys Asp Tyr Phe
            115                 120                 125

Pro Glu Pro Val Thr Val Ser Trp Asn Ser Gly Ala Leu Thr Ser Gly
            130                 135                 140

Val His Thr Phe Pro Ala Val Leu Gln Ser Ser Gly Leu Tyr Ser Leu
145                 150                 155                 160

Ser Ser Val Val Thr Val Pro Ser Ser Ser Leu Gly Thr Gln Thr Tyr
                165                 170                 175

Ile Cys Asn Val Asn His Lys Pro Ser Asn Thr Lys Val Asp Lys Arg
            180                 185                 190

Val Glu Pro Lys Ser Cys Asp Lys Thr His Thr Cys Pro Pro Cys Pro
            195                 200                 205

Ala Pro Glu Leu Leu Gly Gly Pro Ser Val Phe Leu Phe Pro Pro Lys
210                 215                 220

Pro Lys Asp Thr Leu Met Ile Ser Arg Thr Pro Glu Val Thr Cys Val
225                 230                 235                 240

Val Val Asp Val Ser His Glu Asp Pro Glu Val Lys Phe Asn Trp Tyr
            245                 250                 255

Val Asp Gly Val Glu Val His Asn Ala Lys Thr Lys Pro Arg Glu Glu
            260                 265                 270

Gln Tyr Asn Ser Thr Tyr Arg Val Val Ser Val Leu Thr Val Leu His
            275                 280                 285

Gln Asp Trp Leu Asn Gly Lys Glu Tyr Lys Cys Lys Val Ser Asn Lys
            290                 295                 300

Ala Leu Pro Ala Pro Ile Glu Lys Thr Ile Ser Lys Ala Lys Gly Gln

```
              305                 310                 315                 320
Pro Arg Glu Pro Gln Val Tyr Thr Leu Pro Pro Ser Arg Glu Glu Met
                    325                 330                 335

Thr Lys Asn Gln Val Ser Leu Thr Cys Leu Val Lys Gly Phe Tyr Pro
                340                 345                 350

Ser Asp Ile Ala Val Glu Trp Glu Ser Asn Gly Gln Pro Glu Asn Asn
            355                 360                 365

Tyr Lys Thr Thr Pro Pro Val Leu Asp Ser Asp Gly Ser Phe Phe Leu
        370                 375                 380

Tyr Ser Lys Leu Thr Val Asp Lys Ser Arg Trp Gln Gln Gly Asn Val
385                 390                 395                 400

Phe Ser Cys Ser Val Met His Glu Ala Leu His Asn His Tyr Thr Gln
                405                 410                 415

Lys Ser Leu Ser Leu Ser Pro Gly Lys
                420                 425

<210> SEQ ID NO 183
<211> LENGTH: 200
<212> TYPE: PRT
<213> ORGANISM: Homo sapiens

<400> SEQUENCE: 183

Ser Gln Ile Glu Val Lys Asp Val Thr Asp Thr Thr Ala Leu Ile Thr
1               5                   10                  15

Trp Ser Pro Gly Glu Arg Ile Trp Met Phe Thr Gly Cys Glu Leu Thr
                20                  25                  30

Tyr Gly Ile Lys Asp Val Pro Gly Asp Arg Thr Thr Ile Asp Leu Thr
            35                  40                  45

Glu Asp Glu Asn Gln Tyr Ser Ile Gly Asn Leu Lys Pro Asp Thr Glu
        50                  55                  60

Tyr Glu Val Ser Leu Ile Cys Pro Asn Tyr Glu Arg Ile Ser Asn Pro
65                  70                  75                  80

Ala Lys Glu Thr Phe Thr Gly Gly Gly Thr Pro Thr Arg Thr Val
                85                  90                  95

Ala Ala Pro Ser Val Phe Ile Phe Pro Pro Ser Asp Glu Gln Leu Lys
            100                 105                 110

Ser Gly Thr Ala Ser Val Val Cys Leu Leu Asn Asn Phe Tyr Pro Arg
        115                 120                 125

Glu Ala Lys Val Gln Trp Lys Val Asp Asn Ala Leu Gln Ser Gly Asn
    130                 135                 140

Ser Gln Glu Ser Val Thr Glu Gln Asp Ser Lys Asp Ser Thr Tyr Ser
145                 150                 155                 160

Leu Ser Ser Thr Leu Thr Leu Ser Lys Ala Asp Tyr Glu Lys His Lys
                165                 170                 175

Val Tyr Ala Cys Glu Val Thr His Gln Gly Leu Ser Ser Pro Val Thr
            180                 185                 190

Lys Ser Phe Asn Arg Gly Glu Cys
        195                 200

<210> SEQ ID NO 184
<211> LENGTH: 101
<212> TYPE: PRT
<213> ORGANISM: Artificial Sequence
<220> FEATURE:
<223> OTHER INFORMATION: Description of Artificial Sequence: Synthetic
      polypeptide
```

<400> SEQUENCE: 184

```
Ile Glu Val Lys Asp Val Thr Asp Thr Thr Ala Leu Ile Thr Trp Ile
1               5                   10                  15

Pro Pro His Asn Ala Asp Ser Ser Ile Ile Gly Cys Glu Leu Thr Tyr
            20                  25                  30

Gly Ile Lys Asp Val Pro Gly Asp Arg Thr Thr Ile Asp Leu Tyr Asp
        35                  40                  45

Val Ala Phe Asp Tyr Ser Ile Gly Asn Leu Lys Pro Asp Thr Glu Tyr
50                  55                  60

Glu Val Ser Leu Ile Cys Asp Thr Phe Tyr Gly Phe Asp Ser Asn Pro
65                  70                  75                  80

Ala Lys Glu Thr Phe Thr Thr Gly Gly Gly Thr Leu Gly His His His
                85                  90                  95

His His His His His
            100
```

<210> SEQ ID NO 185
<211> LENGTH: 101
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 185

```
Ala Ile Glu Val Lys Asp Val Thr Asp Thr Thr Ala Leu Ile Thr Trp
1               5                   10                  15

Asp Leu Ala Ala Tyr Ser Val Ala Tyr Asn Gly Cys Glu Leu Thr Tyr
            20                  25                  30

Gly Ile Lys Asp Val Pro Gly Asp Arg Thr Thr Ile Asp Leu Phe Asn
        35                  40                  45

Asp Asn Asn Pro Tyr Ser Ile Gly Asn Leu Lys Pro Asp Thr Glu Tyr
50                  55                  60

Glu Val Ser Leu Ile Cys Asn Asn Phe Tyr Gly Ile Leu Ser Asn Pro
65                  70                  75                  80

Ala Lys Glu Thr Phe Thr Thr Gly Gly Gly Thr Leu Gly His His His
                85                  90                  95

His His His His His
            100
```

<210> SEQ ID NO 186
<211> LENGTH: 100
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 186

```
Ala Ile Glu Val Lys Asp Val Thr Asp Thr Thr Ala Leu Ile Thr Trp
1               5                   10                  15

Val Pro Pro Ile Asn Ile Asn Gly Val Ile Ala Gly Cys Glu Leu Thr
            20                  25                  30

Tyr Gly Ile Lys Asp Val Pro Gly Asp Arg Thr Thr Ile Asp Leu Phe
                35                  40                  45

Asp Phe Ser Tyr Val Tyr Ser Ile Gly Asn Leu Lys Pro Asp Thr Glu
50                  55                  60

Tyr Glu Val Ser Leu Ile Cys Phe Thr Thr Asn Gly Asp Ala Val Ser
```

```
                65                  70                  75                  80
Lys Glu Thr Phe Thr Thr Gly Gly Thr Leu Gly His His His
                    85                  90                  95

His His His His
            100

<210> SEQ ID NO 187
<211> LENGTH: 101
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 187

Ala Ile Glu Val Lys Asp Val Thr Asp Thr Thr Ala Leu Ile Thr Trp
1               5                   10                  15

Asn Pro Ser Val Leu Ser Val Tyr Tyr His Gly Cys Glu Leu Thr Tyr
                20                  25                  30

Gly Ile Lys Asp Val Pro Gly Asp Arg Thr Thr Ile Asp Leu Phe Leu
                35                  40                  45

Asp Val Ser Pro Tyr Ser Ile Gly Asn Leu Lys Pro Asp Thr Glu Tyr
    50                  55                  60

Glu Val Ser Leu Ile Cys Ser Thr Phe Thr Gly Asp Tyr Ser Asn Pro
65                  70                  75                  80

Ala Lys Glu Thr Phe Thr Thr Gly Gly Gly Thr Leu Gly His His His
                85                  90                  95

His His His His His
            100

<210> SEQ ID NO 188
<211> LENGTH: 98
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 188

Ala Ile Glu Val Lys Asp Val Thr Asp Thr Thr Ala Leu Ile Thr Trp
1               5                   10                  15

Phe Phe Pro Tyr Ala Tyr His Asp Gly Cys Glu Leu Thr Tyr Gly Ile
                20                  25                  30

Lys Asp Val Pro Gly Asp Arg Thr Thr Ile Asp Leu Asp Leu Leu Leu
                35                  40                  45

Pro Phe Tyr Ser Ile Gly Asn Leu Lys Pro Asp Thr Glu Tyr Glu Val
    50                  55                  60

Ser Leu Ile Cys Ile Thr Asn Ser Phe Asp Gly Asn Pro Ala Lys Glu
65                  70                  75                  80

Thr Phe Thr Thr Gly Gly Gly Thr Leu Gly His His His His His His
                85                  90                  95

His His

<210> SEQ ID NO 189
<211> LENGTH: 101
<212> TYPE: PRT
<213> ORGANISM: Artificial Sequence
<220> FEATURE:
<223> OTHER INFORMATION: Description of Artificial Sequence: Synthetic
      polypeptide
```

<400> SEQUENCE: 189

Ala Ile Glu Val Lys Asp Val Thr Asp Thr Thr Ala Leu Ile Thr Trp
1               5                   10                  15

Ala Phe Pro His Phe Leu Asp Val Leu Thr Gly Cys Glu Leu Thr Tyr
            20                  25                  30

Gly Ile Lys Asp Val Pro Gly Asp Arg Thr Thr Ile Asp Leu Asp Asn
        35                  40                  45

Asp Tyr Ile Ala Tyr Ser Ile Gly Asn Leu Lys Pro Asp Thr Glu Tyr
    50                  55                  60

Glu Val Ser Leu Ile Cys Phe Lys Asp Leu Gly Thr Tyr Ser Asn Pro
65                  70                  75                  80

Ala Lys Glu Thr Phe Thr Thr Gly Gly Gly Thr Leu Gly His His His
                85                  90                  95

His His His His His
            100

<210> SEQ ID NO 190
<211> LENGTH: 100
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 190

Ala Ile Glu Val Lys Asp Val Thr Asp Thr Thr Ala Leu Ile Thr Trp
1               5                   10                  15

Ile Pro Pro Asn Asn Ile Gly Gly Phe Ile Leu Gly Cys Glu Leu Thr
            20                  25                  30

Tyr Gly Ile Lys Asp Val Pro Gly Asp Arg Thr Thr Ile Asp Leu Tyr
        35                  40                  45

Asp Phe Ala Asn Ile Tyr Ser Ile Gly Asn Leu Lys Pro Asp Thr Glu
    50                  55                  60

Tyr Glu Val Ser Leu Ile Cys Ile Thr Asn Asn Gly Tyr Leu Asn Ser
65                  70                  75                  80

Lys Glu Thr Phe Thr Thr Gly Gly Gly Thr Leu Gly His His His His
                85                  90                  95

His His His His
            100

<210> SEQ ID NO 191
<211> LENGTH: 99
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 191

Ala Ile Glu Val Lys Asp Val Thr Asp Thr Thr Ala Leu Ile Thr Trp
1               5                   10                  15

Asp Ile Ser Leu Asp Phe Asp Tyr Ser Ile Gly Cys Glu Leu Thr Tyr
            20                  25                  30

Gly Ile Lys Asp Val Pro Gly Asp Arg Thr Thr Ile Asp Leu His Tyr
        35                  40                  45

Phe Asp Phe Ala Tyr Ser Ile Gly Asn Leu Lys Pro Asp Thr Glu Tyr
    50                  55                  60

```
Glu Val Ser Leu Ile Cys Phe Thr Phe Asp Gly Phe Asn Val Ala Lys
 65                  70                  75                  80

Glu Thr Phe Thr Thr Gly Gly Gly Thr Leu Gly His His His His His
                 85                  90                  95

His His His

<210> SEQ ID NO 192
<211> LENGTH: 639
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 192

Ser Gly Gly Gly Ser Ala Ile Glu Val Lys Asp Val Thr Asp Thr
 1               5                  10                  15

Thr Ala Leu Ile Thr Trp Ala Lys Pro Trp Val Asp Pro Pro Leu
                 20                  25                  30

Trp Gly Cys Glu Leu Ala Tyr Gly Ile Lys Asp Val Pro Gly Asp Arg
                 35                  40                  45

Thr Thr Ile Asp Leu Gln Gln Lys His Thr Ala Tyr Ser Ile Gly Asn
 50                  55                  60

Leu Lys Pro Asp Thr Glu Tyr Glu Val Ser Leu Ile Cys Phe Asp Pro
 65                  70                  75                  80

Tyr Gly Met Arg Ser Lys Pro Ala Lys Glu Thr Phe Thr Thr Gly Gly
                 85                  90                  95

Gly Gly Ser Gly Gly Gly Ser Gly Gly Gly Ser Ala Ile Glu
                100                 105                 110

Val Lys Asp Val Thr Asp Thr Thr Ala Leu Ile Thr Trp Ala Lys Pro
            115                 120                 125

Trp Val Asp Pro Pro Leu Trp Gly Cys Glu Leu Ala Tyr Gly Ile
            130                 135                 140

Lys Asp Val Pro Gly Asp Arg Thr Thr Ile Asp Leu Gln Gln Lys His
145                 150                 155                 160

Thr Ala Tyr Ser Ile Gly Asn Leu Lys Pro Asp Thr Glu Tyr Glu Val
                165                 170                 175

Ser Leu Ile Cys Phe Asp Pro Tyr Gly Met Arg Ser Lys Pro Ala Lys
                180                 185                 190

Glu Thr Phe Thr Thr Gly Gly Gly Ser Gly Gly Gly Ser Gly
                195                 200                 205

Gly Gly Ser Ala Ile Glu Val Lys Asp Val Thr Asp Thr Thr Ala
            210                 215                 220

Leu Ile Thr Trp Ala Lys Pro Trp Val Asp Pro Pro Leu Trp Gly
225                 230                 235                 240

Cys Glu Leu Ala Tyr Gly Ile Lys Asp Val Pro Gly Asp Arg Thr Thr
                245                 250                 255

Ile Asp Leu Gln Gln Lys His Thr Ala Tyr Ser Ile Gly Asn Leu Lys
                260                 265                 270

Pro Asp Thr Glu Tyr Glu Val Ser Leu Ile Cys Phe Asp Pro Tyr Gly
                275                 280                 285

Met Arg Ser Lys Pro Ala Lys Glu Thr Phe Thr Thr Gly Gly Gly Gly
                290                 295                 300

Ser Gly Gly Gly Gly Ser Gly Gly Gly Ser Ala Ile Glu Val Lys
305                 310                 315                 320
```

```
Asp Val Thr Asp Thr Thr Ala Leu Ile Thr Trp Ala Lys Pro Trp Val
            325                 330                 335

Asp Pro Pro Leu Trp Gly Cys Glu Leu Ala Tyr Gly Ile Lys Asp
        340                 345                 350

Val Pro Gly Asp Arg Thr Thr Ile Asp Leu Gln Gln Lys His Thr Ala
        355                 360                 365

Tyr Ser Ile Gly Asn Leu Lys Pro Asp Thr Glu Tyr Glu Val Ser Leu
    370                 375                 380

Ile Cys Phe Asp Pro Tyr Gly Met Arg Ser Lys Pro Ala Lys Glu Thr
385                 390                 395                 400

Phe Thr Thr Gly Gly Gly Ser Gly Gly Gly Ser Gly Thr Gly
                405                 410                 415

Ser Ala Met Ala Ser Gly Gly Gly Ser Ala Ile Glu Val Lys Asp
        420                 425                 430

Val Thr Asp Thr Thr Ala Leu Ile Thr Trp Ala Lys Pro Trp Val Asp
        435                 440                 445

Pro Pro Leu Trp Gly Cys Glu Leu Ala Tyr Gly Ile Lys Asp Val
    450                 455                 460

Pro Gly Asp Arg Thr Thr Ile Asp Leu Gln Gln Lys His Thr Ala Tyr
465                 470                 475                 480

Ser Ile Gly Asn Leu Lys Pro Asp Thr Glu Tyr Glu Val Ser Leu Ile
            485                 490                 495

Cys Phe Asp Pro Tyr Gly Met Arg Ser Lys Pro Ala Lys Glu Thr Phe
                500                 505                 510

Thr Thr Gly Gly Gly Gly Ser Gly Gly Gly Ser Gly Gly Gly Gly
            515                 520                 525

Ser Ala Ile Glu Val Lys Asp Val Thr Asp Thr Thr Ala Leu Ile Thr
    530                 535                 540

Trp Ala Lys Pro Trp Val Asp Pro Pro Leu Trp Gly Cys Glu Leu
545                 550                 555                 560

Ala Tyr Gly Ile Lys Asp Val Pro Gly Asp Arg Thr Thr Ile Asp Leu
                565                 570                 575

Gln Gln Lys His Thr Ala Tyr Ser Ile Gly Asn Leu Lys Pro Asp Thr
            580                 585                 590

Glu Tyr Glu Val Ser Leu Ile Cys Phe Asp Pro Tyr Gly Met Arg Ser
        595                 600                 605

Lys Pro Ala Lys Glu Thr Phe Thr Thr Gly Gly Gly Ser Gly Gly
        610                 615                 620

Gly Gly Ser Gly Thr Leu Gly His His His His His His His
625                 630                 635
```

<210> SEQ ID NO 193
<211> LENGTH: 102
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 193

```
Ala Ile Glu Val Lys Asp Val Thr Asp Thr Thr Ala Leu Ile Thr Trp
1               5                   10                  15

Ala Lys Pro Trp Val Asp Pro Pro Leu Trp Gly Cys Glu Leu Ala
            20                  25                  30

Tyr Gly Ile Lys Asp Val Pro Gly Asp Arg Thr Thr Ile Gly Leu Gln
                35                  40                  45
```

-continued

```
Gln Lys His Thr Ala Tyr Ser Ile Gly Asn Leu Lys Pro Asp Thr Glu
         50                  55                  60

Tyr Glu Val Ser Leu Ile Cys Phe Asp Pro Tyr Gly Leu Lys Ser Arg
 65                  70                  75                  80

Pro Ala Lys Glu Thr Phe Thr Thr Gly Gly Gly Thr Leu Gly His His
                 85                  90                  95

His His His His His His
            100

<210> SEQ ID NO 194
<211> LENGTH: 103
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 194

Ser Gln Ile Glu Val Lys Asp Val Thr Asp Thr Thr Ala Leu Ile Thr
 1               5                  10                  15

Trp Ala Lys Pro Trp Val Asp Pro Pro Leu Trp Gly Cys Glu Leu
                 20                  25                  30

Thr Tyr Gly Ile Lys Asp Val Pro Gly Asp Arg Thr Thr Ile Gly Leu
             35                  40                  45

Gln Gln Lys His Asn Gln Tyr Ser Ile Gly Asn Leu Lys Pro Asp Thr
         50                  55                  60

Glu Tyr Glu Val Ser Leu Ile Cys Phe Asp Pro Tyr Gly Leu Lys Ser
 65                  70                  75                  80

Arg Pro Ala Lys Glu Thr Phe Thr Thr Gly Leu Gly Thr Leu Gly His
                 85                  90                  95

His His His His His His His
            100

<210> SEQ ID NO 195
<211> LENGTH: 88
<212> TYPE: PRT
<213> ORGANISM: Homo sapiens

<400> SEQUENCE: 195

Ala Ile Glu Val Lys Asp Val Thr Asp Thr Thr Ala Leu Ile Thr Trp
 1               5                  10                  15

Ala Lys Pro Trp Val Asp Pro Pro Leu Trp Gly Cys Glu Leu Ala
                 20                  25                  30

Tyr Gly Ile Lys Asp Val Pro Gly Asp Arg Thr Thr Ile Gly Leu Gln
             35                  40                  45

Gln Lys His Thr Ala Tyr Ser Ile Gly Asn Leu Lys Pro Asp Thr Glu
         50                  55                  60

Tyr Glu Val Ser Leu Ile Cys Phe Asp Pro Tyr Gly Arg Ser Ser Arg
 65                  70                  75                  80

Arg Ile Lys Glu Thr Phe Thr Thr
                 85

<210> SEQ ID NO 196
<211> LENGTH: 88
<212> TYPE: PRT
<213> ORGANISM: Homo sapiens

<400> SEQUENCE: 196
```

Ala Ile Glu Val Lys Asp Val Thr Asp Thr Thr Ala Leu Ile Thr Trp
1               5                   10                  15

Gly Gln Pro Trp Val Ser Pro Pro Leu Trp Gly Cys Glu Leu Ala
            20                  25                  30

Tyr Gly Ile Lys Asp Val Pro Gly Asp Arg Thr Thr Ile Gly Leu Gln
            35                  40                  45

Gln Lys His Thr Ala Tyr Ser Ile Gly Asn Leu Lys Pro Asp Thr Glu
        50                  55                  60

Tyr Glu Val Ser Leu Ile Cys Phe Asp Pro Tyr Gly Leu His Ser Arg
65                  70                  75                  80

Leu Thr Lys Glu Thr Phe Thr Thr
                85

<210> SEQ ID NO 197
<211> LENGTH: 88
<212> TYPE: PRT
<213> ORGANISM: Homo sapiens

<400> SEQUENCE: 197

Ala Ile Glu Val Lys Asp Val Thr Asp Thr Thr Ala Leu Ile Thr Trp
1               5                   10                  15

Ala Lys Pro Trp Val Asp Pro Pro Leu Trp Gly Cys Glu Leu Ala
            20                  25                  30

Tyr Gly Ile Lys Asp Val Pro Gly Asp Arg Thr Thr Ile Gly Leu Gln
            35                  40                  45

Gln Lys His Thr Ala Tyr Ser Ile Gly Asn Leu Lys Pro Asp Thr Glu
        50                  55                  60

Tyr Glu Val Ser Leu Ile Cys Phe Asp Pro Tyr Gly Arg Lys Ser Gln
65                  70                  75                  80

Pro Thr Lys Glu Thr Phe Thr Thr
                85

<210> SEQ ID NO 198
<211> LENGTH: 88
<212> TYPE: PRT
<213> ORGANISM: Homo sapiens

<400> SEQUENCE: 198

Ala Ile Glu Val Lys Asp Val Thr Asp Thr Thr Ala Leu Ile Thr Trp
1               5                   10                  15

Ala Lys Pro Trp Val Asp Pro Pro Leu Trp Gly Cys Glu Leu Ala
            20                  25                  30

Tyr Gly Ile Lys Asp Val Pro Gly Asp Arg Thr Thr Ile Gly Leu Gln
            35                  40                  45

Gln Lys His Thr Ala Tyr Ser Ile Gly Asn Leu Lys Pro Asp Thr Glu
        50                  55                  60

Tyr Glu Val Ser Leu Ile Cys Phe Asp Pro Tyr Gly Met Lys Ser Lys
65                  70                  75                  80

Pro Ser Lys Glu Thr Phe Thr Thr
                85

<210> SEQ ID NO 199
<211> LENGTH: 88
<212> TYPE: PRT
<213> ORGANISM: Homo sapiens

<400> SEQUENCE: 199

Ala Ile Glu Val Lys Asp Val Thr Asp Thr Thr Ala Leu Ile Thr Trp

```
                1               5                  10                 15
            Ala Lys Pro Trp Val Asp Pro Pro Leu Trp Gly Cys Glu Leu Ala
                            20                  25                 30

Tyr Gly Ile Lys Asp Val Pro Gly Asp Arg Thr Thr Ile Gly Leu Gln
                            35                  40                 45

Gln Lys His Thr Ala Tyr Ser Ile Gly Asn Leu Lys Pro Asp Thr Glu
                            50                  55                 60

Tyr Glu Val Ser Leu Ile Cys Phe Asp Pro Tyr Gly Gly Lys Ser Arg
            65                  70                  75                 80

Pro Thr Lys Glu Thr Phe Thr Thr
                            85

<210> SEQ ID NO 200
<211> LENGTH: 88
<212> TYPE: PRT
<213> ORGANISM: Homo sapiens

<400> SEQUENCE: 200

Ala Ile Glu Val Lys Asp Val Thr Asp Thr Thr Ala Leu Ile Thr Trp
            1               5                  10                 15

Ala Lys Pro Trp Val Asp Pro Pro Leu Trp Gly Cys Glu Leu Ala
                            20                  25                 30

Tyr Gly Ile Lys Asp Val Pro Gly Asp Arg Thr Thr Ile Gly Leu Gln
                            35                  40                 45

Gln Lys His Thr Ala Tyr Ser Ile Gly Asn Leu Lys Pro Asp Thr Glu
                            50                  55                 60

Tyr Glu Val Ser Leu Ile Cys Phe Asp Pro Tyr Gly His Ser Thr His
            65                  70                  75                 80

Pro Val Lys Gly Thr Phe Thr Thr
                            85

<210> SEQ ID NO 201
<211> LENGTH: 87
<212> TYPE: PRT
<213> ORGANISM: Homo sapiens

<400> SEQUENCE: 201

Ser Gln Ile Glu Val Lys Asp Val Thr Asp Thr Thr Ala Leu Ile Thr
            1               5                  10                 15

Trp Phe Lys Pro Leu Ala Glu Ile Asp Gly Cys Glu Leu Thr Tyr Gly
                            20                  25                 30

Ile Lys Asp Val Pro Gly Asp Arg Thr Thr Ile Asp Leu Thr Glu Asp
                            35                  40                 45

Glu Asn Gln Tyr Ser Ile Gly Asn Leu Lys Pro Asp Thr Glu Tyr Glu
                            50                  55                 60

Val Ser Leu Ile Cys Arg Arg Gly Asp Met Ser Ser Asn Pro Ala Lys
            65                  70                  75                 80

Glu Thr Phe Thr Thr Gly Leu
                            85

<210> SEQ ID NO 202
<211> LENGTH: 90
<212> TYPE: PRT
<213> ORGANISM: Homo sapiens

<400> SEQUENCE: 202

Ala Ile Glu Val Lys Asp Val Thr Asp Thr Thr Ala Leu Ile Thr Trp
            1               5                  10                 15
```

```
Ala Lys Pro Trp Val Asp Pro Pro Leu Trp Gly Cys Glu Leu Ala
             20                  25                  30

Tyr Gly Ile Lys Asp Val Pro Gly Asp Arg Thr Thr Ile Asp Leu Gln
             35                  40                  45

Gln Lys His Thr Ala Tyr Ser Ile Gly Asn Leu Lys Pro Asp Thr Glu
 50                  55                  60

Tyr Glu Val Ser Leu Ile Cys Phe Asp Pro Tyr Gly Leu Lys Ser Arg
 65                  70                  75                  80

Pro Ala Lys Glu Thr Phe Thr Thr Gly Gly
             85                  90

<210> SEQ ID NO 203
<211> LENGTH: 90
<212> TYPE: PRT
<213> ORGANISM: Homo sapiens

<400> SEQUENCE: 203

Ala Ile Glu Val Lys Asp Val Thr Asp Thr Thr Ala Leu Ile Thr Trp
 1               5                  10                  15

Ala Lys Pro Trp Val Asp Pro Pro Leu Trp Gly Cys Glu Leu Ala
             20                  25                  30

Tyr Gly Ile Lys Asp Val Pro Gly Asp Arg Thr Thr Ile Gly Leu Gln
             35                  40                  45

Gln Lys His Thr Ala Tyr Ser Ile Gly Asn Leu Lys Pro Asp Thr Glu
 50                  55                  60

Tyr Glu Val Ser Leu Ile Cys Phe Asp Pro Tyr Gly Leu Lys Ser Arg
 65                  70                  75                  80

Pro Ala Lys Glu Thr Phe Thr Thr Gly Gly
             85                  90

<210> SEQ ID NO 204
<211> LENGTH: 91
<212> TYPE: PRT
<213> ORGANISM: Homo sapiens

<400> SEQUENCE: 204

Ser Gln Ile Glu Val Lys Asp Val Thr Asp Thr Thr Ala Leu Ile Thr
 1               5                  10                  15

Trp Ala Lys Pro Trp Val Asp Pro Pro Leu Trp Gly Cys Glu Leu
             20                  25                  30

Thr Tyr Gly Ile Lys Asp Val Pro Gly Asp Arg Thr Thr Ile Gly Leu
             35                  40                  45

Gln Gln Lys His Asn Gln Tyr Ser Ile Gly Asn Leu Lys Pro Asp Thr
 50                  55                  60

Glu Tyr Glu Val Ser Leu Ile Cys Phe Asp Pro Tyr Gly Leu Lys Ser
 65                  70                  75                  80

Arg Pro Ala Lys Glu Thr Phe Thr Thr Gly Leu
             85                  90

<210> SEQ ID NO 205
<211> LENGTH: 91
<212> TYPE: PRT
<213> ORGANISM: Homo sapiens

<400> SEQUENCE: 205

Ser Gln Ile Glu Val Lys Asp Val Thr Asp Thr Thr Ala Leu Ile Thr
 1               5                  10                  15
```

```
Trp Gly Gln Pro Trp Val Ser Pro Pro Leu Trp Gly Cys Glu Leu
            20                  25                  30

Thr Tyr Gly Ile Lys Asp Val Pro Gly Asp Arg Thr Thr Ile Gly Leu
            35                  40                  45

Gln Gln Lys His Asn Gln Tyr Ser Ile Gly Asn Leu Lys Pro Asp Thr
 50                      55                  60

Glu Tyr Glu Val Ser Leu Ile Cys Phe Asp Pro Tyr Gly Leu His Ser
 65                  70                  75                  80

Arg Leu Thr Lys Glu Thr Phe Thr Thr Gly Leu
             85                  90
```

<210> SEQ ID NO 206
<211> LENGTH: 91
<212> TYPE: PRT
<213> ORGANISM: Homo sapiens

<400> SEQUENCE: 206

```
Ser Gln Ile Glu Val Lys Asp Val Thr Asp Thr Thr Ala Leu Ile Thr
 1               5                  10                  15

Trp Ala Lys Pro Trp Val Asp Pro Pro Leu Trp Gly Cys Glu Leu
            20                  25                  30

Thr Tyr Gly Ile Lys Asp Val Pro Gly Asp Arg Thr Thr Ile Gly Leu
            35                  40                  45

Gln Gln Lys His Asn Gln Tyr Ser Ile Gly Asn Leu Lys Pro Asp Thr
 50                      55                  60

Glu Tyr Glu Val Ser Leu Ile Cys Phe Asp Pro Tyr Gly Arg Lys Ser
 65                  70                  75                  80

Gln Pro Thr Lys Glu Thr Phe Thr Thr Gly Leu
             85                  90
```

<210> SEQ ID NO 207
<211> LENGTH: 91
<212> TYPE: PRT
<213> ORGANISM: Homo sapiens

<400> SEQUENCE: 207

```
Ser Gln Ile Glu Val Lys Asp Val Thr Asp Thr Thr Ala Leu Ile Thr
 1               5                  10                  15

Trp Ala Lys Pro Trp Val Asp Pro Pro Leu Trp Gly Cys Glu Leu
            20                  25                  30

Thr Tyr Gly Ile Lys Asp Val Pro Gly Asp Arg Thr Thr Ile Gly Leu
            35                  40                  45

Gln Gln Lys His Asn Gln Tyr Ser Ile Gly Asn Leu Lys Pro Asp Thr
 50                      55                  60

Glu Tyr Glu Val Ser Leu Ile Cys Phe Asp Pro Tyr Gly Gly Lys Ser
 65                  70                  75                  80

Arg Pro Thr Lys Glu Thr Phe Thr Thr Gly Leu
             85                  90
```

<210> SEQ ID NO 208
<211> LENGTH: 91
<212> TYPE: PRT
<213> ORGANISM: Homo sapiens

<400> SEQUENCE: 208

```
Ser Gln Ile Glu Val Lys Asp Val Thr Asp Thr Thr Ala Leu Ile Thr
 1               5                  10                  15

Trp Ala Lys Pro Trp Val Asp Pro Pro Leu Trp Gly Cys Glu Leu
```

```
                20                  25                  30

Thr Tyr Gly Ile Lys Asp Val Pro Gly Asp Arg Thr Thr Ile Gly Leu
            35                  40                  45

Gln Gln Lys His Asn Gln Tyr Ser Ile Gly Asn Leu Lys Pro Asp Thr
        50                  55                  60

Glu Tyr Glu Val Ser Leu Ile Cys Phe Asp Pro Tyr Gly Met Lys Ser
65                  70                  75                  80

Lys Pro Ser Lys Glu Thr Phe Thr Thr Gly Leu
                85                  90

<210> SEQ ID NO 209
<211> LENGTH: 89
<212> TYPE: PRT
<213> ORGANISM: Homo sapiens

<400> SEQUENCE: 209

Ser Gln Ile Glu Val Lys Asp Val Thr Asp Thr Thr Ala Leu Ile Thr
1               5                   10                  15

Trp Ala Lys Pro Trp Val Asp Pro Pro Leu Trp Gly Cys Glu Leu
            20                  25                  30

Thr Tyr Gly Ile Lys Asp Val Pro Gly Asp Arg Thr Thr Ile Gly Leu
            35                  40                  45

Gln Gln Lys His Asn Gln Tyr Ser Ile Gly Asn Leu Lys Pro Asp Thr
        50                  55                  60

Glu Tyr Glu Val Ser Leu Ile Cys Phe Asp Pro Tyr Gly Leu Lys Ser
65                  70                  75                  80

Arg Pro Ala Lys Glu Thr Phe Thr Thr
                85

<210> SEQ ID NO 210
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 210

Gly Gly Gly Gly Ser
1               5

<210> SEQ ID NO 211
<211> LENGTH: 8
<212> TYPE: PRT
<213> ORGANISM: Artificial Sequence
<220> FEATURE:
<223> OTHER INFORMATION: Description of Artificial Sequence: Synthetic
      8xHis tag

<400> SEQUENCE: 211

His His His His His His His His
1               5

<210> SEQ ID NO 212
<211> LENGTH: 35
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: misc_feature
<222> LOCATION: (1)..(4)
```

```
<223> OTHER INFORMATION: This region may encompass 1-4 residues
<220> FEATURE:
<221> NAME/KEY: misc_feature
<222> LOCATION: (6)..(9)
<223> OTHER INFORMATION: This region may encompass 1-4 residues
<220> FEATURE:
<221> NAME/KEY: misc_feature
<222> LOCATION: (11)..(14)
<223> OTHER INFORMATION: This region may encompass 1-4 residues
<220> FEATURE:
<221> NAME/KEY: misc_feature
<222> LOCATION: (16)..(19)
<223> OTHER INFORMATION: This region may encompass 1-4 residues
<220> FEATURE:
<221> NAME/KEY: misc_feature
<222> LOCATION: (21)..(24)
<223> OTHER INFORMATION: This region may encompass 1-4 residues
<220> FEATURE:
<221> NAME/KEY: misc_feature
<222> LOCATION: (26)..(29)
<223> OTHER INFORMATION: This region may encompass 1-4 residues
<220> FEATURE:
<221> NAME/KEY: misc_feature
<222> LOCATION: (31)..(34)
<223> OTHER INFORMATION: This region may encompass 1-4 residues
<220> FEATURE:
<221> NAME/KEY: misc_feature
<222> LOCATION: (1)..(35)
<223> OTHER INFORMATION: This sequence may encompass 1-7 "Gly-sub.x-Ser"
      repeating units, wherein some positions may be absent

<400> SEQUENCE: 212

Gly Gly Gly Gly Ser Gly Gly Gly Gly Ser Gly Gly Gly Gly Ser Gly
1               5                   10                  15

Gly Gly Gly Ser Gly Gly Gly Gly Ser Gly Gly Gly Gly Ser Gly Gly
            20                  25                  30

Gly Gly Ser
        35

<210> SEQ ID NO 213
<211> LENGTH: 87
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (4)..(10)
<223> OTHER INFORMATION: Any amino acid and this region may preferably
      comprise the sequence "Lys Asp Val Thr Asp Thr Thr"
<220> FEATURE:
<221> NAME/KEY: MOD_RES
<222> LOCATION: (16)..(27)
<223> OTHER INFORMATION: Any amino acid and this region may preferably
      comprise the sequences "Ala Lys Pro Trp Val Asp Pro Pro Pro Leu
      Trp Gly," "Ser Pro Gly Glu Arg Ile Trp Met Phe Thr Gly," "Ala Lys
      Pro Glu Lys Trp Asp Gly Ser Ile Tyr Gly,"
<220> FEATURE:
<221> NAME/KEY: MOD_RES
<222> LOCATION: (16)..(27)
<223> OTHER INFORMATION: continued from above, "His Asp Ala Phe Gly Tyr
      Asp Phe Gly," "Ile Pro Pro His Asn Ala Asp Ser Ser Ile Ile Gly" or
      "Ala Lys Pro Glu Lys Trp Asp Gly Pro Pro Leu Trp," wherein some
      positions may be absent
<220> FEATURE:
<221> NAME/KEY: MOD_RES
<222> LOCATION: (31)..(31)
<223> OTHER INFORMATION: Ala or Thr
<220> FEATURE:
<221> NAME/KEY: MOD_RES
<222> LOCATION: (35)..(41)
<223> OTHER INFORMATION: Any amino acid and this region may preferably
      comprise the sequence "Lys Asp Val Pro Gly Asp Arg"
<220> FEATURE:
```

```
<221> NAME/KEY: MOD_RES
<222> LOCATION: (45)..(45)
<223> OTHER INFORMATION: Asp or Gly
<220> FEATURE:
<221> NAME/KEY: MOD_RES
<222> LOCATION: (47)..(52)
<223> OTHER INFORMATION: Any amino acid and this region may preferably
      comprise the sequence "Gln Gln Lys His Thr Ala," "Thr Glu Asp Glu
      Asn Gln," "Asn Ser Arg His Thr Ala," "Pro Asp His Phe His Asn,"
      "Tyr Asp Val Ala Phe Asp" or "Gln Gln Lys His Asn Gln"
<220> FEATURE:
<221> NAME/KEY: MOD_RES
<222> LOCATION: (56)..(63)
<223> OTHER INFORMATION: Any amino acid and this region may preferably
      comprise the sequence "Gly Asn Leu Lys Pro Asp Thr Glu"
<220> FEATURE:
<221> NAME/KEY: MOD_RES
<222> LOCATION: (71)..(81)
<223> OTHER INFORMATION: Any amino acid and this region may preferably
      comprise the sequence "Phe Asp Pro Tyr Gly Ala Lys Ser Asn Pro
      Ala," "Pro Asn Tyr Glu Arg Ile Ser Asn Pro Ala," "Phe Asp Pro Tyr
      Gly Met Arg Ser Lys Pro Ala," "Phe Thr Pro Tyr Gly Ala Lys Ser Asn
      Pro Ala,"
<220> FEATURE:
<221> NAME/KEY: MOD_RES
<222> LOCATION: (71)..(81)
<223> OTHER INFORMATION: continued from above, "Ala Asn Asp His Gly Phe
      Asp Ser Asn Pro Ala," "Asp Thr Phe Tyr Gly Phe Asp Ser Asn Pro
      Ala" "Phe Asp Pro Tyr Asn Lys Arg Asn Val Pro Ala" or "Phe Asp Pro
      Tyr Gly Leu Lys Ser Arg Pro Ala," wherein some positions may be
      absent
<220> FEATURE:
<221> NAME/KEY: MOD_RES
<222> LOCATION: (83)..(83)
<223> OTHER INFORMATION: Glu or Gly
<220> FEATURE:
<223> OTHER INFORMATION: See specification as filed for detailed
      description of substitutions and preferred embodiments

<400> SEQUENCE: 213

Ile Glu Val Xaa Xaa Xaa Xaa Xaa Xaa Ala Leu Ile Thr Trp Xaa
1               5                   10                  15

Xaa Xaa Xaa Xaa Xaa Xaa Xaa Xaa Xaa Xaa Cys Glu Leu Xaa Tyr
                20                  25                  30

Gly Ile Xaa Xaa Xaa Xaa Xaa Xaa Xaa Thr Thr Ile Xaa Leu Xaa Xaa
            35                  40                  45

Xaa Xaa Xaa Xaa Tyr Ser Ile Xaa Xaa Xaa Xaa Xaa Xaa Xaa Tyr
    50                  55                  60

Glu Val Ser Leu Ile Cys Xaa Xaa Xaa Xaa Xaa Xaa Xaa Xaa Xaa
65                  70                  75                  80

Xaa Lys Xaa Thr Phe Thr Thr
            85

<210> SEQ ID NO 214
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 214

Gly Gly Gly Gly Ser Gly Gly Gly Gly Ser Gly Gly Gly Gly Ser
1               5                   10                  15

<210> SEQ ID NO 215
<211> LENGTH: 87
<212> TYPE: PRT
<213> ORGANISM: Artificial Sequence
<220> FEATURE:
```

```
<223> OTHER INFORMATION: Description of Artificial Sequence: Synthetic
      polypeptide
<220> FEATURE:
<221> NAME/KEY: MOD_RES
<222> LOCATION: (4)..(10)
<223>

```
Xaa Lys Glu Thr Phe Thr Thr
             85
```

<210> SEQ ID NO 216
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(6)
<223> OTHER INFORMATION: Asn, Asp, His, Tyr, Ile, Val, Leu, Phe, Thr,
      Ala, Pro or Ser
<220> FEATURE:
<221> NAME/KEY: MOD_RES
<222> LOCATION: (7)..(7)
<223> OTHER INFORMATION: Ser, Thr, Ala or Gly

<400> SEQUENCE: 216

```
Lys Xaa Xaa Xaa Xaa Xaa Xaa
1               5
```

<210> SEQ ID NO 217
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(8)
<223> OTHER INFORMATION: Asn, Asp, His, Tyr, Ile, Val, Leu, Phe, Thr,
      Ala, Pro or Ser
<220> FEATURE:
<221> NAME/KEY: MOD_RES
<222> LOCATION: (9)..(9)
<223> OTHER INFORMATION: Ser, Thr, Ala or Gly

<400> SEQUENCE: 217

```
Lys Xaa Xaa Xaa Xaa Xaa Xaa Xaa Xaa
1               5
```

<210> SEQ ID NO 218
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: Any amino acid
<220> FEATURE:
<221> NAME/KEY: MOD_RES
<222> LOCATION: (3)..(3)
<223> OTHER INFORMATION: Pro or Ala
<220> FEATURE:
<221> NAME/KEY: MOD_RES
<222> LOCATION: (4)..(4)
<223> OTHER INFORMATION: Any amino acid
<220> FEATURE:
<221> NAME/KEY: MOD_RES
<222> LOCATION: (5)..(5)
<223> OTHER INFORMATION: Ala or Gly
<220> FEATURE:
<221> NAME/KEY: MOD_RES
<222> LOCATION: (6)..(8)
<223> OTHER INFORMATION: Any amino acid

<400> SEQUENCE: 218

```
Ser Xaa Xaa Xaa Xaa Xaa Xaa Xaa Gly
1               5
```

<210> SEQ ID NO 219
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(3)
<223> OTHER INFORMATION: Pro, Ser or Gly
<220> FEATURE:
<221> NAME/KEY: MOD_RES
<222> LOCATION: (4)..(9)
<223> OTHER INFORMATION: Any amino acid

<400> SEQUENCE: 219

```
Ser Pro Xaa Xaa Xaa Xaa Xaa Xaa Xaa Thr Gly
1               5                   10
```

<210> SEQ ID NO 220
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: Pro, Gln or Lys
<220> FEATURE:
<221> NAME/KEY: MOD_RES
<222> LOCATION: (4)..(6)
<223> OTHER INFORMATION: Any amino acid
<220> FEATURE:
<221> NAME/KEY: MOD_RES
<222> LOCATION: (7)..(7)
<223> OTHER INFORMATION: Asn or Gly
<220> FEATURE:
<221> NAME/KEY: MOD_RES
<222> LOCATION: (8)..(8)
<223> OTHER INFORMATION: Ser or Gly
<220> FEATURE:
<221> NAME/KEY: MOD_RES
<222> LOCATION: (9)..(9)
<223> OTHER INFORMATION: Any amino acid
<220> FEATURE:
<221> NAME/KEY: MOD_RES
<222> LOCATION: (11)..(11)
<223> OTHER INFORMATION: Any amino acid

<400> SEQUENCE: 220

```
Ala Xaa Pro Xaa Xaa Xaa Xaa Xaa Xaa Ile Xaa Gly
1               5                   10
```

<210> SEQ ID NO 221
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(10)
<223> OTHER INFORMATION: Any amino acid and this sequence may encompass
      6-10 residues, wherein some positions may be absent

<400> SEQUENCE: 221

```
Xaa Xaa Xaa Xaa Xaa Xaa Xaa Xaa Xaa Xaa
1               5                   10

<210> SEQ ID NO 222
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(6)
<223> OTHER INFORMATION: Any amino acid

<400> SEQUENCE: 222

Xaa Xaa Xaa Xaa Xaa Xaa
1               5

<210> SEQ ID NO 223
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Asn, Asp, His, Tyr, Ile, Val, Leu, Phe, Thr,
      Ala, Pro or Ser
<220> FEATURE:
<221> NAME/KEY: MOD_RES
<222> LOCATION: (2)..(2)
<223> OTHER INFORMATION: Asn, Lys, Arg, Asp, Glu or Gly
<220> FEATURE:
<221> NAME/KEY: MOD_RES
<222> LOCATION: (4)..(4)
<223> OTHER INFORMATION: Asn, Asp, His, Tyr, Ile, Val, Leu, Phe, Thr,
      Ala, Pro or Ser
<220> FEATURE:
<221> NAME/KEY: MOD_RES
<222> LOCATION: (6)..(6)
<223> OTHER INFORMATION: Asn, Asp, His, Tyr, Ile, Val, Leu, Phe, Thr,
      Ala, Pro or Ser
<220> FEATURE:
<221> NAME/KEY: MOD_RES
<222> LOCATION: (7)..(7)
<223> OTHER INFORMATION: Ile, Thr, Ser, Val, Ala or Gly
<220> FEATURE:
<221> NAME/KEY: MOD_RES
<222> LOCATION: (8)..(8)
<223> OTHER INFORMATION: Asn, Asp, His, Tyr, Ile, Val, Leu, Phe, Thr,
      Ala, Pro or Ser

<400> SEQUENCE: 223

Xaa Xaa Leu Xaa Pro Xaa Xaa Xaa
1               5

<210> SEQ ID NO 224
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Any amino acid
<220> FEATURE:
<221> NAME/KEY: MOD_RES
<222> LOCATION: (2)..(2)
```

```
<223> OTHER INFORMATION: Asn, Thr or Lys
<220> FEATURE:
<221> NAME/KEY: MOD_RES
<222> LOCATION: (3)..(4)
<223> OTHER INFORMATION: Any amino acid
<220> FEATURE:
<221> NAME/KEY: MOD_RES
<222> LOCATION: (6)..(8)
<223> OTHER INFORMATION: Any amino acid
<220> FEATURE:
<221> NAME/KEY: MOD_RES
<222> LOCATION: (9)..(9)
<223> OTHER INFORMATION: Ser or Ala

<400> SEQUENCE: 224

Xaa Xaa Xaa Xaa Gly Xaa Xaa Xaa Xaa
1               5

<210> SEQ ID NO 225
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(9)
<223> OTHER INFORMATION: Any amino acid

<400> SEQUENCE: 225

Xaa Xaa Xaa Xaa Xaa Xaa Xaa Xaa Xaa
1               5

<210> SEQ ID NO 226
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Any amino acid
<220> FEATURE:
<221> NAME/KEY: MOD_RES
<222> LOCATION: (2)..(2)
<223> OTHER INFORMATION: Asn, Thr or Lys
<220> FEATURE:
<221> NAME/KEY: MOD_RES
<222> LOCATION: (3)..(6)
<223> OTHER INFORMATION: Any amino acid
<220> FEATURE:
<221> NAME/KEY: MOD_RES
<222> LOCATION: (7)..(7)
<223> OTHER INFORMATION: Ser or Gly

<400> SEQUENCE: 226

Xaa Xaa Xaa Xaa Xaa Xaa Xaa Asn Pro Ala
1               5                   10

<210> SEQ ID NO 227
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Any amino acid
```

-continued

```
<220> FEATURE:
<221> NAME/KEY: MOD_RES
<222> LOCATION: (2)..(2)
<223> OTHER INFORMATION: Asn, Thr or Lys
<220> FEATURE:
<221> NAME/KEY: MOD_RES
<222> LOCATION: (3)..(4)
<223> OTHER INFORMATION: Any amino acid
<220> FEATURE:
<221> NAME/KEY: MOD_RES
<222> LOCATION: (6)..(7)
<223> OTHER INFORMATION: Any amino acid

<400> SEQUENCE: 227

Xaa Xaa Xaa Xaa Gly Xaa Xaa Ser Asn Pro Ala
1               5                   10

<210> SEQ ID NO 228
<211> LENGTH: 6
<212> TYPE: PRT
<213> ORGANISM: Artificial Sequence
<220> FEATURE:
<223> OTHER INFORMATION: Description of Artificial Sequence: Synthetic
      6xHis tag

<400> SEQUENCE: 228

His His His His His His
1               5

<210> SEQ ID NO 229
<211> LENGTH: 87
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (4)..(10)
<223> OTHER INFORMATION: Any amino acid and this region may preferably
      comprise the sequence "Lys Asp Val Thr Asp Thr Thr"
<220> FEATURE:
<221> NAME/KEY: MOD_RES
<222> LOCATION: (16)..(27)
<223> OTHER INFORMATION: Any amino acid and this region may preferably
      comprise the sequences "Ala Lys Pro Trp Val Asp Pro Pro Leu
      Trp Gly," "Ser Pro Gly Glu Arg Ile Trp Met Phe Thr Gly," "Ala Lys
      Pro Glu Lys Trp Asp Gly Ser Ile Tyr Gly,"
<220> FEATURE:
<221> NAME/KEY: MOD_RES
<222> LOCATION: (16)..(27)
<223> OTHER INFORMATION: continued from above, "His Asp Ala Phe Gly Tyr
      Asp Phe Gly," "Ile Pro Pro His Asn Ala Asp Ser Ser Ile Ile Gly" or
      "Ala Lys Pro Glu Lys Trp Asp Gly Pro Pro Leu Trp," wherein some
      positions may be absent
<220> FEATURE:
<221> NAME/KEY: MOD_RES
<222> LOCATION: (31)..(31)
<223> OTHER INFORMATION: Ala or Thr
<220> FEATURE:
<221> NAME/KEY: MOD_RES
<222> LOCATION: (35)..(41)
<223> OTHER INFORMATION: Any amino acid and this region may preferably
      comprise the sequence "Lys Asp Val Pro Gly Asp Arg"
<220> FEATURE:
<221> NAME/KEY: MOD_RES
<222> LOCATION: (47)..(52)
<223> OTHER INFORMATION: Any amino acid and this region may preferably
      comprise the sequence "Gln Gln Lys His Thr Ala," "Thr Glu Asp Glu
      Asn Gln," "Asn Ser Arg His Thr Ala," "Pro Asp His Phe His Asn,"
      "Tyr Asp Val Ala Phe Asp" or "Gln Gln Lys His Asn Gln"
<220> FEATURE:
<221> NAME/KEY: MOD_RES
<222> LOCATION: (56)..(63)
<223> OTHER INFORMATION: Any amino acid and this region may preferably
``` comprise the sequence "Gly Asn Leu Lys Pro Asp Thr Glu"
<220> FEATURE:
<221> NAME/KEY: MOD_RES
<222> LOCATION: (71)..(81)
<223> OTHER INFORMATION: Any amino acid and this region may preferably
       comprise the sequence "Phe Asp Pro Tyr Gly Ala Lys Ser Asn Pro
       Ala," "Pro Asn Tyr Glu Arg Ile Ser Asn Pro Ala," "Phe Asp Pro Tyr
       Gly Met Arg Ser Lys Pro Ala," "Phe Thr Pro Tyr Gly Ala Lys Ser Asn
       Pro Ala,"
<220> FEATURE:
<221> NAME/KEY: MOD_RES
<222> LOCATION: (71)..(81)
<223> OTHER INFORMATION: continued from above, "Ala Asn Asp His Gly Phe
       Asp Ser Asn Pro Ala," "Asp Thr Phe Tyr Gly Phe Asp Ser Asn Pro
       Ala" "Phe Asp Pro Tyr Asn Lys Arg Asn Val Pro Ala" or "Phe Asp Pro
       Tyr Gly Leu Lys Ser Arg Pro Ala," wherein some positions may be
       absent
<220> FEATURE:
<223> OTHER INFORMATION: See specification as filed for detailed
       description of substitutions and preferred embodiments

<400> SEQUENCE: 229

Ile Glu Val Xaa Xaa Xaa Xaa Xaa Xaa Ala Leu Ile Thr Trp Xaa
1               5                   10                  15

Xaa Xaa Xaa Xaa Xaa Xaa Xaa Xaa Xaa Xaa Cys Glu Leu Xaa Tyr
                20                  25                  30

Gly Ile Xaa Xaa Xaa Xaa Xaa Xaa Thr Thr Ile Asp Leu Xaa Xaa
            35                  40                  45

Xaa Xaa Xaa Xaa Tyr Ser Ile Xaa Xaa Xaa Xaa Xaa Xaa Xaa Tyr
50                  55                  60

Glu Val Ser Leu Ile Cys Xaa Xaa Xaa Xaa Xaa Xaa Xaa Xaa Xaa
65                  70                  75                  80

Xaa Lys Glu Thr Phe Thr Thr
                85

<210> SEQ ID NO 230
<211> LENGTH: 5
<212> TYPE: PRT
<213> ORGANISM: Artificial Sequence
<220> FEATURE:
<223> OTHER INFORMATION: Description of Artificial Sequence: Synthetic
       peptide

<400> SEQUENCE: 230

Ile Thr Ile Ser Trp
1               5

<210> SEQ ID NO 231
<211> LENGTH: 35
<212> TYPE: PRT
<213> ORGANISM: Artificial Sequence
<220> FEATURE:
<223> OTHER INFORMATION: Description of Artificial Sequence: Synthetic
       polypeptide
<220> FEATURE:
<221> NAME/KEY: misc_feature
<222> LOCATION: (1)..(35)
<223> OTHER INFORMATION: This sequence may encompass 1-7 "Gly Gly Gly
       Gly Ser" repeating units, wherein some positions may be absent

<400> SEQUENCE: 231

Gly Gly Gly Gly Ser Gly Gly Gly Gly Ser Gly Gly Gly Gly Ser Gly
1               5                   10                  15

Gly Gly Ser Gly Gly Gly Ser Gly Gly Gly Ser Gly Gly
            20                  25                  30

Gly Gly Ser
        35

```
<210> SEQ ID NO 232
<211> LENGTH: 102
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (5)..(11)
<223> OTHER INFORMATION: Any amino acid and this region may preferably
      comprise the sequence "Lys Asp Val Thr Asp Thr Thr"
<220> FEATURE:
<221> NAME/KEY: MOD_RES
<222> LOCATION: (17)..(28)
<223> OTHER INFORMATION: Any amino acid and this region may preferably
      comprise the sequences "Ala Lys Pro Trp Val Asp Pro Pro Pro Leu
      Trp Gly," "Ser Pro Gly Glu Arg Ile Trp Met Phe Thr Gly," "Ala Lys
      Pro Glu Lys Trp Asp Gly Ser Ile Tyr Gly,"
<220> FEATURE:
<221> NAME/KEY: MOD_RES
<222> LOCATION: (17)..(28)
<223> OTHER INFORMATION: continued from above, "His Asp Ala Phe Gly Tyr
      Asp Phe Gly," "Ile Pro Pro His Asn Ala Asp Ser Ser Ile Ile Gly" or
      "Ala Lys Pro Glu Lys Trp Asp Gly Pro Pro Leu Trp," wherein some
      positions may be absent
<220> FEATURE:
<221> NAME/KEY: MOD_RES
<222> LOCATION: (32)..(32)
<223> OTHER INFORMATION: Ala or Thr
<220> FEATURE:
<221> NAME/KEY: MOD_RES
<222> LOCATION: (36)..(42)
<223> OTHER INFORMATION: Any amino acid and this region may preferably
      comprise the sequence "Lys Asp Val Pro Gly Asp Arg"
<220> FEATURE:
<221> NAME/KEY: MOD_RES
<222> LOCATION: (48)..(53)
<223> OTHER INFORMATION: Any amino acid and this region may preferably
      comprise the sequence "Gln Gln Lys His Thr Ala," "Thr Glu Asp Glu
      Asn Gln," "Asn Ser Arg His Thr Ala," "Pro Asp His Phe His Asn,"
      "Tyr Asp Val Ala Phe Asp" or "Gln Gln Lys His Asn Gln"
<220> FEATURE:
<221> NAME/KEY: MOD_RES
<222> LOCATION: (57)..(64)
<223> OTHER INFORMATION: Any amino acid and this region may preferably
      comprise the sequence "Gly Asn Leu Lys Pro Asp Thr Glu"
<220> FEATURE:
<221> NAME/KEY: MOD_RES
<222> LOCATION: (72)..(82)
<223> OTHER INFORMATION: Any amino acid and this region may preferably
      comprise the sequence "Phe Asp Pro Tyr Gly Ala Lys Ser Asn Pro
      Ala," "Pro Asn Tyr Glu Arg Ile Ser Asn Pro Ala," "Phe Asp Pro Tyr
      Gly Met Arg Ser Lys Pro Ala," "Phe Thr Pro Tyr Gly Ala Lys Ser Asn
      Pro Ala,"
<220> FEATURE:
<221> NAME/KEY: MOD_RES
<222> LOCATION: (72)..(82)
<223> OTHER INFORMATION: continued from above, "Ala Asn Asp His Gly Phe
      Asp Ser Asn Pro Ala," "Asp Thr Phe Tyr Gly Phe Asp Ser Asn Pro
      Ala" "Phe Asp Pro Tyr Asn Lys Arg Asn Val Pro Ala" or "Phe Asp Pro
      Tyr Gly Leu Lys Ser Arg Pro Ala," wherein some positions may be
      absent
<220> FEATURE:
<223> OTHER INFORMATION: See specification as filed for detailed
      description of substitutions and preferred embodiments

<400> SEQUENCE: 232

Ala Ile Glu Val Xaa Xaa Xaa Xaa Xaa Xaa Xaa Ala Leu Ile Thr Trp
1               5                   10                  15

Xaa Xaa Xaa Xaa Xaa Xaa Xaa Xaa Xaa Xaa Xaa Cys Glu Leu Xaa
            20                  25                  30

Tyr Gly Ile Xaa Xaa Xaa Xaa Xaa Xaa Xaa Thr Thr Ile Asp Leu Xaa
            35                  40                  45
```

```
Xaa Xaa Xaa Xaa Xaa Tyr Ser Ile Xaa Xaa Xaa Xaa Xaa Xaa Xaa
    50                  55                      60

Tyr Glu Val Ser Leu Ile Cys Xaa Xaa Xaa Xaa Xaa Xaa Xaa Xaa
65                  70                  75                  80

Xaa Xaa Lys Glu Thr Phe Thr Thr Gly Gly Gly Thr Leu Gly His His
            85                  90                  95

His His His His His His
            100

<210> SEQ ID NO 233
<211> LENGTH: 219
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (11)..(17)
<223> OTHER INFORMATION: Any amino acid and this region may preferably
      comprise the sequence "Lys Asp Val Thr Asp Thr Thr"
<220> FEATURE:
<221> NAME/KEY: MOD_RES
<222> LOCATION: (23)..(34)
<223> OTHER INFORMATION: Any amino acid and this region may preferably
      comprise the sequences "Ala Lys Pro Trp Val Asp Pro Pro Pro Leu
      Trp Gly," "Ser Pro Gly Glu Arg Ile Trp Met Phe Thr Gly," "Ala Lys
      Pro Glu Lys Trp Asp Gly Ser Ile Tyr Gly,"
<220> FEATURE:
<221> NAME/KEY: MOD_RES
<222> LOCATION: (23)..(34)
<223> OTHER INFORMATION: continued from above, "His Asp Ala Phe Gly Tyr
      Asp Phe Gly," "Ile Pro Pro His Asn Ala Asp Ser Ser Ile Ile Gly" or
      "Ala Lys Pro Glu Lys Trp Asp Gly Pro Pro Leu Trp," wherein some
      positions may be absent
<220> FEATURE:
<221> NAME/KEY: MOD_RES
<222> LOCATION: (38)..(38)
<223> OTHER INFORMATION: Ala or Thr
<220> FEATURE:
<221> NAME/KEY: MOD_RES
<222> LOCATION: (42)..(48)
<223> OTHER INFORMATION: Any amino acid and this region may preferably
      comprise the sequence "Lys Asp Val Pro Gly Asp Arg"
<220> FEATURE:
<221> NAME/KEY: MOD_RES
<222> LOCATION: (54)..(59)
<223> OTHER INFORMATION: Any amino acid and this region may preferably
      comprise the sequence "Gln Gln Lys His Thr Ala," "Thr Glu Asp Glu
      Asn Gln," "Asn Ser Arg His Thr Ala," "Pro Asp His Phe His Asn,"
      "Tyr Asp Val Ala Phe Asp" or "Gln Gln Lys His Asn Gln"
<220> FEATURE:
<221> NAME/KEY: MOD_RES
<222> LOCATION: (63)..(70)
<223> OTHER INFORMATION: Any amino acid and this region may preferably
      comprise the sequence "Gly Asn Leu Lys Pro Asp Thr Glu"
<220> FEATURE:
<221> NAME/KEY: MOD_RES
<222> LOCATION: (78)..(88)
<223> OTHER INFORMATION: Any amino acid and this region may preferably
      comprise the sequence "Phe Asp Pro Tyr Gly Ala Lys Ser Asn Pro
      Ala," "Pro Asn Tyr Glu Arg Ile Ser Asn Pro Ala," "Phe Asp Pro Tyr
      Gly Met Arg Ser Lys Pro Ala," "Phe Thr Pro Tyr Gly Ala Lys Ser Asn
      Pro Ala,"
<220> FEATURE:
<221> NAME/KEY: MOD_RES
<222> LOCATION: (78)..(88)
<223> OTHER INFORMATION: continued from above, "Ala Asn Asp His Gly Phe
      Asp Ser Asn Pro Ala," "Asp Thr Phe Tyr Gly Phe Asp Ser Asn Pro
      Ala" "Phe Asp Pro Tyr Asn Lys Arg Asn Val Pro Ala" or "Phe Asp Pro
      Tyr Gly Leu Lys Ser Arg Pro Ala," wherein some positions may be
      absent
<220> FEATURE:
<221> NAME/KEY: MOD_RES
```

-continued

```
<222> LOCATION: (114)..(120)
<223> OTHER INFORMATION: Any amino acid and this region may preferably
      comprise the sequence "Lys Asp Val Thr Asp Thr Thr"
<220> FEATURE:
<221> NAME/KEY: MOD_RES
<222> LOCATION: (126)..(137)
<223> OTHER INFORMATION: Any amino acid and this region may preferably
      comprise the sequences "Ala Lys Pro Trp Val Asp Pro Pro Leu
      Trp Gly," "Ser Pro Gly Glu Arg Ile Trp Met Phe Thr Gly," "Ala Lys
      Pro Glu Lys Trp Asp Gly Ser Ile Tyr Gly,"
<220> FEATURE:
<221> NAME/KEY: MOD_RES
<222> LOCATION: (126)..(137)
<223> OTHER INFORMATION: continued from above, "His Asp Ala Phe Gly Tyr
      Asp Phe Gly," "Ile Pro Pro His Asn Ala Asp Ser Ser Ile Ile Gly" or
      "Ala Lys Pro Glu Lys Trp Asp Gly Pro Pro Leu Trp," wherein some
      positions may be absent
<220> FEATURE:
<221> NAME/KEY: MOD_RES
<222> LOCATION: (141)..(141)
<223> OTHER INFORMATION: Ala or Thr
<220> FEATURE:
<221> NAME/KEY: MOD_RES
<222> LOCATION: (145)..(151)
<223> OTHER INFORMATION: Any amino acid and this region may preferably
      comprise the sequence "Lys Asp Val Pro Gly Asp Arg"
<220> FEATURE:
<221> NAME/KEY: MOD_RES
<222> LOCATION: (157)..(162)
<223> OTHER INFORMATION: Any amino acid and this region may preferably
      comprise the sequence "Gln Gln Lys His Thr Ala," "Thr Glu Asp Glu
      Asn Gln," "Asn Ser Arg His Thr Ala," "Pro Asp His Phe His Asn,"
      "Tyr Asp Val Ala Phe Asp" or "Gln Gln Lys His Asn Gln"
<220> FEATURE:
<221> NAME/KEY: MOD_RES
<222> LOCATION: (166)..(173)
<223> OTHER INFORMATION: Any amino acid and this region may preferably
      comprise the sequence "Gly Asn Leu Lys Pro Asp Thr Glu"
<220> FEATURE:
<221> NAME/KEY: MOD_RES
<222> LOCATION: (181)..(191)
<223> OTHER INFORMATION: Any amino acid and this region may preferably
      comprise the sequence "Phe Asp Pro Tyr Gly Ala Lys Ser Asn Pro
      Ala," "Pro Asn Tyr Glu Arg Ile Ser Asn Pro Ala," "Phe Asp Pro Tyr
      Gly Met Arg Ser Lys Pro Ala," "Phe Thr Pro Tyr Gly Ala Lys Ser Asn
      Pro Ala,"
<220> FEATURE:
<221> NAME/KEY: MOD_RES
<222> LOCATION: (181)..(191)
<223> OTHER INFORMATION: continued from above, "Ala Asn Asp His Gly Phe
      Asp Ser Asn Pro Ala," "Asp Thr Phe Tyr Gly Phe Asp Ser Asn Pro
      Ala" "Phe Asp Pro Tyr Asn Lys Arg Asn Val Pro Ala" or "Phe Asp Pro
      Tyr Gly Leu Lys Ser Arg Pro Ala," wherein some positions may be
      absent
<220> FEATURE:
<223> OTHER INFORMATION: See specification as filed for detailed
      description of substitutions and preferred embodiments

<400> SEQUENCE: 233

Ser Gly Gly Gly Gly Ser Ala Ile Glu Val Xaa Xaa Xaa Xaa Xaa Xaa
1               5                   10                  15

Xaa Ala Leu Ile Thr Trp Xaa Xaa Xaa Xaa Xaa Xaa Xaa Xaa
            20                  25                  30

Xaa Xaa Cys Glu Leu Xaa Tyr Gly Ile Xaa Xaa Xaa Xaa Xaa Xaa
        35                  40                  45

Thr Thr Ile Asp Leu Xaa Xaa Xaa Xaa Xaa Xaa Tyr Ser Ile Xaa Xaa
50                  55                  60

Xaa Xaa Xaa Xaa Xaa Xaa Tyr Glu Val Ser Leu Ile Cys Xaa Xaa Xaa
65                  70                  75                  80

Xaa Xaa Xaa Xaa Xaa Xaa Xaa Xaa Lys Glu Thr Phe Thr Thr Gly Gly
            85                  90                  95

Gly Gly Ser Gly Gly Gly Gly Ser Gly Gly Gly Gly Ser Ala Ile Glu
```

```
              100                 105                 110
Val Xaa Xaa Xaa Xaa Xaa Xaa Ala Leu Ile Thr Trp Xaa Xaa Xaa
        115                 120                 125

Xaa Xaa Xaa Xaa Xaa Xaa Xaa Xaa Cys Glu Leu Xaa Tyr Gly Ile
    130                 135                 140

Xaa Xaa Xaa Xaa Xaa Xaa Xaa Thr Thr Ile Asp Leu Xaa Xaa Xaa
145                 150                 155                 160

Xaa Xaa Tyr Ser Ile Xaa Xaa Xaa Xaa Xaa Xaa Xaa Tyr Glu Val
                165                 170                 175

Ser Leu Ile Cys Xaa Xaa Xaa Xaa Xaa Xaa Xaa Xaa Xaa Xaa Lys
            180                 185                 190

Glu Thr Phe Thr Thr Gly Gly Gly Gly Ser Gly Gly Gly Ser Gly
        195                 200                 205

Thr Leu Gly His His His His His His His
        210                 215

<210> SEQ ID NO 234
<211> LENGTH: 322
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (11)..(17)
<223> OTHER INFORMATION: Any amino acid and this region may preferably
      comprise the sequence "Lys Asp Val Thr Asp Thr Thr"
<220> FEATURE:
<221> NAME/KEY: MOD_RES
<222> LOCATION: (23)..(34)
<223> OTHER INFORMATION: Any amino acid and this region may preferably
      comprise the sequences "Ala Lys Pro Trp Val Asp Pro Pro Pro Leu
      Trp Gly," "Ser Pro Gly Glu Arg Ile Trp Met Phe Thr Gly," "Ala Lys
      Pro Glu Lys Trp Asp Gly Ser Ile Tyr Gly,"
<220> FEATURE:
<221> NAME/KEY: MOD_RES
<222> LOCATION: (23)..(34)
<223> OTHER INFORMATION: continued from above, "His Asp Ala Phe Gly Tyr
      Asp Phe Gly," "Ile Pro Pro His Asn Ala Asp Ser Ser Ile Ile Gly" or
      "Ala Lys Pro Glu Lys Trp Asp Gly Pro Pro Leu Trp," wherein some
      positions may be absent
<220> FEATURE:
<221> NAME/KEY: MOD_RES
<222> LOCATION: (38)..(38)
<223> OTHER INFORMATION: Ala or Thr
<220> FEATURE:
<221> NAME/KEY: MOD_RES
<222> LOCATION: (42)..(48)
<223> OTHER INFORMATION: Any amino acid and this region may preferably
      comprise the sequence "Lys Asp Val Pro Gly Asp Arg"
<220> FEATURE:
<221> NAME/KEY: MOD_RES
<222> LOCATION: (54)..(59)
<223> OTHER INFORMATION: Any amino acid and this region may preferably
      comprise the sequence "Gln Gln Lys His Thr Ala," "Thr Glu Asp Glu
      Asn Gln," "Asn Ser Arg His Thr Ala," "Pro Asp His Phe His Asn,"
      "Tyr Asp Val Ala Phe Asp" or "Gln Gln Lys His Asn Gln"
<220> FEATURE:
<221> NAME/KEY: MOD_RES
<222> LOCATION: (63)..(70)
<223> OTHER INFORMATION: Any amino acid and this region may preferably
      comprise the sequence "Gly Asn Leu Lys Pro Asp Thr Glu"
<220> FEATURE:
<221> NAME/KEY: MOD_RES
<222> LOCATION: (78)..(88)
<223> OTHER INFORMATION: Any amino acid and this region may preferably
      comprise the sequence "Phe Asp Pro Tyr Gly Ala Lys Ser Asn Pro
      Ala," "Pro Asn Tyr Glu Arg Ile Ser Asn Pro Ala," "Phe Asp Pro Tyr
      Gly Met Arg Ser Lys Pro Ala," "Phe Thr Pro Tyr Gly Ala Lys Ser Asn
      Pro Ala,"
```

```
<220> FEATURE:
<221> NAME/KEY: MOD_RES
<222> LOCATION: (78)..(88)
<223> OTHER INFORMATION: continued from above, "Ala Asn Asp His Gly Phe
      Asp Ser Asn Pro Ala," "Asp Thr Phe Tyr Gly Phe Asp Ser Asn Pro
      Ala" "Phe Asp Pro Tyr Asn Lys Arg Asn Val Pro Ala" or "Phe Asp Pro
      Tyr Gly Leu Lys Ser Arg Pro Ala," wherein some positions may be
      absent
<220> FEATURE:
<221> NAME/KEY: MOD_RES
<222> LOCATION: (114)..(120)
<223> OTHER INFORMATION: Any amino acid and this region may preferably
      comprise the sequence "Lys Asp Val Thr Asp Thr Thr"
<220> FEATURE:
<221> NAME/KEY: MOD_RES
<222> LOCATION: (126)..(137)
<223> OTHER INFORMATION: Any amino acid and this region may preferably
      comprise the sequences "Ala Lys Pro Trp Val Asp Pro Pro Pro Leu
      Trp Gly," "Ser Pro Gly Glu Arg Ile Trp Met Phe Thr Gly," "Ala Lys
      Pro Glu Lys Trp Asp Gly Ser Ile Tyr Gly,"
<220> FEATURE:
<221> NAME/KEY: MOD_RES
<222> LOCATION: (126)..(137)
<223> OTHER INFORMATION: continued from above, "His Asp Ala Phe Gly Tyr
      Asp Phe Gly," "Ile Pro Pro His Asn Ala Asp Ser Ser Ile Ile Gly" or
      "Ala Lys Pro Glu Lys Trp Asp Gly Pro Pro Leu Trp," wherein some
      positions may be absent
<220> FEATURE:
<221> NAME/KEY: MOD_RES
<222> LOCATION: (141)..(141)
<223> OTHER INFORMATION: Ala or Thr
<220> FEATURE:
<221> NAME/KEY: MOD_RES
<222> LOCATION: (145)..(151)
<223> OTHER INFORMATION: Any amino acid and this region may preferably
      comprise the sequence "Lys Asp Val Pro Gly Asp Arg"
<220> FEATURE:
<221> NAME/KEY: MOD_RES
<222> LOCATION: (157)..(162)
<223> OTHER INFORMATION: Any amino acid and this region may preferably
      comprise the sequence "Gln Gln Lys His Thr Ala," "Thr Glu Asp Glu
      Asn Gln," "Asn Ser Arg His Thr Ala," "Pro Asp His Phe His Asn,"
      "Tyr Asp Val Ala Phe Asp" or "Gln Gln Lys His Asn Gln"
<220> FEATURE:
<221> NAME/KEY: MOD_RES
<222> LOCATION: (166)..(173)
<223> OTHER INFORMATION: Any amino acid and this region may preferably
      comprise the sequence "Gly Asn Leu Lys Pro Asp Thr Glu"
<220> FEATURE:
<221> NAME/KEY: MOD_RES
<222> LOCATION: (181)..(191)
<223> OTHER INFORMATION: Any amino acid and this region may preferably
      comprise the sequence "Phe Asp Pro Tyr Gly Ala Lys Ser Asn Pro
      Ala," "Pro Asn Tyr Glu Arg Ile Ser Asn Pro Ala," "Phe Asp Pro Tyr
      Gly Met Arg Ser Lys Pro Ala," "Phe Thr Pro Tyr Gly Ala Lys Ser Asn
      Pro Ala,"
<220> FEATURE:
<221> NAME/KEY: MOD_RES
<222> LOCATION: (181)..(191)
<223> OTHER INFORMATION: continued from above, "Ala Asn Asp His Gly Phe
      Asp Ser Asn Pro Ala," "Asp Thr Phe Tyr Gly Phe Asp Ser Asn Pro
      Ala" "Phe Asp Pro Tyr Asn Lys Arg Asn Val Pro Ala" or "Phe Asp Pro
      Tyr Gly Leu Lys Ser Arg Pro Ala," wherein some positions may be
      absent
<220> FEATURE:
<221> NAME/KEY: MOD_RES
<222> LOCATION: (217)..(223)
<223> OTHER INFORMATION: Any amino acid and this region may preferably
      comprise the sequence "Lys Asp Val Thr Asp Thr Thr"
<220> FEATURE:
<221> NAME/KEY: MOD_RES
<222> LOCATION: (229)..(240)
<223> OTHER INFORMATION: Any amino acid and this region may preferably
      comprise the sequences "Ala Lys Pro Trp Val Asp Pro Pro Pro Leu
      Trp Gly," "Ser Pro Gly Glu Arg Ile Trp Met Phe Thr Gly," "Ala Lys
      Pro Glu Lys Trp Asp Gly Ser Ile Tyr Gly,"
<220> FEATURE:
<221> NAME/KEY: MOD_RES
<222> LOCATION: (229)..(240)
```

-continued

```
<223> OTHER INFORMATION: continued from above, "His Asp Ala Phe Gly Tyr
      Asp Phe Gly," "Ile Pro Pro His Asn Ala Asp Ser Ser Ile Ile Gly" or
      "Ala Lys Pro Glu Lys Trp Asp Gly Pro Pro Leu Trp," wherein some
      positions may be absent
<220> FEATURE:
<221> NAME/KEY: MOD_RES
<222> LOCATION: (244)..(244)
<223> OTHER INFORMATION: Ala or Thr
<220> FEATURE:
<221> NAME/KEY: MOD_RES
<222> LOCATION: (248)..(254)
<223> OTHER INFORMATION: Any amino acid and this region may preferably
      comprise the sequence "Lys Asp Val Pro Gly Asp Arg"
<220> FEATURE:
<221> NAME/KEY: MOD_RES
<222> LOCATION: (260)..(265)
<223> OTHER INFORMATION: Any amino acid and this region may preferably
      comprise the sequence "Gln Gln Lys His Thr Ala," "Thr Glu Asp Glu
      Asn Gln," "Asn Ser Arg His Thr Ala," "Pro Asp His Phe His Asn,"
      "Tyr Asp Val Ala Phe Asp" or "Gln Gln Lys His Asn Gln"
<220> FEATURE:
<221> NAME/KEY: MOD_RES
<222> LOCATION: (269)..(276)
<223> OTHER INFORMATION: Any amino acid and this region may preferably
      comprise the sequence "Gly Asn Leu Lys Pro Asp Thr Glu"
<220> FEATURE:
<221> NAME/KEY: MOD_RES
<222> LOCATION: (284)..(294)
<223> OTHER INFORMATION: Any amino acid and this region may preferably
      comprise the sequence "Phe Asp Pro Tyr Gly Ala Lys Ser Asn Pro
      Ala," "Pro Asn Tyr Glu Arg Ile Ser Asn Pro Ala," "Phe Asp Pro Tyr
      Gly Met Arg Ser Lys Pro Ala," "Phe Thr Pro Tyr Gly Ala Lys Ser Asn
      Pro Ala,"
<220> FEATURE:
<221> NAME/KEY: MOD_RES
<222> LOCATION: (284)..(294)
<223> OTHER INFORMATION: continued from above, "Ala Asn Asp His Gly Phe
      Asp Ser Asn Pro Ala," "Asp Thr Phe Tyr Gly Phe Asp Ser Asn Pro
      Ala" "Phe Asp Pro Tyr Asn Lys Arg Asn Val Pro Ala" or "Phe Asp Pro
      Tyr Gly Leu Lys Ser Arg Pro Ala," wherein some positions may be
      absent
<220> FEATURE:
<223> OTHER INFORMATION: See specification as filed for detailed
      description of substitutions and preferred embodiments

<400> SEQUENCE: 234

Ser Gly Gly Gly Gly Ser Ala Ile Glu Val Xaa Xaa Xaa Xaa Xaa Xaa
1               5                   10                  15

Xaa Ala Leu Ile Thr Trp Xaa Xaa Xaa Xaa Xaa Xaa Xaa Xaa
                20                  25                  30

Xaa Xaa Cys Glu Leu Xaa Tyr Gly Ile Xaa Xaa Xaa Xaa Xaa Xaa
            35                  40                  45

Thr Thr Ile Asp Leu Xaa Xaa Xaa Xaa Xaa Xaa Tyr Ser Ile Xaa Xaa
    50                  55                  60

Xaa Xaa Xaa Xaa Xaa Xaa Tyr Glu Val Ser Leu Ile Cys Xaa Xaa Xaa
65                  70                  75                  80

Xaa Xaa Xaa Xaa Xaa Xaa Xaa Lys Glu Thr Phe Thr Thr Gly Gly
                85                  90                  95

Gly Gly Ser Gly Gly Gly Gly Ser Gly Gly Gly Gly Ser Ala Ile Glu
            100                 105                 110

Val Xaa Xaa Xaa Xaa Xaa Xaa Xaa Ala Leu Ile Thr Trp Xaa Xaa Xaa
    115                 120                 125

Xaa Xaa Xaa Xaa Xaa Xaa Xaa Xaa Cys Glu Leu Xaa Tyr Gly Ile
    130                 135                 140

Xaa Xaa Xaa Xaa Xaa Xaa Xaa Thr Thr Ile Asp Leu Xaa Xaa Xaa Xaa
145                 150                 155                 160

Xaa Xaa Tyr Ser Ile Xaa Xaa Xaa Xaa Xaa Xaa Xaa Xaa Tyr Glu Val
            165                 170                 175
```

```
Ser Leu Ile Cys Xaa Xaa Xaa Xaa Xaa Xaa Xaa Xaa Xaa Xaa Lys
            180                 185                 190

Glu Thr Phe Thr Thr Gly Gly Gly Gly Ser Gly Gly Gly Ser Gly
                195                 200                 205

Gly Gly Gly Ser Ala Ile Glu Val Xaa Xaa Xaa Xaa Xaa Xaa Ala
    210                 215                 220

Leu Ile Thr Trp Xaa Xaa Xaa Xaa Xaa Xaa Xaa Xaa Xaa Xaa Xaa
225                 230                 235                 240

Cys Glu Leu Xaa Tyr Gly Ile Xaa Xaa Xaa Xaa Xaa Xaa Thr Thr
                245                 250                 255

Ile Asp Leu Xaa Xaa Xaa Xaa Xaa Tyr Ser Ile Xaa Xaa Xaa Xaa
                260                 265                 270

Xaa Xaa Xaa Xaa Tyr Glu Val Ser Leu Ile Cys Xaa Xaa Xaa Xaa
            275                 280                 285

Xaa Xaa Xaa Xaa Xaa Xaa Lys Glu Thr Phe Thr Thr Gly Gly Gly Gly
        290                 295                 300

Ser Gly Gly Gly Gly Ser Gly Thr Leu Gly His His His His His
305                 310                 315                 320

His His
```

<210> SEQ ID NO 235
<211> LENGTH: 639
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (11)..(17)
<223> OTHER INFORMATION: Any amino acid and this region may preferably
      comprise the sequence "Lys Asp Val Thr Asp Thr Thr"
<220> FEATURE:
<221> NAME/KEY: MOD_RES
<222> LOCATION: (23)..(34)
<223> OTHER INFORMATION: Any amino acid and this region may preferably
      comprise the sequences "Ala Lys Pro Trp Val Asp Pro Pro Leu
      Trp Gly," "Ser Pro Gly Glu Arg Ile Trp Met Phe Thr Gly," "Ala Lys
      Pro Glu Lys Trp Asp Gly Ser Ile Tyr Gly,"
<220> FEATURE:
<221> NAME/KEY: MOD_RES
<222> LOCATION: (23)..(34)
<223> OTHER INFORMATION: continued from above, "His Asp Ala Phe Gly Tyr
      Asp Phe Gly," "Ile Pro Pro His Asn Ala Asp Ser Ser Ile Ile Gly" or
      "Ala Lys Pro Glu Lys Trp Asp Gly Pro Pro Leu Trp," wherein some
      positions may be absent
<220> FEATURE:
<221> NAME/KEY: MOD_RES
<222> LOCATION: (38)..(38)
<223> OTHER INFORMATION: Ala or Thr
<220> FEATURE:
<221> NAME/KEY: MOD_RES
<222> LOCATION: (42)..(48)
<223> OTHER INFORMATION: Any amino acid and this region may preferably
      comprise the sequence "Lys Asp Val Pro Gly Asp Arg"
<220> FEATURE:
<221> NAME/KEY: MOD_RES
<222> LOCATION: (54)..(59)
<223> OTHER INFORMATION: Any amino acid and this region may preferably
      comprise the sequence "Gln Gln Lys His Thr Ala," "Thr Glu Asp Glu
      Asn Gln," "Asn Ser Arg His Thr Ala," "Pro Asp His Phe His Asn,"
      "Tyr Asp Val Ala Phe Asp" or "Gln Gln Lys His Asn Gln"
<220> FEATURE:
<221> NAME/KEY: MOD_RES
<222> LOCATION: (63)..(70)
<223> OTHER INFORMATION: Any amino acid and this region may preferably
      comprise the sequence "Gly Asn Leu Lys Pro Asp Thr Glu"
<220> FEATURE:

```
<221> NAME/KEY: MOD_RES
<222> LOCATION: (78)..(88)
<223> OTHER INFORMATION: Any amino acid and this region may preferably
      comprise the sequence "Phe Asp Pro Tyr Gly Ala Lys Ser Asn Pro
      Ala," "Pro Asn Tyr Glu Arg Ile Ser Asn Pro Ala," "Phe Asp Pro Tyr
      Gly Met Arg Ser Lys Pro Ala," "Phe Thr Pro Tyr Gly Ala Lys Ser Asn
      Pro Ala,"
<220> FEATURE:
<221> NAME/KEY: MOD_RES
<222> LOCATION: (78)..(88)
<223> OTHER INFORMATION: continued from above, "Ala Asn Asp His Gly Phe
      Asp Ser Asn Pro Ala," "Asp Thr Phe Tyr Gly Phe Asp Ser Asn Pro
      Ala" "Phe Asp Pro Tyr Asn Lys Arg Asn Val Pro Ala" or "Phe Asp Pro
      Tyr Gly Leu Lys Ser Arg Pro Ala," wherein some positions may be
      absent
<220> FEATURE:
<221> NAME/KEY: MOD_RES
<222> LOCATION: (114)..(120)
<223> OTHER INFORMATION: Any amino acid and this region may preferably
      comprise the sequence "Lys Asp Val Thr Asp Thr Thr"
<220> FEATURE:
<221> NAME/KEY: MOD_RES
<222> LOCATION: (126)..(137)
<223> OTHER INFORMATION: Any amino acid and this region may preferably
      comprise the sequences "Ala Lys Pro Trp Val Asp Pro Pro Leu
      Trp Gly," "Ser Pro Gly Glu Arg Ile Trp Met Phe Thr Gly," "Ala Lys
      Pro Glu Lys Trp Asp Gly Ser Ile Tyr Gly,"
<220> FEATURE:
<221> NAME/KEY: MOD_RES
<222> LOCATION: (126)..(137)
<223> OTHER INFORMATION: continued from above, "His Asp Ala Phe Gly Tyr
      Asp Phe Gly," "Ile Pro Pro His Asn Ala Asp Ser Ser Ile Ile Gly" or
      "Ala Lys Pro Glu Lys Trp Asp Gly Pro Pro Leu Trp," wherein some
      positions may be absent
<220> FEATURE:
<221> NAME/KEY: MOD_RES
<222> LOCATION: (141)..(141)
<223> OTHER INFORMATION: Ala or Thr
<220> FEATURE:
<221> NAME/KEY: MOD_RES
<222> LOCATION: (145)..(151)
<223> OTHER INFORMATION: Any amino acid and this region may preferably
      comprise the sequence "Lys Asp Val Pro Gly Asp Arg"
<220> FEATURE:
<221> NAME/KEY: MOD_RES
<222> LOCATION: (157)..(162)
<223> OTHER INFORMATION: Any amino acid and this region may preferably
      comprise the sequence "Gln Gln Lys His Thr Ala," "Thr Glu Asp Glu
      Asn Gln," "Asn Ser Arg His Thr Ala," "Pro Asp His Phe His Asn,"
      "Tyr Asp Val Ala Phe Asp" or "Gln Gln Lys His Asn Gln"
<220> FEATURE:
<221> NAME/KEY: MOD_RES
<222> LOCATION: (166)..(173)
<223> OTHER INFORMATION: Any amino acid and this region may preferably
      comprise the sequence "Gly Asn Leu Lys Pro Asp Thr Glu"
<220> FEATURE:
<221> NAME/KEY: MOD_RES
<222> LOCATION: (181)..(191)
<223> OTHER INFORMATION: Any amino acid and this region may preferably
      comprise the sequence "Phe Asp Pro Tyr Gly Ala Lys Ser Asn Pro
      Ala," "Pro Asn Tyr Glu Arg Ile Ser Asn Pro Ala," "Phe Asp Pro Tyr
      Gly Met Arg Ser Lys Pro Ala," "Phe Thr Pro Tyr Gly Ala Lys Ser Asn
      Pro Ala,"
<220> FEATURE:
<221> NAME/KEY: MOD_RES
<222> LOCATION: (181)..(191)
<223> OTHER INFORMATION: continued from above, "Ala Asn Asp His Gly Phe
      Asp Ser Asn Pro Ala," "Asp Thr Phe Tyr Gly Phe Asp Ser Asn Pro
      Ala" "Phe Asp Pro Tyr Asn Lys Arg Asn Val Pro Ala" or "Phe Asp Pro
      Tyr Gly Leu Lys Ser Arg Pro Ala," wherein some positions may be
      absent
<220> FEATURE:
<221> NAME/KEY: MOD_RES
<222> LOCATION: (217)..(223)
<223> OTHER INFORMATION: Any amino acid and this region may preferably
      comprise the sequence "Lys Asp Val Thr Asp Thr Thr"
<220> FEATURE:
<221> NAME/KEY: MOD_RES
<222> LOCATION: (229)..(240)
```

```
<223> OTHER INFORMATION: Any amino acid and this region may preferably
      comprise the sequences "Ala Lys Pro Trp Val Asp Pro Pro Leu
      Trp Gly," "Ser Pro Gly Glu Arg Ile Trp Met Phe Thr Gly," "Ala Lys
      Pro Glu Lys Trp Asp Gly Ser Ile Tyr Gly,"
<220> FEATURE:
<221> NAME/KEY: MOD_RES
<222> LOCATION: (229)..(240)
<223> OTHER INFORMATION: continued from above, "His Asp Ala Phe Gly Tyr
      Asp Phe Gly," "Ile Pro Pro His Asn Ala Asp Ser Ser Ile Ile Gly" or
      "Ala Lys Pro Glu Lys Trp Asp Gly Pro Pro Leu Trp," wherein some
      positions may be absent
<220> FEATURE:
<221> NAME/KEY: MOD_RES
<222> LOCATION: (244)..(244)
<223> OTHER INFORMATION: Ala or Thr
<220> FEATURE:
<221> NAME/KEY: MOD_RES
<222> LOCATION: (248)..(254)
<223> OTHER INFORMATION: Any amino acid and this region may preferably
      comprise the sequence "Lys Asp Val Pro Gly Asp Arg"
<220> FEATURE:
<221> NAME/KEY: MOD_RES
<222> LOCATION: (260)..(265)
<223> OTHER INFORMATION: Any amino acid and this region may preferably
      comprise the sequence "Gln Gln Lys His Thr Ala," "Thr Glu Asp Glu
      Asn Gln," "Asn Ser Arg His Thr Ala," "Pro Asp His Phe His Asn,"
      "Tyr Asp Val Ala Phe Asp" or "Gln Gln Lys His Asn Gln"
<220> FEATURE:
<221> NAME/KEY: MOD_RES
<222> LOCATION: (269)..(276)
<223> OTHER INFORMATION: Any amino acid and this region may preferably
      comprise the sequence "Gly Asn Leu Lys Pro Asp Thr Glu"
<220> FEATURE:
<221> NAME/KEY: MOD_RES
<222> LOCATION: (284)..(294)
<223> OTHER INFORMATION: Any amino acid and this region may preferably
      comprise the sequence "Phe Asp Pro Tyr Gly Ala Lys Ser Asn Pro
      Ala," "Pro Asn Tyr Glu Arg Ile Ser Asn Pro Ala," "Phe Asp Pro Tyr
      Gly Met Arg Ser Lys Pro Ala," "Phe Thr Pro Tyr Gly Ala Lys Ser Asn
      Pro Ala,"
<220> FEATURE:
<221> NAME/KEY: MOD_RES
<222> LOCATION: (284)..(294)
<223> OTHER INFORMATION: continued from above, "Ala Asn Asp His Gly Phe
      Asp Ser Asn Pro Ala," "Asp Thr Phe Tyr Gly Phe Asp Ser Asn Pro
      Ala" "Phe Asp Pro Tyr Asn Lys Arg Asn Val Pro Ala" or "Phe Asp Pro
      Tyr Gly Leu Lys Ser Arg Pro Ala," wherein some positions may be
      absent
<220> FEATURE:
<221> NAME/KEY: MOD_RES
<222> LOCATION: (320)..(326)
<223> OTHER INFORMATION: Any amino acid and this region may preferably
      comprise the sequence "Lys Asp Val Thr Asp Thr Thr"
<220> FEATURE:
<221> NAME/KEY: MOD_RES
<222> LOCATION: (332)..(343)
<223> OTHER INFORMATION: Any amino acid and this region may preferably
      comprise the sequences "Ala Lys Pro Trp Val Asp Pro Pro Leu
      Trp Gly," "Ser Pro Gly Glu Arg Ile Trp Met Phe Thr Gly," "Ala Lys
      Pro Glu Lys Trp Asp Gly Ser Ile Tyr Gly,"
<220> FEATURE:
<221> NAME/KEY: MOD_RES
<222> LOCATION: (332)..(343)
<223> OTHER INFORMATION: continued from above, "His Asp Ala Phe Gly Tyr
      Asp Phe Gly," "Ile Pro Pro His Asn Ala Asp Ser Ser Ile Ile Gly" or
      "Ala Lys Pro Glu Lys Trp Asp Gly Pro Pro Leu Trp," wherein some
      positions may be absent
<220> FEATURE:
<221> NAME/KEY: MOD_RES
<222> LOCATION: (347)..(347)
<223> OTHER INFORMATION: Ala or Thr
<220> FEATURE:
<221> NAME/KEY: MOD_RES
<222> LOCATION: (351)..(357)
<223> OTHER INFORMATION: Any amino acid and this region may preferably
      comprise the sequence "Lys Asp Val Pro Gly Asp Arg"
<220> FEATURE:
<221> NAME/KEY: MOD_RES
<222> LOCATION: (363)..(368)
```

```
<223> OTHER INFORMATION: Any amino acid and this region may preferably
      comprise the sequence "Gln Gln Lys His Thr Ala," "Thr Glu Asp Glu
      Asn Gln," "Asn Ser Arg His Thr Ala," "Pro Asp His Phe His Asn,"
      "Tyr Asp Val Ala Phe Asp" or "Gln Gln Lys His Asn Gln"
<220> FEATURE:
<221> NAME/KEY: MOD_RES
<222> LOCATION: (372)..(379)
<223> OTHER INFORMATION: Any amino acid and this region may preferably
      comprise the sequence "Gly Asn Leu Lys Pro Asp Thr Glu"
<220> FEATURE:
<221> NAME/KEY: MOD_RES
<222> LOCATION: (387)..(397)
<223> OTHER INFORMATION: Any amino acid and this region may preferably
      comprise the sequence "Phe Asp Pro Tyr Gly Ala Lys Ser Asn Pro
      Ala," "Pro Asn Tyr Glu Arg Ile Ser Asn Pro Ala," "Phe Asp Pro Tyr
      Gly Met Arg Ser Lys Pro Ala," "Phe Thr Pro Tyr Gly Ala Lys Ser Asn
      Pro Ala,"
<220> FEATURE:
<221> NAME/KEY: MOD_RES
<222> LOCATION: (387)..(397)
<223> OTHER INFORMATION: continued from above, "Ala Asn Asp His Gly Phe
      Asp Ser Asn Pro Ala," "Asp Thr Phe Tyr Gly Phe Asp Ser Asn Pro
      Ala" "Phe Asp Pro Tyr Asn Lys Arg Asn Val Pro Ala" or "Phe Asp Pro
      Tyr Gly Leu Lys Ser Arg Pro Ala," wherein some positions may be
      absent
<220> FEATURE:
<221> NAME/KEY: MOD_RES
<222> LOCATION: (431)..(437)
<223> OTHER INFORMATION: Any amino acid and this region may preferably
      comprise the sequence "Lys Asp Val Thr Asp Thr Thr"
<220> FEATURE:
<221> NAME/KEY: MOD_RES
<222> LOCATION: (443)..(454)
<223> OTHER INFORMATION: Any amino acid and this region may preferably
      comprise the sequences "Ala Lys Pro Trp Val Asp Pro Pro Pro Leu
      Trp Gly," "Ser Pro Gly Glu Arg Ile Trp Met Phe Thr Gly," "Ala Lys
      Pro Glu Lys Trp Asp Gly Ser Ile Tyr Gly,"
<220> FEATURE:
<221> NAME/KEY: MOD_RES
<222> LOCATION: (443)..(454)
<223> OTHER INFORMATION: continued from above, "His Asp Ala Phe Gly Tyr
      Asp Phe Gly," "Ile Pro Pro His Asn Ala Asp Ser Ser Ile Ile Gly" or
      "Ala Lys Pro Glu Lys Trp Asp Gly Pro Pro Leu Trp," wherein some
      positions may be absent
<220> FEATURE:
<221> NAME/KEY: MOD_RES
<222> LOCATION: (458)..(458)
<223> OTHER INFORMATION: Ala or Thr
<220> FEATURE:
<221> NAME/KEY: MOD_RES
<222> LOCATION: (462)..(468)
<223> OTHER INFORMATION: Any amino acid and this region may preferably
      comprise the sequence "Lys Asp Val Pro Gly Asp Arg"
<220> FEATURE:
<221> NAME/KEY: MOD_RES
<222> LOCATION: (474)..(479)
<223> OTHER INFORMATION: Any amino acid and this region may preferably
      comprise the sequence "Gln Gln Lys His Thr Ala," "Thr Glu Asp Glu
      Asn Gln," "Asn Ser Arg His Thr Ala," "Pro Asp His Phe His Asn,"
      "Tyr Asp Val Ala Phe Asp" or "Gln Gln Lys His Asn Gln"
<220> FEATURE:
<221> NAME/KEY: MOD_RES
<222> LOCATION: (483)..(490)
<223> OTHER INFORMATION: Any amino acid and this region may preferably
      comprise the sequence "Gly Asn Leu Lys Pro Asp Thr Glu"
<220> FEATURE:
<221> NAME/KEY: MOD_RES
<222> LOCATION: (498)..(508)
<223> OTHER INFORMATION: Any amino acid and this region may preferably
      comprise the sequence "Phe Asp Pro Tyr Gly Ala Lys Ser Asn Pro
      Ala," "Pro Asn Tyr Glu Arg Ile Ser Asn Pro Ala," "Phe Asp Pro Tyr
      Gly Met Arg Ser Lys Pro Ala," "Phe Thr Pro Tyr Gly Ala Lys Ser Asn
      Pro Ala,"
<220> FEATURE:
<221> NAME/KEY: MOD_RES
<222> LOCATION: (498)..(508)
<223> OTHER INFORMATION: continued from above, "Ala Asn Asp His Gly Phe
      Asp Ser Asn Pro Ala," "Asp Thr Phe Tyr Gly Phe Asp Ser Asn Pro
      Ala" "Phe Asp Pro Tyr Asn Lys Arg Asn Val Pro Ala" or "Phe Asp Pro
```

```
        Tyr Gly Leu Lys Ser Arg Pro Ala," wherein some positions may be
        absent
<220> FEATURE:
<221> NAME/KEY: MOD_RES
<222> LOCATION: (534)..(540)
<223> OTHER INFORMATION: Any amino acid and this region may preferably
        comprise the sequence "Lys Asp Val Thr Asp Thr Thr"
<220> FEATURE:
<221> NAME/KEY: MOD_RES
<222> LOCATION: (546)..(557)
<223> OTHER INFORMATION: Any amino acid and this region may preferably
        comprise the sequences "Ala Lys Pro Trp Val Asp Pro Pro Leu
        Trp Gly," "Ser Pro Gly Glu Arg Ile Trp Met Phe Thr Gly," "Ala Lys
        Pro Glu Lys Trp Asp Gly Ser Ile Tyr Gly,"
<220> FEATURE:
<221> NAME/KEY: MOD_RES
<222> LOCATION: (546)..(557)
<223> OTHER INFORMATION: continued from above, "His Asp Ala Phe Gly Tyr
        Asp Phe Gly," "Ile Pro Pro His Asn Ala Asp Ser Ser Ile Ile Gly" or
        "Ala Lys Pro Glu Lys Trp Asp Gly Pro Pro Leu Trp," wherein some
        positions may be absent
<220> FEATURE:
<221> NAME/KEY: MOD_RES
<222> LOCATION: (561)..(561)
<223> OTHER INFORMATION: Ala or Thr
<220> FEATURE:
<221> NAME/KEY: MOD_RES
<222> LOCATION: (565)..(571)
<223> OTHER INFORMATION: Any amino acid and this region may preferably
        comprise the sequence "Lys Asp Val Pro Gly Asp Arg"
<220> FEATURE:
<221> NAME/KEY: MOD_RES
<222> LOCATION: (577)..(582)
<223> OTHER INFORMATION: Any amino acid and this region may preferably
        comprise the sequence "Gln Gln Lys His Thr Ala," "Thr Glu Asp Glu
        Asn Gln," "Asn Ser Arg His Thr Ala," "Pro Asp His Phe His Asn,"
        "Tyr Asp Val Ala Phe Asp" or "Gln Gln Lys His Asn Gln"
<220> FEATURE:
<221> NAME/KEY: MOD_RES
<222> LOCATION: (586)..(593)
<223> OTHER INFORMATION: Any amino acid and this region may preferably
        comprise the sequence "Gly Asn Leu Lys Pro Asp Thr Glu"
<220> FEATURE:
<221> NAME/KEY: MOD_RES
<222> LOCATION: (601)..(611)
<223> OTHER INFORMATION: Any amino acid and this region may preferably
        comprise the sequence "Phe Asp Pro Tyr Gly Ala Lys Ser Asn Pro
        Ala," "Pro Asn Tyr Glu Arg Ile Ser Asn Pro Ala," "Phe Asp Pro Tyr
        Gly Met Arg Ser Lys Pro Ala," "Phe Thr Pro Tyr Gly Ala Lys Ser Asn
        Pro Ala,"
<220> FEATURE:
<221> NAME/KEY: MOD_RES
<222> LOCATION: (601)..(611)
<223> OTHER INFORMATION: continued from above, "Ala Asn Asp His Gly Phe
        Asp Ser Asn Pro Ala," "Asp Thr Phe Tyr Gly Phe Asp Ser Asn Pro
        Ala" "Phe Asp Pro Tyr Asn Lys Arg Asn Val Pro Ala" or "Phe Asp Pro
        Tyr Gly Leu Lys Ser Arg Pro Ala," wherein some positions may be
        absent
<220> FEATURE:
<223> OTHER INFORMATION: See specification as filed for detailed
        description of substitutions and preferred embodiments

<400> SEQUENCE: 235

Ser Gly Gly Gly Gly Ser Ala Ile Glu Val Xaa Xaa Xaa Xaa Xaa Xaa
1               5                   10                  15

Xaa Ala Leu Ile Thr Trp Xaa Xaa Xaa Xaa Xaa Xaa Xaa Xaa
                20                  25                  30

Xaa Xaa Cys Glu Leu Xaa Tyr Gly Ile Xaa Xaa Xaa Xaa Xaa Xaa
            35                  40                  45

Thr Thr Ile Asp Leu Xaa Xaa Xaa Xaa Xaa Xaa Tyr Ser Ile Xaa Xaa
        50                  55                  60

Xaa Xaa Xaa Xaa Xaa Xaa Tyr Glu Val Ser Leu Ile Cys Xaa Xaa Xaa
65                  70                  75                  80
```

```
Xaa Xaa Xaa Xaa Xaa Xaa Xaa Lys Glu Thr Phe Thr Thr Gly
            85                  90                  95
Gly Gly Ser Gly Gly Gly Ser Gly Gly Gly Ser Ala Ile Glu
            100                 105                 110
Val Xaa Xaa Xaa Xaa Xaa Xaa Ala Leu Ile Thr Trp Xaa Xaa Xaa
        115                 120                 125
Xaa Xaa Xaa Xaa Xaa Xaa Xaa Xaa Cys Glu Leu Xaa Tyr Gly Ile
            130                 135                 140
Xaa Xaa Xaa Xaa Xaa Xaa Xaa Thr Thr Ile Asp Leu Xaa Xaa Xaa
145                 150                 155                 160
Xaa Xaa Tyr Ser Ile Xaa Xaa Xaa Xaa Xaa Xaa Xaa Tyr Glu Val
                165                 170                 175
Ser Leu Ile Cys Xaa Xaa Xaa Xaa Xaa Xaa Xaa Xaa Xaa Lys
                180                 185                 190
Glu Thr Phe Thr Thr Gly Gly Gly Ser Gly Gly Gly Ser Gly
                195                 200                 205
Gly Gly Ser Ala Ile Glu Val Xaa Xaa Xaa Xaa Xaa Xaa Ala
    210                 215                 220
Leu Ile Thr Trp Xaa Xaa Xaa Xaa Xaa Xaa Xaa Xaa Xaa Xaa
225                 230                 235                 240
Cys Glu Leu Xaa Tyr Gly Ile Xaa Xaa Xaa Xaa Xaa Xaa Thr Thr
            245                 250                 255
Ile Asp Leu Xaa Xaa Xaa Xaa Xaa Tyr Ser Ile Xaa Xaa Xaa
            260                 265                 270
Xaa Xaa Xaa Xaa Tyr Glu Val Ser Leu Ile Cys Xaa Xaa Xaa Xaa
            275                 280                 285
Xaa Xaa Xaa Xaa Xaa Xaa Lys Glu Thr Phe Thr Thr Gly Gly Gly Gly
            290                 295                 300
Ser Gly Gly Gly Gly Ser Gly Gly Gly Gly Ser Ala Ile Glu Val Xaa
305                 310                 315                 320
Xaa Xaa Xaa Xaa Xaa Xaa Ala Leu Ile Thr Trp Xaa Xaa Xaa Xaa
            325                 330                 335
Xaa Xaa Xaa Xaa Xaa Xaa Xaa Cys Glu Leu Xaa Tyr Gly Ile Xaa Xaa
            340                 345                 350
Xaa Xaa Xaa Xaa Xaa Thr Thr Ile Asp Leu Xaa Xaa Xaa Xaa Xaa
            355                 360                 365
Tyr Ser Ile Xaa Xaa Xaa Xaa Xaa Xaa Xaa Tyr Glu Val Ser Leu
            370                 375                 380
Ile Cys Xaa Xaa Xaa Xaa Xaa Xaa Xaa Xaa Xaa Lys Glu Thr
385                 390                 395                 400
Phe Thr Thr Gly Gly Gly Gly Ser Gly Gly Gly Gly Ser Gly Thr Gly
                405                 410                 415
Ser Ala Met Ala Ser Gly Gly Gly Gly Ser Ala Ile Glu Val Xaa Xaa
            420                 425                 430
Xaa Xaa Xaa Xaa Xaa Ala Leu Ile Thr Trp Xaa Xaa Xaa Xaa Xaa
            435                 440                 445
Xaa Xaa Xaa Xaa Xaa Xaa Cys Glu Leu Xaa Tyr Gly Ile Xaa Xaa Xaa
            450                 455                 460
Xaa Xaa Xaa Xaa Thr Thr Ile Asp Leu Xaa Xaa Xaa Xaa Xaa Tyr
465                 470                 475                 480
Ser Ile Xaa Xaa Xaa Xaa Xaa Xaa Xaa Tyr Glu Val Ser Leu Ile
                485                 490                 495
Cys Xaa Xaa Xaa Xaa Xaa Xaa Xaa Xaa Xaa Xaa Lys Glu Thr Phe
```

```
                    500             505             510
Thr Thr Gly Gly Gly Gly Ser Gly Gly Gly Gly Ser Gly Gly Gly
        515             520             525

Ser Ala Ile Glu Val Xaa Xaa Xaa Xaa Xaa Xaa Ala Leu Ile Thr
    530             535             540

Trp Xaa Xaa Xaa Xaa Xaa Xaa Xaa Xaa Xaa Xaa Xaa Cys Glu Leu
545             550             555             560

Xaa Tyr Gly Ile Xaa Xaa Xaa Xaa Xaa Xaa Thr Thr Ile Asp Leu
            565             570             575

Xaa Xaa Xaa Xaa Xaa Xaa Tyr Ser Ile Xaa Xaa Xaa Xaa Xaa Xaa
                580             585             590

Xaa Tyr Glu Val Ser Leu Ile Cys Xaa Xaa Xaa Xaa Xaa Xaa Xaa
            595             600             605

Xaa Xaa Xaa Lys Glu Thr Phe Thr Thr Gly Gly Gly Ser Gly Gly
        610             615             620

Gly Gly Ser Gly Thr Leu Gly His His His His His His His
625             630             635

<210> SEQ ID NO 236
<211> LENGTH: 845
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (11)..(17)
<223> OTHER INFORMATION: Any amino acid and this region may preferably
      comprise the sequence "Lys Asp Val Thr Asp Thr Thr"
<220> FEATURE:
<221> NAME/KEY: MOD_RES
<222> LOCATION: (23)..(34)
<223> OTHER INFORMATION: Any amino acid and this region may preferably
      comprise the sequences "Ala Lys Pro Trp Val Asp Pro Pro Leu
      Trp Gly," "Ser Pro Gly Glu Arg Ile Trp Met Phe Thr Gly," "Ala Lys
      Pro Glu Lys Trp Asp Gly Ser Ile Tyr Gly,"
<220> FEATURE:
<221> NAME/KEY: MOD_RES
<222> LOCATION: (23)..(34)
<223> OTHER INFORMATION: continued from above, "His Asp Ala Phe Gly Tyr
      Asp Phe Gly," "Ile Pro Pro His Asn Ala Asp Ser Ser Ile Ile Gly" or
      "Ala Lys Pro Glu Lys Trp Asp Gly Pro Pro Leu Trp," wherein some
      positions may be absent
<220> FEATURE:
<221> NAME/KEY: MOD_RES
<222> LOCATION: (38)..(38)
<223> OTHER INFORMATION: Ala or Thr
<220> FEATURE:
<221> NAME/KEY: MOD_RES
<222> LOCATION: (42)..(48)
<223> OTHER INFORMATION: Any amino acid and this region may preferably
      comprise the sequence "Lys Asp Val Pro Gly Asp Arg"
<220> FEATURE:
<221> NAME/KEY: MOD_RES
<222> LOCATION: (54)..(59)
<223> OTHER INFORMATION: Any amino acid and this region may preferably
      comprise the sequence "Gln Gln Lys His Thr Ala," "Thr Glu Asp Glu
      Asn Gln," "Asn Ser Arg His Thr Ala," "Pro Asp His Phe His Asn,"
      "Tyr Asp Val Ala Phe Asp" or "Gln Gln Lys His Asn Gln"
<220> FEATURE:
<221> NAME/KEY: MOD_RES
<222> LOCATION: (63)..(70)
<223> OTHER INFORMATION: Any amino acid and this region may preferably
      comprise the sequence "Gly Asn Leu Lys Pro Asp Thr Glu"
<220> FEATURE:
<221> NAME/KEY: MOD_RES
<222> LOCATION: (78)..(88)
<223> OTHER INFORMATION: Any amino acid and this region may preferably
      comprise the sequence "Phe Asp Pro Tyr Gly Ala Lys Ser Asn Pro
```

Ala," "Pro Asn Tyr Glu Arg Ile Ser Asn Pro Ala," "Phe Asp Pro Tyr
Gly Met Arg Ser Lys Pro Ala," "Phe Thr Pro Tyr Gly Ala Lys Ser Asn
Pro Ala,"
<220> FEATURE:
<221> NAME/KEY: MOD_RES
<222> LOCATION: (78)..(88)
<223> OTHER INFORMATION: continued from above, "Ala Asn Asp His Gly Phe
Asp Ser Asn Pro Ala," "Asp Thr Phe Tyr Gly Phe Asp Ser Asn Pro
Ala" "Phe Asp Pro Tyr Asn Lys Arg Asn Val Pro Ala" or "Phe Asp Pro
Tyr Gly Leu Lys Ser Arg Pro Ala," wherein some positions may be
absent
<220> FEATURE:
<221> NAME/KEY: MOD_RES
<222> LOCATION: (114)..(120)
<223> OTHER INFORMATION: Any amino acid and this region may preferably
comprise the sequence "Lys Asp Val Thr Asp Thr Thr"
<220> FEATURE:
<221> NAME/KEY: MOD_RES
<222> LOCATION: (126)..(137)
<223> OTHER INFORMATION: Any amino acid and this region may preferably
comprise the sequences "Ala Lys Pro Trp Val Asp Pro Pro Leu
Trp Gly," "Ser Pro Gly Glu Arg Ile Trp Met Phe Thr Gly," "Ala Lys
Pro Glu Lys Trp Asp Gly Ser Ile Tyr Gly,"
<220> FEATURE:
<221> NAME/KEY: MOD_RES
<222> LOCATION: (126)..(137)
<223> OTHER INFORMATION: continued from above, "His Asp Ala Phe Gly Tyr
Asp Phe Gly," "Ile Pro Pro His Asn Ala Asp Ser Ser Ile Ile Gly" or
"Ala Lys Pro Glu Lys Trp Asp Gly Pro Pro Leu Trp," wherein some
positions may be absent
<220> FEATURE:
<221> NAME/KEY: MOD_RES
<222> LOCATION: (141)..(141)
<223> OTHER INFORMATION: Ala or Thr
<220> FEATURE:
<221> NAME/KEY: MOD_RES
<222> LOCATION: (145)..(151)
<223> OTHER INFORMATION: Any amino acid and this region may preferably
comprise the sequence "Lys Asp Val Pro Gly Asp Arg"
<220> FEATURE:
<221> NAME/KEY: MOD_RES
<222> LOCATION: (157)..(162)
<223> OTHER INFORMATION: Any amino acid and this region may preferably
comprise the sequence "Gln Gln Lys His Thr Ala," "Thr Glu Asp Glu
Asn Gln," "Asn Ser Arg His Thr Ala," "Pro Asp His Phe His Asn,"
"Tyr Asp Val Ala Phe Asp" or "Gln Gln Lys His Asn Gln"
<220> FEATURE:
<221> NAME/KEY: MOD_RES
<222> LOCATION: (166)..(173)
<223> OTHER INFORMATION: Any amino acid and this region may preferably
comprise the sequence "Gly Asn Leu Lys Pro Asp Thr Glu"
<220> FEATURE:
<221> NAME/KEY: MOD_RES
<222> LOCATION: (181)..(191)
<223> OTHER INFORMATION: Any amino acid and this region may preferably
comprise the sequence "Phe Asp Pro Tyr Gly Ala Lys Ser Asn Pro
Ala," "Pro Asn Tyr Glu Arg Ile Ser Asn Pro Ala," "Phe Asp Pro Tyr
Gly Met Arg Ser Lys Pro Ala," "Phe Thr Pro Tyr Gly Ala Lys Ser Asn
Pro Ala,"
<220> FEATURE:
<221> NAME/KEY: MOD_RES
<222> LOCATION: (181)..(191)
<223> OTHER INFORMATION: continued from above, "Ala Asn Asp His Gly Phe
Asp Ser Asn Pro Ala," "Asp Thr Phe Tyr Gly Phe Asp Ser Asn Pro
Ala" "Phe Asp Pro Tyr Asn Lys Arg Asn Val Pro Ala" or "Phe Asp Pro
Tyr Gly Leu Lys Ser Arg Pro Ala," wherein some positions may be
absent
<220> FEATURE:
<221> NAME/KEY: MOD_RES
<222> LOCATION: (217)..(223)
<223> OTHER INFORMATION: Any amino acid and this region may preferably
comprise the sequence "Lys Asp Val Thr Asp Thr Thr"
<220> FEATURE:
<221> NAME/KEY: MOD_RES
<222> LOCATION: (229)..(240)
<223> OTHER INFORMATION: Any amino acid and this region may preferably
comprise the sequences "Ala Lys Pro Trp Val Asp Pro Pro Leu
Trp Gly," "Ser Pro Gly Glu Arg Ile Trp Met Phe Thr Gly," "Ala Lys
Pro Glu Lys Trp Asp Gly Ser Ile Tyr Gly,"

```
<220> FEATURE:
<221> NAME/KEY: MOD_RES
<222> LOCATION: (229)..(240)
<223> OTHER INFORMATION: continued from above, "His Asp Ala Phe Gly Tyr
      Asp Phe Gly," "Ile Pro Pro His Asn Ala Asp Ser Ser Ile Ile Gly" or
      "Ala Lys Pro Glu Lys Trp Asp Gly Pro Pro Leu Trp," wherein some
      positions may be absent
<220> FEATURE:
<221> NAME/KEY: MOD_RES
<222> LOCATION: (244)..(244)
<223> OTHER INFORMATION: Ala or Thr
<220> FEATURE:
<221> NAME/KEY: MOD_RES
<222> LOCATION: (248)..(254)
<223> OTHER INFORMATION: Any amino acid and this region may preferably
      comprise the sequence "Lys Asp Val Pro Gly Asp Arg"
<220> FEATURE:
<221> NAME/KEY: MOD_RES
<222> LOCATION: (260)..(265)
<223> OTHER INFORMATION: Any amino acid and this region may preferably
      comprise the sequence "Gln Gln Lys His Thr Ala," "Thr Glu Asp Glu
      Asn Gln," "Asn Ser Arg His Thr Ala," "Pro Asp His Phe His Asn,"
      "Tyr Asp Val Ala Phe Asp" or "Gln Gln Lys His Asn Gln"
<220> FEATURE:
<221> NAME/KEY: MOD_RES
<222> LOCATION: (269)..(276)
<223> OTHER INFORMATION: Any amino acid and this region may preferably
      comprise the sequence "Gly Asn Leu Lys Pro Asp Thr Glu"
<220> FEATURE:
<221> NAME/KEY: MOD_RES
<222> LOCATION: (284)..(294)
<223> OTHER INFORMATION: Any amino acid and this region may preferably
      comprise the sequence "Phe Asp Pro Tyr Gly Ala Lys Ser Asn Pro
      Ala," "Pro Asn Tyr Glu Arg Ile Ser Asn Pro Ala," "Phe Asp Pro Tyr
      Gly Met Arg Ser Lys Pro Ala," "Phe Thr Pro Tyr Gly Ala Lys Ser Asn
      Pro Ala,"
<220> FEATURE:
<221> NAME/KEY: MOD_RES
<222> LOCATION: (284)..(294)
<223> OTHER INFORMATION: continued from above, "Ala Asn Asp His Gly Phe
      Asp Ser Asn Pro Ala," "Asp Thr Phe Tyr Gly Phe Asp Ser Asn Pro
      Ala" "Phe Asp Pro Tyr Asn Lys Arg Asn Val Pro Ala" or "Phe Asp Pro
      Tyr Gly Leu Lys Ser Arg Pro Ala," wherein some positions may be
      absent
<220> FEATURE:
<221> NAME/KEY: MOD_RES
<222> LOCATION: (320)..(326)
<223> OTHER INFORMATION: Any amino acid and this region may preferably
      comprise the sequence "Lys Asp Val Thr Asp Thr Thr"
<220> FEATURE:
<221> NAME/KEY: MOD_RES
<222> LOCATION: (332)..(343)
<223> OTHER INFORMATION: Any amino acid and this region may preferably
      comprise the sequences "Ala Lys Pro Trp Val Asp Pro Pro Leu
      Trp Gly," "Ser Pro Gly Glu Arg Ile Trp Met Phe Thr Gly," "Ala Lys
      Pro Glu Lys Trp Asp Gly Ser Ile Tyr Gly,"
<220> FEATURE:
<221> NAME/KEY: MOD_RES
<222> LOCATION: (332)..(343)
<223> OTHER INFORMATION: continued from above, "His Asp Ala Phe Gly Tyr
      Asp Phe Gly," "Ile Pro Pro His Asn Ala Asp Ser Ser Ile Ile Gly" or
      "Ala Lys Pro Glu Lys Trp Asp Gly Pro Pro Leu Trp," wherein some
      positions may be absent
<220> FEATURE:
<221> NAME/KEY: MOD_RES
<222> LOCATION: (347)..(347)
<223> OTHER INFORMATION: Ala or Thr
<220> FEATURE:
<221> NAME/KEY: MOD_RES
<222> LOCATION: (351)..(357)
<223> OTHER INFORMATION: Any amino acid and this region may preferably
      comprise the sequence "Lys Asp Val Pro Gly Asp Arg"
<220> FEATURE:
<221> NAME/KEY: MOD_RES
<222> LOCATION: (363)..(368)
<223> OTHER INFORMATION: Any amino acid and this region may preferably
      comprise the sequence "Gln Gln Lys His Thr Ala," "Thr Glu Asp Glu
      Asn Gln," "Asn Ser Arg His Thr Ala," "Pro Asp His Phe His Asn,"
      "Tyr Asp Val Ala Phe Asp" or "Gln Gln Lys His Asn Gln"
```

```
<220> FEATURE:
<221> NAME/KEY: MOD_RES
<222> LOCATION: (372)..(379)
<223> OTHER INFORMATION: Any amino acid and this region may preferably
      comprise the sequence "Gly Asn Leu Lys Pro Asp Thr Glu"
<220> FEATURE:
<221> NAME/KEY: MOD_RES
<222> LOCATION: (387)..(397)
<223> OTHER INFORMATION: Any amino acid and this region may preferably
      comprise the sequence "Phe Asp Pro Tyr Gly Ala Lys Ser Asn Pro
      Ala," "Pro Asn Tyr Glu Arg Ile Ser Asn Pro Ala," "Phe Asp Pro Tyr
      Gly Met Arg Ser Lys Pro Ala," "Phe Thr Pro Tyr Gly Ala Lys Ser Asn
      Pro Ala,"
<220> FEATURE:
<221> NAME/KEY: MOD_RES
<222> LOCATION: (387)..(397)
<223> OTHER INFORMATION: continued from above, "Ala Asn Asp His Gly Phe
      Asp Ser Asn Pro Ala," "Asp Thr Phe Tyr Gly Phe Asp Ser Asn Pro
      Ala" "Phe Asp Pro Tyr Asn Lys Arg Asn Val Pro Ala" or "Phe Asp Pro
      Tyr Gly Leu Lys Ser Arg Pro Ala," wherein some positions may be
      absent
<220> FEATURE:
<221> NAME/KEY: MOD_RES
<222> LOCATION: (431)..(437)
<223> OTHER INFORMATION: Any amino acid and this region may preferably
      comprise the sequence "Lys Asp Val Thr Asp Thr Thr"
<220> FEATURE:
<221> NAME/KEY: MOD_RES
<222> LOCATION: (443)..(454)
<223> OTHER INFORMATION: Any amino acid and this region may preferably
      comprise the sequences "Ala Lys Pro Trp Val Asp Pro Pro Pro Leu
      Trp Gly," "Ser Pro Gly Glu Arg Ile Trp Met Phe Thr Gly," "Ala Lys
      Pro Glu Lys Trp Asp Gly Ser Ile Tyr Gly,"
<220> FEATURE:
<221> NAME/KEY: MOD_RES
<222> LOCATION: (443)..(454)
<223> OTHER INFORMATION: continued from above, "His Asp Ala Phe Gly Tyr
      Asp Phe Gly," "Ile Pro Pro His Asn Ala Asp Ser Ser Ile Ile Gly" or
      "Ala Lys Pro Glu Lys Trp Asp Gly Pro Pro Leu Trp," wherein some
      positions may be absent
<220> FEATURE:
<221> NAME/KEY: MOD_RES
<222> LOCATION: (458)..(458)
<223> OTHER INFORMATION: Ala or Thr
<220> FEATURE:
<221> NAME/KEY: MOD_RES
<222> LOCATION: (462)..(468)
<223> OTHER INFORMATION: Any amino acid and this region may preferably
      comprise the sequence "Lys Asp Val Pro Gly Asp Arg"
<220> FEATURE:
<221> NAME/KEY: MOD_RES
<222> LOCATION: (474)..(479)
<223> OTHER INFORMATION: Any amino acid and this region may preferably
      comprise the sequence "Gln Gln Lys His Thr Ala," "Thr Glu Asp Glu
      Asn Gln," "Asn Ser Arg His Thr Ala," "Pro Asp His Phe His Asn,"
      "Tyr Asp Val Ala Phe Asp" or "Gln Gln Lys His Asn Gln"
<220> FEATURE:
<221> NAME/KEY: MOD_RES
<222> LOCATION: (483)..(490)
<223> OTHER INFORMATION: Any amino acid and this region may preferably
      comprise the sequence "Gly Asn Leu Lys Pro Asp Thr Glu"
<220> FEATURE:
<221> NAME/KEY: MOD_RES
<222> LOCATION: (498)..(508)
<223> OTHER INFORMATION: Any amino acid and this region may preferably
      comprise the sequence "Phe Asp Pro Tyr Gly Ala Lys Ser Asn Pro
      Ala," "Pro Asn Tyr Glu Arg Ile Ser Asn Pro Ala," "Phe Asp Pro Tyr
      Gly Met Arg Ser Lys Pro Ala," "Phe Thr Pro Tyr Gly Ala Lys Ser Asn
      Pro Ala,"
<220> FEATURE:
<221> NAME/KEY: MOD_RES
<222> LOCATION: (498)..(508)
<223> OTHER INFORMATION: continued from above, "Ala Asn Asp His Gly Phe
      Asp Ser Asn Pro Ala," "Asp Thr Phe Tyr Gly Phe Asp Ser Asn Pro
      Ala" "Phe Asp Pro Tyr Asn Lys Arg Asn Val Pro Ala" or "Phe Asp Pro
      Tyr Gly Leu Lys Ser Arg Pro Ala," wherein some positions may be
      absent
<220> FEATURE:
<221> NAME/KEY: MOD_RES
```

```
<222> LOCATION: (534)..(540)
<223> OTHER INFORMATION: Any amino acid and this region may preferably
      comprise the sequence "Lys Asp Val Thr Asp Thr Thr"
<220> FEATURE:
<221> NAME/KEY: MOD_RES
<222> LOCATION: (546)..(557)
<223> OTHER INFORMATION: Any amino acid and this region may preferably
      comprise the sequences "Ala Lys Pro Trp Val Asp Pro Pro Leu
      Trp Gly," "Ser Pro Gly Glu Arg Ile Trp Met Phe Thr Gly," "Ala Lys
      Pro Glu Lys Trp Asp Gly Ser Ile Tyr Gly,"
<220> FEATURE:
<221> NAME/KEY: MOD_RES
<222> LOCATION: (546)..(557)
<223> OTHER INFORMATION: continued from above, "His Asp Ala Phe Gly Tyr
      Asp Phe Gly," "Ile Pro Pro His Asn Ala Asp Ser Ser Ile Ile Gly" or
      "Ala Lys Pro Glu Lys Trp Asp Gly Pro Pro Leu Trp," wherein some
      positions may be absent
<220> FEATURE:
<221> NAME/KEY: MOD_RES
<222> LOCATION: (561)..(561)
<223> OTHER INFORMATION: Ala or Thr
<220> FEATURE:
<221> NAME/KEY: MOD_RES
<222> LOCATION: (565)..(571)
<223> OTHER INFORMATION: Any amino acid and this region may preferably
      comprise the sequence "Lys Asp Val Pro Gly Asp Arg"
<220> FEATURE:
<221> NAME/KEY: MOD_RES
<222> LOCATION: (577)..(582)
<223> OTHER INFORMATION: Any amino acid and this region may preferably
      comprise the sequence "Gln Gln Lys His Thr Ala," "Thr Glu Asp Glu
      Asn Gln," "Asn Ser Arg His Thr Ala," "Pro Asp His Phe His Asn,"
      "Tyr Asp Val Ala Phe Asp" or "Gln Gln Lys His Asn Gln"
<220> FEATURE:
<221> NAME/KEY: MOD_RES
<222> LOCATION: (586)..(593)
<223> OTHER INFORMATION: Any amino acid and this region may preferably
      comprise the sequence "Gly Asn Leu Lys Pro Asp Thr Glu"
<220> FEATURE:
<221> NAME/KEY: MOD_RES
<222> LOCATION: (601)..(611)
<223> OTHER INFORMATION: Any amino acid and this region may preferably
      comprise the sequence "Phe Asp Pro Tyr Gly Ala Lys Ser Asn Pro
      Ala," "Pro Asn Tyr Glu Arg Ile Ser Asn Pro Ala," "Phe Asp Pro Tyr
      Gly Met Arg Ser Lys Pro Ala," "Phe Thr Pro Tyr Gly Ala Lys Ser Asn
      Pro Ala,"
<220> FEATURE:
<221> NAME/KEY: MOD_RES
<222> LOCATION: (601)..(611)
<223> OTHER INFORMATION: continued from above, "Ala Asn Asp His Gly Phe
      Asp Ser Asn Pro Ala," "Asp Thr Phe Tyr Gly Phe Asp Ser Asn Pro
      Ala" "Phe Asp Pro Tyr Asn Lys Arg Asn Val Pro Ala" or "Phe Asp Pro
      Tyr Gly Leu Lys Ser Arg Pro Ala," wherein some positions may be
      absent
<220> FEATURE:
<221> NAME/KEY: MOD_RES
<222> LOCATION: (637)..(643)
<223> OTHER INFORMATION: Any amino acid and this region may preferably
      comprise the sequence "Lys Asp Val Thr Asp Thr Thr"
<220> FEATURE:
<221> NAME/KEY: MOD_RES
<222> LOCATION: (649)..(660)
<223> OTHER INFORMATION: Any amino acid and this region may preferably
      comprise the sequences "Ala Lys Pro Trp Val Asp Pro Pro Leu
      Trp Gly," "Ser Pro Gly Glu Arg Ile Trp Met Phe Thr Gly," "Ala Lys
      Pro Glu Lys Trp Asp Gly Ser Ile Tyr Gly,"
<220> FEATURE:
<221> NAME/KEY: MOD_RES
<222> LOCATION: (649)..(660)
<223> OTHER INFORMATION: continued from above, "His Asp Ala Phe Gly Tyr
      Asp Phe Gly," "Ile Pro Pro His Asn Ala Asp Ser Ser Ile Ile Gly" or
      "Ala Lys Pro Glu Lys Trp Asp Gly Pro Pro Leu Trp," wherein some
      positions may be absent
<220> FEATURE:
<221> NAME/KEY: MOD_RES
<222> LOCATION: (664)..(664)
<223> OTHER INFORMATION: Ala or Thr
<220> FEATURE:
<221> NAME/KEY: MOD_RES
```

```
<222> LOCATION: (668)..(674)
<223> OTHER INFORMATION: Any amino acid and this region may preferably
      comprise the sequence "Lys Asp Val Pro Gly Asp Arg"
<220> FEATURE:
<221> NAME/KEY: MOD_RES
<222> LOCATION: (680)..(685)
<223> OTHER INFORMATION: Any amino acid and this region may preferably
      comprise the sequence "Gln Gln Lys His Thr Ala," "Thr Glu Asp Glu
      Asn Gln," "Asn Ser Arg His Thr Ala," "Pro Asp His Phe His Asn,"
      "Tyr Asp Val Ala Phe Asp" or "Gln Gln Lys His Asn Gln"
<220> FEATURE:
<221> NAME/KEY: MOD_RES
<222> LOCATION: (689)..(696)
<223> OTHER INFORMATION: Any amino acid and this region may preferably
      comprise the sequence "Gly Asn Leu Lys Pro Asp Thr Glu"
<220> FEATURE:
<221> NAME/KEY: MOD_RES
<222> LOCATION: (704)..(714)
<223> OTHER INFORMATION: Any amino acid and this region may preferably
      comprise the sequence "Phe Asp Pro Tyr Gly Ala Lys Ser Asn Pro
      Ala," "Pro Asn Tyr Glu Arg Ile Ser Asn Pro Ala," "Phe Asp Pro Tyr
      Gly Met Arg Ser Lys Pro Ala," "Phe Thr Pro Tyr Gly Ala Lys Ser Asn
      Pro Ala,"
<220> FEATURE:
<221> NAME/KEY: MOD_RES
<222> LOCATION: (704)..(714)
<223> OTHER INFORMATION: continued from above, "Ala Asn Asp His Gly Phe
      Asp Ser Asn Pro Ala," "Asp Thr Phe Tyr Gly Phe Asp Ser Asn Pro
      Ala" "Phe Asp Pro Tyr Asn Lys Arg Asn Val Pro Ala" or "Phe Asp Pro
      Tyr Gly Leu Lys Ser Arg Pro Ala," wherein some positions may be
      absent
<220> FEATURE:
<221> NAME/KEY: MOD_RES
<222> LOCATION: (740)..(746)
<223> OTHER INFORMATION: Any amino acid and this region may preferably
      comprise the sequence "Lys Asp Val Thr Asp Thr Thr"
<220> FEATURE:
<221> NAME/KEY: MOD_RES
<222> LOCATION: (752)..(763)
<223> OTHER INFORMATION: Any amino acid and this region may preferably
      comprise the sequences "Ala Lys Pro Trp Val Asp Pro Pro Leu
      Trp Gly," "Ser Pro Gly Glu Arg Ile Trp Met Phe Thr Gly," "Ala Lys
      Pro Glu Lys Trp Asp Gly Ser Ile Tyr Gly,"
<220> FEATURE:
<221> NAME/KEY: MOD_RES
<222> LOCATION: (752)..(763)
<223> OTHER INFORMATION: continued from above, "His Asp Ala Phe Gly Tyr
      Asp Phe Gly," "Ile Pro Pro His Asn Ala Asp Ser Ser Ile Ile Gly" or
      "Ala Lys Pro Glu Lys Trp Asp Gly Pro Pro Leu Trp," wherein some
      positions may be absent
<220> FEATURE:
<221> NAME/KEY: MOD_RES
<222> LOCATION: (767)..(767)
<223> OTHER INFORMATION: Ala or Thr
<220> FEATURE:
<221> NAME/KEY: MOD_RES
<222> LOCATION: (771)..(777)
<223> OTHER INFORMATION: Any amino acid and this region may preferably
      comprise the sequence "Lys Asp Val Pro Gly Asp Arg"
<220> FEATURE:
<221> NAME/KEY: MOD_RES
<222> LOCATION: (783)..(788)
<223> OTHER INFORMATION: Any amino acid and this region may preferably
      comprise the sequence "Gln Gln Lys His Thr Ala," "Thr Glu Asp Glu
      Asn Gln," "Asn Ser Arg His Thr Ala," "Pro Asp His Phe His Asn,"
      "Tyr Asp Val Ala Phe Asp" or "Gln Gln Lys His Asn Gln"
<220> FEATURE:
<221> NAME/KEY: MOD_RES
<222> LOCATION: (792)..(799)
<223> OTHER INFORMATION: Any amino acid and this region may preferably
      comprise the sequence "Gly Asn Leu Lys Pro Asp Thr Glu"
<220> FEATURE:
<221> NAME/KEY: MOD_RES
<222> LOCATION: (807)..(817)
<223> OTHER INFORMATION: Any amino acid and this region may preferably
      comprise the sequence "Phe Asp Pro Tyr Gly Ala Lys Ser Asn Pro
      Ala," "Pro Asn Tyr Glu Arg Ile Ser Asn Pro Ala," "Phe Asp Pro Tyr
      Gly Met Arg Ser Lys Pro Ala," "Phe Thr Pro Tyr Gly Ala Lys Ser Asn
      Pro Ala,"
```

```
<220> FEATURE:
<221> NAME/KEY: MOD_RES
<222> LOCATION: (807)..(817)
<223> OTHER INFORMATION: continued from above, "Ala Asn Asp His Gly Phe
      Asp Ser Asn Pro Ala," "Asp Thr Phe Tyr Gly Phe Asp Ser Asn Pro
      Ala" "Phe Asp Pro Tyr Asn Lys Arg Asn Val Pro Ala" or "Phe Asp Pro
      Tyr Gly Leu Lys Ser Arg Pro Ala," wherein some positions may be
      absent
<220> FEATURE:
<223> OTHER INFORMATION: See specification as filed for detailed
      description of substitutions and preferred embodiments

<400> SEQUENCE: 236

Ser Gly Gly Gly Gly Ser Ala Ile Glu Val Xaa Xaa Xaa Xaa Xaa
1               5                  10                  15

Xaa Ala Leu Ile Thr Trp Xaa Xaa Xaa Xaa Xaa Xaa Xaa Xaa Xaa
            20                  25                  30

Xaa Xaa Cys Glu Leu Xaa Tyr Gly Ile Xaa Xaa Xaa Xaa Xaa Xaa
        35                  40                  45

Thr Thr Ile Asp Leu Xaa Xaa Xaa Xaa Xaa Xaa Tyr Ser Ile Xaa Xaa
    50                  55                  60

Xaa Xaa Xaa Xaa Xaa Xaa Tyr Glu Val Ser Leu Ile Cys Xaa Xaa Xaa
65                  70                  75                  80

Xaa Xaa Xaa Xaa Xaa Xaa Xaa Lys Glu Thr Phe Thr Thr Gly Gly
                85                  90                  95

Gly Gly Ser Gly Gly Gly Gly Ser Gly Gly Gly Ser Ala Ile Glu
            100                 105                 110

Val Xaa Xaa Xaa Xaa Xaa Xaa Xaa Ala Leu Ile Thr Trp Xaa Xaa Xaa
    115                 120                 125

Xaa Xaa Xaa Xaa Xaa Xaa Xaa Xaa Cys Glu Leu Xaa Tyr Gly Ile
    130                 135                 140

Xaa Xaa Xaa Xaa Xaa Xaa Xaa Thr Thr Ile Asp Leu Xaa Xaa Xaa Xaa
145                 150                 155                 160

Xaa Xaa Tyr Ser Ile Xaa Xaa Xaa Xaa Xaa Xaa Xaa Xaa Tyr Glu Val
            165                 170                 175

Ser Leu Ile Cys Xaa Xaa Xaa Xaa Xaa Xaa Xaa Xaa Xaa Xaa Lys
            180                 185                 190

Glu Thr Phe Thr Thr Gly Gly Gly Gly Ser Gly Gly Gly Gly Ser Gly
            195                 200                 205

Gly Gly Ser Ala Ile Glu Val Xaa Xaa Xaa Xaa Xaa Xaa Ala
    210                 215                 220

Leu Ile Thr Trp Xaa Xaa Xaa Xaa Xaa Xaa Xaa Xaa Xaa Xaa Xaa
225                 230                 235                 240

Cys Glu Leu Xaa Tyr Gly Ile Xaa Xaa Xaa Xaa Xaa Xaa Thr Thr
            245                 250                 255

Ile Asp Leu Xaa Xaa Xaa Xaa Xaa Tyr Ser Ile Xaa Xaa Xaa
            260                 265                 270

Xaa Xaa Xaa Xaa Tyr Glu Val Ser Leu Ile Cys Xaa Xaa Xaa Xaa
        275                 280                 285

Xaa Xaa Xaa Xaa Xaa Xaa Lys Glu Thr Phe Thr Thr Gly Gly Gly Gly
290                 295                 300

Ser Gly Gly Gly Gly Ser Gly Gly Gly Ser Ala Ile Glu Val Xaa
305                 310                 315                 320

Xaa Xaa Xaa Xaa Xaa Ala Leu Ile Thr Trp Xaa Xaa Xaa Xaa
            325                 330                 335

Xaa Xaa Xaa Xaa Xaa Xaa Cys Glu Leu Xaa Tyr Gly Ile Xaa Xaa
            340                 345                 350
```

```
Xaa Xaa Xaa Xaa Xaa Thr Thr Ile Asp Leu Xaa Xaa Xaa Xaa Xaa
            355                 360                 365

Tyr Ser Ile Xaa Xaa Xaa Xaa Xaa Xaa Xaa Tyr Glu Val Ser Leu
        370                 375                 380

Ile Cys Xaa Xaa Xaa Xaa Xaa Xaa Xaa Xaa Xaa Lys Glu Thr
385                 390                 395                 400

Phe Thr Thr Gly Gly Gly Gly Ser Gly Gly Gly Ser Gly Thr Gly
                405                 410                 415

Ser Ala Met Ala Ser Gly Gly Gly Ser Ala Ile Glu Val Xaa Xaa
            420                 425                 430

Xaa Xaa Xaa Xaa Xaa Ala Leu Ile Thr Trp Xaa Xaa Xaa Xaa Xaa
            435                 440                 445

Xaa Xaa Xaa Xaa Xaa Xaa Cys Glu Leu Xaa Tyr Gly Ile Xaa Xaa
            450                 455                 460

Xaa Xaa Xaa Xaa Thr Thr Ile Asp Leu Xaa Xaa Xaa Xaa Xaa Tyr
465                 470                 475                 480

Ser Ile Xaa Xaa Xaa Xaa Xaa Xaa Xaa Tyr Glu Val Ser Leu Ile
        485                 490                 495

Cys Xaa Xaa Xaa Xaa Xaa Xaa Xaa Xaa Xaa Lys Glu Thr Phe
        500                 505                 510

Thr Thr Gly Gly Gly Gly Ser Gly Gly Gly Ser Gly Gly Gly
        515                 520                 525

Ser Ala Ile Glu Val Xaa Xaa Xaa Xaa Xaa Xaa Ala Leu Ile Thr
530                 535                 540

Trp Xaa Xaa Xaa Xaa Xaa Xaa Xaa Xaa Xaa Xaa Cys Glu Leu
545                 550                 555                 560

Xaa Tyr Gly Ile Xaa Xaa Xaa Xaa Xaa Xaa Thr Thr Ile Asp Leu
            565                 570                 575

Xaa Xaa Xaa Xaa Xaa Xaa Tyr Ser Ile Xaa Xaa Xaa Xaa Xaa Xaa
            580                 585                 590

Xaa Tyr Glu Val Ser Leu Ile Cys Xaa Xaa Xaa Xaa Xaa Xaa Xaa
    595                 600                 605

Xaa Xaa Xaa Lys Glu Thr Phe Thr Thr Gly Gly Gly Gly Ser Gly Gly
            610                 615                 620

Gly Gly Ser Gly Gly Gly Gly Ser Ala Ile Glu Val Xaa Xaa Xaa Xaa
625                 630                 635                 640

Xaa Xaa Xaa Ala Leu Ile Thr Trp Xaa Xaa Xaa Xaa Xaa Xaa
            645                 650                 655

Xaa Xaa Xaa Xaa Cys Glu Leu Xaa Tyr Gly Ile Xaa Xaa Xaa Xaa
            660                 665                 670

Xaa Xaa Thr Thr Ile Asp Leu Xaa Xaa Xaa Xaa Xaa Tyr Ser Ile
        675                 680                 685

Xaa Xaa Xaa Xaa Xaa Xaa Xaa Tyr Glu Val Ser Leu Ile Cys Xaa
690                 695                 700

Xaa Xaa Xaa Xaa Xaa Xaa Xaa Xaa Lys Glu Thr Phe Thr Thr
705                 710                 715                 720

Gly Gly Gly Gly Ser Gly Gly Gly Gly Ser Gly Gly Gly Ser Ala
            725                 730                 735

Ile Glu Val Xaa Xaa Xaa Xaa Xaa Xaa Ala Leu Ile Thr Trp Xaa
            740                 745                 750

Xaa Xaa Xaa Xaa Xaa Xaa Xaa Xaa Xaa Xaa Cys Glu Leu Xaa Tyr
            755                 760                 765
```

```
Gly Ile Xaa Xaa Xaa Xaa Xaa Xaa Thr Thr Ile Asp Leu Xaa Xaa
    770                 775                 780

Xaa Xaa Xaa Xaa Tyr Ser Ile Xaa Xaa Xaa Xaa Xaa Xaa Xaa Tyr
785                 790                 795                 800

Glu Val Ser Leu Ile Cys Xaa Xaa Xaa Xaa Xaa Xaa Xaa Xaa Xaa
            805                 810                 815

Xaa Lys Glu Thr Phe Thr Thr Gly Gly Gly Ser Gly Gly Gly Gly
        820                 825                 830

Ser Gly Thr Leu Gly His His His His His His His
        835                 840                 845
```

<210> SEQ ID NO 237
<211> LENGTH: 321
<212> TYPE: PRT
<213> ORGANISM: Artificial Sequence
<220> FEATURE:
<223> OTHER INFORMATION: Description of Artificial Sequence: Synthetic polypeptide
<220> FEATURE:
<221> NAME/KEY: MOD_RES
<222> LOCATION: (4)..(10)
<223> OTHER INFORMATION: Any amino acid and this region may preferably comprise the sequence "Lys Asp Val Thr Asp Thr Thr"
<220> FEATURE:
<221> NAME/KEY: MOD_RES
<222> LOCATION: (16)..(27)
<223> OTHER INFORMATION: Any amino acid and this region may preferably comprise the sequences "Ala Lys Pro Trp Val Asp Pro Pro Pro Leu Trp Gly," "Ser Pro Gly Glu Arg Ile Trp Met Phe Thr Gly," "Ala Lys Pro Glu Lys Trp Asp Gly Ser Ile Tyr Gly,"
<220> FEATURE:
<221> NAME/KEY: MOD_RES
<222> LOCATION: (16)..(27)
<223> OTHER INFORMATION: continued from above, "His Asp Ala Phe Gly Tyr Asp Phe Gly," "Ile Pro Pro His Asn Ala Asp Ser Ser Ile Ile Gly" or "Ala Lys Pro Glu Lys Trp Asp Gly Pro Pro Leu Trp," wherein some positions may be absent
<220> FEATURE:
<221> NAME/KEY: MOD_RES
<222> LOCATION: (31)..(31)
<223> OTHER INFORMATION: Ala or Thr
<220> FEATURE:
<221> NAME/KEY: MOD_RES
<222> LOCATION: (35)..(41)
<223> OTHER INFORMATION: Any amino acid and this region may preferably comprise the sequence "Lys Asp Val Pro Gly Asp Arg"
<220> FEATURE:
<221> NAME/KEY: MOD_RES
<222> LOCATION: (47)..(52)
<223> OTHER INFORMATION: Any amino acid and this region may preferably comprise the sequence "Gln Gln Lys His Thr Ala," "Thr Glu Asp Glu Asn Gln," "Asn Ser Arg His Thr Ala," "Pro Asp His Phe His Asn," "Tyr Asp Val Ala Phe Asp" or "Gln Gln Lys His Asn Gln"
<220> FEATURE:
<221> NAME/KEY: MOD_RES
<222> LOCATION: (56)..(63)
<223> OTHER INFORMATION: Any amino acid and this region may preferably comprise the sequence "Gly Asn Leu Lys Pro Asp Thr Glu"
<220> FEATURE:
<221> NAME/KEY: MOD_RES
<222> LOCATION: (71)..(81)
<223> OTHER INFORMATION: Any amino acid and this region may preferably comprise the sequence "Phe Asp Pro Tyr Gly Ala Lys Ser Asn Pro Ala," "Pro Asn Tyr Glu Arg Ile Ser Asn Pro Ala," "Phe Asp Pro Tyr Gly Met Arg Ser Lys Pro Ala," "Phe Thr Pro Tyr Gly Ala Lys Ser Asn Pro Ala,"
<220> FEATURE:
<221> NAME/KEY: MOD_RES
<222> LOCATION: (71)..(81)
<223> OTHER INFORMATION: continued from above, "Ala Asn Asp His Gly Phe Asp Ser Asn Pro Ala," "Asp Thr Phe Tyr Gly Phe Asp Ser Asn Pro Ala" "Phe Asp Pro Tyr Asn Lys Arg Asn Val Pro Ala" or "Phe Asp Pro Tyr Gly Leu Lys Ser Arg Pro Ala," wherein some positions may be absent
<220> FEATURE:
<223> OTHER INFORMATION: See specification as filed for detailed description of substitutions and preferred embodiments

<400> SEQUENCE: 237

```
Ile Glu Val Xaa Xaa Xaa Xaa Xaa Xaa Ala Leu Ile Thr Trp Xaa
1               5                   10                  15

Xaa Xaa Xaa Xaa Xaa Xaa Xaa Xaa Xaa Cys Glu Leu Xaa Tyr
            20                  25                  30

Gly Ile Xaa Xaa Xaa Xaa Xaa Xaa Thr Thr Ile Asp Leu Xaa Xaa
        35                  40                  45

Xaa Xaa Xaa Xaa Tyr Ser Ile Xaa Xaa Xaa Xaa Xaa Xaa Xaa Tyr
50                  55                  60

Glu Val Ser Leu Ile Cys Xaa Xaa Xaa Xaa Xaa Xaa Xaa Xaa
65                  70                  75                  80

Xaa Lys Glu Thr Phe Thr Thr Gly Ala Glu Pro Lys Ser Cys Asp Lys
                85                  90                  95

Thr His Thr Cys Pro Pro Cys Pro Ala Pro Glu Leu Leu Gly Gly Pro
            100                 105                 110

Ser Val Phe Leu Phe Pro Pro Lys Pro Lys Asp Thr Leu Met Ile Ser
        115                 120                 125

Arg Thr Pro Glu Val Thr Cys Val Val Val Asp Val Ser His Glu Asp
130                 135                 140

Pro Glu Val Lys Phe Asn Trp Tyr Val Asp Gly Val Glu Val His Asn
145                 150                 155                 160

Ala Lys Thr Lys Pro Arg Glu Glu Gln Tyr Asn Ser Thr Tyr Arg Val
                165                 170                 175

Val Ser Val Leu Thr Val Leu His Gln Asp Trp Leu Asn Gly Lys Glu
            180                 185                 190

Tyr Lys Cys Lys Val Ser Asn Lys Ala Leu Pro Ala Pro Ile Glu Lys
        195                 200                 205

Thr Ile Ser Lys Ala Lys Gly Gln Pro Arg Glu Pro Gln Val Tyr Thr
210                 215                 220

Leu Pro Pro Ser Arg Glu Glu Met Thr Lys Asn Gln Val Ser Leu Thr
225                 230                 235                 240

Cys Leu Val Lys Gly Phe Tyr Pro Ser Asp Ile Ala Val Glu Trp Glu
                245                 250                 255

Ser Asn Gly Gln Pro Glu Asn Asn Tyr Lys Thr Thr Pro Pro Val Leu
            260                 265                 270

Asp Ser Asp Gly Ser Phe Phe Leu Tyr Ser Lys Leu Thr Val Asp Lys
        275                 280                 285

Ser Arg Trp Gln Gln Gly Asn Val Phe Ser Cys Ser Val Met His Glu
290                 295                 300

Ala Leu His Asn His Tyr Thr Gln Lys Ser Leu Ser Leu Ser Pro Gly
305                 310                 315                 320

Lys
```

<210> SEQ ID NO 238
<211> LENGTH: 446
<212> TYPE: PRT
<213> ORGANISM: Artificial Sequence
<220> FEATURE:
<223> OTHER INFORMATION: Description of Artificial Sequence: Synthetic polypeptide
<220> FEATURE:
<221> NAME/KEY: MOD_RES
<222> LOCATION: (14)..(20)

-continued

```
<223> OTHER INFORMATION: Any amino acid and this region may preferably
      comprise the sequence "Lys Asp Val Thr Asp Thr Thr"
<220> FEATURE:
<221> NAME/KEY: MOD_RES
<222> LOCATION: (26)..(37)
<223> OTHER INFORMATION: Any amino acid and this region may preferably
      comprise the sequences "Ala Lys Pro Trp Val Asp Pro Pro Pro Leu
      Trp Gly," "Ser Pro Gly Glu Arg Ile Trp Met Phe Thr Gly," "Ala Lys
      Pro Glu Lys Trp Asp Gly Ser Ile Tyr Gly,"
<220> FEATURE:
<221> NAME/KEY: MOD_RES
<222> LOCATION: (26)..(37)
<223> OTHER INFORMATION: continued from above, "His Asp Ala Phe Gly Tyr
      Asp Phe Gly," "Ile Pro Pro His Asn Ala Asp Ser Ser Ile Ile Gly" or
      "Ala Lys Pro Glu Lys Trp Asp Gly Pro Pro Leu Trp," wherein some
      positions may be absent
<220> FEATURE:
<221> NAME/KEY: MOD_RES
<222> LOCATION: (41)..(41)
<223> OTHER INFORMATION: Ala or Thr
<220> FEATURE:
<221> NAME/KEY: MOD_RES
<222> LOCATION: (45)..(51)
<223> OTHER INFORMATION: Any amino acid and this region may preferably
      comprise the sequence "Lys Asp Val Pro Gly Asp Arg"
<220> FEATURE:
<221> NAME/KEY: MOD_RES
<222> LOCATION: (57)..(62)
<223> OTHER INFORMATION: Any amino acid and this region may preferably
      comprise the sequence "Gln Gln Lys His Thr Ala," "Thr Glu Asp Glu
      Asn Gln," "Asn Ser Arg His Thr Ala," "Pro Asp His Phe His Asn,"
      "Tyr Asp Val Ala Phe Asp" or "Gln Gln Lys His Asn Gln"
<220> FEATURE:
<221> NAME/KEY: MOD_RES
<222> LOCATION: (66)..(73)
<223> OTHER INFORMATION: Any amino acid and this region may preferably
      comprise the sequence "Gly Asn Leu Lys Pro Asp Thr Glu"
<220> FEATURE:
<221> NAME/KEY: MOD_RES
<222> LOCATION: (81)..(91)
<223> OTHER INFORMATION: Any amino acid and this region may preferably
      comprise the sequence "Phe Asp Pro Tyr Gly Ala Lys Ser Asn Pro
      Ala," "Pro Asn Tyr Glu Arg Ile Ser Asn Pro Ala," "Phe Asp Pro Tyr
      Gly Met Arg Ser Lys Pro Ala," "Phe Thr Pro Tyr Gly Ala Lys Ser Asn
      Pro Ala,"
<220> FEATURE:
<221> NAME/KEY: MOD_RES
<222> LOCATION: (81)..(91)
<223> OTHER INFORMATION: continued from above, "Ala Asn Asp His Gly Phe
      Asp Ser Asn Pro Ala," "Asp Thr Phe Tyr Gly Phe Asp Ser Asn Pro
      Ala" "Phe Asp Pro Tyr Asn Lys Arg Asn Val Pro Ala" or "Phe Asp Pro
      Tyr Gly Leu Lys Ser Arg Pro Ala," wherein some positions may be
      absent
<220> FEATURE:
<221> NAME/KEY: MOD_RES
<222> LOCATION: (117)..(123)
<223> OTHER INFORMATION: Any amino acid and this region may preferably
      comprise the sequence "Lys Asp Val Thr Asp Thr Thr"
<220> FEATURE:
<221> NAME/KEY: MOD_RES
<222> LOCATION: (129)..(140)
<223> OTHER INFORMATION: Any amino acid and this region may preferably
      comprise the sequences "Ala Lys Pro Trp Val Asp Pro Pro Pro Leu
      Trp Gly," "Ser Pro Gly Glu Arg Ile Trp Met Phe Thr Gly," "Ala Lys
      Pro Glu Lys Trp Asp Gly Ser Ile Tyr Gly,"
<220> FEATURE:
<221> NAME/KEY: MOD_RES
<222> LOCATION: (129)..(140)
<223> OTHER INFORMATION: continued from above, "His Asp Ala Phe Gly Tyr
      Asp Phe Gly," "Ile Pro Pro His Asn Ala Asp Ser Ser Ile Ile Gly" or
      "Ala Lys Pro Glu Lys Trp Asp Gly Pro Pro Leu Trp," wherein some
      positions may be absent
<220> FEATURE:
<221> NAME/KEY: MOD_RES
<222> LOCATION: (144)..(144)
<223> OTHER INFORMATION: Ala or Thr
<220> FEATURE:
<221> NAME/KEY: MOD_RES
<222> LOCATION: (148)..(154)
```

-continued

```
<223> OTHER INFORMATION: Any amino acid and this region may preferably
      comprise the sequence "Lys Asp Val Pro Gly Asp Arg"
<220> FEATURE:
<221> NAME/KEY: MOD_RES
<222> LOCATION: (160)..(165)
<223> OTHER INFORMATION: Any amino acid and this region may preferably
      comprise the sequence "Gln Gln Lys His Thr Ala," "Thr Glu Asp Glu
      Asn Gln," "Asn Ser Arg His Thr Ala," "Pro Asp His Phe His Asn,"
      "Tyr Asp Val Ala Phe Asp" or "Gln Gln Lys His Asn Gln"
<220> FEATURE:
<221> NAME/KEY: MOD_RES
<222> LOCATION: (169)..(176)
<223> OTHER INFORMATION: Any amino acid and this region may preferably
      comprise the sequence "Gly Asn Leu Lys Pro Asp Thr Glu"
<220> FEATURE:
<221> NAME/KEY: MOD_RES
<222> LOCATION: (184)..(194)
<223> OTHER INFORMATION: Any amino acid and this region may preferably
      comprise the sequence "Phe Asp Pro Tyr Gly Ala Lys Ser Asn Pro
      Ala," "Pro Asn Tyr Glu Arg Ile Ser Asn Pro Ala," "Phe Asp Pro Tyr
      Gly Met Arg Ser Lys Pro Ala," "Phe Thr Pro Tyr Gly Ala Lys Ser Asn
      Pro Ala,"
<220> FEATURE:
<221> NAME/KEY: MOD_RES
<222> LOCATION: (184)..(194)
<223> OTHER INFORMATION: continued from above, "Ala Asn Asp His Gly Phe
      Asp Ser Asn Pro Ala," "Asp Thr Phe Tyr Gly Phe Asp Ser Asn Pro
      Ala" "Phe Asp Pro Tyr Asn Lys Arg Asn Val Pro Ala" or "Phe Asp Pro
      Tyr Gly Leu Lys Ser Arg Pro Ala," wherein some positions may be
      absent
<220> FEATURE:
<223> OTHER INFORMATION: See specification as filed for detailed
      description of substitutions and preferred embodiments

<400> SEQUENCE: 238

Ala Met Ala Ser Gly Gly Gly Ser Ala Ile Glu Val Xaa Xaa Xaa
1               5                   10                  15

Xaa Xaa Xaa Xaa Ala Leu Ile Thr Trp Xaa Xaa Xaa Xaa Xaa Xaa
            20                  25                  30

Xaa Xaa Xaa Xaa Xaa Cys Glu Leu Xaa Tyr Gly Ile Xaa Xaa Xaa
            35                  40                  45

Xaa Xaa Xaa Thr Thr Ile Asp Leu Xaa Xaa Xaa Xaa Xaa Tyr Ser
        50                  55                  60

Ile Xaa Xaa Xaa Xaa Xaa Xaa Xaa Tyr Glu Val Ser Leu Ile Cys
65                  70                  75                  80

Xaa Xaa Xaa Xaa Xaa Xaa Xaa Xaa Xaa Xaa Lys Glu Thr Phe Thr
            85                  90                  95

Thr Gly Gly Gly Gly Ser Gly Gly Gly Ser Gly Gly Gly Gly Ser
            100                 105                 110

Ala Ile Glu Val Xaa Xaa Xaa Xaa Xaa Xaa Xaa Ala Leu Ile Thr Trp
        115                 120                 125

Xaa Xaa Xaa Xaa Xaa Xaa Xaa Xaa Xaa Xaa Xaa Cys Glu Leu Xaa
        130                 135                 140

Tyr Gly Ile Xaa Xaa Xaa Xaa Xaa Xaa Xaa Thr Thr Ile Asp Leu Xaa
145                 150                 155                 160

Xaa Xaa Xaa Xaa Xaa Tyr Ser Ile Xaa Xaa Xaa Xaa Xaa Xaa Xaa
            165                 170                 175

Tyr Glu Val Ser Leu Ile Cys Xaa Xaa Xaa Xaa Xaa Xaa Xaa Xaa
            180                 185                 190

Xaa Xaa Lys Glu Thr Phe Thr Thr Gly Gly Gly Gly Ser Gly Gly Gly
        195                 200                 205

Gly Ser Gly Thr Gly Ala Glu Pro Lys Ser Cys Asp Lys Thr His Thr
    210                 215                 220

Cys Pro Pro Cys Pro Ala Pro Glu Leu Leu Gly Gly Pro Ser Val Phe
```

```
                225                 230                 235                 240
Leu Phe Pro Pro Lys Pro Lys Asp Thr Leu Met Ile Ser Arg Thr Pro
                245                 250                 255
Glu Val Thr Cys Val Val Val Asp Val Ser His Glu Asp Pro Glu Val
            260                 265                 270
Lys Phe Asn Trp Tyr Val Asp Gly Val Glu Val His Asn Ala Lys Thr
        275                 280                 285
Lys Pro Arg Glu Glu Gln Tyr Asn Ser Thr Tyr Arg Val Val Ser Val
    290                 295                 300
Leu Thr Val Leu His Gln Asp Trp Leu Asn Gly Lys Glu Tyr Lys Cys
305                 310                 315                 320
Lys Val Ser Asn Lys Ala Leu Pro Ala Pro Ile Glu Lys Thr Ile Ser
                325                 330                 335
Lys Ala Lys Gly Gln Pro Arg Glu Pro Gln Val Tyr Thr Leu Pro Pro
            340                 345                 350
Ser Arg Glu Glu Met Thr Lys Asn Gln Val Ser Leu Thr Cys Leu Val
        355                 360                 365
Lys Gly Phe Tyr Pro Ser Asp Ile Ala Val Glu Trp Glu Ser Asn Gly
    370                 375                 380
Gln Pro Glu Asn Asn Tyr Lys Thr Thr Pro Pro Val Leu Asp Ser Asp
385                 390                 395                 400
Gly Ser Phe Phe Leu Tyr Ser Lys Leu Thr Val Asp Lys Ser Arg Trp
                405                 410                 415
Gln Gln Gly Asn Val Phe Ser Cys Ser Val Met His Glu Ala Leu His
            420                 425                 430
Asn His Tyr Thr Gln Lys Ser Leu Ser Leu Ser Pro Gly Lys
        435                 440                 445

<210> SEQ ID NO 239
<211> LENGTH: 652
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (14)..(20)
<223> OTHER INFORMATION: Any amino acid and this region may preferably
      comprise the sequence "Lys Asp Val Thr Asp Thr Thr"
<220> FEATURE:
<221> NAME/KEY: MOD_RES
<222> LOCATION: (26)..(37)
<223> OTHER INFORMATION: Any amino acid and this region may preferably
      comprise the sequences "Ala Lys Pro Trp Val Asp Pro Pro Leu
      Trp Gly," "Ser Pro Gly Glu Arg Ile Trp Met Phe Thr Gly," "Ala Lys
      Pro Glu Lys Trp Asp Gly Ser Ile Tyr Gly,"
<220> FEATURE:
<221> NAME/KEY: MOD_RES
<222> LOCATION: (26)..(37)
<223> OTHER INFORMATION: continued from above, "His Asp Ala Phe Gly Tyr
      Asp Phe Gly," "Ile Pro Pro His Asn Ala Asp Ser Ser Ile Ile Gly" or
      "Ala Lys Pro Glu Lys Trp Asp Gly Pro Pro Leu Trp," wherein some
      positions may be absent
<220> FEATURE:
<221> NAME/KEY: MOD_RES
<222> LOCATION: (41)..(41)
<223> OTHER INFORMATION: Ala or Thr
<220> FEATURE:
<221> NAME/KEY: MOD_RES
<222> LOCATION: (45)..(51)
<223> OTHER INFORMATION: Any amino acid and this region may preferably
      comprise the sequence "Lys Asp Val Pro Gly Asp Arg"
<220> FEATURE:
<221> NAME/KEY: MOD_RES
```

```
<222> LOCATION: (57)..(62)
<223> OTHER INFORMATION: Any amino acid and this region may preferably
      comprise the sequence "Gln Gln Lys His Thr Ala," "Thr Glu Asp Glu
      Asn Gln," "Asn Ser Arg His Thr Ala," "Pro Asp His Phe His Asn,"
      "Tyr Asp Val Ala Phe Asp" or "Gln Gln Lys His Asn Gln"
<220> FEATURE:
<221> NAME/KEY: MOD_RES
<222> LOCATION: (66)..(73)
<223> OTHER INFORMATION: Any amino acid and this region may preferably
      comprise the sequence "Gly Asn Leu Lys Pro Asp Thr Glu"
<220> FEATURE:
<221> NAME/KEY: MOD_RES
<222> LOCATION: (81)..(91)
<223> OTHER INFORMATION: Any amino acid and this region may preferably
      comprise the sequence "Phe Asp Pro Tyr Gly Ala Lys Ser Asn Pro
      Ala," "Pro Asn Tyr Glu Arg Ile Ser Asn Pro Ala," "Phe Asp Pro Tyr
      Gly Met Arg Ser Lys Pro Ala," "Phe Thr Pro Tyr Gly Ala Lys Ser Asn
      Pro Ala,"
<220> FEATURE:
<221> NAME/KEY: MOD_RES
<222> LOCATION: (81)..(91)
<223> OTHER INFORMATION: continued from above, "Ala Asn Asp His Gly Phe
      Asp Ser Asn Pro Ala," "Asp Thr Phe Tyr Gly Phe Asp Ser Asn Pro
      Ala" "Phe Asp Pro Tyr Asn Lys Arg Asn Val Pro Ala" or "Phe Asp Pro
      Tyr Gly Leu Lys Ser Arg Pro Ala," wherein some positions may be
      absent
<220> FEATURE:
<221> NAME/KEY: MOD_RES
<222> LOCATION: (117)..(123)
<223> OTHER INFORMATION: Any amino acid and this region may preferably
      comprise the sequence "Lys Asp Val Thr Asp Thr Thr"
<220> FEATURE:
<221> NAME/KEY: MOD_RES
<222> LOCATION: (129)..(140)
<223> OTHER INFORMATION: Any amino acid and this region may preferably
      comprise the sequences "Ala Lys Pro Trp Val Asp Pro Pro Pro Leu
      Trp Gly," "Ser Pro Gly Glu Arg Ile Trp Met Phe Thr Gly," "Ala Lys
      Pro Glu Lys Trp Asp Gly Ser Ile Tyr Gly,"
<220> FEATURE:
<221> NAME/KEY: MOD_RES
<222> LOCATION: (129)..(140)
<223> OTHER INFORMATION: continued from above, "His Asp Ala Phe Gly Tyr
      Asp Phe Gly," "Ile Pro Pro His Asn Ala Asp Ser Asn Ser Ile Ile Gly" or
      "Ala Lys Pro Glu Lys Trp Asp Gly Pro Pro Leu Trp," wherein some
      positions may be absent
<220> FEATURE:
<221> NAME/KEY: MOD_RES
<222> LOCATION: (144)..(144)
<223> OTHER INFORMATION: Ala or Thr
<220> FEATURE:
<221> NAME/KEY: MOD_RES
<222> LOCATION: (148)..(154)
<223> OTHER INFORMATION: Any amino acid and this region may preferably
      comprise the sequence "Lys Asp Val Pro Gly Asp Arg"
<220> FEATURE:
<221> NAME/KEY: MOD_RES
<222> LOCATION: (160)..(165)
<223> OTHER INFORMATION: Any amino acid and this region may preferably
      comprise the sequence "Gln Gln Lys His Thr Ala," "Thr Glu Asp Glu
      Asn Gln," "Asn Ser Arg His Thr Ala," "Pro Asp His Phe His Asn,"
      "Tyr Asp Val Ala Phe Asp" or "Gln Gln Lys His Asn Gln"
<220> FEATURE:
<221> NAME/KEY: MOD_RES
<222> LOCATION: (169)..(176)
<223> OTHER INFORMATION: Any amino acid and this region may preferably
      comprise the sequence "Gly Asn Leu Lys Pro Asp Thr Glu"
<220> FEATURE:
<221> NAME/KEY: MOD_RES
<222> LOCATION: (184)..(194)
<223> OTHER INFORMATION: Any amino acid and this region may preferably
      comprise the sequence "Phe Asp Pro Tyr Gly Ala Lys Ser Asn Pro
      Ala," "Pro Asn Tyr Glu Arg Ile Ser Asn Pro Ala," "Phe Asp Pro Tyr
      Gly Met Arg Ser Lys Pro Ala," "Phe Thr Pro Tyr Gly Ala Lys Ser Asn
      Pro Ala,"
<220> FEATURE:
<221> NAME/KEY: MOD_RES
<222> LOCATION: (184)..(194)
<223> OTHER INFORMATION: continued from above, "Ala Asn Asp His Gly Phe
      Asp Ser Asn Pro Ala," "Asp Thr Phe Tyr Gly Phe Asp Ser Asn Pro
```

```
        Ala" "Phe Asp Pro Tyr Asn Lys Arg Asn Val Pro Ala" or "Phe Asp Pro
        Tyr Gly Leu Lys Ser Arg Pro Ala," wherein some positions may be
        absent
<220> FEATURE:
<221> NAME/KEY: MOD_RES
<222> LOCATION: (220)..(226)
<223> OTHER INFORMATION: Any amino acid and this region may preferably
        comprise the sequence "Lys Asp Val Thr Asp Thr Thr"
<220> FEATURE:
<221> NAME/KEY: MOD_RES
<222> LOCATION: (232)..(243)
<223> OTHER INFORMATION: Any amino acid and this region may preferably
        comprise the sequences "Ala Lys Pro Trp Val Asp Pro Pro Pro Leu
        Trp Gly," "Ser Pro Gly Glu Arg Ile Trp Met Phe Thr Gly," "Ala Lys
        Pro Glu Lys Trp Asp Gly Ser Ile Tyr Gly,"
<220> FEATURE:
<221> NAME/KEY: MOD_RES
<222> LOCATION: (232)..(243)
<223> OTHER INFORMATION: continued from above, "His Asp Ala Phe Gly Tyr
        Asp Phe Gly," "Ile Pro Pro His Asn Ala Asp Ser Ser Ile Ile Gly" or
        "Ala Lys Pro Glu Lys Trp Asp Gly Pro Pro Leu Trp," wherein some
        positions may be absent
<220> FEATURE:
<221> NAME/KEY: MOD_RES
<222> LOCATION: (247)..(247)
<223> OTHER INFORMATION: Ala or Thr
<220> FEATURE:
<221> NAME/KEY: MOD_RES
<222> LOCATION: (251)..(257)
<223> OTHER INFORMATION: Any amino acid and this region may preferably
        comprise the sequence "Lys Asp Val Pro Gly Asp Arg"
<220> FEATURE:
<221> NAME/KEY: MOD_RES
<222> LOCATION: (263)..(268)
<223> OTHER INFORMATION: Any amino acid and this region may preferably
        comprise the sequence "Gln Gln Lys His Thr Ala," "Thr Glu Asp Glu
        Asn Gln," "Asn Ser Arg His Thr Ala," "Pro Asp His Phe His Asn,"
        "Tyr Asp Val Ala Phe Asp" or "Gln Gln Lys His Asn Gln"
<220> FEATURE:
<221> NAME/KEY: MOD_RES
<222> LOCATION: (272)..(279)
<223> OTHER INFORMATION: Any amino acid and this region may preferably
        comprise the sequence "Gly Asn Leu Lys Pro Asp Thr Glu"
<220> FEATURE:
<221> NAME/KEY: MOD_RES
<222> LOCATION: (287)..(297)
<223> OTHER INFORMATION: Any amino acid and this region may preferably
        comprise the sequence "Phe Asp Pro Tyr Gly Ala Lys Ser Asn Pro
        Ala," "Pro Asn Tyr Glu Arg Ile Ser Asn Pro Ala," "Phe Asp Pro Tyr
        Gly Met Arg Ser Lys Pro Ala," "Phe Thr Pro Tyr Gly Ala Lys Ser Asn
        Pro Ala,"
<220> FEATURE:
<221> NAME/KEY: MOD_RES
<222> LOCATION: (287)..(297)
<223> OTHER INFORMATION: continued from above, "Ala Asn Asp His Gly Phe
        Asp Ser Asn Pro Ala," "Asp Thr Phe Tyr Gly Phe Asp Ser Asn Pro
        Ala" "Phe Asp Pro Tyr Asn Lys Arg Asn Val Pro Ala" or "Phe Asp Pro
        Tyr Gly Leu Lys Ser Arg Pro Ala," wherein some positions may be
        absent
<220> FEATURE:
<221> NAME/KEY: MOD_RES
<222> LOCATION: (323)..(329)
<223> OTHER INFORMATION: Any amino acid and this region may preferably
        comprise the sequence "Lys Asp Val Thr Asp Thr Thr"
<220> FEATURE:
<221> NAME/KEY: MOD_RES
<222> LOCATION: (335)..(346)
<223> OTHER INFORMATION: Any amino acid and this region may preferably
        comprise the sequences "Ala Lys Pro Trp Val Asp Pro Pro Pro Leu
        Trp Gly," "Ser Pro Gly Glu Arg Ile Trp Met Phe Thr Gly," "Ala Lys
        Pro Glu Lys Trp Asp Gly Ser Ile Tyr Gly,"
<220> FEATURE:
<221> NAME/KEY: MOD_RES
<222> LOCATION: (335)..(346)
<223> OTHER INFORMATION: continued from above, "His Asp Ala Phe Gly Tyr
        Asp Phe Gly," "Ile Pro Pro His Asn Ala Asp Ser Ser Ile Ile Gly" or
        "Ala Lys Pro Glu Lys Trp Asp Gly Pro Pro Leu Trp," wherein some
        positions may be absent
<220> FEATURE:
```

```
<221> NAME/KEY: MOD_RES
<222> LOCATION: (350)..(350)
<223> OTHER INFORMATION: Ala or Thr
<220> FEATURE:
<221> NAME/KEY: MOD_RES
<222> LOCATION: (354)..(360)
<223> OTHER INFORMATION: Any amino acid and this region may preferably
      comprise the sequence "Lys Asp Val Pro Gly Asp Arg"
<220> FEATURE:
<221> NAME/KEY: MOD_RES
<222> LOCATION: (366)..(371)
<223> OTHER INFORMATION: Any amino acid and this region may preferably
      comprise the sequence "Gln Gln Lys His Thr Ala," "Thr Glu Asp Glu
      Asn Gln," "Asn Ser Arg His Thr Ala," "Pro Asp His Phe His Asn,"
      "Tyr Asp Val Ala Phe Asp" or "Gln Gln Lys His Asn Gln"
<220> FEATURE:
<221> NAME/KEY: MOD_RES
<222> LOCATION: (375)..(382)
<223> OTHER INFORMATION: Any amino acid and this region may preferably
      comprise the sequence "Gly Asn Leu Lys Pro Asp Thr Glu"
<220> FEATURE:
<221> NAME/KEY: MOD_RES
<222> LOCATION: (390)..(400)
<223> OTHER INFORMATION: Any amino acid and this region may preferably
      comprise the sequence "Phe Asp Pro Tyr Gly Ala Lys Ser Asn Pro
      Ala," "Pro Asn Tyr Glu Arg Ile Ser Asn Pro Ala," "Phe Asp Pro Tyr
      Gly Met Arg Ser Lys Pro Ala," "Phe Thr Pro Tyr Gly Ala Lys Ser Asn
      Pro Ala,"
<220> FEATURE:
<221> NAME/KEY: MOD_RES
<222> LOCATION: (390)..(400)
<223> OTHER INFORMATION: continued from above, "Ala Asn Asp His Gly Phe
      Asp Ser Asn Pro Ala," "Asp Thr Phe Tyr Gly Phe Asp Ser Asn Pro
      Ala" "Phe Asp Pro Tyr Asn Lys Arg Asn Val Pro Ala" or "Phe Asp Pro
      Tyr Gly Leu Lys Ser Arg Pro Ala," wherein some positions may be
      absent
<220> FEATURE:
<223> OTHER INFORMATION: See specification as filed for detailed
      description of substitutions and preferred embodiments

<400> SEQUENCE: 239

Ala Met Ala Ser Gly Gly Gly Gly Ser Ala Ile Glu Val Xaa Xaa Xaa
1               5                   10                  15

Xaa Xaa Xaa Xaa Ala Leu Ile Thr Trp Xaa Xaa Xaa Xaa Xaa Xaa Xaa
                20                  25                  30

Xaa Xaa Xaa Xaa Xaa Cys Glu Leu Xaa Tyr Gly Ile Xaa Xaa Xaa Xaa
            35                  40                  45

Xaa Xaa Xaa Thr Thr Ile Asp Leu Xaa Xaa Xaa Xaa Xaa Xaa Tyr Ser
        50                  55                  60

Ile Xaa Xaa Xaa Xaa Xaa Xaa Xaa Tyr Glu Val Ser Leu Ile Cys
65                  70                  75                  80

Xaa Xaa Xaa Xaa Xaa Xaa Xaa Xaa Xaa Xaa Lys Glu Thr Phe Thr
                85                  90                  95

Thr Gly Gly Gly Gly Ser Gly Gly Gly Ser Gly Gly Gly Gly Ser
            100                 105                 110

Ala Ile Glu Val Xaa Xaa Xaa Xaa Xaa Xaa Xaa Ala Leu Ile Thr Trp
        115                 120                 125

Xaa Xaa Xaa Xaa Xaa Xaa Xaa Xaa Xaa Xaa Cys Glu Leu Xaa
    130                 135                 140

Tyr Gly Ile Xaa Xaa Xaa Xaa Xaa Xaa Xaa Thr Thr Ile Asp Leu Xaa
145                 150                 155                 160

Xaa Xaa Xaa Xaa Xaa Tyr Ser Ile Xaa Xaa Xaa Xaa Xaa Xaa Xaa
                165                 170                 175

Tyr Glu Val Ser Leu Ile Cys Xaa Xaa Xaa Xaa Xaa Xaa Xaa Xaa
            180                 185                 190

Xaa Xaa Lys Glu Thr Phe Thr Thr Gly Gly Gly Gly Ser Gly Gly Gly
```

-continued

```
            195                 200                 205
Gly Ser Gly Gly Gly Ser Ala Ile Glu Val Xaa Xaa Xaa Xaa
210                 215                 220
Xaa Xaa Ala Leu Ile Thr Trp Xaa Xaa Xaa Xaa Xaa Xaa Xaa
225                 230                 235                 240
Xaa Xaa Xaa Cys Glu Leu Xaa Tyr Gly Ile Xaa Xaa Xaa Xaa
                245                 250                 255
Xaa Thr Thr Ile Asp Leu Xaa Xaa Xaa Xaa Xaa Tyr Ser Ile Xaa
                260                 265                 270
Xaa Xaa Xaa Xaa Xaa Xaa Xaa Tyr Glu Val Ser Leu Ile Cys Xaa Xaa
            275                 280                 285
Xaa Xaa Xaa Xaa Xaa Xaa Xaa Xaa Lys Glu Thr Phe Thr Thr Gly
290                 295                 300
Gly Gly Gly Ser Gly Gly Gly Ser Gly Gly Gly Ser Ala Ile
305                 310                 315                 320
Glu Val Xaa Xaa Xaa Xaa Xaa Xaa Xaa Ala Leu Ile Thr Trp Xaa Xaa
                325                 330                 335
Xaa Xaa Xaa Xaa Xaa Xaa Xaa Xaa Xaa Cys Glu Leu Xaa Tyr Gly
                340                 345                 350
Ile Xaa Xaa Xaa Xaa Xaa Xaa Xaa Thr Thr Ile Asp Leu Xaa Xaa Xaa
            355                 360                 365
Xaa Xaa Xaa Tyr Ser Ile Xaa Xaa Xaa Xaa Xaa Xaa Xaa Tyr Glu
            370                 375                 380
Val Ser Leu Ile Cys Xaa Xaa Xaa Xaa Xaa Xaa Xaa Xaa Xaa
385                 390                 395                 400
Lys Glu Thr Phe Thr Thr Gly Gly Gly Ser Gly Gly Gly Ser
                405                 410                 415
Gly Thr Gly Ala Glu Pro Lys Ser Cys Asp Lys Thr His Thr Cys Pro
                420                 425                 430
Pro Cys Pro Ala Pro Glu Leu Leu Gly Gly Pro Ser Val Phe Leu Phe
            435                 440                 445
Pro Pro Lys Pro Lys Asp Thr Leu Met Ile Ser Arg Thr Pro Glu Val
450                 455                 460
Thr Cys Val Val Val Asp Val Ser His Glu Asp Pro Glu Val Lys Phe
465                 470                 475                 480
Asn Trp Tyr Val Asp Gly Val Glu Val His Asn Ala Lys Thr Lys Pro
                485                 490                 495
Arg Glu Glu Gln Tyr Asn Ser Thr Tyr Arg Val Val Ser Val Leu Thr
                500                 505                 510
Val Leu His Gln Asp Trp Leu Asn Gly Lys Glu Tyr Lys Cys Lys Val
            515                 520                 525
Ser Asn Lys Ala Leu Pro Ala Pro Ile Glu Lys Thr Ile Ser Lys Ala
            530                 535                 540
Lys Gly Gln Pro Arg Glu Pro Gln Val Tyr Thr Leu Pro Pro Ser Arg
545                 550                 555                 560
Glu Glu Met Thr Lys Asn Gln Val Ser Leu Thr Cys Leu Val Lys Gly
                565                 570                 575
Phe Tyr Pro Ser Asp Ile Ala Val Glu Trp Glu Ser Asn Gly Gln Pro
                580                 585                 590
Glu Asn Asn Tyr Lys Thr Thr Pro Pro Val Leu Asp Ser Asp Gly Ser
            595                 600                 605
Phe Phe Leu Tyr Ser Lys Leu Thr Val Asp Lys Ser Arg Trp Gln Gln
            610                 615                 620
```

-continued

```
Gly Asn Val Phe Ser Cys Ser Val Met His Glu Ala Leu His Asn His
625                 630                 635                 640

Tyr Thr Gln Lys Ser Leu Ser Leu Ser Pro Gly Lys
                645                 650

<210> SEQ ID NO 240
<211> LENGTH: 427
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (6)..(12)
<223> OTHER INFORMATION: Any amino acid and this region may preferably
      comprise the sequence "Lys Asp Val Thr Asp Thr Thr"
<220> FEATURE:
<221> NAME/KEY: MOD_RES
<222> LOCATION: (18)..(29)
<223> OTHER INFORMATION: Any amino acid and this region may preferably
      comprise the sequences "Ala Lys Pro Trp Val Asp Pro Pro Leu
      Trp Gly," "Ser Pro Gly Glu Arg Ile Trp Met Phe Thr Gly," "Ala Lys
      Pro Glu Lys Trp Asp Gly Ser Ile Tyr Gly,"
<220> FEATURE:
<221> NAME/KEY: MOD_RES
<222> LOCATION: (18)..(29)
<223> OTHER INFORMATION: continued from above, "His Asp Ala Phe Gly Tyr
      Asp Phe Gly," "Ile Pro Pro His Asn Ala Asp Ser Ser Ile Ile Gly" or
      "Ala Lys Pro Glu Lys Trp Asp Gly Pro Pro Leu Trp," wherein some
      positions may be absent
<220> FEATURE:
<221> NAME/KEY: MOD_RES
<222> LOCATION: (33)..(33)
<223> OTHER INFORMATION: Ala or Thr
<220> FEATURE:
<221> NAME/KEY: MOD_RES
<222> LOCATION: (37)..(43)
<223> OTHER INFORMATION: Any amino acid and this region may preferably
      comprise the sequence "Lys Asp Val Pro Gly Asp Arg"
<220> FEATURE:
<221> NAME/KEY: MOD_RES
<222> LOCATION: (49)..(54)
<223> OTHER INFORMATION: Any amino acid and this region may preferably
      comprise the sequence "Gln Gln Lys His Thr Ala," "Thr Glu Asp Glu
      Asn Gln," "Asn Ser Arg His Thr Ala," "Pro Asp His Phe His Asn,"
      "Tyr Asp Val Ala Phe Asp" or "Gln Gln Lys His Asn Gln"
<220> FEATURE:
<221> NAME/KEY: MOD_RES
<222> LOCATION: (58)..(65)
<223> OTHER INFORMATION: Any amino acid and this region may preferably
      comprise the sequence "Gly Asn Leu Lys Pro Asp Thr Glu"
<220> FEATURE:
<221> NAME/KEY: MOD_RES
<222> LOCATION: (73)..(83)
<223> OTHER INFORMATION: Any amino acid and this region may preferably
      comprise the sequence "Phe Asp Pro Tyr Gly Ala Lys Ser Asn Pro
      Ala," "Pro Asn Tyr Glu Arg Ile Ser Asn Pro Ala," "Phe Asp Pro Tyr
      Gly Met Arg Ser Lys Pro Ala," "Phe Thr Pro Tyr Gly Ala Lys Ser Asn
      Pro Ala,"
<220> FEATURE:
<221> NAME/KEY: MOD_RES
<222> LOCATION: (73)..(83)
<223> OTHER INFORMATION: continued from above, "Ala Asn Asp His Gly Phe
      Asp Ser Asn Pro Ala," "Asp Thr Phe Tyr Gly Phe Asp Ser Asn Pro
      Ala" "Phe Asp Pro Tyr Asn Lys Arg Asn Val Pro Ala" or "Phe Asp Pro
      Tyr Gly Leu Lys Ser Arg Pro Ala," wherein some positions may be
      absent
<220> FEATURE:
<223> OTHER INFORMATION: See specification as filed for detailed
      description of substitutions and preferred embodiments

<400> SEQUENCE: 240

Ser Gln Ile Glu Val Xaa Xaa Xaa Xaa Xaa Xaa Xaa Ala Leu Ile Thr
1               5                   10                  15
```

Trp Xaa Xaa Xaa Xaa Xaa Xaa Xaa Xaa Xaa Xaa Cys Glu Leu
        20                  25                  30

Xaa Tyr Gly Ile Xaa Xaa Xaa Xaa Xaa Xaa Thr Thr Ile Asp Leu
    35                  40                  45

Xaa Xaa Xaa Xaa Xaa Xaa Tyr Ser Ile Xaa Xaa Xaa Xaa Xaa Xaa
50                      55                  60

Xaa Tyr Glu Val Ser Leu Ile Cys Xaa Xaa Xaa Xaa Xaa Xaa Xaa
65                      70                  75                  80

Xaa Xaa Xaa Lys Glu Thr Phe Thr Thr Gly Gly Thr Pro Thr Ser
            85                  90                  95

Ser Ala Ser Thr Lys Gly Pro Ser Val Phe Pro Leu Ala Pro Ser Ser
            100                 105                 110

Lys Ser Thr Ser Gly Gly Thr Ala Ala Leu Gly Cys Leu Val Lys Asp
            115                 120                 125

Tyr Phe Pro Glu Pro Val Thr Val Ser Trp Asn Ser Gly Ala Leu Thr
    130                 135                 140

Ser Gly Val His Thr Phe Pro Ala Val Leu Gln Ser Ser Gly Leu Tyr
145                 150                 155                 160

Ser Leu Ser Ser Val Val Thr Val Pro Ser Ser Ser Leu Gly Thr Gln
                165                 170                 175

Thr Tyr Ile Cys Asn Val Asn His Lys Pro Ser Asn Thr Lys Val Asp
            180                 185                 190

Lys Arg Val Glu Pro Lys Ser Cys Asp Lys Thr His Thr Cys Pro Pro
            195                 200                 205

Cys Pro Ala Pro Glu Leu Leu Gly Gly Pro Ser Val Phe Leu Phe Pro
            210                 215                 220

Pro Lys Pro Lys Asp Thr Leu Met Ile Ser Arg Thr Pro Glu Val Thr
225                 230                 235                 240

Cys Val Val Val Asp Val Ser His Glu Asp Pro Glu Val Lys Phe Asn
                245                 250                 255

Trp Tyr Val Asp Gly Val Glu Val His Asn Ala Lys Thr Lys Pro Arg
            260                 265                 270

Glu Glu Gln Tyr Asn Ser Thr Tyr Arg Val Val Ser Val Leu Thr Val
            275                 280                 285

Leu His Gln Asp Trp Leu Asn Gly Lys Glu Tyr Lys Cys Lys Val Ser
            290                 295                 300

Asn Lys Ala Leu Pro Ala Pro Ile Glu Lys Thr Ile Ser Lys Ala Lys
305                 310                 315                 320

Gly Gln Pro Arg Glu Pro Gln Val Tyr Thr Leu Pro Pro Ser Arg Glu
                325                 330                 335

Glu Met Thr Lys Asn Gln Val Ser Leu Thr Cys Leu Val Lys Gly Phe
            340                 345                 350

Tyr Pro Ser Asp Ile Ala Val Glu Trp Glu Ser Asn Gly Gln Pro Glu
            355                 360                 365

Asn Asn Tyr Lys Thr Thr Pro Pro Val Leu Asp Ser Asp Gly Ser Phe
            370                 375                 380

Phe Leu Tyr Ser Lys Leu Thr Val Asp Lys Ser Arg Trp Gln Gln Gly
385                 390                 395                 400

Asn Val Phe Ser Cys Ser Val Met His Glu Ala Leu His Asn His Tyr
                405                 410                 415

Thr Gln Lys Ser Leu Ser Leu Ser Pro Gly Lys
            420                 425

```
<210> SEQ ID NO 241
<211> LENGTH: 202
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (6)..(12)
<223> OTHER INFORMATION: Any amino acid and this region may preferably
      comprise the sequence "Lys Asp Val Thr Asp Thr Thr"
<220> FEATURE:
<221> NAME/KEY: MOD_RES
<222> LOCATION: (18)..(29)
<223> OTHER INFORMATION: Any amino acid and this region may preferably
      comprise the sequences "Ala Lys Pro Trp Val Asp Pro Pro Leu
      Trp Gly," "Ser Pro Gly Glu Arg Ile Trp Met Phe Thr Gly," "Ala Lys
      Pro Glu Lys Trp Asp Gly Ser Ile Tyr Gly,"
<220> FEATURE:
<221> NAME/KEY: MOD_RES
<222> LOCATION: (18)..(29)
<223> OTHER INFORMATION: continued from above, "His Asp Ala Phe Gly Tyr
      Asp Phe Gly," "Ile Pro Pro His Asn Ala Asp Ser Ser Ile Ile Gly" or
      "Ala Lys Pro Glu Lys Trp Asp Gly Pro Pro Leu Trp," wherein some
      positions may be absent
<220> FEATURE:
<221> NAME/KEY: MOD_RES
<222> LOCATION: (33)..(33)
<223> OTHER INFORMATION: Ala or Thr
<220> FEATURE:
<221> NAME/KEY: MOD_RES
<222> LOCATION: (37)..(43)
<223> OTHER INFORMATION: Any amino acid and this region may preferably
      comprise the sequence "Lys Asp Val Pro Gly Asp Arg"
<220> FEATURE:
<221> NAME/KEY: MOD_RES
<222> LOCATION: (49)..(54)
<223> OTHER INFORMATION: Any amino acid and this region may preferably
      comprise the sequence "Gln Gln Lys His Thr Ala," "Thr Glu Asp Glu
      Asn Gln," "Asn Ser Arg His Thr Ala," "Pro Asp His Phe His Asn,"
      "Tyr Asp Val Ala Phe Asp" or "Gln Gln Lys His Asn Gln"
<220> FEATURE:
<221> NAME/KEY: MOD_RES
<222> LOCATION: (58)..(65)
<223> OTHER INFORMATION: Any amino acid and this region may preferably
      comprise the sequence "Gly Asn Leu Lys Pro Asp Thr Glu"
<220> FEATURE:
<221> NAME/KEY: MOD_RES
<222> LOCATION: (73)..(83)
<223> OTHER INFORMATION: Any amino acid and this region may preferably
      comprise the sequence "Phe Asp Pro Tyr Gly Ala Lys Ser Asn Pro
      Ala," "Pro Asn Tyr Glu Arg Ile Ser Asn Pro Ala," "Phe Asp Pro Tyr
      Gly Met Arg Ser Lys Pro Ala," "Phe Thr Pro Tyr Gly Ala Lys Ser Asn
      Pro Ala,"
<220> FEATURE:
<221> NAME/KEY: MOD_RES
<222> LOCATION: (73)..(83)
<223> OTHER INFORMATION: continued from above, "Ala Asn Asp His Gly Phe
      Asp Ser Asn Pro Ala," "Asp Thr Phe Tyr Gly Phe Asp Ser Asn Pro
      Ala" "Phe Asp Pro Tyr Asn Lys Arg Asn Val Pro Ala" or "Phe Asp Pro
      Tyr Gly Leu Lys Ser Arg Pro Ala," wherein some positions may be
      absent
<220> FEATURE:
<223> OTHER INFORMATION: See specification as filed for detailed
      description of substitutions and preferred embodiments

<400> SEQUENCE: 241

Ser Gln Ile Glu Val Xaa Xaa Xaa Xaa Xaa Xaa Xaa Ala Leu Ile Thr
1               5                   10                  15

Trp Xaa Xaa Xaa Xaa Xaa Xaa Xaa Xaa Xaa Xaa Xaa Cys Glu Leu
            20                  25                  30

Xaa Tyr Gly Ile Xaa Xaa Xaa Xaa Xaa Xaa Xaa Thr Thr Ile Asp Leu
        35                  40                  45
```

```
Xaa Xaa Xaa Xaa Xaa Tyr Ser Ile Xaa Xaa Xaa Xaa Xaa Xaa
    50              55              60

Xaa Tyr Glu Val Ser Leu Ile Cys Xaa Xaa Xaa Xaa Xaa Xaa Xaa
65              70              75              80

Xaa Xaa Xaa Lys Glu Thr Phe Thr Thr Gly Gly Gly Thr Pro Thr Arg
            85              90              95

Thr Val Ala Ala Pro Ser Val Phe Ile Phe Pro Pro Ser Asp Glu Gln
            100             105             110

Leu Lys Ser Gly Thr Ala Ser Val Val Cys Leu Leu Asn Asn Phe Tyr
            115             120             125

Pro Arg Glu Ala Lys Val Gln Trp Lys Val Asp Asn Ala Leu Gln Ser
            130             135             140

Gly Asn Ser Gln Glu Ser Val Thr Glu Gln Asp Ser Lys Asp Ser Thr
145             150             155             160

Tyr Ser Leu Ser Ser Thr Leu Thr Leu Ser Lys Ala Asp Tyr Glu Lys
                165             170             175

His Lys Val Tyr Ala Cys Glu Val Thr His Gln Gly Leu Ser Ser Pro
            180             185             190

Val Thr Lys Ser Phe Asn Arg Gly Glu Cys
            195             200
```

<210> SEQ ID NO 242
<211> LENGTH: 102
<212> TYPE: PRT
<213> ORGANISM: Artificial Sequence
<220> FEATURE:
<223> OTHER INFORMATION: Description of Artificial Sequence: Synthetic polypeptide
<220> FEATURE:
<221> NAME/KEY: MOD_RES
<222> LOCATION: (5)..(11)
<223> OTHER INFORMATION: Any amino acid and this region may preferably comprise the sequence "Lys Asp Val Thr Asp Thr Thr"
<220> FEATURE:
<221> NAME/KEY: MOD_RES
<222> LOCATION: (17)..(28)
<223> OTHER INFORMATION: Any amino acid and this region may preferably comprise the sequences "Ala Lys Pro Trp Val Asp Pro Pro Leu Trp Gly," "Ser Pro Gly Glu Arg Ile Trp Met Phe Thr Gly," "Ala Lys Pro Glu Lys Trp Asp Gly Ser Ile Tyr Gly,"
<220> FEATURE:
<221> NAME/KEY: MOD_RES
<222> LOCATION: (17)..(28)
<223> OTHER INFORMATION: continued from above, "His Asp Ala Phe Gly Tyr Asp Asp Phe Gly," "Ile Pro Pro His Asn Ala Asp Ser Ser Ile Ile Gly" or "Ala Lys Pro Glu Lys Trp Asp Gly Pro Pro Leu Trp," wherein some positions may be absent
<220> FEATURE:
<221> NAME/KEY: MOD_RES
<222> LOCATION: (32)..(32)
<223> OTHER INFORMATION: Ala or Thr
<220> FEATURE:
<221> NAME/KEY: MOD_RES
<222> LOCATION: (36)..(42)
<223> OTHER INFORMATION: Any amino acid and this region may preferably comprise the sequence "Lys Asp Val Pro Gly Asp Arg"
<220> FEATURE:
<221> NAME/KEY: MOD_RES
<222> LOCATION: (48)..(53)
<223> OTHER INFORMATION: Any amino acid and this region may preferably comprise the sequence "Gln Gln Lys His Thr Ala," "Thr Glu Asp Glu Asn Gln," "Asn Ser Arg His Thr Ala," "Pro Asp His Phe His Asn," "Tyr Asp Val Ala Phe Asp" or "Gln Gln Lys His Asn Gln"
<220> FEATURE:
<221> NAME/KEY: MOD_RES
<222> LOCATION: (57)..(64)
<223> OTHER INFORMATION: Any amino acid and this region may preferably comprise the sequence "Gly Asn Leu Lys Pro Asp Thr Glu"
<220> FEATURE:

<221> NAME/KEY: MOD_RES
<222> LOCATION: (72)..(82)
<223> OTHER INFORMATION: Any amino acid and this region may preferably comprise the sequence "Phe Asp Pro Tyr Gly Ala Lys Ser Asn Pro Ala," "Pro Asn Tyr Glu Arg Ile Ser Asn Pro Ala," "Phe Asp Pro Tyr Gly Met Arg Ser Lys Pro Ala," "Phe Thr Pro Tyr Gly Ala Lys Ser Asn Pro Ala,"
<220> FEATURE:
<221> NAME/KEY: MOD_RES
<222> LOCATION: (72)..(82)
<223> OTHER INFORMATION: continued from above, "Ala Asn Asp His Gly Phe Asp Ser Asn Pro Ala," "Asp Thr Phe Tyr Gly Phe Asp Ser Asn Pro Ala" "Phe Asp Pro Tyr Asn Lys Arg Asn Val Pro Ala" or "Phe Asp Pro Tyr Gly Leu Lys Ser Arg Pro Ala," wherein some positions may be absent
<220> FEATURE:
<223> OTHER INFORMATION: See specification as filed for detailed description of substitutions and preferred embodiments

<400> SEQUENCE: 242

Ala Ile Glu Val Xaa Xaa Xaa Xaa Xaa Xaa Xaa Ala Leu Ile Thr Trp
1               5                   10                  15

Xaa Xaa Xaa Xaa Xaa Xaa Xaa Xaa Xaa Xaa Xaa Xaa Cys Glu Leu Xaa
            20                  25                  30

Tyr Gly Ile Xaa Xaa Xaa Xaa Xaa Xaa Xaa Thr Thr Ile Asp Leu Xaa
            35                  40                  45

Xaa Xaa Xaa Xaa Xaa Tyr Ser Ile Xaa Xaa Xaa Xaa Xaa Xaa Xaa Xaa
        50                  55                  60

Tyr Glu Val Ser Leu Ile Cys Xaa Xaa Xaa Xaa Xaa Xaa Xaa Xaa Xaa
65                  70                  75                  80

Xaa Xaa Lys Glu Thr Phe Thr Thr Gly Gly Gly Thr Leu Gly His His
            85                  90                  95

His His His His His His
            100

<210> SEQ ID NO 243
<211> LENGTH: 202
<212> TYPE: PRT
<213> ORGANISM: Artificial Sequence
<220> FEATURE:
<223> OTHER INFORMATION: Description of Artificial Sequence: Synthetic polypeptide
<220> FEATURE:
<221> NAME/KEY: MOD_RES
<222> LOCATION: (5)..(11)
<223> OTHER INFORMATION: Any amino acid and this region may preferably comprise the sequence "Lys Asp Val Thr Asp Thr Thr"
<220> FEATURE:
<221> NAME/KEY: MOD_RES
<222> LOCATION: (17)..(28)
<223> OTHER INFORMATION: Any amino acid and this region may preferably comprise the sequences "Ala Lys Pro Trp Val Asp Pro Pro Pro Leu Trp Gly," "Ser Pro Gly Glu Arg Ile Trp Met Phe Thr Gly," "Ala Lys Pro Glu Lys Trp Asp Gly Ser Ile Tyr Gly,"
<220> FEATURE:
<221> NAME/KEY: MOD_RES
<222> LOCATION: (17)..(28)
<223> OTHER INFORMATION: continued from above, "His Asp Ala Phe Gly Tyr Asp Phe Gly," "Ile Pro Pro His Asn Ala Asp Ser Ser Ile Ile Gly" or "Ala Lys Pro Glu Lys Trp Asp Gly Pro Pro Leu Trp," wherein some positions may be absent
<220> FEATURE:
<221> NAME/KEY: MOD_RES
<222> LOCATION: (32)..(32)
<223> OTHER INFORMATION: Ala or Thr
<220> FEATURE:
<221> NAME/KEY: MOD_RES
<222> LOCATION: (36)..(42)
<223> OTHER INFORMATION: Any amino acid and this region may preferably comprise the sequence "Lys Asp Val Pro Gly Asp Arg"
<220> FEATURE:

```
<221> NAME/KEY: MOD_RES
<222> LOCATION: (48)..(53)
<223> OTHER INFORMATION: Any amino acid and this region may preferably
      comprise the sequence "Gln Gln Lys His Thr Ala," "Thr Glu Asp Glu
      Asn Gln," "Asn Ser Arg His Thr Ala," "Pro Asp His Phe His Asn,"
      "Tyr Asp Val Ala Phe Asp" or "Gln Gln Lys His Asn Gln"
<220> FEATURE:
<221> NAME/KEY: MOD_RES
<222> LOCATION: (57)..(64)
<223> OTHER INFORMATION: Any amino acid and this region may preferably
      comprise the sequence "Gly Asn Leu Lys Pro Asp Thr Glu"
<220> FEATURE:
<221> NAME/KEY: MOD_RES
<222> LOCATION: (72)..(82)
<223> OTHER INFORMATION: Any amino acid and this region may preferably
      comprise the sequence "Phe Asp Pro Tyr Gly Ala Lys Ser Asn Pro
      Ala," "Pro Asn Tyr Glu Arg Ile Ser Asn Pro Ala," "Phe Asp Pro Tyr
      Gly Met Arg Ser Lys Pro Ala," "Phe Thr Pro Tyr Gly Ala Lys Ser Asn
      Pro Ala,"
<220> FEATURE:
<221> NAME/KEY: MOD_RES
<222> LOCATION: (72)..(82)
<223> OTHER INFORMATION: continued from above, "Ala Asn Asp His Gly Phe
      Asp Ser Asn Pro Ala," "Asp Thr Phe Tyr Gly Phe Asp Ser Asn Pro
      Ala" "Phe Asp Pro Tyr Asn Lys Arg Asn Val Pro Ala" or "Phe Asp Pro
      Tyr Gly Leu Lys Ser Arg Pro Ala," wherein some positions may be
      absent
<220> FEATURE:
<221> NAME/KEY: MOD_RES
<222> LOCATION: (105)..(111)
<223> OTHER INFORMATION: Any amino acid and this region may preferably
      comprise the sequence "Lys Asp Val Thr Asp Thr Thr"
<220> FEATURE:
<221> NAME/KEY: MOD_RES
<222> LOCATION: (117)..(128)
<223> OTHER INFORMATION: Any amino acid and this region may preferably
      comprise the sequences "Ala Lys Pro Trp Val Asp Pro Pro Pro Leu
      Trp Gly," "Ser Pro Gly Glu Arg Ile Trp Met Phe Thr Gly," "Ala Lys
      Pro Glu Lys Trp Asp Gly Ser Ile Tyr Gly,"
<220> FEATURE:
<221> NAME/KEY: MOD_RES
<222> LOCATION: (117)..(128)
<223> OTHER INFORMATION: continued from above, "His Asp Ala Phe Gly Tyr
      Asp Phe Gly," "Ile Pro Pro His Asn Ala Asp Ser Ser Ile Ile Gly" or
      "Ala Lys Pro Glu Lys Trp Asp Gly Pro Pro Leu Trp," wherein some
      positions may be absent
<220> FEATURE:
<221> NAME/KEY: MOD_RES
<222> LOCATION: (132)..(132)
<223> OTHER INFORMATION: Ala or Thr
<220> FEATURE:
<221> NAME/KEY: MOD_RES
<222> LOCATION: (136)..(142)
<223> OTHER INFORMATION: Any amino acid and this region may preferably
      comprise the sequence "Lys Asp Val Pro Gly Asp Arg"
<220> FEATURE:
<221> NAME/KEY: MOD_RES
<222> LOCATION: (148)..(153)
<223> OTHER INFORMATION: Any amino acid and this region may preferably
      comprise the sequence "Gln Gln Lys His Thr Ala," "Thr Glu Asp Glu
      Asn Gln," "Asn Ser Arg His Thr Ala," "Pro Asp His Phe His Asn,"
      "Tyr Asp Val Ala Phe Asp" or "Gln Gln Lys His Asn Gln"
<220> FEATURE:
<221> NAME/KEY: MOD_RES
<222> LOCATION: (157)..(164)
<223> OTHER INFORMATION: Any amino acid and this region may preferably
      comprise the sequence "Gly Asn Leu Lys Pro Asp Thr Glu"
<220> FEATURE:
<221> NAME/KEY: MOD_RES
<222> LOCATION: (172)..(182)
<223> OTHER INFORMATION: Any amino acid and this region may preferably
      comprise the sequence "Phe Asp Pro Tyr Gly Ala Lys Ser Asn Pro
      Ala," "Pro Asn Tyr Glu Arg Ile Ser Asn Pro Ala," "Phe Asp Pro Tyr
      Gly Met Arg Ser Lys Pro Ala," "Phe Thr Pro Tyr Gly Ala Lys Ser Asn
      Pro Ala,"
<220> FEATURE:
<221> NAME/KEY: MOD_RES
<222> LOCATION: (172)..(182)
<223> OTHER INFORMATION: continued from above, "Ala Asn Asp His Gly Phe
```

Asp Ser Asn Pro Ala," "Asp Thr Phe Tyr Gly Phe Asp Ser Asn Pro Ala" "Phe Asp Pro Tyr Asn Lys Arg Asn Val Pro Ala" or "Phe Asp Pro Tyr Gly Leu Lys Ser Arg Pro Ala," wherein some positions may be absent
<220> FEATURE:
<223> OTHER INFORMATION: See specification as filed for detailed description of substitutions and preferred embodiments

<400> SEQUENCE: 243

Ala Ile Glu Val Xaa Xaa Xaa Xaa Xaa Xaa Ala Leu Ile Thr Trp
1               5                   10                  15

Xaa Xaa Xaa Xaa Xaa Xaa Xaa Xaa Xaa Xaa Xaa Cys Glu Leu Xaa
            20                  25                  30

Tyr Gly Ile Xaa Xaa Xaa Xaa Xaa Xaa Xaa Thr Thr Ile Asp Leu Xaa
            35                  40                  45

Xaa Xaa Xaa Xaa Xaa Tyr Ser Ile Xaa Xaa Xaa Xaa Xaa Xaa Xaa
        50                  55                  60

Tyr Glu Val Ser Leu Ile Cys Xaa Xaa Xaa Xaa Xaa Xaa Xaa Xaa
65              70                  75                  80

Xaa Xaa Lys Glu Thr Phe Thr Thr Ala Gly Gly Gly Ser Arg Leu
            85                  90                  95

Asp Ala Pro Gly Gln Ile Glu Val Xaa Xaa Xaa Xaa Xaa Xaa Xaa Ala
            100                 105                 110

Leu Ile Thr Trp Xaa Xaa Xaa Xaa Xaa Xaa Xaa Xaa Xaa Xaa Xaa
            115                 120                 125

Cys Glu Leu Xaa Tyr Gly Ile Xaa Xaa Xaa Xaa Xaa Xaa Xaa Thr Thr
130             135                 140

Ile Asp Leu Xaa Xaa Xaa Xaa Xaa Xaa Tyr Ser Ile Xaa Xaa Xaa Xaa
145                 150                 155                 160

Xaa Xaa Xaa Xaa Tyr Glu Val Ser Leu Ile Cys Xaa Xaa Xaa Xaa
                165                 170                 175

Xaa Xaa Xaa Xaa Xaa Xaa Lys Glu Thr Phe Thr Thr Gly Gly Gly Thr
            180                 185                 190

Leu Gly His His His His His His His
            195                 200

<210> SEQ ID NO 244
<211> LENGTH: 211
<212> TYPE: PRT
<213> ORGANISM: Artificial Sequence
<220> FEATURE:
<223> OTHER INFORMATION: Description of Artificial Sequence: Synthetic polypeptide
<220> FEATURE:
<221> NAME/KEY: MOD_RES
<222> LOCATION: (5)..(11)
<223> OTHER INFORMATION: Any amino acid and this region may preferably comprise the sequence "Lys Asp Val Thr Asp Thr Thr"
<220> FEATURE:
<221> NAME/KEY: MOD_RES
<222> LOCATION: (17)..(28)
<223> OTHER INFORMATION: Any amino acid and this region may preferably comprise the sequences "Ala Lys Pro Trp Val Asp Pro Pro Pro Leu Trp Gly," "Ser Pro Gly Glu Arg Ile Trp Met Phe Thr Gly," "Ala Lys Pro Glu Lys Trp Asp Gly Ser Ile Tyr Gly,"
<220> FEATURE:
<221> NAME/KEY: MOD_RES
<222> LOCATION: (17)..(28)
<223> OTHER INFORMATION: continued from above, "His Asp Ala Phe Gly Tyr Asp Phe Gly," "Ile Pro Pro His Asn Ala Asp Ser Ser Ile Ile Gly" or "Ala Lys Pro Glu Lys Trp Asp Gly Pro Pro Leu Trp," wherein some positions may be absent
<220> FEATURE:
<221> NAME/KEY: MOD_RES
<222> LOCATION: (32)..(32)

```
<223> OTHER INFORMATION: Ala or Thr
<220> FEATURE:
<221> NAME/KEY: MOD_RES
<222> LOCATION: (36)..(42)
<223> OTHER INFORMATION: Any amino acid and this region may preferably
      comprise the sequence "Lys Asp Val Pro Gly Asp Arg"
<220> FEATURE:
<221> NAME/KEY: MOD_RES
<222> LOCATION: (48)..(53)
<223> OTHER INFORMATION: Any amino acid and this region may preferably
      comprise the sequence "Gln Gln Lys His Thr Ala," "Thr Glu Asp Glu
      Asn Gln," "Asn Ser Arg His Thr Ala," "Pro Asp His Phe His Asn,"
      "Tyr Asp Val Ala Phe Asp" or "Gln Gln Lys His Asn Gln"
<220> FEATURE:
<221> NAME/KEY: MOD_RES
<222> LOCATION: (57)..(64)
<223> OTHER INFORMATION: Any amino acid and this region may preferably
      comprise the sequence "Gly Asn Leu Lys Pro Asp Thr Glu"
<220> FEATURE:
<221> NAME/KEY: MOD_RES
<222> LOCATION: (72)..(82)
<223> OTHER INFORMATION: Any amino acid and this region may preferably
      comprise the sequence "Phe Asp Pro Tyr Gly Ala Lys Ser Asn Pro
      Ala," "Pro Asn Tyr Glu Arg Ile Ser Asn Pro Ala," "Phe Asp Pro Tyr
      Gly Met Arg Ser Lys Pro Ala," "Phe Thr Pro Tyr Gly Ala Lys Ser Asn
      Pro Ala,"
<220> FEATURE:
<221> NAME/KEY: MOD_RES
<222> LOCATION: (72)..(82)
<223> OTHER INFORMATION: continued from above, "Ala Asn Asp His Gly Phe
      Asp Ser Asn Pro Ala," "Asp Thr Phe Tyr Gly Phe Asp Ser Asn Pro
      Ala" "Phe Asp Pro Tyr Asn Lys Arg Asn Val Pro Ala" or "Phe Asp Pro
      Tyr Gly Leu Lys Ser Arg Pro Ala," wherein some positions may be
      absent
<220> FEATURE:
<221> NAME/KEY: MOD_RES
<222> LOCATION: (114)..(120)
<223> OTHER INFORMATION: Any amino acid and this region may preferably
      comprise the sequence "Lys Asp Val Thr Asp Thr Thr"
<220> FEATURE:
<221> NAME/KEY: MOD_RES
<222> LOCATION: (126)..(137)
<223> OTHER INFORMATION: Any amino acid and this region may preferably
      comprise the sequences "Ala Lys Pro Trp Val Asp Pro Pro Leu
      Trp Gly," "Ser Pro Gly Glu Arg Ile Trp Met Phe Thr Gly," "Ala Lys
      Pro Glu Lys Trp Asp Gly Ser Ile Tyr Gly,"
<220> FEATURE:
<221> NAME/KEY: MOD_RES
<222> LOCATION: (126)..(137)
<223> OTHER INFORMATION: continued from above, "His Asp Ala Phe Gly Tyr
      Asp Phe Gly," "Ile Pro Pro His Asn Ala Asp Ser Ser Ile Ile Gly" or
      "Ala Lys Pro Glu Lys Trp Asp Gly Pro Pro Leu Trp," wherein some
      positions may be absent
<220> FEATURE:
<221> NAME/KEY: MOD_RES
<222> LOCATION: (141)..(141)
<223> OTHER INFORMATION: Ala or Thr
<220> FEATURE:
<221> NAME/KEY: MOD_RES
<222> LOCATION: (145)..(151)
<223> OTHER INFORMATION: Any amino acid and this region may preferably
      comprise the sequence "Lys Asp Val Pro Gly Asp Arg"
<220> FEATURE:
<221> NAME/KEY: MOD_RES
<222> LOCATION: (157)..(162)
<223> OTHER INFORMATION: Any amino acid and this region may preferably
      comprise the sequence "Gln Gln Lys His Thr Ala," "Thr Glu Asp Glu
      Asn Gln," "Asn Ser Arg His Thr Ala," "Pro Asp His Phe His Asn,"
      "Tyr Asp Val Ala Phe Asp" or "Gln Gln Lys His Asn Gln"
<220> FEATURE:
<221> NAME/KEY: MOD_RES
<222> LOCATION: (166)..(173)
<223> OTHER INFORMATION: Any amino acid and this region may preferably
      comprise the sequence "Gly Asn Leu Lys Pro Asp Thr Glu"
<220> FEATURE:
<221> NAME/KEY: MOD_RES
<222> LOCATION: (181)..(191)
<223> OTHER INFORMATION: Any amino acid and this region may preferably
      comprise the sequence "Phe Asp Pro Tyr Gly Ala Lys Ser Asn Pro
```

Ala," "Pro Asn Tyr Glu Arg Ile Ser Asn Pro Ala," "Phe Asp Pro Tyr Gly Met Arg Ser Lys Pro Ala," "Phe Thr Pro Tyr Gly Ala Lys Ser Asn Pro Ala,"
<220> FEATURE:
<221> NAME/KEY: MOD_RES
<222> LOCATION: (181)..(191)
<223> OTHER INFORMATION: continued from above, "Ala Asn Asp His Gly Phe Asp Ser Asn Pro Ala," "Asp Thr Phe Tyr Gly Phe Asp Ser Asn Pro Ala" "Phe Asp Pro Tyr Asn Lys Arg Asn Val Pro Ala" or "Phe Asp Pro Tyr Gly Leu Lys Ser Arg Pro Ala," wherein some positions may be absent
<220> FEATURE:
<223> OTHER INFORMATION: See specification as filed for detailed description of substitutions and preferred embodiments

<400> SEQUENCE: 244

Ala Ile Glu Val Xaa Xaa Xaa Xaa Xaa Xaa Xaa Ala Leu Ile Thr Trp
1               5                   10                  15

Xaa Xaa Xaa Xaa Xaa Xaa Xaa Xaa Xaa Xaa Xaa Cys Glu Leu Xaa
            20                  25                  30

Tyr Gly Ile Xaa Xaa Xaa Xaa Xaa Xaa Xaa Thr Thr Ile Asp Leu Xaa
                35                  40                  45

Xaa Xaa Xaa Xaa Xaa Tyr Ser Ile Xaa Xaa Xaa Xaa Xaa Xaa Xaa
    50                  55                  60

Tyr Glu Val Ser Leu Ile Cys Xaa Xaa Xaa Xaa Xaa Xaa Xaa Xaa Xaa
65                  70                  75                  80

Xaa Xaa Lys Glu Thr Phe Thr Thr Gly Gly Gly Ser Gly Gly Gly
            85                  90                  95

Gly Ser Gly Gly Gly Gly Ser Arg Leu Asp Ala Pro Gly Gln Ile Glu
                100                 105                 110

Val Xaa Xaa Xaa Xaa Xaa Xaa Xaa Ala Leu Ile Thr Trp Xaa Xaa Xaa
    115                 120                 125

Xaa Xaa Xaa Xaa Xaa Xaa Xaa Xaa Cys Glu Leu Xaa Tyr Gly Ile
    130                 135                 140

Xaa Xaa Xaa Xaa Xaa Xaa Xaa Thr Thr Ile Asp Leu Xaa Xaa Xaa Xaa
145                 150                 155                 160

Xaa Xaa Tyr Ser Ile Xaa Xaa Xaa Xaa Xaa Xaa Xaa Tyr Glu Val
            165                 170                 175

Ser Leu Ile Cys Xaa Xaa Xaa Xaa Xaa Xaa Xaa Xaa Xaa Xaa Lys
            180                 185                 190

Glu Thr Phe Thr Thr Gly Gly Gly Thr Leu Gly His His His His His
            195                 200                 205

His His His
    210

<210> SEQ ID NO 245
<211> LENGTH: 221
<212> TYPE: PRT
<213> ORGANISM: Artificial Sequence
<220> FEATURE:
<223> OTHER INFORMATION: Description of Artificial Sequence: Synthetic polypeptide
<220> FEATURE:
<221> NAME/KEY: MOD_RES
<222> LOCATION: (5)..(11)
<223> OTHER INFORMATION: Any amino acid and this region may preferably comprise the sequence "Lys Asp Val Thr Asp Thr Thr"
<220> FEATURE:
<221> NAME/KEY: MOD_RES
<222> LOCATION: (17)..(28)
<223> OTHER INFORMATION: Any amino acid and this region may preferably comprise the sequences "Ala Lys Pro Trp Val Asp Pro Pro Leu Trp Gly," "Ser Pro Gly Glu Arg Ile Trp Met Phe Thr Gly," "Ala Lys Pro Glu Lys Trp Asp Gly Ser Ile Tyr Gly,"

```
<220> FEATURE:
<221> NAME/KEY: MOD_RES
<222> LOCATION: (17)..(28)
<223> OTHER INFORMATION: continued from above, "His Asp Ala Phe Gly Tyr
      Asp Phe Gly," "Ile Pro Pro His Asn Ala Asp Ser Ser Ile Ile Gly" or
      "Ala Lys Pro Glu Lys Trp Asp Gly Pro Pro Leu Trp," wherein some
      positions may be absent
<220> FEATURE:
<221> NAME/KEY: MOD_RES
<222> LOCATION: (32)..(32)
<223> OTHER INFORMATION: Ala or Thr
<220> FEATURE:
<221> NAME/KEY: MOD_RES
<222> LOCATION: (36)..(42)
<223> OTHER INFORMATION: Any amino acid and this region may preferably
      comprise the sequence "Lys Asp Val Pro Gly Asp Arg"
<220> FEATURE:
<221> NAME/KEY: MOD_RES
<222> LOCATION: (48)..(53)
<223> OTHER INFORMATION: Any amino acid and this region may preferably
      comprise the sequence "Gln Gln Lys His Thr Ala," "Thr Glu Asp Glu
      Asn Gln," "Asn Ser Arg His Thr Ala," "Pro Asp His Phe His Asn,"
      "Tyr Asp Val Ala Phe Asp" or "Gln Gln Lys His Asn Gln"
<220> FEATURE:
<221> NAME/KEY: MOD_RES
<222> LOCATION: (57)..(64)
<223> OTHER INFORMATION: Any amino acid and this region may preferably
      comprise the sequence "Gly Asn Leu Lys Pro Asp Thr Glu"
<220> FEATURE:
<221> NAME/KEY: MOD_RES
<222> LOCATION: (72)..(82)
<223> OTHER INFORMATION: Any amino acid and this region may preferably
      comprise the sequence "Phe Asp Pro Tyr Gly Ala Lys Ser Asn Pro
      Ala," "Pro Asn Tyr Glu Arg Ile Ser Asn Pro Ala," "Phe Asp Pro Tyr
      Gly Met Arg Ser Lys Pro Ala," "Phe Thr Pro Tyr Gly Ala Lys Ser Asn
      Pro Ala,"
<220> FEATURE:
<221> NAME/KEY: MOD_RES
<222> LOCATION: (72)..(82)
<223> OTHER INFORMATION: continued from above, "Ala Asn Asp His Gly Phe
      Asp Ser Asn Pro Ala," "Asp Thr Phe Tyr Gly Phe Asp Ser Asn Pro
      Ala" "Phe Asp Pro Tyr Asn Lys Arg Asn Val Pro Ala" or "Phe Asp Pro
      Tyr Gly Leu Lys Ser Arg Pro Ala," wherein some positions may be
      absent
<220> FEATURE:
<221> NAME/KEY: MOD_RES
<222> LOCATION: (124)..(130)
<223> OTHER INFORMATION: Any amino acid and this region may preferably
      comprise the sequence "Lys Asp Val Thr Asp Thr Thr"
<220> FEATURE:
<221> NAME/KEY: MOD_RES
<222> LOCATION: (136)..(147)
<223> OTHER INFORMATION: Any amino acid and this region may preferably
      comprise the sequences "Ala Lys Pro Trp Val Asp Pro Pro Leu
      Trp Gly," "Ser Pro Gly Glu Arg Ile Trp Met Phe Thr Gly," "Ala Lys
      Pro Glu Lys Trp Asp Gly Ser Ile Tyr Gly,"
<220> FEATURE:
<221> NAME/KEY: MOD_RES
<222> LOCATION: (136)..(147)
<223> OTHER INFORMATION: continued from above, "His Asp Ala Phe Gly Tyr
      Asp Phe Gly," "Ile Pro Pro His Asn Ala Asp Ser Ser Ile Ile Gly" or
      "Ala Lys Pro Glu Lys Trp Asp Gly Pro Pro Leu Trp," wherein some
      positions may be absent
<220> FEATURE:
<221> NAME/KEY: MOD_RES
<222> LOCATION: (151)..(151)
<223> OTHER INFORMATION: Ala or Thr
<220> FEATURE:
<221> NAME/KEY: MOD_RES
<222> LOCATION: (155)..(161)
<223> OTHER INFORMATION: Any amino acid and this region may preferably
      comprise the sequence "Lys Asp Val Pro Gly Asp Arg"
<220> FEATURE:
<221> NAME/KEY: MOD_RES
<222> LOCATION: (167)..(172)
<223> OTHER INFORMATION: Any amino acid and this region may preferably
      comprise the sequence "Gln Gln Lys His Thr Ala," "Thr Glu Asp Glu
      Asn Gln," "Asn Ser Arg His Thr Ala," "Pro Asp His Phe His Asn,"
      "Tyr Asp Val Ala Phe Asp" or "Gln Gln Lys His Asn Gln"
```

```
<220> FEATURE:
<221> NAME/KEY: MOD_RES
<222> LOCATION: (176)..(183)
<223> OTHER INFORMATION: Any amino acid and this region may preferably
      comprise the sequence "Gly Asn Leu Lys Pro Asp Thr Glu"
<220> FEATURE:
<221> NAME/KEY: MOD_RES
<222> LOCATION: (191)..(201)
<223> OTHER INFORMATION: Any amino acid and this region may preferably
      comprise the sequence "Phe Asp Pro Tyr Gly Ala Lys Ser Asn Pro
      Ala," "Pro Asn Tyr Glu Arg Ile Ser Asn Pro Ala," "Phe Asp Pro Tyr
      Gly Met Arg Ser Lys Pro Ala," "Phe Thr Pro Tyr Gly Ala Lys Ser Asn
      Pro Ala,"
<220> FEATURE:
<221> NAME/KEY: MOD_RES
<222> LOCATION: (191)..(201)
<223> OTHER INFORMATION: continued from above, "Ala Asn Asp His Gly Phe
      Asp Ser Asn Pro Ala," "Asp Thr Phe Tyr Gly Phe Asp Ser Asn Pro
      Ala" "Phe Asp Pro Tyr Asn Lys Arg Asn Val Pro Ala" or "Phe Asp Pro
      Tyr Gly Leu Lys Ser Arg Pro Ala," wherein some positions may be
      absent
<220> FEATURE:
<223> OTHER INFORMATION: See specification as filed for detailed
      description of substitutions and preferred embodiments

<400> SEQUENCE: 245

Ala Ile Glu Val Xaa Xaa Xaa Xaa Xaa Xaa Xaa Ala Leu Ile Thr Trp
 1               5                   10                  15

Xaa Xaa Xaa Xaa Xaa Xaa Xaa Xaa Xaa Xaa Xaa Cys Glu Leu Xaa
            20                  25                  30

Tyr Gly Ile Xaa Xaa Xaa Xaa Xaa Xaa Thr Thr Ile Asp Leu Xaa
        35                  40                  45

Xaa Xaa Xaa Xaa Xaa Tyr Ser Ile Xaa Xaa Xaa Xaa Xaa Xaa Xaa
50                  55                  60

Tyr Glu Val Ser Leu Ile Cys Xaa Xaa Xaa Xaa Xaa Xaa Xaa Xaa
65                  70                  75                  80

Xaa Xaa Lys Glu Thr Phe Thr Thr Gly Gly Gly Ser Gly Gly Gly
            85                  90                  95

Gly Ser Gly Gly Gly Gly Ser Gly Gly Gly Ser Gly Gly Gly Gly
            100                 105                 110

Ser Arg Leu Asp Ala Pro Gly Gln Ile Glu Val Xaa Xaa Xaa Xaa Xaa
            115                 120                 125

Xaa Xaa Ala Leu Ile Thr Trp Xaa Xaa Xaa Xaa Xaa Xaa Xaa Xaa Xaa
145             130                 135                 140

Xaa Xaa Xaa Cys Glu Leu Xaa Tyr Gly Ile Xaa Xaa Xaa Xaa Xaa Xaa
145                 150                 155                 160

Xaa Thr Thr Ile Asp Leu Xaa Xaa Xaa Xaa Xaa Xaa Tyr Ser Ile Xaa
                165                 170                 175

Xaa Xaa Xaa Xaa Xaa Xaa Xaa Tyr Glu Val Ser Leu Ile Cys Xaa Xaa
            180                 185                 190

Xaa Xaa Xaa Xaa Xaa Xaa Xaa Xaa Lys Glu Thr Phe Thr Thr Gly
        195                 200                 205

Gly Gly Thr Leu Gly His His His His His His
210                 215                 220

<210> SEQ ID NO 246
<211> LENGTH: 231
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
```

```
<222> LOCATION: (5)..(11)
<223> OTHER INFORMATION: Any amino acid and this region may preferably
      comprise the sequence "Lys Asp Val Thr Asp Thr Thr"
<220> FEATURE:
<221> NAME/KEY: MOD_RES
<222> LOCATION: (17)..(28)
<223> OTHER INFORMATION: Any amino acid and this region may preferably
      comprise the sequences "Ala Lys Pro Trp Val Asp Pro Pro Leu
      Trp Gly," "Ser Pro Gly Glu Arg Ile Trp Met Phe Thr Gly," "Ala Lys
      Pro Glu Lys Trp Asp Gly Ser Ile Tyr Gly,"
<220> FEATURE:
<221> NAME/KEY: MOD_RES
<222> LOCATION: (17)..(28)
<223> OTHER INFORMATION: continued from above, "His Asp Ala Phe Gly Tyr
      Asp Phe Gly," "Ile Pro Pro His Asn Ala Asp Ser Ser Ile Ile Gly" or
      "Ala Lys Pro Glu Lys Trp Asp Gly Pro Pro Leu Trp," wherein some
      positions may be absent
<220> FEATURE:
<221> NAME/KEY: MOD_RES
<222> LOCATION: (32)..(32)
<223> OTHER INFORMATION: Ala or Thr
<220> FEATURE:
<221> NAME/KEY: MOD_RES
<222> LOCATION: (36)..(42)
<223> OTHER INFORMATION: Any amino acid and this region may preferably
      comprise the sequence "Lys Asp Val Pro Gly Asp Arg"
<220> FEATURE:
<221> NAME/KEY: MOD_RES
<222> LOCATION: (48)..(53)
<223> OTHER INFORMATION: Any amino acid and this region may preferably
      comprise the sequence "Gln Gln Lys His Thr Ala," "Thr Glu Asp Glu
      Asn Gln," "Asn Ser Arg His Thr Ala," "Pro Asp His Phe His Asn,"
      "Tyr Asp Val Ala Phe Asp" or "Gln Gln Lys His Asn Gln"
<220> FEATURE:
<221> NAME/KEY: MOD_RES
<222> LOCATION: (57)..(64)
<223> OTHER INFORMATION: Any amino acid and this region may preferably
      comprise the sequence "Gly Asn Leu Lys Pro Asp Thr Glu"
<220> FEATURE:
<221> NAME/KEY: MOD_RES
<222> LOCATION: (72)..(82)
<223> OTHER INFORMATION: Any amino acid and this region may preferably
      comprise the sequence "Phe Asp Pro Tyr Gly Ala Lys Ser Asn Pro
      Ala," "Pro Asn Tyr Glu Arg Ile Ser Asn Pro Ala," "Phe Asp Pro Tyr
      Gly Met Arg Ser Lys Pro Ala," "Phe Thr Pro Tyr Gly Ala Lys Ser Asn
      Pro Ala,"
<220> FEATURE:
<221> NAME/KEY: MOD_RES
<222> LOCATION: (72)..(82)
<223> OTHER INFORMATION: continued from above, "Ala Asn Asp His Gly Phe
      Asp Ser Asn Pro Ala," "Asp Thr Phe Tyr Gly Phe Asp Ser Asn Pro
      Ala" "Phe Asp Pro Tyr Asn Lys Arg Asn Val Pro Ala" or "Phe Asp Pro
      Tyr Gly Leu Lys Ser Arg Pro Ala," wherein some positions may be
      absent
<220> FEATURE:
<221> NAME/KEY: MOD_RES
<222> LOCATION: (134)..(140)
<223> OTHER INFORMATION: Any amino acid and this region may preferably
      comprise the sequence "Lys Asp Val Thr Asp Thr Thr"
<220> FEATURE:
<221> NAME/KEY: MOD_RES
<222> LOCATION: (146)..(157)
<223> OTHER INFORMATION: Any amino acid and this region may preferably
      comprise the sequences "Ala Lys Pro Trp Val Asp Pro Pro Leu
      Trp Gly," "Ser Pro Gly Glu Arg Ile Trp Met Phe Thr Gly," "Ala Lys
      Pro Glu Lys Trp Asp Gly Ser Ile Tyr Gly,"
<220> FEATURE:
<221> NAME/KEY: MOD_RES
<222> LOCATION: (146)..(157)
<223> OTHER INFORMATION: continued from above, "His Asp Ala Phe Gly Tyr
      Asp Phe Gly," "Ile Pro Pro His Asn Ala Asp Ser Ser Ile Ile Gly" or
      "Ala Lys Pro Glu Lys Trp Asp Gly Pro Pro Leu Trp," wherein some
      positions may be absent
<220> FEATURE:
<221> NAME/KEY: MOD_RES
<222> LOCATION: (161)..(161)
<223> OTHER INFORMATION: Ala or Thr
<220> FEATURE:
<221> NAME/KEY: MOD_RES
```

-continued

```
<222> LOCATION: (165)..(171)
<223> OTHER INFORMATION: Any amino acid and this region may preferably
      comprise the sequence "Lys Asp Val Pro Gly Asp Arg"
<220> FEATURE:
<221> NAME/KEY: MOD_RES
<222> LOCATION: (177)..(182)
<223> OTHER INFORMATION: Any amino acid and this region may preferably
      comprise the sequence "Gln Gln Lys His Thr Ala," "Thr Glu Asp Glu
      Asn Gln," "Asn Ser Arg His Thr Ala," "Pro Asp His Phe His Asn,"
      "Tyr Asp Val Ala Phe Asp" or "Gln Gln Lys His Asn Gln"
<220> FEATURE:
<221> NAME/KEY: MOD_RES
<222> LOCATION: (186)..(193)
<223> OTHER INFORMATION: Any amino acid and this region may preferably
      comprise the sequence "Gly Asn Leu Lys Pro Asp Thr Glu"
<220> FEATURE:
<221> NAME/KEY: MOD_RES
<222> LOCATION: (201)..(211)
<223> OTHER INFORMATION: Any amino acid and this region may preferably
      comprise the sequence "Phe Asp Pro Tyr Gly Ala Lys Ser Asn Pro
      Ala," "Pro Asn Tyr Glu Arg Ile Ser Asn Pro Ala," "Phe Asp Pro Tyr
      Gly Met Arg Ser Lys Pro Ala," "Phe Thr Pro Tyr Gly Ala Lys Ser Asn
      Pro Ala,"
<220> FEATURE:
<221> NAME/KEY: MOD_RES
<222> LOCATION: (201)..(211)
<223> OTHER INFORMATION: continued from above, "Ala Asn Asp His Gly Phe
      Asp Ser Asn Pro Ala," "Asp Thr Phe Tyr Gly Phe Asp Ser Asn Pro
      Ala" "Phe Asp Pro Tyr Asn Lys Arg Asn Val Pro Ala" or "Phe Asp Pro
      Tyr Gly Leu Lys Ser Arg Pro Ala," wherein some positions may be
      absent
<220> FEATURE:
<223> OTHER INFORMATION: See specification as filed for detailed
      description of substitutions and preferred embodiments

<400> SEQUENCE: 246

Ala Ile Glu Val Xaa Xaa Xaa Xaa Xaa Xaa Ala Leu Ile Thr Trp
1               5                   10                  15

Xaa Xaa Xaa Xaa Xaa Xaa Xaa Xaa Xaa Xaa Xaa Cys Glu Leu Xaa
            20                  25                  30

Tyr Gly Ile Xaa Xaa Xaa Xaa Xaa Xaa Xaa Thr Thr Ile Asp Leu Xaa
            35                  40                  45

Xaa Xaa Xaa Xaa Xaa Tyr Ser Ile Xaa Xaa Xaa Xaa Xaa Xaa Xaa
        50                  55                  60

Tyr Glu Val Ser Leu Ile Cys Xaa Xaa Xaa Xaa Xaa Xaa Xaa Xaa
65                  70                  75                  80

Xaa Xaa Lys Glu Thr Phe Thr Thr Gly Gly Gly Gly Ser Gly Gly Gly
                85                  90                  95

Gly Ser Gly Gly Gly Gly Ser Gly Gly Gly Ser Gly Gly Gly Gly
            100                 105                 110

Ser Gly Gly Gly Gly Ser Gly Gly Gly Ser Arg Leu Asp Ala Pro
            115                 120                 125

Gly Gln Ile Glu Val Xaa Xaa Xaa Xaa Xaa Xaa Xaa Ala Leu Ile Thr
130                 135                 140

Trp Xaa Xaa Xaa Xaa Xaa Xaa Xaa Xaa Xaa Xaa Xaa Cys Glu Leu
145                 150                 155                 160

Xaa Tyr Gly Ile Xaa Xaa Xaa Xaa Xaa Xaa Xaa Thr Thr Ile Asp Leu
                165                 170                 175

Xaa Xaa Xaa Xaa Xaa Xaa Tyr Ser Ile Xaa Xaa Xaa Xaa Xaa Xaa
            180                 185                 190

Xaa Tyr Glu Val Ser Leu Ile Cys Xaa Xaa Xaa Xaa Xaa Xaa Xaa
            195                 200                 205

Xaa Xaa Xaa Lys Glu Thr Phe Thr Thr Gly Gly Gly Thr Leu Gly His
210                 215                 220
```

His His His His His His His
225                 230

<210> SEQ ID NO 247
<211> LENGTH: 197
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (5)..(11)
<223> OTHER INFORMATION: Any amino acid and this region may preferably
      comprise the sequence "Lys Asp Val Thr Asp Thr Thr"
<220> FEATURE:
<221> NAME/KEY: MOD_RES
<222> LOCATION: (17)..(28)
<223> OTHER INFORMATION: Any amino acid and this region may preferably
      comprise the sequences "Ala Lys Pro Trp Val Asp Pro Pro Pro Leu
      Trp Gly," "Ser Pro Gly Glu Arg Ile Trp Met Phe Thr Gly," "Ala Lys
      Pro Glu Lys Trp Asp Gly Ser Ile Tyr Gly,"
<220> FEATURE:
<221> NAME/KEY: MOD_RES
<222> LOCATION: (17)..(28)
<223> OTHER INFORMATION: continued from above, "His Asp Ala Phe Gly Tyr
      Asp Phe Gly," "Ile Pro Pro His Asn Ala Asp Ser Ser Ile Ile Gly" or
      "Ala Lys Pro Glu Lys Trp Asp Gly Pro Pro Leu Trp," wherein some
      positions may be absent
<220> FEATURE:
<221> NAME/KEY: MOD_RES
<222> LOCATION: (32)..(32)
<223> OTHER INFORMATION: Ala or Thr
<220> FEATURE:
<221> NAME/KEY: MOD_RES
<222> LOCATION: (36)..(42)
<223> OTHER INFORMATION: Any amino acid and this region may preferably
      comprise the sequence "Lys Asp Val Pro Gly Asp Arg"
<220> FEATURE:
<221> NAME/KEY: MOD_RES
<222> LOCATION: (48)..(53)
<223> OTHER INFORMATION: Any amino acid and this region may preferably
      comprise the sequence "Gln Gln Lys His Thr Ala," "Thr Glu Asp Glu
      Asn Gln," "Asn Ser Arg His Thr Ala," "Pro Asp His Phe His Asn,"
      "Tyr Asp Val Ala Phe Asp" or "Gln Gln Lys His Asn Gln"
<220> FEATURE:
<221> NAME/KEY: MOD_RES
<222> LOCATION: (57)..(64)
<223> OTHER INFORMATION: Any amino acid and this region may preferably
      comprise the sequence "Gly Asn Leu Lys Pro Asp Thr Glu"
<220> FEATURE:
<221> NAME/KEY: MOD_RES
<222> LOCATION: (72)..(82)
<223> OTHER INFORMATION: Any amino acid and this region may preferably
      comprise the sequence "Phe Asp Pro Tyr Gly Ala Lys Ser Asn Pro
      Ala," "Pro Asn Tyr Glu Arg Ile Ser Asn Pro Ala," "Phe Asp Pro Tyr
      Gly Met Arg Ser Lys Pro Ala," "Phe Thr Pro Tyr Gly Ala Lys Ser Asn
      Pro Ala,"
<220> FEATURE:
<221> NAME/KEY: MOD_RES
<222> LOCATION: (72)..(82)
<223> OTHER INFORMATION: continued from above, "Ala Asn Asp His Gly Phe
      Asp Ser Asn Pro Ala," "Asp Thr Phe Tyr Gly Phe Asp Ser Asn Pro
      Ala" "Phe Asp Pro Tyr Asn Lys Arg Asn Val Pro Ala" or "Phe Asp Pro
      Tyr Gly Leu Lys Ser Arg Pro Ala," wherein some positions may be
      absent
<220> FEATURE:
<221> NAME/KEY: MOD_RES
<222> LOCATION: (100)..(106)
<223> OTHER INFORMATION: Any amino acid and this region may preferably
      comprise the sequence "Lys Asp Val Thr Asp Thr Thr"
<220> FEATURE:
<221> NAME/KEY: MOD_RES
<222> LOCATION: (112)..(123)
<223> OTHER INFORMATION: Any amino acid and this region may preferably
      comprise the sequences "Ala Lys Pro Trp Val Asp Pro Pro Pro Leu
      Trp Gly," "Ser Pro Gly Glu Arg Ile Trp Met Phe Thr Gly," "Ala Lys
      Pro Glu Lys Trp Asp Gly Ser Ile Tyr Gly,"

```
<220> FEATURE:
<221> NAME/KEY: MOD_RES
<222> LOCATION: (112)..(123)
<223> OTHER INFORMATION: continued from above, "His Asp Ala Phe Gly Tyr
      Asp Phe Gly," "Ile Pro Pro His Asn Ala Asp Ser Ser Ile Ile Gly" or
      "Ala Lys Pro Glu Lys Trp Asp Gly Pro Pro Leu Trp," wherein some
      positions may be absent
<220> FEATURE:
<221> NAME/KEY: MOD_RES
<222> LOCATION: (127)..(127)
<223> OTHER INFORMATION: Ala or Thr
<220> FEATURE:
<221> NAME/KEY: MOD_RES
<222> LOCATION: (131)..(137)
<223> OTHER INFORMATION: Any amino acid and this region may preferably
      comprise the sequence "Lys Asp Val Pro Gly Asp Arg"
<220> FEATURE:
<221> NAME/KEY: MOD_RES
<222> LOCATION: (143)..(148)
<223> OTHER INFORMATION: Any amino acid and this region may preferably
      comprise the sequence "Gln Gln Lys His Thr Ala," "Thr Glu Asp Glu
      Asn Gln," "Asn Ser Arg His Thr Ala," "Pro Asp His Phe His Asn,"
      "Tyr Asp Val Ala Phe Asp" or "Gln Gln Lys His Asn Gln"
<220> FEATURE:
<221> NAME/KEY: MOD_RES
<222> LOCATION: (152)..(159)
<223> OTHER INFORMATION: Any amino acid and this region may preferably
      comprise the sequence "Gly Asn Leu Lys Pro Asp Thr Glu"
<220> FEATURE:
<221> NAME/KEY: MOD_RES
<222> LOCATION: (167)..(177)
<223> OTHER INFORMATION: Any amino acid and this region may preferably
      comprise the sequence "Phe Asp Pro Tyr Gly Ala Lys Ser Asn Pro
      Ala," "Pro Asn Tyr Glu Arg Ile Ser Asn Pro Ala," "Phe Asp Pro Tyr
      Gly Met Arg Ser Lys Pro Ala," "Phe Thr Pro Tyr Gly Ala Lys Ser Asn
      Pro Ala,"
<220> FEATURE:
<221> NAME/KEY: MOD_RES
<222> LOCATION: (167)..(177)
<223> OTHER INFORMATION: continued from above, "Ala Asn Asp His Gly Phe
      Asp Ser Asn Pro Ala," "Asp Thr Phe Tyr Gly Phe Asp Ser Asn Pro
      Ala" "Phe Asp Pro Tyr Asn Lys Arg Asn Val Pro Ala" or "Phe Asp Pro
      Tyr Gly Leu Lys Ser Arg Pro Ala," wherein some positions may be
      absent
<220> FEATURE:
<223> OTHER INFORMATION: See specification as filed for detailed
      description of substitutions and preferred embodiments

<400> SEQUENCE: 247

Ala Ile Glu Val Xaa Xaa Xaa Xaa Xaa Xaa Xaa Ala Leu Ile Thr Trp
1               5                   10                  15

Xaa Xaa Xaa Xaa Xaa Xaa Xaa Xaa Xaa Xaa Xaa Cys Glu Leu Xaa
            20                  25                  30

Tyr Gly Ile Xaa Xaa Xaa Xaa Xaa Xaa Xaa Thr Thr Ile Asp Leu Xaa
                35                  40                  45

Xaa Xaa Xaa Xaa Xaa Tyr Ser Ile Xaa Xaa Xaa Xaa Xaa Xaa Xaa Xaa
    50                  55                  60

Tyr Glu Val Ser Leu Ile Cys Xaa Xaa Xaa Xaa Xaa Xaa Xaa Xaa Xaa
65                  70                  75                  80

Xaa Xaa Lys Glu Thr Phe Thr Thr Thr Arg Leu Asp Ala Pro Gly Gln
                85                  90                  95

Ile Glu Val Xaa Xaa Xaa Xaa Xaa Xaa Xaa Ala Leu Ile Thr Trp Xaa
            100                 105                 110

Xaa Xaa Xaa Xaa Xaa Xaa Xaa Xaa Xaa Xaa Cys Glu Leu Xaa Tyr
        115                 120                 125

Gly Ile Xaa Xaa Xaa Xaa Xaa Xaa Xaa Thr Thr Ile Asp Leu Xaa Xaa
    130                 135                 140

Xaa Xaa Xaa Xaa Tyr Ser Ile Xaa Xaa Xaa Xaa Xaa Xaa Xaa Tyr
145                 150                 155                 160
```

```
Glu Val Ser Leu Ile Cys Xaa Xaa Xaa Xaa Xaa Xaa Xaa Xaa Xaa
                165                 170                 175

Xaa Lys Glu Thr Phe Thr Thr Gly Gly Gly Thr Leu Gly His His His
        180                 185                 190

His His His His His
        195

<210> SEQ ID NO 248
<211> LENGTH: 201
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (5)..(11)
<223> OTHER INFORMATION: Any amino acid and this region may preferably
      comprise the sequence "Lys Asp Val Thr Asp Thr Thr"
<220> FEATURE:
<221> NAME/KEY: MOD_RES
<222> LOCATION: (17)..(28)
<223> OTHER INFORMATION: Any amino acid and this region may preferably
      comprise the sequences "Ala Lys Pro Trp Val Asp Pro Pro Pro Leu
      Trp Gly," "Ser Pro Gly Glu Arg Ile Trp Met Phe Thr Gly," "Ala Lys
      Pro Glu Lys Trp Asp Gly Ser Ile Tyr Gly,"
<220> FEATURE:
<221> NAME/KEY: MOD_RES
<222> LOCATION: (17)..(28)
<223> OTHER INFORMATION: continued from above, "His Asp Ala Phe Gly Tyr
      Asp Phe Gly," "Ile Pro Pro His Asn Ala Asp Ser Ser Ile Ile Gly" or
      "Ala Lys Pro Glu Lys Trp Asp Gly Pro Pro Leu Trp," wherein some
      positions may be absent
<220> FEATURE:
<221> NAME/KEY: MOD_RES
<222> LOCATION: (32)..(32)
<223> OTHER INFORMATION: Ala or Thr
<220> FEATURE:
<221> NAME/KEY: MOD_RES
<222> LOCATION: (36)..(42)
<223> OTHER INFORMATION: Any amino acid and this region may preferably
      comprise the sequence "Lys Asp Val Pro Gly Asp Arg"
<220> FEATURE:
<221> NAME/KEY: MOD_RES
<222> LOCATION: (48)..(53)
<223> OTHER INFORMATION: Any amino acid and this region may preferably
      comprise the sequence "Gln Gln Lys His Thr Ala," "Thr Glu Asp Glu
      Asn Gln," "Asn Ser Arg His Thr Ala," "Pro Asp His Phe His Asn,"
      "Tyr Asp Val Ala Phe Asp" or "Gln Gln Lys His Asn Gln"
<220> FEATURE:
<221> NAME/KEY: MOD_RES
<222> LOCATION: (57)..(64)
<223> OTHER INFORMATION: Any amino acid and this region may preferably
      comprise the sequence "Gly Asn Leu Lys Pro Asp Thr Glu"
<220> FEATURE:
<221> NAME/KEY: MOD_RES
<222> LOCATION: (72)..(82)
<223> OTHER INFORMATION: Any amino acid and this region may preferably
      comprise the sequence "Phe Asp Pro Tyr Gly Ala Lys Ser Asn Pro
      Ala," "Pro Asn Tyr Glu Arg Ile Ser Asn Pro Ala," "Phe Asp Pro Tyr
      Gly Met Arg Ser Lys Pro Ala," "Phe Thr Pro Tyr Gly Ala Lys Ser Asn
      Pro Ala,"
<220> FEATURE:
<221> NAME/KEY: MOD_RES
<222> LOCATION: (72)..(82)
<223> OTHER INFORMATION: continued from above, "Ala Asn Asp His Gly Phe
      Asp Ser Asn Pro Ala," "Asp Thr Phe Tyr Gly Phe Asp Ser Asn Pro
      Ala" "Phe Asp Pro Tyr Asn Lys Arg Asn Val Pro Ala" or "Phe Asp Pro
      Tyr Gly Leu Lys Ser Arg Pro Ala," wherein some positions may be
      absent
<220> FEATURE:
<221> NAME/KEY: MOD_RES
<222> LOCATION: (104)..(110)
<223> OTHER INFORMATION: Any amino acid and this region may preferably
      comprise the sequence "Lys Asp Val Thr Asp Thr Thr"
```

-continued

```
<220> FEATURE:
<221> NAME/KEY: MOD_RES
<222> LOCATION: (116)..(127)
<223> OTHER INFORMATION: Any amino acid and this region may preferably
      comprise the sequences "Ala Lys Pro Trp Val Asp Pro Pro Leu
      Trp Gly," "Ser Pro Gly Glu Arg Ile Trp Met Phe Thr Gly," "Ala Lys
      Pro Glu Lys Trp Asp Gly Ser Ile Tyr Gly,"
<220> FEATURE:
<221> NAME/KEY: MOD_RES
<222> LOCATION: (116)..(127)
<223> OTHER INFORMATION: continued from above, "His Asp Ala Phe Gly Tyr
      Asp Phe Gly," "Ile Pro Pro His Asn Ala Asp Ser Ser Ile Ile Gly" or
      "Ala Lys Pro Glu Lys Trp Asp Gly Pro Pro Leu Trp," wherein some
      positions may be absent
<220> FEATURE:
<221> NAME/KEY: MOD_RES
<222> LOCATION: (131)..(131)
<223> OTHER INFORMATION: Ala or Thr
<220> FEATURE:
<221> NAME/KEY: MOD_RES
<222> LOCATION: (135)..(141)
<223> OTHER INFORMATION: Any amino acid and this region may preferably
      comprise the sequence "Lys Asp Val Pro Gly Asp Arg"
<220> FEATURE:
<221> NAME/KEY: MOD_RES
<222> LOCATION: (147)..(152)
<223> OTHER INFORMATION: Any amino acid and this region may preferably
      comprise the sequence "Gln Gln Lys His Thr Ala," "Thr Glu Asp Glu
      Asn Gln," "Asn Ser Arg His Thr Ala," "Pro Asp His Phe His Asn,"
      "Tyr Asp Val Ala Phe Asp" or "Gln Gln Lys His Asn Gln"
<220> FEATURE:
<221> NAME/KEY: MOD_RES
<222> LOCATION: (156)..(163)
<223> OTHER INFORMATION: Any amino acid and this region may preferably
      comprise the sequence "Gly Asn Leu Lys Pro Asp Thr Glu"
<220> FEATURE:
<221> NAME/KEY: MOD_RES
<222> LOCATION: (171)..(181)
<223> OTHER INFORMATION: Any amino acid and this region may preferably
      comprise the sequence "Phe Asp Pro Tyr Gly Ala Lys Ser Asn Pro
      Ala," "Pro Asn Tyr Glu Arg Ile Ser Asn Pro Ala," "Phe Asp Pro Tyr
      Gly Met Arg Ser Lys Pro Ala," "Phe Thr Pro Tyr Gly Ala Lys Ser Asn
      Pro Ala,"
<220> FEATURE:
<221> NAME/KEY: MOD_RES
<222> LOCATION: (171)..(181)
<223> OTHER INFORMATION: continued from above, "Ala Asn Asp His Gly Phe
      Asp Ser Asn Pro Ala," "Asp Thr Phe Tyr Gly Phe Asp Ser Asn Pro
      Ala" "Phe Asp Pro Tyr Asn Lys Arg Asn Val Pro Ala" or "Phe Asp Pro
      Tyr Gly Leu Lys Ser Arg Pro Ala," wherein some positions may be
      absent
<220> FEATURE:
<223> OTHER INFORMATION: See specification as filed for detailed
      description of substitutions and preferred embodiments

<400> SEQUENCE: 248

Ala Ile Glu Val Xaa Xaa Xaa Xaa Xaa Xaa Xaa Ala Leu Ile Thr Trp
1               5                   10                  15

Xaa Xaa Xaa Xaa Xaa Xaa Xaa Xaa Xaa Xaa Xaa Xaa Cys Glu Leu Xaa
            20                  25                  30

Tyr Gly Ile Xaa Xaa Xaa Xaa Xaa Xaa Xaa Thr Thr Ile Asp Leu Xaa
            35                  40                  45

Xaa Xaa Xaa Xaa Xaa Tyr Ser Ile Xaa Xaa Xaa Xaa Xaa Xaa Xaa Xaa
        50                  55                  60

Tyr Glu Val Ser Leu Ile Cys Xaa Xaa Xaa Xaa Xaa Xaa Xaa Xaa Xaa
65                  70                  75                  80

Xaa Xaa Lys Glu Thr Phe Thr Thr Gly Gly Gly Gly Ser Arg Leu Asp
            85                  90                  95

Ala Pro Gly Gln Ile Glu Val Xaa Xaa Xaa Xaa Xaa Xaa Xaa Ala Leu
            100                 105                 110

Ile Thr Trp Xaa Xaa Xaa Xaa Xaa Xaa Xaa Xaa Xaa Xaa Xaa Xaa Cys
```

```
                115                 120                 125
Glu Leu Xaa Tyr Gly Ile Xaa Xaa Xaa Xaa Xaa Xaa Thr Thr Ile
        130                 135                 140

Asp Leu Xaa Xaa Xaa Xaa Xaa Xaa Tyr Ser Ile Xaa Xaa Xaa Xaa
145                 150                 155                 160

Xaa Xaa Xaa Tyr Glu Val Ser Leu Ile Cys Xaa Xaa Xaa Xaa Xaa
                165                 170                 175

Xaa Xaa Xaa Xaa Xaa Lys Glu Thr Phe Thr Thr Gly Gly Thr Leu
            180                 185                 190

Gly His His His His His His His
        195                 200

<210> SEQ ID NO 249
<211> LENGTH: 206
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (5)..(11)
<223> OTHER INFORMATION: Any amino acid and this region may preferably
      comprise the sequence "Lys Asp Val Thr Asp Thr Thr"
<220> FEATURE:
<221> NAME/KEY: MOD_RES
<222> LOCATION: (17)..(28)
<223> OTHER INFORMATION: Any amino acid and this region may preferably
      comprise the sequences "Ala Lys Pro Trp Val Asp Pro Pro Leu
      Trp Gly," "Ser Pro Gly Glu Arg Ile Trp Met Phe Thr Gly," "Ala Lys
      Pro Glu Lys Trp Asp Gly Ser Ile Tyr Gly,"
<220> FEATURE:
<221> NAME/KEY: MOD_RES
<222> LOCATION: (17)..(28)
<223> OTHER INFORMATION: continued from above, "His Asp Ala Phe Gly Tyr
      Asp Phe Gly," "Ile Pro Pro His Asn Ala Asp Ser Ser Ile Ile Gly" or
      "Ala Lys Pro Glu Lys Trp Asp Gly Pro Pro Leu Trp," wherein some
      positions may be absent
<220> FEATURE:
<221> NAME/KEY: MOD_RES
<222> LOCATION: (32)..(32)
<223> OTHER INFORMATION: Ala or Thr
<220> FEATURE:
<221> NAME/KEY: MOD_RES
<222> LOCATION: (36)..(42)
<223> OTHER INFORMATION: Any amino acid and this region may preferably
      comprise the sequence "Lys Asp Val Pro Gly Asp Arg"
<220> FEATURE:
<221> NAME/KEY: MOD_RES
<222> LOCATION: (48)..(53)
<223> OTHER INFORMATION: Any amino acid and this region may preferably
      comprise the sequence "Gln Gln Lys His Thr Ala," "Thr Glu Asp Glu
      Asn Gln," "Asn Ser Arg His Thr Ala," "Pro Asp His Phe His Asn,"
      "Tyr Asp Val Ala Phe Asp" or "Gln Gln Lys His Asn Gln"
<220> FEATURE:
<221> NAME/KEY: MOD_RES
<222> LOCATION: (57)..(64)
<223> OTHER INFORMATION: Any amino acid and this region may preferably
      comprise the sequence "Gly Asn Leu Lys Pro Asp Thr Glu"
<220> FEATURE:
<221> NAME/KEY: MOD_RES
<222> LOCATION: (72)..(82)
<223> OTHER INFORMATION: Any amino acid and this region may preferably
      comprise the sequence "Phe Asp Pro Tyr Gly Ala Lys Ser Asn Pro
      Ala," "Pro Asn Tyr Glu Arg Ile Ser Asn Pro Ala," "Phe Asp Pro Tyr
      Gly Met Arg Ser Lys Pro Ala," "Phe Thr Pro Tyr Gly Ala Lys Ser Asn
      Pro Ala,"
<220> FEATURE:
<221> NAME/KEY: MOD_RES
<222> LOCATION: (72)..(82)
<223> OTHER INFORMATION: continued from above, "Ala Asn Asp His Gly Phe
      Asp Ser Asn Pro Ala," "Asp Thr Phe Tyr Gly Phe Asp Ser Asn Pro
      Ala" "Phe Asp Pro Tyr Asn Lys Arg Asn Val Pro Ala" or "Phe Asp Pro
```

-continued

```
      Tyr Gly Leu Lys Ser Arg Pro Ala," wherein some positions may be
      absent
<220> FEATURE:
<221> NAME/KEY: MOD_RES
<222> LOCATION: (109)..(115)
<223> OTHER INFORMATION: Any amino acid and this region may preferably
      comprise the sequence "Lys Asp Val Thr Asp Thr Thr"
<220> FEATURE:
<221> NAME/KEY: MOD_RES
<222> LOCATION: (121)..(132)
<223> OTHER INFORMATION: Any amino acid and this region may preferably
      comprise the sequences "Ala Lys Pro Trp Val Asp Pro Pro Pro Leu
      Trp Gly," "Ser Pro Gly Glu Arg Ile Trp Met Phe Thr Gly," "Ala Lys
      Pro Glu Lys Trp Asp Gly Ser Ile Tyr Gly,"
<220> FEATURE:
<221> NAME/KEY: MOD_RES
<222> LOCATION: (121)..(132)
<223> OTHER INFORMATION: continued from above, "His Asp Ala Phe Gly Tyr
      Asp Phe Gly," "Ile Pro Pro His Asn Ala Asp Ser Ser Ile Ile Gly" or
      "Ala Lys Pro Glu Lys Trp Asp Gly Pro Pro Leu Trp," wherein some
      positions may be absent
<220> FEATURE:
<221> NAME/KEY: MOD_RES
<222> LOCATION: (136)..(136)
<223> OTHER INFORMATION: Ala or Thr
<220> FEATURE:
<221> NAME/KEY: MOD_RES
<222> LOCATION: (140)..(146)
<223> OTHER INFORMATION: Any amino acid and this region may preferably
      comprise the sequence "Lys Asp Val Pro Gly Asp Arg"
<220> FEATURE:
<221> NAME/KEY: MOD_RES
<222> LOCATION: (152)..(157)
<223> OTHER INFORMATION: Any amino acid and this region may preferably
      comprise the sequence "Gln Gln Lys His Thr Ala," "Thr Glu Asp Glu
      Asn Gln," "Asn Ser Arg His Thr Ala," "Pro Asp His Phe His Asn,"
      "Tyr Asp Val Ala Phe Asp" or "Gln Gln Lys His Asn Gln"
<220> FEATURE:
<221> NAME/KEY: MOD_RES
<222> LOCATION: (161)..(168)
<223> OTHER INFORMATION: Any amino acid and this region may preferably
      comprise the sequence "Gly Asn Leu Lys Pro Asp Thr Glu"
<220> FEATURE:
<221> NAME/KEY: MOD_RES
<222> LOCATION: (176)..(186)
<223> OTHER INFORMATION: Any amino acid and this region may preferably
      comprise the sequence "Phe Asp Pro Tyr Gly Ala Lys Ser Asn Pro
      Ala," "Pro Asn Tyr Glu Arg Ile Ser Asn Pro Ala," "Phe Asp Pro Tyr
      Gly Met Arg Ser Lys Pro Ala," "Phe Thr Pro Tyr Gly Ala Lys Ser Asn
      Pro Ala,"
<220> FEATURE:
<221> NAME/KEY: MOD_RES
<222> LOCATION: (176)..(186)
<223> OTHER INFORMATION: continued from above, "Ala Asn Asp His Gly Phe
      Asp Ser Asn Pro Ala," "Asp Thr Phe Tyr Gly Phe Asp Ser Asn Pro
      Ala" "Phe Asp Pro Tyr Asn Lys Arg Asn Val Pro Ala" or "Phe Asp Pro
      Tyr Gly Leu Lys Ser Arg Pro Ala," wherein some positions may be
      absent
<220> FEATURE:
<223> OTHER INFORMATION: See specification as filed for detailed
      description of substitutions and preferred embodiments

<400> SEQUENCE: 249

Ala Ile Glu Val Xaa Xaa Xaa Xaa Xaa Xaa Xaa Ala Leu Ile Thr Trp
1               5                   10                  15

Xaa Xaa Xaa Xaa Xaa Xaa Xaa Xaa Xaa Xaa Xaa Cys Glu Leu Xaa
            20                  25                  30

Tyr Gly Ile Xaa Xaa Xaa Xaa Xaa Xaa Xaa Thr Thr Ile Asp Leu Xaa
        35                  40                  45

Xaa Xaa Xaa Xaa Xaa Tyr Ser Ile Xaa Xaa Xaa Xaa Xaa Xaa Xaa
    50                  55                  60

Tyr Glu Val Ser Leu Ile Cys Xaa Xaa Xaa Xaa Xaa Xaa Xaa Xaa
65                  70                  75                  80
```

```
Xaa Xaa Lys Glu Thr Phe Thr Thr Gly Gly Gly Ser Gly Gly Gly
            85                  90                  95

Gly Ser Arg Leu Asp Ala Pro Gly Gln Ile Glu Val Xaa Xaa Xaa Xaa
            100                 105                 110

Xaa Xaa Xaa Ala Leu Ile Thr Trp Xaa Xaa Xaa Xaa Xaa Xaa Xaa
            115                 120                 125

Xaa Xaa Xaa Xaa Cys Glu Leu Xaa Tyr Gly Ile Xaa Xaa Xaa Xaa
            130                 135                 140

Xaa Xaa Thr Thr Ile Asp Leu Xaa Xaa Xaa Xaa Xaa Tyr Ser Ile
145                 150                 155                 160

Xaa Xaa Xaa Xaa Xaa Xaa Xaa Xaa Tyr Glu Val Ser Leu Ile Cys Xaa
                165                 170                 175

Xaa Xaa Xaa Xaa Xaa Xaa Xaa Xaa Xaa Xaa Lys Glu Thr Phe Thr Thr
            180                 185                 190

Gly Gly Gly Thr Leu Gly His His His His His His His
            195                 200                 205

<210> SEQ ID NO 250
<211> LENGTH: 211
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (5)..(11)
<223> OTHER INFORMATION: Any amino acid and this region may preferably
      comprise the sequence "Lys Asp Val Thr Asp Thr Thr"
<220> FEATURE:
<221> NAME/KEY: MOD_RES
<222> LOCATION: (17)..(28)
<223> OTHER INFORMATION: Any amino acid and this region may preferably
      comprise the sequences "Ala Lys Pro Trp Val Asp Pro Pro Leu
      Trp Gly," "Ser Pro Gly Glu Arg Ile Trp Met Phe Thr Gly," "Ala Lys
      Pro Glu Lys Trp Asp Gly Ser Ile Tyr Gly,"
<220> FEATURE:
<221> NAME/KEY: MOD_RES
<222> LOCATION: (17)..(28)
<223> OTHER INFORMATION: continued from above, "His Asp Ala Phe Gly Tyr
      Asp Phe Gly," "Ile Pro Pro His Asn Ala Asp Ser Ser Ile Ile Gly" or
      "Ala Lys Pro Glu Lys Trp Asp Gly Pro Pro Leu Trp," wherein some
      positions may be absent
<220> FEATURE:
<221> NAME/KEY: MOD_RES
<222> LOCATION: (32)..(32)
<223> OTHER INFORMATION: Ala or Thr
<220> FEATURE:
<221> NAME/KEY: MOD_RES
<222> LOCATION: (36)..(42)
<223> OTHER INFORMATION: Any amino acid and this region may preferably
      comprise the sequence "Lys Asp Val Pro Gly Asp Arg"
<220> FEATURE:
<221> NAME/KEY: MOD_RES
<222> LOCATION: (48)..(53)
<223> OTHER INFORMATION: Any amino acid and this region may preferably
      comprise the sequence "Gln Gln Lys His Thr Ala," "Thr Glu Asp Glu
      Asn Gln," "Asn Ser Arg His Thr Ala," "Pro Asp His Phe His Asn,"
      "Tyr Asp Val Ala Phe Asp" or "Gln Gln Lys His Asn Gln"
<220> FEATURE:
<221> NAME/KEY: MOD_RES
<222> LOCATION: (57)..(64)
<223> OTHER INFORMATION: Any amino acid and this region may preferably
      comprise the sequence "Gly Asn Leu Lys Pro Asp Thr Glu"
<220> FEATURE:
<221> NAME/KEY: MOD_RES
<222> LOCATION: (72)..(82)
<223> OTHER INFORMATION: Any amino acid and this region may preferably
      comprise the sequence "Phe Asp Pro Tyr Gly Ala Lys Ser Asn Pro
      Ala," "Pro Asn Tyr Glu Arg Ile Ser Asn Pro Ala," "Phe Asp Pro Tyr
      Gly Met Arg Ser Lys Pro Ala," "Phe Thr Pro Tyr Gly Ala Lys Ser Asn
```

```
              Pro Ala,"
<220> FEATURE:
<221> NAME/KEY: MOD_RES
<222> LOCATION: (72)..(82)
<223> OTHER INFORMATION: continued from above, "Ala Asn Asp His Gly Phe
      Asp Ser Asn Pro Ala," "Asp Thr Phe Tyr Gly Phe Asp Ser Asn Pro
      Ala" "Phe Asp Pro Tyr Asn Lys Arg Asn Val Pro Ala" or "Phe Asp Pro
      Tyr Gly Leu Lys Ser Arg Pro Ala," wherein some positions may be
      absent
<220> FEATURE:
<221> NAME/KEY: MOD_RES
<222> LOCATION: (114)..(120)
<223> OTHER INFORMATION: Any amino acid and this region may preferably
      comprise the sequence "Lys Asp Val Thr Asp Thr Thr"
<220> FEATURE:
<221> NAME/KEY: MOD_RES
<222> LOCATION: (126)..(137)
<223> OTHER INFORMATION: Any amino acid and this region may preferably
      comprise the sequences "Ala Lys Pro Trp Val Asp Pro Pro Pro Leu
      Trp Gly," "Ser Pro Gly Glu Arg Ile Trp Met Phe Thr Gly," "Ala Lys
      Pro Glu Lys Trp Asp Gly Ser Ile Tyr Gly,"
<220> FEATURE:
<221> NAME/KEY: MOD_RES
<222> LOCATION: (126)..(137)
<223> OTHER INFORMATION: continued from above, "His Asp Ala Phe Gly Tyr
      Asp Phe Gly," "Ile Pro Pro His Asn Ala Asp Ser Ser Ile Ile Gly" or
      "Ala Lys Pro Glu Lys Trp Asp Gly Pro Pro Leu Trp," wherein some
      positions may be absent
<220> FEATURE:
<221> NAME/KEY: MOD_RES
<222> LOCATION: (141)..(141)
<223> OTHER INFORMATION: Ala or Thr
<220> FEATURE:
<221> NAME/KEY: MOD_RES
<222> LOCATION: (145)..(151)
<223> OTHER INFORMATION: Any amino acid and this region may preferably
      comprise the sequence "Lys Asp Val Pro Gly Asp Arg"
<220> FEATURE:
<221> NAME/KEY: MOD_RES
<222> LOCATION: (157)..(162)
<223> OTHER INFORMATION: Any amino acid and this region may preferably
      comprise the sequence "Gln Gln Lys His Thr Ala," "Thr Glu Asp Glu
      Asn Gln," "Asn Ser Arg His Thr Ala," "Pro Asp His Phe His Asn,"
      "Tyr Asp Val Ala Phe Asp" or "Gln Gln Lys His Asn Gln"
<220> FEATURE:
<221> NAME/KEY: MOD_RES
<222> LOCATION: (166)..(173)
<223> OTHER INFORMATION: Any amino acid and this region may preferably
      comprise the sequence "Gly Asn Leu Lys Pro Asp Thr Glu"
<220> FEATURE:
<221> NAME/KEY: MOD_RES
<222> LOCATION: (181)..(191)
<223> OTHER INFORMATION: Any amino acid and this region may preferably
      comprise the sequence "Phe Asp Pro Tyr Gly Ala Lys Ser Asn Pro
      Ala," "Pro Asn Tyr Glu Arg Ile Ser Asn Pro Ala," "Phe Asp Pro Tyr
      Gly Met Arg Ser Lys Pro Ala," "Phe Thr Pro Tyr Gly Ala Lys Ser Asn
      Pro Ala,"
<220> FEATURE:
<221> NAME/KEY: MOD_RES
<222> LOCATION: (181)..(191)
<223> OTHER INFORMATION: continued from above, "Ala Asn Asp His Gly Phe
      Asp Ser Asn Pro Ala," "Asp Thr Phe Tyr Gly Phe Asp Ser Asn Pro
      Ala" "Phe Asp Pro Tyr Asn Lys Arg Asn Val Pro Ala" or "Phe Asp Pro
      Tyr Gly Leu Lys Ser Arg Pro Ala," wherein some positions may be
      absent
<220> FEATURE:
<223> OTHER INFORMATION: See specification as filed for detailed
      description of substitutions and preferred embodiments

<400> SEQUENCE: 250

Ala Ile Glu Val Xaa Xaa Xaa Xaa Xaa Xaa Xaa Ala Leu Ile Thr Trp
1               5                   10                  15

Xaa Xaa Xaa Xaa Xaa Xaa Xaa Xaa Xaa Xaa Xaa Cys Glu Leu Xaa
            20                  25                  30

Tyr Gly Ile Xaa Xaa Xaa Xaa Xaa Xaa Xaa Thr Thr Ile Asp Leu Xaa
        35                  40                  45
```

```
Xaa Xaa Xaa Xaa Xaa Tyr Ser Ile Xaa Xaa Xaa Xaa Xaa Xaa Xaa
            50              55                  60

Tyr Glu Val Ser Leu Ile Cys Xaa Xaa Xaa Xaa Xaa Xaa Xaa Xaa
 65              70              75                      80

Xaa Xaa Lys Glu Thr Phe Thr Thr Gly Gly Gly Ser Gly Gly Gly
                 85              90              95

Gly Ser Gly Gly Gly Gly Ser Arg Leu Asp Ala Pro Gly Gln Ile Glu
            100             105                 110

Val Xaa Xaa Xaa Xaa Xaa Xaa Ala Leu Ile Thr Trp Xaa Xaa Xaa
        115             120             125

Xaa Xaa Xaa Xaa Xaa Xaa Xaa Xaa Cys Glu Leu Xaa Tyr Gly Ile
    130             135             140

Xaa Xaa Xaa Xaa Xaa Xaa Xaa Thr Thr Ile Asp Leu Xaa Xaa Xaa
145             150             155                     160

Xaa Xaa Tyr Ser Ile Xaa Xaa Xaa Xaa Xaa Xaa Xaa Tyr Glu Val
            165             170             175

Ser Leu Ile Cys Xaa Xaa Xaa Xaa Xaa Xaa Xaa Xaa Xaa Xaa Lys
            180             185             190

Glu Thr Phe Thr Thr Gly Gly Gly Thr Leu Gly His His His His
            195             200             205

His His His
    210

<210> SEQ ID NO 251
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 251

Gly Gly Gly Gly His His His His His His His His
1               5                   10
```